United States Patent
Cao et al.

(10) Patent No.: US 7,314,974 B2
(45) Date of Patent: Jan. 1, 2008

(54) EXPRESSION OF MICROBIAL PROTEINS IN PLANTS FOR PRODUCTION OF PLANTS WITH IMPROVED PROPERTIES

(75) Inventors: Yongwei Cao, Chesterfield, MO (US); Gregory J. Hinkle, Plymouth, MA (US); Steven C. Slater, Middleton, WI (US); Xianfeng Chen, Wildwood, MO (US); Barry S. Goldman, St. Louis, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 422 days.

(21) Appl. No.: 10/369,493

(22) Filed: Feb. 20, 2003

(65) Prior Publication Data

US 2003/0233675 A1 Dec. 18, 2003

Related U.S. Application Data

(60) Provisional application No. 60/360,039, filed on Feb. 21, 2002.

(51) Int. Cl.
*C12N 15/82* (2006.01)
*A01H 5/00* (2006.01)

(52) U.S. Cl. .......................... 800/289; 800/288; 800/290; 800/298; 800/312; 800/320.1

(58) Field of Classification Search ................. 435/419, 435/320.1; 536/23.74; 800/298, 312, 320.1
See application file for complete search history.

(56) References Cited

OTHER PUBLICATIONS

Dietrich F.S. et al. Uniprot Accession P39954, Feb. 1, 1995, Adenosylhomocysteinase (S-adenosyl-L-homocysteine hydrolase) (AdoHcyase), from *Saccharomyces cereviseae*, amino acid sequence from Nucleotide Sequence [Large Scale Genomic DNA].*
Bell M.H. et al. Tobacco plants transformed with cdc25, a mitotic inducer gene from fission yeast. Plant Mol Biol. Nov. 1993; 23(3):445-51.*
Kawalleck P. et al. Induction by fungal elicitor of S-adenosyl-L-methionine synthetase and S-adenosyl-L-homocysteine hydrolase mRNAs in cultured cells and leaves of *Petroselinum crispum*. Proc Natl Acad Sci U S A. May 15, 1992;89(10):4713-7.*
Bell M.H. et al. Tobacco plants transformed with cdc25, a mitotic inducer gene from fission yeast. Plant Mol Biol. Nov. 1993; 23(3):445-51.*
Kawalleck P. et al. Induction by fungal elicitor of S-adenosyl-L-methionine synthetase and S-adenosyl-L-homocysteine hydrolase mRNAs in cultured cells and leaves of *Petroselinum crispum*. Proc Natl Acad Sci U S A. May 15, 1992;89(10):4713-7.*
Dietrich F.S. et al.Uniprot Accession P39954, Feb. 1, 1995, Adenosylhomocysteinase (S-adenosyl-L-homocysteine hydrolase) (AdoHcyase), from *Saccharomyces cereviseae*, amino acid sequence from Nucleotide Sequence [Large Scale Genomic DNA].*

* cited by examiner

*Primary Examiner*—Cynthia Collins
(74) *Attorney, Agent, or Firm*—Donna E. Scherer; Thomas E. Kelley

(57) ABSTRACT

Recombinant constructs and methods useful for improvement of plants are provided. In particular, recombinant constructs comprising promoters functional in plant cells positioned for expression of polynucleotides encoding polypeptides from microbial sources are provided. The disclosed constructs and methods find use in production of transgenic plants to provide plants, particularly crop plants, having improved properties.

8 Claims, No Drawings

EXPRESSION OF MICROBIAL PROTEINS IN PLANTS FOR PRODUCTION OF PLANTS WITH IMPROVED PROPERTIES

CROSS-REFERENCE TO RELATED APPLICATIONS

This application claims priority under 35 U.S.C. § 119 (e) of U.S. Provisional Application No. 60/360,039 filed Feb. 21, 2002, the disclosure of which application is incorporated herein by reference in its entirety.

INCORPORATION OF SEQUENCE LISTING

Two copies of the sequence listing (Copy 1 and Copy 2) and a computer readable form (CRF) of the sequence listing, all on CD-ROMs, each containing the file named pa_00433.rpt, which is 136,695,099 bytes (measured in MS-WINDOWS) and was created on Feb. 7, 2003, are herein incorporated by reference.

INCORPORATION OF TABLES

Two copies of Tables 1 and 2 on CD-ROMs, each containing the file named pa_00420.txt, which is 28,959,455 bytes (measured in MS-WINDOWS) and was created on Feb. 18, 2002, are herein incorporated by reference.

FIELD OF THE INVENTION

Disclosed herein are inventions in the field of plant biochemistry and genetics. More specifically methods of producing transgenic plants having improved properties as the result of expression of microbial polypeptides are provided.

BACKGROUND OF THE INVENTION

The ability to develop transgenic plants with improved traits depends in part on the identification of genes that are useful for production of transformed plants for expression of novel polypeptides. Microbial genes are of interest for expression in transgenic plants for a number of reasons. Bacteria and fungi have been well characterized as model organisms. Therefore there is a wide array of knowledge about the biochemical properties of the genes and pathways in these organisms that allows selection of target genes for expression in plants to produce specific effects on pathways of interest and generate transgenic plants having improved phenotypic properties. In addition, there is a great diversity of genes from which to choose in microorganisms. Of particular interest is the ability to express genes in plants that encode proteins that are not subject to the same types of enzymatic feedback as the native plant genes.

SUMMARY OF THE INVENTION

This invention provides recombinant DNA constructs which provide for expression in plant cells of polypeptides encoded by microbial genes. Expression of such polypeptides in transgenic plants leads to plants having improved phenotypic properties and/or improved response to stressful environmental conditions. Of particular interest are recombinant DNA constructs, wherein said constructs comprise a promoter functional in a plant cell, wherein said promoter is positioned to provide for expression of a polynucleotide encoding a polypeptide from a microbial source, wherein said polynucleotide is selected from the group consisting of:

(a) a polynucleotide comprising a nucleic acid sequence selected from the group consisting of SEQ ID NO:1 through SEQ ID NO:23687;
(b) a polynucleotide encoding a polypeptide having an amino acid sequence selected from the group consisting of SEQ ID NO:23688 through SEQ ID NO:47374;
(c) a polynucleotide having at least 70% sequence identity to a polynucleotide of (a) or (b);
(d) a polynucleotide encoding a polypeptide having at least 80% sequence identity to a polypeptide having an amino acid sequence selected from the group consisting of SEQ ID NO:23688 through SEQ ID NO:47374, wherein said encoded polypeptide is a functional homolog of said polypeptide having an amino acid sequence selected from the group consisting of SEQ ID NO:23688 through SEQ ID NO:47374.

Such constructs are useful for production of transgenic plants having at least one improved biological property as the result of expression of a polypeptide using a construct of this invention. Improved properties of interest include yield, disease resistance, growth rate, stress tolerance and others as set forth in more detail herein.

The present invention also provides a method of improving a biological property of a plant by inserting into cells of said plant a recombinant DNA construct of the present invention.

This invention also provides transformed plants, preferably transformed crop plants, comprising a recombinant DNA construct of the present invention, and having an improved biological property as the result of the expression of a microbial polypeptide from said recombinant DNA construct.

DETAILED DESCRIPTION OF THE INVENTION

The present invention provides recombinant DNA constructs, wherein said constructs comprise a promoter functional in a plant cell, positioned to provide for expression of a polynucleotide encoding a polypeptide from a microbial source. Microbial polypeptides of interest for expression from such constructs are provided herein and are selected for their ability to impart improved properties to transformed plants as the result of modification of any one or more of a variety of plant phenotypes.

The constructs of the present invention find use in generation of transgenic plants to provide for expression of polypeptides encoded by polynucleotides, including the native microbial polynucleotides described herein. As a result of such biotechnological applications, plants, particularly crop plants, having improved properties are obtained. Crop plants of interest in the present invention include, but are not limited to soy, cotton, canola, maize, wheat, sunflower, sorghum, alfalfa, barley, millet, rice, tobacco, fruit and vegetable crops, and turf grass. Of particular interest are expression of the disclosed polypeptides to provide plants having improved yield resulting from improved utilization of key biochemical compounds, such as nitrogen, phosphorous or carbohydrate, or resulting from improved responses to environmental stresses, such as cold, heat, drought or salt, or improved response to attack by pests or pathogens. Constructs of the present invention may also be used to provide plants having improved growth and development, and ultimately increased yield, as the result of modified expression of growth regulators or modification of cell cycle or photosynthesis pathways. Other traits of interest that may be modified in plants using constructs of the present invention include seed oil and protein quantity and quality, herbicide tolerance and rate of homologous recombination.

The polynucleotides or polypeptides from a microbial source as used in this invention may be isolated from the source organism or may be obtained in some other manner, for example by de novo synthesis of polynucleotides. Thus, as used herein, the term "microbial source" indicates that the molecule was identified as naturally existing in a microbe, but does not necessarily indicate the molecule itself was specifically isolated from the source organism.

As used herein a "transgenic" organism is one whose genome has been altered by the incorporation of foreign genetic material or additional copies of native genetic material, e.g. by transformation or recombination.

It is understood that the molecules of the invention may be labeled with reagents that facilitate detection of the molecule. As used herein, a label can be any reagent that facilitates detection, including fluorescent labels (Prober, et al., *Science* 238:336-340 (1987); Albarella et al., EP 144914), chemical labels (Sheldon et al., U.S. Pat. No. 4,582,789; Albarella et al., U.S. Pat. No. 4,563,417), or modified bases (Miyoshi et al., EP 119448), including nucleotides with radioactive elements, e.g. $^{32}P$, $^{33}P$, $^{35}S$ or $^{125}I$ such as $^{32}P$ deoxycytidine-5'-triphosphate ($^{32}PdCTP$).

Polynucleotides are capable of specifically hybridizing to other polynucleotides under certain circumstances. As used herein, two polynucleotides are said to be capable of specifically hybridizing to one another if the two molecules are capable of forming an anti-parallel, double-stranded nucleic acid structure. A nucleic acid molecule is said to be the "complement" of another nucleic acid molecule if the molecules exhibit complete complementarity. As used herein, molecules are said to exhibit "complete complementarity" when every nucleotide in each of the molecules is complementary to the corresponding nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haynes et al., *Nucleic Acid Hybridization, A Practical Approach*, IRL Press, Washington, D.C. (1985).

Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology*, John Wiley & Sons, N.Y. (1989), 6.3.1-6.3.6. Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

As used herein "sequence identity" refers to the extent to which two optimally aligned polynucleotide or peptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as those in the BLAST suite of sequence analysis programs.

Polynucleotides—This invention utilizes polynucleotides that encode polypeptides identified from a microbial source. The encoded polypeptides may be the complete protein encoded by an identified microbial gene, or may be fragments of the encoded protein. Preferably, polynucleotides utilized herein encode polypeptides constituting a substantial portion of the complete protein, and more preferentially, constituting a sufficient portion of the complete protein to provide the relevant biological activity.

Of particular interest are polynucleotides that encode polypeptides involved in one or more important biological functions that are common between microbes and plants. Such polynucleotides may be expressed in transgenic plants to produce plants having improved phenotypic properties and/or improved response to stressful environmental conditions. See, for example, Tables 3-21 for a list of improved plant properties and responses and the SEQ ID NOs representing exemplary polynucleotides that may be expressed in transgenic plants to impart such improvements.

Polynucleotides of the present invention are generally used to impart such biological properties by providing for enhanced protein activity in a transgenic organism, preferably a transgenic plant. Enhanced protein activity is evaluated by reference to a wild type cell or organism and can be determined by direct or indirect measurement. Direct measurement of protein activity might include an analytical assay for the protein, per se, or enzymatic product of protein activity. Indirect assay might include measurement of a property affected by the protein.

The polynucleotides that find use in this invention represent genes from a variety of bacterial and fungal sources as shown in Table 1. Nucleic acid sequences of polynucleotides for use in the constructs of the present invention are exemplified herein by the native microbial polynucleotide sequences provided as SEQ ID NO: 1 through SEQ ID NO: 23687.

Also of interest for use in the constructs of the present invention are variants of the polynucleotides provided herein. Such variants may be naturally occurring, including homologous polynucleotides from the same or a different species, or may be non-natural variants, for example polynucleotides synthesized using chemical synthesis methods, or generated using recombinant DNA techniques. Degeneracy of the genetic code provides the possibility to substitute at least one base of the protein encoding sequence of a gene with a different base without causing the amino acid sequence of the polypeptide produced from the gene to be changed. Hence, the DNA utilized in the present invention may also have any base sequence that has been changed from SEQ ID NO: 1 through SEQ ID NO: 23687 by substitution in accordance with degeneracy of the genetic code.

Also of interest regarding variant sequences for expression of microbial polypeptides in plants is the use of polynucleotides optimized for efficient expression of the encoded polypeptide in plants. For example, the encoding polynucleotides can be synthesized or modified using plant preferred codons for improved expression. It is recognized that all or any part of the encoding sequence may be optimized by synthesis or modification, and that partially optimized polynucleotides are also of interest for expression of microbial polypeptides for modification of plant properties. Codon usage tables may be used to identify plant preferred codons, for example by identifying the codons of highest frequency in the proteins expressed in the largest amount in the particular plant species of interest, and to avoid the use of codons that are rarely found in plants. References describing codon usage include: U.S. Pat. No. 5,500,365, Nakamura et al. (2000) *Nucl. Acids Res.* 28:292, Perlak et al. (1991) *Proc. Natl. Acad. Sci. USA* 88:3324-3328, Carels et al. (1998) *J. Mol. Evol.* 46: 45 and Fennoy et al. (993) *Nucl. Acids Res.* 21(23):5294. Codon usage tables for a number of plant species are also available from the Department of Plant Gene Research at the Kazusa DNA Research Institute, Japan, for example at www.kazusa.or.jp/codon/.

Additional sequence modifications are known to enhance gene expression in plant hosts. These include elimination of sequences encoding spurious polyadenylation signals, exon-intron splice site signals, transposon-like repeats, hairpin secondary mRNA structures and other such well-characterized sequences which may be deleterious to gene expression. The G–C content of the sequence may also be adjusted to levels generally used by the target plant host. For example, some microbial genes are very rich (>60%) in adenine (A) and thymine (T) while plant genes are on the order of 45-55% A+T. It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

As discussed above, modification of the DNA sequences of wild-type genes and construction of t a completely synthetic gene for a given amino acid sequence are both desirable methods for increasing the expression level of non-plant genes in plant cells. In general, regions with multiple consecutive A+T or G+C nucleotides should be avoided. Codons should be selected avoiding the TA and CG doublets where possible. Codon usage can be normalized against a plant preferred codon usage table and the G+C content preferably adjusted to about 50%. The resulting sequence should also be examined to ensure that there are minimal putative plant polyadenylation signals and ATTTA sequences.

Polynucleotides for use in constructs of the present invention that are variants of the polynucleotides described herein will generally demonstrate significant identity with the polynucleotides provided herein. Of particular interest are polynucleotide homologs having at least about 60% sequence identity, at least about 70% sequence identity, at least about 80% sequence identity, at least about 85% sequence identity, and more preferably at least about 90%, 95% or even greater, such as 98% or 99% sequence identity with polynucleotide sequences described herein.

Protein and Polypeptide Molecules—This invention encompasses recombinant DNA expression constructs that provide for production of polypeptides from microbial sources in plants and/or plant cells. Amino acid sequences of the polypeptides of interest for expression using constructs of the present invention are provided herein as SEQ ID NO:23688 through SEQ ID NO:47374.

As used herein, the term "polypeptide" means an unbranched chain of amino acid residues that are covalently linked by an amide linkage between the carboxyl group of one amino acid and the amino group of another. The term polypeptide can encompass whole proteins (i.e. a functional protein encoded by a particular gene), as well as fragments of proteins. Of particular interest are polypeptides which represent whole proteins or a sufficient portion of the entire protein to impart the relevant biological activity of the protein. The term "protein" also includes molecules consisting of one or more polypeptide chains. Thus, a polypeptide for use in constructs of the present invention may also constitute an entire gene product, but only a portion of a functional oligomeric protein having multiple polypeptide chains.

Of particular interest for expression from constructs of the present invention are polypeptides involved in one or more important biological properties in plants. Such polypeptides may be produced in transgenic plants to provide plants having improved phenotypic properties and/or improved response to stressful environmental conditions. See, Tables 3-21 for improved plant properties and responses and the SEQ ID NOs for the polypeptides whose expression in transgenic plants is of interest to impart such improvements. A summary of such improved properties and polypeptides of interest is provided below.

Yield/Nitrogen: Yield improvement by improved nitrogen flow, sensing, uptake, storage and/or transport. Polypeptides useful for imparting such properties include those involved in aspartate and glutamate biosynthesis, polypeptides involved in aspartate and glutamate transport, polypeptides associated with the TOR (Target of Rapamycin) pathway, nitrate transporters, ammonium transporters, chlorate transporters and polypeptides involved in tetrapyrrole biosynthesis.

Yield/Carbohydrate: Yield improvement by effects on carbohydrate metabolism, for example by increased sucrose production and/or transport. Polypeptides useful for improved yield by effects on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, and polypeptides involved in glucose signaling, such as SNF1 complex proteins.

Yield/Photosynthesis: Yield improvement resulting from increased photosynthesis. Polypeptides useful for increasing the rate of photosynthesis include phytochrome, photosystem I and II proteins, electron carriers, ATP synthase, NADH dehydrogenase and cytochrome oxidase.

Yield/Phosphorus: Yield improvement resulting from increased phosphorus uptake, transport or utilization. Polypeptides useful for improving yield in this manner include phosphatases and phosphate transporters.

Yield/Stress tolerance: Yield improvement resulting from improved plant growth and development by helping plants to tolerate stressful growth conditions. Polypeptides useful for improved stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and homoglobin. Enhanced activity of such polypeptides in transgenic plants will provide changes in the ability of a plant to respond to a variety of environmental stresses, such as chemical stress, drought stress and pest stress.

Cold tolerance: Polypeptides of interest for improving plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins and uncoupling protein.

Heat tolerance: Polypeptides of interest for improving plant tolerance to heat include polypeptides involved in biosynthesis of trehalose, polypeptides involved in glycerolipid biosynthesis or membrane lipid metabolism (for altering membrane fatty acid composition), heat shock proteins and mitochondrial NDK.

Osmotic tolerance: Polypeptides of interest for improving plant tolerance to extreme osmotic conditions include polypeptides involved in proline biosynthesis.

Drought tolerance: Polypeptides of interest for improving plant tolerance to drought conditions include aquaporins, polypeptides involved in biosynthesis of trehalose or wax, LEA proteins and invertase.

Pathogen or pest tolerance: Polypeptides of interest for improving plant tolerance to effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects.

Cell cycle modification: Polypeptides encoding cell cycle enzymes and regulators of the cell cycle pathway are useful for manipulating growth rate in plants to provide early vigor and accelerated maturation leading to improved yield. Improvements in quality traits, such as seed oil content, may also be obtained by expression of cell cycle enzymes and cell cycle regulators. Polypeptides of interest for modification of cell cycle pathway include cyclins and EIF5alpha pathway proteins, polypeptides involved in polyamine metabolism, polypeptides which act as regulators of the cell cycle pathway, including cyclin-dependent kinases (CDKs), CDK-activating kinases, CDK-inhibitors, Rb and Rb-binding proteins, and transcription factors that activate genes involved in cell proliferation and division, such as the E2F family of transcription factors, proteins involved in degradation of cyclins, such as cullins, and plant homologs of tumor suppressor polypeptides.

Seed protein yield/content: Polypeptides useful for providing increased seed protein quantity and/or quality include polypeptides involved in the metabolism of amino acids in plants, particularly polypeptides involved in biosynthesis of methionine/cystein and lysine, amino acid transporters, amino acid efflux carriers, seed storage proteins, proteases, and polypeptides involved in phytic acid metabolism.

Seed oil yield/content: Polypeptides useful for providing increased seed oil quantity and/or quality include polypeptides involved in fatty acid and glycerolipid biosynthesis, beta-oxidation enzymes, enzymes involved in biosynthesis of nutritional compounds, such as carotenoids and tocopherols, and polypeptides that increase embryo size or number or thickness of aleurone.

Disease response in plants: Polypeptides useful for imparting improved disease responses to plants include polypeptides encoded by cercosporin induced genes, antifungal proteins and proteins encoded by R-genes or SAR genes. Expression of such polypeptides in transgenic plants will provide an increase in disease resistance ability of plants.

Galactomannanan biosynthesis: Polypeptides involved in production of galactomannans are of interest for providing plants having increased and/or modified reserve polysaccharides for use in food, pharmaceutical, cosmetic, paper and paint industries.

Flavonoid/isoflavonoid metabolism in plants: Polypeptides of interest for modification of flavonoid/isoflavonoid metabolism in plants include cinnamate-4-hydroxylase, chalcone synthase and flavonol synthase. Enhanced activity of such polypeptides in transgenic plants will provide changes in the quantity and/or speed of flavonoid metabolism in plants and may improve disease resistance by enhancing synthesis of protective secondary metabolites or improving signaling pathways governing disease resistance.

Growth regulators: Polypeptides involved in production of substances that regulate the growth of various plant tissues are of interest in the present invention and may be used to provide transgenic plants having altered morphologies and improved plant growth and development profiles leading to improvements in yield and stress response. Of particular interest are polypeptides involved in the biosynthesis of plant growth hormones, such as gibberellins, cytokinins, auxins, ethylene and abscisic acid, and other proteins involved in the activity and/or transport of such polypeptides, including for example, cytokinin oxidase, cytokinin/purine permeases, F-box proteins, G-protiens and phytosulfokines.

Herbicide tolerance: Polypeptides of interest for producing plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, including for example, resolvases and polypeptide members of the RAD52 epistasis group.

Lignin biosynthesis: Polypeptides involved in lignin biosynthesis are of interest for increasing plants' resistance to lodging and for increasing the usefulness of plant materials as biofuels.

The function of polypeptides used in constructs of the present invention may be known from previous experimental evidence, or may be determined by comparison of the amino acid sequence of the polypeptides to amino acid sequences of other polypeptides for which a function is known. A variety of homology based search algorithms are available to compare a query sequence to a protein database, including for example, BLAST, FASTA, and Smith-Waterman. In the present application, BLASTX and BLASTP algorithms are used to provide protein function information. A number of values are examined in order to assess the confidence of the function assignment. Useful measurements include "E-value" (also shown as "hit_p"), "percent identity", "percent query coverage", and "percent hit coverage".

In BLAST, E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GenBank, have generally increased over time for any given query/entry match. In setting criteria for confidence of polypeptide function prediction, a "high" BLAST match is considered herein as having an E-value for the top BLAST hit provided in Table 1 of less than 1E-30; a medium BLASTX E-value is 1E-30 to 1E-8; and a low BLASTX E-value is greater than 1E-8.

Percent identity refers to the percentage of identically matched amino acid residues that exist along the length of that portion of the sequences which is aligned by the BLAST algorithm. In setting criteria for confidence of polypeptide function prediction, a "high" BLAST match is considered herein as having percent identity for the top BLAST hit provided in Table 1 of at least 70%; a medium percent identity value is 35% to 70%; and a low percent identity is less than 35%.

Of particular interest in protein function assignment in the present invention is the use of combinations of E-values, percent identity, query coverage and hit coverage. Query coverage refers to the percent of the query sequence that is represented in the BLAST alignment. Hit coverage refers to the percent of the database entry that is represented in the BLAST alignment. In the present invention, function of a query polypeptide is inferred from function of a protein homolog where either (1) (hit_p<1e-30 or % identity>35%) AND query_coverage>50% AND hit_coverage>50%, or (2) hit_p<1e-8 AND query_coverage>70% AND hit_coverage>70%.

Functional homologs which differ in one or more amino acids from those of a polypeptide described herein as the result of one or more conservative amino acid substitutions are also of interest for expression in plants using the constructs of the present invention. It is well known in the art that one or more amino acids in a native sequence can be substituted with at least one other amino acid, the charge and polarity of which are similar to that of the native amino acid, resulting in a silent change. For instance, valine is a conservative substitute for alanine and threonine is a conservative substitute for serine. Conservative substitutions for an amino acid within the native polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. Also of interest for expression in transgenic plants using constructs as described herein are polypeptides which differ in one or more amino acids from those of a microbial polypeptide described herein as the result of deletion or insertion of one or more amino acids in a native sequence.

Also of interest for use in constructs of the present invention are functional homologs of the polypeptides described herein which have the same function as a microbial polypeptide provided herein, but with increased or decreased activity or altered specificity. Such variations in protein activity may exist naturally in polypeptides encoded by related genes, for example in a related polypeptide encoded by a different allele or in a different species, or can be achieved by mutagenesis. Naturally occurring variant polypeptides may be obtained by well known nucleic acid or protein screening methods using DNA or antibody probes, for example by screening libraries for genes encoding related polypeptides, or in the case of expression libraries, by screening directly for variant polypeptides. Screening methods for obtaining a modified protein or enzymatic activity of interest by mutagenesis are disclosed in U.S. Pat. No. 5,939,250. An alternative approach to the generation of variants uses random recombination techniques such as "DNA shuffling" as disclosed in U.S. Pat. Nos. 5,605,793; 5,811,238; 5,830,721 and 5,837,458; and International Applications WO 98/31837 and WO 99/65927, all of which are incorporated herein by reference. An alternative method of molecular evolution involves a staggered extension process (StEP) for in vitro mutagenesis and recombination of nucleic acid molecule sequences, as disclosed in U.S. Pat. No. 5,965,408 and International Application WO 98/42832, both of which are incorporated herein by reference.

Polypeptide variants useful for expression in transgenic plants will generally demonstrate significant identity with the polypeptides described herein. Of particular interest are polypeptides having at least about 35% sequence identity, at least about 50% sequence identity, at least about 60% sequence identity, at least about 70% sequence identity, at least about 80% sequence identity, and more preferably at least about 85%, 90%, 95% or even greater, sequence identity with polypeptide sequences described herein. Of particular interest in the present invention are polypeptides having amino acid sequences provided herein (reference polypeptides) and functional homologs of such reference polypeptides, wherein such functional homologs comprises at least 50 consecutive amino acids having at least 80% identity to a 50 amino acid polypeptide fragment of said reference polypeptide.

Recombinant DNA Constructs—The present invention encompasses the use of polynucleotides described herein in recombinant constructs, i.e. constructs comprising polynucleotides that are constructed or modified outside of cells and that join nucleic acids that are not found joined in nature. Using methods known to those of ordinary skill in the art, polypeptide encoding sequences of this invention can be inserted into recombinant DNA constructs that can be introduced into a host cell of choice for expression of the encoded protein. Of particular interest in the present invention is the use of the polynucleotides of the present invention for preparation of constructs for use in plant transformation.

In plant transformation, exogenous genetic material is transferred into a plant cell. By "exogenous" it is meant that a nucleic acid molecule, for example a recombinant DNA construct comprising a polynucleotide of the present invention, is produced outside the organism, e.g. plant, into which it is introduced. An exogenous nucleic acid molecule can have a naturally occurring or non-naturally occurring nucleotide sequence. One skilled in the art recognizes that an exogenous nucleic acid molecule can be derived from the same species into which it is introduced or from a different species. Such exogenous genetic material may be transferred into either monocot or dicot plants including, but not limited to, soy, cotton, canola, maize, teosinte, wheat, rice and *Arabidopsis* plants. Transformed plant cells comprising such exogenous genetic material may be regenerated to produce whole transformed plants.

Exogenous genetic material may be transferred into a plant cell by the use of a DNA vector or construct designed for such a purpose. A construct can comprise a number of sequence elements, including promoters, encoding regions, and selectable markers. Vectors are available which have been designed to replicate in both *E. coli* and *A. tumefaciens* and have all of the features required for transferring large inserts of DNA into plant chromosomes. Design of such vectors is generally within the skill of the art. See, for example, *Plant Molecular Biology: A Laboratory Manual*, Clark (ed.), Springier, New York (1997).

A construct will generally include a plant promoter to direct transcription of the protein encoding region of choice. Numerous promoters that are active in plant cells have been described in the literature. These include the nopaline synthase (NOS) promoter and octopine synthase (OCS) promoters carried on tumor-inducing plasmids of *Agrobacterium tumefaciens*, caulimovirus promoters such as the cauliflower mosaic virus (CaMV) 19S promoter (Lawton et al., *Plant Mol. Biol.* 9:315-324 (1987) and 35S promoter (Odell et al., *Nature* 313:810-812 (1985), CaMV enhanced 35s promoter and the figwort mosaic virus 35S-promoter. Other desirable promoters include the light-inducible promoter from the small subunit of ribulose-1,5-bis-phosphate carboxylase (ssRUBISCO), the actin 1 promoter from rice (McElroy et al. (1991) *Mol. Gen. Genet.* 231:150-160) or maize (Wang et al. (1992) *Molecular and Cellular Biology* 12:3399-3406), the Adh promoter (Walker et al., *Proc. Natl. Acad. Sci. (U.S.A.)* 84:6624-6628 (1987), the sucrose synthase promoter (Yang et al. (1990) *Proc. Natl. Acad. Sci. (U.S.A.)* 87:4144-4148), the R gene complex promoter (Chandler et al. (1989) *The Plant Cell* 1:1175-1183), and the chlorophyll a/b binding protein gene promoter. These promoters and numerous others have been used to create DNA constructs for expression in plants. See, for example, PCT publication WO 84/02913. Any promoter known or found to cause transcription of DNA in plant cells can be used in the invention. Other useful promoters are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are incorporated herein by reference.

In addition, promoter enhancers, such as the CaMV 35S enhancer (Kay et al. (1987) *Science* 236:1299-1302) or a tissue specific enhancer (Fromm et al. (1989) *The Plant Cell* 1:977-984), may be used to enhance gene transcription levels. Enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers which can be used in accordance with the invention include elements from octopine synthase genes (Ellis et al. (1987) *EMBO Journal* 6:3203-3208), the maize alcohol dehydrogenase gene intron 1 (Callis et al. (1987) *Genes and Develop.* 1:1183-1200), elements from the maize shrunken 1 gene, the sucrose synthase intron (Vasil et al. (1989) *Plant Physiol.* 91:1575-1579) and the TMV omega element (Gallie et al. (1989) *The Plant Cell* 1:301-311), and promoters from non-plant eukaryotes (e.g., yeast; Ruden et al. (1988) *Proc Natl. Acad. Sci.* 85:4262-4266). DNA constructs can also contain one or more 5' non-translated leader sequences which serve to enhance polypeptide production from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al. (1996) *Plant Mol. Biol.* 32:393-405).

Constructs and vectors may also include, with the coding region of interest, a nucleic acid sequence that acts, in whole or in part, to terminate transcription of that region. One type of 3' untranslated sequence which may be used is a 3' UTR from the nopaline synthase gene (nos 3') of *Agrobacterium tumefaciens* (Bevan et al. (1983) *Nucleic Acids Res.* 11:369-385). Other 3' termination regions of interest include those from a gene encoding the small subunit of a ribulose-1,5-bisphosphate carboxylase-oxygenase (rbcS), and more specifically, from a rice rbcS gene (PCT Publication WO 00/70066), the 3' UTR for the T7 transcript of *Agrobacterium tumefaciens* (Dhaese et al. (1983) *EMBO J* 2:419-426), the 3' end of the protease inhibitor I or II genes from potato (An et al. (1989) *Plant Cell* 1:115-122) or tomato (Pearce et al. (1991) *Science* 253:895-898), and the 3' region isolated from Cauliflower Mosaic Virus (Timmermans et al. (1990) *J Biotechnol* 14:333-344). Alternatively, one also can use a gamma coixin, oleosin 3 or other 3' UTRs from the genus *Coix* (PCT Publication WO 99/58659).

Constructs and vectors may also include a selectable marker. Selectable markers may be used to select for plants or plant cells that contain the exogenous genetic material. Examples of such include, but are not limited to, a nptII gene (Potrykus et al. (1985) *Mol. Gen. Genet.* 199:183-188)

which codes for kanamycin resistance and can be selected for using kanamycin, G418, etc.; a bar gene which codes for bialaphos resistance; a mutant EPSP synthase gene (Hinchee et al. (1988) *Bio/Technology* 6:915-922) which encodes glyphosate resistance; a nitrilase gene which confers resistance to bromoxynil (Stalker et al. (1988) *J. Biol. Chem.* 263:6310-6314); a mutant acetolactate synthase gene (ALS) which confers imidazolinone or sulphonylurea resistance (European Patent Application 154,204 (Sep. 11, 1985)); and a methotrexate resistant DHFR gene (Thillet et al. (1988) *J. Biol. Chem.* 263:12500-12508.

Constructs and vectors may also include a screenable marker. Screenable markers may be used to monitor transformation. Exemplary screenable markers include a β-glucuronidase or uidA gene (GUS) which encodes an enzyme for which various chromogenic substrates are known (Jefferson (1987) *Plant Mol. Biol, Rep.* 5:387-405); Jefferson et al. (1987) *EMBO J.* 6:3901-3907); an R-locus gene, which encodes a product that regulates the production of anthocyanin pigments (red color) in plant tissues (Dellaporta et al. (1988) *Stadler Symposium* 11:263-282); Other possible selectable and/or screenable marker genes will be apparent to those of skill in the art.

Constructs and vectors may also include a transit peptide for targeting of a gene target to a plant organelle, particularly to a chloroplast, leucoplast or other plastid organelle (European Patent Application Publication Number 0218571).

For use in *Agrobacterium* mediated transformation methods, constructs of the present invention will also include T-DNA border regions flanking the DNA to be inserted into the plant genome to provide for transfer of the DNA into the plant host chromosome as discussed in more detail below. An exemplary plasmid that finds use in such transformation methods is pCGN8640, a T-DNA vector that can be used to clone exogenous genes and transfer them into plants using *Agrobacterium*-mediated transformation. pCGN8640 has the restriction sites BamH1, Not1, HindIII, PstI, and SacI positioned between a 35S promoter element and a transcription terminator. Flanking this DNA are the left border and right border sequences necessary for *Agrobacterium* transformation. The plasmid also has origins of replication for maintaining the plasmid in both *E. coli* and *Agrobacterium tumefaciens* strains. A spectinomycin resistance gene on the plasmid can be used to select for the presence of the plasmid in both *E. coli* and *Agrobacterium tumefaciens*.

A candidate gene is prepared for insertion into the T-DNA vector, for example using well-known gene cloning techniques such as PCR. Restriction sites may be introduced onto each end of the gene to facilitate cloning. For example, candidate genes may be amplified by PCR techniques using a set of primers. Both the amplified DNA and the cloning vector are cut with the same restriction enzymes, for example, NotI and PstI. The resulting fragments are gel-purified, ligated together, and transformed into *E. coli*. Plasmid DNA containing the vector with inserted gene may be isolated from *E. coli* cells selected for spectinomycin resistance, and the presence to the desired insert in pCGN8640 verified by digestion with the appropriate restriction enzymes. Undigested plasmid may then be transformed into *Agrobacterium tumefaciens* using techniques well known to those in the art, and transformed *Agrobacterium* cells containing the vector of interest selected based on spectinomycin resistance. These and other similar constructs useful for plant transformation may be readily prepared by one skilled in the art.

Transformation Methods and Transgenic Plants—Methods and compositions for transforming bacteria and other microorganisms are known in the art. See for example Sambrook et al. (1989) *Molecular Cloning: A Laboratory Manual*, Second Edition, Cold Spring Harbor Laboratory Press, Cold Spring Harbor, N.Y.).

Technology for introduction of DNA into cells is well known to those of skill in the art. Known methods for delivering a gene into cells include: (a) chemical methods (Graham and van der Eb (1973) *Virology* 54:536-539); (b) physical methods such as microinjection (Capecchi (1980) *Cell* 22:479-488), electroporation (Wong and Neumann (1982) *Biochem. Biophys. Res. Commun.* 107:584-587); Fromm et al. (1985) *Proc. Natl. Acad. Sci. (U.S.A.)* 82:5824-5828); U.S. Pat. No. 5,384,253); the gene gun (Johnston and Tang (1994) *Methods Cell Biol.* 43:353-365); (c) viral vectors (Clapp (1993) *Clin. Perinatol.* 20:155-168); Lu et al. (1993) *J. Exp. Med.* 178:2089-2096); Eglitis and Anderson (1988) *Biotechniques* 6:608-614); (d) receptor-mediated mechanisms (Curiel et al. (1992) *Hum. Gen. Ther.* 3:147-154), Wagner et al. (1992) *Proc. Natl. Acad. Sci. (USA)* 89:6099-6103); and (e) *Agrobacterium tumefaciens*-mediated transformation of plants (Fraley et al., *Bio/Technology* 3:629-635 (1985); and Rogers et al. (1987) *Methods Enzymol.* 153:253-277). In addition, DNA constructs and methods for stably transforming plant plastids have been described; see, for example U.S. Pat. No. 5,877,402, incorporated herein by reference.

After transformation, the transformed plant cells or tissues may be grown in an appropriate medium to promote cell proliferation and regeneration. In the case of protoplasts the cell wall will first be allowed to reform under appropriate osmotic conditions, and the resulting callus introduced into a nutrient regeneration medium to promote the formation of shoots and roots. For gene gun transformation of wheat and maize see U.S. Pat. Nos. 6,153,812 and 6,160,208, both of which are incorporated herein by reference. See also, Chistou (1996) *Particle Bombardment for Genetic Engineering of Plants*, Biotechnology Intelligence Unit, Academic Press, San Diego, Calif.), and in particular, pp. 63-69 (maize), and pp50-60 (rice).

The use of *Agrobacterium*-mediated plant integrating vectors to introduce DNA into plant cells for production of stably transformed whole plants is well known in the art. The region of DNA to be transferred into the host genome is defined by the tDNA border sequences in *Agrobacterium*-mediated plant integrating vectors and intervening DNA is usually inserted into the plant genome as described (Spielmann et al. (1986) *Mol. Gen. Genet.* 205:34). See also U.S. Pat. Nos. 5,416,011; 5,463,174; and 5,959,179 for *Agrobacterium* mediated transformation of soy; U.S. Pat. Nos. 5,591,616 and 5,731,179 for *Agrobacterium* mediated transformation of monocots such as maize; and U.S. Pat. No. 6,037,527 for *Agrobacterium* mediated transformation of cotton, all of which are incorporated herein by reference. Modern *Agrobacterium* transformation vectors are capable of replication in *E. coli* as well as *Agrobacterium*, allowing for convenient manipulations (Klee et al. (1985) In: *Plant DNA Infectious Agents*, Hohn and Schell (eds.), Springer-Verlag, New York, pp. 179-203).

Microprojectile bombardment techniques are also widely applicable, and may be used to transform virtually any plant species. Examples of species which have been transformed by microprojectile bombardment include monocot species such as maize (PCT Publication WO 95/06128), barley, wheat (U.S. Pat. No. 5,563,055), rice, oats, rye, sugarcane, and sorghum, and dicot species including tobacco, soybean (U.S. Pat. No. 5,322,783), sunflower, cotton, tomato, and legumes in general (U.S. Pat. No. 5,563,055).

Any of the constructs of the present invention may be introduced into a plant cell in a permanent or transient manner in combination with other genetic elements such as vectors, promoters enhancers etc. Further any of the constructs of the present invention may be introduced into a plant cell in a manner that allows for production in the plant cell of one or more polypeptides encoded by microbial polynucleotides in the construct.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Expression of microbial polynucleotides using constructs of the present invention and the concomitant production of polypeptides encoded by the polynucleotides is of interest for production of transgenic plants having improved properties, particularly, improved properties which result in crop plant yield improvement. Expression of polypeptides in plant cells may be evaluated by specifically identifying the protein products of the introduced genes or evaluating the phenotypic changes brought about by their expression.

Assays for the production and identification of specific proteins make use of various physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, particularly where the expressed protein is an enzyme capable of catalyzing chemical reactions involving specific substrates and products. These reactions may be measured, for example in plant extracts, by providing and quantifying the loss of substrates or the generation of products of the reactions by physical and/or chemical procedures.

In many cases, the expression of a gene product is determined by evaluating the phenotypic results of its expression. Such evaluations may be simply as visual observations, or may involve assays. Such assays may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995; Birren et al., *Genome Analysis: Analyzing DNA*, 1, Cold Spring Harbor, N.Y. (1998)).

Having now generally described the invention, the same will be more readily understood through reference to the following example which is provided by way of illustration, and are not intended to be limiting of the present invention, unless specified.

EXAMPLE

Functions of polypeptides encoded by the microbial polynucleotide sequences described herein are determined using a hierarchical classification tool, termed FunCAT, for Functional Categories Annotation Tool. Most categories collected in FunCAT are classified by function, although other criteria are used, for example, cellular localization or temporal process. The assignment of a functional category to a query sequence is based on BLASTX sequence search, which compares two protein sequences. FunCAT assigns categories by iteratively scanning through all BLAST hits, starting with the most significant match, and reporting the first category assignment for each FunCAT source classification scheme. In the present invention, function of a query polypeptide is inferred from the function of a protein homolog where either (1) (hit_p<1e-30 or % identity>35%) AND query_coverage>50% AND hit_coverage>50%, or (2) hit_p<1e-8 AND query_coverage>70% AND hit_coverage>70%.

Functional assignments from five public classification schemes, GO_BP, GO_CC, GO_MF, KEGG and EC, and one internal Monsanto classification scheme, POI, are provided in Table 1. The column under the heading "cat_type" indicates the source of the classification. GO_BP=Gene Ontology Consortium–biological process; GO_CC=Gene Ontology Consortium–cellular component; GO_MF=Gene Ontology Consortium–molecular function; KEGG=KEGG functional hierarchy; EC=Enzyme Classification from ENZYME data bank release 25.0; POI=Pathways of Interest. The column under the heading "cat_desc" provides the name of the subcategory into which the query sequence was classified. The column under the heading "hit_desc" provides a description of the BLAST hit to the query sequences that led to the specific classification. The column under the heading "hit_p" provides the e-value for the BLAST hit.

Table 2 provides the SEQ ID NO (SEQ NUM), sequence designation (SEQ ID) of exemplary DNA sequence encoding the polypeptides described in Table 1. Table 2 also provides the SEQ ID NO (Prot Num) and sequence designation (Prot ID) of the proteins encoded by the nucleotide sequences.

Sequences useful for producing transgenic plants having improved biological properties are identified from their FunCAT annotations and are provided in Tables 3-21. a biological property of particular interest is plant yield. Plant yield may be improved by alteration of a variety of plant pathways, including those involving nitrogen, carbohydrate, or phosphorus utilization and/or uptake. Plant yield may also be improved by alteration of a plant's photosynthetic capacity or by improving a plant's ability to tolerate a variety of environmental stresses, including cold, heat, drought and osmotic stresses. Other biological properties of interest that may be improved using sequences of the present invention include pathogen or pest tolerance, herbicide tolerance, disease resistance, growth rate (for example by modification of cell cycle or expression of growth regulators), seed oil and/or protein yield and quality, rate and control of recombination, and lignin content.

TABLE 3

Cold Tolerance

Table 3A SEQ ID NOs of Polypeptides useful for improving Cold Tolerance

| 4 | 5 | 6 | 11 | 19 | 26 | 31 | 36 | 39 | 52 | 56 | 81 |
|---|---|---|----|----|----|----|----|----|----|----|----|
| 88 | 90 | 91 | 101 | 109 | 117 | 118 | 121 | 122 | 128 | 145 | 146 |
| 147 | 151 | 153 | 154 | 156 | 178 | 191 | 195 | 204 | 230 | 238 | 247 |
| 257 | 272 | 274 | 275 | 295 | 310 | 321 | 325 | 332 | 338 | 342 | 350 |
| 356 | 378 | 379 | 390 | 393 | 395 | 396 | 400 | 413 | 418 | 436 | 437 |
| 443 | 449 | 456 | 459 | 466 | 477 | 479 | 491 | 508 | 510 | 515 | 516 |
| 525 | 526 | 531 | 541 | 543 | 544 | 548 | 549 | 555 | 570 | 571 | 576 |
| 585 | 587 | 599 | 609 | 623 | 631 | 636 | 646 | 648 | 664 | 665 | 672 |
| 681 | 682 | 684 | 696 | 725 | 744 | 752 | 756 | 757 | 761 | 782 | 787 |
| 788 | 815 | 822 | 835 | 852 | 854 | 859 | 871 | 874 | 883 | 885 | 890 |
| 895 | 897 | 903 | 904 | 909 | 937 | 964 | 975 | 976 | 980 | 983 | 985 |
| 987 | 993 | 995 | 997 | 1007 | 1024 | 1025 | 1035 | 1036 | 1041 | 1047 | 1055 |
| 1057 | 1070 | 1094 | 1105 | 1113 | 1123 | 1130 | 1132 | 1135 | 1145 | 1149 | 1173 |
| 1174 | 1183 | 1184 | 1185 | 1186 | 1200 | 1207 | 1214 | 1217 | 1220 | 1229 | 1241 |
| 1245 | 1250 | 1255 | 1292 | 1309 | 1310 | 1312 | 1313 | 1337 | 1341 | 1346 | 1347 |
| 1349 | 1358 | 1402 | 1403 | 1417 | 1434 | 1437 | 1459 | 1463 | 1464 | 1476 | 1477 |
| 1500 | 1507 | 1510 | 1552 | 1556 | 1564 | 1578 | 1597 | 1604 | 1615 | 1617 | 1624 |
| 1627 | 1632 | 1636 | 1664 | 1673 | 1685 | 1699 | 1702 | 1712 | 1740 | 1746 | 1748 |
| 1797 | 1834 | 1878 | 1883 | 1899 | 1903 | 1920 | 1928 | 1934 | 1952 | 1953 | 2007 |
| 2023 | 2042 | 2044 | 2051 | 2084 | 2097 | 2105 | 2107 | 2118 | 2124 | 2139 | 2146 |
| 2147 | 2148 | 2163 | 2174 | 2184 | 2186 | 2194 | 2198 | 2211 | 2212 | 2230 | 2233 |
| 2245 | 2254 | 2259 | 2263 | 2268 | 2270 | 2280 | 2286 | 2294 | 2302 | 2303 | 2304 |
| 2306 | 2311 | 2315 | 2321 | 2333 | 2377 | 2394 | 2413 | 2425 | 2430 | 2445 | 2450 |
| 2457 | 2485 | 2496 | 2497 | 2503 | 2517 | 2518 | 2546 | 2566 | 2567 | 2568 | 2599 |
| 2602 | 2612 | 2622 | 2625 | 2626 | 2632 | 2634 | 2642 | 2651 | 2687 | 2706 | 2708 |
| 2731 | 2739 | 2746 | 2750 | 2751 | 2752 | 2755 | 2768 | 2773 | 2788 | 2818 | 2824 |
| 2828 | 2835 | 2846 | 2847 | 2851 | 2853 | 2860 | 2864 | 2878 | 2882 | 2887 | 2894 |
| 2895 | 2896 | 2900 | 2905 | 2907 | 2916 | 2919 | 2929 | 2936 | 2945 | 2947 | 2959 |
| 2960 | 2968 | 2984 | 2987 | 2990 | 2991 | 3005 | 3012 | 3031 | 3035 | 3044 | 3047 |
| 3052 | 3057 | 3066 | 3069 | 3070 | 3100 | 3137 | 3138 | 3139 | 3156 | 3165 | 3180 |
| 3184 | 3191 | 3198 | 3200 | 3231 | 3234 | 3236 | 3240 | 3260 | 3271 | 3288 | 3291 |
| 3305 | 3334 | 3343 | 3357 | 3363 | 3366 | 3389 | 3395 | 3419 | 3441 | 3442 | 3469 |
| 3481 | 3482 | 3485 | 3488 | 3518 | 3522 | 3559 | 3561 | 3563 | 3570 | 3575 | 3588 |
| 3592 | 3597 | 3603 | 3658 | 3663 | 3683 | 3688 | 3700 | 3703 | 3705 | 3715 | 3722 |
| 3724 | 3733 | 3736 | 3741 | 3747 | 3751 | 3752 | 3757 | 3775 | 3780 | 3845 | 3853 |
| 3880 | 3888 | 3892 | 3931 | 3932 | 3938 | 3958 | 3966 | 3968 | 3976 | 3978 | 3987 |
| 3995 | 4006 | 4019 | 4021 | 4041 | 4075 | 4076 | 4078 | 4079 | 4093 | 4098 | 4100 |
| 4110 | 4117 | 4122 | 4142 | 4145 | 4154 | 4160 | 4178 | 4189 | 4195 | 4198 | 4202 |
| 4205 | 4234 | 4236 | 4272 | 4277 | 4280 | 4290 | 4291 | 4294 | 4295 | 4301 | 4302 |
| 4311 | 4312 | 4313 | 4316 | 4334 | 4362 | 4366 | 4375 | 4388 | 4391 | 4398 | 4416 |
| 4433 | 4438 | 4464 | 4487 | 4491 | 4496 | 4497 | 4505 | 4506 | 4507 | 4521 | 4548 |
| 4569 | 4580 | 4582 | 4590 | 4591 | 4599 | 4644 | 4657 | 4676 | 4686 | 4701 | 4706 |
| 4709 | 4721 | 4727 | 4729 | 4748 | 4762 | 4781 | 4783 | 4805 | 4806 | 4807 | 4811 |
| 4815 | 4818 | 4826 | 4829 | 4833 | 4837 | 4850 | 4866 | 4874 | 4885 | 4897 | 4898 |
| 4899 | 4911 | 4912 | 4920 | 4926 | 4960 | 4970 | 4979 | 4990 | 4991 | 4994 | 5002 |
| 5007 | 5012 | 5022 | 5035 | 5038 | 5045 | 5065 | 5089 | 5093 | 5097 | 5105 | 5116 |
| 5117 | 5118 | 5125 | 5154 | 5158 | 5180 | 5181 | 5183 | 5208 | 5212 | 5216 | 5226 |
| 5230 | 5233 | 5238 | 5239 | 5240 | 5241 | 5247 | 5248 | 5249 | 5250 | 5251 | 5252 |
| 5254 | 5255 | 5257 | 5268 | 5275 | 5278 | 5279 | 5298 | 5306 | 5320 | 5338 | 5339 |
| 5363 | 5378 | 5380 | 5394 | 5397 | 5399 | 5408 | 5423 | 5450 | 5468 | 5480 | 5485 |
| 5493 | 5496 | 5501 | 5516 | 5544 | 5547 | 5548 | 5550 | 5553 | 5567 | 5576 | 5588 |
| 5613 | 5614 | 5615 | 5616 | 5617 | 5618 | 5638 | 5640 | 5644 | 5650 | 5659 | 5660 |
| 5669 | 5686 | 5695 | 5698 | 5699 | 5700 | 5709 | 5713 | 5714 | 5717 | 5718 | 5723 |
| 5726 | 5727 | 5736 | 5769 | 5772 | 5777 | 5784 | 5785 | 5789 | 5795 | 5805 | 5812 |
| 5814 | 5827 | 5828 | 5855 | 5858 | 5866 | 5935 | 5936 | 5937 | 5950 | 5951 | 5955 |
| 5966 | 5968 | 5974 | 5993 | 6000 | 6001 | 6002 | 6007 | 6011 | 6014 | 6017 | 6018 |
| 6024 | 6028 | 6036 | 6042 | 6057 | 6076 | 6077 | 6086 | 6089 | 6095 | 6096 | 6115 |
| 6123 | 6135 | 6136 | 6144 | 6160 | 6163 | 6173 | 6174 | 6177 | 6188 | 6190 | 6193 |
| 6194 | 6219 | 6223 | 6231 | 6240 | 6241 | 6260 | 6287 | 6310 | 6312 | 6314 | 6315 |
| 6316 | 6317 | 6318 | 6322 | 6338 | 6343 | 6347 | 6348 | 6349 | 6350 | 6351 | 6352 |
| 6365 | 6366 | 6367 | 6374 | 6376 | 6378 | 6381 | 6388 | 6400 | 6421 | 6435 | 6442 |
| 6443 | 6449 | 6455 | 6456 | 6467 | 6470 | 6509 | 6510 | 6511 | 6515 | 6518 | 6520 |
| 6531 | 6532 | 6535 | 6536 | 6546 | 6549 | 6558 | 6587 | 6588 | 6589 | 6590 | 6591 |
| 6592 | 6596 | 6602 | 6617 | 6630 | 6637 | 6654 | 6668 | 6682 | 6702 | 6703 | 6706 |
| 6728 | 6730 | 6734 | 6749 | 6750 | 6756 | 6766 | 6768 | 6773 | 6776 | 6780 | 6796 |
| 6804 | 6819 | 6820 | 6828 | 6829 | 6836 | 6839 | 6845 | 6851 | 6854 | 6870 | 6879 |
| 6880 | 6922 | 6927 | 6940 | 6941 | 6977 | 6978 | 6979 | 6983 | 6991 | 7000 | 7001 |
| 7031 | 7035 | 7046 | 7047 | 7050 | 7051 | 7057 | 7058 | 7067 | 7068 | 7069 | 7072 |
| 7090 | 7116 | 7120 | 7129 | 7136 | 7143 | 7146 | 7153 | 7172 | 7191 | 7197 | 7224 |

TABLE 3-continued

Cold Tolerance

| | | | | | | | | | | | |
|---|---|---|---|---|---|---|---|---|---|---|---|
| 7246 | 7250 | 7255 | 7256 | 7263 | 7264 | 7265 | 7266 | 7280 | 7326 | 7337 | 7339 |
| 7347 | 7348 | 7356 | 7402 | 7415 | 7432 | 7435 | 7445 | 7459 | 7465 | 7468 | 7480 |
| 7486 | 7488 | 7508 | 7521 | 7541 | 7543 | 7564 | 7565 | 7566 | 7570 | 7574 | 7577 |
| 7585 | 7588 | 7592 | 7597 | 7609 | 7625 | 7634 | 7643 | 7655 | 7656 | 7657 | 7669 |
| 7670 | 7678 | 7684 | 7718 | 7737 | 7743 | 7771 | 7772 | 7777 | 7782 | 7784 | 7794 |
| 7795 | 7805 | 7807 | 7808 | 7809 | 7810 | 7813 | 7815 | 7837 | 7840 | 7869 | 7873 |
| 7892 | 7896 | 7912 | 7913 | 7922 | 7939 | 7951 | 7966 | 7967 | 7973 | 7979 | 7993 |
| 8007 | 8011 | 8012 | 8015 | 8019 | 8022 | 8024 | 8039 | 8041 | 8047 | 8051 | 8057 |
| 8063 | 8074 | 8080 | 8083 | 8084 | 8093 | 8108 | 8112 | 8114 | 8133 | 8141 | 8159 |
| 8194 | 8195 | 8202 | 8203 | 8210 | 8219 | 8220 | 8224 | 8226 | 8241 | 8248 | 8249 |
| 8255 | 8256 | 8259 | 8260 | 8261 | 8262 | 8263 | 8265 | 8266 | 8270 | 8275 | 8276 |
| 8288 | 8290 | 8291 | 8297 | 8298 | 8304 | 8309 | 8319 | 8321 | 8323 | 8362 | 8374 |
| 8375 | 8406 | 8479 | 8484 | 8485 | 8488 | 8496 | 8502 | 8503 | 8513 | 8520 | 8530 |
| 8531 | 8545 | 8576 | 8578 | 8579 | 8581 | 8582 | 8589 | 8604 | 8606 | 8610 | 8611 |
| 8626 | 8631 | 8654 | 8676 | 8680 | 8685 | 8688 | 8692 | 8695 | 8699 | 8706 | 8707 |
| 8747 | 8750 | 8759 | 8760 | 8763 | 8767 | 8783 | 8806 | 8828 | 8843 | 8844 | 8852 |
| 8855 | 8859 | 8876 | 8880 | 8899 | 8901 | 8906 | 8913 | 8914 | 8922 | 8928 | 8939 |
| 8958 | 8977 | 8984 | 9005 | 9006 | 9017 | 9018 | 9019 | 9022 | 9023 | 9026 | 9029 |
| 9042 | 9061 | 9083 | 9088 | 9103 | 9105 | 9108 | 9123 | 9127 | 9134 | 9135 | 9136 |
| 9153 | 9156 | 9165 | 9167 | 9175 | 9186 | 9190 | 9193 | 9194 | 9195 | 9197 | 9198 |
| 9212 | 9227 | 9228 | 9236 | 9239 | 9240 | 9241 | 9243 | 9244 | 9245 | 9255 | 9257 |
| 9269 | 9270 | 9274 | 9276 | 9279 | 9280 | 9282 | 9303 | 9304 | 9320 | 9321 | 9329 |
| 9334 | 9352 | 9368 | 9369 | 9371 | 9372 | 9385 | 9386 | 9389 | 9390 | 9404 | 9409 |
| 9419 | 9420 | 9423 | 9424 | 9425 | 9435 | 9439 | 9440 | 9453 | 9460 | 9461 | 9462 |
| 9484 | 9490 | 9498 | 9507 | 9511 | 9520 | 9521 | 9524 | 9530 | 9539 | 9558 | 9575 |
| 9576 | 9586 | 9588 | 9589 | 9599 | 9612 | 9635 | 9645 | 9646 | 9650 | 9652 | 9669 |
| 9689 | 9690 | 9701 | 9713 | 9725 | 9732 | 9750 | 9751 | 9754 | 9758 | 9759 | 9774 |
| 9798 | 9814 | 9839 | 9856 | 9864 | 9866 | 9870 | 9874 | 9902 | 9928 | 9934 | 9960 |
| 9963 | 9976 | 9977 | 9981 | 9993 | 9995 | 9997 | 10026 | 10029 | 10038 | 10049 | 10061 |
| 10098 | 10099 | 10102 | 10104 | 10109 | 10114 | 10115 | 10121 | 10132 | 10135 | 10136 | 10143 |
| 10147 | 10151 | 10159 | 10163 | 10174 | 10181 | 10182 | 10185 | 10190 | 10204 | 10213 | 10223 |
| 10232 | 10262 | 10265 | 10266 | 10268 | 10285 | 10296 | 10304 | 10305 | 10311 | 10318 | 10319 |
| 10330 | 10336 | 10338 | 10339 | 10348 | 10357 | 10364 | 10365 | 10368 | 10370 | 10374 | 10381 |
| 10403 | 10404 | 10410 | 10411 | 10413 | 10417 | 10422 | 10431 | 10434 | 10438 | 10439 | 10445 |
| 10471 | 10478 | 10479 | 10487 | 10492 | 10514 | 10519 | 10521 | 10524 | 10530 | 10534 | 10543 |
| 10545 | 10572 | 10599 | 10600 | 10602 | 10603 | 10607 | 10615 | 10622 | 10629 | 10630 | 10646 |
| 10671 | 10672 | 10687 | 10690 | 10691 | 10705 | 10708 | 10736 | 10747 | 10750 | 10763 | 10765 |
| 10776 | 10782 | 10788 | 10789 | 10797 | 10798 | 10805 | 10814 | 10816 | 10850 | 10859 | 10872 |
| 10879 | 10880 | 10882 | 10898 | 10909 | 10910 | 10928 | 10968 | 10969 | 10970 | 10989 | 10990 |
| 10996 | 11005 | 11014 | 11028 | 11045 | 11050 | 11051 | 11058 | 11066 | 11073 | 11076 | 11079 |
| 11099 | 11102 | 11103 | 11105 | 11117 | 11119 | 11137 | 11160 | 11185 | 11188 | 11197 | 11216 |
| 11237 | 11245 | 11249 | 11251 | 11257 | 11262 | 11277 | 11285 | 11286 | 11297 | 11308 | 11309 |
| 11320 | 11321 | 11327 | 11329 | 11336 | 11338 | 11345 | 11364 | 11374 | 11381 | 11387 |
| 11407 | 11413 | 11427 | 11432 | 11433 | 11439 | 11442 | 11443 | 11463 | 11465 | 11466 | 11468 |
| 11469 | 11475 | 11478 | 11490 | 11498 | 11506 | 11518 | 11535 | 11537 | 11538 | 11539 | 11540 |
| 11542 | 11550 | 11554 | 11555 | 11559 | 11565 | 11578 | 11594 | 11595 | 11597 | 11598 | 11614 |
| 11623 | 11629 | 11653 | 11661 | 11663 | 11667 | 11709 | 11719 | 11722 | 11747 | 11749 | 11766 |
| 11768 | 11769 | 11774 | 11783 | 11786 | 11795 | 11796 | 11800 | 11813 | 11830 | 11837 | 11838 |
| 11839 | 11840 | 11848 | 11850 | 11859 | 11875 | 11876 | 11881 | 11887 | 11897 | 11911 | 11932 |
| 11936 | 11950 | 11951 | 11977 | 11988 | 11997 | 12013 | 12021 | 12033 | 12034 | 12041 | 12052 |
| 12053 | 12058 | 12062 | 12071 | 12078 | 12079 | 12083 | 12086 | 12096 | 12099 | 12102 | 12104 |
| 12106 | 12108 | 12109 | 12110 | 12112 | 12124 | 12135 | 12138 | 12149 | 12159 | 12167 | 12176 |
| 12178 | 12186 | 12195 | 12200 | 12212 | 12213 | 12241 | 12275 | 12282 | 12302 | 12304 | 12312 |
| 12316 | 12324 | 12341 | 12363 | 12398 | 12400 | 12408 | 12418 | 12427 | 12438 | 12472 | 12482 |
| 12486 | 12492 | 12494 | 12496 | 12506 | 12509 | 12513 | 12517 | 12554 | 12566 | 12589 | 12593 |
| 12598 | 12605 | 12607 | 12610 | 12611 | 12626 | 12664 | 12673 | 12692 | 12704 | 12709 | 12723 |
| 12728 | 12730 | 12733 | 12736 | 12758 | 12771 | 12777 | 12835 | 12836 | 12889 | 12891 | 12903 |
| 12911 | 12926 | 12943 | 12949 | 12952 | 12968 | 12969 | 12984 | 12987 | 12989 | 13023 | 13037 |
| 13040 | 13064 | 13073 | 13090 | 13091 | 13100 | 13106 | 13108 | 13111 | 13126 | 13136 | 13141 |
| 13159 | 13166 | 13169 | 13171 | 13179 | 13192 | 13195 | 13212 | 13225 | 13234 | 13241 | 13247 |
| 13257 | 13280 | 13285 | 13295 | 13301 | 13313 | 13319 | 13329 | 13387 | 13401 | 13453 | 13454 |
| 13459 | 13473 | 13479 | 13480 | 13484 | 13499 | 13532 | 13534 | 13535 | 13536 | 13538 | 13539 |
| 13543 | 13554 | 13556 | 13557 | 13562 | 13568 | 13592 | 13596 | 13598 | 13603 | 13612 | 13633 |
| 13643 | 13648 | 13650 | 13653 | 13679 | 13688 | 13694 | 13717 | 13719 | 13720 | 13728 | 13749 |
| 13755 | 13758 | 13783 | 13786 | 13787 | 13797 | 13798 | 13806 | 13813 | 13817 | 13837 | 13845 |
| 13846 | 13851 | 13865 | 13866 | 13868 | 13873 | 13874 | 13880 | 13881 | 13887 | 13901 | 13903 |
| 13904 | 13906 | 13912 | 13920 | 13927 | 13932 | 13948 | 13953 | 13971 | 14030 | 14045 | 14048 |
| 14049 | 14053 | 14062 | 14067 | 14068 | 14113 | 14143 | 14145 | 14149 | 14152 | 14157 | 14175 |
| 14181 | 14195 | 14216 | 14232 | 14233 | 14234 | 14238 | 14242 | 14246 | 14247 | 14248 | 14255 |
| 14259 | 14266 | 14277 | 14283 | 14293 | 14304 | 14308 | 14309 | 14313 | 14322 | 14324 | 14331 |
| 14332 | 14333 | 14346 | 14348 | 14356 | 14364 | 14381 | 14383 | 14392 | 14400 | 14421 | 14431 |
| 14452 | 14453 | 14473 | 14474 | 14482 | 14484 | 14487 | 14488 | 14491 | 14501 | 14510 | 14517 |
| 14522 | 14523 | 14526 | 14528 | 14529 | 14534 | 14535 | 14540 | 14551 | 14565 | 14568 | 14575 |
| 14586 | 14588 | 14594 | 14598 | 14613 | 14615 | 14616 | 14649 | 14650 | 14652 | 14657 | 14662 |
| 14663 | 14664 | 14678 | 14700 | 14705 | 14707 | 14708 | 14711 | 14717 | 14723 | 14746 | 14752 |
| 14780 | 14795 | 14810 | 14820 | 14840 | 14847 | 14863 | 14864 | 14867 | 14869 | 14871 | 14873 |
| 14876 | 14882 | 14885 | 14894 | 14901 | 14920 | 14934 | 14938 | 14943 | 14962 | 14963 | 14964 |

TABLE 3-continued

Cold Tolerance

| | | | | | | | | | | | |
|---|---|---|---|---|---|---|---|---|---|---|---|
| 14978 | 14983 | 14986 | 14991 | 15008 | 15016 | 15025 | 15029 | 15037 | 15047 | 15051 | 15058 |
| 15059 | 15060 | 15064 | 15079 | 15093 | 15103 | 15120 | 15123 | 15124 | 15125 | 15132 | 15140 |
| 15141 | 15142 | 15160 | 15183 | 15189 | 15190 | 15191 | 15193 | 15198 | 15202 | 15224 | 15229 |
| 15271 | 15289 | 15293 | 15310 | 15311 | 15312 | 15316 | 15317 | 15322 | 15334 | 15335 | 15336 |
| 15358 | 15360 | 15365 | 15374 | 15376 | 15377 | 15380 | 15388 | 15392 | 15398 | 15401 | 15406 |
| 15409 | 15415 | 15416 | 15422 | 15423 | 15428 | 15442 | 15454 | 15471 | 15482 | 15490 | 15492 |
| 15500 | 15518 | 15519 | 15526 | 15530 | 15534 | 15545 | 15553 | 15554 | 15561 | 15562 | 15575 |
| 15580 | 15582 | 15585 | 15587 | 15597 | 15601 | 15604 | 15609 | 15617 | 15624 | 15630 | 15634 |
| 15639 | 15642 | 15646 | 15647 | 15648 | 15649 | 15650 | 15651 | 15652 | 15654 | 15655 | 15656 |
| 15658 | 15659 | 15676 | 15677 | 15678 | 15682 | 15683 | 15688 | 15702 | 15703 | 15708 | 15725 |
| 15727 | 15732 | 15741 | 15744 | 15745 | 15748 | 15756 | 15760 | 15766 | 15769 | 15774 | 15777 |
| 15783 | 15784 | 15790 | 15791 | 15796 | 15799 | 15808 | 15811 | 15822 | 15841 | 15853 | 15862 |
| 15863 | 15871 | 15890 | 15891 | 15897 | 15901 | 15905 | 15917 | 15926 | 15927 | 15934 | 15935 |
| 15949 | 15951 | 15956 | 15958 | 15961 | 15963 | 15974 | 15979 | 15984 | 15992 | 15999 | 16005 |
| 16009 | 16014 | 16017 | 16021 | 16023 | 16024 | 16025 | 16026 | 16027 | 16028 | 16029 | 16030 |
| 16031 | 16033 | 16034 | 16035 | 16036 | 16037 | 16039 | 16041 | 16042 | 16045 | 16046 | 16047 |
| 16048 | 16049 | 16067 | 16068 | 16073 | 16074 | 16079 | 16092 | 16093 | 16094 | 16110 | 16111 |
| 16117 | 16126 | 16128 | 16129 | 16132 | 16139 | 16143 | 16150 | 16153 | 16157 | 16164 | 16166 |
| 16172 | 16173 | 16178 | 16181 | 16189 | 16190 | 16204 | 16233 | 16236 | 16238 | 16246 | 16263 |
| 16264 | 16269 | 16273 | 16284 | 16293 | 16294 | 16302 | 16303 | 16314 | 16315 | 16319 | 16324 |
| 16328 | 16336 | 16338 | 16342 | 16351 | 16352 | 16359 | 16363 | 16367 | 16370 | 16373 | 16376 |
| 16383 | 16386 | 16388 | 16389 | 16391 | 16407 | 16420 | 16421 | 16428 | 16429 | 16437 | 16445 |
| 16446 | 16457 | 16463 | 16478 | 16480 | 16481 | 16497 | 16519 | 16525 | 16550 | 16552 | 16558 |
| 16560 | 16561 | 16571 | 16576 | 16580 | 16590 | 16595 | 16598 | 16603 | 16610 | 16646 | 16662 |
| 16669 | 16679 | 16687 | 16690 | 16691 | 16693 | 16702 | 16703 | 16707 | 16709 | 16731 | 16735 |
| 16749 | 16756 | 16757 | 16776 | 16777 | 16783 | 16787 | 16799 | 16804 | 16805 | 16809 | 16825 |
| 16828 | 16844 | 16854 | 16864 | 16865 | 16866 | 16895 | 16901 | 16909 | 16915 | 16917 | 16920 |
| 16933 | 16935 | 16941 | 16946 | 16949 | 16959 | 16970 | 16980 | 16981 | 16987 | 16995 | 17009 |
| 17011 | 17015 | 17017 | 17024 | 17040 | 17058 | 17059 | 17065 | 17067 | 17068 | 17069 | 17088 |
| 17089 | 17093 | 17103 | 17125 | 17126 | 17155 | 17158 | 17182 | 17183 | 17184 | 17196 | 17198 |
| 17201 | 17204 | 17220 | 17226 | 17231 | 17234 | 17235 | 17237 | 17273 | 17284 | 17319 |
| 17321 | 17330 | 17345 | 17348 | 17352 | 17359 | 17375 | 17388 | 17389 | 17399 | 17410 | 17427 |
| 17439 | 17440 | 17442 | 17447 | 17454 | 17466 | 17467 | 17476 | 17510 | 17515 | 17519 | 17522 |
| 17523 | 17551 | 17552 | 17554 | 17555 | 17556 | 17564 | 17565 | 17568 | 17570 | 17571 | 17572 |
| 17579 | 17587 | 17605 | 17614 | 17615 | 17619 | 17623 | 17626 | 17635 | 17636 | 17656 | 17658 |
| 17660 | 17661 | 17670 | 17671 | 17701 | 17722 | 17724 | 17725 | 17731 | 17738 | 17739 | 17742 |
| 17745 | 17749 | 17762 | 17786 | 17788 | 17790 | 17803 | 17807 | 17809 | 17822 | 17837 | 17840 |
| 17849 | 17863 | 17868 | 17870 | 17889 | 17898 | 17899 | 17901 | 17913 | 17914 | 17921 | 17926 |
| 17927 | 17934 | 17948 | 17958 | 17967 | 17971 | 17978 | 17981 | 17985 | 17993 | 17995 |
| 18012 | 18015 | 18018 | 18025 | 18026 | 18030 | 18031 | 18034 | 18041 | 18043 | 18045 | 18049 |
| 18050 | 18051 | 18054 | 18055 | 18060 | 18063 | 18067 | 18069 | 18070 | 18071 | 18073 | 18074 |
| 18075 | 18076 | 18077 | 18078 | 18079 | 18080 | 18081 | 18082 | 18101 | 18113 | 18135 | 18143 |
| 18145 | 18149 | 18156 | 18176 | 18180 | 18192 | 18195 | 18204 | 18205 | 18213 | 18226 | 18227 |
| 18228 | 18241 | 18245 | 18255 | 18265 | 18267 | 18281 | 18308 | 18311 | 18330 | 18338 | 18345 |
| 18363 | 18367 | 18390 | 18397 | 18401 | 18402 | 18405 | 18410 | 18411 | 18417 | 18418 | 18424 |
| 18431 | 18432 | 18435 | 18442 | 18444 | 18447 | 18451 | 18473 | 18474 | 18475 | 18486 | 18487 |
| 18491 | 18500 | 18517 | 18522 | 18529 | 18537 | 18551 | 18569 | 18588 | 18595 | 18598 | 18608 |
| 18612 | 18617 | 18618 | 18625 | 18636 | 18640 | 18655 | 18660 | 18672 | 18673 | 18688 | 18692 |
| 18697 | 18699 | 18710 | 18718 | 18719 | 18731 | 18733 | 18740 | 18741 | 18751 | 18759 | 18761 |
| 18766 | 18768 | 18771 | 18804 | 18813 | 18824 | 18828 | 18838 | 18846 | 18858 | 18861 | 18862 |
| 18863 | 18869 | 18884 | 18904 | 18916 | 18925 | 18926 | 18930 | 18937 | 18941 | 18952 | 18953 |
| 18961 | 18963 | 18978 | 19005 | 19007 | 19008 | 19022 | 19023 | 19055 | 19059 | 19069 | 19073 |
| 19078 | 19118 | 19120 | 19137 | 19156 | 19158 | 19160 | 19169 | 19195 | 19198 | 19199 | 19200 |
| 19202 | 19203 | 19205 | 19216 | 19222 | 19233 | 19261 | 19264 | 19269 | 19276 | 19277 | 19280 |
| 19294 | 19300 | 19301 | 19317 | 19338 | 19351 | 19363 | 19364 | 19365 | 19366 | 19381 | 19383 |
| 19389 | 19390 | 19391 | 19394 | 19420 | 19433 | 19461 | 19464 | 19465 | 19472 | 19483 | 19486 |
| 19493 | 19502 | 19522 | 19549 | 19550 | 19553 | 19557 | 19572 | 19573 | 19575 | 19578 | 19580 |
| 19585 | 19593 | 19595 | 19599 | 19614 | 19616 | 19617 | 19620 | 19628 | 19644 | 19645 | 19656 |
| 19664 | 19666 | 19672 | 19684 | 19686 | 19698 | 19699 | 19703 | 19704 | 19708 | 19711 | 19714 |
| 19719 | 19754 | 19772 | 19791 | 19795 | 19799 | 19808 | 19831 | 19838 | 19844 | 19846 | 19847 |
| 19850 | 19852 | 19853 | 19854 | 19857 | 19860 | 19866 | 19915 | 19918 | 19921 | 19929 | 19930 |
| 19946 | 19956 | 19990 | 20007 | 20032 | 20035 | 20050 | 20055 | 20056 | 20068 | 20074 | 20086 |
| 20101 | 20103 | 20108 | 20110 | 20118 | 20119 | 20126 | 20133 | 20146 | 20155 | 20162 | 20192 |
| 20195 | 20207 | 20216 | 20220 | 20221 | 20229 | 20241 | 20253 | 20262 | 20278 | 20280 | 20297 |
| 20298 | 20301 | 20312 | 20317 | 20322 | 20358 | 20374 | 20375 | 20377 | 20378 | 20400 | 20404 |
| 20409 | 20410 | 20412 | 20417 | 20418 | 20419 | 20428 | 20437 | 20460 | 20461 | 20480 | 20515 |
| 20539 | 20543 | 20548 | 20580 | 20586 | 20603 | 20627 | 20637 | 20643 | 20646 | 20648 | 20655 |
| 20668 | 20709 | 20731 | 20736 | 20737 | 20739 | 20744 | 20745 | 20750 | 20757 | 20758 | 20765 |
| 20772 | 20784 | 20787 | 20793 | 20797 | 20801 | 20802 | 20805 | 20806 | 20811 | 20827 | 20828 |
| 20829 | 20835 | 20836 | 20840 | 20841 | 20848 | 20854 | 20868 | 20871 | 20878 | 20892 | 20894 |
| 20895 | 20910 | 20919 | 20921 | 20942 | 20943 | 20952 | 20963 | 20987 | 20988 | 20989 | 20991 |
| 20992 | 20993 | 21004 | 21008 | 21010 | 21032 | 21042 | 21045 | 21059 | 21062 | 21068 | 21073 |
| 21091 | 21103 | 21119 | 21124 | 21129 | 21147 | 21161 | 21167 | 21170 | 21185 | 21186 | 21190 |
| 21196 | 21200 | 21204 | 21209 | 21210 | 21243 | 21244 | 21256 | 21257 | 21260 | 21263 | 21267 |
| 21280 | 21281 | 21284 | 21285 | 21296 | 21313 | 21314 | 21323 | 21324 | 21328 | 21331 | 21340 |
| 21354 | 21364 | 21368 | 21371 | 21373 | 21379 | 21387 | 21396 | 21410 | 21425 | 21432 | 21441 |
| 21443 | 21446 | 21447 | 21460 | 21462 | 21464 | 21466 | 21481 | 21485 | 21503 | 21507 | 21513 |

TABLE 3-continued

Cold Tolerance

| | | | | | | | | | | | |
|---|---|---|---|---|---|---|---|---|---|---|---|
| 21527 | 21533 | 21552 | 21557 | 21574 | 21585 | 21586 | 21588 | 21590 | 21607 | 21637 | 21639 |
| 21655 | 21664 | 21670 | 21677 | 21680 | 21682 | 21683 | 21689 | 21691 | 21692 | 21694 | 21701 |
| 21704 | 21711 | 21717 | 21722 | 21726 | 21729 | 21757 | 21758 | 21760 | 21763 | 21778 | 21781 |
| 21794 | 21795 | 21803 | 21809 | 21817 | 21822 | 21824 | 21825 | 21867 | 21872 | 21882 | 21883 |
| 21896 | 21900 | 21911 | 21929 | 21937 | 21941 | 21960 | 21973 | 21987 | 21988 | 21993 | 21994 |
| 21998 | 22006 | 22011 | 22013 | 22015 | 22034 | 22035 | 22036 | 22038 | 22066 | 22071 | 22078 |
| 22094 | 22101 | 22102 | 22107 | 22124 | 22126 | 22147 | 22165 | 22170 | 22186 | 22205 | 22206 |
| 22214 | 22220 | 22221 | 22232 | 22238 | 22253 | 22279 | 22291 | 22295 | 22332 | 22335 | 22346 |
| 22370 | 22378 | 22379 | 22386 | 22389 | 22391 | 22402 | 22406 | 22425 | 22428 | 22432 | 22436 |
| 22439 | 22446 | 22492 | 22497 | 22509 | 22538 | 22544 | 22545 | 22551 | 22552 | 22565 | 22582 |
| 22583 | 22594 | 22609 | 22617 | 22632 | 22642 | 22653 | 22675 | 22685 | 22712 | 22717 | 22737 |
| 22748 | 22759 | 22768 | 22782 | 22787 | 22799 | 22817 | 22823 | 22834 | 22839 | 22840 | 22843 |
| 22854 | 22864 | 22865 | 22870 | 22873 | 22895 | 22905 | 22928 | 22962 | 22980 | 23000 | 23013 |
| 23019 | 23052 | 23071 | 23073 | 23095 | 23110 | 23126 | 23127 | 23145 | 23146 | 23147 | 23176 |
| 23179 | 23181 | 23182 | 23183 | 23185 | 23202 | 23214 | 23217 | 23226 | 23227 | 23233 | 23241 |
| 23259 | 23263 | 23272 | 23290 | 23308 | 23312 | 23313 | 23318 | 23319 | 23321 | 23322 | 23326 |
| 23329 | 23350 | 23358 | 23363 | 23376 | 23392 | 23401 | 23420 | 23421 | 23426 | 23445 | 23459 |
| 23467 | 23474 | 23479 | 23480 | 23497 | 23498 | 23502 | 23505 | 23514 | 23516 | 23520 | 23524 |
| 23531 | 23535 | 23551 | 23578 | 23583 | 23598 | 23601 | 23604 | 23610 | 23612 | 23613 | 23619 |
| 23638 | 23640 | 23650 | 23651 | 23652 | 23653 | 23666 | 23667 | 23671 | 23673 | | |

Table 3B SEQ ID NOs of Polynucleotides useful for improving Cold Tolerance

| | | | | | | | | | | | |
|---|---|---|---|---|---|---|---|---|---|---|---|
| 23691 | 23692 | 23693 | 23698 | 23706 | 23713 | 23718 | 23723 | 23726 | 23739 | 23743 | 23768 |
| 23775 | 23777 | 23778 | 23788 | 23796 | 23804 | 23805 | 23808 | 23809 | 23815 | 23832 | 23833 |
| 23834 | 23838 | 23840 | 23841 | 23843 | 23865 | 23878 | 23882 | 23891 | 23917 | 23925 | 23934 |
| 23944 | 23959 | 23961 | 23962 | 23982 | 23997 | 24008 | 24012 | 24019 | 24025 | 24029 | 24037 |
| 24043 | 24065 | 24066 | 24077 | 24080 | 24082 | 24083 | 24087 | 24100 | 24105 | 24123 | 24124 |
| 24130 | 24136 | 24143 | 24146 | 24153 | 24164 | 24166 | 24178 | 24195 | 24197 | 24202 | 24203 |
| 24212 | 24213 | 24218 | 24228 | 24230 | 24231 | 24235 | 24236 | 24242 | 24257 | 24258 | 24263 |
| 24272 | 24274 | 24286 | 24296 | 24310 | 24318 | 24323 | 24333 | 24335 | 24351 | 24352 | 24359 |
| 24368 | 24369 | 24371 | 24383 | 24412 | 24431 | 24439 | 24443 | 24444 | 24448 | 24469 | 24474 |
| 24475 | 24502 | 24509 | 24522 | 24539 | 24541 | 24546 | 24558 | 24561 | 24570 | 24572 | 24577 |
| 24582 | 24584 | 24590 | 24591 | 24596 | 24624 | 24651 | 24662 | 24663 | 24667 | 24670 | 24672 |
| 24674 | 24680 | 24682 | 24684 | 24694 | 24711 | 24712 | 24722 | 24723 | 24728 | 24734 | 24742 |
| 24744 | 24757 | 24781 | 24792 | 24800 | 24810 | 24817 | 24819 | 24822 | 24832 | 24836 | 24860 |
| 24861 | 24870 | 24871 | 24872 | 24873 | 24887 | 24894 | 24901 | 24904 | 24907 | 24916 | 24928 |
| 24932 | 24937 | 24942 | 24979 | 24996 | 24997 | 24999 | 25000 | 25024 | 25028 | 25033 | 25034 |
| 25036 | 25045 | 25089 | 25090 | 25104 | 25121 | 25124 | 25146 | 25150 | 25151 | 25163 | 25164 |
| 25187 | 25194 | 25197 | 25239 | 25243 | 25251 | 25265 | 25284 | 25291 | 25302 | 25304 | 25311 |
| 25314 | 25319 | 25323 | 25351 | 25360 | 25372 | 25386 | 25389 | 25399 | 25427 | 25433 | 25435 |
| 25484 | 25521 | 25565 | 25570 | 25586 | 25590 | 25607 | 25615 | 25621 | 25639 | 25640 | 25694 |
| 25710 | 25729 | 25731 | 25738 | 25771 | 25784 | 25792 | 25794 | 25805 | 25811 | 25826 | 25833 |
| 25834 | 25835 | 25850 | 25861 | 25871 | 25873 | 25881 | 25885 | 25898 | 25899 | 25917 | 25920 |
| 25932 | 25941 | 25946 | 25950 | 25955 | 25957 | 25967 | 25973 | 25981 | 25989 | 25990 | 25991 |
| 25993 | 25998 | 26002 | 26008 | 26020 | 26064 | 26081 | 26100 | 26112 | 26117 | 26132 | 26137 |
| 26144 | 26172 | 26183 | 26184 | 26190 | 26204 | 26205 | 26233 | 26253 | 26254 | 26255 | 26286 |
| 26289 | 26299 | 26309 | 26312 | 26313 | 26319 | 26321 | 26329 | 26338 | 26374 | 26393 | 26395 |
| 26418 | 26426 | 26433 | 26437 | 26438 | 26439 | 26442 | 26455 | 26460 | 26475 | 26505 | 26511 |
| 26515 | 26522 | 26533 | 26534 | 26538 | 26540 | 26547 | 26551 | 26565 | 26569 | 26574 | 26581 |
| 26582 | 26583 | 26587 | 26592 | 26594 | 26603 | 26606 | 26616 | 26623 | 26632 | 26634 | 26646 |
| 26647 | 26655 | 26671 | 26674 | 26677 | 26678 | 26692 | 26699 | 26722 | 26731 | 26734 | |
| 26739 | 26744 | 26753 | 26756 | 26757 | 26787 | 26824 | 26825 | 26826 | 26843 | 26852 | 26867 |
| 26871 | 26878 | 26885 | 26887 | 26918 | 26921 | 26923 | 26927 | 26947 | 26958 | 26975 | 26978 |
| 26992 | 27021 | 27030 | 27044 | 27050 | 27053 | 27076 | 27082 | 27106 | 27128 | 27129 | 27156 |
| 27168 | 27169 | 27172 | 27175 | 27205 | 27209 | 27246 | 27248 | 27250 | 27257 | 27262 | 27275 |
| 27279 | 27284 | 27290 | 27345 | 27350 | 27370 | 27375 | 27387 | 27390 | 27392 | 27402 | 27409 |
| 27411 | 27420 | 27423 | 27428 | 27434 | 27438 | 27439 | 27444 | 27462 | 27467 | 27532 | 27540 |
| 27567 | 27575 | 27579 | 27618 | 27619 | 27625 | 27645 | 27653 | 27655 | 27663 | 27665 | 27674 |
| 27682 | 27693 | 27706 | 27708 | 27728 | 27762 | 27763 | 27765 | 27780 | 27785 | 27787 | |
| 27797 | 27804 | 27809 | 27829 | 27832 | 27841 | 27847 | 27865 | 27876 | 27882 | 27885 | 27889 |
| 27892 | 27921 | 27923 | 27959 | 27964 | 27967 | 27977 | 27978 | 27981 | 27982 | 27988 | 27989 |
| 27998 | 27999 | 28000 | 28003 | 28021 | 28049 | 28053 | 28062 | 28075 | 28078 | 28085 | 28103 |
| 28120 | 28125 | 28151 | 28174 | 28178 | 28183 | 28184 | 28192 | 28193 | 28194 | 28208 | 28235 |
| 28256 | 28267 | 28269 | 28277 | 28278 | 28286 | 28331 | 28344 | 28363 | 28373 | 28388 | 28393 |
| 28396 | 28408 | 28414 | 28416 | 28435 | 28449 | 28468 | 28470 | 28492 | 28493 | 28494 | 28498 |
| 28502 | 28505 | 28513 | 28516 | 28520 | 28524 | 28537 | 28553 | 28561 | 28572 | 28584 | 28585 |
| 28586 | 28598 | 28599 | 28607 | 28613 | 28647 | 28657 | 28666 | 28677 | 28678 | 28681 | 28689 |
| 28694 | 28699 | 28709 | 28722 | 28725 | 28732 | 28752 | 28776 | 28780 | 28784 | 28792 | 28803 |
| 28804 | 28805 | 28812 | 28841 | 28845 | 28867 | 28868 | 28870 | 28895 | 28899 | 28903 | 28913 |
| 28917 | 28920 | 28925 | 28926 | 28927 | 28928 | 28934 | 28935 | 28936 | 28937 | 28938 | 28939 |
| 28941 | 28942 | 28944 | 28955 | 28962 | 28966 | 28985 | 28993 | 29007 | 29025 | 29026 | |
| 29050 | 29065 | 29067 | 29081 | 29084 | 29086 | 29095 | 29110 | 29137 | 29155 | 29167 | 29172 |
| 29180 | 29183 | 29188 | 29203 | 29231 | 29234 | 29235 | 29237 | 29240 | 29254 | 29263 | 29275 |
| 29300 | 29301 | 29302 | 29303 | 29304 | 29305 | 29325 | 29327 | 29331 | 29337 | 29346 | 29347 |
| 29356 | 29373 | 29382 | 29385 | 29386 | 29387 | 29396 | 29400 | 29401 | 29404 | 29405 | 29410 |
| 29413 | 29414 | 29423 | 29456 | 29459 | 29464 | 29471 | 29472 | 29476 | 29482 | 29492 | 29499 |

TABLE 3-continued

Cold Tolerance

| | | | | | | | | | | | |
|---|---|---|---|---|---|---|---|---|---|---|---|
| 29501 | 29514 | 29515 | 29542 | 29545 | 29553 | 29622 | 29623 | 29624 | 29637 | 29638 | 29642 |
| 29653 | 29655 | 29661 | 29680 | 29687 | 29688 | 29689 | 29694 | 29698 | 29701 | 29704 | 29705 |
| 29711 | 29715 | 29723 | 29729 | 29744 | 29763 | 29764 | 29773 | 29776 | 29782 | 29783 | 29802 |
| 29810 | 29822 | 29823 | 29831 | 29847 | 29850 | 29860 | 29861 | 29864 | 29875 | 29877 | 29880 |
| 29881 | 29906 | 29910 | 29918 | 29927 | 29928 | 29947 | 29974 | 29997 | 29999 | 30001 | 30002 |
| 30003 | 30004 | 30005 | 30009 | 30025 | 30030 | 30034 | 30035 | 30036 | 30037 | 30038 | 30039 |
| 30052 | 30053 | 30054 | 30061 | 30063 | 30065 | 30068 | 30075 | 30087 | 30108 | 30122 | 30129 |
| 30130 | 30136 | 30142 | 30143 | 30154 | 30157 | 30196 | 30197 | 30198 | 30202 | 30205 | 30207 |
| 30218 | 30219 | 30222 | 30223 | 30233 | 30236 | 30245 | 30274 | 30275 | 30276 | 30277 | 30278 |
| 30279 | 30283 | 30289 | 30304 | 30317 | 30324 | 30341 | 30355 | 30369 | 30389 | 30390 | 30393 |
| 30415 | 30417 | 30421 | 30436 | 30437 | 30443 | 30453 | 30455 | 30460 | 30463 | 30467 | 30483 |
| 30491 | 30506 | 30507 | 30515 | 30516 | 30523 | 30526 | 30532 | 30538 | 30541 | 30557 | 30566 |
| 30567 | 30609 | 30614 | 30627 | 30628 | 30664 | 30665 | 30666 | 30670 | 30678 | 30687 | 30688 |
| 30718 | 30722 | 30733 | 30734 | 30737 | 30738 | 30744 | 30745 | 30754 | 30755 | 30756 | 30759 |
| 30777 | 30803 | 30807 | 30816 | 30823 | 30830 | 30833 | 30840 | 30859 | 30878 | 30884 | 30911 |
| 30933 | 30937 | 30942 | 30943 | 30950 | 30951 | 30952 | 30953 | 30967 | 31013 | 31024 | 31026 |
| 31034 | 31035 | 31043 | 31089 | 31102 | 31119 | 31122 | 31132 | 31146 | 31152 | 31155 | 31167 |
| 31173 | 31175 | 31195 | 31208 | 31228 | 31230 | 31251 | 31252 | 31253 | 31257 | 31261 | 31264 |
| 31272 | 31275 | 31279 | 31284 | 31296 | 31312 | 31321 | 31330 | 31342 | 31343 | 31344 | 31356 |
| 31357 | 31365 | 31371 | 31405 | 31424 | 31430 | 31458 | 31459 | 31464 | 31469 | 31471 | 31481 |
| 31482 | 31492 | 31494 | 31495 | 31496 | 31497 | 31500 | 31502 | 31524 | 31527 | 31556 | 31560 |
| 31579 | 31583 | 31599 | 31600 | 31609 | 31626 | 31638 | 31653 | 31654 | 31660 | 31666 | 31680 |
| 31694 | 31698 | 31699 | 31702 | 31706 | 31709 | 31711 | 31726 | 31728 | 31734 | 31738 | 31744 |
| 31750 | 31761 | 31767 | 31770 | 31771 | 31780 | 31795 | 31799 | 31801 | 31820 | 31828 | 31846 |
| 31881 | 31882 | 31889 | 31890 | 31897 | 31906 | 31907 | 31911 | 31913 | 31928 | 31935 | 31936 |
| 31942 | 31943 | 31946 | 31947 | 31948 | 31949 | 31950 | 31952 | 31953 | 31957 | 31962 | 31963 |
| 31975 | 31977 | 31978 | 31984 | 31985 | 31991 | 31996 | 32006 | 32008 | 32010 | 32049 | 32061 |
| 32062 | 32093 | 32166 | 32171 | 32172 | 32175 | 32183 | 32189 | 32190 | 32200 | 32207 | 32217 |
| 32218 | 32232 | 32263 | 32265 | 32266 | 32268 | 32269 | 32276 | 32291 | 32293 | 32297 | 32298 |
| 32313 | 32318 | 32341 | 32363 | 32367 | 32372 | 32375 | 32379 | 32382 | 32386 | 32393 | 32394 |
| 32434 | 32437 | 32446 | 32447 | 32450 | 32454 | 32470 | 32493 | 32515 | 32530 | 32531 | 32539 |
| 32542 | 32546 | 32563 | 32567 | 32586 | 32588 | 32593 | 32600 | 32601 | 32609 | 32615 | 32626 |
| 32645 | 32664 | 32671 | 32692 | 32693 | 32704 | 32705 | 32706 | 32709 | 32710 | 32713 | 32716 |
| 32729 | 32748 | 32770 | 32775 | 32790 | 32792 | 32795 | 32810 | 32814 | 32821 | 32822 | 32823 |
| 32840 | 32843 | 32852 | 32854 | 32862 | 32873 | 32877 | 32880 | 32881 | 32882 | 32884 | 32885 |
| 32899 | 32914 | 32915 | 32923 | 32926 | 32927 | 32928 | 32930 | 32931 | 32932 | 32942 | 32944 |
| 32956 | 32957 | 32961 | 32963 | 32966 | 32967 | 32969 | 32990 | 32991 | 33007 | 33008 | 33016 |
| 33021 | 33039 | 33055 | 33056 | 33058 | 33059 | 33072 | 33073 | 33076 | 33077 | 33091 | 33096 |
| 33106 | 33107 | 33110 | 33111 | 33112 | 33122 | 33126 | 33127 | 33140 | 33147 | 33148 | 33149 |
| 33171 | 33177 | 33185 | 33194 | 33198 | 33207 | 33208 | 33211 | 33217 | 33226 | 33245 | 33262 |
| 33263 | 33273 | 33275 | 33276 | 33286 | 33299 | 33322 | 33332 | 33333 | 33337 | 33339 | 33356 |
| 33376 | 33377 | 33388 | 33400 | 33412 | 33419 | 33437 | 33438 | 33441 | 33445 | 33446 | 33461 |
| 33485 | 33501 | 33526 | 33543 | 33551 | 33553 | 33557 | 33561 | 33589 | 33615 | 33621 | 33647 |
| 33650 | 33663 | 33664 | 33668 | 33680 | 33682 | 33684 | 33713 | 33716 | 33725 | 33736 | 33748 |
| 33785 | 33786 | 33789 | 33791 | 33796 | 33801 | 33802 | 33808 | 33819 | 33822 | 33823 | 33830 |
| 33834 | 33838 | 33846 | 33850 | 33861 | 33868 | 33869 | 33872 | 33877 | 33891 | 33900 | 33910 |
| 33919 | 33949 | 33952 | 33953 | 33955 | 33972 | 33983 | 33991 | 33992 | 33998 | 34005 | 34006 |
| 34017 | 34023 | 34025 | 34026 | 34035 | 34044 | 34051 | 34052 | 34055 | 34057 | 34061 | 34068 |
| 34090 | 34091 | 34097 | 34098 | 34100 | 34104 | 34109 | 34118 | 34121 | 34125 | 34126 | 34132 |
| 34158 | 34165 | 34166 | 34174 | 34179 | 34201 | 34206 | 34208 | 34211 | 34217 | 34221 | 34230 |
| 34232 | 34259 | 34286 | 34287 | 34289 | 34290 | 34294 | 34302 | 34309 | 34316 | 34317 | 34333 |
| 34358 | 34359 | 34374 | 34377 | 34378 | 34392 | 34395 | 34423 | 34434 | 34437 | 34450 | 34452 |
| 34463 | 34469 | 34475 | 34476 | 34484 | 34485 | 34492 | 34501 | 34503 | 34537 | 34546 | 34559 |
| 34566 | 34567 | 34569 | 34585 | 34596 | 34597 | 34615 | 34655 | 34656 | 34657 | 34676 | 34677 |
| 34683 | 34692 | 34701 | 34715 | 34732 | 34737 | 34738 | 34745 | 34753 | 34760 | 34763 | 34766 |
| 34786 | 34789 | 34790 | 34792 | 34804 | 34806 | 34824 | 34847 | 34872 | 34875 | 34884 | 34903 |
| 34924 | 34932 | 34936 | 34938 | 34944 | 34949 | 34964 | 34972 | 34973 | 34984 | 34995 | 34996 |
| 35007 | 35008 | 35014 | 35016 | 35023 | 35025 | 35032 | 35051 | 35058 | 35061 | 35068 | 35074 |
| 35094 | 35100 | 35114 | 35119 | 35120 | 35126 | 35129 | 35130 | 35150 | 35152 | 35153 | 35155 |
| 35156 | 35162 | 35165 | 35177 | 35185 | 35193 | 35205 | 35222 | 35224 | 35225 | 35226 | 35227 |
| 35229 | 35237 | 35241 | 35242 | 35246 | 35252 | 35265 | 35281 | 35282 | 35284 | 35285 | 35301 |
| 35310 | 35316 | 35340 | 35348 | 35350 | 35354 | 35396 | 35406 | 35409 | 35434 | 35436 | 35453 |
| 35455 | 35456 | 35461 | 35470 | 35473 | 35482 | 35483 | 35487 | 35500 | 35517 | 35524 | 35525 |
| 35526 | 35527 | 35535 | 35557 | 35546 | 35562 | 35563 | 35574 | 35584 | 35598 | 35619 |
| 35623 | 35637 | 35638 | 35664 | 35675 | 35684 | 35700 | 35708 | 35720 | 35721 | 35728 | 35739 |
| 35740 | 35745 | 35749 | 35758 | 35765 | 35766 | 35770 | 35773 | 35783 | 35786 | 35789 | 35791 |
| 35793 | 35795 | 35796 | 35797 | 35799 | 35811 | 35822 | 35825 | 35836 | 35846 | 35854 | 35863 |
| 35865 | 35873 | 35882 | 35887 | 35899 | 35900 | 35928 | 35962 | 35969 | 35989 | 35991 | 35999 |
| 36003 | 36011 | 36028 | 36050 | 36085 | 36087 | 36095 | 36105 | 36114 | 36125 | 36159 | 36169 |
| 36173 | 36179 | 36181 | 36183 | 36193 | 36196 | 36200 | 36204 | 36241 | 36253 | 36276 | 36280 |
| 36285 | 36292 | 36294 | 36297 | 36298 | 36313 | 36351 | 36360 | 36379 | 36391 | 36396 | 36410 |
| 36415 | 36417 | 36420 | 36423 | 36445 | 36458 | 36464 | 36523 | 36576 | 36578 | 36590 |
| 36598 | 36613 | 36630 | 36636 | 36639 | 36655 | 36656 | 36671 | 36674 | 36676 | 36710 | 36724 |
| 36727 | 36751 | 36760 | 36777 | 36778 | 36787 | 36793 | 36795 | 36798 | 36813 | 36823 | 36828 |
| 36846 | 36853 | 36856 | 36858 | 36866 | 36879 | 36882 | 36899 | 36912 | 36921 | 36928 | 36934 |
| 36944 | 36967 | 36972 | 36982 | 36988 | 37000 | 37006 | 37016 | 37074 | 37088 | 37140 | 37141 |
| 37146 | 37160 | 37166 | 37167 | 37171 | 37186 | 37219 | 37221 | 37222 | 37223 | 37225 | 37226 |

TABLE 3-continued

Cold Tolerance

| | | | | | | | | | | | |
|---|---|---|---|---|---|---|---|---|---|---|---|
| 37230 | 37241 | 37243 | 37244 | 37249 | 37255 | 37279 | 37283 | 37285 | 37290 | 37299 | 37320 |
| 37330 | 37335 | 37337 | 37340 | 37366 | 37375 | 37381 | 37404 | 37406 | 37407 | 37415 | 37436 |
| 37442 | 37445 | 37470 | 37473 | 37474 | 37484 | 37485 | 37493 | 37500 | 37504 | 37524 | 37532 |
| 37533 | 37538 | 37552 | 37553 | 37555 | 37560 | 37561 | 37567 | 37568 | 37574 | 37588 | 37590 |
| 37591 | 37593 | 37599 | 37607 | 37614 | 37619 | 37635 | 37640 | 37658 | 37717 | 37732 | 37735 |
| 37736 | 37740 | 37749 | 37754 | 37755 | 37800 | 37830 | 37832 | 37836 | 37839 | 37844 | 37862 |
| 37868 | 37882 | 37903 | 37919 | 37920 | 37921 | 37925 | 37929 | 37933 | 37934 | 37935 | 37942 |
| 37946 | 37953 | 37964 | 37970 | 37980 | 37991 | 37995 | 37996 | 38000 | 38009 | 38011 | 38018 |
| 38019 | 38020 | 38033 | 38035 | 38043 | 38051 | 38068 | 38070 | 38079 | 38087 | 38108 | 38118 |
| 38139 | 38140 | 38160 | 38161 | 38169 | 38171 | 38174 | 38175 | 38178 | 38188 | 38197 | 38204 |
| 38209 | 38210 | 38213 | 38215 | 38216 | 38221 | 38222 | 38227 | 38238 | 38252 | 38255 | 38262 |
| 38273 | 38275 | 38281 | 38285 | 38300 | 38302 | 38303 | 38336 | 38337 | 38339 | 38344 | 38349 |
| 38350 | 38351 | 38365 | 38387 | 38392 | 38394 | 38395 | 38398 | 38404 | 38410 | 38433 | 38439 |
| 38467 | 38482 | 38497 | 38507 | 38527 | 38534 | 38550 | 38551 | 38554 | 38556 | 38558 | 38560 |
| 38563 | 38569 | 38572 | 38581 | 38588 | 38607 | 38621 | 38625 | 38630 | 38649 | 38650 | 38651 |
| 38665 | 38670 | 38673 | 38678 | 38695 | 38703 | 38712 | 38716 | 38724 | 38734 | 38738 | 38745 |
| 38746 | 38747 | 38751 | 38766 | 38780 | 38790 | 38807 | 38810 | 38811 | 38812 | 38819 | 38827 |
| 38828 | 38829 | 38847 | 38870 | 38876 | 38877 | 38878 | 38880 | 38885 | 38889 | 38911 | 38916 |
| 38958 | 38976 | 38980 | 38997 | 38998 | 38999 | 39003 | 39004 | 39009 | 39021 | 39022 | 39023 |
| 39045 | 39047 | 39052 | 39061 | 39063 | 39064 | 39067 | 39075 | 39079 | 39085 | 39088 | 39093 |
| 39096 | 39102 | 39103 | 39109 | 39110 | 39115 | 39129 | 39141 | 39158 | 39169 | 39177 | 39179 |
| 39187 | 39205 | 39206 | 39213 | 39217 | 39221 | 39232 | 39240 | 39241 | 39248 | 39249 | 39262 |
| 39267 | 39269 | 39272 | 39274 | 39284 | 39288 | 39291 | 39296 | 39304 | 39311 | 39317 | 39321 |
| 39326 | 39329 | 39333 | 39334 | 39335 | 39336 | 39337 | 39338 | 39339 | 39341 | 39342 | 39343 |
| 39345 | 39346 | 39363 | 39364 | 39365 | 39369 | 39370 | 39375 | 39389 | 39390 | 39395 | 39412 |
| 39414 | 39419 | 39428 | 39431 | 39432 | 39435 | 39443 | 39447 | 39453 | 39456 | 39461 | 39464 |
| 39470 | 39471 | 39477 | 39478 | 39483 | 39486 | 39495 | 39509 | 39528 | 39540 | 39549 |
| 39550 | 39558 | 39577 | 39578 | 39584 | 39588 | 39592 | 39604 | 39613 | 39614 | 39621 | 39622 |
| 39636 | 39638 | 39643 | 39645 | 39648 | 39650 | 39661 | 39666 | 39671 | 39679 | 39686 | 39692 |
| 39696 | 39701 | 39704 | 39708 | 39710 | 39711 | 39712 | 39713 | 39714 | 39715 | 39716 | 39717 |
| 39718 | 39720 | 39721 | 39722 | 39723 | 39724 | 39726 | 39728 | 39729 | 39732 | 39733 | 39734 |
| 39735 | 39736 | 39754 | 39755 | 39760 | 39761 | 39766 | 39779 | 39780 | 39781 | 39797 | 39798 |
| 39804 | 39813 | 39815 | 39816 | 39819 | 39826 | 39830 | 39837 | 39840 | 39844 | 39851 | 39853 |
| 39859 | 39860 | 39865 | 39868 | 39876 | 39877 | 39891 | 39920 | 39923 | 39925 | 39933 | 39950 |
| 39951 | 39956 | 39960 | 39971 | 39980 | 39981 | 39989 | 39999 | 40001 | 40002 | 40006 | 40011 |
| 40015 | 40023 | 40025 | 40029 | 40038 | 40039 | 40046 | 40050 | 40054 | 40057 | 40060 | 40063 |
| 40070 | 40073 | 40075 | 40076 | 40078 | 40094 | 40107 | 40108 | 40115 | 40116 | 40124 | 40132 |
| 40133 | 40144 | 40150 | 40165 | 40167 | 40168 | 40184 | 40206 | 40212 | 40237 | 40239 | 40245 |
| 40247 | 40248 | 40258 | 40263 | 40267 | 40277 | 40282 | 40290 | 40297 | 40333 | 40349 |
| 40356 | 40366 | 40374 | 40377 | 40378 | 40380 | 40389 | 40390 | 40394 | 40396 | 40418 | 40422 |
| 40436 | 40443 | 40444 | 40463 | 40464 | 40470 | 40474 | 40486 | 40491 | 40492 | 40496 | 40512 |
| 40515 | 40531 | 40541 | 40551 | 40552 | 40553 | 40582 | 40588 | 40596 | 40602 | 40604 | 40607 |
| 40620 | 40622 | 40628 | 40633 | 40636 | 40646 | 40657 | 40667 | 40674 | 40682 | 40696 |
| 40698 | 40702 | 40704 | 40711 | 40727 | 40745 | 40746 | 40752 | 40754 | 40755 | 40756 | 40775 |
| 40776 | 40780 | 40790 | 40812 | 40813 | 40842 | 40845 | 40869 | 40870 | 40871 | 40883 | 40885 |
| 40888 | 40891 | 40907 | 40913 | 40918 | 40921 | 40922 | 40924 | 40927 | 40960 | 40971 | 41006 |
| 41008 | 41017 | 41032 | 41035 | 41039 | 41046 | 41062 | 41076 | 41086 | 41097 | 41114 |
| 41126 | 41127 | 41129 | 41134 | 41141 | 41153 | 41154 | 41163 | 41197 | 41202 | 41206 | 41209 |
| 41210 | 41238 | 41239 | 41241 | 41242 | 41243 | 41251 | 41252 | 41255 | 41257 | 41258 | 41259 |
| 41266 | 41274 | 41292 | 41301 | 41302 | 41306 | 41310 | 41313 | 41322 | 41323 | 41343 | 41345 |
| 41347 | 41348 | 41357 | 41358 | 41388 | 41409 | 41411 | 41412 | 41418 | 41425 | 41426 | 41429 |
| 41432 | 41436 | 41449 | 41473 | 41475 | 41477 | 41490 | 41494 | 41496 | 41509 | 41524 | 41527 |
| 41536 | 41550 | 41555 | 41557 | 41576 | 41585 | 41586 | 41588 | 41600 | 41601 | 41608 | 41613 |
| 41614 | 41621 | 41635 | 41645 | 41654 | 41658 | 41665 | 41668 | 41671 | 41672 | 41680 | 41682 |
| 41699 | 41702 | 41705 | 41712 | 41713 | 41717 | 41718 | 41721 | 41728 | 41730 | 41732 | 41736 |
| 41737 | 41738 | 41741 | 41742 | 41747 | 41750 | 41754 | 41756 | 41757 | 41758 | 41760 | 41761 |
| 41762 | 41763 | 41764 | 41765 | 41766 | 41767 | 41768 | 41769 | 41788 | 41800 | 41822 | 41830 |
| 41832 | 41836 | 41843 | 41863 | 41867 | 41879 | 41882 | 41891 | 41892 | 41900 | 41913 | 41914 |
| 41915 | 41928 | 41932 | 41942 | 41952 | 41954 | 41968 | 41995 | 41998 | 42017 | 42025 | 42032 |
| 42050 | 42054 | 42077 | 42084 | 42088 | 42089 | 42092 | 42097 | 42104 | 42105 | 42111 |
| 42118 | 42119 | 42122 | 42129 | 42131 | 42134 | 42138 | 42160 | 42161 | 42162 | 42173 | 42174 |
| 42178 | 42187 | 42204 | 42209 | 42216 | 42224 | 42238 | 42256 | 42275 | 42282 | 42285 | 42295 |
| 42299 | 42304 | 42305 | 42312 | 42323 | 42327 | 42342 | 42347 | 42359 | 42360 | 42375 | 42379 |
| 42384 | 42386 | 42397 | 42405 | 42406 | 42418 | 42420 | 42427 | 42428 | 42438 | 42446 | 42448 |
| 42453 | 42455 | 42458 | 42491 | 42500 | 42511 | 42515 | 42525 | 42533 | 42545 | 42548 | 42549 |
| 42550 | 42556 | 42571 | 42591 | 42603 | 42612 | 42613 | 42617 | 42624 | 42628 | 42639 | 42640 |
| 42648 | 42650 | 42665 | 42692 | 42694 | 42695 | 42709 | 42710 | 42742 | 42746 | 42756 | 42760 |
| 42765 | 42805 | 42807 | 42824 | 42843 | 42845 | 42847 | 42856 | 42882 | 42885 | 42886 | 42887 |
| 42889 | 42890 | 42892 | 42903 | 42909 | 42920 | 42948 | 42951 | 42956 | 42963 | 42964 | 42967 |
| 42981 | 42987 | 42988 | 43004 | 43025 | 43038 | 43050 | 43051 | 43052 | 43053 | 43068 | 43070 |
| 43076 | 43077 | 43078 | 43081 | 43107 | 43120 | 43148 | 43151 | 43152 | 43159 | 43170 | 43173 |
| 43180 | 43189 | 43209 | 43236 | 43237 | 43240 | 43244 | 43259 | 43260 | 43262 | 43265 | 43267 |
| 43272 | 43280 | 43282 | 43286 | 43301 | 43303 | 43304 | 43307 | 43315 | 43331 | 43332 | 43343 |
| 43351 | 43353 | 43359 | 43371 | 43373 | 43385 | 43386 | 43390 | 43391 | 43395 | 43398 | 43401 |
| 43406 | 43441 | 43459 | 43478 | 43482 | 43486 | 43495 | 43518 | 43525 | 43531 | 43533 | 43534 |
| 43537 | 43539 | 43540 | 43541 | 43544 | 43547 | 43553 | 43602 | 43605 | 43608 | 43616 | 43617 |
| 43633 | 43643 | 43677 | 43694 | 43719 | 43722 | 43737 | 43742 | 43743 | 43755 | 43761 | 43773 |

TABLE 3-continued

Cold Tolerance

| | | | | | | | | | | | |
|---|---|---|---|---|---|---|---|---|---|---|---|
| 43788 | 43790 | 43795 | 43797 | 43805 | 43806 | 43813 | 43820 | 43833 | 43842 | 43849 | 43879 |
| 43882 | 43894 | 43903 | 43907 | 43908 | 43916 | 43928 | 43940 | 43949 | 43965 | 43967 | 43984 |
| 43985 | 43988 | 43999 | 44004 | 44009 | 44045 | 44061 | 44062 | 44064 | 44065 | 44087 | 44091 |
| 44096 | 44097 | 44099 | 44104 | 44105 | 44106 | 44115 | 44124 | 44147 | 44148 | 44167 | 44202 |
| 44226 | 44230 | 44235 | 44267 | 44273 | 44290 | 44314 | 44324 | 44330 | 44333 | 44335 | 44342 |
| 44355 | 44396 | 44418 | 44423 | 44424 | 44426 | 44431 | 44432 | 44437 | 44444 | 44445 | 44452 |
| 44459 | 44471 | 44474 | 44480 | 44484 | 44488 | 44489 | 44492 | 44493 | 44498 | 44514 | 44515 |
| 44516 | 44522 | 44523 | 44527 | 44528 | 44535 | 44541 | 44555 | 44558 | 44565 | 44579 | 44581 |
| 44582 | 44597 | 44606 | 44608 | 44629 | 44630 | 44639 | 44650 | 44674 | 44675 | 44676 | 44678 |
| 44679 | 44680 | 44691 | 44695 | 44697 | 44719 | 44729 | 44732 | 44746 | 44749 | 44755 | 44760 |
| 44778 | 44790 | 44806 | 44811 | 44816 | 44834 | 44848 | 44854 | 44857 | 44872 | 44873 | 44877 |
| 44883 | 44887 | 44891 | 44896 | 44897 | 44930 | 44931 | 44943 | 44944 | 44947 | 44950 | 44954 |
| 44967 | 44968 | 44971 | 44972 | 44983 | 45000 | 45001 | 45010 | 45011 | 45015 | 45018 | 45027 |
| 45041 | 45051 | 45055 | 45058 | 45060 | 45066 | 45074 | 45083 | 45097 | 45112 | 45119 | 45128 |
| 45130 | 45133 | 45134 | 45147 | 45149 | 45151 | 45153 | 45168 | 45172 | 45190 | 45194 | 45200 |
| 45214 | 45220 | 45239 | 45244 | 45261 | 45272 | 45273 | 45275 | 45277 | 45294 | 45324 | 45326 |
| 45342 | 45351 | 45357 | 45364 | 45367 | 45369 | 45370 | 45376 | 45378 | 45379 | 45381 | 45388 |
| 45391 | 45398 | 45404 | 45409 | 45413 | 45416 | 45444 | 45445 | 45447 | 45450 | 45465 | 45468 |
| 45481 | 45482 | 45490 | 45496 | 45504 | 45509 | 45511 | 45512 | 45554 | 45559 | 45569 | 45570 |
| 45583 | 45587 | 45598 | 45616 | 45624 | 45628 | 45647 | 45660 | 45674 | 45675 | 45680 | 45681 |
| 45685 | 45693 | 45698 | 45700 | 45702 | 45721 | 45722 | 45723 | 45725 | 45753 | 45758 | 45765 |
| 45781 | 45788 | 45789 | 45794 | 45811 | 45813 | 45834 | 45857 | 45873 | 45892 | 45893 | |
| 45901 | 45907 | 45908 | 45919 | 45925 | 45940 | 45966 | 45978 | 45982 | 46019 | 46022 | 46033 |
| 46057 | 46065 | 46066 | 46073 | 46076 | 46078 | 46089 | 46093 | 46112 | 46115 | 46119 | 46123 |
| 46126 | 46133 | 46179 | 46184 | 46196 | 46225 | 46231 | 46232 | 46238 | 46239 | 46252 | 46269 |
| 46270 | 46281 | 46296 | 46304 | 46319 | 46329 | 46340 | 46362 | 46372 | 46399 | 46404 | 46424 |
| 46435 | 46446 | 46455 | 46469 | 46474 | 46486 | 46504 | 46510 | 46521 | 46526 | 46527 | 46530 |
| 46541 | 46551 | 46552 | 46557 | 46560 | 46582 | 46592 | 46615 | 46649 | 46667 | 46687 | 46700 |
| 46706 | 46739 | 46758 | 46760 | 46782 | 46797 | 46813 | 46814 | 46832 | 46833 | 46834 | 46863 |
| 46866 | 46868 | 46869 | 46870 | 46872 | 46889 | 46901 | 46904 | 46913 | 46914 | 46920 | 46928 |
| 46946 | 46950 | 46959 | 46977 | 46995 | 46999 | 47000 | 47005 | 47006 | 47008 | 47009 | 47013 |
| 47016 | 47037 | 47045 | 47050 | 47063 | 47079 | 47088 | 47107 | 47108 | 47113 | 47132 | 47146 |
| 47154 | 47161 | 47166 | 47167 | 47184 | 47185 | 47189 | 47192 | 47201 | 47203 | 47207 | 47211 |
| 47218 | 47222 | 47238 | 47265 | 47270 | 47285 | 47288 | 47291 | 47297 | 47299 | 47300 | 47306 |
| 47325 | 47327 | 47337 | 47338 | 47339 | 47340 | 47353 | 47354 | 47358 | 47360 | | |

TABLE 4

Disease Control

Table 4A SEQ ID NOs of Polypeptides useful for Improving Disease Control

| | | | | | | | | | | |
|---|---|---|---|---|---|---|---|---|---|---|
| 415 | 492 | 507 | 653 | 721 | 833 | 1355 | 1356 | 1472 | 1539 | 1545 | 1684 |
| 1802 | 1878 | 1928 | 1932 | 1957 | 2023 | 2335 | 2337 | 2880 | 2924 | 3089 | 3135 |
| 3308 | 3399 | 3492 | 3566 | 3785 | 3812 | 3831 | 3951 | 4035 | 4049 | 4051 | 4114 |
| 4125 | 4167 | 4288 | 4408 | 4456 | 4659 | 4680 | 4711 | 4743 | 4756 | 4824 | 4838 |
| 4949 | 5146 | 5302 | 5381 | 5421 | 5520 | 5521 | 5522 | 5523 | 5524 | 5525 | 5664 |
| 5897 | 5984 | 6023 | 6195 | 6215 | 6248 | 6303 | 6353 | 6391 | 6450 | 6507 | 6508 |
| 6581 | 6582 | 6583 | 6743 | 6901 | 7044 | 7164 | 7216 | 7418 | 7439 | 7471 | 7503 |
| 7515 | 7583 | 7707 | 7816 | 7890 | 7983 | 7993 | 8158 | 8165 | 8236 | 8244 | 8470 |
| 8547 | 8599 | 8641 | 8700 | 8722 | 8812 | 8961 | 9115 | 9117 | 9120 | 9281 | 9309 |
| 9398 | 9399 | 10218 | 10228 | 10461 | 10562 | 10717 | 10803 | 10892 | 10919 | 11040 | 11058 |
| 11065 | 11114 | 11177 | 11298 | 11345 | 11395 | 11462 | 11500 | 11527 | 11556 | 11684 | 11765 |
| 11807 | 11860 | 11865 | 11889 | 11934 | 12024 | 12262 | 12263 | 12329 | 12339 | 12435 | 12478 |
| 12511 | 12631 | 12670 | 12727 | 12804 | 12818 | 12910 | 12950 | 13012 | 13016 | 13060 | 13100 |
| 13135 | 13147 | 13220 | 13288 | 13372 | 13482 | 13557 | 13631 | 13656 | 13690 | 13691 | 13805 |
| 13850 | 13927 | 14042 | 14080 | 14111 | 14179 | 14207 | 14347 | 14420 | 14475 | 14511 | |
| 14593 | 14671 | 14728 | 14787 | 14789 | 14922 | 14948 | 14953 | 14961 | 15106 | 15152 | 15208 |
| 15360 | 15414 | 15727 | 15782 | 15948 | 16111 | 16165 | 16394 | 16399 | 16459 | 16514 | 16538 |
| 16543 | 16644 | 16742 | 16746 | 16840 | 16849 | 16889 | 16891 | 17022 | 17136 | 17162 | 17274 |
| 17479 | 17563 | 17612 | 17614 | 17735 | 17952 | 18118 | 18204 | 18212 | 18262 | 18473 | 18493 |
| 18503 | 18584 | 18585 | 18613 | 18984 | 19136 | 19211 | 19361 | 19400 | 19484 | 19507 | |
| 19514 | 19529 | 19684 | 19726 | 19739 | 19750 | 19803 | 19830 | 19890 | 19963 | 19972 | 20183 |
| 20187 | 20189 | 20271 | 20427 | 20462 | 20499 | 20552 | 20590 | 20624 | 20721 | 20851 | 20915 |
| 21113 | 21172 | 21317 | 21318 | 21322 | 22719 | 22735 | 22884 | 22908 | 22951 | 23041 | 23167 |
| 23211 | 23365 | 23452 | 23465 | 23680 | 23682 | 23685 | | | | | |

Table 4B SEQ ID NOs of Polynucleotides useful for Improving Disease Control

| | | | | | | | | | | |
|---|---|---|---|---|---|---|---|---|---|---|
| 24102 | 24179 | 24194 | 24340 | 24408 | 24520 | 25042 | 25043 | 25159 | 25226 | 25232 | 25371 |
| 25489 | 25565 | 25615 | 25619 | 25644 | 25710 | 26022 | 26024 | 26567 | 26611 | 26776 | 26822 |
| 26995 | 27086 | 27179 | 27253 | 27472 | 27499 | 27518 | 27638 | 27722 | 27736 | 27738 | 27801 |
| 27812 | 27854 | 27975 | 28095 | 28143 | 28346 | 28367 | 28398 | 28430 | 28443 | 28511 | 28525 |
| 28636 | 28833 | 28989 | 29068 | 29108 | 29207 | 29208 | 29209 | 29210 | 29211 | 29212 | 29351 |

TABLE 4-continued

Disease Control

| | | | | | | | | | | | |
|---|---|---|---|---|---|---|---|---|---|---|---|
| 29584 | 29671 | 29710 | 29882 | 29902 | 29935 | 29990 | 30040 | 30078 | 30137 | 30194 | 30195 |
| 30268 | 30269 | 30270 | 30430 | 30588 | 30731 | 30851 | 30903 | 31105 | 31126 | 31158 | 31190 |
| 31202 | 31270 | 31394 | 31503 | 31577 | 31670 | 31680 | 31845 | 31852 | 31923 | 31931 | 32157 |
| 32234 | 32286 | 32328 | 32387 | 32409 | 32499 | 32648 | 32802 | 32804 | 32807 | 32968 | 32996 |
| 33085 | 33086 | 33905 | 33915 | 34148 | 34249 | 34404 | 34490 | 34579 | 34606 | 34727 | 34745 |
| 34752 | 34801 | 34864 | 34985 | 35032 | 35082 | 35149 | 35187 | 35214 | 35243 | 35371 | 35452 |
| 35494 | 35547 | 35552 | 35576 | 35621 | 35711 | 35949 | 35950 | 36016 | 36026 | 36122 | 36165 |
| 36198 | 36318 | 36357 | 36414 | 36491 | 36505 | 36597 | 36637 | 36699 | 36703 | 36747 | 36787 |
| 36822 | 36834 | 36907 | 36975 | 37059 | 37169 | 37244 | 37318 | 37343 | 37377 | 37378 | 37492 |
| 37537 | 37614 | 37729 | 37767 | 37798 | 37866 | 37894 | 37967 | 38034 | 38107 | 38162 | 38198 |
| 38280 | 38358 | 38415 | 38474 | 38476 | 38609 | 38635 | 38640 | 38648 | 38793 | 38839 | 38895 |
| 39047 | 39101 | 39414 | 39469 | 39635 | 39798 | 39852 | 40081 | 40086 | 40146 | 40201 | 40225 |
| 40230 | 40331 | 40429 | 40433 | 40527 | 40536 | 40576 | 40578 | 40709 | 40823 | 40849 | 40961 |
| 41166 | 41250 | 41299 | 41301 | 41422 | 41639 | 41805 | 41891 | 41949 | 42080 | 42180 |
| 42190 | 42271 | 42272 | 42300 | 42671 | 42823 | 42898 | 42976 | 43048 | 43087 | 43171 | 43194 |
| 43201 | 43216 | 43371 | 43413 | 43426 | 43437 | 43490 | 43517 | 43577 | 43650 | 43659 | 43870 |
| 43874 | 43876 | 43958 | 44114 | 44149 | 44186 | 44239 | 44277 | 44311 | 44408 | 44538 | 44602 |
| 44800 | 44859 | 45004 | 45005 | 45009 | 46406 | 46422 | 46571 | 46595 | 46638 | 46728 | 46854 |
| 46898 | 47052 | 47139 | 47152 | 47367 | 47369 | 47372 | | | | | |

TABLE 5

Drought Tolerance

Table 5A SEQ ID NOs of Polypeptides useful for Improving Drought Tolerance

| | | | | | | | | | | | |
|---|---|---|---|---|---|---|---|---|---|---|---|
| 390 | 752 | 874 | 1463 | 1624 | 1883 | 1920 | 2245 | 2268 | 2311 | 2546 | 2751 |
| 2968 | 3030 | 3191 | 3411 | 3588 | 3853 | 4019 | 4375 | 4438 | 4644 | 4706 | 4960 |
| 5268 | 5378 | 7129 | 7197 | 7402 | 7465 | 7718 | 7973 | 8022 | 8321 | 8654 | 9976 |
| 10422 | 10519 | 10572 | 10616 | 11099 | 11374 | 11737 | 11837 | 12302 | 12438 | 12607 | 12704 |
| 12968 | 13045 | 13234 | 13603 | 14304 | 14427 | 14780 | 14793 | 14934 | 14959 | 15271 | 15597 |
| 15604 | 15974 | 15979 | 16336 | 16338 | 16731 | 17184 | 17803 | 18255 | 18766 | 19269 | 19383 |
| 19844 | 19866 | 20146 | 20637 | 20793 | 20943 | 21062 | 21190 | 21533 | 21717 | 22074 | 22238 |
| 22749 | 22787 | 23212 | 23310 | 23354 | 23445 | | | | | | |

Table 5B SEQ ID NOs of Polynucleotides useful for Improving Drought Tolerance

| | | | | | | | | | | | |
|---|---|---|---|---|---|---|---|---|---|---|---|
| 24077 | 24439 | 24561 | 25150 | 25311 | 25570 | 25607 | 25932 | 25955 | 25998 | 26233 | 26438 |
| 26655 | 26717 | 26878 | 27098 | 27275 | 27540 | 27706 | 28062 | 28125 | 28331 | 28393 | 28647 |
| 28955 | 29065 | 30816 | 30884 | 31089 | 31152 | 31405 | 31660 | 31709 | 32008 | 32341 | 33663 |
| 34109 | 34206 | 34259 | 34303 | 34786 | 35061 | 35424 | 35524 | 35989 | 36125 | 36294 | 36391 |
| 36655 | 36732 | 36921 | 37290 | 37991 | 38114 | 38467 | 38480 | 38621 | 38646 | 38958 | 39284 |
| 39291 | 39661 | 39666 | 40023 | 40025 | 40418 | 40871 | 41490 | 41942 | 42453 | 42956 | 43070 |
| 43531 | 43553 | 43833 | 44324 | 44480 | 44630 | 44749 | 44877 | 45220 | 45404 | 45761 | 45925 |
| 46436 | 46474 | 46899 | 46997 | 47041 | 47132 | | | | | | |

TABLE 6

Plant Growth/Cell Cycle

Table 6A SEQ ID NOs of Polypeptides useful for improving Plant Growth - Cell Cycle

| | | | | | | | | | | | |
|---|---|---|---|---|---|---|---|---|---|---|---|
| 38 | 52 | 83 | 91 | 152 | 160 | 167 | 184 | 212 | 229 | 258 | 284 |
| 295 | 300 | 355 | 363 | 444 | 553 | 614 | 617 | 623 | 627 | 628 | 658 |
| 670 | 723 | 746 | 844 | 859 | 865 | 866 | 870 | 872 | 921 | 929 | 939 |
| 942 | 944 | 959 | 960 | 963 | 974 | 984 | 985 | 1005 | 1006 | 1031 | 1041 |
| 1056 | 1062 | 1083 | 1098 | 1103 | 1116 | 1117 | 1124 | 1125 | 1168 | 1180 | 1213 |
| 1217 | 1230 | 1242 | 1246 | 1247 | 1249 | 1251 | 1272 | 1273 | 1279 | 1286 | 1287 |
| 1293 | 1305 | 1306 | 1312 | 1318 | 1322 | 1350 | 1351 | 1352 | 1353 | 1354 | 1355 |
| 1356 | 1357 | 1358 | 1359 | 1360 | 1361 | 1362 | 1363 | 1364 | 1365 | 1366 | 1367 |
| 1368 | 1369 | 1370 | 1371 | 1372 | 1373 | 1374 | 1375 | 1376 | 1377 | 1378 | 1379 |
| 1380 | 1381 | 1382 | 1383 | 1384 | 1385 | 1386 | 1387 | 1388 | 1389 | 1390 | 1398 |
| 1399 | 1400 | 1407 | 1422 | 1424 | 1438 | 1448 | 1452 | 1455 | 1467 | 1475 | 1487 |
| 1493 | 1503 | 1524 | 1533 | 1535 | 1540 | 1542 | 1551 | 1553 | 1561 | 1563 | 1568 |
| 1569 | 1570 | 1576 | 1581 | 1585 | 1586 | 1591 | 1619 | 1620 | 1621 | 1625 | 1627 |
| 1628 | 1630 | 1650 | 1653 | 1655 | 1678 | 1715 | 1735 | 1744 | 1761 | 1768 | 1770 |
| 1776 | 1790 | 1798 | 1800 | 1842 | 1852 | 1855 | 1870 | 1875 | 1891 | 1894 | 1901 |
| 1908 | 1919 | 1938 | 1942 | 1965 | 1984 | 1990 | 2001 | 2009 | 2012 | 2030 | 2033 |
| 2036 | 2037 | 2040 | 2061 | 2070 | 2072 | 2073 | 2076 | 2088 | 2099 | 2101 | 2114 |
| 2116 | 2133 | 2135 | 2136 | 2138 | 2150 | 2157 | 2161 | 2179 | 2184 | 2187 | 2188 |
| 2210 | 2213 | 2217 | 2219 | 2224 | 2234 | 2239 | 2240 | 2248 | 2257 | 2258 | 2276 |
| 2290 | 2294 | 2302 | 2309 | 2317 | 2318 | 2323 | 2324 | 2326 | 2335 | 2337 | 2342 |

TABLE 6-continued

Plant Growth/Cell Cycle

| | | | | | | | | | | |
|---|---|---|---|---|---|---|---|---|---|---|
| 2344 | 2347 | 2348 | 2353 | 2362 | 2370 | 2371 | 2375 | 2376 | 2382 | 2390 | 2391 |
| 2395 | 2400 | 2401 | 2405 | 2434 | 2447 | 2452 | 2454 | 2465 | 2468 | 2469 | 2472 |
| 2473 | 2479 | 2487 | 2491 | 2498 | 2502 | 2505 | 2525 | 2544 | 2553 | 2556 | 2563 |
| 2565 | 2577 | 2581 | 2582 | 2584 | 2590 | 2591 | 2593 | 2594 | 2691 | 2693 | 2823 |
| 2840 | 2846 | 2853 | 2904 | 2906 | 2924 | 2940 | 2987 | 3033 | 3035 | 3070 | 3075 |
| 3084 | 3092 | 3093 | 3101 | 3112 | 3118 | 3134 | 3142 | 3151 | 3162 | 3174 | 3195 |
| 3209 | 3210 | 3227 | 3230 | 3242 | 3247 | 3255 | 3256 | 3268 | 3272 | 3275 | 3279 |
| 3293 | 3294 | 3318 | 3319 | 3329 | 3340 | 3345 | 3346 | 3347 | 3349 | 3368 | 3370 |
| 3371 | 3374 | 3375 | 3377 | 3386 | 3388 | 3402 | 3405 | 3406 | 3408 | 3417 | 3433 |
| 3434 | 3438 | 3449 | 3456 | 3464 | 3467 | 3477 | 3487 | 3491 | 3494 | 3503 | 3519 |
| 3526 | 3539 | 3553 | 3557 | 3564 | 3565 | 3569 | 3572 | 3574 | 3585 | 3587 | 3606 |
| 3607 | 3613 | 3626 | 3648 | 3649 | 3650 | 3653 | 3676 | 3691 | 3700 | 3706 | 3707 |
| 3713 | 3716 | 3718 | 3719 | 3729 | 3732 | 3734 | 3738 | 3753 | 3767 | 3768 | 3790 |
| 3791 | 3801 | 3802 | 3807 | 3822 | 3829 | 3841 | 3847 | 3870 | 3883 | 3892 | 3903 |
| 3904 | 3909 | 3922 | 3926 | 3933 | 3935 | 3938 | 3941 | 3942 | 3944 | 3950 | 3959 |
| 3961 | 3963 | 3965 | 3975 | 3989 | 4007 | 4025 | 4026 | 4036 | 4039 | 4053 | 4055 |
| 4058 | 4062 | 4067 | 4070 | 4073 | 4087 | 4089 | 4090 | 4091 | 4102 | 4120 | 4132 |
| 4148 | 4151 | 4155 | 4156 | 4170 | 4174 | 4193 | 4195 | 4197 | 4199 | 4208 | 4222 |
| 4239 | 4261 | 4314 | 4347 | 4363 | 4371 | 4385 | 4389 | 4408 | 4416 | 4435 | 4509 |
| 4511 | 4525 | 4548 | 4634 | 4636 | 4658 | 4666 | 4692 | 4703 | 4735 | 4736 | 4773 |
| 4813 | 4850 | 4859 | 4920 | 4934 | 4947 | 4967 | 4977 | 4980 | 4988 | 4992 | 4995 |
| 5002 | 5014 | 5018 | 5030 | 5053 | 5094 | 5101 | 5102 | 5109 | 5110 | 5113 | 5128 |
| 5129 | 5137 | 5138 | 5141 | 5156 | 5159 | 5162 | 5163 | 5172 | 5173 | 5174 | 5175 |
| 5186 | 5190 | 5191 | 5192 | 5207 | 5227 | 5234 | 5235 | 5236 | 5237 | 5271 | 5296 |
| 5297 | 5305 | 5307 | 5308 | 5341 | 5342 | 5357 | 5366 | 5368 | 5372 | 5388 | 5400 |
| 5413 | 5414 | 5420 | 5447 | 5455 | 5459 | 5460 | 5478 | 5482 | 5505 | 5506 | 5514 |
| 5517 | 5519 | 5526 | 5552 | 5558 | 5566 | 5571 | 5601 | 5607 | 5609 | 5620 | 5639 |
| 5643 | 5653 | 5663 | 5671 | 5672 | 5680 | 5690 | 5692 | 5696 | 5697 | 5705 | 5719 |
| 5721 | 5733 | 5739 | 5743 | 5746 | 5769 | 5781 | 5791 | 5797 | 5822 | 5838 | 5839 |
| 5840 | 5848 | 5849 | 5853 | 5854 | 5855 | 5874 | 5875 | 5877 | 5881 | 5887 | 5890 |
| 5894 | 5895 | 5901 | 5902 | 5904 | 5920 | 5929 | 5930 | 5940 | 5949 | 5955 | 5964 |
| 5972 | 5973 | 5975 | 5977 | 5979 | 5990 | 6020 | 6026 | 6027 | 6063 | 6064 | 6067 |
| 6074 | 6092 | 6106 | 6117 | 6118 | 6119 | 6143 | 6150 | 6156 | 6157 | 6161 | 6187 |
| 6188 | 6189 | 6194 | 6200 | 6201 | 6209 | 6210 | 6237 | 6246 | 6247 | 6248 | 6270 |
| 6289 | 6298 | 6304 | 6328 | 6330 | 6343 | 6346 | 6362 | 6364 | 6376 | 6390 | 6395 |
| 6397 | 6432 | 6440 | 6449 | 6453 | 6460 | 6479 | 6480 | 6481 | 6501 | 6516 | 6527 |
| 6564 | 6573 | 6586 | 6597 | 6604 | 6612 | 6621 | 6625 | 6631 | 6638 | 6639 | 6665 |
| 6676 | 6724 | 6727 | 6729 | 6751 | 6770 | 6774 | 6821 | 6832 | 6834 | 6840 | 6841 |
| 6844 | 6888 | 6922 | 6924 | 6925 | 6926 | 6928 | 6929 | 6943 | 6963 | 6964 |
| 6973 | 6974 | 6975 | 6995 | 6998 | 7016 | 7017 | 7027 | 7029 | 7030 | 7070 | 7102 |
| 7117 | 7125 | 7140 | 7144 | 7164 | 7172 | 7194 | 7267 | 7269 | 7284 | 7322 | 7389 |
| 7392 | 7394 | 7416 | 7417 | 7461 | 7495 | 7533 | 7572 | 7609 | 7618 | 7678 | 7692 |
| 7705 | 7725 | 7751 | 7765 | 7797 | 7800 | 7824 | 7852 | 7931 | 7951 | 7964 |
| 8029 | 8067 | 8074 | 8115 | 8119 | 8131 | 8199 | 8215 | 8228 | 8233 | 8259 | 8267 |
| 8278 | 8286 | 8458 | 8467 | 8474 | 8493 | 8650 | 8678 | 8685 | 8695 | 8702 | 8731 |
| 8773 | 8794 | 8804 | 8832 | 8847 | 8849 | 8851 | 8878 | 8880 | 8933 | 8961 | 8973 |
| 8974 | 9007 | 9015 | 9075 | 9076 | 9088 | 9103 | 9114 | 9141 | 9250 | 9265 | 9271 |
| 9282 | 9287 | 9297 | 9301 | 9376 | 9430 | 9476 | 9505 | 9524 | 9536 | 9541 | 9625 |
| 9646 | 9731 | 9770 | 9790 | 9839 | 9853 | 9876 | 9899 | 9967 | 10053 | 10100 | 10109 |
| 10111 | 10140 | 10154 | 10158 | 10249 | 10254 | 10259 | 10287 | 10321 | 10375 | 10395 | 10404 |
| 10414 | 10454 | 10472 | 10545 | 10562 | 10583 | 10621 | 10644 | 10646 | 10683 | 10684 | 10855 |
| 10878 | 10887 | 10890 | 10892 | 10901 | 10914 | 10917 | 10933 | 10954 | 10959 | 10987 | 11000 |
| 11003 | 11005 | 11023 | 11031 | 11044 | 11060 | 11071 | 11104 | 11105 | 11107 | 11108 | 11119 |
| 11148 | 11160 | 11164 | 11228 | 11236 | 11275 | 11277 | 11279 | 11291 | 11295 | 11302 | 11312 |
| 11330 | 11333 | 11335 | 11354 | 11379 | 11384 | 11411 | 11453 | 11462 | 11487 | 11505 | 11539 |
| 11565 | 11606 | 11623 | 11660 | 11663 | 11689 | 11700 | 11798 | 11841 | 11849 | 11860 | 11869 |
| 11887 | 11907 | 11951 | 11980 | 11988 | 12017 | 12040 | 12114 | 12128 | 12150 | 12192 | 12215 |
| 12249 | 12336 | 12365 | 12387 | 12411 | 12415 | 12424 | 12429 | 12442 | 12443 | 12464 | 12474 |
| 12512 | 12534 | 12545 | 12547 | 12555 | 12557 | 12560 | 12561 | 12564 | 12567 | 12571 | 12578 |
| 12581 | 12582 | 12584 | 12588 | 12591 | 12604 | 12609 | 12616 | 12649 | 12651 | 12654 |
| 12660 | 12677 | 12685 | 12687 | 12705 | 12719 | 12724 | 12732 | 12740 | 12745 | 12752 | 12754 |
| 12755 | 12756 | 12775 | 12779 | 12785 | 12831 | 12839 | 12856 | 12862 | 12867 | 12885 | 12886 |
| 12888 | 12898 | 12915 | 12917 | 12931 | 12940 | 12945 | 12948 | 12951 | 12954 | 12955 | 12961 |
| 12965 | 12966 | 12972 | 12977 | 12992 | 12998 | 13005 | 13007 | 13066 | 13077 | 13082 | 13083 |
| 13084 | 13088 | 13093 | 13103 | 13114 | 13117 | 13118 | 13132 | 13133 | 13141 | 13159 | 13162 |
| 13178 | 13208 | 13223 | 13227 | 13231 | 13238 | 13243 | 13248 | 13270 | 13273 | 13290 | 13300 |
| 13302 | 13315 | 13342 | 13363 | 13372 | 13374 | 13376 | 13383 | 13398 | 13399 | 13402 | 13404 |
| 13407 | 13412 | 13413 | 13414 | 13415 | 13445 | 13464 | 13482 | 13487 | 13489 | 13490 | 13495 |
| 13500 | 13504 | 13513 | 13538 | 13539 | 13543 | 13570 | 13572 | 13580 | 13581 | 13583 | 13590 |
| 13593 | 13606 | 13607 | 13609 | 13635 | 13640 | 13653 | 13683 | 13708 | 13726 | 13730 | 13737 |
| 13773 | 13776 | 13808 | 13840 | 13857 | 13919 | 13947 | 13955 | 13971 | 13985 | 14059 | 14084 |
| 14156 | 14254 | 14280 | 14283 | 14293 | 14309 | 14313 | 14315 | 14318 | 14387 | 14390 | 14428 |
| 14473 | 14474 | 14482 | 14532 | 14540 | 14552 | 14606 | 14661 | 14702 | 14728 | 14731 | 14742 |
| 14867 | 15007 | 15054 | 15079 | 15093 | 15103 | 15121 | 15138 | 15184 | 15208 | 15211 | 15477 |
| 15503 | 15512 | 15548 | 15559 | 15601 | 15635 | 15808 | 15847 | 15875 | 15884 | 15920 | 15921 |
| 15932 | 15970 | 16010 | 16022 | 16040 | 16044 | 16189 | 16226 | 16250 | 16257 | 16287 | 16289 |
| 16299 | 16364 | 16382 | 16431 | 16504 | 16508 | 16524 | 16543 | 16545 | 16582 | 16638 | 16647 |

TABLE 6-continued

Plant Growth/Cell Cycle

| | | | | | | | | | | | |
|---|---|---|---|---|---|---|---|---|---|---|---|
| 16692 | 16733 | 16787 | 16837 | 16940 | 16984 | 17007 | 17048 | 17073 | 17091 | 17107 | 17108 |
| 17155 | 17189 | 17192 | 17226 | 17231 | 17271 | 17284 | 17348 | 17398 | 17403 | 17405 | 17428 |
| 17476 | 17479 | 17482 | 17499 | 17503 | 17524 | 17537 | 17645 | 17676 | 17704 | 17796 | 17809 |
| 17845 | 17971 | 18005 | 18013 | 18057 | 18060 | 18109 | 18110 | 18116 | 18137 | 18148 | 18176 |
| 18184 | 18190 | 18192 | 18195 | 18198 | 18211 | 18215 | 18216 | 18218 | 18225 | 18229 | 18244 |
| 18253 | 18256 | 18257 | 18258 | 18268 | 18284 | 18288 | 18350 | 18393 | 18424 | 18430 | 18450 |
| 18481 | 18537 | 18538 | 18542 | 18543 | 18544 | 18559 | 18566 | 18569 | 18579 | 18589 | 18594 |
| 18602 | 18612 | 18638 | 18645 | 18664 | 18666 | 18670 | 18676 | 18677 | 18685 | 18686 | 18689 |
| 18702 | 18755 | 18771 | 18775 | 18818 | 18823 | 18897 | 18932 | 18939 | 18994 | 18997 | 19033 |
| 19034 | 19044 | 19074 | 19126 | 19139 | 19146 | 19152 | 19166 | 19176 | 19218 | 19262 | 19310 |
| 19319 | 19330 | 19381 | 19415 | 19417 | 19433 | 19495 | 19522 | 19527 | 19548 | 19565 | 19576 |
| 19581 | 19616 | 19640 | 19655 | 19656 | 19662 | 19690 | 19831 | 19859 | 19935 | 19939 | 19947 |
| 19958 | 19972 | 19984 | 19993 | 20050 | 20102 | 20109 | 20141 | 20143 | 20185 | 20203 | 20256 |
| 20281 | 20313 | 20314 | 20316 | 20318 | 20338 | 20339 | 20345 | 20352 | 20353 | 20359 | 20371 |
| 20377 | 20383 | 20387 | 20450 | 20482 | 20486 | 20527 | 20547 | 20553 | 20554 | 20557 | 20581 |
| 20643 | 20706 | 20707 | 20721 | 20746 | 20787 | 20817 | 20826 | 20851 | 20910 | 20920 | 20946 |
| 21075 | 21077 | 21123 | 21130 | 21221 | 21247 | 21269 | 21304 | 21322 | 21348 | 21352 | 21359 |
| 21388 | 21389 | 21407 | 21409 | 21414 | 21436 | 21437 | 21451 | 21452 | 21457 | 21469 | 21482 |
| 21490 | 21521 | 21522 | 21524 | 21538 | 21575 | 21580 | 21586 | 21594 | 21595 | 21606 | 21609 |
| 21621 | 21634 | 21635 | 21636 | 21663 | 21665 | 21666 | 21668 | 21695 | 21779 | 21813 | 21816 |
| 21817 | 21868 | 21874 | 21888 | 21890 | 21899 | 21902 | 21904 | 21907 | 21910 | 21923 | 21924 |
| 21927 | 21931 | 21940 | 21949 | 21955 | 21957 | 21964 | 21967 | 21970 | 21976 | 21977 | 21978 |
| 21981 | 21985 | 21989 | 21995 | 21997 | 22005 | 22025 | 22030 | 22042 | 22059 | 22068 | 22069 |
| 22073 | 22080 | 22084 | 22087 | 22092 | 22103 | 22104 | 22105 | 22108 | 22133 | 22142 | 22149 |
| 22150 | 22151 | 22153 | 22171 | 22173 | 22174 | 22179 | 22189 | 22199 | 22211 | 22221 | 22228 |
| 22235 | 22246 | 22247 | 22262 | 22272 | 22276 | 22285 | 22288 | 22292 | 22304 | 22311 | 22312 |
| 22317 | 22318 | 22319 | 22327 | 22338 | 22343 | 22349 | 22354 | 22356 | 22360 | 22364 | 22387 |
| 22421 | 22422 | 22423 | 22426 | 22427 | 22429 | 22430 | 22434 | 22435 | 22437 | 22439 | 22449 |
| 22453 | 22456 | 22457 | 22462 | 22488 | 22500 | 22502 | 22505 | 22511 | 22513 | 22520 | 22526 |
| 22530 | 22531 | 22548 | 22556 | 22559 | 22561 | 22562 | 22564 | 22578 | 22595 | 22604 | 22616 |
| 22618 | 22624 | 22625 | 22627 | 22641 | 22656 | 22669 | 22673 | 22686 | 22695 | 22702 | |
| 22703 | 22704 | 22712 | 22718 | 22725 | 22734 | 22741 | 22742 | 22745 | 22747 | 22771 | 22778 |
| 22784 | 22785 | 22802 | 22806 | 22811 | 22818 | 22820 | 22829 | 22832 | 22838 | 22841 | 22842 |
| 22860 | 22866 | 22869 | 22884 | 22892 | 22895 | 22929 | 22939 | 22942 | 22950 | 22960 | 22961 |
| 22974 | 23038 | 23039 | 23095 | 23098 | 23128 | 23134 | 23183 | 23185 | 23230 | 23240 | 23247 |
| 23249 | 23261 | 23276 | 23284 | 23350 | 23423 | 23435 | 23458 | 23473 | 23535 | 23543 | 23564 |
| 23606 | 23658 | 23680 | 23685 | | | | | | | | |

Table 6B SEQ ID NOs of Polynucleotides useful for improving Plant Growth - Cell Cycle

| | | | | | | | | | | | |
|---|---|---|---|---|---|---|---|---|---|---|---|
| 23725 | 23739 | 23770 | 23778 | 23839 | 23847 | 23854 | 23871 | 23899 | 23916 | 23945 | 23971 |
| 23982 | 23987 | 24042 | 24050 | 24131 | 24240 | 24301 | 24304 | 24310 | 24314 | 24315 | 24345 |
| 24357 | 24410 | 24433 | 24531 | 24546 | 24552 | 24553 | 24557 | 24559 | 24608 | 24616 | 24626 |
| 24629 | 24631 | 24646 | 24647 | 24650 | 24661 | 24671 | 24672 | 24692 | 24693 | 24718 | 24728 |
| 24743 | 24749 | 24770 | 24785 | 24790 | 24803 | 24804 | 24811 | 24812 | 24855 | 24867 | 24900 |
| 24904 | 24917 | 24929 | 24933 | 24934 | 24936 | 24938 | 24959 | 24960 | 24966 | 24973 | 24974 |
| 24980 | 24992 | 24993 | 24999 | 25005 | 25009 | 25037 | 25038 | 25039 | 25040 | 25041 | 25042 |
| 25043 | 25044 | 25045 | 25046 | 25047 | 25048 | 25049 | 25050 | 25051 | 25052 | 25053 | 25054 |
| 25055 | 25056 | 25057 | 25058 | 25059 | 25060 | 25061 | 25062 | 25063 | 25064 | 25065 | 25066 |
| 25067 | 25068 | 25069 | 25070 | 25071 | 25072 | 25073 | 25074 | 25075 | 25076 | 25077 | 25085 |
| 25086 | 25087 | 25094 | 25109 | 25111 | 25125 | 25135 | 25139 | 25142 | 25154 | 25162 | 25174 |
| 25180 | 25190 | 25211 | 25220 | 25222 | 25227 | 25229 | 25238 | 25248 | 25250 | 25255 | |
| 25256 | 25257 | 25263 | 25268 | 25272 | 25273 | 25278 | 25306 | 25307 | 25308 | 25312 | 25314 |
| 25315 | 25317 | 25337 | 25340 | 25342 | 25365 | 25402 | 25422 | 25431 | 25448 | 25455 | 25457 |
| 25463 | 25477 | 25485 | 25487 | 25529 | 25539 | 25542 | 25557 | 25562 | 25578 | 25581 | 25588 |
| 25595 | 25606 | 25625 | 25629 | 25652 | 25671 | 25677 | 25688 | 25695 | 25699 | 25717 | 25720 |
| 25723 | 25724 | 25727 | 25748 | 25757 | 25759 | 25760 | 25763 | 25775 | 25786 | 25788 | 25801 |
| 25803 | 25820 | 25822 | 25823 | 25825 | 25837 | 25844 | 25848 | 25866 | 25871 | 25874 | 25875 |
| 25897 | 25900 | 25904 | 25906 | 25911 | 25921 | 25926 | 25927 | 25935 | 25944 | 25945 | 25963 |
| 25977 | 25981 | 25989 | 25996 | 26004 | 26005 | 26010 | 26011 | 26013 | 26022 | 26024 | 26029 |
| 26031 | 26034 | 26035 | 26040 | 26049 | 26057 | 26058 | 26062 | 26063 | 26069 | 26077 | 26078 |
| 26082 | 26087 | 26088 | 26092 | 26121 | 26134 | 26139 | 26141 | 26152 | 26155 | 26156 | 26159 |
| 26160 | 26166 | 26174 | 26178 | 26185 | 26189 | 26192 | 26212 | 26231 | 26240 | 26243 | 26250 |
| 26252 | 26264 | 26268 | 26269 | 26271 | 26277 | 26278 | 26378 | 26380 | 26510 | | |
| 26527 | 26533 | 26540 | 26591 | 26593 | 26611 | 26627 | 26674 | 26720 | 26722 | 26757 | 26762 |
| 26771 | 26779 | 26780 | 26788 | 26799 | 26805 | 26821 | 26829 | 26838 | 26849 | 26861 | 26882 |
| 26896 | 26897 | 26914 | 26917 | 26929 | 26934 | 26942 | 26943 | 26955 | 26959 | 26962 | 26966 |
| 26980 | 26981 | 27005 | 27006 | 27016 | 27027 | 27032 | 27033 | 27034 | 27036 | 27055 | 27057 |
| 27058 | 27061 | 27062 | 27064 | 27073 | 27075 | 27089 | 27092 | 27093 | 27095 | 27104 | 27120 |
| 27121 | 27125 | 27136 | 27143 | 27151 | 27154 | 27164 | 27174 | 27178 | 27181 | 27190 | 27206 |
| 27213 | 27226 | 27240 | 27244 | 27251 | 27252 | 27256 | 27259 | 27261 | 27272 | 27274 | 27293 |
| 27294 | 27300 | 27313 | 27335 | 27336 | 27337 | 27340 | 27363 | 27378 | 27387 | 27393 | 27394 |
| 27400 | 27403 | 27405 | 27406 | 27416 | 27419 | 27421 | 27425 | 27440 | 27454 | 27455 | 27477 |
| 27478 | 27488 | 27489 | 27494 | 27509 | 27516 | 27528 | 27534 | 27557 | 27570 | 27579 | 27590 |
| 27591 | 27596 | 27609 | 27613 | 27620 | 27622 | 27625 | 27628 | 27629 | 27631 | 27637 | 27646 |
| 27648 | 27650 | 27652 | 27662 | 27676 | 27694 | 27712 | 27713 | 27723 | 27726 | 27740 | 27742 |
| 27745 | 27749 | 27754 | 27757 | 27760 | 27774 | 27776 | 27777 | 27778 | 27789 | 27807 | 27819 |

TABLE 6-continued

Plant Growth/Cell Cycle

| | | | | | | | | | | | |
|---|---|---|---|---|---|---|---|---|---|---|---|
| 27835 | 27838 | 27842 | 27843 | 27857 | 27861 | 27880 | 27882 | 27884 | 27886 | 27895 | 27909 |
| 27926 | 27948 | 28001 | 28034 | 28050 | 28058 | 28072 | 28076 | 28095 | 28103 | 28122 | 28196 |
| 28198 | 28212 | 28235 | 28321 | 28323 | 28345 | 28353 | 28379 | 28390 | 28422 | 28423 | 28460 |
| 28500 | 28537 | 28546 | 28607 | 28621 | 28634 | 28654 | 28664 | 28667 | 28675 | 28679 | 28682 |
| 28689 | 28701 | 28705 | 28717 | 28740 | 28781 | 28788 | 28789 | 28796 | 28797 | 28800 | 28815 |
| 28816 | 28824 | 28825 | 28828 | 28843 | 28846 | 28849 | 28850 | 28859 | 28860 | 28861 | 28862 |
| 28873 | 28877 | 28878 | 28879 | 28894 | 28914 | 28921 | 28922 | 28923 | 28924 | 28958 | 28983 |
| 28984 | 28992 | 28994 | 28995 | 29028 | 29029 | 29044 | 29053 | 29055 | 29059 | 29075 | 29087 |
| 29100 | 29101 | 29107 | 29134 | 29142 | 29146 | 29147 | 29165 | 29169 | 29192 | 29193 | 29201 |
| 29204 | 29206 | 29213 | 29239 | 29245 | 29253 | 29258 | 29288 | 29294 | 29296 | 29307 | 29326 |
| 29330 | 29340 | 29350 | 29358 | 29359 | 29367 | 29377 | 29379 | 29383 | 29384 | 29392 | 29406 |
| 29408 | 29420 | 29426 | 29430 | 29433 | 29456 | 29468 | 29478 | 29484 | 29509 | 29525 | 29526 |
| 29527 | 29535 | 29536 | 29540 | 29541 | 29542 | 29561 | 29562 | 29564 | 29568 | 29574 | 29577 |
| 29581 | 29582 | 29588 | 29589 | 29591 | 29607 | 29616 | 29617 | 29627 | 29636 | 29642 | 29651 |
| 29659 | 29660 | 29662 | 29664 | 29666 | 29677 | 29707 | 29713 | 29714 | 29750 | 29751 | 29754 |
| 29761 | 29779 | 29793 | 29804 | 29805 | 29806 | 29830 | 29837 | 29843 | 29844 | 29848 | 29874 |
| 29875 | 29876 | 29881 | 29887 | 29888 | 29896 | 29897 | 29924 | 29933 | 29934 | 29935 | 29957 |
| 29976 | 29985 | 29991 | 30015 | 30017 | 30030 | 30033 | 30049 | 30051 | 30063 | 30077 | 30082 |
| 30084 | 30119 | 30127 | 30136 | 30140 | 30147 | 30166 | 30167 | 30168 | 30188 | 30203 | 30214 |
| 30251 | 30260 | 30273 | 30284 | 30291 | 30299 | 30308 | 30312 | 30318 | 30325 | 30326 | 30352 |
| 30363 | 30411 | 30414 | 30416 | 30438 | 30457 | 30461 | 30508 | 30519 | 30521 | 30527 | 30528 |
| 30531 | 30575 | 30609 | 30611 | 30612 | 30613 | 30615 | 30616 | 30629 | 30630 | 30650 | 30651 |
| 30660 | 30661 | 30662 | 30682 | 30685 | 30703 | 30704 | 30714 | 30716 | 30717 | 30757 | 30789 |
| 30804 | 30812 | 30827 | 30831 | 30851 | 30859 | 30881 | 30954 | 30956 | 30971 | 31009 | 31076 |
| 31079 | 31081 | 31103 | 31104 | 31148 | 31182 | 31220 | 31259 | 31296 | 31305 | 31365 | 31379 |
| 31392 | 31412 | 31438 | 31452 | 31484 | 31487 | 31511 | 31539 | 31574 | 31618 | 31638 | 31651 |
| 31716 | 31754 | 31761 | 31802 | 31806 | 31818 | 31886 | 31902 | 31915 | 31920 | 31946 | 31954 |
| 31965 | 31973 | 32145 | 32154 | 32161 | 32180 | 32337 | 32365 | 32372 | 32382 | 32389 | 32418 |
| 32460 | 32481 | 32491 | 32519 | 32534 | 32536 | 32538 | 32565 | 32567 | 32620 | 32648 | 32660 |
| 32661 | 32694 | 32702 | 32762 | 32763 | 32775 | 32790 | 32801 | 32828 | 32937 | 32952 | 32958 |
| 32969 | 32974 | 32984 | 32988 | 33063 | 33117 | 33163 | 33192 | 33211 | 33223 | 33228 | 33312 |
| 33333 | 33418 | 33457 | 33477 | 33526 | 33540 | 33563 | 33586 | 33654 | 33740 | 33787 | 33796 |
| 33798 | 33827 | 33841 | 33845 | 33936 | 33941 | 33946 | 33974 | 34008 | 34062 | 34082 | 34091 |
| 34101 | 34141 | 34159 | 34232 | 34249 | 34270 | 34308 | 34331 | 34333 | 34370 | 34371 | 34542 |
| 34565 | 34574 | 34577 | 34579 | 34588 | 34601 | 34604 | 34620 | 34641 | 34646 | 34674 | 34687 |
| 34690 | 34692 | 34710 | 34718 | 34731 | 34747 | 34758 | 34791 | 34792 | 34794 | 34795 | 34806 |
| 34835 | 34847 | 34851 | 34915 | 34923 | 34962 | 34964 | 34966 | 34978 | 34982 | 34989 | 34999 |
| 35017 | 35020 | 35022 | 35041 | 35066 | 35071 | 35098 | 35140 | 35149 | 35174 | 35192 | 35226 |
| 35252 | 35293 | 35310 | 35347 | 35350 | 35376 | 35387 | 35455 | 35485 | 35536 | 35547 | 35556 |
| 35574 | 35594 | 35638 | 35667 | 35675 | 35704 | 35727 | 35801 | 35815 | 35837 | 35879 | 35902 |
| 35936 | 36023 | 36052 | 36074 | 36098 | 36102 | 36111 | 36116 | 36129 | 36130 | 36151 | 36161 |
| 36199 | 36221 | 36232 | 36234 | 36242 | 36244 | 36247 | 36248 | 36251 | 36254 | 36258 | 36265 |
| 36268 | 36269 | 36271 | 36275 | 36278 | 36291 | 36296 | 36303 | 36333 | 36336 | 36338 | 36341 |
| 36347 | 36364 | 36372 | 36374 | 36392 | 36406 | 36411 | 36419 | 36427 | 36432 | 36439 | 36441 |
| 36442 | 36443 | 36462 | 36466 | 36472 | 36518 | 36526 | 36543 | 36549 | 36554 | 36572 | 36573 |
| 36575 | 36585 | 36602 | 36604 | 36618 | 36627 | 36632 | 36635 | 36638 | 36641 | 36642 | 36648 |
| 36652 | 36653 | 36659 | 36664 | 36679 | 36685 | 36692 | 36694 | 36753 | 36764 | 36769 | 36770 |
| 36771 | 36775 | 36780 | 36790 | 36801 | 36804 | 36805 | 36819 | 36820 | 36828 | 36846 | 36849 |
| 36865 | 36895 | 36910 | 36914 | 36918 | 36925 | 36930 | 36935 | 36957 | 36960 | 36977 | 36987 |
| 36989 | 37002 | 37029 | 37050 | 37059 | 37061 | 37063 | 37070 | 37085 | 37086 | 37089 | 37091 |
| 37094 | 37099 | 37100 | 37101 | 37102 | 37132 | 37151 | 37169 | 37174 | 37176 | 37177 | 37182 |
| 37187 | 37191 | 37200 | 37225 | 37226 | 37230 | 37257 | 37259 | 37267 | 37268 | 37270 | 37277 |
| 37280 | 37293 | 37294 | 37296 | 37322 | 37327 | 37340 | 37370 | 37395 | 37413 | 37417 | 37424 |
| 37460 | 37463 | 37495 | 37527 | 37544 | 37606 | 37634 | 37642 | 37658 | 37672 | 37746 | 37771 |
| 37843 | 37941 | 37967 | 37970 | 37980 | 37996 | 38000 | 38002 | 38005 | 38074 | 38077 | 38115 |
| 38160 | 38161 | 38169 | 38219 | 38227 | 38239 | 38293 | 38348 | 38389 | 38415 | 38418 | 38429 |
| 38554 | 38694 | 38741 | 38766 | 38780 | 38790 | 38808 | 38825 | 38871 | 38895 | 38898 | 39164 |
| 39190 | 39199 | 39235 | 39246 | 39288 | 39322 | 39495 | 39534 | 39562 | 39571 | 39607 | 39608 |
| 39619 | 39657 | 39697 | 39709 | 39727 | 39731 | 39876 | 39913 | 39937 | 39944 | 39974 | 39976 |
| 39986 | 40051 | 40069 | 40118 | 40191 | 40195 | 40211 | 40230 | 40232 | 40269 | 40325 | 40334 |
| 40379 | 40420 | 40474 | 40524 | 40627 | 40671 | 40694 | 40735 | 40760 | 40778 | 40794 | 40795 |
| 40842 | 40876 | 40879 | 40913 | 40918 | 40958 | 40971 | 41035 | 41085 | 41090 | 41092 | 41115 |
| 41163 | 41166 | 41169 | 41186 | 41190 | 41211 | 41224 | 41332 | 41363 | 41391 | 41483 | 41496 |
| 41532 | 41658 | 41692 | 41700 | 41744 | 41747 | 41796 | 41803 | 41824 | 41855 | 41863 | 41863 |
| 41871 | 41877 | 41879 | 41882 | 41885 | 41898 | 41902 | 41903 | 41905 | 41912 | 41916 | 41931 |
| 41940 | 41943 | 41944 | 41945 | 41955 | 41971 | 41975 | 42037 | 42080 | 42111 | 42117 | 42137 |
| 42168 | 42224 | 42225 | 42229 | 42230 | 42231 | 42246 | 42253 | 42256 | 42266 | 42276 | 42281 |
| 42289 | 42299 | 42325 | 42332 | 42351 | 42357 | 42363 | 42364 | 42372 | 42373 | 42376 | |
| 42389 | 42442 | 42458 | 42462 | 42505 | 42510 | 42584 | 42619 | 42626 | 42681 | 42684 | 42720 |
| 42721 | 42731 | 42761 | 42813 | 42826 | 42833 | 42839 | 42853 | 42863 | 42905 | 42949 | 42997 |
| 43006 | 43017 | 43068 | 43102 | 43104 | 43120 | 43182 | 43209 | 43214 | 43235 | 43252 | 43263 |
| 43268 | 43303 | 43327 | 43342 | 43343 | 43377 | 43518 | 43546 | 43622 | 43626 | 43634 | |
| 43645 | 43659 | 43671 | 43680 | 43737 | 43789 | 43796 | 43828 | 43830 | 43872 | 43890 | 43943 |
| 43968 | 44000 | 44001 | 44003 | 44005 | 44025 | 44026 | 44032 | 44039 | 44040 | 44046 | 44058 |
| 44064 | 44070 | 44074 | 44137 | 44169 | 44173 | 44214 | 44234 | 44240 | 44241 | 44244 | 44268 |
| 44330 | 44393 | 44394 | 44408 | 44433 | 44474 | 44504 | 44513 | 44538 | 44597 | 44607 | 44633 |
| 44762 | 44764 | 44810 | 44817 | 44908 | 44934 | 44956 | 44991 | 45009 | 45035 | 45039 | 45046 |

TABLE 6-continued

Plant Growth/Cell Cycle

| | | | | | | | | | | | |
|---|---|---|---|---|---|---|---|---|---|---|---|
| 45075 | 45076 | 45094 | 45096 | 45101 | 45123 | 45124 | 45138 | 45139 | 45144 | 45156 | 45169 |
| 45177 | 45208 | 45209 | 45211 | 45225 | 45262 | 45267 | 45273 | 45281 | 45282 | 45293 | 45296 |
| 45308 | 45321 | 45322 | 45323 | 45350 | 45352 | 45353 | 45355 | 45382 | 45466 | 45500 | 45503 |
| 45504 | 45555 | 45561 | 45575 | 45577 | 45586 | 45589 | 45591 | 45594 | 45597 | 45610 | 45611 |
| 45614 | 45618 | 45627 | 45636 | 45642 | 45644 | 45651 | 45654 | 45657 | 45663 | 45664 | 45665 |
| 45668 | 45672 | 45676 | 45682 | 45684 | 45692 | 45712 | 45717 | 45729 | 45746 | 45755 | 45756 |
| 45760 | 45767 | 45771 | 45774 | 45779 | 45790 | 45791 | 45792 | 45795 | 45820 | 45829 | 45836 |
| 45837 | 45838 | 45840 | 45858 | 45860 | 45861 | 45866 | 45876 | 45886 | 45898 | 45908 | 45915 |
| 45922 | 45933 | 45934 | 45949 | 45959 | 45963 | 45972 | 45975 | 45979 | 45991 | 45998 | 45999 |
| 46004 | 46005 | 46006 | 46014 | 46025 | 46030 | 46036 | 46041 | 46043 | 46047 | 46051 | 46074 |
| 46108 | 46109 | 46110 | 46113 | 46114 | 46116 | 46117 | 46121 | 46122 | 46124 | 46126 | 46136 |
| 46140 | 46143 | 46144 | 46149 | 46175 | 46187 | 46189 | 46192 | 46198 | 46200 | 46207 | 46213 |
| 46217 | 46218 | 46235 | 46243 | 46246 | 46248 | 46249 | 46251 | 46265 | 46282 | 46291 | 46303 |
| 46305 | 46311 | 46312 | 46314 | 46328 | 46343 | 46356 | 46360 | 46361 | 46373 | 46382 | 46389 |
| 46390 | 46391 | 46399 | 46405 | 46412 | 46421 | 46428 | 46429 | 46432 | 46434 | 46458 | 46465 |
| 46471 | 46472 | 46489 | 46493 | 46498 | 46505 | 46507 | 46516 | 46519 | 46525 | 46528 | 46529 |
| 46547 | 46553 | 46556 | 46571 | 46579 | 46582 | 46616 | 46626 | 46629 | 46637 | 46647 | 46648 |
| 46661 | 46725 | 46726 | 46782 | 46785 | 46815 | 46821 | 46870 | 46872 | 46917 | 46927 | 46934 |
| 46936 | 46948 | 46963 | 46971 | 47037 | 47110 | 47122 | 47145 | 47160 | 47222 | 47230 | 47251 |
| 47293 | 47345 | 47367 | 47372 | | | | | | | | |

TABLE 7

Plant Growth/Growth Regulators

Table 7A SEQ ID NOs of Polypeptides useful for improving Plant Growth - Growth Regulators

| | | | | | | | | | | | |
|---|---|---|---|---|---|---|---|---|---|---|---|
| 13 | 35 | 55 | 61 | 63 | 65 | 135 | 173 | 183 | 201 | 211 | 251 |
| 305 | 349 | 372 | 383 | 417 | 420 | 440 | 448 | 467 | 480 | 481 | 483 |
| 496 | 504 | 518 | 529 | 547 | 565 | 586 | 588 | 598 | 610 | 619 | 622 |
| 704 | 711 | 731 | 732 | 737 | 773 | 802 | 816 | 863 | 877 | 892 | 941 |
| 953 | 1044 | 1091 | 1097 | 1101 | 1114 | 1127 | 1136 | 1215 | 1233 | 1240 | 1276 |
| 1280 | 1335 | 1427 | 1471 | 1484 | 1526 | 1607 | 1654 | 1660 | 1694 | 1859 | 1868 |
| 1923 | 1974 | 2050 | 2080 | 2134 | 2176 | 2346 | 2351 | 2378 | 2433 | 2495 | 2506 |
| 2526 | 2534 | 2586 | 2597 | 2607 | 2608 | 2618 | 2645 | 2652 | 2664 | 2716 | 2717 |
| 2724 | 2732 | 2740 | 2748 | 2753 | 2810 | 2817 | 2852 | 2898 | 2903 | 2908 | 2952 |
| 2985 | 3024 | 3025 | 3028 | 3043 | 3056 | 3058 | 3102 | 3116 | 3134 | 3153 | 3163 |
| 3239 | 3267 | 3281 | 3313 | 3373 | 3435 | 3475 | 3496 | 3504 | 3551 | 3576 | 3612 |
| 3617 | 3620 | 3649 | 3679 | 3842 | 3854 | 3885 | 3893 | 3921 | 3945 | 4024 |
| 4061 | 4124 | 4143 | 4150 | 4165 | 4221 | 4298 | 4387 | 4492 | 4494 | 4495 | 4498 |
| 4540 | 4615 | 4623 | 4627 | 4651 | 4669 | 4670 | 4682 | 4730 | 4779 | 4808 | 4825 |
| 4856 | 4876 | 4877 | 4891 | 4900 | 4906 | 4921 | 4932 | 4959 | 5040 | 5046 | 5048 |
| 5051 | 5055 | 5099 | 5111 | 5151 | 5246 | 5256 | 5335 | 5529 | 5530 | 5531 | 5532 |
| 5584 | 5648 | 5670 | 5732 | 5775 | 5952 | 6131 | 6175 | 6301 | 6324 | 6331 | 6513 |
| 6538 | 6539 | 6568 | 6584 | 6678 | 6679 | 6787 | 6869 | 6932 | 6966 | 6967 | 6968 |
| 7054 | 7142 | 7178 | 7251 | 7253 | 7254 | 7257 | 7298 | 7372 | 7381 | 7385 | 7409 |
| 7428 | 7429 | 7441 | 7489 | 7490 | 7539 | 7567 | 7584 | 7615 | 7636 | 7649 | 7658 |
| 7664 | 7679 | 7690 | 7717 | 7730 | 7736 | 7744 | 7748 | 7761 | 7804 | 7818 | 7828 |
| 7851 | 7857 | 7858 | 7893 | 7894 | 7907 | 7945 | 7961 | 7990 | 8043 | 8070 | 8090 |
| 8106 | 8172 | 8173 | 8178 | 8190 | 8225 | 8227 | 8293 | 8348 | 8360 | 8419 | 8421 |
| 8472 | 8506 | 8507 | 8550 | 8630 | 8669 | 8682 | 8687 | 8689 | 8690 | 8772 | 8778 |
| 8893 | 8930 | 8946 | 8955 | 8957 | 8962 | 8982 | 9003 | 9033 | 9077 | 9079 | 9085 |
| 9143 | 9151 | 9172 | 9178 | 9184 | 9188 | 9211 | 9272 | 9290 | 9299 | 9300 | 9307 |
| 9343 | 9356 | 9359 | 9367 | 9375 | 9429 | 9451 | 9452 | 9503 | 9509 | 9513 | 9546 |
| 9550 | 9571 | 9596 | 9617 | 9622 | 9630 | 9660 | 9686 | 9695 | 9710 | 9711 | 9749 |
| 9769 | 9782 | 9867 | 9897 | 9924 | 9932 | 9935 | 9940 | 9952 | 9956 | 9962 | 9972 |
| 9973 | 9978 | 9979 | 9992 | 10000 | 10008 | 10012 | 10013 | 10025 | 10028 | 10030 | 10036 |
| 10046 | 10047 | 10048 | 10056 | 10057 | 10062 | 10068 | 10071 | 10074 | 10076 | 10077 | 10081 |
| 10082 | 10085 | 10087 | 10088 | 10093 | 10094 | 10095 | 10096 | 10101 | 10123 | 10124 | 10127 |
| 10128 | 10129 | 10137 | 10138 | 10146 | 10152 | 10166 | 10176 | 10177 | 10180 | 10186 | 10187 |
| 10188 | 10202 | 10219 | 10247 | 10269 | 10280 | 10292 | 10298 | 10308 | 10316 | 10317 | 10332 |
| 10341 | 10353 | 10362 | 10363 | 10366 | 10367 | 10377 | 10452 | 10464 | 10518 | 10554 | 10577 |
| 10617 | 10625 | 10637 | 10645 | 10724 | 10795 | 10806 | 10848 | 10875 | 10894 | 10961 | 10973 |
| 10983 | 11057 | 11136 | 11143 | 11175 | 11231 | 11233 | 11235 | 11239 | 11276 | 11280 | 11355 |
| 11356 | 11359 | 11370 | 11390 | 11397 | 11418 | 11449 | 11544 | 11547 | 11549 | 11573 | 11580 |
| 11581 | 11611 | 11622 | 11753 | 11763 | 11764 | 11779 | 11785 | 11799 | 11811 | 11816 | 11896 |
| 11938 | 11968 | 11989 | 12009 | 12016 | 12134 | 12139 | 12164 | 12184 | 12185 | 12201 | 12202 |
| 12231 | 12239 | 12283 | 12284 | 12290 | 12405 | 12421 | 12466 | 12476 | 12523 | 12549 | 12559 |
| 12595 | 12606 | 12622 | 12625 | 12641 | 12663 | 12680 | 12714 | 12748 | 12759 | 12785 | 12796 |
| 12799 | 12809 | 12853 | 12858 | 12865 | 12900 | 12905 | 12919 | 12970 | 12974 | 12982 | 12988 |
| 12991 | 13034 | 13046 | 13061 | 13096 | 13125 | 13153 | 13181 | 13272 | 13305 | 13332 | 13363 |
| 13385 | 13388 | 13417 | 13448 | 13481 | 13578 | 13616 | 13649 | 13681 | 13725 | 13756 | 13766 |
| 13771 | 13803 | 13814 | 13816 | 13823 | 13854 | 13879 | 13882 | 13940 | 13944 | 13946 | 13965 |

TABLE 7-continued

Plant Growth/Growth Regulators

| | | | | | | | | | | | |
|---|---|---|---|---|---|---|---|---|---|---|---|
| 13986 | 13998 | 13999 | 14003 | 14013 | 14020 | 14043 | 14112 | 14114 | 14148 | 14169 | 14191 |
| 14198 | 14237 | 14281 | 14306 | 14362 | 14369 | 14373 | 14376 | 14380 | 14419 | 14435 | 14451 |
| 14493 | 14539 | 14546 | 14569 | 14582 | 14583 | 14591 | 14620 | 14669 | 14670 | 14672 | 14759 |
| 14768 | 14775 | 14816 | 14829 | 14853 | 14862 | 14881 | 14886 | 14897 | 14916 | 14921 | 14928 |
| 14957 | 15003 | 15011 | 15034 | 15067 | 15078 | 15108 | 15149 | 15150 | 15245 | 15248 | 15249 |
| 15250 | 15251 | 15252 | 15253 | 15254 | 15255 | 15262 | 15266 | 15267 | 15274 | 15277 | 15278 |
| 15279 | 15280 | 15281 | 15282 | 15284 | 15292 | 15298 | 15304 | 15324 | 15331 | 15333 | 15351 |
| 15354 | 15355 | 15396 | 15432 | 15440 | 15449 | 15476 | 15489 | 15537 | 15540 | 15568 | 15594 |
| 15619 | 15628 | 15637 | 15657 | 15662 | 15664 | 15670 | 15690 | 15698 | 15700 | 15718 | 15721 |
| 15722 | 15764 | 15809 | 15817 | 15846 | 15861 | 15872 | 15908 | 15911 | 15941 | 15971 | 15994 |
| 16003 | 16012 | 16053 | 16054 | 16060 | 16082 | 16089 | 16091 | 16105 | 16107 | 16138 | 16148 |
| 16191 | 16200 | 16225 | 16240 | 16247 | 16279 | 16281 | 16307 | 16358 | 16365 | 16393 | 16461 |
| 16496 | 16509 | 16523 | 16526 | 16541 | 16548 | 16549 | 16573 | 16584 | 16604 | 16652 | 16665 |
| 16697 | 16723 | 16739 | 16750 | 16768 | 16773 | 16800 | 16822 | 16831 | 16836 | 16839 | 16874 |
| 16925 | 16937 | 16942 | 16943 | 16948 | 16960 | 16994 | 17001 | 17004 | 17008 | 17025 | 17038 |
| 17041 | 17076 | 17084 | 17087 | 17097 | 17099 | 17191 | 17202 | 17210 | 17227 | 17236 | 17275 |
| 17308 | 17313 | 17334 | 17346 | 17357 | 17358 | 17379 | 17450 | 17478 | 17501 | 17502 | 17504 |
| 17527 | 17561 | 17589 | 17621 | 17644 | 17734 | 17751 | 17755 | 17829 | 17842 | 17871 | 17895 |
| 17925 | 17939 | 17944 | 17957 | 18000 | 18010 | 18021 | 18022 | 18029 | 18033 | 18040 | 18044 |
| 18090 | 18132 | 18150 | 18207 | 18261 | 18289 | 18306 | 18326 | 18335 | 18347 | 18391 | 18404 |
| 18434 | 18440 | 18445 | 18463 | 18467 | 18468 | 18472 | 18556 | 18567 | 18606 | 18651 | 18674 |
| 18727 | 18750 | 18752 | 18753 | 18757 | 18784 | 18787 | 18799 | 18803 | 18833 | 18843 | 18849 |
| 18853 | 18860 | 18875 | 18894 | 18911 | 18920 | 18923 | 18931 | 18947 | 18949 | 19001 | 19003 |
| 19006 | 19027 | 19041 | 19058 | 19068 | 19095 | 19096 | 19188 | 19189 | 19190 | 19191 | 19194 |
| 19206 | 19227 | 19306 | 19313 | 19329 | 19356 | 19399 | 19468 | 19471 | 19520 | 19552 | 19561 |
| 19586 | 19588 | 19643 | 19661 | 19670 | 19675 | 19687 | 19696 | 19717 | 19761 | 19798 | 19827 |
| 19835 | 19836 | 19837 | 19843 | 19851 | 19864 | 19883 | 19886 | 19922 | 19926 | 19933 | 19934 |
| 19952 | 19976 | 19987 | 19991 | 20004 | 20015 | 20017 | 20023 | 20029 | 20052 | 20076 | 20094 |
| 20098 | 20142 | 20145 | 20168 | 20176 | 20179 | 20188 | 20196 | 20206 | 20209 | 20212 | 20255 |
| 20265 | 20283 | 20290 | 20342 | 20346 | 20399 | 20441 | 20483 | 20510 | 20569 | 20579 | 20595 |
| 20596 | 20601 | 20620 | 20686 | 20697 | 20734 | 20763 | 20788 | 20796 | 20832 | 20853 | 20893 |
| 20900 | 20918 | 20926 | 20928 | 20939 | 20944 | 20945 | 20973 | 21022 | 21033 | 21056 | 21079 |
| 21083 | 21089 | 21105 | 21137 | 21173 | 21174 | 21195 | 21197 | 21211 | 21225 | 21264 | 21289 |
| 21319 | 21366 | 21419 | 21422 | 21459 | 21484 | 21492 | 21512 | 21529 | 21542 | 21562 | 21615 |
| 21633 | 21696 | 21719 | 21725 | 21759 | 21768 | 21770 | 21782 | 21805 | 21821 | 21913 | 21917 |
| 21934 | 21997 | 22041 | 22060 | 22137 | 22145 | 22203 | 22271 | 22280 | 22362 | 22390 | 22473 |
| 22474 | 22475 | 22476 | 22477 | 22478 | 22479 | 22480 | 22481 | 22482 | 22483 | 22484 | 22485 |
| 22486 | 22487 | 22488 | 22489 | 22494 | 22524 | 22558 | 22566 | 22567 | 22572 | 22598 | 22680 |
| 22687 | 22691 | 22711 | 22716 | 22757 | 22794 | 22798 | 22815 | 22920 | 22977 | 22984 | 23025 |
| 23046 | 23048 | 23090 | 23096 | 23108 | 23114 | 23149 | 23153 | 23168 | 23180 | 23200 | 23201 |
| 23205 | 23216 | 23279 | 23325 | 23364 | 23369 | 23381 | 23414 | 23494 | 23506 | 23528 | 23540 |
| 23548 | 23568 | 23618 | 23629 | 23655 | | | | | | | |

Table 7B SEQ ID NOs of Polynucleotides useful for improving Plant Growth - Growth Regulators

| | | | | | | | | | | | |
|---|---|---|---|---|---|---|---|---|---|---|---|
| 23700 | 23722 | 23742 | 23748 | 23750 | 23752 | 23822 | 23860 | 23870 | 23888 | 23898 | 23938 |
| 23992 | 24036 | 24059 | 24070 | 24104 | 24107 | 24127 | 24135 | 24154 | 24167 | 24168 | 24170 |
| 24183 | 24191 | 24205 | 24216 | 24234 | 24252 | 24273 | 24275 | 24285 | 24297 | 24306 | 24309 |
| 24391 | 24398 | 24418 | 24419 | 24424 | 24460 | 24489 | 24503 | 24550 | 24564 | 24579 | 24628 |
| 24640 | 24731 | 24778 | 24784 | 24788 | 24801 | 24814 | 24823 | 24902 | 24920 | 24927 | 24963 |
| 24967 | 25022 | 25114 | 25158 | 25171 | 25213 | 25294 | 25341 | 25347 | 25381 | 25546 | 25555 |
| 25610 | 25661 | 25737 | 25767 | 25821 | 25863 | 26033 | 26038 | 26065 | 26120 | 26182 | 26193 |
| 26213 | 26221 | 26273 | 26284 | 26294 | 26295 | 26305 | 26332 | 26347 | 26351 | 26403 | 26404 |
| 26411 | 26419 | 26427 | 26435 | 26440 | 26497 | 26504 | 26539 | 26585 | 26590 | 26595 | 26639 |
| 26672 | 26711 | 26712 | 26715 | 26730 | 26743 | 26745 | 26789 | 26803 | 26821 | 26840 | 26850 |
| 26926 | 26954 | 26968 | 27000 | 27060 | 27122 | 27162 | 27183 | 27191 | 27238 | 27263 | 27299 |
| 27304 | 27307 | 27336 | 27366 | 27529 | 27541 | 27572 | 27580 | 27587 | 27608 | 27632 | 27711 |
| 27748 | 27811 | 27830 | 27837 | 27852 | 27908 | 27985 | 28074 | 28179 | 28181 | 28182 | 28185 |
| 28227 | 28302 | 28310 | 28314 | 28338 | 28356 | 28357 | 28369 | 28417 | 28466 | 28495 | 28512 |
| 28543 | 28563 | 28564 | 28578 | 28587 | 28593 | 28608 | 28619 | 28646 | 28727 | 28733 | 28735 |
| 28738 | 28742 | 28786 | 28798 | 28838 | 28933 | 28943 | 29022 | 29216 | 29217 | 29218 | 29219 |
| 29271 | 29335 | 29357 | 29419 | 29462 | 29639 | 29818 | 29862 | 29988 | 30011 | 30018 | 30200 |
| 30225 | 30226 | 30255 | 30271 | 30365 | 30366 | 30474 | 30506 | 30519 | 30653 | 30654 | 30655 |
| 30741 | 30829 | 30865 | 30938 | 30940 | 30941 | 30944 | 30985 | 31059 | 31068 | 31072 | 31096 |
| 31115 | 31116 | 31128 | 31176 | 31177 | 31226 | 31254 | 31271 | 31302 | 31323 | 31336 | 31345 |
| 31351 | 31366 | 31377 | 31404 | 31417 | 31423 | 31431 | 31435 | 31448 | 31491 | 31505 | 31515 |
| 31538 | 31544 | 31545 | 31580 | 31581 | 31594 | 31632 | 31648 | 31677 | 31730 | 31757 | 31777 |
| 31793 | 31859 | 31860 | 31865 | 31877 | 31912 | 31914 | 31980 | 32035 | 32047 | 32106 | 32108 |
| 32159 | 32193 | 32194 | 32237 | 32317 | 32356 | 32369 | 32374 | 32376 | 32377 | 32459 | 32465 |
| 32580 | 32617 | 32633 | 32642 | 32644 | 32649 | 32669 | 32690 | 32720 | 32764 | 32766 | 32772 |
| 32830 | 32838 | 32859 | 32865 | 32871 | 32875 | 32898 | 32959 | 32986 | 32987 | 32994 |
| 33030 | 33043 | 33046 | 33054 | 33062 | 33116 | 33138 | 33139 | 33190 | 33196 | 33200 | 33233 |
| 33237 | 33258 | 33283 | 33304 | 33309 | 33317 | 33347 | 33373 | 33382 | 33397 | 33398 | 33436 |
| 33456 | 33469 | 33554 | 33584 | 33611 | 33619 | 33622 | 33627 | 33639 | 33643 | 33649 | 33659 |
| 33660 | 33665 | 33666 | 33679 | 33687 | 33695 | 33699 | 33700 | 33712 | 33715 | 33717 | 33723 |
| 33733 | 33734 | 33735 | 33743 | 33744 | 33749 | 33755 | 33758 | 33761 | 33763 | 33764 | 33768 |

TABLE 7-continued

Plant Growth/Growth Regulators

| | | | | | | | | | | | |
|---|---|---|---|---|---|---|---|---|---|---|---|
| 33769 | 33772 | 33774 | 33775 | 33780 | 33781 | 33782 | 33783 | 33788 | 33810 | 33811 | 33814 |
| 33815 | 33816 | 33824 | 33825 | 33833 | 33839 | 33853 | 33863 | 33864 | 33867 | 33873 | 33874 |
| 33875 | 33889 | 33906 | 33934 | 33956 | 33967 | 33979 | 33985 | 33995 | 34003 | 34004 | 34019 |
| 34028 | 34040 | 34049 | 34050 | 34053 | 34054 | 34064 | 34139 | 34151 | 34205 | 34241 | 34264 |
| 34304 | 34312 | 34324 | 34332 | 34411 | 34482 | 34493 | 34535 | 34562 | 34581 | 34648 | 34660 |
| 34670 | 34744 | 34823 | 34830 | 34862 | 34918 | 34920 | 34922 | 34926 | 34963 | 34967 | 35042 |
| 35043 | 35046 | 35057 | 35077 | 35084 | 35105 | 35136 | 35231 | 35234 | 35236 | 35260 | 35267 |
| 35268 | 35298 | 35309 | 35440 | 35450 | 35451 | 35466 | 35472 | 35486 | 35498 | 35503 | 35583 |
| 35625 | 35655 | 35676 | 35696 | 35703 | 35821 | 35826 | 35851 | 35871 | 35872 | 35888 | 35889 |
| 35918 | 35926 | 35970 | 35971 | 35977 | 36092 | 36108 | 36153 | 36163 | 36210 | 36236 | 36246 |
| 36282 | 36293 | 36309 | 36312 | 36328 | 36350 | 36367 | 36401 | 36435 | 36446 | 36472 | 36483 |
| 36486 | 36496 | 36540 | 36545 | 36552 | 36587 | 36592 | 36606 | 36657 | 36661 | 36669 | 36675 |
| 36678 | 36721 | 36733 | 36748 | 36783 | 36812 | 36840 | 36868 | 36959 | 36992 | 37019 | 37050 |
| 37072 | 37075 | 37104 | 37135 | 37168 | 37265 | 37303 | 37336 | 37368 | 37412 | 37443 | 37453 |
| 37458 | 37490 | 37501 | 37503 | 37510 | 37541 | 37566 | 37569 | 37627 | 37631 | 37633 | 37652 |
| 37673 | 37685 | 37686 | 37690 | 37700 | 37707 | 37730 | 37799 | 37801 | 37835 | 37856 | 37878 |
| 37885 | 37924 | 37968 | 37993 | 38049 | 38056 | 38060 | 38063 | 38067 | 38106 | 38122 | 38138 |
| 38180 | 38226 | 38233 | 38256 | 38269 | 38270 | 38278 | 38307 | 38356 | 38357 | 38359 | 38446 |
| 38455 | 38462 | 38503 | 38516 | 38540 | 38549 | 38568 | 38573 | 38584 | 38603 | 38608 | 38615 |
| 38644 | 38690 | 38698 | 38721 | 38754 | 38765 | 38795 | 38836 | 38837 | 38932 | 38935 | 38936 |
| 38937 | 38938 | 38939 | 38940 | 38941 | 38942 | 38949 | 38953 | 38954 | 38961 | 38964 | 38965 |
| 38966 | 38967 | 38968 | 38969 | 38971 | 38979 | 38985 | 38991 | 39011 | 39018 | 39020 | 39038 |
| 39041 | 39042 | 39083 | 39119 | 39127 | 39136 | 39163 | 39176 | 39224 | 39227 | 39255 | 39281 |
| 39306 | 39315 | 39324 | 39344 | 39349 | 39351 | 39357 | 39377 | 39385 | 39387 | 39405 | 39408 |
| 39409 | 39451 | 39496 | 39504 | 39533 | 39548 | 39559 | 39595 | 39598 | 39628 | 39658 | 39681 |
| 39690 | 39699 | 39740 | 39741 | 39747 | 39769 | 39776 | 39778 | 39792 | 39794 | 39825 | 39835 |
| 39878 | 39887 | 39912 | 39927 | 39934 | 39966 | 39968 | 39994 | 40045 | 40052 | 40080 | 40148 |
| 40183 | 40196 | 40210 | 40213 | 40228 | 40235 | 40236 | 40260 | 40271 | 40291 | 40339 | 40352 |
| 40384 | 40410 | 40426 | 40437 | 40455 | 40460 | 40487 | 40509 | 40518 | 40523 | 40526 | 40561 |
| 40612 | 40624 | 40629 | 40630 | 40635 | 40647 | 40681 | 40688 | 40691 | 40695 | 40712 | 40725 |
| 40728 | 40763 | 40771 | 40774 | 40784 | 40786 | 40878 | 40889 | 40897 | 40914 | 40923 | 40962 |
| 40995 | 41000 | 41021 | 41033 | 41044 | 41045 | 41066 | 41137 | 41165 | 41188 | 41189 | 41191 |
| 41214 | 41248 | 41276 | 41308 | 41331 | 41421 | 41438 | 41442 | 41516 | 41529 | 41558 | 41582 |
| 41612 | 41626 | 41631 | 41644 | 41687 | 41697 | 41708 | 41709 | 41716 | 41720 | 41727 | 41731 |
| 41777 | 41819 | 41837 | 41894 | 41948 | 41976 | 41993 | 42013 | 42022 | 42034 | 42078 | 42091 |
| 42121 | 42127 | 42132 | 42150 | 42154 | 42155 | 42159 | 42243 | 42254 | 42293 | 42338 | 42361 |
| 42414 | 42437 | 42439 | 42440 | 42444 | 42471 | 42474 | 42486 | 42490 | 42520 | 42530 | 42536 |
| 42540 | 42547 | 42562 | 42581 | 42598 | 42607 | 42610 | 42618 | 42634 | 42636 | 42688 | 42690 |
| 42693 | 42714 | 42728 | 42745 | 42755 | 42782 | 42783 | 42875 | 42877 | 42878 | 42881 | |
| 42893 | 42914 | 42993 | 43000 | 43016 | 43043 | 43086 | 43155 | 43158 | 43207 | 43239 | 43248 |
| 43273 | 43275 | 43330 | 43348 | 43357 | 43362 | 43374 | 43383 | 43404 | 43448 | 43485 | 43514 |
| 43522 | 43523 | 43524 | 43530 | 43538 | 43551 | 43570 | 43573 | 43609 | 43613 | 43620 | 43621 |
| 43639 | 43663 | 43674 | 43678 | 43691 | 43702 | 43704 | 43710 | 43716 | 43739 | 43763 | 43781 |
| 43785 | 43829 | 43832 | 43855 | 43863 | 43866 | 43875 | 43883 | 43893 | 43896 | 43899 | 43942 |
| 43952 | 43970 | 43977 | 44029 | 44033 | 44086 | 44128 | 44170 | 44197 | 44256 | 44266 | 44282 |
| 44283 | 44288 | 44307 | 44373 | 44384 | 44421 | 44450 | 44475 | 44483 | 44519 | 44540 | 44580 |
| 44587 | 44605 | 44613 | 44615 | 44626 | 44631 | 44632 | 44660 | 44709 | 44720 | 44743 | 44766 |
| 44770 | 44776 | 44792 | 44824 | 44860 | 44861 | 44882 | 44884 | 44898 | 44912 | 44951 | 44976 |
| 45006 | 45053 | 45106 | 45109 | 45146 | 45171 | 45179 | 45199 | 45216 | 45229 | 45249 | 45302 |
| 45320 | 45383 | 45406 | 45412 | 45446 | 45455 | 45457 | 45469 | 45492 | 45508 | 45600 | 45604 |
| 45621 | 45684 | 45728 | 45747 | 45824 | 45832 | 45890 | 45958 | 45967 | 46049 | 46077 | 46160 |
| 46161 | 46162 | 46163 | 46164 | 46165 | 46166 | 46167 | 46168 | 46169 | 46170 | 46171 | 46172 |
| 46173 | 46174 | 46175 | 46176 | 46181 | 46211 | 46245 | 46253 | 46254 | 46259 | 46285 | 46367 |
| 46374 | 46378 | 46398 | 46403 | 46444 | 46481 | 46485 | 46502 | 46607 | 46664 | 46671 | 46712 |
| 46733 | 46735 | 46777 | 46783 | 46795 | 46801 | 46836 | 46840 | 46855 | 46867 | 46887 | 46888 |
| 46892 | 46903 | 46966 | 47012 | 47051 | 47056 | 47068 | 47101 | 47181 | 47193 | 47215 | 47227 |
| 47235 | 47255 | 47305 | 47316 | 47342 | | | | | | | |

TABLE 8

Heat Tolerance

Table 8A SEQ ID NOs of Polypeptides useful for improving Heat Tolerance

| | | | | | | | | | | | |
|---|---|---|---|---|---|---|---|---|---|---|---|
| 20 | 31 | 47 | 72 | 73 | 98 | 122 | 126 | 134 | 166 | 181 | 189 |
| 205 | 244 | 268 | 280 | 298 | 311 | 351 | 356 | 365 | 373 | 386 | 387 |
| 390 | 414 | 421 | 449 | 459 | 477 | 513 | 558 | 562 | 566 | 591 | 636 |
| 645 | 682 | 688 | 689 | 733 | 734 | 738 | 750 | 752 | 777 | 790 | 822 |
| 835 | 839 | 874 | 923 | 931 | 989 | 993 | 1132 | 1155 | 1211 | 1212 | 1394 |
| 1409 | 1423 | 1434 | 1439 | 1440 | 1445 | 1463 | 1474 | 1476 | 1479 | 1522 | 1544 |
| 1568 | 1589 | 1591 | 1597 | 1609 | 1624 | 1625 | 1632 | 1641 | 1649 | 1665 | 1673 |
| 1716 | 1728 | 1760 | 1768 | 1798 | 1821 | 1838 | 1839 | 1847 | 1883 | 1899 | 1904 |
| 1907 | 1917 | 1920 | 1943 | 1956 | 1971 | 1975 | 1998 | 2001 | 2018 | 2047 | 2053 |
| 2079 | 2119 | 2121 | 2130 | 2157 | 2158 | 2171 | 2202 | 2205 | 2208 | 2211 | 2213 |

TABLE 8-continued

Heat Tolerance

| | | | | | | | | | | | |
|---|---|---|---|---|---|---|---|---|---|---|---|
| 2245 | 2268 | 2270 | 2304 | 2311 | 2359 | 2397 | 2419 | 2420 | 2453 | 2524 | 2536 |
| 2546 | 2551 | 2574 | 2639 | 2642 | 2647 | 2648 | 2738 | 2745 | 2751 | 2752 | 2762 |
| 2766 | 2769 | 2779 | 2791 | 2799 | 2805 | 2834 | 2856 | 2878 | 2894 | 2902 | 2916 |
| 2937 | 2945 | 2949 | 2950 | 2968 | 2975 | 2984 | 3026 | 3031 | 3050 | 3087 | 3103 |
| 3120 | 3130 | 3133 | 3191 | 3198 | 3203 | 3206 | 3232 | 3236 | 3249 | 3292 | 3299 |
| 3305 | 3345 | 3357 | 3376 | 3462 | 3465 | 3478 | 3487 | 3491 | 3505 | 3526 | 3527 |
| 3561 | 3571 | 3588 | 3592 | 3603 | 3615 | 3629 | 3698 | 3724 | 3762 | 3788 | 3834 |
| 3835 | 3847 | 3853 | 3871 | 3950 | 3990 | 4019 | 4056 | 4083 | 4086 | 4100 | 4116 |
| 4137 | 4144 | 4146 | 4198 | 4216 | 4227 | 4236 | 4259 | 4284 | 4291 | 4314 | 4337 |
| 4361 | 4363 | 4369 | 4375 | 4413 | 4424 | 4438 | 4455 | 4506 | 4510 | 4573 | 4574 |
| 4593 | 4618 | 4644 | 4663 | 4689 | 4694 | 4706 | 4720 | 4727 | 4781 | 4806 | 4844 |
| 4960 | 4968 | 4970 | 4988 | 4992 | 4994 | 5003 | 5023 | 5027 | 5068 | 5090 | 5104 |
| 5184 | 5225 | 5268 | 5298 | 5330 | 5334 | 5338 | 5339 | 5363 | 5378 | 5415 | 5448 |
| 5491 | 5533 | 5534 | 5540 | 5544 | 5548 | 5552 | 5576 | 5592 | 5593 | 5609 | 5644 |
| 5693 | 5743 | 5745 | 5773 | 5777 | 5780 | 5791 | 5796 | 5798 | 5858 | 5862 | 5863 |
| 5901 | 5902 | 5904 | 5915 | 5916 | 5922 | 5975 | 5990 | 5993 | 6014 | 6018 | 6026 |
| 6027 | 6042 | 6057 | 6062 | 6081 | 6104 | 6107 | 6108 | 6133 | 6134 | 6143 | 6152 |
| 6163 | 6189 | 6210 | 6214 | 6233 | 6240 | 6241 | 6253 | 6272 | 6274 | 6309 | 6315 |
| 6316 | 6317 | 6318 | 6322 | 6325 | 6326 | 6348 | 6349 | 6350 | 6351 | 6352 | 6355 |
| 6356 | 6361 | 6365 | 6366 | 6367 | 6384 | 6388 | 6394 | 6397 | 6400 | 6413 | 6422 |
| 6423 | 6424 | 6425 | 6438 | 6471 | 6472 | 6473 | 6484 | 6485 | 6503 | 6578 | 6579 |
| 6587 | 6588 | 6589 | 6590 | 6591 | 6592 | 6597 | 6607 | 6617 | 6625 | 6636 | 6663 |
| 6664 | 6740 | 6749 | 6759 | 6766 | 6788 | 6790 | 6792 | 6796 | 6819 | 6829 | 6955 |
| 6978 | 6979 | 6983 | 6986 | 7031 | 7039 | 7047 | 7070 | 7092 | 7102 | 7115 | 7117 |
| 7123 | 7129 | 7169 | 7182 | 7197 | 7264 | 7268 | 7330 | 7331 | 7350 | 7375 | 7402 |
| 7422 | 7448 | 7465 | 7479 | 7486 | 7541 | 7565 | 7603 | 7718 | 7726 | 7776 | 7778 |
| 7784 | 7799 | 7831 | 7869 | 7908 | 7916 | 7917 | 7973 | 8000 | 8022 | 8041 | 8063 |
| 8064 | 8065 | 8094 | 8095 | 8096 | 8109 | 8114 | 8242 | 8260 | 8289 | 8309 | 8319 |
| 8321 | 8322 | 8434 | 8450 | 8487 | 8495 | 8498 | 8575 | 8579 | 8617 | 8654 | 8706 |
| 8792 | 8814 | 8874 | 8888 | 8902 | 8915 | 8926 | 8927 | 8932 | 9019 | 9038 | 9080 |
| 9112 | 9140 | 9156 | 9166 | 9196 | 9240 | 9269 | 9287 | 9305 | 9306 | 9313 | 9337 |
| 9347 | 9374 | 9378 | 9385 | 9439 | 9459 | 9467 | 9493 | 9496 | 9597 | 9606 | 9635 |
| 9641 | 9654 | 9656 | 9697 | 9759 | 9767 | 9794 | 9870 | 9898 | 9928 | 9938 | 9944 |
| 9961 | 9976 | 9982 | 9983 | 10014 | 10015 | 10058 | 10060 | 10066 | 10163 | 10170 | 10172 |
| 10244 | 10294 | 10295 | 10297 | 10300 | 10336 | 10368 | 10371 | 10380 | 10386 | 10398 | 10422 |
| 10492 | 10519 | 10534 | 10572 | 10603 | 10608 | 10623 | 10648 | 10649 | 10657 | 10673 | 10763 |
| 10798 | 10802 | 10814 | 10849 | 10862 | 10863 | 10870 | 10890 | 10928 | 11007 | 11087 | 11088 |
| 11099 | 11135 | 11178 | 11204 | 11232 | 11374 | 11393 | 11475 | 11478 | 11483 | 11504 | 11535 |
| 11550 | 11595 | 11598 | 11643 | 11704 | 11710 | 11759 | 11760 | 11797 | 11817 | 11834 | 11837 |
| 11838 | 11895 | 11908 | 11916 | 11917 | 11920 | 11921 | 11971 | 11982 | 12087 | 12088 | 12096 |
| 12106 | 12108 | 12170 | 12294 | 12302 | 12330 | 12331 | 12348 | 12349 | 12366 | 12426 | 12438 |
| 12482 | 12506 | 12517 | 12535 | 12536 | 12554 | 12592 | 12607 | 12614 | 12619 | 12640 | 12645 |
| 12665 | 12703 | 12704 | 12741 | 12788 | 12817 | 12830 | 12873 | 12911 | 12922 | 12968 | 12992 |
| 12995 | 12997 | 13007 | 13011 | 13097 | 13099 | 13185 | 13234 | 13279 | 13280 | 13281 | 13285 |
| 13292 | 13301 | 13393 | 13503 | 13532 | 13592 | 13603 | 13643 | 13657 | 13658 | 13666 | 13684 |
| 13718 | 13722 | 13736 | 13739 | 13744 | 13764 | 13817 | 13818 | 13867 | 14027 | 14055 | 14061 |
| 14063 | 14068 | 14074 | 14104 | 14113 | 14131 | 14157 | 14206 | 14213 | 14265 | 14304 | 14356 |
| 14436 | 14449 | 14459 | 14521 | 14535 | 14543 | 14565 | 14588 | 14613 | 14656 | 14769 | 14780 |
| 14882 | 14919 | 14934 | 14943 | 14980 | 14987 | 15051 | 15059 | 15087 | 15130 | 15163 | 15247 |
| 15263 | 15264 | 15265 | 15271 | 15310 | 15311 | 15312 | 15347 | 15374 | 15389 | 15468 | 15487 |
| 15488 | 15521 | 15524 | 15554 | 15561 | 15580 | 15597 | 15599 | 15604 | 15639 | 15645 | 15676 |
| 15677 | 15678 | 15714 | 15741 | 15757 | 15838 | 15859 | 15860 | 15892 | 15895 | 15927 | 15934 |
| 15956 | 15974 | 15976 | 15979 | 16014 | 16020 | 16067 | 16068 | 16126 | 16141 | 16217 | 16235 |
| 16265 | 16268 | 16293 | 16302 | 16319 | 16333 | 16336 | 16338 | 16343 | 16367 | 16372 | 16445 |
| 16515 | 16519 | 16530 | 16558 | 16571 | 16622 | 16635 | 16731 | 16749 | 16753 | 16754 | 16818 |
| 16825 | 16834 | 16865 | 16917 | 16934 | 16990 | 17101 | 17132 | 17172 | 17182 | 17184 | 17208 |
| 17209 | 17234 | 17272 | 17294 | 17305 | 17345 | 17352 | 17386 | 17392 | 17514 | 17524 | 17546 |
| 17551 | 17569 | 17593 | 17615 | 17643 | 17660 | 17710 | 17725 | 17733 | 17803 | 17826 | 17841 |
| 17874 | 17875 | 17907 | 17908 | 17910 | 17945 | 17958 | 17967 | 17978 | 18017 | 18050 | 18239 |
| 18240 | 18241 | 18255 | 18341 | 18348 | 18363 | 18418 | 18432 | 18444 | 18448 | 18517 | 18523 |
| 18560 | 18561 | 18660 | 18669 | 18728 | 18744 | 18756 | 18766 | 18769 | 18770 | 18772 | 18794 |
| 18813 | 18826 | 18874 | 18913 | 18937 | 18988 | 18989 | 19014 | 19070 | 19076 | 19077 | 19111 |
| 19116 | 19121 | 19140 | 19144 | 19148 | 19153 | 19154 | 19157 | 19161 | 19170 | 19183 | 19186 |
| 19204 | 19217 | 19226 | 19247 | 19254 | 19267 | 19269 | 19277 | 19290 | 19335 | 19351 | 19372 |
| 19377 | 19383 | 19384 | 19403 | 19420 | 19421 | 19432 | 19458 | 19460 | 19473 | 19502 | 19516 |
| 19534 | 19544 | 19574 | 19578 | 19591 | 19596 | 19614 | 19625 | 19646 | 19647 | 19665 | 19725 |
| 19735 | 19756 | 19762 | 19786 | 19820 | 19832 | 19833 | 19844 | 19854 | 19866 | 19884 | 19909 |
| 19962 | 20032 | 20046 | 20047 | 20064 | 20070 | 20072 | 20073 | 20099 | 20100 | 20146 | 20184 |
| 20211 | 20216 | 20217 | 20276 | 20488 | 20490 | 20521 | 20609 | 20611 | 20616 | 20637 | 20653 |
| 20654 | 20711 | 20733 | 20739 | 20776 | 20793 | 20809 | 20826 | 20841 | 20843 | 20854 | 20873 |
| 20886 | 20889 | 20911 | 20941 | 20942 | 20943 | 20953 | 20981 | 20987 | 21005 | 21018 | 21024 |
| 21062 | 21076 | 21109 | 21121 | 21167 | 21190 | 21204 | 21218 | 21223 | 21226 | 21245 | 21305 |
| 21306 | 21323 | 21354 | 21363 | 21379 | 21381 | 21428 | 21533 | 21552 | 21717 | 21758 | 21767 |
| 21775 | 21781 | 21798 | 21824 | 21848 | 21849 | 21863 | 21867 | 21871 | 21872 | 21936 | 21993 |
| 22015 | 22016 | 22040 | 22053 | 22106 | 22110 | 22115 | 22150 | 22167 | 22185 | 22231 | 22238 |
| 22252 | 22297 | 22298 | 22325 | 22335 | 22350 | 22355 | 22384 | 22411 | 22412 | 22419 | 22446 |
| 22452 | 22463 | 22490 | 22497 | 22551 | 22555 | 22578 | 22583 | 22587 | 22595 | 22651 | 22655 |

TABLE 8-continued

Heat Tolerance

| | | | | | | | | | | | |
|---|---|---|---|---|---|---|---|---|---|---|---|
| 22664 | 22684 | 22697 | 22699 | 22768 | 22772 | 22783 | 22787 | 22801 | 22823 | 22890 | 23050 |
| 23094 | 23147 | 23182 | 23206 | 23224 | 23233 | 23308 | 23372 | 23376 | 23402 | 23416 | 23420 |
| 23431 | 23445 | 23464 | 23500 | 23508 | 23531 | 23598 | 23601 | 23604 | 23630 | 23640 | |

Table 8B SEQ ID NOs of Polynucleotides useful for improving Heat Tolerance

| | | | | | | | | | | | |
|---|---|---|---|---|---|---|---|---|---|---|---|
| 23707 | 23718 | 23734 | 23759 | 23760 | 23785 | 23809 | 23813 | 23821 | 23853 | 23868 | 23876 |
| 23892 | 23931 | 23955 | 23967 | 23985 | 23998 | 24038 | 24043 | 24052 | 24060 | 24073 | 24074 |
| 24077 | 24101 | 24108 | 24136 | 24146 | 24164 | 24200 | 24245 | 24249 | 24253 | 24278 | 24323 |
| 24332 | 24369 | 24375 | 24376 | 24420 | 24421 | 24425 | 24437 | 24439 | 24464 | 24477 | 24509 |
| 24522 | 24526 | 24561 | 24610 | 24618 | 24676 | 24680 | 24819 | 24842 | 24898 | 24899 | 25081 |
| 25096 | 25110 | 25121 | 25126 | 25127 | 25132 | 25150 | 25161 | 25163 | 25166 | 25209 | 25231 |
| 25255 | 25276 | 25278 | 25284 | 25296 | 25311 | 25312 | 25319 | 25328 | 25336 | 25352 | 25360 |
| 25403 | 25415 | 25447 | 25455 | 25485 | 25508 | 25525 | 25526 | 25534 | 25570 | 25586 | 25591 |
| 25594 | 25604 | 25607 | 25630 | 25643 | 25658 | 25662 | 25685 | 25688 | 25705 | 25734 | 25740 |
| 25766 | 25806 | 25808 | 25817 | 25844 | 25845 | 25858 | 25889 | 25892 | 25895 | 25898 | 25900 |
| 25932 | 25955 | 25957 | 25991 | 25998 | 26046 | 26084 | 26106 | 26107 | 26140 | 26211 | 26223 |
| 26233 | 26238 | 26261 | 26326 | 26329 | 26334 | 26335 | 26425 | 26432 | 26438 | 26439 | 26449 |
| 26453 | 26456 | 26466 | 26478 | 26486 | 26492 | 26521 | 26543 | 26565 | 26581 | 26589 | 26603 |
| 26624 | 26632 | 26636 | 26637 | 26655 | 26662 | 26671 | 26713 | 26718 | 26737 | 26774 | 26790 |
| 26807 | 26817 | 26820 | 26878 | 26885 | 26890 | 26893 | 26919 | 26923 | 26936 | 26979 | 26986 |
| 26992 | 27032 | 27044 | 27063 | 27149 | 27152 | 27165 | 27174 | 27178 | 27192 | 27213 | 27214 |
| 27248 | 27258 | 27275 | 27279 | 27290 | 27302 | 27316 | 27385 | 27411 | 27449 | 27475 | 27521 |
| 27522 | 27534 | 27540 | 27558 | 27637 | 27677 | 27706 | 27743 | 27770 | 27773 | 27787 | 27803 |
| 27824 | 27831 | 27833 | 27885 | 27903 | 27914 | 27923 | 27946 | 27971 | 27978 | 28001 | 28024 |
| 28048 | 28050 | 28056 | 28062 | 28100 | 28111 | 28125 | 28142 | 28193 | 28197 | 28260 | 28261 |
| 28280 | 28305 | 28331 | 28350 | 28376 | 28381 | 28393 | 28407 | 28414 | 28468 | 28493 | 28531 |
| 28647 | 28655 | 28657 | 28675 | 28679 | 28681 | 28690 | 28710 | 28714 | 28755 | 28777 | 28791 |
| 28871 | 28912 | 28955 | 28985 | 29017 | 29021 | 29025 | 29026 | 29050 | 29065 | 29102 | 29135 |
| 29178 | 29220 | 29221 | 29227 | 29231 | 29235 | 29239 | 29263 | 29279 | 29280 | 29296 | 29331 |
| 29380 | 29430 | 29432 | 29460 | 29464 | 29467 | 29478 | 29483 | 29485 | 29545 | 29549 | 29550 |
| 29588 | 29589 | 29591 | 29602 | 29603 | 29609 | 29662 | 29677 | 29680 | 29701 | 29705 | 29713 |
| 29714 | 29729 | 29744 | 29749 | 29768 | 29791 | 29794 | 29795 | 29820 | 29821 | 29830 | 29839 |
| 29850 | 29876 | 29897 | 29901 | 29920 | 29927 | 29928 | 29940 | 29959 | 29961 | 29996 | 30002 |
| 30003 | 30004 | 30005 | 30009 | 30012 | 30013 | 30035 | 30036 | 30037 | 30038 | 30039 | 30042 |
| 30043 | 30048 | 30052 | 30053 | 30054 | 30071 | 30075 | 30081 | 30084 | 30087 | 30100 | 30109 |
| 30110 | 30111 | 30112 | 30125 | 30158 | 30159 | 30160 | 30171 | 30172 | 30190 | 30265 | 30266 |
| 30274 | 30275 | 30276 | 30277 | 30278 | 30279 | 30284 | 30294 | 30304 | 30312 | 30323 | 30350 |
| 30351 | 30427 | 30436 | 30446 | 30453 | 30475 | 30477 | 30479 | 30483 | 30506 | 30516 | 30642 |
| 30665 | 30666 | 30670 | 30673 | 30718 | 30726 | 30734 | 30757 | 30779 | 30789 | 30802 | 30804 |
| 30810 | 30816 | 30856 | 30869 | 30884 | 30951 | 30955 | 31017 | 31018 | 31037 | 31062 | 31089 |
| 31109 | 31135 | 31152 | 31166 | 31173 | 31228 | 31252 | 31290 | 31405 | 31413 | 31463 | 31465 |
| 31471 | 31486 | 31518 | 31556 | 31595 | 31603 | 31604 | 31660 | 31687 | 31709 | 31728 | 31750 |
| 31751 | 31752 | 31781 | 31782 | 31783 | 31796 | 31801 | 31929 | 31947 | 31976 | 31996 | 32006 |
| 32008 | 32009 | 32121 | 32137 | 32174 | 32182 | 32185 | 32262 | 32266 | 32304 | 32341 | 32393 |
| 32479 | 32501 | 32561 | 32575 | 32589 | 32602 | 32613 | 32614 | 32619 | 32706 | 32725 | 32767 |
| 32799 | 32827 | 32843 | 32853 | 32883 | 32927 | 32956 | 32974 | 32992 | 32993 | 33000 | 33024 |
| 33034 | 33061 | 33065 | 33072 | 33126 | 33146 | 33154 | 33180 | 33183 | 33284 | 33293 | 33322 |
| 33328 | 33341 | 33343 | 33384 | 33446 | 33454 | 33481 | 33557 | 33585 | 33615 | 33625 | 33631 |
| 33648 | 33663 | 33669 | 33670 | 33701 | 33702 | 33745 | 33747 | 33753 | 33850 | 33857 | 33859 |
| 33931 | 33981 | 33982 | 33984 | 33987 | 34023 | 34055 | 34058 | 34067 | 34073 | 34085 | 34109 |
| 34179 | 34206 | 34221 | 34259 | 34290 | 34295 | 34310 | 34335 | 34336 | 34344 | 34360 | 34450 |
| 34485 | 34489 | 34501 | 34536 | 34549 | 34550 | 34557 | 34577 | 34615 | 34694 | 34774 | 34775 |
| 34786 | 34822 | 34865 | 34891 | 34919 | 35061 | 35080 | 35162 | 35165 | 35170 | 35191 | 35222 |
| 35237 | 35282 | 35285 | 35330 | 35391 | 35397 | 35446 | 35447 | 35484 | 35504 | 35521 | 35524 |
| 35525 | 35582 | 35595 | 35603 | 35604 | 35607 | 35608 | 35658 | 35669 | 35774 | 35775 | 35783 |
| 35793 | 35795 | 35857 | 35981 | 35989 | 36017 | 36018 | 36035 | 36036 | 36053 | 36113 | 36125 |
| 36169 | 36193 | 36204 | 36222 | 36223 | 36241 | 36279 | 36294 | 36301 | 36306 | 36327 | 36332 |
| 36352 | 36390 | 36391 | 36428 | 36475 | 36504 | 36517 | 36560 | 36598 | 36609 | 36655 | 36679 |
| 36682 | 36684 | 36694 | 36698 | 36784 | 36786 | 36872 | 36921 | 36966 | 36967 | 36968 | 36972 |
| 36979 | 36988 | 37080 | 37190 | 37219 | 37279 | 37290 | 37330 | 37344 | 37345 | 37353 | 37371 |
| 37405 | 37409 | 37423 | 37426 | 37431 | 37451 | 37504 | 37505 | 37554 | 37714 | 37742 | 37748 |
| 37750 | 37755 | 37761 | 37791 | 37800 | 37818 | 37844 | 37893 | 37900 | 37952 | 37991 | 38043 |
| 38123 | 38136 | 38146 | 38208 | 38222 | 38230 | 38252 | 38275 | 38300 | 38343 | 38456 | 38467 |
| 38569 | 38606 | 38621 | 38630 | 38667 | 38674 | 38738 | 38746 | 38774 | 38817 | 38850 | 38934 |
| 38950 | 38951 | 38952 | 38958 | 38997 | 38998 | 38999 | 39034 | 39061 | 39076 | 39155 | 39174 |
| 39175 | 39208 | 39211 | 39241 | 39248 | 39267 | 39284 | 39286 | 39291 | 39326 | 39332 | 39363 |
| 39364 | 39365 | 39401 | 39428 | 39444 | 39525 | 39546 | 39547 | 39579 | 39582 | 39614 | 39621 |
| 39643 | 39661 | 39663 | 39666 | 39701 | 39707 | 39754 | 39755 | 39813 | 39828 | 39904 | 39922 |
| 39952 | 39955 | 39980 | 39989 | 40006 | 40020 | 40023 | 40025 | 40030 | 40054 | 40059 | 40132 |
| 40202 | 40206 | 40217 | 40245 | 40258 | 40309 | 40322 | 40418 | 40436 | 40440 | 40441 | 40505 |
| 40512 | 40521 | 40552 | 40604 | 40621 | 40677 | 40788 | 40859 | 40869 | 40819 | 40871 | 40895 |
| 40896 | 40921 | 40959 | 40981 | 40992 | 41032 | 41039 | 41073 | 41079 | 41201 | 41211 | 41233 |
| 41238 | 41256 | 41280 | 41302 | 41330 | 41347 | 41397 | 41412 | 41420 | 41490 | 41513 | 41528 |
| 41561 | 41562 | 41594 | 41595 | 41597 | 41632 | 41645 | 41654 | 41665 | 41704 | 41737 | 41926 |
| 41927 | 41928 | 41942 | 42028 | 42035 | 42050 | 42105 | 42119 | 42131 | 42135 | 42204 | 42210 |
| 42247 | 42248 | 42347 | 42356 | 42415 | 42431 | 42443 | 42453 | 42456 | 42457 | 42459 | 42481 |

TABLE 8-continued

Heat Tolerance

| | | | | | | | | | | | |
|---|---|---|---|---|---|---|---|---|---|---|---|
| 42500 | 42513 | 42561 | 42600 | 42624 | 42675 | 42676 | 42701 | 42757 | 42763 | 42764 | 42798 |
| 42803 | 42808 | 42827 | 42831 | 42835 | 42840 | 42841 | 42844 | 42848 | 42857 | 42870 | 42873 |
| 42891 | 42904 | 42913 | 42934 | 42941 | 42954 | 42956 | 42964 | 42977 | 43022 | 43038 | 43059 |
| 43064 | 43070 | 43071 | 43090 | 43107 | 43108 | 43119 | 43145 | 43147 | 43160 | 43189 | 43203 |
| 43221 | 43231 | 43261 | 43265 | 43278 | 43283 | 43301 | 43312 | 43333 | 43334 | 43352 | 43412 |
| 43422 | 43443 | 43449 | 43473 | 43507 | 43519 | 43520 | 43531 | 43541 | 43553 | 43571 | 43596 |
| 43649 | 43719 | 43733 | 43734 | 43751 | 43757 | 43759 | 43760 | 43786 | 43787 | 43833 | 43871 |
| 43898 | 43903 | 43904 | 43963 | 44175 | 44177 | 44208 | 44296 | 44298 | 44303 | 44324 | 44340 |
| 44341 | 44398 | 44420 | 44426 | 44463 | 44480 | 44496 | 44513 | 44528 | 44530 | 44541 | 44560 |
| 44573 | 44576 | 44598 | 44628 | 44629 | 44630 | 44640 | 44668 | 44674 | 44692 | 44705 | 44711 |
| 44749 | 44763 | 44796 | 44808 | 44854 | 44877 | 44891 | 44905 | 44910 | 44913 | 44932 | 44992 |
| 44993 | 45010 | 45041 | 45050 | 45066 | 45068 | 45115 | 45220 | 45239 | 45404 | 45445 | 45454 |
| 45462 | 45468 | 45485 | 45511 | 45535 | 45536 | 45550 | 45554 | 45558 | 45559 | 45623 | 45680 |
| 45702 | 45703 | 45727 | 45740 | 45793 | 45797 | 45802 | 45837 | 45854 | 45872 | 45918 | 45925 |
| 45939 | 45984 | 45985 | 46012 | 46022 | 46037 | 46042 | 46071 | 46098 | 46099 | 46106 | 46133 |
| 46139 | 46150 | 46177 | 46184 | 46238 | 46242 | 46265 | 46270 | 46274 | 46282 | 46338 | 46342 |
| 46351 | 46371 | 46384 | 46386 | 46455 | 46459 | 46470 | 46474 | 46488 | 46510 | 46577 | 46737 |
| 46781 | 46834 | 46869 | 46893 | 46911 | 46920 | 46995 | 47059 | 47063 | 47089 | 47103 | 47107 |
| 47118 | 47132 | 47151 | 47187 | 47195 | 47218 | 47285 | 47288 | 47291 | 47317 | 47327 | |

TABLE 9

Herbicide Tolerance

Table 9A SEQ ID NOs of Polypeptides useful for improving Herbicide Tolerance

| | | | | | | | | | | | |
|---|---|---|---|---|---|---|---|---|---|---|---|
| 3 | 5 | 10 | 22 | 23 | 26 | 30 | 42 | 57 | 59 | 69 | 92 |
| 96 | 99 | 113 | 120 | 121 | 123 | 125 | 138 | 145 | 148 | 149 | 150 |
| 158 | 161 | 165 | 170 | 196 | 200 | 203 | 206 | 223 | 227 | 233 | 241 |
| 242 | 243 | 246 | 254 | 259 | 273 | 292 | 297 | 302 | 322 | 323 | 324 |
| 326 | 331 | 336 | 354 | 358 | 382 | 384 | 389 | 397 | 399 | 400 | 404 |
| 406 | 412 | 422 | 441 | 445 | 450 | 451 | 463 | 482 | 510 | 511 | 514 |
| 532 | 533 | 536 | 563 | 567 | 568 | 569 | 570 | 573 | 575 | 576 | 589 |
| 594 | 595 | 629 | 646 | 654 | 655 | 659 | 660 | 661 | 663 | 669 | 678 |
| 680 | 700 | 703 | 706 | 714 | 726 | 728 | 739 | 743 | 751 | 758 | 760 |
| 761 | 762 | 770 | 771 | 775 | 783 | 801 | 803 | 804 | 814 | 826 | 850 |
| 854 | 857 | 880 | 881 | 882 | 884 | 898 | 912 | 916 | 925 | 930 | 947 |
| 962 | 971 | 992 | 1007 | 1030 | 1049 | 1051 | 1055 | 1058 | 1059 | 1066 | 1067 |
| 1071 | 1076 | 1078 | 1080 | 1102 | 1104 | 1108 | 1113 | 1118 | 1119 | 1120 | 1128 |
| 1131 | 1138 | 1139 | 1144 | 1147 | 1149 | 1156 | 1159 | 1162 | 1163 | 1164 | 1165 |
| 1179 | 1181 | 1196 | 1198 | 1206 | 1210 | 1218 | 1221 | 1232 | 1239 | 1260 | 1261 |
| 1288 | 1294 | 1298 | 1302 | 1308 | 1319 | 1323 | 1340 | 1410 | 1443 | 1444 | 1465 |
| 1501 | 1511 | 1513 | 1548 | 1582 | 1610 | 1614 | 1616 | 1617 | 1622 | 1635 | 1645 |
| 1659 | 1664 | 1701 | 1707 | 1727 | 1743 | 1757 | 1783 | 1832 | 1869 | 1946 | 1947 |
| 2005 | 2041 | 2048 | 2063 | 2064 | 2098 | 2175 | 2227 | 2237 | 2247 | 2305 | 2334 |
| 2336 | 2417 | 2435 | 2461 | 2484 | 2496 | 2580 | 2616 | 2620 | 2628 | 2630 | 2637 |
| 2641 | 2643 | 2650 | 2652 | 2674 | 2677 | 2681 | 2701 | 2704 | 2712 | 2721 | 2729 |
| 2755 | 2758 | 2764 | 2784 | 2789 | 2793 | 2794 | 2796 | 2802 | 2804 | 2812 | 2819 |
| 2821 | 2822 | 2827 | 2835 | 2837 | 2838 | 2849 | 2851 | 2872 | 2883 | 2891 | 2931 |
| 2933 | 2989 | 2991 | 2992 | 2993 | 3013 | 3022 | 3049 | 3063 | 3069 | 3071 | 3076 |
| 3098 | 3106 | 3111 | 3140 | 3143 | 3157 | 3167 | 3199 | 3200 | 3214 | 3218 | 3244 |
| 3250 | 3260 | 3363 | 3383 | 3390 | 3397 | 3455 | 3466 | 3474 | 3524 | 3556 | 3578 |
| 3579 | 3699 | 3702 | 3705 | 3708 | 3782 | 3814 | 3850 | 3905 | 3906 | 3916 | 3970 |
| 3972 | 4079 | 4080 | 4113 | 4133 | 4153 | 4172 | 4178 | 4179 | 4181 | 4196 | 4214 |
| 4230 | 4232 | 4245 | 4247 | 4264 | 4273 | 4274 | 4293 | 4300 | 4323 | 4348 | 4368 |
| 4372 | 4386 | 4415 | 4417 | 4419 | 4431 | 4433 | 4469 | 4470 | 4476 | 4477 | 4507 |
| 4513 | 4516 | 4533 | 4538 | 4545 | 4547 | 4551 | 4571 | 4575 | 4576 | 4580 | 4588 |
| 4589 | 4590 | 4592 | 4607 | 4616 | 4649 | 4650 | 4655 | 4726 | 4728 | 4759 | 4764 |
| 4778 | 4810 | 4811 | 4821 | 4826 | 4878 | 4922 | 4927 | 4929 | 4930 | 4941 | 4966 |
| 5037 | 5211 | 5445 | 5454 | 5501 | 5588 | 5628 | 5650 | 5676 | 5736 | 5747 | 5752 |
| 5776 | 5778 | 5942 | 5978 | 6052 | 6071 | 6151 | 6188 | 6228 | 6245 | 6327 | 6360 |
| 6392 | 6526 | 6530 | 6577 | 6691 | 6902 | 6905 | 6922 | 6987 | 7001 | 7049 | 7056 |
| 7079 | 7103 | 7122 | 7126 | 7141 | 7171 | 7173 | 7175 | 7189 | 7191 | 7229 | 7230 |
| 7235 | 7236 | 7265 | 7271 | 7275 | 7291 | 7296 | 7303 | 7305 | 7308 | 7328 | 7332 |
| 7333 | 7337 | 7345 | 7346 | 7347 | 7349 | 7364 | 7373 | 7407 | 7408 | 7413 | 7485 |
| 7518 | 7524 | 7538 | 7569 | 7570 | 7580 | 7585 | 7637 | 7680 | 7685 | 7687 | 7688 |
| 7699 | 7724 | 7743 | 7746 | 7749 | 7779 | 7790 | 7801 | 7802 | 7803 | 7814 | 7820 |
| 7830 | 7853 | 7861 | 7872 | 7876 | 7886 | 7888 | 7903 | 7914 | 7950 | 7953 | 7958 |
| 7966 | 7968 | 7971 | 7996 | 7997 | 7999 | 8013 | 8014 | 8015 | 8016 | 8023 | 8028 |
| 8038 | 8044 | 8046 | 8062 | 8069 | 8079 | 8080 | 8081 | 8086 | 8087 | 8102 | 8110 |
| 8111 | 8120 | 8134 | 8135 | 8136 | 8137 | 8161 | 8185 | 8197 | 8200 | 8201 | 8202 |
| 8210 | 8248 | 8276 | 8277 | 8279 | 8301 | 8302 | 8313 | 8327 | 8333 | 8339 | 8358 |
| 8362 | 8363 | 8403 | 8406 | 8418 | 8420 | 8436 | 8448 | 8453 | 8460 | 8461 | 8465 |
| 8480 | 8481 | 8497 | 8529 | 8558 | 8583 | 8584 | 8613 | 8623 | 8642 | 8644 | 8647 |

TABLE 9-continued

Herbicide Tolerance

| | | | | | | | | | | | |
|---|---|---|---|---|---|---|---|---|---|---|---|
| 8658 | 8660 | 8666 | 8670 | 8676 | 8681 | 8691 | 8692 | 8694 | 8696 | 8736 | 8737 |
| 8754 | 8758 | 8760 | 8761 | 8762 | 8763 | 8775 | 8776 | 8790 | 8818 | 8844 | 8852 |
| 8858 | 8868 | 8883 | 8887 | 8904 | 8920 | 8942 | 8948 | 8967 | 8970 | 8975 | 8976 |
| 8977 | 8978 | 8989 | 8993 | 8996 | 9011 | 9022 | 9045 | 9047 | 9052 | 9053 | 9054 |
| 9065 | 9098 | 9099 | 9105 | 9125 | 9127 | 9130 | 9137 | 9146 | 9152 | 9155 | 9180 |
| 9181 | 9183 | 9185 | 9192 | 9206 | 9212 | 9214 | 9215 | 9223 | 9224 | 9234 | 9252 |
| 9259 | 9261 | 9263 | 9273 | 9274 | 9288 | 9298 | 9302 | 9314 | 9317 | 9318 | 9319 |
| 9320 | 9322 | 9345 | 9351 | 9360 | 9361 | 9362 | 9363 | 9368 | 9379 | 9382 | 9388 |
| 9390 | 9391 | 9392 | 9393 | 9394 | 9421 | 9426 | 9441 | 9442 | 9446 | 9448 | 9449 |
| 9453 | 9463 | 9471 | 9474 | 9499 | 9504 | 9523 | 9538 | 9543 | 9548 | 9552 | 9555 |
| 9557 | 9567 | 9572 | 9580 | 9581 | 9585 | 9591 | 9599 | 9610 | 9628 | 9638 | 9642 |
| 9647 | 9649 | 9650 | 9655 | 9659 | 9677 | 9678 | 9688 | 9690 | 9691 | 9692 | 9694 |
| 9705 | 9712 | 9713 | 9719 | 9726 | 9727 | 9733 | 9745 | 9764 | 9768 | 9777 | 9778 |
| 9779 | 9780 | 9819 | 9835 | 9836 | 9837 | 9856 | 9864 | 9865 | 9880 | 9904 | 9930 |
| 9933 | 9937 | 9943 | 9957 | 9959 | 9971 | 9974 | 9985 | 9994 | 9995 | 10024 | 10029 |
| 10032 | 10033 | 10034 | 10051 | 10054 | 10078 | 10080 | 10083 | 10105 | 10117 | 10118 | 10119 |
| 10120 | 10121 | 10122 | 10139 | 10155 | 10162 | 10213 | 10215 | 10220 | 10221 | 10265 | 10276 |
| 10284 | 10290 | 10301 | 10313 | 10323 | 10335 | 10339 | 10340 | 10344 | 10358 | 10374 | 10378 |
| 10392 | 10393 | 10394 | 10401 | 10407 | 10408 | 10416 | 10419 | 10441 | 10449 | 10471 | 10476 |
| 10491 | 10495 | 10508 | 10511 | 10523 | 10524 | 10525 | 10535 | 10606 | 10609 | 10639 | 10647 |
| 10675 | 10678 | 10680 | 10729 | 10768 | 10779 | 10780 | 10788 | 10790 | 10791 | 10796 | 10801 |
| 10833 | 10834 | 10835 | 10838 | 10840 | 10853 | 10865 | 10868 | 10877 | 10884 | 10885 | 10896 |
| 10903 | 10936 | 10945 | 10955 | 10958 | 10967 | 10970 | 10971 | 10980 | 10988 | 10989 | 10991 |
| 11019 | 11029 | 11030 | 11059 | 11077 | 11078 | 11086 | 11094 | 11101 | 11102 | 11116 | 11144 |
| 11151 | 11155 | 11168 | 11172 | 11173 | 11179 | 11196 | 11198 | 11209 | 11210 | 11216 | 11238 |
| 11241 | 11250 | 11254 | 11255 | 11257 | 11261 | 11262 | 11267 | 11268 | 11269 | 11270 | 11271 |
| 11272 | 11297 | 11305 | 11306 | 11310 | 11311 | 11329 | 11353 | 11367 | 11386 | 11405 | 11421 |
| 11431 | 11438 | 11439 | 11440 | 11441 | 11444 | 11460 | 11461 | 11463 | 11464 | 11469 | 11476 |
| 11508 | 11515 | 11529 | 11533 | 11534 | 11569 | 11571 | 11576 | 11604 | 11616 | 11618 | 11621 |
| 11627 | 11652 | 11656 | 11658 | 11662 | 11718 | 11733 | 11752 | 11762 | 11771 | 11777 | 11787 |
| 11792 | 11830 | 11831 | 11843 | 11852 | 11872 | 11873 | 11874 | 11875 | 11877 | 11883 | 11892 |
| 11911 | 11933 | 11937 | 11941 | 11954 | 11991 | 11994 | 12003 | 12050 | 12057 | 12058 | 12059 |
| 12060 | 12071 | 12072 | 12084 | 12100 | 12102 | 12105 | 12113 | 12115 | 12116 | 12147 | 12156 |
| 12160 | 12166 | 12175 | 12182 | 12183 | 12187 | 12189 | 12190 | 12194 | 12209 | 12210 | 12216 |
| 12220 | 12224 | 12243 | 12257 | 12259 | 12264 | 12289 | 12313 | 12335 | 12342 | 12367 | 12374 |
| 12398 | 12412 | 12425 | 12445 | 12456 | 12472 | 12475 | 12502 | 12510 | 12514 | 12519 | 12537 |
| 12544 | 12572 | 12579 | 12603 | 12621 | 12652 | 12673 | 12675 | 12692 | 12701 | 12735 | 12736 |
| 12757 | 12792 | 12811 | 12814 | 12829 | 12851 | 12891 | 12903 | 12944 | 13015 | 13017 | 13059 |
| 13068 | 13079 | 13104 | 13124 | 13196 | 13216 | 13266 | 13267 | 13278 | 13328 | 13346 | 13368 |
| 13397 | 13408 | 13437 | 13451 | 13484 | 13485 | 13494 | 13514 | 13519 | 13520 | 13521 | 13533 |
| 13565 | 13573 | 13582 | 13585 | 13587 | 13612 | 13613 | 13625 | 13651 | 13668 | 13669 | 13679 |
| 13724 | 13759 | 13760 | 13762 | 13765 | 13775 | 13782 | 13787 | 13788 | 13806 | 13813 | 13833 |
| 13834 | 13835 | 13838 | 13868 | 13869 | 13872 | 13883 | 13884 | 13923 | 13933 | 13934 |
| 13937 | 13941 | 13943 | 13948 | 13958 | 13961 | 13976 | 13977 | 13978 | 13983 | 13987 | 13988 |
| 13995 | 13997 | 14002 | 14006 | 14026 | 14046 | 14050 | 14060 | 14064 | 14065 | 14099 | 14100 |
| 14105 | 14118 | 14133 | 14146 | 14155 | 14171 | 14190 | 14203 | 14217 | 14244 | 14247 | 14272 |
| 14290 | 14292 | 14323 | 14324 | 14325 | 14326 | 14331 | 14334 | 14351 | 14367 | 14374 | 14378 |
| 14379 | 14395 | 14407 | 14409 | 14411 | 14414 | 14430 | 14434 | 14441 | 14442 | 14443 | 14477 |
| 14479 | 14489 | 14490 | 14491 | 14492 | 14495 | 14515 | 14523 | 14524 | 14544 | 14548 | 14553 |
| 14554 | 14557 | 14574 | 14595 | 14600 | 14602 | 14605 | 14609 | 14649 | 14668 | 14675 | 14677 |
| 14690 | 14699 | 14704 | 14726 | 14727 | 14729 | 14756 | 14763 | 14764 | 14776 | 14804 | 14813 |
| 14822 | 14850 | 14874 | 14875 | 14876 | 14877 | 14890 | 14902 | 14929 | 14951 | 14969 | 14981 |
| 14990 | 14991 | 14992 | 14995 | 14998 | 15000 | 15013 | 15032 | 15041 | 15090 | 15110 | 15112 |
| 15116 | 15123 | 15128 | 15134 | 15151 | 15153 | 15159 | 15173 | 15182 | 15187 | 15205 | 15207 |
| 15209 | 15235 | 15240 | 15244 | 15286 | 15290 | 15299 | 15315 | 15317 | 15318 | 15319 | 15320 |
| 15321 | 15323 | 15325 | 15349 | 15352 | 15356 | 15371 | 15383 | 15404 | 15408 | 15412 |
| 15413 | 15430 | 15454 | 15455 | 15464 | 15484 | 15500 | 15504 | 15505 | 15506 | 15533 | 15542 |
| 15573 | 15587 | 15589 | 15593 | 15596 | 15610 | 15624 | 15632 | 15633 | 15634 | 15643 | 15665 |
| 15681 | 15683 | 15684 | 15685 | 15686 | 15687 | 15689 | 15691 | 15716 | 15719 | 15723 | 15738 |
| 15751 | 15761 | 15772 | 15776 | 15780 | 15781 | 15798 | 15822 | 15823 | 15833 | 15855 | 15871 |
| 15876 | 15877 | 15878 | 15904 | 15913 | 15946 | 15963 | 15965 | 15969 | 15973 | 15986 | 15999 |
| 16007 | 16008 | 16009 | 16018 | 16055 | 16072 | 16074 | 16075 | 16076 | 16077 | 16078 | 17242 |
| 17245 | 17273 | 17295 | 17297 | 17321 | 17322 | 17347 | 17377 | 17381 | 17382 | 17383 | 17384 |
| 17385 | 17393 | 17395 | 17416 | 17438 | 17440 | 17441 | 17452 | 17457 | 17471 | 17474 | 17477 |
| 17485 | 17486 | 17520 | 17525 | 17532 | 17535 | 17573 | 17579 | 17581 | 17582 | 17583 | 17585 |
| 17591 | 17603 | 17608 | 17634 | 17636 | 17637 | 17638 | 17639 | 17642 | 17655 | 17656 | 17659 |
| 17671 | 17672 | 17673 | 17690 | 17703 | 17714 | 17727 | 17728 | 17730 | 17741 | 17742 | 17750 |
| 17752 | 17758 | 17767 | 17786 | 17787 | 17789 | 17791 | 17793 | 17794 | 17799 | 17800 | 17812 |
| 17814 | 17824 | 17836 | 17837 | 17838 | 17843 | 17851 | 17852 | 17855 | 17904 | 17911 | 17922 |
| 17965 | 17973 | 17975 | 17977 | 17992 | 18014 | 18018 | 18019 | 18039 | 18055 | 18056 | 18065 |
| 18066 | 18085 | 18095 | 18124 | 18135 | 18136 | 18161 | 18163 | 18166 | 18167 | 18202 | 18217 |
| 18220 | 18222 | 18238 | 18251 | 18252 | 18265 | 18266 | 18291 | 18299 | 18322 | 18327 | 18328 |
| 18329 | 18330 | 18340 | 18380 | 18385 | 18402 | 18408 | 18409 | 18410 | 18412 | 18419 | 18429 |
| 18456 | 18481 | 18482 | 18483 | 18485 | 18495 | 18508 | 18514 | 18519 | 18526 | 18558 | 18570 |
| 18596 | 18603 | 18607 | 18615 | 18616 | 18627 | 18635 | 18636 | 18637 | 18648 | 18679 | 18687 |
| 18692 | 18694 | 18695 | 18697 | 18714 | 18721 | 18722 | 18729 | 18734 | 18742 | 18746 | 18774 |
| 18790 | 18797 | 18798 | 18805 | 18810 | 18814 | 18816 | 18834 | 18836 | 18838 | 18841 | 18842 |

TABLE 9-continued

Herbicide Tolerance

| | | | | | | | | | | | |
|---|---|---|---|---|---|---|---|---|---|---|---|
| 18847 | 18857 | 18858 | 18862 | 18863 | 18866 | 18867 | 18868 | 18870 | 18873 | 18877 | 18880 |
| 18895 | 18900 | 18903 | 18909 | 18919 | 18934 | 18960 | 18969 | 18974 | 18976 | 18987 | 18991 |
| 19018 | 19029 | 19054 | 19061 | 19110 | 19119 | 19127 | 19147 | 19149 | 19160 | 19167 | 19168 |
| 19169 | 19175 | 19177 | 19200 | 19201 | 19215 | 19229 | 19232 | 19244 | 19272 | 19285 | 19294 |
| 19314 | 19327 | 19347 | 19350 | 19357 | 19371 | 19380 | 19423 | 19426 | 19427 | 19474 | 19481 |
| 19489 | 19506 | 19526 | 19536 | 19569 | 19593 | 19594 | 19606 | 19609 | 19610 | 19622 | 19634 |
| 19636 | 19639 | 19641 | 19649 | 19651 | 19657 | 19671 | 19672 | 19673 | 19674 | 19676 | 19678 |
| 19683 | 19685 | 19692 | 19694 | 19697 | 19699 | 19700 | 19711 | 19722 | 19731 | 19738 | 19746 |
| 19749 | 19764 | 19767 | 19778 | 19800 | 19813 | 19815 | 19816 | 19819 | 19824 | 19838 | 19850 |
| 19895 | 19896 | 19918 | 19924 | 19938 | 19950 | 19953 | 19967 | 19971 | 19994 | 20000 | 20002 |
| 20038 | 20055 | 20061 | 20075 | 20078 | 20113 | 20124 | 20130 | 20131 | 20137 | 20162 | 20164 |
| 20181 | 20204 | 20208 | 20210 | 20225 | 20226 | 20230 | 20231 | 20234 | 20238 | 20239 | 20252 |
| 20254 | 20278 | 20289 | 20292 | 20296 | 20305 | 20327 | 20328 | 20354 | 20360 | 20364 | 20368 |
| 20373 | 20384 | 20388 | 20403 | 20434 | 20435 | 20436 | 20437 | 20439 | 20442 | 20443 | 20445 |
| 20446 | 20447 | 20448 | 20472 | 20478 | 20479 | 20487 | 20524 | 20539 | 20549 | 20550 | 20564 |
| 20572 | 20582 | 20587 | 20613 | 20629 | 20630 | 20633 | 20634 | 20641 | 20644 | 20651 | 20658 |
| 20659 | 20675 | 20684 | 20694 | 20702 | 20727 | 20735 | 20737 | 20748 | 20749 | 20750 | 20751 |
| 20766 | 20767 | 20768 | 20790 | 20799 | 20803 | 20818 | 20847 | 20862 | 20864 | 20877 | 20879 |
| 20881 | 20891 | 20902 | 20914 | 20917 | 20930 | 20933 | 20934 | 20937 | 20952 | 20954 | 20958 |
| 20961 | 20964 | 20965 | 20966 | 20967 | 20969 | 20975 | 20978 | 20979 | 20984 | 20994 | 20995 |
| 20996 | 21001 | 21012 | 21017 | 21043 | 21045 | 21053 | 21065 | 21069 | 21078 | 21080 | 21081 |
| 21091 | 21092 | 21120 | 21126 | 21128 | 21134 | 21145 | 21148 | 21150 | 21152 | 21155 | 21159 |
| 21160 | 21184 | 21194 | 21198 | 21203 | 21215 | 21216 | 21217 | 21227 | 21228 | 21229 | 21234 |
| 21239 | 21255 | 21257 | 21258 | 21259 | 21261 | 21266 | 21270 | 21280 | 21290 | 21321 | 21329 |
| 21341 | 21342 | 21358 | 21361 | 21364 | 21365 | 21370 | 21383 | 21392 | 21393 | 21397 | 21401 |
| 21408 | 21410 | 21411 | 21413 | 21427 | 21431 | 21439 | 21445 | 21454 | 21466 | 21468 | 21473 |
| 21476 | 21480 | 21485 | 21488 | 21495 | 21496 | 21500 | 21503 | 21504 | 21508 | 21514 | 21515 |
| 21519 | 21531 | 21544 | 21567 | 21572 | 21573 | 21578 | 21592 | 21598 | 21601 | 21605 | 21610 |
| 21649 | 21650 | 21684 | 21685 | 21699 | 21703 | 21708 | 21724 | 21727 | 21739 | 21750 | 21755 |
| 21756 | 21773 | 21774 | 21799 | 21808 | 21811 | 21814 | 21829 | 21832 | 21836 | 21837 | 21838 |
| 21853 | 21884 | 21897 | 21922 | 21945 | 21959 | 21973 | 21991 | 22018 | 22091 | 22095 | |
| 22162 | 22223 | 22248 | 22275 | 22290 | 22334 | 22342 | 22345 | 22378 | 22382 | 22389 | 22410 |
| 22431 | 22442 | 22447 | 22518 | 22597 | 22602 | 22617 | 22626 | 22639 | 22659 | 22685 | 22738 |
| 22746 | 22761 | 22779 | 22780 | 22792 | 22817 | 22844 | 22849 | 22850 | 22851 | 22856 | 22857 |
| 22872 | 22873 | 22896 | 22903 | 22926 | 22937 | 22948 | 22955 | 22957 | 22958 | 22970 | |
| 22990 | 22995 | 23002 | 23005 | 23019 | 23033 | 23047 | 23051 | 23057 | 23058 | 23064 | 23073 |
| 23074 | 23079 | 23099 | 23125 | 23126 | 23135 | 23160 | 23165 | 23166 | 23171 | 23174 | 23175 |
| 23178 | 23213 | 23219 | 23220 | 23221 | 23222 | 23223 | 23237 | 23248 | 23255 | 23256 | 23258 |
| 23317 | 23319 | 23320 | 23328 | 23335 | 23346 | 23348 | 23358 | 23363 | 23367 | 23382 | 23383 |
| 23410 | 23413 | 23421 | 23424 | 23425 | 23429 | 23441 | 23459 | 23461 | 23467 | 23472 | 23478 |
| 23483 | 23486 | 23488 | 23491 | 23509 | 23512 | 23513 | 23560 | 23569 | 23571 | 23573 | 23575 |
| 23580 | 23600 | 23607 | 23621 | 23622 | 23623 | 23634 | 23643 | 23653 | 23670 | | |

| Table 9B SEQ ID NOs of Polynucleotides useful for improving Herbicide Tolerance | | | | | | | | | | | |
|---|---|---|---|---|---|---|---|---|---|---|---|
| 23690 | 23692 | 23697 | 23709 | 23710 | 23713 | 23717 | 23729 | 23744 | 23746 | 23756 | 23779 |
| 23783 | 23786 | 23800 | 23807 | 23808 | 23810 | 23812 | 23825 | 23832 | 23835 | 23836 | 23837 |
| 23845 | 23848 | 23852 | 23857 | 23883 | 23887 | 23890 | 23893 | 23910 | 23914 | 23920 | 23928 |
| 23929 | 23930 | 23933 | 23941 | 23946 | 23960 | 23979 | 23984 | 23989 | 24009 | 24010 | 24011 |
| 24013 | 24018 | 24023 | 24041 | 24045 | 24069 | 24071 | 24076 | 24084 | 24086 | 24087 | 24091 |
| 24093 | 24099 | 24109 | 24128 | 24132 | 24137 | 24138 | 24150 | 24169 | 24197 | 24198 | 24201 |
| 24219 | 24220 | 24223 | 24250 | 24254 | 24255 | 24256 | 24257 | 24260 | 24262 | 24263 | 24276 |
| 24281 | 24282 | 24316 | 24333 | 24341 | 24342 | 24346 | 24347 | 24348 | 24350 | 24356 | 24365 |
| 24367 | 24387 | 24390 | 24393 | 24401 | 24413 | 24415 | 24426 | 24430 | 24438 | 24445 | 24447 |
| 24448 | 24449 | 24457 | 24458 | 24462 | 24470 | 24488 | 24490 | 24491 | 24501 | 24513 | 24537 |
| 24541 | 24544 | 24567 | 24568 | 24569 | 24571 | 24585 | 24599 | 24603 | 24612 | 24617 | 24634 |
| 24649 | 24658 | 24679 | 24694 | 24717 | 24736 | 24738 | 24742 | 24745 | 24746 | 24753 | 24754 |
| 24758 | 24763 | 24765 | 24767 | 24789 | 24791 | 24795 | 24800 | 24805 | 24806 | 24807 | 24815 |
| 24818 | 24825 | 24826 | 24831 | 24834 | 24836 | 24843 | 24846 | 24849 | 24850 | 24851 | 24852 |
| 24866 | 24868 | 24883 | 24885 | 24893 | 24897 | 24905 | 24908 | 24919 | 24926 | 24947 | 24948 |
| 24975 | 24981 | 24985 | 24989 | 24995 | 25006 | 25010 | 25027 | 25097 | 25130 | 25131 | 25152 |
| 25188 | 25198 | 25200 | 25235 | 25269 | 25297 | 25301 | 25303 | 25304 | 25309 | 25322 | 25332 |
| 25346 | 25351 | 25388 | 25394 | 25414 | 25430 | 25444 | 25470 | 25519 | 25556 | 25633 | 25634 |
| 25692 | 25728 | 25735 | 25750 | 25751 | 25785 | 25862 | 25914 | 25924 | 25934 | 25992 | 26021 |
| 26023 | 26104 | 26122 | 26148 | 26171 | 26183 | 26267 | 26303 | 26307 | 26315 | 26317 | 26324 |
| 26328 | 26330 | 26337 | 26339 | 26361 | 26364 | 26368 | 26388 | 26391 | 26399 | 26408 | 26416 |
| 26442 | 26445 | 26451 | 26471 | 26476 | 26480 | 26481 | 26483 | 26489 | 26491 | 26499 | 26506 |
| 26508 | 26509 | 26514 | 26522 | 26524 | 26525 | 26536 | 26538 | 26559 | 26570 | 26578 | 26618 |
| 26620 | 26676 | 26678 | 26679 | 26680 | 26700 | 26709 | 26736 | 26750 | 26756 | 26758 | 26763 |
| 26785 | 26793 | 26798 | 26827 | 26830 | 26844 | 26854 | 26886 | 26887 | 26901 | 26905 | 26931 |
| 26937 | 26947 | 27050 | 27070 | 27077 | 27084 | 27142 | 27153 | 27161 | 27211 | 27243 | 27265 |
| 27266 | 27386 | 27389 | 27392 | 27395 | 27469 | 27501 | 27537 | 27592 | 27593 | 27603 | 27657 |
| 27659 | 27766 | 27767 | 27800 | 27820 | 27840 | 27859 | 27865 | 27866 | 27868 | 27883 | 27901 |
| 27917 | 27919 | 27932 | 27934 | 27951 | 27960 | 27961 | 27980 | 27987 | 28010 | 28035 | 28055 |
| 28059 | 28073 | 28102 | 28104 | 28106 | 28118 | 28120 | 28156 | 28157 | 28163 | 28164 | 28194 |
| 28200 | 28203 | 28220 | 28225 | 28232 | 28234 | 28238 | 28258 | 28262 | 28263 | 28267 | 28275 |
| 28276 | 28277 | 28279 | 28294 | 28303 | 28336 | 28337 | 28342 | 28413 | 28415 | 28446 | 28451 |

TABLE 9-continued

Herbicide Tolerance

| | | | | | | | | | | | |
|---|---|---|---|---|---|---|---|---|---|---|---|
| 28465 | 28497 | 28498 | 28508 | 28513 | 28565 | 28609 | 28614 | 28616 | 28617 | 28628 | 28653 |
| 28724 | 28898 | 29132 | 29141 | 29188 | 29275 | 29315 | 29337 | 29363 | 29423 | 29434 | 29439 |
| 29463 | 29465 | 29629 | 29665 | 29739 | 29758 | 29838 | 29875 | 29915 | 29932 | 30014 | 30047 |
| 30079 | 30213 | 30217 | 30264 | 30378 | 30589 | 30592 | 30609 | 30674 | 30688 | 30736 | 30743 |
| 30766 | 30790 | 30809 | 30813 | 30828 | 30858 | 30860 | 30862 | 30876 | 30878 | 30916 | 30917 |
| 30922 | 30923 | 30952 | 30958 | 30962 | 30978 | 30983 | 30990 | 30992 | 30995 | 31015 | 31019 |
| 31020 | 31024 | 31032 | 31033 | 31034 | 31036 | 31051 | 31060 | 31094 | 31095 | 31100 | 31172 |
| 31205 | 31211 | 31225 | 31256 | 31257 | 31267 | 31272 | 31324 | 31367 | 31372 | 31374 | 31375 |
| 31386 | 31411 | 31430 | 31433 | 31436 | 31466 | 31477 | 31488 | 31489 | 31490 | 31501 | 31507 |
| 31517 | 31540 | 31548 | 31559 | 31563 | 31573 | 31575 | 31590 | 31601 | 31637 | 31640 | 31645 |
| 31653 | 31655 | 31658 | 31683 | 31684 | 31686 | 31700 | 31701 | 31702 | 31703 | 31710 | 31715 |
| 31725 | 31731 | 31733 | 31749 | 31756 | 31766 | 31767 | 31768 | 31773 | 31774 | 31789 | 31797 |
| 31798 | 31807 | 31821 | 31822 | 31823 | 31824 | 31848 | 31872 | 31884 | 31887 | 31888 | 31889 |
| 31897 | 31935 | 31963 | 31964 | 31966 | 31988 | 31989 | 32000 | 32014 | 32020 | 32026 | 32045 |
| 32049 | 32050 | 32090 | 32093 | 32105 | 32107 | 32123 | 32135 | 32140 | 32147 | 32148 | 32152 |
| 32167 | 32168 | 32184 | 32216 | 32245 | 32270 | 32271 | 32300 | 32310 | 32329 | 32331 | 32334 |
| 32345 | 32347 | 32353 | 32357 | 32363 | 32368 | 32378 | 32379 | 32381 | 32383 | 32423 | 32424 |
| 32441 | 32445 | 32447 | 32448 | 32449 | 32450 | 32462 | 32463 | 32477 | 32505 | 32531 | 32539 |
| 32545 | 32555 | 32570 | 32574 | 32591 | 32607 | 32629 | 32635 | 32654 | 32657 | 32662 | 32663 |
| 32664 | 32665 | 32676 | 32680 | 32683 | 32698 | 32709 | 32732 | 32734 | 32739 | 32740 | 32741 |
| 32752 | 32785 | 32786 | 32792 | 32812 | 32814 | 32817 | 32824 | 32833 | 32839 | 32842 | 32867 |
| 32868 | 32870 | 32872 | 32879 | 32883 | 32899 | 32901 | 32902 | 32910 | 32911 | 32921 | 32939 |
| 32946 | 32948 | 32950 | 32960 | 32961 | 32975 | 32985 | 32989 | 33001 | 33004 | 33005 | 33006 |
| 33007 | 33009 | 33032 | 33038 | 33047 | 33048 | 33049 | 33050 | 33055 | 33066 | 33069 | 33075 |
| 33077 | 33078 | 33079 | 33080 | 33081 | 33108 | 33113 | 33128 | 33129 | 33133 | 33135 | 33136 |
| 33140 | 33150 | 33158 | 33161 | 33186 | 33191 | 33210 | 33225 | 33230 | 33235 | 33239 | 33242 |
| 33244 | 33254 | 33259 | 33267 | 33268 | 33272 | 33278 | 33286 | 33297 | 33315 | 33325 | 33329 |
| 33334 | 33336 | 33337 | 33342 | 33346 | 33364 | 33365 | 33375 | 33377 | 33378 | 33379 | 33381 |
| 33392 | 33399 | 33400 | 33406 | 33413 | 33414 | 33420 | 33432 | 33451 | 33455 | 33464 | 33465 |
| 33466 | 33467 | 33506 | 33522 | 33523 | 33524 | 33543 | 33551 | 33552 | 33567 | 33591 | 33617 |
| 33620 | 33624 | 33630 | 33644 | 33646 | 33658 | 33661 | 33672 | 33681 | 33682 | 33711 | 33716 |
| 33719 | 33720 | 33721 | 33738 | 33741 | 33765 | 33767 | 33770 | 33792 | 33804 | 33805 | 33806 |
| 33807 | 33808 | 33809 | 33826 | 33842 | 33849 | 33900 | 33902 | 33907 | 33908 | 33952 | 33963 |
| 33971 | 33977 | 33988 | 34000 | 34010 | 34022 | 34026 | 34027 | 34031 | 34045 | 34061 | 34065 |
| 34079 | 34080 | 34081 | 34088 | 34094 | 34095 | 34103 | 34106 | 34128 | 34136 | 34158 | 34163 |
| 34178 | 34182 | 34195 | 34198 | 34210 | 34211 | 34212 | 34222 | 34293 | 34296 | 34326 | 34334 |
| 34362 | 34365 | 34367 | 34416 | 34455 | 34466 | 34467 | 34475 | 34477 | 34478 | 34483 | 34488 |
| 34520 | 34521 | 34522 | 34525 | 34527 | 34540 | 34552 | 34555 | 34564 | 34571 | 34572 | 34583 |
| 34590 | 34623 | 34632 | 34642 | 34645 | 34654 | 34657 | 34658 | 34674 | 34675 | 34676 | 34678 |
| 34706 | 34716 | 34717 | 34746 | 34764 | 34765 | 34773 | 34781 | 34788 | 34789 | 34803 | 34831 |
| 34838 | 34842 | 34855 | 34859 | 34860 | 34866 | 34883 | 34885 | 34896 | 34897 | 34903 | 34925 |
| 34928 | 34937 | 34941 | 34942 | 34944 | 34948 | 34949 | 34954 | 34955 | 34956 | 34957 | 34958 |
| 34959 | 34984 | 34992 | 34993 | 34997 | 34998 | 35016 | 35040 | 35054 | 35073 | 35092 | 35108 |
| 35118 | 35125 | 35126 | 35127 | 35128 | 35131 | 35147 | 35148 | 35150 | 35151 | 35156 | 35163 |
| 35195 | 35202 | 35216 | 35220 | 35221 | 35256 | 35258 | 35263 | 35291 | 35303 | 35305 | 35308 |
| 35314 | 35339 | 35343 | 35345 | 35349 | 35405 | 35420 | 35439 | 35449 | 35458 | 35464 | 35474 |
| 35479 | 35517 | 35518 | 35530 | 35539 | 35559 | 35560 | 35561 | 35562 | 35564 | 35570 | 35579 |
| 35598 | 35620 | 35624 | 35628 | 35641 | 35678 | 35681 | 35690 | 35737 | 35744 | 35745 | 35746 |
| 35747 | 35758 | 35759 | 35771 | 35787 | 35789 | 35792 | 35800 | 35802 | 35803 | 35834 | 35843 |
| 35847 | 35853 | 35862 | 35869 | 35870 | 35874 | 35876 | 35877 | 35881 | 35896 | 35897 | 35903 |
| 35907 | 35911 | 35930 | 35944 | 35946 | 35951 | 35976 | 36000 | 36022 | 36029 | 36054 | 36061 |
| 36085 | 36099 | 36112 | 36132 | 36143 | 36159 | 36162 | 36189 | 36197 | 36201 | 36206 | 36224 |
| 36231 | 36259 | 36266 | 36290 | 36308 | 36339 | 36360 | 36362 | 36379 | 36388 | 36422 | 36423 |
| 36444 | 36479 | 36498 | 36501 | 36516 | 36538 | 36578 | 36590 | 36631 | 36702 | 36704 | 36746 |
| 36755 | 36766 | 36791 | 36811 | 36883 | 36903 | 36953 | 36954 | 36965 | 37015 | 37033 | 37055 |
| 37084 | 37095 | 37124 | 37138 | 37171 | 37172 | 37181 | 37206 | 37207 | 37208 | 37220 |
| 37252 | 37260 | 37269 | 37272 | 37274 | 37299 | 37300 | 37312 | 37338 | 37355 | 37356 | 37366 |
| 37411 | 37446 | 37447 | 37449 | 37452 | 37462 | 37469 | 37474 | 37475 | 37493 | 37500 | 37520 |
| 37521 | 37522 | 37525 | 37555 | 37556 | 37559 | 37570 | 37571 | 37605 | 37610 | 37620 | 37621 |
| 37624 | 37628 | 37630 | 37635 | 37645 | 37648 | 37663 | 37664 | 37665 | 37670 | 37674 | 37675 |
| 37682 | 37684 | 37689 | 37693 | 37713 | 37733 | 37737 | 37747 | 37751 | 37752 | 37786 | 37787 |
| 37792 | 37805 | 37820 | 37833 | 37842 | 37858 | 37877 | 37890 | 37904 | 37931 | 37934 | 37959 |
| 37977 | 37979 | 38010 | 38011 | 38012 | 38013 | 38018 | 38021 | 38038 | 38054 | 38061 | 38065 |
| 38066 | 38082 | 38094 | 38096 | 38098 | 38101 | 38117 | 38121 | 38128 | 38129 | 38130 | 38164 |
| 38166 | 38176 | 38177 | 38178 | 38179 | 38182 | 38202 | 38210 | 38211 | 38231 | 38235 | 38240 |
| 38241 | 38244 | 38261 | 38282 | 38287 | 38289 | 38292 | 38296 | 38336 | 38355 | 38362 | 38364 |
| 38377 | 38386 | 38391 | 38413 | 38414 | 38416 | 38443 | 38450 | 38451 | 38463 | 38491 | 38500 |
| 38509 | 38537 | 38561 | 38562 | 38563 | 38564 | 38574 | 38589 | 38638 | 38656 | 38668 |
| 38677 | 38678 | 38679 | 38682 | 38685 | 38687 | 38700 | 38719 | 38728 | 38777 | 38797 | 38799 |
| 38803 | 38810 | 38815 | 38821 | 38838 | 38840 | 38846 | 38860 | 38869 | 38874 | 38892 | 38894 |
| 38896 | 38922 | 38927 | 38931 | 38973 | 38977 | 38986 | 39002 | 39004 | 39005 | 39006 | 39007 |
| 39008 | 39010 | 39012 | 39036 | 39039 | 39043 | 39058 | 39070 | 39080 | 39091 | 39095 | 39099 |
| 39100 | 39117 | 39141 | 39142 | 39151 | 39171 | 39187 | 39191 | 39192 | 39193 | 39220 | 39229 |
| 39260 | 39274 | 39276 | 39280 | 39283 | 39297 | 39311 | 39319 | 39320 | 39321 | 39330 | 39352 |
| 39368 | 39370 | 39371 | 39372 | 39373 | 39374 | 39376 | 39378 | 39403 | 39406 | 39410 | 39425 |
| 39438 | 39448 | 39459 | 39463 | 39467 | 39468 | 39485 | 39509 | 39510 | 39520 | 39542 | 39558 |
| 39563 | 39564 | 39565 | 39591 | 39600 | 39633 | 39650 | 39652 | 39656 | 39660 | 39673 | 39686 |

TABLE 9-continued

Herbicide Tolerance

| | | | | | | | | | | | |
|---|---|---|---|---|---|---|---|---|---|---|---|
| 39694 | 39695 | 39696 | 39705 | 39742 | 39759 | 39761 | 39762 | 39763 | 39764 | 39765 | 40929 |
| 40932 | 40960 | 40982 | 40984 | 41008 | 41009 | 41034 | 41064 | 41068 | 41069 | 41070 | 41071 |
| 41072 | 41080 | 41082 | 41103 | 41125 | 41127 | 41128 | 41139 | 41144 | 41158 | 41161 | 41164 |
| 41172 | 41173 | 41207 | 41212 | 41219 | 41222 | 41260 | 41266 | 41268 | 41269 | 41270 | 41272 |
| 41278 | 41290 | 41295 | 41321 | 41323 | 41324 | 41325 | 41326 | 41329 | 41342 | 41343 | 41346 |
| 41358 | 41359 | 41360 | 41377 | 41390 | 41401 | 41414 | 41415 | 41417 | 41428 | 41429 | 41437 |
| 41439 | 41445 | 41454 | 41473 | 41474 | 41476 | 41478 | 41480 | 41481 | 41486 | 41487 | 41499 |
| 41501 | 41511 | 41523 | 41524 | 41525 | 41530 | 41538 | 41539 | 41542 | 41591 | 41598 | 41609 |
| 41652 | 41660 | 41662 | 41664 | 41679 | 41701 | 41705 | 41706 | 41726 | 41742 | 41743 | 41752 |
| 41753 | 41772 | 41782 | 41811 | 41822 | 41823 | 41848 | 41850 | 41853 | 41854 | 41889 | 41904 |
| 41907 | 41909 | 41925 | 41938 | 41939 | 41952 | 41953 | 41978 | 41986 | 42009 | 42014 | 42015 |
| 42016 | 42017 | 42027 | 42067 | 42072 | 42089 | 42095 | 42096 | 42097 | 42099 | 42106 | 42116 |
| 42143 | 42168 | 42169 | 42170 | 42172 | 42182 | 42195 | 42201 | 42206 | 42213 | 42245 | 42257 |
| 42283 | 42290 | 42294 | 42302 | 42303 | 42314 | 42322 | 42323 | 42335 | 42366 | 42374 | |
| 42379 | 42381 | 42382 | 42384 | 42401 | 42408 | 42409 | 42416 | 42421 | 42429 | 42433 | 42461 |
| 42477 | 42484 | 42485 | 42492 | 42497 | 42501 | 42503 | 42521 | 42523 | 42525 | 42528 | 42529 |
| 42534 | 42544 | 42545 | 42549 | 42550 | 42553 | 42554 | 42555 | 42557 | 42560 | 42564 | 42567 |
| 42582 | 42587 | 42590 | 42596 | 42606 | 42621 | 42647 | 42656 | 42661 | 42663 | 42674 | 42678 |
| 42705 | 42716 | 42741 | 42748 | 42797 | 42806 | 42814 | 42834 | 42836 | 42847 | 42854 | 42855 |
| 42856 | 42862 | 42864 | 42887 | 42888 | 42902 | 42916 | 42919 | 42931 | 42959 | 42972 | 42981 |
| 43001 | 43014 | 43034 | 43037 | 43044 | 43058 | 43067 | 43110 | 43113 | 43114 | 43161 | 43168 |
| 43176 | 43193 | 43213 | 43223 | 43256 | 43280 | 43281 | 43293 | 43296 | 43297 | 43309 | 43321 |
| 43323 | 43326 | 43328 | 43336 | 43338 | 43344 | 43358 | 43359 | 43360 | 43361 | 43363 | 43365 |
| 43370 | 43372 | 43379 | 43381 | 43384 | 43386 | 43387 | 43398 | 43409 | 43418 | 43425 | 43433 |
| 43436 | 43451 | 43454 | 43465 | 43487 | 43500 | 43502 | 43503 | 43506 | 43511 | 43525 | 43537 |
| 43582 | 43583 | 43605 | 43611 | 43625 | 43637 | 43640 | 43654 | 43681 | 43687 | 43689 | |
| 43725 | 43742 | 43748 | 43762 | 43765 | 43800 | 43811 | 43817 | 43818 | 43824 | 43849 | 43851 |
| 43868 | 43891 | 43895 | 43897 | 43912 | 43913 | 43917 | 43918 | 43921 | 43925 | 43926 | 43939 |
| 43941 | 43965 | 43976 | 43979 | 43983 | 43992 | 44014 | 44015 | 44041 | 44047 | 44051 | 44055 |
| 44060 | 44071 | 44075 | 44090 | 44121 | 44122 | 44123 | 44124 | 44126 | 44129 | 44130 | 44132 |
| 44133 | 44134 | 44135 | 44159 | 44165 | 44166 | 44174 | 44211 | 44226 | 44236 | 44237 | 44251 |
| 44259 | 44269 | 44274 | 44300 | 44316 | 44317 | 44320 | 44321 | 44328 | 44331 | 44338 | 44345 |
| 44346 | 44362 | 44371 | 44381 | 44389 | 44414 | 44422 | 44424 | 44435 | 44436 | 44437 | 44438 |
| 44453 | 44454 | 44455 | 44477 | 44486 | 44490 | 44505 | 44534 | 44549 | 44551 | 44564 | 44566 |
| 44568 | 44578 | 44589 | 44601 | 44604 | 44617 | 44620 | 44624 | 44639 | 44641 | 44645 | |
| 44648 | 44651 | 44652 | 44653 | 44654 | 44656 | 44662 | 44665 | 44666 | 44671 | 44681 | 44682 |
| 44683 | 44688 | 44699 | 44704 | 44730 | 44732 | 44740 | 44752 | 44756 | 44765 | 44767 | 44768 |
| 44778 | 44779 | 44807 | 44813 | 44815 | 44821 | 44832 | 44835 | 44837 | 44839 | 44842 | 44846 |
| 44847 | 44871 | 44881 | 44885 | 44890 | 44902 | 44903 | 44914 | 44915 | 44916 | 44921 | |
| 44926 | 44942 | 44944 | 44945 | 44946 | 44948 | 44953 | 44957 | 44967 | 44977 | 45008 | 45016 |
| 45028 | 45029 | 45045 | 45048 | 45051 | 45052 | 45057 | 45070 | 45079 | 45080 | 45084 | 45088 |
| 45095 | 45097 | 45098 | 45100 | 45114 | 45118 | 45126 | 45132 | 45141 | 45153 | 45155 | 45160 |
| 45163 | 45167 | 45172 | 45175 | 45182 | 45183 | 45187 | 45190 | 45191 | 45195 | 45201 | 45202 |
| 45206 | 45218 | 45231 | 45254 | 45259 | 45260 | 45265 | 45279 | 45285 | 45288 | 45292 | 45297 |
| 45336 | 45337 | 45371 | 45372 | 45386 | 45390 | 45395 | 45411 | 45414 | 45426 | 45437 | 45442 |
| 45443 | 45460 | 45461 | 45486 | 45495 | 45498 | 45501 | 45516 | 45519 | 45523 | 45524 | 45525 |
| 45540 | 45571 | 45584 | 45609 | 45632 | 45646 | 45660 | 45678 | 45686 | 45705 | 45778 | 45782 |
| 45849 | 45910 | 45935 | 45962 | 45977 | 46021 | 46029 | 46032 | 46065 | 46069 | 46076 | 46097 |
| 46118 | 46129 | 46134 | 46205 | 46284 | 46289 | 46304 | 46313 | 46326 | 46346 | 46372 | 46425 |
| 46433 | 46448 | 46466 | 46467 | 46479 | 46504 | 46531 | 46536 | 46537 | 46538 | 46543 | 46544 |
| 46559 | 46560 | 46583 | 46590 | 46613 | 46624 | 46635 | 46642 | 46643 | 46644 | 46645 | 46657 |
| 46677 | 46682 | 46689 | 46692 | 46706 | 46720 | 46734 | 46738 | 46744 | 46745 | 46751 | 46760 |
| 46761 | 46766 | 46786 | 46812 | 46813 | 46822 | 46847 | 46852 | 46853 | 46858 | 46861 | 46862 |
| 46865 | 46900 | 46906 | 46907 | 46908 | 46909 | 46910 | 46924 | 46935 | 46942 | 46943 | 46945 |
| 47004 | 47006 | 47007 | 47015 | 47022 | 47033 | 47035 | 47045 | 47050 | 47054 | 47069 | 47070 |
| 47097 | 47100 | 47108 | 47111 | 47112 | 47116 | 47128 | 47146 | 47148 | 47154 | 47159 | 47165 |
| 47170 | 47173 | 47175 | 47178 | 47196 | 47199 | 47200 | 47247 | 47256 | 47258 | 47260 | 47262 |
| 47267 | 47287 | 47294 | 47308 | 47309 | 47310 | 47321 | 47330 | 47340 | 47357 | | |

TABLE 10A

Homologous Recombination

Table 10A SEQ ID NOs of Polypeptides useful for improving Homologous Recombination

| | | | | | | | | | | | |
|---|---|---|---|---|---|---|---|---|---|---|---|
| 11 | 25 | 43 | 45 | 58 | 70 | 75 | 105 | 109 | 116 | 179 | 219 |
| 236 | 263 | 269 | 270 | 271 | 272 | 286 | 346 | 431 | 453 | 468 | 517 |
| 524 | 525 | 539 | 615 | 624 | 652 | 665 | 697 | 774 | 786 | 797 | 817 |
| 858 | 860 | 903 | 904 | 911 | 917 | 932 | 939 | 955 | 958 | 959 | 961 |
| 966 | 967 | 1009 | 1016 | 1024 | 1048 | 1061 | 1075 | 1083 | 1084 | 1095 | 1096 |
| 1115 | 1121 | 1141 | 1143 | 1151 | 1154 | 1184 | 1195 | 1197 | 1213 | 1219 | 1223 |
| 1227 | 1237 | 1238 | 1247 | 1248 | 1251 | 1253 | 1254 | 1271 | 1289 | 1301 | 1314 |
| 1317 | 1320 | 1330 | 1333 | 1338 | 1343 | 1347 | 1365 | 1366 | 1372 | 1373 | 1385 |
| 1391 | 1392 | 1395 | 1405 | 1407 | 1413 | 1414 | 1416 | 1420 | 1422 | 1424 | 1432 |

TABLE 10A-continued

| Homologous Recombination | | | | | | | | | | | |
|---|---|---|---|---|---|---|---|---|---|---|---|
| 1436 | 1442 | 1447 | 1448 | 1452 | 1456 | 1457 | 1458 | 1459 | 1462 | 1466 | 1467 |
| 1468 | 1475 | 1477 | 1482 | 1483 | 1485 | 1487 | 1502 | 1509 | 1512 | 1514 | 1516 |
| 1517 | 1523 | 1528 | 1530 | 1534 | 1536 | 1537 | 1545 | 1546 | 1547 | 1551 | 1552 |
| 1557 | 1558 | 1561 | 1562 | 1567 | 1568 | 1569 | 1571 | 1576 | 1577 | 1581 | 1585 |
| 1586 | 1587 | 1591 | 1594 | 1595 | 1602 | 1620 | 1621 | 1625 | 1627 | 1629 | 1633 |
| 1638 | 1640 | 1644 | 1646 | 1647 | 1648 | 1652 | 1656 | 1657 | 1658 | 1666 | 1671 |
| 1672 | 1676 | 1677 | 1678 | 1682 | 1687 | 1691 | 1693 | 1700 | 1708 | 1709 | 1714 |
| 1715 | 1723 | 1729 | 1738 | 1748 | 1752 | 1755 | 1758 | 1761 | 1763 | 1766 | 1767 |
| 1768 | 1771 | 1773 | 1777 | 1779 | 1782 | 1786 | 1787 | 1788 | 1790 | 1791 | 1793 |
| 1794 | 1799 | 1800 | 1804 | 1807 | 1808 | 1809 | 1810 | 1811 | 1822 | 1825 | 1827 |
| 1840 | 1843 | 1845 | 1848 | 1852 | 1853 | 1854 | 1855 | 1858 | 1860 | 1861 | 1863 |
| 1864 | 1870 | 1871 | 1873 | 1875 | 1881 | 1886 | 1888 | 1889 | 1891 | 1900 | 1901 |
| 1908 | 1911 | 1913 | 1914 | 1915 | 1916 | 1919 | 1925 | 1934 | 1937 | 1939 | 1940 |
| 1941 | 1943 | 1945 | 1948 | 1950 | 1954 | 1957 | 1959 | 1961 | 1963 | 1965 | 1967 |
| 1968 | 1972 | 1976 | 1978 | 1979 | 1980 | 1981 | 1982 | 1985 | 1990 | 1991 | 1996 |
| 2001 | 2011 | 2012 | 2015 | 2016 | 2018 | 2020 | 2021 | 2022 | 2035 | 2036 | 2038 |
| 2039 | 2046 | 2049 | 2052 | 2054 | 2055 | 2056 | 2060 | 2061 | 2075 | 2081 | 2088 |
| 2089 | 2090 | 2092 | 2093 | 2094 | 2097 | 2100 | 2101 | 2103 | 2105 | 2106 | 2107 |
| 2108 | 2113 | 2114 | 2125 | 2128 | 2131 | 2132 | 2135 | 2136 | 2138 | 2141 | 2142 |
| 2145 | 2146 | 2149 | 2153 | 2157 | 2161 | 2163 | 2170 | 2172 | 2173 | 2178 | 2179 |
| 2180 | 2183 | 2185 | 2187 | 2188 | 2189 | 2190 | 2193 | 2196 | 2197 | 2203 | 2213 |
| 2215 | 2219 | 2221 | 2222 | 2224 | 2234 | 2236 | 2240 | 2242 | 2248 | 2253 | 2254 |
| 2256 | 2259 | 2261 | 2266 | 2271 | 2274 | 2275 | 2281 | 2286 | 2287 | 2288 | 2290 |
| 2295 | 2296 | 2298 | 2302 | 2307 | 2309 | 2312 | 2317 | 2318 | 2323 | 2324 | 2326 |
| 2329 | 2332 | 2344 | 2348 | 2353 | 2360 | 2361 | 2370 | 2371 | 2372 | 2376 | 2377 |
| 2379 | 2380 | 2385 | 2386 | 2389 | 2395 | 2396 | 2399 | 2401 | 2405 | 2412 | 2416 |
| 2419 | 2420 | 2434 | 2436 | 2437 | 2443 | 2449 | 2454 | 2456 | 2459 | 2460 | 2462 |
| 2464 | 2465 | 2467 | 2471 | 2477 | 2480 | 2483 | 2493 | 2498 | 2501 | 2505 | 2509 |
| 2516 | 2519 | 2520 | 2525 | 2532 | 2535 | 2539 | 2540 | 2541 | 2542 | 2543 | 2545 |
| 2548 | 2552 | 2555 | 2558 | 2561 | 2572 | 2573 | 2574 | 2577 | 2579 | 2581 | 2583 |
| 2585 | 2587 | 2594 | 2595 | 2671 | 2673 | 2686 | 2697 | 2709 | 2713 | 2746 | 2763 |
| 2772 | 2882 | 2886 | 2895 | 2911 | 2962 | 3001 | 3006 | 3011 | 3018 | 3053 | 3081 |
| 3084 | 3099 | 3101 | 3112 | 3114 | 3117 | 3123 | 3141 | 3146 | 3149 | 3164 | 3170 |
| 3183 | 3184 | 3192 | 3204 | 3207 | 3212 | 3213 | 3215 | 3222 | 3223 | 3238 | 3242 |
| 3243 | 3255 | 3258 | 3261 | 3265 | 3268 | 3272 | 3275 | 3287 | 3296 | 3297 | 3303 |
| 3314 | 3317 | 3319 | 3329 | 3336 | 3341 | 3342 | 3345 | 3349 | 3365 | 3366 | 3367 |
| 3369 | 3370 | 3374 | 3375 | 3400 | 3402 | 3403 | 3405 | 3408 | 3412 | 3413 | 3427 |
| 3432 | 3434 | 3438 | 3439 | 3443 | 3447 | 3448 | 3459 | 3464 | 3467 | 3472 | 3477 |
| 3487 | 3488 | 3491 | 3492 | 3497 | 3499 | 3502 | 3503 | 3509 | 3510 | 3525 | 3526 |
| 3536 | 3537 | 3539 | 3542 | 3546 | 3550 | 3552 | 3564 | 3567 | 3569 | 3572 | 3574 |
| 3577 | 3582 | 3584 | 3586 | 3593 | 3594 | 3598 | 3602 | 3604 | 3606 | 3613 | 3614 |
| 3622 | 3631 | 3633 | 3645 | 3651 | 3655 | 3664 | 3668 | 3672 | 3691 | 3693 | 3706 |
| 3712 | 3716 | 3718 | 3719 | 3720 | 3721 | 3735 | 3738 | 3741 | 3743 | 3750 | 3754 |
| 3755 | 3756 | 3763 | 3767 | 3775 | 3779 | 3789 | 3790 | 3791 | 3795 | 3796 | 3797 |
| 3801 | 3807 | 3813 | 3823 | 3826 | 3832 | 3841 | 3845 | 3847 | 3849 | 3851 | 3858 |
| 3861 | 3862 | 3863 | 3873 | 3874 | 3877 | 3878 | 3882 | 3883 | 3892 | 3897 | 3898 |
| 3910 | 3914 | 3917 | 3918 | 3923 | 3935 | 3942 | 3947 | 3949 | 3950 | 3952 | 3952 |
| 3953 | 3961 | 3962 | 3971 | 3980 | 3983 | 3988 | 3992 | 4007 | 4008 | 4010 | 4021 |
| 4023 | 4027 | 4028 | 4036 | 4037 | 4042 | 4050 | 4056 | 4057 | 4058 | 4063 | 4067 |
| 4069 | 4071 | 4072 | 4078 | 4088 | 4090 | 4091 | 4092 | 4099 | 4105 | 4109 | 4112 |
| 4119 | 4120 | 4122 | 4127 | 4132 | 4135 | 4138 | 4139 | 4141 | 4145 | 4147 | 4151 |
| 4155 | 4160 | 4170 | 4171 | 4174 | 4175 | 4190 | 4193 | 4197 | 4208 | 4210 | 4210 |
| 4212 | 4219 | 4225 | 4226 | 4231 | 4237 | 4239 | 4281 | 4333 | 4374 | 4378 | 4396 |
| 4436 | 4491 | 4496 | 4497 | 4518 | 4537 | 4570 | 4662 | 4774 | 4839 | 4867 | 4971 |
| 4974 | 4977 | 4988 | 4992 | 4995 | 4997 | 4999 | 5001 | 5003 | 5004 | 5019 | 5023 |
| 5024 | 5030 | 5031 | 5032 | 5035 | 5036 | 5043 | 5047 | 5053 | 5054 | 5058 | 5065 |
| 5066 | 5068 | 5076 | 5077 | 5079 | 5082 | 5085 | 5101 | 5102 | 5104 | 5106 | 5123 |
| 5124 | 5130 | 5131 | 5132 | 5134 | 5136 | 5137 | 5138 | 5139 | 5141 | 5146 | 5156 |
| 5159 | 5160 | 5182 | 5186 | 5190 | 5191 | 5192 | 5193 | 5195 | 5196 | 5197 | 5200 |
| 5201 | 5207 | 5218 | 5219 | 5224 | 5227 | 5234 | 5235 | 5236 | 5237 | 5243 | 5253 |
| 5254 | 5255 | 5261 | 5271 | 5292 | 5293 | 5303 | 5305 | 5315 | 5317 | 5342 | 5359 |
| 5360 | 5368 | 5369 | 5383 | 5384 | 5385 | 5388 | 5393 | 5397 | 5401 | 5403 | 5404 |
| 5405 | 5406 | 5420 | 5422 | 5424 | 5425 | 5427 | 5430 | 5435 | 5438 | 5447 | 5456 |
| 5457 | 5461 | 5466 | 5468 | 5469 | 5472 | 5473 | 5475 | 5479 | 5485 | 5489 | 5499 |
| 5511 | 5517 | 5526 | 5533 | 5534 | 5538 | 5540 | 5551 | 5552 | 5554 | 5555 | 5559 |
| 5560 | 5561 | 5563 | 5566 | 5574 | 5577 | 5578 | 5580 | 5581 | 5585 | 5594 | 5596 |
| 5597 | 5598 | 5601 | 5603 | 5609 | 5620 | 5643 | 5647 | 5649 | 5653 | 5663 | 5675 |
| 5683 | 5685 | 5686 | 5689 | 5690 | 5691 | 5692 | 5694 | 5702 | 5704 | 5716 | 5720 |
| 5722 | 5739 | 5743 | 5744 | 5760 | 5762 | 5767 | 5780 | 5790 | 5791 | 5792 | 5793 |
| 5796 | 5814 | 5822 | 5828 | 5837 | 5838 | 5839 | 5846 | 5847 | 5848 | 5849 | 5853 |
| 5854 | 5861 | 5862 | 5863 | 5869 | 5870 | 5878 | 5880 | 5881 | 5882 | 5891 | 5901 |
| 5902 | 5904 | 5913 | 5920 | 5927 | 5928 | 5929 | 5930 | 5931 | 5943 | 5945 | 5953 |
| 5961 | 5962 | 5963 | 5964 | 5967 | 5968 | 5972 | 5973 | 5975 | 5977 | 5981 | 5987 |
| 5988 | 5989 | 5990 | 5994 | 5995 | 5997 | 6004 | 6005 | 6006 | 6025 | 6026 | 6027 |
| 6031 | 6037 | 6045 | 6054 | 6056 | 6062 | 6063 | 6064 | 6065 | 6074 | 6079 | 6081 |
| 6083 | 6092 | 6117 | 6118 | 6119 | 6121 | 6126 | 6132 | 6143 | 6144 | 6147 | 6150 |
| 6152 | 6155 | 6157 | 6161 | 6162 | 6170 | 6176 | 6185 | 6187 | 6189 | 6201 | 6204 |

TABLE 10A-continued

| Homologous Recombination | | | | | | | | | | | |
|---|---|---|---|---|---|---|---|---|---|---|---|
| 6205 | 6209 | 6210 | 6212 | 6217 | 6229 | 6230 | 6236 | 6237 | 6242 | 6261 | 6267 |
| 6304 | 6307 | 6328 | 6341 | 6375 | 6394 | 6395 | 6397 | 6409 | 6426 | 6434 | 6438 |
| 6442 | 6453 | 6457 | 6461 | 6462 | 6465 | 6471 | 6472 | 6473 | 6474 | 6478 | 6482 |
| 6483 | 6498 | 6499 | 6519 | 6524 | 6527 | 6528 | 6529 | 6535 | 6536 | 6537 | 6573 |
| 6597 | 6600 | 6601 | 6602 | 6603 | 6605 | 6606 | 6612 | 6614 | 6621 | 6631 | 6632 |
| 6633 | 6665 | 6694 | 6700 | 6708 | 6725 | 6729 | 6731 | 6744 | 6745 | 6756 | 6757 |
| 6765 | 6770 | 6774 | 6791 | 6846 | 6851 | 6881 | 6882 | 6908 | 6909 | 6920 | 6923 |
| 6928 | 6929 | 6931 | 6946 | 6947 | 6973 | 6974 | 6975 | 6991 | 6992 | 6993 | 6998 |
| 7012 | 7015 | 7027 | 7028 | 7029 | 7030 | 7036 | 7042 | 7089 | 7128 | 7132 | 7151 |
| 7195 | 7250 | 7255 | 7256 | 7277 | 7295 | 7322 | 7327 | 7421 | 7534 | 7598 | 7626 |
| 7741 | 7767 | 7780 | 7808 | 7821 | 7849 | 7865 | 7880 | 7889 | 8042 | 8059 | 8118 |
| 8133 | 8212 | 8217 | 8297 | 8298 | 8316 | 8325 | 8336 | 8389 | 8463 | 8511 | 8543 |
| 8559 | 8570 | 8581 | 8610 | 8611 | 8656 | 8693 | 8745 | 8784 | 8808 | 8811 | 8824 |
| 8846 | 8889 | 8905 | 8956 | 8986 | 8992 | 9009 | 9025 | 9044 | 9071 | 9131 | 9134 |
| 9157 | 9179 | 9187 | 9194 | 9195 | 9199 | 9207 | 9219 | 9247 | 9275 | 9353 | 9432 |
| 9433 | 9434 | 9455 | 9460 | 9461 | 9486 | 9510 | 9579 | 9618 | 9651 | 9683 | 9696 |
| 9722 | 9739 | 9740 | 9755 | 9770 | 9874 | 9905 | 9951 | 10043 | 10072 | 10090 | 10126 |
| 10147 | 10148 | 10189 | 10206 | 10251 | 10271 | 10289 | 10291 | 10320 | 10324 | 10331 | 10364 |
| 10365 | 10387 | 10391 | 10400 | 10455 | 10633 | 10676 | 10706 | 10737 | 10767 | 10778 | 10846 |
| 10874 | 10879 | 10880 | 10918 | 10948 | 10954 | 10963 | 10964 | 10965 | 11015 | 11016 | 11047 |
| 11051 | 11080 | 11081 | 11082 | 11083 | 11100 | 11104 | 11133 | 11135 | 11145 | 11146 | 11150 |
| 11158 | 11159 | 11197 | 11199 | 11201 | 11220 | 11222 | 11224 | 11228 | 11243 | 11256 | 11266 |
| 11278 | 11285 | 11289 | 11290 | 11292 | 11313 | 11315 | 11316 | 11319 | 11322 | 11323 | 11324 |
| 11334 | 11341 | 11342 | 11348 | 11354 | 11423 | 11454 | 11510 | 11541 | 11561 | 11585 | 11654 |
| 11746 | 11758 | 11784 | 11800 | 11858 | 11884 | 11910 | 11930 | 11976 | 12051 | 12076 | 12133 |
| 12292 | 12325 | 12334 | 12354 | 12355 | 12357 | 12359 | 12363 | 12365 | 12369 | 12372 | 12378 |
| 12392 | 12406 | 12415 | 12432 | 12444 | 12462 | 12464 | 12474 | 12479 | 12490 | 12493 | 12497 |
| 12504 | 12508 | 12515 | 12522 | 12525 | 12531 | 12543 | 12547 | 12550 | 12552 | 12555 | 12557 |
| 12560 | 12564 | 12567 | 12571 | 12581 | 12582 | 12584 | 12587 | 12588 | 12599 | 12604 | 12609 |
| 12611 | 12615 | 12616 | 12632 | 12633 | 12637 | 12647 | 12649 | 12651 | 12654 | 12655 | 12656 |
| 12660 | 12667 | 12668 | 12669 | 12674 | 12677 | 12691 | 12702 | 12705 | 12707 | 12709 | 12717 |
| 12718 | 12729 | 12731 | 12740 | 12747 | 12749 | 12752 | 12754 | 12755 | 12776 | 12777 | 12787 |
| 12788 | 12795 | 12798 | 12805 | 12816 | 12822 | 12826 | 12838 | 12839 | 12852 | 12860 | 12866 |
| 12875 | 12878 | 12881 | 12884 | 12898 | 12906 | 12909 | 12915 | 12916 | 12930 | 12931 | 12935 |
| 12937 | 12943 | 12945 | 12948 | 12951 | 12964 | 12965 | 12966 | 12973 | 12981 | 12992 | 12993 |
| 12998 | 13007 | 13009 | 13021 | 13024 | 13041 | 13052 | 13058 | 13073 | 13077 | 13080 | 13082 |
| 13108 | 13110 | 13112 | 13116 | 13123 | 13130 | 13138 | 13141 | 13143 | 13149 | 13157 | 13165 |
| 13172 | 13174 | 13175 | 13176 | 13178 | 13186 | 13189 | 13207 | 13208 | 13213 | 13218 | 13219 |
| 13223 | 13228 | 13232 | 13248 | 13257 | 13268 | 13270 | 13271 | 13298 | 13299 | 13302 |
| 13309 | 13312 | 13315 | 13321 | 13331 | 13338 | 13345 | 13364 | 13366 | 13367 | 13369 | 13374 |
| 13377 | 13378 | 13387 | 13398 | 13399 | 13401 | 13402 | 13404 | 13409 | 13411 | 13413 | 13421 |
| 13425 | 13441 | 13449 | 13452 | 13453 | 13454 | 13457 | 13459 | 13468 | 13477 | 13491 | 13501 |
| 13511 | 13512 | 13544 | 13545 | 13558 | 13572 | 13580 | 13589 | 13602 | 13637 | 13687 | 13701 |
| 13727 | 13758 | 13830 | 13840 | 13852 | 13858 | 13886 | 13891 | 13920 | 13954 | 14023 | 14056 |
| 14076 | 14108 | 14188 | 14189 | 14224 | 14229 | 14253 | 14255 | 14282 | 14305 | 14311 | 14558 |
| 14568 | 14570 | 14572 | 14627 | 14635 | 14653 | 14655 | 14745 | 14751 | 14767 | 14855 | 14885 |
| 14890 | 14899 | 15044 | 15086 | 15097 | 15126 | 15129 | 15145 | 15227 | 15230 | 15246 | 15330 |
| 15381 | 15384 | 15411 | 15429 | 15518 | 15519 | 15528 | 15549 | 15588 | 15618 | 15638 | 15697 |
| 15749 | 15752 | 15779 | 15797 | 15890 | 15891 | 15899 | 15922 | 15964 | 15970 | 15993 | 16013 |
| 16066 | 16088 | 16133 | 16136 | 16162 | 16179 | 16263 | 16264 | 16270 | 16287 | 16288 | 16325 |
| 16366 | 16432 | 16439 | 16456 | 16475 | 16503 | 16557 | 16572 | 16602 | 16617 | 16623 | 16627 |
| 16633 | 16638 | 16648 | 16672 | 16673 | 16702 | 16722 | 16745 | 16755 | 16777 | 16788 | 16820 |
| 16894 | 16936 | 17065 | 17083 | 17096 | 17125 | 17126 | 17138 | 17173 | 17311 | 17312 | 17320 |
| 17323 | 17363 | 17406 | 17465 | 17482 | 17490 | 17497 | 17533 | 17570 | 17571 | 17620 | 17628 |
| 17683 | 17697 | 17709 | 17717 | 17743 | 17748 | 17753 | 17754 | 17823 | 17831 | 17962 | 17972 |
| 18023 | 18025 | 18026 | 18053 | 18057 | 18058 | 18081 | 18091 | 18093 | 18097 | 18106 | 18194 |
| 18198 | 18203 | 18214 | 18215 | 18224 | 18231 | 18243 | 18246 | 18249 | 18279 | 18281 | 18283 |
| 18286 | 18287 | 18312 | 18331 | 18339 | 18376 | 18383 | 18392 | 18397 | 18400 | 18415 | 18428 |
| 18439 | 18520 | 18521 | 18536 | 18539 | 18541 | 18546 | 18547 | 18562 | 18563 | 18564 | 18591 |
| 18623 | 18624 | 18628 | 18629 | 18631 | 18640 | 18641 | 18642 | 18643 | 18659 | 18663 | 18665 |
| 18667 | 18672 | 18673 | 18689 | 18691 | 18699 | 18707 | 18708 | 18737 | 18738 | 18747 | 18755 |
| 18795 | 18806 | 18821 | 18845 | 18871 | 18883 | 18891 | 18905 | 18907 | 18927 | 18939 | 18951 |
| 18965 | 19032 | 19034 | 19046 | 19050 | 19053 | 19064 | 19098 | 19112 | 19113 | 19123 | 19125 |
| 19218 | 19236 | 19278 | 19279 | 19319 | 19354 | 19362 | 19363 | 19364 | 19385 | 19415 | 19437 |
| 19454 | 19457 | 19463 | 19467 | 19476 | 19592 | 19600 | 19650 | 19677 | 19720 | 19730 | 19732 |
| 19744 | 19773 | 19775 | 19792 | 19794 | 19795 | 19855 | 19865 | 19869 | 19898 | 19899 | 19941 |
| 19944 | 19945 | 19974 | 19983 | 20058 | 20059 | 20066 | 20079 | 20081 | 20091 | 20095 | 20096 |
| 20122 | 20143 | 20148 | 20149 | 20166 | 20175 | 20205 | 20224 | 20242 | 20246 | 20247 | 20287 |
| 20288 | 20291 | 20295 | 20301 | 20314 | 20315 | 20318 | 20320 | 20321 | 20337 | 20355 | 20367 |
| 20379 | 20382 | 20385 | 20394 | 20397 | 20401 | 20406 | 20409 | 20410 | 20484 | 20538 | 20571 |
| 20638 | 20667 | 20669 | 20738 | 20794 | 20819 | 20976 | 21030 | 21040 | 21055 | 21099 | 21100 |
| 21107 | 21138 | 21139 | 21169 | 21231 | 21237 | 21240 | 21251 | 21265 | 21279 | 21299 | 21347 |
| 21351 | 21360 | 21367 | 21371 | 21382 | 21404 | 21406 | 21438 | 21440 | 21447 | 21451 | 21453 |
| 21457 | 21493 | 21499 | 21502 | 21517 | 21523 | 21528 | 21537 | 21538 | 21547 | 21550 | 21554 |
| 21558 | 21561 | 21577 | 21581 | 21584 | 21599 | 21611 | 21643 | 21656 | 21660 | 21663 | 21667 |
| 21668 | 21677 | 21688 | 21692 | 21764 | 21830 | 21874 | 21875 | 21876 | 21877 | 21885 | 21887 |
| 21888 | 21890 | 21899 | 21901 | 21902 | 21903 | 21905 | 21910 | 21911 | 21912 | 21915 | 21927 |

TABLE 10A-continued

Homologous Recombination

| | | | | | | | | | | |
|---|---|---|---|---|---|---|---|---|---|---|
| 21928 | 21929 | 21932 | 21933 | 21935 | 21940 | 21944 | 21949 | 21955 | 21957 | 21961 | 21964 |
| 21969 | 21971 | 21974 | 21977 | 21978 | 21979 | 21981 | 21987 | 21989 | 22004 | 22007 | 22008 |
| 22016 | 22019 | 22020 | 22025 | 22030 | 22031 | 22050 | 22052 | 22054 | 22056 | 22057 | 22058 |
| 22059 | 22076 | 22079 | 22083 | 22085 | 22094 | 22099 | 22100 | 22101 | 22105 | 22108 | 22111 |
| 22112 | 22117 | 22118 | 22129 | 22136 | 22138 | 22142 | 22148 | 22151 | 22153 | 22155 | 22157 |
| 22158 | 22159 | 22160 | 22169 | 22170 | 22172 | 22175 | 22178 | 22182 | 22188 | 22190 | 22191 |
| 22192 | 22195 | 22199 | 22217 | 22218 | 22228 | 22235 | 22243 | 22250 | 22255 | 22256 | 22258 |
| 22262 | 22272 | 22274 | 22278 | 22279 | 22296 | 22299 | 22301 | 22305 | 22314 | 22315 | 22319 |
| 22320 | 22324 | 22330 | 22339 | 22341 | 22344 | 22348 | 22350 | 22356 | 22358 | 22360 | 22363 |
| 22364 | 22365 | 22368 | 22369 | 22375 | 22376 | 22383 | 22384 | 22385 | 22387 | 22388 | 22395 |
| 22396 | 22406 | 22422 | 22427 | 22445 | 22449 | 22450 | 22460 | 22463 | 22465 | 22466 | 22467 |
| 22469 | 22475 | 22484 | 22500 | 22502 | 22505 | 22507 | 22511 | 22513 | 22515 | 22520 | 22521 |
| 22522 | 22523 | 22528 | 22530 | 22531 | 22534 | 22535 | 22538 | 22540 | 22541 | 22545 | 22550 |
| 22554 | 22556 | 22557 | 22564 | 22565 | 22570 | 22571 | 22575 | 22576 | 22578 | 22579 | 22580 |
| 22588 | 22589 | 22590 | 22595 | 22600 | 22604 | 22605 | 22615 | 22629 | 22637 | 22638 | 22641 |
| 22642 | 22643 | 22647 | 22650 | 22654 | 22656 | 22660 | 22661 | 22662 | 22663 | 22665 | 22667 |
| 22668 | 22669 | 22671 | 22676 | 22692 | 22693 | 22701 | 22703 | 22704 | 22705 | 22706 | 22713 |
| 22714 | 22719 | 22721 | 22727 | 22728 | 22731 | 22734 | 22741 | 22742 | 22744 | 22752 | 22758 |
| 22760 | 22771 | 22774 | 22775 | 22795 | 22800 | 22808 | 22811 | 22812 | 22825 | 22826 | 22827 |
| 22829 | 22832 | 22840 | 22842 | 22847 | 22867 | 22868 | 22874 | 22894 | 22906 | 22923 | 22943 |
| 22944 | 22950 | 22966 | 22979 | 23010 | 23013 | 23045 | 23085 | 23101 | 23124 | 23127 | 23136 |
| 23137 | 23145 | 23146 | 23199 | 23250 | 23353 | 23357 | 23380 | 23386 | 23417 | 23458 | 23474 |
| 23475 | 23507 | 23514 | 23519 | 23617 | 23625 | | | | | | |

Table 10B SEQ ID NOs of Polynucleotides useful for improving Homologous Recombination

| | | | | | | | | | | |
|---|---|---|---|---|---|---|---|---|---|---|
| 23698 | 23712 | 23730 | 23732 | 23745 | 23757 | 23762 | 23792 | 23796 | 23803 | 23866 | 23906 |
| 23923 | 23950 | 23956 | 23957 | 23958 | 23959 | 23973 | 24033 | 24118 | 24140 | 24155 | 24204 |
| 24211 | 24212 | 24226 | 24302 | 24311 | 24339 | 24352 | 24384 | 24461 | 24473 | 24484 | 24504 |
| 24545 | 24547 | 24590 | 24591 | 24598 | 24604 | 24619 | 24626 | 24642 | 24645 | 24646 | 24648 |
| 24653 | 24654 | 24696 | 24703 | 24711 | 24735 | 24748 | 24770 | 24771 | 24782 | 24783 |
| 24802 | 24808 | 24828 | 24830 | 24838 | 24841 | 24871 | 24882 | 24884 | 24900 | 24906 | 24910 |
| 24914 | 24924 | 24925 | 24934 | 24935 | 24938 | 24940 | 24941 | 24958 | 24976 | 24988 | 25001 |
| 25004 | 25007 | 25017 | 25020 | 25025 | 25030 | 25034 | 25052 | 25053 | 25059 | 25060 | 25072 |
| 25078 | 25079 | 25082 | 25092 | 25094 | 25100 | 25101 | 25103 | 25107 | 25109 | 25111 | 25119 |
| 25123 | 25129 | 25134 | 25135 | 25139 | 25143 | 25144 | 25145 | 25146 | 25149 | 25153 | 25154 |
| 25155 | 25162 | 25164 | 25169 | 25170 | 25172 | 25174 | 25189 | 25196 | 25199 | 25201 | 25203 |
| 25204 | 25210 | 25215 | 25217 | 25221 | 25223 | 25224 | 25232 | 25233 | 25234 | 25238 | 25239 |
| 25244 | 25245 | 25248 | 25249 | 25254 | 25255 | 25256 | 25258 | 25263 | 25264 | 25268 | 25272 |
| 25273 | 25274 | 25278 | 25281 | 25282 | 25289 | 25307 | 25308 | 25312 | 25314 | 25316 | 25320 |
| 25325 | 25327 | 25331 | 25333 | 25334 | 25335 | 25339 | 25343 | 25344 | 25345 | 25353 | 25358 |
| 25359 | 25363 | 25364 | 25365 | 25369 | 25374 | 25378 | 25380 | 25387 | 25395 | 25396 | 25401 |
| 25402 | 25410 | 25416 | 25425 | 25435 | 25439 | 25442 | 25448 | 25450 | 25453 | 25454 |
| 25455 | 25458 | 25460 | 25464 | 25466 | 25469 | 25473 | 25474 | 25475 | 25477 | 25478 | 25480 |
| 25481 | 25486 | 25487 | 25491 | 25494 | 25495 | 25496 | 25497 | 25498 | 25509 | 25512 | 25514 |
| 25527 | 25530 | 25532 | 25535 | 25539 | 25540 | 25541 | 25542 | 25545 | 25547 | 25548 | 25550 |
| 25551 | 25557 | 25558 | 25560 | 25562 | 25568 | 25573 | 25575 | 25578 | 25587 | 25588 |
| 25595 | 25598 | 25600 | 25601 | 25602 | 25603 | 25606 | 25612 | 25621 | 25624 | 25626 | 25627 |
| 25628 | 25630 | 25632 | 25635 | 25637 | 25641 | 25644 | 25646 | 25648 | 25650 | 25652 | 25654 |
| 25655 | 25659 | 25663 | 25665 | 25666 | 25667 | 25668 | 25669 | 25672 | 25677 | 25678 | 25683 |
| 25688 | 25698 | 25699 | 25702 | 25703 | 25705 | 25707 | 25708 | 25709 | 25722 | 25723 | 25725 |
| 25726 | 25733 | 25736 | 25739 | 25741 | 25742 | 25743 | 25747 | 25748 | 25762 | 25768 | 25775 |
| 25776 | 25777 | 25779 | 25780 | 25781 | 25784 | 25787 | 25788 | 25790 | 25792 | 25793 | 25794 |
| 25795 | 25800 | 25801 | 25812 | 25815 | 25818 | 25819 | 25822 | 25823 | 25825 | 25828 | 25829 |
| 25832 | 25833 | 25836 | 25840 | 25844 | 25848 | 25850 | 25857 | 25859 | 25860 | 25865 | 25866 |
| 25867 | 25870 | 25872 | 25874 | 25875 | 25876 | 25877 | 25880 | 25883 | 25884 | 25890 | 25900 |
| 25902 | 25906 | 25908 | 25909 | 25911 | 25921 | 25923 | 25927 | 25929 | 25935 | 25940 | 25941 |
| 25943 | 25946 | 25948 | 25953 | 25958 | 25961 | 25962 | 25968 | 25973 | 25974 | 25975 | 25977 |
| 25982 | 25983 | 25985 | 25989 | 25994 | 25996 | 25999 | 26004 | 26005 | 26010 | 26011 | 26013 |
| 26016 | 26019 | 26031 | 26035 | 26040 | 26047 | 26048 | 26057 | 26058 | 26059 | 26063 | 26064 |
| 26066 | 26067 | 26072 | 26073 | 26076 | 26082 | 26083 | 26086 | 26088 | 26092 | 26099 | 26103 |
| 26106 | 26107 | 26121 | 26123 | 26124 | 26130 | 26136 | 26141 | 26143 | 26146 | 26147 | 26149 |
| 26151 | 26152 | 26154 | 26158 | 26164 | 26167 | 26170 | 26180 | 26185 | 26188 | 26192 | 26196 |
| 26203 | 26206 | 26207 | 26212 | 26219 | 26222 | 26226 | 26227 | 26228 | 26229 | 26230 | 26232 |
| 26235 | 26239 | 26242 | 26245 | 26248 | 26259 | 26260 | 26261 | 26264 | 26266 | 26268 | 26270 |
| 26272 | 26274 | 26281 | 26282 | 26358 | 26360 | 26373 | 26384 | 26396 | 26400 | 26433 | 26450 |
| 26459 | 26569 | 26573 | 26582 | 26598 | 26649 | 26688 | 26693 | 26698 | 26705 | 26740 | 26768 |
| 26771 | 26786 | 26788 | 26799 | 26801 | 26804 | 26810 | 26828 | 26833 | 26836 | 26851 | 26857 |
| 26870 | 26871 | 26879 | 26891 | 26894 | 26899 | 26900 | 26902 | 26909 | 26910 | 26925 | 26929 |
| 26930 | 26942 | 26945 | 26948 | 26952 | 26955 | 26959 | 26962 | 26974 | 26983 | 26984 | 26990 |
| 27001 | 27004 | 27006 | 27016 | 27023 | 27028 | 27029 | 27032 | 27036 | 27052 | 27053 | 27054 |
| 27056 | 27057 | 27061 | 27062 | 27087 | 27089 | 27090 | 27092 | 27095 | 27099 | 27100 | 27114 |
| 27119 | 27121 | 27125 | 27126 | 27130 | 27134 | 27135 | 27146 | 27151 | 27154 | 27159 | 27164 |
| 27174 | 27175 | 27178 | 27179 | 27184 | 27186 | 27189 | 27190 | 27196 | 27197 | 27212 | 27213 |
| 27223 | 27224 | 27226 | 27229 | 27233 | 27237 | 27239 | 27251 | 27254 | 27256 | 27259 | 27261 |
| 27264 | 27269 | 27271 | 27273 | 27280 | 27281 | 27285 | 27289 | 27291 | 27293 | 27300 | 27301 |
| 27309 | 27318 | 27320 | 27332 | 27338 | 27342 | 27351 | 27355 | 27359 | 27378 | 27380 | 27393 |

TABLE 10A-continued

Homologous Recombination

| | | | | | | | | | | | |
|---|---|---|---|---|---|---|---|---|---|---|---|
| 27399 | 27403 | 27405 | 27406 | 27407 | 27408 | 27422 | 27425 | 27428 | 27430 | 27437 | 27441 |
| 27442 | 27443 | 27450 | 27454 | 27462 | 27466 | 27476 | 27477 | 27478 | 27482 | 27483 | 27484 |
| 27488 | 27494 | 27500 | 27510 | 27513 | 27519 | 27528 | 27532 | 27534 | 27536 | 27538 | 27545 |
| 27548 | 27549 | 27550 | 27560 | 27561 | 27564 | 27565 | 27569 | 27570 | 27579 | 27584 | 27585 |
| 27597 | 27601 | 27604 | 27605 | 27610 | 27622 | 27629 | 27631 | 27634 | 27636 | 27637 | 27639 |
| 27640 | 27648 | 27649 | 27658 | 27667 | 27670 | 27675 | 27679 | 27694 | 27695 | 27697 | 27708 |
| 27710 | 27714 | 27715 | 27723 | 27724 | 27729 | 27737 | 27743 | 27744 | 27745 | 27750 | 27754 |
| 27756 | 27758 | 27759 | 27765 | 27775 | 27777 | 27778 | 27779 | 27786 | 27792 | 27796 | 27799 |
| 27806 | 27807 | 27809 | 27814 | 27819 | 27822 | 27825 | 27826 | 27828 | 27832 | 27834 | 27838 |
| 27842 | 27847 | 27857 | 27858 | 27861 | 27862 | 27877 | 27878 | 27880 | 27884 | 27895 | 27897 |
| 27899 | 27906 | 27912 | 27913 | 27918 | 27924 | 27926 | 27968 | 28020 | 28061 | 28065 | 28083 |
| 28123 | 28178 | 28183 | 28184 | 28205 | 28224 | 28257 | 28349 | 28461 | 28526 | 28554 | 28658 |
| 28661 | 28664 | 28675 | 28679 | 28682 | 28684 | 28686 | 28688 | 28690 | 28691 | 28706 | 28710 |
| 28711 | 28717 | 28718 | 28719 | 28722 | 28723 | 28730 | 28734 | 28740 | 28741 | 28745 | 28752 |
| 28753 | 28755 | 28763 | 28764 | 28766 | 28769 | 28772 | 28788 | 28789 | 28791 | 28793 | 28810 |
| 28811 | 28817 | 28818 | 28819 | 28821 | 28823 | 28824 | 28825 | 28826 | 28828 | 28833 | 28843 |
| 28846 | 28847 | 28869 | 28873 | 28877 | 28878 | 28879 | 28880 | 28882 | 28883 | 28884 | 28887 |
| 28888 | 28894 | 28905 | 28906 | 28911 | 28914 | 28921 | 28922 | 28923 | 28924 | 28930 | 28940 |
| 28941 | 28942 | 28948 | 28958 | 28979 | 28980 | 28990 | 28992 | 29002 | 29004 | 29029 | 29046 |
| 29047 | 29055 | 29056 | 29070 | 29071 | 29072 | 29075 | 29080 | 29084 | 29088 | 29090 | 29091 |
| 29092 | 29093 | 29107 | 29109 | 29111 | 29112 | 29114 | 29117 | 29122 | 29125 | 29134 | 29143 |
| 29144 | 29153 | 29155 | 29156 | 29159 | 29160 | 29162 | 29166 | 29172 | 29176 | 29186 |
| 29198 | 29204 | 29213 | 29220 | 29221 | 29225 | 29227 | 29238 | 29239 | 29241 | 29242 | 29246 |
| 29247 | 29248 | 29250 | 29253 | 29261 | 29264 | 29265 | 29267 | 29268 | 29272 | 29281 | 29283 |
| 29284 | 29285 | 29288 | 29290 | 29296 | 29307 | 29330 | 29334 | 29336 | 29340 | 29350 | 29362 |
| 29370 | 29372 | 29373 | 29376 | 29377 | 29378 | 29379 | 29381 | 29389 | 29391 | 29403 | 29407 |
| 29409 | 29426 | 29430 | 29431 | 29447 | 29449 | 29454 | 29467 | 29477 | 29478 | 29479 | 29480 |
| 29483 | 29501 | 29509 | 29515 | 29524 | 29525 | 29526 | 29533 | 29534 | 29535 | 29536 | 29540 |
| 29541 | 29548 | 29549 | 29550 | 29556 | 29557 | 29565 | 29567 | 29568 | 29569 | 29578 | 29588 |
| 29589 | 29591 | 29600 | 29607 | 29614 | 29615 | 29616 | 29617 | 29618 | 29630 | 29632 | 29640 |
| 29648 | 29649 | 29650 | 29651 | 29654 | 29655 | 29659 | 29660 | 29662 | 29664 | 29668 | 29674 |
| 29675 | 29676 | 29677 | 29681 | 29682 | 29684 | 29691 | 29692 | 29693 | 29712 | 29713 | 29714 |
| 29718 | 29724 | 29732 | 29741 | 29743 | 29749 | 29750 | 29751 | 29752 | 29761 | 29766 | 29768 |
| 29770 | 29779 | 29804 | 29805 | 29806 | 29808 | 29813 | 29819 | 29830 | 29831 | 29834 | 29837 |
| 29839 | 29842 | 29844 | 29848 | 29849 | 29857 | 29863 | 29872 | 29874 | 29876 | 29888 | 29891 |
| 29892 | 29896 | 29897 | 29899 | 29904 | 29916 | 29917 | 29923 | 29924 | 29929 | 29948 | 29954 |
| 29991 | 29994 | 30015 | 30028 | 30062 | 30081 | 30082 | 30084 | 30096 | 30113 | 30121 | 30125 |
| 30129 | 30140 | 30144 | 30148 | 30149 | 30152 | 30158 | 30159 | 30160 | 30161 | 30165 | 30169 |
| 30170 | 30185 | 30186 | 30206 | 30211 | 30214 | 30215 | 30216 | 30222 | 30223 | 30224 | 30260 |
| 30284 | 30287 | 30288 | 30289 | 30290 | 30292 | 30293 | 30299 | 30301 | 30308 | 30318 | 30319 |
| 30320 | 30352 | 30381 | 30387 | 30395 | 30412 | 30416 | 30418 | 30431 | 30432 | 30443 | 30444 |
| 30452 | 30457 | 30461 | 30478 | 30533 | 30538 | 30568 | 30569 | 30595 | 30596 | 30607 | 30610 |
| 30615 | 30616 | 30618 | 30633 | 30634 | 30660 | 30661 | 30662 | 30679 | 30680 | 30685 |
| 30699 | 30702 | 30714 | 30715 | 30716 | 30717 | 30723 | 30729 | 30776 | 30815 | 30819 | 30838 |
| 30882 | 30937 | 30942 | 30943 | 30964 | 30982 | 31009 | 31014 | 31108 | 31221 | 31285 | 31313 |
| 31428 | 31454 | 31467 | 31495 | 31508 | 31536 | 31552 | 31567 | 31576 | 31729 | 31746 | 31805 |
| 31820 | 31899 | 31904 | 31984 | 31985 | 32003 | 32012 | 32023 | 32150 | 32198 | 32230 |
| 32246 | 32257 | 32268 | 32297 | 32298 | 32343 | 32380 | 32432 | 32471 | 32495 | 32498 | 32511 |
| 32533 | 32576 | 32592 | 32643 | 32673 | 32679 | 32696 | 32712 | 32731 | 32758 | 32818 | 32821 |
| 32844 | 32866 | 32874 | 32881 | 32882 | 32886 | 32894 | 32906 | 32934 | 32962 | 33040 | 33119 |
| 33120 | 33121 | 33142 | 33147 | 33148 | 33173 | 33197 | 33266 | 33305 | 33338 | 33370 | 33383 |
| 33409 | 33426 | 33427 | 33442 | 33457 | 33561 | 33592 | 33638 | 33730 | 33759 | 33777 | 33813 |
| 33834 | 33835 | 33876 | 33893 | 33938 | 33958 | 33976 | 33978 | 34007 | 34011 | 34018 | 34051 |
| 34052 | 34074 | 34078 | 34087 | 34142 | 34320 | 34363 | 34393 | 34424 | 34454 | 34465 | 34533 |
| 34561 | 34566 | 34567 | 34605 | 34635 | 34641 | 34650 | 34651 | 34652 | 34702 | 34703 | 34734 |
| 34738 | 34767 | 34768 | 34769 | 34770 | 34787 | 34791 | 34820 | 34822 | 34832 | 34833 | 34837 |
| 34845 | 34846 | 34884 | 34886 | 34888 | 34907 | 34909 | 34911 | 34915 | 34930 | 34943 | 34953 |
| 34965 | 34972 | 34976 | 34977 | 34979 | 35000 | 35002 | 35003 | 35006 | 35009 | 35010 | 35011 |
| 35021 | 35028 | 35029 | 35035 | 35041 | 35110 | 35141 | 35197 | 35228 | 35248 | 35272 | 35341 |
| 35433 | 35445 | 35471 | 35487 | 35545 | 35571 | 35597 | 35617 | 35663 | 35738 | 35763 | 35820 |
| 35979 | 36012 | 36021 | 36041 | 36042 | 36044 | 36046 | 36050 | 36052 | 36056 | 36059 | 36065 |
| 36079 | 36093 | 36102 | 36119 | 36131 | 36149 | 36151 | 36161 | 36166 | 36177 | 36180 | 36184 |
| 36191 | 36195 | 36202 | 36209 | 36212 | 36218 | 36230 | 36234 | 36237 | 36239 | 36242 | 36244 |
| 36247 | 36251 | 36254 | 36258 | 36268 | 36269 | 36271 | 36274 | 36276 | 36286 | 36291 | 36296 |
| 36298 | 36302 | 36303 | 36319 | 36320 | 36324 | 36334 | 36336 | 36338 | 36341 | 36342 | 36343 |
| 36347 | 36354 | 36355 | 36356 | 36361 | 36364 | 36378 | 36389 | 36392 | 36394 | 36396 | 36404 |
| 36405 | 36416 | 36418 | 36427 | 36434 | 36436 | 36439 | 36441 | 36442 | 36463 | 36464 | 36474 |
| 36475 | 36482 | 36485 | 36492 | 36503 | 36509 | 36513 | 36525 | 36526 | 36539 | 36547 | 36553 |
| 36562 | 36565 | 36568 | 36571 | 36585 | 36593 | 36596 | 36602 | 36603 | 36617 | 36618 | 36622 |
| 36624 | 36630 | 36632 | 36635 | 36638 | 36651 | 36652 | 36653 | 36660 | 36668 | 36679 | 36680 |
| 36685 | 36694 | 36696 | 36708 | 36711 | 36728 | 36739 | 36745 | 36760 | 36764 | 36767 | 36769 |
| 36795 | 36797 | 36799 | 36803 | 36810 | 36817 | 36825 | 36828 | 36830 | 36836 | 36844 | 36852 |
| 36859 | 36861 | 36862 | 36863 | 36865 | 36873 | 36876 | 36894 | 36895 | 36900 | 36905 | 36906 |
| 36910 | 36915 | 36919 | 36935 | 36944 | 36955 | 36957 | 36958 | 36964 | 36985 | 36986 | 36989 |
| 36996 | 36999 | 37002 | 37008 | 37018 | 37025 | 37032 | 37051 | 37053 | 37054 | 37056 | 37061 |
| 37064 | 37065 | 37074 | 37085 | 37086 | 37088 | 37089 | 37091 | 37096 | 37098 | 37100 | 37108 |
| 37112 | 37128 | 37136 | 37139 | 37140 | 37141 | 37144 | 37146 | 37155 | 37164 | 37178 | 37188 |

TABLE 10A-continued

Homologous Recombination

| | | | | | | | | | | | |
|---|---|---|---|---|---|---|---|---|---|---|---|
| 37198 | 37199 | 37231 | 37232 | 37245 | 37259 | 37267 | 37276 | 37289 | 37324 | 37374 | 37388 |
| 37414 | 37445 | 37517 | 37527 | 37539 | 37545 | 37573 | 37578 | 37607 | 37641 | 37710 | 37743 |
| 37763 | 37795 | 37875 | 37876 | 37911 | 37916 | 37940 | 37942 | 37969 | 37992 | 37998 | 38245 |
| 38255 | 38257 | 38259 | 38314 | 38322 | 38340 | 38342 | 38432 | 38438 | 38454 | 38542 | 38572 |
| 38577 | 38586 | 38731 | 38773 | 38784 | 38813 | 38816 | 38832 | 38914 | 38917 | 38933 | 39017 |
| 39068 | 39071 | 39098 | 39116 | 39205 | 39206 | 39215 | 39236 | 39275 | 39305 | 39325 | 39384 |
| 39436 | 39439 | 39466 | 39484 | 39577 | 39578 | 39586 | 39609 | 39651 | 39657 | 39680 | 39700 |
| 39753 | 39775 | 39820 | 39823 | 39849 | 39866 | 39950 | 39951 | 39957 | 39974 | 39975 | 40012 |
| 40053 | 40119 | 40126 | 40143 | 40162 | 40190 | 40244 | 40259 | 40289 | 40304 | 40310 | 40314 |
| 40320 | 40325 | 40335 | 40359 | 40360 | 40389 | 40409 | 40432 | 40442 | 40464 | 40475 | 40507 |
| 40581 | 40623 | 40752 | 40770 | 40783 | 40812 | 40813 | 40825 | 40860 | 40998 | 40999 | 41007 |
| 41010 | 41050 | 41093 | 41152 | 41169 | 41177 | 41184 | 41220 | 41257 | 41258 | 41307 | 41315 |
| 41370 | 41384 | 41396 | 41404 | 41430 | 41435 | 41440 | 41441 | 41510 | 41518 | 41649 | 41659 |
| 41710 | 41712 | 41713 | 41740 | 41744 | 41745 | 41768 | 41778 | 41780 | 41784 | 41793 | 41881 |
| 41885 | 41890 | 41901 | 41902 | 41911 | 41918 | 41930 | 41933 | 41936 | 41966 | 41968 | 41970 |
| 41973 | 41974 | 41999 | 42018 | 42026 | 42063 | 42070 | 42079 | 42084 | 42087 | 42102 | 42115 |
| 42126 | 42207 | 42208 | 42223 | 42226 | 42228 | 42233 | 42234 | 42249 | 42250 | 42251 | 42278 |
| 42310 | 42311 | 42315 | 42316 | 42318 | 42327 | 42328 | 42329 | 42330 | 42346 | 42350 | 42352 |
| 42354 | 42359 | 42360 | 42376 | 42378 | 42386 | 42394 | 42395 | 42424 | 42425 | 42434 | 42442 |
| 42482 | 42493 | 42508 | 42532 | 42558 | 42570 | 42578 | 42592 | 42594 | 42614 | 42626 | 42638 |
| 42652 | 42719 | 42721 | 42733 | 42737 | 42740 | 42751 | 42785 | 42799 | 42800 | 42810 | 42812 |
| 42905 | 42923 | 42965 | 42966 | 43006 | 43041 | 43049 | 43050 | 43051 | 43072 | 43102 | 43124 |
| 43141 | 43144 | 43150 | 43154 | 43163 | 43279 | 43287 | 43337 | 43364 | 43407 | 43417 | 43419 |
| 43431 | 43460 | 43462 | 43479 | 43481 | 43482 | 43542 | 43552 | 43556 | 43585 | 43586 | 43628 |
| 43631 | 43632 | 43661 | 43670 | 43745 | 43746 | 43753 | 43766 | 43768 | 43778 | 43782 | 43783 |
| 43809 | 43830 | 43835 | 43836 | 43853 | 43862 | 43892 | 43911 | 43929 | 43933 | 43934 | 43974 |
| 43975 | 43978 | 43982 | 43988 | 44001 | 44002 | 44005 | 44007 | 44008 | 44024 | 44042 | 44054 |
| 44066 | 44069 | 44072 | 44081 | 44084 | 44088 | 44093 | 44096 | 44097 | 44171 | 44225 | 44258 |
| 44325 | 44354 | 44356 | 44425 | 44481 | 44506 | 44663 | 44717 | 44727 | 44742 | 44786 | 44787 |
| 44794 | 44825 | 44826 | 44856 | 44918 | 44924 | 44927 | 44938 | 44952 | 44966 | 44986 | 45034 |
| 45038 | 45047 | 45054 | 45058 | 45069 | 45091 | 45093 | 45125 | 45127 | 45134 | 45138 | 45140 |
| 45144 | 45180 | 45186 | 45189 | 45204 | 45210 | 45215 | 45224 | 45225 | 45234 | 45237 | 45241 |
| 45245 | 45248 | 45264 | 45268 | 45271 | 45286 | 45298 | 45330 | 45343 | 45347 | 45350 | 45354 |
| 45355 | 45364 | 45375 | 45379 | 45451 | 45517 | 45561 | 45562 | 45563 | 45564 | 45572 | 45574 |
| 45575 | 45577 | 45586 | 45588 | 45589 | 45590 | 45592 | 45597 | 45598 | 45599 | 45602 | 45614 |
| 45615 | 45616 | 45619 | 45620 | 45622 | 45627 | 45631 | 45636 | 45642 | 45644 | 45648 | 45651 |
| 45656 | 45658 | 45661 | 45664 | 45665 | 45666 | 45668 | 45674 | 45676 | 45691 | 45694 | 45695 |
| 45703 | 45706 | 45707 | 45712 | 45717 | 45718 | 45737 | 45739 | 45741 | 45743 | 45744 | 45745 |
| 45746 | 45763 | 45766 | 45770 | 45772 | 45781 | 45786 | 45787 | 45788 | 45792 | 45795 | 45798 |
| 45799 | 45804 | 45805 | 45816 | 45823 | 45825 | 45829 | 45835 | 45838 | 45840 | 45842 | 45844 |
| 45845 | 45846 | 45847 | 45856 | 45857 | 45859 | 45862 | 45865 | 45869 | 45875 | 45877 | 45878 |
| 45879 | 45882 | 45886 | 45904 | 45905 | 45915 | 45922 | 45930 | 45937 | 45942 | 45943 | 45945 |
| 45949 | 45959 | 45961 | 45965 | 45966 | 45983 | 45986 | 45992 | 46001 | 46002 | 46006 |
| 46007 | 46011 | 46017 | 46026 | 46028 | 46031 | 46035 | 46037 | 46043 | 46045 | 46047 | 46050 |
| 46051 | 46052 | 46055 | 46056 | 46062 | 46063 | 46070 | 46071 | 46072 | 46074 | 46075 | 46082 |
| 46083 | 46093 | 46109 | 46114 | 46132 | 46136 | 46137 | 46147 | 46150 | 46152 | 46153 | 46154 |
| 46156 | 46162 | 46171 | 46187 | 46189 | 46192 | 46194 | 46198 | 46200 | 46202 | 46207 | 46208 |
| 46209 | 46210 | 46215 | 46217 | 46218 | 46221 | 46222 | 46225 | 46227 | 46228 | 46232 | 46237 |
| 46241 | 46243 | 46244 | 46251 | 46252 | 46257 | 46258 | 46262 | 46263 | 46265 | 46266 | 46267 |
| 46275 | 46276 | 46277 | 46282 | 46287 | 46291 | 46292 | 46302 | 46316 | 46324 | 46325 | 46328 |
| 46329 | 46330 | 46334 | 46337 | 46341 | 46343 | 46347 | 46348 | 46349 | 46350 | 46352 | 46354 |
| 46355 | 46356 | 46358 | 46363 | 46379 | 46380 | 46388 | 46390 | 46391 | 46392 | 46393 | 46400 |
| 46401 | 46406 | 46408 | 46414 | 46415 | 46418 | 46421 | 46428 | 46429 | 46431 | 46439 | 46445 |
| 46447 | 46458 | 46461 | 46462 | 46482 | 46487 | 46495 | 46498 | 46499 | 46512 | 46513 | 46514 |
| 46516 | 46519 | 46527 | 46529 | 46534 | 46554 | 46555 | 46561 | 46581 | 46593 | 46610 | 46630 |
| 46631 | 46637 | 46653 | 46666 | 46697 | 46700 | 46732 | 46772 | 46788 | 46811 | 46814 | 46823 |
| 46824 | 46832 | 46833 | 46886 | 46937 | 47040 | 47044 | 47067 | 47073 | 47104 | 47145 | 47161 |
| 47162 | 47194 | 47201 | 47206 | 47304 | 47312 | | | | | | |

TABLE 11

Osmotic Tolerance

Table 11A SEQ ID NOs of Polypeptides useful for improving Osmotic Tolerance

| | | | | | | | | | | |
|---|---|---|---|---|---|---|---|---|---|---|
| 15 | 101 | 122 | 227 | 242 | 273 | 350 | 356 | 406 | 413 | 429 | 445 |
| 463 | 682 | 700 | 714 | 727 | 826 | 898 | 1132 | 1341 | 1385 | 1414 | 1432 |
| 1436 | 1443 | 1444 | 1462 | 1465 | 1513 | 1519 | 1532 | 1586 | 1597 | 1602 | 1616 |
| 1636 | 1645 | 1690 | 1701 | 1707 | 1733 | 1746 | 1750 | 1765 | 1783 | 1786 | 1810 |
| 1813 | 1881 | 1885 | 1945 | 1946 | 1947 | 1959 | 1985 | 2000 | 2035 | 2038 | 2046 |
| 2177 | 2178 | 2224 | 2228 | 2264 | 2271 | 2275 | 2304 | 2390 | 2396 | 2408 | 2410 |
| 2419 | 2420 | 2436 | 2477 | 2512 | 2516 | 2559 | 2566 | 2580 | 2642 | 2699 | 2867 |
| 2957 | 3012 | 3119 | 3141 | 3146 | 3157 | 3180 | 3198 | 3199 | 3212 | 3213 | 3244 |
| 3250 | 3288 | 3297 | 3302 | 3334 | 3387 | 3412 | 3413 | 3416 | 3455 | 3466 | 3472 |

TABLE 11-continued

Osmotic Tolerance

| 3549 | 3638 | 3699 | 3702 | 3744 | 3767 | 3797 | 3833 | 3850 | 3859 | 3861 | 3891 |
|---|---|---|---|---|---|---|---|---|---|---|---|
| 3917 | 3955 | 3962 | 4069 | 4080 | 4092 | 4105 | 4112 | 4141 | 4505 | 4726 | 4762 |
| 5164 | 5298 | 5469 | 5562 | 5647 | 5684 | 5704 | 5858 | 5927 | 5943 | 6030 | 6092 |
| 6219 | 6395 | 6457 | 6527 | 6614 | 6707 | 6729 | 6745 | 6752 | 6930 | 7263 | 7485 |
| 7521 | 7756 | 8140 | 8265 | 8319 | 8448 | 8453 | 8620 | 8658 | 8660 | 8778 | 9008 |
| 9043 | 9138 | 9153 | 9156 | 9580 | 9635 | 9812 | 9940 | 9973 | 9979 | 10025 | 10030 |
| 10031 | 10068 | 10104 | 10123 | 10137 | 10163 | 10177 | 10180 | 10296 | 10314 | 10336 | 10511 |
| 10534 | 10643 | 10978 | 11171 | 11249 | 11309 | 11570 | 11661 | 11997 | 12041 | 12211 | 12372 |
| 12374 | 12425 | 12445 | 12482 | 12508 | 12522 | 12537 | 12560 | 12572 | 12621 | 12636 | 12652 |
| 12675 | 12681 | 12684 | 12729 | 12747 | 12757 | 12792 | 12829 | 12860 | 12880 | 12935 | 12964 |
| 12973 | 13049 | 13068 | 13123 | 13124 | 13126 | 13179 | 13186 | 13218 | 13280 | 13283 | 13287 |
| 13295 | 13301 | 13326 | 13328 | 13382 | 13397 | 13573 | 13591 | 13713 | 13724 | 13788 | 13816 |
| 13817 | 13953 | 14046 | 14065 | 14075 | 14232 | 14371 | 14551 | 14610 | 14615 | 15040 | 15060 |
| 15120 | 15442 | 15653 | 15811 | 16038 | 16043 | 16190 | 16484 | 16515 | 16595 | 16608 | 16653 |
| 16728 | 16836 | 17159 | 17221 | 17234 | 17326 | 17442 | 17572 | 17615 | 17658 | 18015 | 18054 |
| 18072 | 18103 | 18327 | 18328 | 18329 | 18367 | 18432 | 18498 | 18519 | 18804 | 18978 | 19028 |
| 19086 | 19095 | 19133 | 19216 | 19222 | 19277 | 19399 | 19578 | 19931 | 19933 | 20023 | 20133 |
| 20243 | 20404 | 20449 | 20734 | 20739 | 20798 | 20801 | 20885 | 21137 | 21147 | 21148 | 21208 |
| 21215 | 21261 | 21267 | 21323 | 21329 | 21701 | 21872 | 21991 | 22025 | 22035 | 22036 | 22054 |
| 22076 | 22082 | 22102 | 22109 | 22148 | 22158 | 22190 | 22237 | 22255 | 22266 | 22275 | 22290 |
| 22306 | 22314 | 22335 | 22345 | 22350 | 22373 | 22385 | 22392 | 22422 | 22431 | 22442 | 22447 |
| 22515 | 22583 | 22602 | 22693 | 22701 | 22704 | 22738 | 22760 | 22767 | 22792 | 22799 | 22828 |
| 23057 | 23058 | 23064 | 23099 | 23157 | 23182 | 23188 | 23207 | 23213 | 23258 | 23321 | 23348 |
| 23367 | 23382 | 23479 | 23513 | 23516 | 23578 | 23604 | 23610 | 23621 | 23670 | | |

Table 11B SEQ ID NOs of Polynucleotides useful for improving Osmotic Tolerance

| 23702 | 23788 | 23809 | 23914 | 23929 | 23960 | 24037 | 24043 | 24093 | 24100 | 24116 | 24132 |
|---|---|---|---|---|---|---|---|---|---|---|---|
| 24150 | 24369 | 24387 | 24401 | 24414 | 24513 | 24585 | 24819 | 25028 | 25072 | 25101 | 25119 |
| 25123 | 25130 | 25131 | 25149 | 25152 | 25200 | 25206 | 25219 | 25273 | 25284 | 25289 | 25303 |
| 25323 | 25332 | 25377 | 25388 | 25394 | 25420 | 25433 | 25437 | 25452 | 25470 | 25473 | 25497 |
| 25500 | 25568 | 25572 | 25632 | 25633 | 25634 | 25646 | 25672 | 25687 | 25722 | 25725 | 25733 |
| 25864 | 25865 | 25911 | 25915 | 25951 | 25958 | 25962 | 25991 | 26077 | 26083 | 26095 | 26097 |
| 26106 | 26107 | 26123 | 26164 | 26199 | 26203 | 26246 | 26253 | 26267 | 26329 | 26386 | 26554 |
| 26644 | 26699 | 26806 | 26828 | 26833 | 26844 | 26867 | 26885 | 26886 | 26899 | 26900 | 26931 |
| 26937 | 26975 | 26984 | 26989 | 27021 | 27074 | 27099 | 27100 | 27103 | 27142 | 27153 | 27159 |
| 27236 | 27325 | 27386 | 27389 | 27431 | 27454 | 27484 | 27520 | 27537 | 27546 | 27548 | 27578 |
| 27604 | 27642 | 27649 | 27756 | 27767 | 27779 | 27792 | 27799 | 27828 | 28192 | 28413 | 28449 |
| 28851 | 28985 | 29156 | 29249 | 29334 | 29371 | 29391 | 29545 | 29614 | 29630 | 29717 | 29779 |
| 29906 | 30082 | 30144 | 30214 | 30301 | 30394 | 30416 | 30432 | 30439 | 30617 | 30950 | 31172 |
| 31208 | 31443 | 31827 | 31952 | 32006 | 32135 | 32140 | 32307 | 32345 | 32347 | 32465 | 32695 |
| 32730 | 32825 | 32840 | 32843 | 33267 | 33322 | 33499 | 33627 | 33660 | 33666 | 33712 | 33717 |
| 33718 | 33755 | 33791 | 33810 | 33824 | 33850 | 33864 | 33867 | 33983 | 34001 | 34023 | 34198 |
| 34221 | 34330 | 34665 | 34858 | 34936 | 34996 | 35257 | 35348 | 35684 | 35728 | 35898 | 36059 |
| 36061 | 36112 | 36132 | 36169 | 36195 | 36209 | 36224 | 36247 | 36259 | 36308 | 36323 | 36339 |
| 36362 | 36368 | 36371 | 36416 | 36434 | 36444 | 36479 | 36516 | 36547 | 36567 | 36622 | 36651 |
| 36660 | 36736 | 36755 | 36810 | 36811 | 36813 | 36866 | 36873 | 36905 | 36967 | 36970 | 36974 |
| 36982 | 36988 | 37013 | 37015 | 37069 | 37084 | 37260 | 37278 | 37400 | 37411 | 37475 | 37503 |
| 37504 | 37640 | 37733 | 37752 | 37762 | 37919 | 38058 | 38238 | 38297 | 38302 | 38727 | 38747 |
| 38807 | 39129 | 39340 | 39498 | 39725 | 39730 | 39877 | 40171 | 40206 | 40282 | 40295 | 40340 |
| 40415 | 40523 | 40846 | 40908 | 40921 | 41013 | 41129 | 41259 | 41302 | 41345 | 41702 | 41741 |
| 41759 | 41790 | 42014 | 42015 | 42016 | 42054 | 42119 | 42185 | 42206 | 42491 | 42665 | 42715 |
| 42773 | 42782 | 42820 | 42903 | 42909 | 42964 | 43086 | 43265 | 43618 | 43620 | 43710 | 43820 |
| 43930 | 44091 | 44136 | 44421 | 44426 | 44485 | 44488 | 44572 | 44824 | 44834 | 44835 | 44895 |
| 44902 | 44948 | 44954 | 45010 | 45016 | 45388 | 45559 | 45678 | 45712 | 45722 | 45723 | 45741 |
| 45763 | 45769 | 45789 | 45796 | 45835 | 45845 | 45877 | 45924 | 45942 | 45953 | 45962 | 45977 |
| 45993 | 46001 | 46022 | 46032 | 46037 | 46060 | 46072 | 46079 | 46109 | 46118 | 46129 | 46134 |
| 46202 | 46270 | 46289 | 46380 | 46388 | 46391 | 46425 | 46447 | 46454 | 46479 | 46486 | 46515 |
| 46744 | 46745 | 46751 | 46786 | 46844 | 46869 | 46875 | 46894 | 46900 | 46945 | 47008 | 47035 |
| 47054 | 47069 | 47166 | 47200 | 47203 | 47265 | 47291 | 47297 | 47308 | 47357 | | |

TABLE 12

Pathogen/Pest Tolerance

Table 12A SEQ ID NOs of Polypeptides useful for improving Pathogen/Pest Tolerance

| 20 | 67 | 71 | 98 | 102 | 126 | 168 | 176 | 189 | 191 | 195 | 221 |
|---|---|---|---|---|---|---|---|---|---|---|---|
| 239 | 245 | 298 | 308 | 309 | 330 | 338 | 351 | 365 | 373 | 414 | 509 |
| 539 | 555 | 556 | 558 | 566 | 571 | 585 | 592 | 611 | 616 | 621 | 631 |
| 645 | 648 | 734 | 750 | 777 | 838 | 955 | 956 | 957 | 1022 | 1048 | 1050 |
| 1054 | 1084 | 1110 | 1157 | 1161 | 1195 | 1205 | 1253 | 1275 | 1300 | 1311 | 1333 |
| 1358 | 1394 | 1401 | 1403 | 1409 | 1411 | 1417 | 1418 | 1419 | 1423 | 1425 | 1441 |
| 1447 | 1453 | 1454 | 1459 | 1469 | 1479 | 1486 | 1488 | 1494 | 1507 | 1508 | 1517 |

TABLE 12-continued

| \multicolumn{12}{c}{Pathogen/Pest Tolerance} |
|---|---|---|---|---|---|---|---|---|---|---|---|
| 1535 | 1544 | 1546 | 1571 | 1573 | 1590 | 1596 | 1599 | 1601 | 1623 | 1636 | 1639 |
| 1657 | 1661 | 1665 | 1685 | 1691 | 1697 | 1716 | 1724 | 1725 | 1730 | 1732 | 1751 |
| 1754 | 1756 | 1759 | 1760 | 1769 | 1772 | 1773 | 1786 | 1809 | 1814 | 1821 | 1822 |
| 1826 | 1827 | 1831 | 1846 | 1855 | 1872 | 1877 | 1880 | 1885 | 1892 | 1893 | 1899 |
| 1910 | 1914 | 1926 | 1929 | 1930 | 1931 | 1935 | 1943 | 1951 | 1953 | 1956 | 1962 |
| 1963 | 1979 | 1985 | 1987 | 1989 | 2004 | 2007 | 2018 | 2051 | 2057 | 2059 | 2067 |
| 2071 | 2079 | 2083 | 2089 | 2095 | 2100 | 2105 | 2107 | 2115 | 2121 | 2126 | 2131 |
| 2146 | 2157 | 2158 | 2180 | 2184 | 2192 | 2205 | 2212 | 2226 | 2230 | 2233 | 2243 |
| 2244 | 2249 | 2252 | 2253 | 2254 | 2260 | 2262 | 2264 | 2269 | 2272 | 2274 | 2279 |
| 2286 | 2294 | 2301 | 2306 | 2308 | 2315 | 2321 | 2333 | 2338 | 2341 | 2345 | 2352 |
| 2355 | 2357 | 2369 | 2373 | 2384 | 2387 | 2390 | 2392 | 2397 | 2402 | 2406 | 2419 |
| 2420 | 2436 | 2457 | 2464 | 2476 | 2477 | 2481 | 2482 | 2483 | 2490 | 2494 | 2499 |
| 2503 | 2510 | 2516 | 2517 | 2518 | 2530 | 2531 | 2536 | 2538 | 2540 | 2549 | 2554 |
| 2566 | 2569 | 2570 | 2579 | 2588 | 2638 | 2653 | 2683 | 2702 | 2708 | 2741 | 2750 |
| 2757 | 2762 | 2769 | 2770 | 2791 | 2798 | 2805 | 2806 | 2857 | 2862 | 2866 | 2878 |
| 2902 | 2925 | 2936 | 2958 | 3018 | 3026 | 3050 | 3061 | 3066 | 3074 | 3079 | 3088 |
| 3096 | 3100 | 3105 | 3109 | 3115 | 3120 | 3121 | 3126 | 3146 | 3150 | 3156 | 3166 |
| 3169 | 3170 | 3171 | 3172 | 3173 | 3175 | 3182 | 3185 | 3202 | 3203 | 3207 | 3216 |
| 3217 | 3221 | 3226 | 3231 | 3238 | 3240 | 3259 | 3266 | 3269 | 3273 | 3282 | 3284 |
| 3288 | 3292 | 3302 | 3307 | 3312 | 3342 | 3344 | 3345 | 3350 | 3353 | 3354 | 3355 |
| 3365 | 3389 | 3394 | 3404 | 3410 | 3413 | 3422 | 3425 | 3426 | 3427 | 3430 | 3431 |
| 3452 | 3461 | 3471 | 3481 | 3483 | 3485 | 3488 | 3489 | 3495 | 3520 | 3525 | 3527 |
| 3542 | 3558 | 3563 | 3583 | 3597 | 3599 | 3602 | 3615 | 3618 | 3619 | 3632 | 3634 |
| 3655 | 3658 | 3661 | 3694 | 3700 | 3703 | 3715 | 3722 | 3741 | 3775 | 3778 | 3783 |
| 3785 | 3788 | 3792 | 3797 | 3798 | 3803 | 3808 | 3813 | 3843 | 3845 | 3851 | 3868 |
| 3872 | 3877 | 3879 | 3886 | 3891 | 3907 | 3911 | 3912 | 3913 | 3917 | 3934 | 3938 |
| 3955 | 3966 | 3979 | 3983 | 3990 | 3993 | 3998 | 4001 | 4002 | 4016 | 4018 | 4031 |
| 4032 | 4041 | 4043 | 4075 | 4078 | 4083 | 4086 | 4091 | 4098 | 4100 | 4105 | 4111 |
| 4117 | 4130 | 4145 | 4146 | 4154 | 4161 | 4166 | 4169 | 4173 | 4209 | 4216 | 4225 |
| 4228 | 4240 | 4337 | 4361 | 4369 | 4391 | 4397 | 4413 | 4444 | 4450 | 4493 | 4663 |
| 4664 | 4689 | 4713 | 4804 | 4807 | 4833 | 4849 | 4874 | 4885 | 4897 | 4955 | 4968 |
| 4975 | 4976 | 4989 | 5007 | 5008 | 5012 | 5015 | 5035 | 5045 | 5050 | 5062 | 5065 |
| 5067 | 5068 | 5070 | 5071 | 5072 | 5073 | 5074 | 5093 | 5098 | 5103 | 5105 | 5116 |
| 5117 | 5118 | 5126 | 5134 | 5154 | 5155 | 5157 | 5164 | 5176 | 5177 | 5184 | 5202 |
| 5208 | 5213 | 5217 | 5225 | 5228 | 5230 | 5238 | 5239 | 5241 | 5244 | 5245 | 5245 |
| 5247 | 5248 | 5249 | 5250 | 5251 | 5252 | 5275 | 5277 | 5286 | 5294 | 5300 | 5302 |
| 5306 | 5313 | 5314 | 5317 | 5332 | 5333 | 5335 | 5340 | 5343 | 5344 | 5348 | 5349 |
| 5350 | 5351 | 5352 | 5353 | 5354 | 5355 | 5358 | 5361 | 5371 | 5374 | 5379 | 5382 |
| 5383 | 5390 | 5394 | 5397 | 5398 | 5408 | 5411 | 5415 | 5419 | 5423 | 5446 | 5448 |
| 5452 | 5469 | 5472 | 5473 | 5491 | 5494 | 5499 | 5515 | 5535 | 5542 | 5545 | 5546 |
| 5550 | 5551 | 5562 | 5583 | 5586 | 5587 | 5590 | 5592 | 5593 | 5606 | 5611 | 5625 |
| 5626 | 5638 | 5657 | 5658 | 5659 | 5660 | 5684 | 5695 | 5698 | 5699 | 5700 | 5709 |
| 5714 | 5717 | 5725 | 5738 | 5749 | 5753 | 5756 | 5775 | 5784 | 5785 | 5789 |  |
| 5795 | 5799 | 5804 | 5814 | 5827 | 5837 | 5850 | 5855 | 5864 | 5865 | 5866 | 5879 |
| 5903 | 5927 | 5935 | 5936 | 5937 | 5951 | 5961 | 5965 | 5968 | 5990 | 5998 | 6007 |
| 6008 | 6013 | 6016 | 6026 | 6030 | 6036 | 6044 | 6062 | 6068 | 6083 | 6088 | 6089 |
| 6095 | 6096 | 6115 | 6126 | 6142 | 6143 | 6144 | 6160 | 6163 | 6198 | 6210 | 6223 |
| 6229 | 6231 | 6233 | 6257 | 6258 | 6259 | 6260 | 6264 | 6265 | 6266 | 6285 | 6286 |
| 6287 | 6309 | 6310 | 6314 | 6329 | 6334 | 6336 | 6337 | 6341 | 6343 | 6358 | 6359 |
| 6363 | 6374 | 6381 | 6402 | 6403 | 6404 | 6405 | 6416 | 6417 | 6418 | 6421 | 6427 |
| 6436 | 6441 | 6442 | 6443 | 6451 | 6452 | 6454 | 6455 | 6456 | 6457 | 6459 | 6461 |
| 6462 | 6476 | 6509 | 6510 | 6512 | 6514 | 6515 | 6517 | 6518 | 6520 | 6531 | 6532 |
| 6535 | 6536 | 6538 | 6539 | 6543 | 6546 | 6548 | 6549 | 6560 | 6567 | 6593 | 6595 |
| 6610 | 6611 | 6619 | 6622 | 6623 | 6643 | 6645 | 6672 | 6675 | 6680 | 6681 | 6695 |
| 6702 | 6703 | 6706 | 6728 | 6734 | 6740 | 6773 | 6776 | 6777 | 6780 | 6792 | 6795 |
| 6798 | 6799 | 6802 | 6810 | 6828 | 6836 | 6842 | 6850 | 6851 | 6854 | 6869 | 6870 |
| 6879 | 6880 | 6886 | 6920 | 6945 | 6959 | 6960 | 6962 | 6977 | 6981 | 6982 | 6991 |
| 6992 | 7000 | 7002 | 7003 | 7004 | 7006 | 7011 | 7024 | 7092 | 7115 | 7123 | 7146 |
| 7152 | 7169 | 7203 | 7210 | 7252 | 7422 | 7423 | 7432 | 7448 | 7473 | 7563 | 7566 |
| 7592 | 7608 | 7634 | 7643 | 7655 | 7713 | 7726 | 7794 | 7799 | 7831 | 7837 | 7908 |
| 7959 | 7992 | 8000 | 8024 | 8039 | 8064 | 8066 | 8082 | 8096 | 8100 | 8128 | 8159 |
| 8177 | 8219 | 8241 | 8289 | 8292 | 8311 | 8375 | 8376 | 8381 | 8434 | 8462 | 8489 |
| 8511 | 8575 | 8578 | 8615 | 8707 | 8792 | 8897 | 8902 | 8907 | 8915 | 8922 | 8932 |
| 8969 | 9004 | 9010 | 9018 | 9029 | 9035 | 9112 | 9124 | 9135 | 9140 | 9160 | 9161 |
| 9166 | 9191 | 9196 | 9203 | 9204 | 9205 | 9270 | 9328 | 9347 | 9353 | 9374 | 9384 |
| 9417 | 9440 | 9459 | 9493 | 9506 | 9522 | 9529 | 9553 | 9589 | 9616 | 9654 | 9656 |
| 9696 | 9700 | 9707 | 9717 | 9794 | 9806 | 9881 | 9925 | 9928 | 9961 | 9982 | 9983 |
| 10001 | 10018 | 10026 | 10058 | 10073 | 10143 | 10157 | 10159 | 10172 | 10178 | 10183 | 10234 |
| 10236 | 10239 | 10240 | 10242 | 10243 | 10244 | 10249 | 10268 | 10286 | 10297 | 10319 | 10368 |
| 10381 | 10398 | 10440 | 10443 | 10446 | 10514 | 10515 | 10521 | 10602 | 10608 | 10615 | 10623 |
| 10670 | 10676 | 10687 | 10797 | 10800 | 10802 | 10827 | 10845 | 10854 | 10899 | 10922 | 10929 |
| 10942 | 10985 | 11014 | 11032 | 11047 | 11088 | 11135 | 11146 | 11150 | 11154 | 11178 |  |
| 11200 | 11202 | 11222 | 11282 | 11298 | 11313 | 11347 | 11351 | 11352 | 11364 | 11365 | 11366 |
| 11371 | 11393 | 11483 | 11498 | 11506 | 11578 | 11590 | 11594 | 11597 | 11612 | 11629 | 11632 |
| 11681 | 11704 | 11710 | 11748 | 11768 | 11795 | 11834 | 11839 | 11920 | 11976 | 11978 | 11982 |
| 11985 | 12006 | 12023 | 12042 | 12062 | 12086 | 12112 | 12275 | 12282 | 12291 | 12304 | 12316 |
| 12332 | 12333 | 12348 | 12349 | 12366 | 12372 | 12390 | 12393 | 12401 | 12408 | 12414 | 12422 |

TABLE 12-continued

| Pathogen/Pest Tolerance | | | | | | | | | | | |
|---|---|---|---|---|---|---|---|---|---|---|---|
| 12426 | 12427 | 12430 | 12437 | 12449 | 12451 | 12453 | 12468 | 12477 | 12480 | 12496 | 12503 |
| 12509 | 12516 | 12531 | 12556 | 12566 | 12598 | 12611 | 12613 | 12643 | 12655 | 12683 | 12693 |
| 12702 | 12708 | 12713 | 12717 | 12729 | 12730 | 12741 | 12747 | 12750 | 12778 | 12786 | 12788 |
| 12802 | 12808 | 12828 | 12838 | 12849 | 12857 | 12866 | 12871 | 12874 | 12887 | 12894 | 12902 |
| 12906 | 12916 | 12918 | 12923 | 12937 | 12938 | 12949 | 12987 | 12990 | 12995 | 13011 | 13040 |
| 13054 | 13057 | 13072 | 13073 | 13074 | 13090 | 13091 | 13092 | 13099 | 13102 | 13106 | 13108 |
| 13136 | 13140 | 13146 | 13167 | 13179 | 13188 | 13195 | 13197 | 13203 | 13204 | 13212 | 13225 |
| 13230 | 13233 | 13239 | 13240 | 13242 | 13247 | 13256 | 13257 | 13258 | 13271 | 13277 | 13287 |
| 13295 | 13304 | 13319 | 13324 | 13327 | 13331 | 13333 | 13338 | 13365 | 13371 | 13379 | 13387 |
| 13393 | 13406 | 13421 | 13429 | 13432 | 13434 | 13435 | 13488 | 13491 | 13540 | 13554 | 13558 |
| 13614 | 13615 | 13662 | 13666 | 13688 | 13707 | 13709 | 13712 | 13722 | 13739 | 13744 | 13749 |
| 13764 | 13770 | 13825 | 13906 | 13955 | 13980 | 13994 | 14009 | 14055 | 14061 | 14063 | 14067 |
| 14131 | 14145 | 14194 | 14242 | 14265 | 14266 | 14322 | 14384 | 14385 | 14403 | 14404 | 14431 |
| 14449 | 14501 | 14510 | 14526 | 14529 | 14534 | 14543 | 14615 | 14644 | 14696 | 14747 | 14769 |
| 14785 | 14795 | 14810 | 14832 | 14847 | 14848 | 14849 | 14894 | 14920 | 14962 | 14980 | 14983 |
| 15016 | 15020 | 15037 | 15038 | 15047 | 15058 | 15060 | 15087 | 15109 | 15177 | 15225 | 15247 |
| 15310 | 15339 | 15345 | 15358 | 15364 | 15365 | 15366 | 15386 | 15387 | 15389 | 15409 | 15418 |
| 15431 | 15445 | 15447 | 15451 | 15452 | 15453 | 15499 | 15507 | 15508 | 15517 | 15524 | 15543 |
| 15562 | 15592 | 15599 | 15605 | 15631 | 15642 | 15647 | 15648 | 15649 | 15650 | 15651 | 15652 |
| 15654 | 15655 | 15656 | 15659 | 15676 | 15706 | 15712 | 15725 | 15731 | 15732 | 15754 | 15755 |
| 15757 | 15777 | 15786 | 15800 | 15813 | 15815 | 15819 | 15820 | 15821 | 15870 | 15879 | 15880 |
| 15889 | 15895 | 15915 | 15935 | 15951 | 15968 | 15976 | 15980 | 16006 | 16017 | 16023 | 16024 |
| 16025 | 16026 | 16027 | 16028 | 16029 | 16030 | 16031 | 16033 | 16034 | 16035 | 16036 | 16037 |
| 16039 | 16041 | 16042 | 16045 | 16046 | 16047 | 16067 | 16096 | 16101 | 16110 | 16116 | 16117 |
| 16140 | 16141 | 16168 | 16182 | 16195 | 16197 | 16201 | 16202 | 16245 | 16252 | 16260 | 16268 |
| 16286 | 16303 | 16315 | 16330 | 16333 | 16340 | 16360 | 16370 | 16391 | 16410 | 16420 | 16421 |
| 16426 | 16429 | 16435 | 16450 | 16453 | 16457 | 16463 | 16530 | 16579 | 16622 | 16635 | 16671 |
| 16715 | 16732 | 16824 | 16828 | 16834 | 16849 | 16866 | 16891 | 16920 | 16934 | 16953 | 16970 |
| 16990 | 17020 | 17042 | 17054 | 17066 | 17082 | 17100 | 17101 | 17141 | 17158 | 17183 | 17220 |
| 17268 | 17282 | 17294 | 17304 | 17318 | 17373 | 17375 | 17376 | 17386 | 17467 | 17491 | 17492 |
| 17514 | 17521 | 17569 | 17576 | 17593 | 17597 | 17624 | 17627 | 17682 | 17688 | 17710 |
| 17724 | 17765 | 17797 | 17802 | 17826 | 17828 | 17844 | 17874 | 17875 | 17879 | 17889 | 17890 |
| 17894 | 17915 | 17919 | 17926 | 17930 | 17937 | 17945 | 17948 | 17969 | 17981 | 18030 | 18031 |
| 18035 | 18048 | 18049 | 18058 | 18063 | 18067 | 18070 | 18071 | 18073 | 18074 | 18075 | 18076 |
| 18077 | 18078 | 18079 | 18080 | 18133 | 18134 | 18172 | 18180 | 18200 | 18203 | 18260 | 18290 |
| 18319 | 18341 | 18348 | 18379 | 18417 | 18442 | 18448 | 18460 | 18473 | 18474 | 18475 | 18492 |
| 18540 | 18562 | 18590 | 18628 | 18629 | 18641 | 18643 | 18665 | 18667 | 18749 | 18772 | 18773 |
| 18795 | 18796 | 18800 | 18824 | 18854 | 18882 | 18886 | 18892 | 18913 | 18914 | 18936 | 18985 |
| 18992 | 18993 | 18999 | 19000 | 19052 | 19109 | 19111 | 19123 | 19132 | 19135 | 19137 | 19140 |
| 19141 | 19148 | 19153 | 19162 | 19170 | 19186 | 19192 | 19195 | 19205 | 19209 | 19217 | 19241 |
| 19247 | 19254 | 19264 | 19266 | 19267 | 19270 | 19284 | 19299 | 19320 | 19323 | 19335 | 19349 |
| 19353 | 19374 | 19375 | 19382 | 19389 | 19402 | 19403 | 19413 | 19430 | 19432 | 19434 | 19443 |
| 19452 | 19462 | 19463 | 19467 | 19475 | 19515 | 19535 | 19537 | 19553 | 19568 | 19579 | 19591 |
| 19596 | 19607 | 19618 | 19625 | 19629 | 19725 | 19734 | 19762 | 19772 | 19779 | 19780 | 19789 |
| 19791 | 19795 | 19826 | 19842 | 19846 | 19852 | 19878 | 19887 | 19909 | 19916 | 19979 | 19989 |
| 20021 | 20033 | 20047 | 20114 | 20115 | 20117 | 20171 | 20192 | 20211 | 20216 | 20217 | 20221 |
| 20232 | 20264 | 20291 | 20294 | 20320 | 20341 | 20366 | 20376 | 20488 | 20521 | 20562 |
| 20607 | 20627 | 20642 | 20645 | 20653 | 20654 | 20784 | 20797 | 20819 | 20848 | 20872 | 20896 |
| 20911 | 20935 | 20942 | 20947 | 20953 | 20957 | 20988 | 20989 | 21005 | 21007 | 21052 | 21076 |
| 21098 | 21109 | 21121 | 21201 | 21218 | 21222 | 21223 | 21268 | 21292 | 21347 | 21351 | 21394 |
| 21406 | 21442 | 21475 | 21528 | 21547 | 21549 | 21561 | 21587 | 21600 | 21619 | 21632 | 21660 |
| 21711 | 21726 | 21775 | 21798 | 21807 | 21823 | 21825 | 21850 | 21879 | 21880 | 21881 | 21892 |
| 21894 | 21909 | 21929 | 21943 | 21946 | 21948 | 21951 | 21961 | 21962 | 21969 | 21971 | 21980 |
| 21982 | 21990 | 21994 | 22000 | 22010 | 22011 | 22013 | 22016 | 22026 | 22028 | 22029 | 22034 |
| 22037 | 22040 | 22050 | 22054 | 22055 | 22064 | 22066 | 22070 | 22071 | 22077 | 22078 | 22086 |
| 22094 | 22096 | 22098 | 22109 | 22111 | 22113 | 22123 | 22124 | 22126 | 22131 | 22135 | 22139 |
| 22140 | 22141 | 22144 | 22158 | 22166 | 22167 | 22176 | 22177 | 22190 | 22194 | 22195 | 22197 |
| 22202 | 22206 | 22207 | 22220 | 22226 | 22227 | 22229 | 22233 | 22236 | 22237 | 22244 | 22252 |
| 22266 | 22279 | 22281 | 22287 | 22293 | 22296 | 22297 | 22298 | 22314 | 22322 | 22323 | 22328 |
| 22340 | 22350 | 22351 | 22352 | 22367 | 22371 | 22374 | 22381 | 22397 | 22399 | 22406 | 22407 |
| 22408 | 22433 | 22436 | 22470 | 22490 | 22493 | 22498 | 22512 | 22515 | 22527 | 22532 | 22538 |
| 22545 | 22546 | 22555 | 22560 | 22581 | 22590 | 22595 | 22599 | 22603 | 22606 | 22614 | 22616 |
| 22619 | 22640 | 22642 | 22644 | 22645 | 22646 | 22652 | 22681 | 22682 | 22688 | 22689 | 22690 |
| 22701 | 22705 | 22706 | 22710 | 22724 | 22725 | 22726 | 22727 | 22728 | 22739 | 22755 | 22759 |
| 22772 | 22775 | 22782 | 22786 | 22791 | 22793 | 22797 | 22805 | 22806 | 22807 | 22808 | 22816 |
| 22848 | 22868 | 22894 | 22897 | 22936 | 22966 | 23003 | 23021 | 23049 | 23050 | 23071 | 23110 |
| 23129 | 23224 | 23272 | 23290 | 23313 | 23416 | 23430 | 23431 | 23463 | 23500 | 23504 | 23508 |
| 23533 | 23544 | 23567 | 23583 | 23593 | 23608 | 23633 | 23673 | | | | |

| Table 12B SEQ ID NOs of Polynucleotides useful for improving Pathogen/Pest Tolerance | | | | | | | | | | | |
|---|---|---|---|---|---|---|---|---|---|---|---|
| 23707 | 23754 | 23758 | 23785 | 23789 | 23813 | 23855 | 23863 | 23876 | 23878 | 23882 | 23908 |
| 23926 | 23932 | 23985 | 23995 | 23996 | 24017 | 24025 | 24038 | 24052 | 24060 | 24101 | 24196 |
| 24226 | 24242 | 24243 | 24245 | 24253 | 24258 | 24272 | 24279 | 24298 | 24303 | 24308 | 24318 |
| 24332 | 24335 | 24421 | 24437 | 24464 | 24525 | 24642 | 24643 | 24644 | 24709 | 24735 | 24737 |
| 24741 | 24771 | 24797 | 24844 | 24848 | 24882 | 24892 | 24940 | 24962 | 24987 | 24998 | 25020 |
| 25045 | 25081 | 25088 | 25090 | 25096 | 25098 | 25104 | 25105 | 25106 | 25110 | 25112 | 25128 |

TABLE 12-continued

Pathogen/Pest Tolerance

| | | | | | | | | | | | |
|---|---|---|---|---|---|---|---|---|---|---|---|
| 25134 | 25140 | 25141 | 25146 | 25156 | 25166 | 25173 | 25175 | 25181 | 25194 | 25195 | 25204 |
| 25222 | 25231 | 25233 | 25258 | 25260 | 25277 | 25283 | 25286 | 25288 | 25310 | 25323 | 25326 |
| 25344 | 25348 | 25352 | 25372 | 25378 | 25384 | 25403 | 25411 | 25412 | 25417 | 25419 | 25438 |
| 25441 | 25443 | 25446 | 25447 | 25456 | 25459 | 25460 | 25473 | 25496 | 25501 | 25508 | 25509 |
| 25513 | 25514 | 25518 | 25533 | 25542 | 25559 | 25564 | 25567 | 25572 | 25579 | 25580 | 25586 |
| 25597 | 25601 | 25613 | 25616 | 25617 | 25618 | 25622 | 25630 | 25638 | 25640 | 25643 | 25649 |
| 25650 | 25666 | 25672 | 25674 | 25676 | 25691 | 25694 | 25705 | 25738 | 25744 | 25746 | 25754 |
| 25758 | 25766 | 25770 | 25776 | 25782 | 25787 | 25792 | 25794 | 25802 | 25808 | 25813 | 25818 |
| 25833 | 25844 | 25845 | 25867 | 25871 | 25879 | 25892 | 25899 | 25913 | 25917 | 25920 | 25930 |
| 25931 | 25936 | 25939 | 25940 | 25941 | 25947 | 25949 | 25951 | 25956 | 25959 | 25961 | 25966 |
| 25973 | 25981 | 25988 | 25993 | 25995 | 26002 | 26008 | 26020 | 26025 | 26028 | 26032 | 26039 |
| 26042 | 26044 | 26056 | 26060 | 26071 | 26074 | 26077 | 26079 | 26084 | 26089 | 26093 | 26106 |
| 26107 | 26123 | 26144 | 26151 | 26163 | 26164 | 26168 | 26169 | 26170 | 26177 | 26181 | 26186 |
| 26190 | 26197 | 26203 | 26204 | 26205 | 26217 | 26218 | 26223 | 26225 | 26227 | 26236 | 26241 |
| 26253 | 26256 | 26257 | 26266 | 26275 | 26325 | 26340 | 26370 | 26389 | 26395 | 26428 | 26437 |
| 26444 | 26449 | 26456 | 26457 | 26478 | 26485 | 26492 | 26493 | 26544 | 26549 | 26553 | 26565 |
| 26589 | 26612 | 26623 | 26645 | 26705 | 26713 | 26737 | 26748 | 26753 | 26761 | 26766 | 26775 |
| 26783 | 26787 | 26792 | 26796 | 26802 | 26807 | 26808 | 26813 | 26833 | 26837 | 26843 | 26853 |
| 26856 | 26857 | 26858 | 26859 | 26860 | 26862 | 26869 | 26872 | 26889 | 26890 | 26894 | 26903 |
| 26904 | 26908 | 26913 | 26918 | 26925 | 26927 | 26946 | 26953 | 26956 | 26960 | 26969 | 26971 |
| 26975 | 26979 | 26989 | 26994 | 26999 | 27029 | 27031 | 27032 | 27037 | 27040 | 27041 | 27042 |
| 27052 | 27076 | 27081 | 27091 | 27097 | 27100 | 27109 | 27112 | 27113 | 27114 | 27117 | 27118 |
| 27139 | 27148 | 27158 | 27168 | 27170 | 27172 | 27175 | 27176 | 27182 | 27207 | 27212 | 27214 |
| 27229 | 27245 | 27250 | 27270 | 27284 | 27286 | 27289 | 27302 | 27305 | 27306 | 27319 | 27321 |
| 27342 | 27345 | 27348 | 27381 | 27387 | 27390 | 27402 | 27409 | 27428 | 27462 | 27465 | 27470 |
| 27472 | 27475 | 27479 | 27484 | 27485 | 27490 | 27495 | 27500 | 27530 | 27532 | 27538 | 27555 |
| 27559 | 27564 | 27566 | 27573 | 27578 | 27594 | 27598 | 27599 | 27600 | 27604 | 27621 | 27625 |
| 27642 | 27653 | 27666 | 27670 | 27677 | 27680 | 27685 | 27688 | 27689 | 27703 | 27705 | 27718 |
| 27719 | 27728 | 27730 | 27762 | 27765 | 27770 | 27773 | 27778 | 27785 | 27787 | 27792 | 27798 |
| 27804 | 27817 | 27832 | 27833 | 27841 | 27848 | 27853 | 27856 | 27860 | 27896 | 27903 | 27912 |
| 27915 | 27927 | 28024 | 28048 | 28056 | 28078 | 28084 | 28100 | 28131 | 28137 | 28180 | 28350 |
| 28351 | 28376 | 28400 | 28491 | 28494 | 28520 | 28536 | 28561 | 28572 | 28584 | 28642 | 28655 |
| 28662 | 28663 | 28676 | 28694 | 28695 | 28699 | 28702 | 28722 | 28732 | 28737 | 28749 | 28752 |
| 28754 | 28755 | 28757 | 28758 | 28759 | 28760 | 28761 | 28780 | 28785 | 28790 | 28792 | 28803 |
| 28804 | 28805 | 28813 | 28821 | 28841 | 28842 | 28844 | 28863 | 28864 | 28871 | 28889 | |
| 28895 | 28900 | 28904 | 28912 | 28915 | 28917 | 28925 | 28926 | 28927 | 28928 | 28931 | 28932 |
| 28934 | 28935 | 28936 | 28937 | 28938 | 28939 | 28962 | 28964 | 28973 | 28981 | 28987 | 28989 |
| 28993 | 29000 | 29001 | 29004 | 29019 | 29020 | 29022 | 29027 | 29030 | 29031 | 29035 | 29036 |
| 29037 | 29038 | 29039 | 29040 | 29041 | 29042 | 29045 | 29048 | 29058 | 29061 | 29066 | 29069 |
| 29070 | 29077 | 29081 | 29084 | 29085 | 29095 | 29098 | 29102 | 29106 | 29110 | 29133 | 29135 |
| 29139 | 29156 | 29159 | 29160 | 29178 | 29181 | 29186 | 29202 | 29222 | 29229 | 29232 | 29233 |
| 29237 | 29238 | 29249 | 29270 | 29273 | 29274 | 29277 | 29279 | 29280 | 29293 | 29298 | 29312 |
| 29313 | 29325 | 29344 | 29345 | 29346 | 29347 | 29371 | 29382 | 29385 | 29386 | 29387 | 29396 |
| 29401 | 29404 | 29412 | 29425 | 29436 | 29440 | 29443 | 29462 | 29464 | 29471 | 29472 | 29476 |
| 29482 | 29486 | 29491 | 29501 | 29514 | 29524 | 29537 | 29542 | 29551 | 29552 | 29553 | 29566 |
| 29590 | 29614 | 29622 | 29623 | 29624 | 29638 | 29648 | 29652 | 29655 | 29677 | 29685 | 29694 |
| 29695 | 29700 | 29703 | 29713 | 29717 | 29723 | 29731 | 29749 | 29755 | 29770 | 29775 | 29776 |
| 29782 | 29783 | 29802 | 29813 | 29829 | 29830 | 29831 | 29847 | 29850 | 29885 | 29897 | 29910 |
| 29916 | 29918 | 29920 | 29944 | 29945 | 29946 | 29947 | 29951 | 29952 | 29953 | 29972 | 29973 |
| 29974 | 29996 | 29997 | 30001 | 30016 | 30021 | 30023 | 30024 | 30028 | 30030 | 30045 | 30046 |
| 30050 | 30061 | 30068 | 30089 | 30090 | 30091 | 30092 | 30103 | 30104 | 30105 | 30108 | 30114 |
| 30123 | 30128 | 30129 | 30130 | 30138 | 30139 | 30141 | 30142 | 30143 | 30144 | 30146 | 30148 |
| 30149 | 30163 | 30196 | 30197 | 30199 | 30201 | 30202 | 30204 | 30205 | 30207 | 30218 | 30219 |
| 30222 | 30223 | 30225 | 30226 | 30230 | 30233 | 30235 | 30236 | 30247 | 30254 | 30280 | 30282 |
| 30297 | 30298 | 30306 | 30309 | 30310 | 30330 | 30332 | 30359 | 30362 | 30367 | 30368 | 30382 |
| 30389 | 30390 | 30393 | 30415 | 30421 | 30427 | 30460 | 30463 | 30464 | 30467 | 30479 | 30482 |
| 30485 | 30486 | 30489 | 30497 | 30515 | 30523 | 30529 | 30537 | 30538 | 30541 | 30556 | 30557 |
| 30566 | 30567 | 30573 | 30607 | 30632 | 30646 | 30647 | 30649 | 30664 | 30668 | 30669 | 30678 |
| 30679 | 30687 | 30689 | 30690 | 30691 | 30693 | 30698 | 30711 | 30779 | 30802 | 30810 | 30833 |
| 30839 | 30856 | 30890 | 30897 | 30939 | 31109 | 31110 | 31119 | 31135 | 31160 | 31250 | 31253 |
| 31279 | 31295 | 31321 | 31330 | 31342 | 31400 | 31413 | 31481 | 31486 | 31518 | 31524 | 31595 |
| 31646 | 31679 | 31687 | 31711 | 31726 | 31751 | 31753 | 31769 | 31783 | 31787 | 31815 | 31846 |
| 31864 | 31906 | 31928 | 31976 | 31979 | 31998 | 32062 | 32063 | 32068 | 32121 | 32149 | 32176 |
| 32198 | 32262 | 32265 | 32302 | 32394 | 32479 | 32584 | 32594 | 32602 | 32609 | 32619 | |
| 32656 | 32691 | 32697 | 32705 | 32716 | 32722 | 32799 | 32811 | 32822 | 32827 | 32847 | 32848 |
| 32853 | 32878 | 32883 | 32890 | 32891 | 32892 | 32957 | 33015 | 33034 | 33040 | 33061 | 33071 |
| 33104 | 33127 | 33146 | 33180 | 33193 | 33209 | 33216 | 33240 | 33276 | 33303 | 33341 | 33343 |
| 33383 | 33387 | 33394 | 33404 | 33481 | 33493 | 33568 | 33612 | 33615 | 33648 | 33669 | 33670 |
| 33688 | 33705 | 33713 | 33745 | 33760 | 33830 | 33844 | 33846 | 33859 | 33865 | 33870 | 33921 |
| 33923 | 33926 | 33927 | 33929 | 33930 | 33931 | 33936 | 33955 | 33973 | 33984 | 34006 | 34055 |
| 34068 | 34085 | 34127 | 34130 | 34133 | 34201 | 34202 | 34208 | 34289 | 34295 | 34302 | 34310 |
| 34357 | 34363 | 34374 | 34484 | 34487 | 34489 | 34514 | 34532 | 34541 | 34586 | 34609 | 34616 |
| 34629 | 34672 | 34701 | 34719 | 34734 | 34775 | 34822 | 34832 | 34833 | 34837 | 34841 | 34865 |
| 34887 | 34889 | 34909 | 34969 | 34985 | 35000 | 35034 | 35038 | 35039 | 35051 | 35052 | 35053 |
| 35058 | 35080 | 35170 | 35185 | 35193 | 35265 | 35277 | 35281 | 35284 | 35299 | 35316 | 35319 |
| 35368 | 35391 | 35397 | 35435 | 35455 | 35482 | 35521 | 35526 | 35607 | 35663 | 35665 | 35669 |
| 35672 | 35693 | 35710 | 35729 | 35749 | 35773 | 35799 | 35962 | 35969 | 35978 | 35991 | 36003 |

TABLE 12-continued

Pathogen/Pest Tolerance

| | | | | | | | | | | |
|---|---|---|---|---|---|---|---|---|---|---|
| 36019 | 36020 | 36035 | 36036 | 36053 | 36059 | 36077 | 36080 | 36088 | 36095 | 36101 | 36109 |
| 36113 | 36114 | 36117 | 36124 | 36136 | 36138 | 36140 | 36155 | 36164 | 36167 | 36183 | 36190 |
| 36196 | 36203 | 36218 | 36243 | 36253 | 36285 | 36298 | 36300 | 36330 | 36342 | 36370 | 36380 |
| 36389 | 36395 | 36400 | 36404 | 36416 | 36417 | 36428 | 36434 | 36437 | 36465 | 36473 | 36475 |
| 36489 | 36495 | 36515 | 36525 | 36536 | 36544 | 36553 | 36558 | 36561 | 36574 | 36581 | 36589 |
| 36593 | 36603 | 36605 | 36610 | 36624 | 36625 | 36636 | 36674 | 36677 | 36682 | 36698 | 36727 |
| 36741 | 36744 | 36759 | 36760 | 36761 | 36777 | 36778 | 36779 | 36786 | 36789 | 36793 | 36795 |
| 36823 | 36827 | 36833 | 36854 | 36866 | 36875 | 36882 | 36884 | 36890 | 36891 | 36899 | 36912 |
| 36917 | 36920 | 36926 | 36927 | 36929 | 36934 | 36943 | 36944 | 36945 | 36958 | 36964 | 36974 |
| 36982 | 36991 | 37006 | 37011 | 37014 | 37018 | 37020 | 37025 | 37052 | 37058 | 37066 | 37074 |
| 37080 | 37093 | 37108 | 37116 | 37119 | 37121 | 37122 | 37175 | 37178 | 37227 | 37241 | 37245 |
| 37301 | 37302 | 37349 | 37353 | 37375 | 37394 | 37396 | 37399 | 37409 | 37426 | 37431 | 37436 |
| 37451 | 37457 | 37512 | 37593 | 37642 | 37667 | 37681 | 37696 | 37742 | 37748 | 37750 | 37754 |
| 37818 | 37832 | 37881 | 37929 | 37952 | 37953 | 38009 | 38071 | 38072 | 38090 | 38091 | 38118 |
| 38136 | 38188 | 38197 | 38213 | 38216 | 38221 | 38230 | 38302 | 38331 | 38383 | 38434 | 38456 |
| 38472 | 38482 | 38497 | 38519 | 38534 | 38535 | 38536 | 38581 | 38607 | 38649 | 38667 | 38670 |
| 38703 | 38707 | 38724 | 38725 | 38734 | 38745 | 38747 | 38774 | 38796 | 38864 | 38912 | 38934 |
| 38997 | 39026 | 39032 | 39045 | 39051 | 39052 | 39053 | 39073 | 39074 | 39076 | 39096 | 39105 |
| 39118 | 39132 | 39134 | 39138 | 39139 | 39140 | 39186 | 39194 | 39195 | 39204 | 39211 | 39230 |
| 39249 | 39279 | 39286 | 39292 | 39318 | 39329 | 39334 | 39335 | 39336 | 39337 | 39338 | 39339 |
| 39341 | 39342 | 39343 | 39346 | 39363 | 39393 | 39399 | 39412 | 39418 | 39419 | 39441 | 39442 |
| 39444 | 39464 | 39473 | 39487 | 39500 | 39502 | 39506 | 39507 | 39508 | 39557 | 39566 | 39567 |
| 39576 | 39582 | 39602 | 39622 | 39638 | 39655 | 39663 | 39667 | 39693 | 39704 | 39710 | 39711 |
| 39712 | 39713 | 39714 | 39715 | 39716 | 39717 | 39718 | 39720 | 39721 | 39722 | 39723 | 39724 |
| 39726 | 39728 | 39729 | 39732 | 39733 | 39734 | 39754 | 39783 | 39788 | 39797 | 39803 | 39804 |
| 39827 | 39828 | 39855 | 39869 | 39882 | 39884 | 39888 | 39889 | 39932 | 39939 | 39947 | 39955 |
| 39973 | 39990 | 40002 | 40017 | 40020 | 40027 | 40047 | 40057 | 40078 | 40097 | 40107 | 40108 |
| 40113 | 40116 | 40122 | 40137 | 40140 | 40144 | 40150 | 40217 | 40266 | 40309 | 40322 | 40358 |
| 40402 | 40419 | 40511 | 40515 | 40521 | 40536 | 40553 | 40578 | 40607 | 40621 | 40640 | 40657 |
| 40677 | 40707 | 40729 | 40741 | 40753 | 40769 | 40787 | 40788 | 40828 | 40845 | 40870 | 40907 |
| 40955 | 40969 | 40981 | 40991 | 41005 | 41060 | 41062 | 41063 | 41073 | 41154 | 41178 | 41179 |
| 41201 | 41208 | 41256 | 41263 | 41280 | 41284 | 41311 | 41314 | 41348 | 41369 | 41375 | 41397 |
| 41411 | 41452 | 41484 | 41489 | 41513 | 41515 | 41531 | 41561 | 41562 | 41566 | 41576 | 41577 |
| 41581 | 41602 | 41606 | 41613 | 41617 | 41624 | 41632 | 41635 | 41656 | 41668 | 41717 | 41718 |
| 41722 | 41735 | 41736 | 41745 | 41750 | 41754 | 41757 | 41758 | 41761 | 41762 | 41763 |
| 41764 | 41765 | 41766 | 41767 | 41820 | 41821 | 41859 | 41867 | 41887 | 41890 | 41947 | 41977 |
| 42006 | 42028 | 42035 | 42066 | 42104 | 42129 | 42135 | 42147 | 42160 | 42161 | 42162 | 42179 |
| 42227 | 42249 | 42277 | 42315 | 42316 | 42328 | 42330 | 42352 | 42354 | 42436 | 42459 | 42460 |
| 42482 | 42483 | 42487 | 42511 | 42541 | 42569 | 42573 | 42579 | 42600 | 42601 | 42623 | 42672 |
| 42679 | 42680 | 42686 | 42687 | 42739 | 42796 | 42798 | 42810 | 42819 | 42822 | 42824 | 42827 |
| 42828 | 42835 | 42840 | 42849 | 42857 | 42873 | 42879 | 42882 | 42892 | 42896 | 42904 | 42928 |
| 42934 | 42941 | 42951 | 42953 | 42954 | 42957 | 42971 | 42986 | 43007 | 43010 | 43022 | 43036 |
| 43040 | 43061 | 43062 | 43069 | 43076 | 43089 | 43090 | 43100 | 43117 | 43119 | 43121 | 43130 |
| 43139 | 43149 | 43150 | 43154 | 43162 | 43202 | 43222 | 43224 | 43240 | 43255 | 43266 | 43278 |
| 43283 | 43294 | 43305 | 43312 | 43316 | 43412 | 43421 | 43449 | 43459 | 43466 | 43467 | 43476 |
| 43478 | 43482 | 43513 | 43529 | 43533 | 43539 | 43565 | 43574 | 43596 | 43603 | 43666 | 43676 |
| 43708 | 43720 | 43734 | 43801 | 43802 | 43804 | 43858 | 43879 | 43898 | 43903 | 43904 | 43908 |
| 43919 | 43951 | 43978 | 43981 | 44007 | 44028 | 44053 | 44063 | 44084 | 44175 | 44208 | 44249 |
| 44294 | 44314 | 44329 | 44332 | 44340 | 44341 | 44471 | 44484 | 44506 | 44535 | 44559 | 44583 |
| 44598 | 44622 | 44629 | 44634 | 44640 | 44644 | 44675 | 44676 | 44692 | 44694 | 44739 | 44763 |
| 44785 | 44796 | 44808 | 44888 | 44905 | 44909 | 44910 | 44955 | 44979 | 45034 | 45038 | 45081 |
| 45093 | 45129 | 45162 | 45215 | 45234 | 45236 | 45248 | 45274 | 45287 | 45306 | 45319 | 45347 |
| 45398 | 45413 | 45462 | 45485 | 45494 | 45510 | 45512 | 45537 | 45566 | 45567 | 45568 | 45579 |
| 45581 | 45596 | 45616 | 45630 | 45633 | 45635 | 45638 | 45648 | 45649 | 45656 | 45658 | 45667 |
| 45669 | 45677 | 45681 | 45687 | 45697 | 45698 | 45700 | 45703 | 45713 | 45715 | 45716 | 45721 |
| 45724 | 45727 | 45737 | 45741 | 45742 | 45751 | 45753 | 45757 | 45758 | 45764 | 45765 | 45773 |
| 45781 | 45783 | 45785 | 45796 | 45798 | 45800 | 45810 | 45811 | 45813 | 45818 | 45822 | 45826 |
| 45827 | 45828 | 45831 | 45845 | 45853 | 45854 | 45863 | 45864 | 45877 | 45881 | 45882 | 45884 |
| 45889 | 45893 | 45894 | 45907 | 45913 | 45914 | 45916 | 45920 | 45923 | 45924 | 45931 | 45939 |
| 45953 | 45966 | 45968 | 45974 | 45980 | 45983 | 45984 | 45985 | 46001 | 46009 | 46010 | 46015 |
| 46027 | 46037 | 46038 | 46039 | 46054 | 46058 | 46061 | 46068 | 46084 | 46086 | 46093 | 46094 |
| 46095 | 46120 | 46123 | 46157 | 46177 | 46180 | 46185 | 46199 | 46202 | 46214 | 46219 | 46225 |
| 46232 | 46233 | 46242 | 46247 | 46268 | 46277 | 46282 | 46286 | 46290 | 46293 | 46301 | 46303 |
| 46306 | 46327 | 46329 | 46331 | 46332 | 46333 | 46339 | 46368 | 46369 | 46375 | 46376 | 46377 |
| 46388 | 46392 | 46393 | 46397 | 46411 | 46412 | 46413 | 46414 | 46415 | 46426 | 46442 | 46446 |
| 46459 | 46462 | 46469 | 46473 | 46478 | 46480 | 46484 | 46492 | 46493 | 46494 | 46495 | 46503 |
| 46535 | 46555 | 46581 | 46584 | 46623 | 46653 | 46690 | 46708 | 46736 | 46737 | 46758 | 46797 |
| 46816 | 46911 | 46959 | 46977 | 47000 | 47103 | 47117 | 47118 | 47150 | 47187 | 47191 | 47195 |
| 47220 | 47231 | 47254 | 47270 | 47280 | 47295 | 47320 | 47360 | | | | |

TABLE 13A

Seed Oil Yield/Content

Table 13A SEQ ID NOs of Polypeptides useful for improving Seed Oil Yield/Content

| | | | | | | | | | | | |
|---|---|---|---|---|---|---|---|---|---|---|---|
| 1 | 2 | 4 | 5 | 6 | 7 | 8 | 11 | 12 | 13 | 17 | 19 |
| 26 | 27 | 31 | 32 | 34 | 36 | 37 | 39 | 50 | 52 | 55 | 56 |
| 60 | 62 | 63 | 64 | 73 | 77 | 81 | 82 | 86 | 88 | 90 | 91 |
| 99 | 100 | 101 | 108 | 109 | 111 | 112 | 113 | 114 | 117 | 118 | 119 |
| 120 | 121 | 122 | 124 | 125 | 128 | 131 | 132 | 133 | 138 | 145 | 146 |
| 147 | 151 | 153 | 154 | 156 | 157 | 160 | 163 | 169 | 175 | 178 | 183 |
| 184 | 187 | 188 | 191 | 192 | 193 | 194 | 195 | 197 | 202 | 204 | 207 |
| 208 | 211 | 212 | 215 | 223 | 224 | 225 | 226 | 227 | 228 | 230 | 237 |
| 238 | 242 | 244 | 246 | 247 | 256 | 257 | 258 | 266 | 272 | 273 | 274 |
| 275 | 276 | 277 | 278 | 279 | 281 | 282 | 287 | 289 | 290 | 291 | 292 |
| 295 | 297 | 302 | 310 | 311 | 318 | 320 | 321 | 325 | 327 | 329 | 332 |
| 335 | 338 | 340 | 341 | 342 | 350 | 356 | 357 | 363 | 366 | 367 | 370 |
| 371 | 375 | 376 | 377 | 378 | 379 | 384 | 385 | 388 | 391 | 392 | 393 |
| 395 | 396 | 398 | 400 | 403 | 406 | 410 | 413 | 418 | 424 | 427 | 428 |
| 432 | 433 | 436 | 437 | 439 | 442 | 443 | 444 | 445 | 449 | 456 | 459 |
| 460 | 461 | 463 | 466 | 474 | 477 | 478 | 479 | 480 | 484 | 490 | 491 |
| 493 | 494 | 495 | 497 | 498 | 500 | 501 | 502 | 504 | 505 | 508 | 510 |
| 515 | 516 | 519 | 525 | 526 | 529 | 531 | 534 | 535 | 537 | 538 | 539 |
| 541 | 543 | 544 | 546 | 548 | 549 | 552 | 554 | 555 | 559 | 560 | 561 |
| 562 | 563 | 570 | 571 | 572 | 573 | 574 | 575 | 576 | 577 | 579 | 580 |
| 581 | 582 | 583 | 585 | 587 | 593 | 599 | 600 | 602 | 604 | 605 | 609 |
| 613 | 622 | 623 | 629 | 630 | 631 | 632 | 636 | 637 | 638 | 639 | 640 |
| 641 | 642 | 643 | 644 | 646 | 648 | 662 | 664 | 665 | 670 | 671 | 672 |
| 673 | 674 | 675 | 679 | 681 | 682 | 684 | 685 | 693 | 694 | 695 | 696 |
| 700 | 701 | 703 | 707 | 713 | 714 | 720 | 723 | 725 | 729 | 732 | 742 |
| 744 | 745 | 746 | 748 | 749 | 753 | 756 | 757 | 759 | 761 | 762 | 767 |
| 781 | 782 | 783 | 785 | 787 | 788 | 792 | 793 | 794 | 795 | 796 | 800 |
| 812 | 813 | 815 | 818 | 819 | 820 | 823 | 825 | 826 | 834 | 835 | 837 |
| 839 | 844 | 845 | 846 | 847 | 848 | 849 | 850 | 851 | 852 | 853 | 854 |
| 855 | 856 | 859 | 861 | 863 | 867 | 870 | 871 | 872 | 876 | 879 | 883 |
| 885 | 890 | 894 | 895 | 897 | 898 | 899 | 900 | 902 | 903 | 904 | 905 |
| 906 | 907 | 908 | 909 | 920 | 921 | 922 | 923 | 924 | 926 | 928 | 931 |
| 933 | 934 | 935 | 937 | 938 | 940 | 941 | 942 | 943 | 946 | 948 | 949 |
| 950 | 951 | 953 | 964 | 965 | 972 | 974 | 975 | 976 | 977 | 979 | 980 |
| 983 | 985 | 987 | 989 | 991 | 992 | 993 | 995 | 997 | 998 | 1003 | 1004 |
| 1005 | 1006 | 1007 | 1008 | 1011 | 1012 | 1013 | 1014 | 1015 | 1017 | 1020 | 1021 |
| 1024 | 1025 | 1027 | 1028 | 1029 | 1035 | 1036 | 1037 | 1038 | 1041 | 1043 | 1047 |
| 1052 | 1053 | 1055 | 1057 | 1060 | 1070 | 1073 | 1079 | 1081 | 1085 | 1086 | 1087 |
| 1093 | 1094 | 1099 | 1101 | 1105 | 1107 | 1113 | 1116 | 1122 | 1123 | 1127 | 1129 |
| 1130 | 1132 | 1133 | 1135 | 1136 | 1142 | 1145 | 1146 | 1149 | 1150 | 1155 | 1158 |
| 1160 | 1164 | 1166 | 1167 | 1173 | 1174 | 1183 | 1184 | 1185 | 1186 | 1188 | 1189 |
| 1194 | 1198 | 1199 | 1200 | 1203 | 1204 | 1207 | 1214 | 1217 | 1220 | 1229 | 1236 |
| 1240 | 1241 | 1245 | 1246 | 1250 | 1252 | 1255 | 1259 | 1274 | 1276 | 1283 | 1284 |
| 1291 | 1292 | 1299 | 1303 | 1304 | 1309 | 1310 | 1312 | 1313 | 1321 | 1332 | 1334 |
| 1337 | 1339 | 1341 | 1342 | 1346 | 1347 | 1349 | 1358 | 1361 | 1375 | 1397 | 1402 |
| 1403 | 1412 | 1417 | 1428 | 1434 | 1437 | 1438 | 1443 | 1444 | 1458 | 1459 | 1464 |
| 1465 | 1474 | 1477 | 1478 | 1482 | 1484 | 1489 | 1491 | 1492 | 1493 | 1494 | 1495 |
| 1497 | 1500 | 1501 | 1506 | 1507 | 1510 | 1513 | 1521 | 1525 | 1526 | 1541 | 1543 |
| 1552 | 1556 | 1564 | 1565 | 1574 | 1580 | 1582 | 1584 | 1589 | 1597 | 1604 | 1610 |
| 1615 | 1616 | 1617 | 1618 | 1627 | 1632 | 1635 | 1641 | 1642 | 1645 | 1664 |
| 1670 | 1679 | 1680 | 1681 | 1685 | 1688 | 1689 | 1698 | 1699 | 1701 | 1702 | 1704 |
| 1706 | 1707 | 1711 | 1712 | 1719 | 1720 | 1721 | 1728 | 1731 | 1734 | 1736 | 1740 |
| 1742 | 1745 | 1746 | 1748 | 1749 | 1781 | 1783 | 1784 | 1785 | 1789 | 1795 | 1797 |
| 1816 | 1823 | 1824 | 1834 | 1838 | 1839 | 1841 | 1847 | 1850 | 1857 | 1865 | 1866 |
| 1867 | 1878 | 1883 | 1884 | 1890 | 1895 | 1896 | 1897 | 1899 | 1903 | 1904 | 1905 |
| 1912 | 1916 | 1917 | 1921 | 1928 | 1933 | 1934 | 1936 | 1946 | 1947 | 1948 | 1952 |
| 1953 | 1966 | 1971 | 1973 | 1975 | 1983 | 1992 | 1993 | 1994 | 1998 | 2006 | 2007 |
| 2008 | 2013 | 2014 | 2017 | 2019 | 2023 | 2026 | 2027 | 2028 | 2031 | 2042 | 2043 |
| 2044 | 2045 | 2051 | 2062 | 2063 | 2064 | 2066 | 2068 | 2074 | 2084 | 2097 | 2104 |
| 2105 | 2107 | 2109 | 2110 | 2118 | 2119 | 2120 | 2122 | 2124 | 2130 | 2139 | 2140 |
| 2146 | 2147 | 2148 | 2155 | 2163 | 2174 | 2182 | 2184 | 2186 | 2191 | 2194 | 2198 |
| 2202 | 2203 | 2208 | 2212 | 2220 | 2225 | 2229 | 2230 | 2233 | 2254 | 2259 | 2263 |
| 2265 | 2267 | 2270 | 2280 | 2281 | 2283 | 2286 | 2294 | 2302 | 2303 | 2304 | 2305 |
| 2306 | 2315 | 2316 | 2319 | 2321 | 2322 | 2325 | 2327 | 2333 | 2350 | 2359 | 2364 |
| 2377 | 2394 | 2403 | 2413 | 2414 | 2418 | 2422 | 2425 | 2430 | 2438 | 2445 | 2450 |
| 2453 | 2455 | 2457 | 2466 | 2480 | 2485 | 2488 | 2489 | 2496 | 2497 | 2503 | 2504 |
| 2508 | 2517 | 2518 | 2524 | 2537 | 2546 | 2547 | 2551 | 2562 | 2566 | 2567 | 2568 |
| 2578 | 2580 | 2589 | 2592 | 2596 | 2599 | 2602 | 2606 | 2608 | 2609 | 2612 | 2622 |
| 2625 | 2626 | 2631 | 2632 | 2634 | 2639 | 2640 | 2642 | 2649 | 2651 | 2654 | 2658 |
| 2665 | 2666 | 2668 | 2672 | 2675 | 2676 | 2679 | 2687 | 2689 | 2691 | 2692 |
| 2694 | 2695 | 2698 | 2703 | 2706 | 2708 | 2715 | 2719 | 2722 | 2726 | 2730 | 2731 |
| 2734 | 2737 | 2738 | 2739 | 2745 | 2746 | 2748 | 2749 | 2750 | 2752 | 2755 | 2756 |
| 2760 | 2761 | 2766 | 2767 | 2768 | 2771 | 2773 | 2774 | 2775 | 2780 | 2781 | 2782 |
| 2785 | 2787 | 2788 | 2790 | 2797 | 2807 | 2818 | 2822 | 2823 | 2824 | 2828 | 2832 |
| 2833 | 2835 | 2840 | 2842 | 2846 | 2847 | 2848 | 2851 | 2852 | 2853 | 2860 | 2863 |

TABLE 13A-continued

Seed Oil Yield/Content

| | | | | | | | | | | | |
|---|---|---|---|---|---|---|---|---|---|---|---|
| 2864 | 2870 | 2873 | 2878 | 2879 | 2882 | 2885 | 2887 | 2889 | 2891 | 2892 | 2894 |
| 2895 | 2896 | 2898 | 2900 | 2904 | 2905 | 2907 | 2909 | 2910 | 2912 | 2916 | 2919 |
| 2922 | 2923 | 2925 | 2928 | 2929 | 2930 | 2931 | 2932 | 2934 | 2935 | 2936 | 2941 |
| 2942 | 2944 | 2945 | 2947 | 2959 | 2960 | 2961 | 2963 | 2964 | 2965 | 2966 | 2967 |
| 2968 | 2970 | 2971 | 2972 | 2973 | 2974 | 2977 | 2981 | 2984 | 2985 | 2987 | 2990 |
| 2991 | 2996 | 3002 | 3004 | 3005 | 3012 | 3016 | 3020 | 3021 | 3027 | 3030 | 3031 |
| 3032 | 3034 | 3035 | 3042 | 3043 | 3044 | 3045 | 3047 | 3052 | 3054 | 3057 | 3064 |
| 3066 | 3067 | 3069 | 3070 | 3075 | 3077 | 3087 | 3097 | 3100 | 3103 | 3107 | 3110 |
| 3113 | 3115 | 3124 | 3125 | 3130 | 3137 | 3138 | 3139 | 3145 | 3154 | 3156 | 3157 |
| 3165 | 3176 | 3178 | 3180 | 3184 | 3186 | 3188 | 3189 | 3198 | 3199 | 3200 | 3201 |
| 3206 | 3211 | 3219 | 3231 | 3232 | 3234 | 3235 | 3237 | 3240 | 3244 | 3246 | 3249 |
| 3250 | 3260 | 3270 | 3271 | 3276 | 3285 | 3286 | 3288 | 3290 | 3291 | 3295 | 3299 |
| 3301 | 3304 | 3305 | 3309 | 3311 | 3315 | 3318 | 3320 | 3322 | 3323 | 3324 | 3325 |
| 3326 | 3328 | 3331 | 3334 | 3338 | 3339 | 3343 | 3348 | 3357 | 3363 | 3366 | 3372 |
| 3381 | 3389 | 3392 | 3393 | 3395 | 3397 | 3411 | 3415 | 3419 | 3421 | 3423 | 3424 |
| 3436 | 3437 | 3440 | 3441 | 3442 | 3453 | 3455 | 3458 | 3466 | 3468 | 3469 | 3473 |
| 3474 | 3476 | 3478 | 3481 | 3482 | 3484 | 3485 | 3488 | 3490 | 3507 | 3511 | 3513 |
| 3514 | 3515 | 3518 | 3522 | 3529 | 3541 | 3544 | 3555 | 3559 | 3560 | 3563 | 3570 |
| 3571 | 3573 | 3575 | 3580 | 3590 | 3591 | 3592 | 3593 | 3597 | 3601 | 3605 | 3609 |
| 3616 | 3621 | 3623 | 3629 | 3635 | 3637 | 3639 | 3640 | 3647 | 3652 | 3654 | 3658 |
| 3662 | 3663 | 3667 | 3678 | 3682 | 3683 | 3686 | 3688 | 3689 | 3697 | 3698 | 3699 |
| 3700 | 3701 | 3702 | 3703 | 3705 | 3711 | 3713 | 3714 | 3715 | 3717 | 3722 | 3724 |
| 3725 | 3733 | 3735 | 3736 | 3739 | 3741 | 3745 | 3746 | 3747 | 3751 | 3757 | 3761 |
| 3762 | 3772 | 3774 | 3775 | 3777 | 3780 | 3792 | 3793 | 3794 | 3800 | 3805 | 3811 |
| 3815 | 3819 | 3830 | 3834 | 3835 | 3836 | 3840 | 3845 | 3846 | 3850 | 3865 | 3866 |
| 3867 | 3871 | 3876 | 3878 | 3881 | 3884 | 3887 | 3888 | 3890 | 3892 | 3898 | 3904 |
| 3908 | 3915 | 3920 | 3924 | 3925 | 3931 | 3932 | 3937 | 3938 | 3948 | 3954 | 3956 |
| 3957 | 3958 | 3964 | 3966 | 3967 | 3968 | 3969 | 3976 | 3978 | 3982 | 3984 | 3986 |
| 3987 | 3995 | 3999 | 4003 | 4005 | 4006 | 4013 | 4019 | 4021 | 4022 | 4023 | 4025 |
| 4030 | 4033 | 4041 | 4044 | 4045 | 4047 | 4048 | 4052 | 4057 | 4061 | 4066 | 4074 |
| 4075 | 4076 | 4077 | 4078 | 4079 | 4080 | 4084 | 4093 | 4098 | 4100 | 4106 | 4110 |
| 4111 | 4117 | 4118 | 4122 | 4123 | 4126 | 4127 | 4131 | 4134 | 4137 | 4140 | 4142 |
| 4143 | 4145 | 4152 | 4154 | 4160 | 4164 | 4166 | 4168 | 4176 | 4178 | 4180 | 4181 |
| 4183 | 4186 | 4188 | 4189 | 4192 | 4195 | 4198 | 4200 | 4201 | 4202 | 4205 | 4218 |
| 4220 | 4222 | 4227 | 4232 | 4233 | 4234 | 4238 | 4242 | 4243 | 4248 | 4250 | 4251 |
| 4252 | 4254 | 4256 | 4258 | 4259 | 4261 | 4262 | 4263 | 4264 | 4265 | 4266 | 4271 |
| 4272 | 4274 | 4275 | 4277 | 4278 | 4279 | 4280 | 4282 | 4283 | 4284 | 4285 | 4287 |
| 4289 | 4290 | 4291 | 4293 | 4294 | 4295 | 4297 | 4301 | 4302 | 4304 | 4305 | 4306 |
| 4307 | 4308 | 4309 | 4311 | 4312 | 4313 | 4314 | 4315 | 4316 | 4318 | 4322 | 4326 |
| 4327 | 4330 | 4331 | 4332 | 4334 | 4338 | 4339 | 4341 | 4343 | 4344 | 4347 | 4350 |
| 4351 | 4352 | 4353 | 4354 | 4356 | 4358 | 4360 | 4362 | 4363 | 4365 | 4366 | 4367 |
| 4373 | 4376 | 4379 | 4380 | 4381 | 4383 | 4384 | 4387 | 4388 | 4390 | 4391 | 4398 |
| 4399 | 4400 | 4401 | 4405 | 4411 | 4416 | 4418 | 4422 | 4424 | 4425 | 4427 | 4428 |
| 4429 | 4430 | 4432 | 4433 | 4453 | 4454 | 4455 | 4460 | 4461 | 4462 | 4463 | 4464 |
| 4466 | 4467 | 4471 | 4474 | 4477 | 4479 | 4483 | 4484 | 4486 | 4487 | 4490 | 4491 |
| 4496 | 4497 | 4499 | 4500 | 4502 | 4503 | 4504 | 4505 | 4506 | 4507 | 4514 | 4521 |
| 4524 | 4526 | 4527 | 4528 | 4530 | 4534 | 4536 | 4539 | 4541 | 4542 | 4548 | 4549 |
| 4550 | 4553 | 4555 | 4556 | 4557 | 4558 | 4561 | 4562 | 4563 | 4567 | 4568 | 4569 |
| 4572 | 4576 | 4580 | 4581 | 4582 | 4584 | 4590 | 4591 | 4596 | 4599 | 4601 | 4602 |
| 4604 | 4605 | 4606 | 4607 | 4608 | 4609 | 4611 | 4614 | 4618 | 4619 | 4621 | 4622 |
| 4625 | 4626 | 4628 | 4629 | 4630 | 4631 | 4632 | 4633 | 4634 | 4635 | 4637 | 4638 |
| 4639 | 4641 | 4642 | 4645 | 4651 | 4654 | 4656 | 4657 | 4658 | 4667 | 4668 | 4674 |
| 4676 | 4681 | 4684 | 4686 | 4688 | 4690 | 4691 | 4693 | 4696 | 4699 | 4700 | 4701 |
| 4702 | 4704 | 4705 | 4708 | 4709 | 4711 | 4712 | 4715 | 4716 | 4721 | 4725 | 4726 |
| 4727 | 4729 | 4731 | 4732 | 4733 | 4736 | 4739 | 4740 | 4742 | 4744 | 4745 | 4746 |
| 4747 | 4748 | 4749 | 4751 | 4752 | 4753 | 4755 | 4758 | 4762 | 4763 | 4769 | 4770 |
| 4771 | 4772 | 4773 | 4776 | 4777 | 4781 | 4783 | 4785 | 4787 | 4789 | 4792 | 4793 |
| 4794 | 4795 | 4798 | 4799 | 4802 | 4805 | 4806 | 4807 | 4809 | 4811 | 4812 | 4813 |
| 4815 | 4818 | 4821 | 4826 | 4829 | 4833 | 4834 | 4836 | 4837 | 4843 | 4845 | 4846 |
| 4847 | 4850 | 4854 | 4855 | 4860 | 4865 | 4866 | 4869 | 4870 | 4874 | 4878 | 4885 |
| 4886 | 4888 | 4889 | 4894 | 4895 | 4897 | 4898 | 4899 | 4901 | 4902 | 4903 | 4905 |
| 4907 | 4909 | 4910 | 4911 | 4912 | 4914 | 4917 | 4918 | 4920 | 4923 | 4924 | 4926 |
| 4929 | 4930 | 4933 | 4935 | 4939 | 4944 | 4946 | 4947 | 4948 | 4950 | 4951 | 4952 |
| 4954 | 4957 | 4958 | 4962 | 4969 | 4985 | 4987 | 4991 | 4998 | 5002 | 5005 | |
| 5006 | 5007 | 5012 | 5021 | 5022 | 5027 | 5033 | 5034 | 5035 | 5038 | 5045 | 5057 |
| 5060 | 5065 | 5078 | 5080 | 5083 | 5088 | 5089 | 5090 | 5093 | 5095 | 5097 | 5105 |
| 5115 | 5116 | 5117 | 5118 | 5120 | 5125 | 5135 | 5140 | 5147 | 5153 | 5154 | 5158 |
| 5161 | 5165 | 5170 | 5171 | 5172 | 5173 | 5180 | 5181 | 5183 | 5204 | 5208 | 5209 |
| 5212 | 5216 | 5226 | 5229 | 5230 | 5233 | 5238 | 5239 | 5240 | 5241 | 5247 | 5248 |
| 5249 | 5250 | 5251 | 5252 | 5254 | 5255 | 5257 | 5258 | 5259 | 5260 | 5263 | 5264 |
| 5265 | 5266 | 5268 | 5269 | 5270 | 5275 | 5278 | 5279 | 5281 | 5282 | 5283 | 5284 |
| 5298 | 5299 | 5306 | 5309 | 5310 | 5311 | 5312 | 5316 | 5318 | 5320 | 5322 | 5323 |
| 5326 | 5327 | 5329 | 5330 | 5331 | 5334 | 5336 | 5337 | 5345 | 5346 | 5363 | 5364 |
| 5370 | 5372 | 5373 | 5378 | 5379 | 5380 | 5387 | 5394 | 5397 | 5399 | 5402 | 5407 |
| 5408 | 5416 | 5423 | 5426 | 5428 | 5429 | 5433 | 5437 | 5439 | 5440 | 5441 | 5442 |
| 5444 | 5450 | 5451 | 5465 | 5468 | 5470 | 5480 | 5481 | 5485 | 5486 | 5487 | 5488 |
| 5493 | 5496 | 5497 | 5501 | 5507 | 5513 | 5516 | 5518 | 5527 | 5536 | 5537 | 5539 |

TABLE 13A-continued

Seed Oil Yield/Content

| | | | | | | | | | | | |
|---|---|---|---|---|---|---|---|---|---|---|---|
| 5541 | 5543 | 5544 | 5547 | 5548 | 5549 | 5550 | 5553 | 5567 | 5575 | 5578 | 5579 |
| 5584 | 5588 | 5589 | 5595 | 5599 | 5602 | 5604 | 5610 | 5612 | 5613 | 5614 | 5615 |
| 5616 | 5617 | 5618 | 5627 | 5631 | 5634 | 5638 | 5640 | 5642 | 5644 | 5646 | 5650 |
| 5652 | 5659 | 5660 | 5665 | 5669 | 5680 | 5686 | 5688 | 5693 | 5695 | 5698 | 5699 |
| 5700 | 5706 | 5709 | 5710 | 5713 | 5714 | 5715 | 5716 | 5717 | 5718 | 5723 | 5726 |
| 5727 | 5729 | 5734 | 5735 | 5736 | 5741 | 5745 | 5752 | 5758 | 5769 | 5770 | 5772 |
| 5773 | 5774 | 5777 | 5779 | 5784 | 5785 | 5787 | 5789 | 5795 | 5800 | 5803 | 5805 |
| 5812 | 5814 | 5817 | 5823 | 5825 | 5827 | 5828 | 5829 | 5830 | 5831 | 5834 | 5836 |
| 5844 | 5855 | 5857 | 5858 | 5866 | 5867 | 5871 | 5872 | 5873 | 5877 | 5884 | 5886 |
| 5911 | 5912 | 5914 | 5919 | 5922 | 5923 | 5932 | 5933 | 5934 | 5935 | 5936 | 5937 |
| 5938 | 5941 | 5947 | 5951 | 5958 | 5966 | 5968 | 5974 | 5976 | 5980 | 5982 | 5991 |
| 5992 | 5999 | 6000 | 6001 | 6002 | 6007 | 6010 | 6011 | 6017 | 6021 | 6022 | 6024 |
| 6028 | 6029 | 6032 | 6034 | 6036 | 6041 | 6042 | 6045 | 6047 | 6052 | 6057 | 6058 |
| 6059 | 6066 | 6072 | 6073 | 6076 | 6077 | 6084 | 6085 | 6086 | 6089 | 6090 | 6093 |
| 6094 | 6095 | 6096 | 6098 | 6103 | 6104 | 6107 | 6108 | 6112 | 6113 | 6114 | 6115 |
| 6116 | 6120 | 6122 | 6123 | 6129 | 6130 | 6133 | 6134 | 6137 | 6138 | 6139 | 6140 |
| 6141 | 6144 | 6148 | 6149 | 6156 | 6158 | 6159 | 6160 | 6163 | 6168 | 6169 | 6173 |
| 6174 | 6175 | 6177 | 6188 | 6190 | 6191 | 6192 | 6193 | 6194 | 6196 | 6197 | 6200 |
| 6206 | 6207 | 6214 | 6219 | 6220 | 6221 | 6222 | 6223 | 6227 | 6231 | 6234 | 6235 |
| 6243 | 6244 | 6252 | 6256 | 6260 | 6262 | 6263 | 6268 | 6271 | 6272 | 6274 | 6279 |
| 6280 | 6281 | 6283 | 6287 | 6289 | 6299 | 6300 | 6310 | 6312 | 6314 | 6319 | 6320 |
| 6322 | 6333 | 6335 | 6338 | 6343 | 6347 | 6354 | 6355 | 6357 | 6360 | 6361 | |
| 6368 | 6369 | 6374 | 6376 | 6378 | 6381 | 6382 | 6386 | 6387 | 6406 | 6408 | 6410 |
| 6412 | 6413 | 6421 | 6428 | 6430 | 6431 | 6433 | 6435 | 6437 | 6441 | 6442 | 6443 |
| 6446 | 6449 | 6455 | 6456 | 6463 | 6464 | 6466 | 6467 | 6470 | 6475 | 6477 | 6484 |
| 6485 | 6486 | 6487 | 6491 | 6503 | 6504 | 6509 | 6510 | 6511 | 6515 | 6518 | 6520 |
| 6521 | 6522 | 6523 | 6524 | 6525 | 6531 | 6532 | 6535 | 6536 | 6537 | 6540 | 6541 |
| 6542 | 6544 | 6545 | 6546 | 6549 | 6550 | 6551 | 6557 | 6558 | 6561 | 6567 | 6574 |
| 6575 | 6578 | 6579 | 6580 | 6586 | 6594 | 6596 | 6598 | 6599 | 6602 | 6606 | 6615 |
| 6616 | 6617 | 6625 | 6630 | 6634 | 6636 | 6637 | 6646 | 6647 | 6648 | 6649 | 6654 |
| 6655 | 6656 | 6657 | 6658 | 6659 | 6660 | 6661 | 6662 | 6666 | 6668 | 6670 | 6671 |
| 6673 | 6674 | 6682 | 6683 | 6684 | 6685 | 6687 | 6689 | 6690 | 6692 | 6693 | 6695 |
| 6701 | 6702 | 6703 | 6704 | 6705 | 6706 | 6714 | 6715 | 6716 | 6719 | 6728 | 6730 |
| 6732 | 6733 | 6734 | 6736 | 6737 | 6739 | 6741 | 6747 | 6749 | 6750 | 6753 | 6756 |
| 6759 | 6760 | 6768 | 6771 | 6773 | 6776 | 6779 | 6780 | 6788 | 6797 | 6804 | 6806 |
| 6807 | 6814 | 6819 | 6820 | 6821 | 6826 | 6828 | 6829 | 6830 | 6836 | 6839 | 6845 |
| 6847 | 6849 | 6851 | 6854 | 6855 | 6862 | 6865 | 6870 | 6879 | 6880 | 6884 | 6885 |
| 6890 | 6893 | 6907 | 6917 | 6918 | 6919 | 6922 | 6927 | 6939 | 6961 | 6970 | 6971 |
| 6977 | 6985 | 6986 | 6991 | 7000 | 7001 | 7005 | 7008 | 7009 | 7018 | 7023 | 7025 |
| 7026 | 7027 | 7033 | 7034 | 7035 | 7037 | 7038 | 7039 | 7040 | 7043 | 7045 | 7046 |
| 7047 | 7049 | 7050 | 7051 | 7053 | 7057 | 7058 | 7061 | 7062 | 7063 | 7064 | 7065 |
| 7067 | 7068 | 7069 | 7070 | 7071 | 7072 | 7074 | 7076 | 7078 | 7083 | 7086 | 7087 |
| 7088 | 7090 | 7093 | 7094 | 7096 | 7098 | 7099 | 7102 | 7105 | 7106 | 7107 | 7108 |
| 7110 | 7112 | 7114 | 7116 | 7117 | 7119 | 7120 | 7121 | 7127 | 7130 | 7133 | 7134 |
| 7135 | 7136 | 7138 | 7139 | 7140 | 7142 | 7143 | 7145 | 7146 | 7153 | 7154 | 7155 |
| 7156 | 7158 | 7161 | 7167 | 7172 | 7174 | 7179 | 7182 | 7183 | 7185 | 7186 | 7187 |
| 7188 | 7190 | 7191 | 7193 | 7207 | 7213 | 7214 | 7220 | 7221 | 7222 | 7223 | 7224 |
| 7226 | 7227 | 7231 | 7233 | 7236 | 7238 | 7242 | 7243 | 7245 | 7246 | 7249 | 7250 |
| 7255 | 7256 | 7258 | 7259 | 7261 | 7262 | 7263 | 7264 | 7265 | 7266 | 7272 | 7280 |
| 7283 | 7284 | 7285 | 7286 | 7287 | 7288 | 7292 | 7294 | 7297 | 7299 | 7300 | 7304 |
| 7307 | 7310 | 7312 | 7313 | 7314 | 7315 | 7317 | 7319 | 7320 | 7321 | 7324 | 7325 |
| 7326 | 7329 | 7333 | 7337 | 7338 | 7339 | 7341 | 7347 | 7348 | 7353 | 7356 | 7358 |
| 7359 | 7361 | 7362 | 7363 | 7364 | 7365 | 7368 | 7370 | 7371 | 7375 | 7376 | 7379 |
| 7383 | 7384 | 7386 | 7387 | 7388 | 7389 | 7390 | 7391 | 7392 | 7393 | 7395 | 7396 |
| 7397 | 7399 | 7400 | 7403 | 7409 | 7410 | 7412 | 7414 | 7415 | 7417 | 7426 | 7427 |
| 7432 | 7433 | 7435 | 7440 | 7442 | 7443 | 7445 | 7447 | 7449 | 7450 | 7454 | 7457 |
| 7458 | 7459 | 7460 | 7462 | 7463 | 7467 | 7468 | 7471 | 7472 | 7474 | 7475 | 7480 |
| 7484 | 7485 | 7486 | 7488 | 7491 | 7492 | 7493 | 7495 | 7498 | 7499 | 7501 | 7502 |
| 7504 | 7505 | 7506 | 7507 | 7508 | 7510 | 7511 | 7512 | 7514 | 7517 | 7521 | 7523 |
| 7529 | 7530 | 7531 | 7532 | 7533 | 7536 | 7537 | 7541 | 7543 | 7545 | 7547 | 7549 |
| 7552 | 7553 | 7554 | 7555 | 7557 | 7558 | 7559 | 7561 | 7564 | 7565 | 7566 | 7568 |
| 7570 | 7571 | 7572 | 7574 | 7577 | 7580 | 7585 | 7588 | 7589 | 7592 | 7593 | 7595 |
| 7597 | 7602 | 7604 | 7605 | 7606 | 7609 | 7613 | 7614 | 7619 | 7624 | 7625 | 7629 |
| 7630 | 7634 | 7637 | 7643 | 7644 | 7646 | 7647 | 7652 | 7653 | 7655 | 7656 | 7657 |
| 7659 | 7660 | 7661 | 7663 | 7665 | 7667 | 7668 | 7669 | 7670 | 7672 | 7675 | 7676 |
| 7678 | 7681 | 7682 | 7684 | 7687 | 7688 | 7691 | 7695 | 7697 | 7702 | 7704 | 7705 |
| 7706 | 7708 | 7709 | 7710 | 7712 | 7715 | 7716 | 7720 | 7727 | 7729 | 7730 | 7733 |
| 7734 | 7737 | 7738 | 7743 | 7745 | 7747 | 7752 | 7753 | 7754 | 7755 | 7759 | 7760 |
| 7762 | 7764 | 7765 | 7766 | 7768 | 7769 | 7771 | 7772 | 7773 | 7777 | 7778 | 7782 |
| 7783 | 7784 | 7786 | 7789 | 7791 | 7794 | 7795 | 7805 | 7806 | 7807 | 7808 | 7809 |
| 7810 | 7813 | 7814 | 7815 | 7818 | 7822 | 7824 | 7827 | 7832 | 7833 | 7834 | 7836 |
| 7837 | 7839 | 7840 | 7844 | 7845 | 7846 | 7848 | 7852 | 7858 | 7859 | 7860 | 7868 |
| 7869 | 7870 | 7873 | 7875 | 7881 | 7882 | 7883 | 7884 | 7885 | 7892 | 7894 | 7896 |
| 7897 | 7905 | 7906 | 7912 | 7913 | 7919 | 7920 | 7922 | 7923 | 7925 | 7927 | 7929 |
| 7933 | 7936 | 7938 | 7939 | 7940 | 7944 | 7945 | 7946 | 7949 | 7951 | 7963 | 7964 |
| 7966 | 7967 | 7969 | 7970 | 7972 | 7973 | 7974 | 7976 | 7977 | 7979 | 7982 | 7985 |
| 7993 | 7995 | 7998 | 8001 | 8002 | 8003 | 8004 | 8007 | 8009 | 8011 | 8012 | 8013 |

TABLE 13A-continued

| Seed Oil Yield/Content | | | | | | | | | | | |
|---|---|---|---|---|---|---|---|---|---|---|---|
| 8015 | 8017 | 8019 | 8024 | 8026 | 8027 | 8030 | 8031 | 8032 | 8038 | 8039 | 8041 |
| 8045 | 8046 | 8047 | 8048 | 8051 | 8053 | 8054 | 8055 | 8057 | 8058 | 8063 | 8070 |
| 8071 | 8072 | 8073 | 8074 | 8080 | 8083 | 8084 | 8086 | 8088 | 8092 | 8093 | 8097 |
| 8105 | 8107 | 8108 | 8109 | 8110 | 8111 | 8112 | 8114 | 8115 | 8117 | 8119 | 8122 |
| 8125 | 8128 | 8132 | 8133 | 8141 | 8143 | 8144 | 8145 | 8146 | 8148 | 8149 | 8150 |
| 8155 | 8156 | 8157 | 8159 | 8162 | 8163 | 8164 | 8167 | 8169 | 8170 | 8179 | 8180 |
| 8181 | 8182 | 8183 | 8184 | 8187 | 8188 | 8189 | 8194 | 8195 | 8196 | 8198 | 8202 |
| 8203 | 8206 | 8209 | 8210 | 8211 | 8213 | 8216 | 8218 | 8219 | 8220 | 8223 | 8224 |
| 8226 | 8227 | 8228 | 8234 | 8237 | 8238 | 8241 | 8243 | 8245 | 8248 | 8249 | 8250 |
| 8252 | 8253 | 8255 | 8256 | 8259 | 8261 | 8262 | 8263 | 8264 | 8265 | 8266 | 8269 |
| 8270 | 8271 | 8272 | 8274 | 8275 | 8276 | 8277 | 8279 | 8281 | 8282 | 8283 | 8286 |
| 8287 | 8288 | 8290 | 8291 | 8297 | 8298 | 8304 | 8305 | 8306 | 8307 | 8309 | 8312 |
| 8314 | 8319 | 8323 | 8324 | 8326 | 8328 | 8330 | 8338 | 8340 | 8342 | 8344 | 8345 |
| 8346 | 8349 | 8354 | 8355 | 8356 | 8361 | 8362 | 8364 | 8365 | 8370 | 8371 | 8372 |
| 8374 | 8375 | 8378 | 8382 | 8383 | 8384 | 8386 | 8387 | 8392 | 8394 | 8397 | 8398 |
| 8402 | 8404 | 8405 | 8406 | 8408 | 8410 | 8411 | 8413 | 8416 | 8417 | 8430 | 8431 |
| 8432 | 8438 | 8439 | 8440 | 8441 | 8442 | 8443 | 8444 | 8446 | 8447 | 8448 | 8449 |
| 8452 | 8453 | 8457 | 8458 | 8464 | 8466 | 8467 | 8468 | 8471 | 8472 | 8473 | 8479 |
| 8483 | 8484 | 8485 | 8488 | 8490 | 8493 | 8494 | 8496 | 8498 | 8499 | 8501 | 8502 |
| 8503 | 8509 | 8513 | 8514 | 8515 | 8516 | 8517 | 8518 | 8520 | 8521 | 8522 | 8523 |
| 8524 | 8525 | 8529 | 8530 | 8531 | 8532 | 8533 | 8534 | 8535 | 8537 | 8538 | 8539 |
| 8545 | 8551 | 8553 | 8556 | 8561 | 8562 | 8563 | 8564 | 8567 | 8568 | 8569 | 8571 |
| 8572 | 8576 | 8578 | 8579 | 8580 | 8581 | 8582 | 8584 | 8585 | 8586 | 8587 | 8588 |
| 8589 | 8590 | 8591 | 8592 | 8595 | 8600 | 8603 | 8604 | 8606 | 8607 | 8608 | 8609 |
| 8610 | 8611 | 8614 | 8621 | 8622 | 8625 | 8626 | 8627 | 8631 | 8645 | 8646 | 8648 |
| 8649 | 8650 | 8652 | 8653 | 8658 | 8659 | 8660 | 8663 | 8664 | 8665 | 8666 | 8667 |
| 8671 | 8672 | 8673 | 8674 | 8675 | 8676 | 8678 | 8680 | 8683 | 8685 | 8688 | 8691 |
| 8692 | 8695 | 8697 | 8698 | 8699 | 8701 | 8702 | 8706 | 8707 | 8710 | 8711 | 8712 |
| 8713 | 8717 | 8718 | 8719 | 8720 | 8721 | 8723 | 8724 | 8725 | 8726 | 8727 | 8728 |
| 8729 | 8730 | 8731 | 8738 | 8741 | 8742 | 8747 | 8748 | 8750 | 8755 | 8757 | 8759 |
| 8760 | 8763 | 8765 | 8766 | 8767 | 8768 | 8769 | 8770 | 8771 | 8774 | 8775 | 8777 |
| 8780 | 8781 | 8783 | 8786 | 8789 | 8793 | 8795 | 8796 | 8797 | 8800 | 8801 | 8803 |
| 8806 | 8807 | 8813 | 8814 | 8815 | 8816 | 8817 | 8822 | 8823 | 8826 | 8827 | 8828 |
| 8832 | 8833 | 8834 | 8835 | 8836 | 8839 | 8843 | 8844 | 8847 | 8852 | 8855 | 8856 |
| 8859 | 8860 | 8861 | 8862 | 8864 | 8865 | 8866 | 8868 | 8869 | 8872 | 8873 | 8876 |
| 8880 | 8885 | 8893 | 8894 | 8896 | 8899 | 8901 | 8903 | 8906 | 8909 | 8911 | 8913 |
| 8914 | 8916 | 8917 | 8918 | 8919 | 8921 | 8922 | 8923 | 8924 | 8927 | 8928 | 8933 |
| 8934 | 8936 | 8938 | 8939 | 8940 | 8945 | 8953 | 8958 | 8959 | 8960 | 8966 | 8970 |
| 8973 | 8974 | 8977 | 8980 | 8981 | 8984 | 8994 | 8998 | 8999 | 9000 | 9005 | 9006 |
| 9012 | 9013 | 9014 | 9015 | 9017 | 9018 | 9019 | 9020 | 9021 | 9022 | 9023 | 9026 |
| 9028 | 9029 | 9031 | 9035 | 9036 | 9037 | 9042 | 9045 | 9046 | 9048 | 9049 | 9051 |
| 9056 | 9061 | 9067 | 9068 | 9072 | 9073 | 9076 | 9080 | 9081 | 9082 | 9083 | 9086 |
| 9088 | 9089 | 9103 | 9104 | 9105 | 9106 | 9107 | 9108 | 9109 | 9110 | 9111 | 9114 |
| 9116 | 9118 | 9119 | 9123 | 9126 | 9127 | 9130 | 9132 | 9134 | 9135 | 9136 | 9142 |
| 9145 | 9148 | 9151 | 9153 | 9156 | 9164 | 9165 | 9167 | 9175 | 9182 | 9186 | 9189 |
| 9190 | 9192 | 9193 | 9194 | 9195 | 9197 | 9198 | 9201 | 9202 | 9212 | 9213 | 9216 |
| 9218 | 9220 | 9221 | 9222 | 9223 | 9227 | 9228 | 9235 | 9236 | 9239 | 9240 | 9241 |
| 9242 | 9243 | 9244 | 9245 | 9251 | 9253 | 9254 | 9255 | 9257 | 9264 | 9265 | 9266 |
| 9269 | 9270 | 9271 | 9273 | 9274 | 9276 | 9279 | 9280 | 9282 | 9288 | 9289 | 9291 |
| 9292 | 9293 | 9294 | 9296 | 9300 | 9302 | 9303 | 9304 | 9310 | 9320 | 9321 | 9323 |
| 9324 | 9329 | 9330 | 9333 | 9334 | 9335 | 9336 | 9348 | 9352 | 9354 | 9358 | 9362 |
| 9364 | 9368 | 9369 | 9371 | 9372 | 9373 | 9376 | 9381 | 9383 | 9385 | 9386 | 9387 |
| 9389 | 9390 | 9395 | 9404 | 9405 | 9409 | 9419 | 9420 | 9423 | 9424 | 9425 | 9429 |
| 9435 | 9439 | 9440 | 9443 | 9453 | 9456 | 9457 | 9458 | 9460 | 9461 | 9462 | 9463 |
| 9464 | 9465 | 9468 | 9469 | 9470 | 9472 | 9475 | 9476 | 9477 | 9484 | 9485 | 9489 |
| 9490 | 9492 | 9498 | 9499 | 9507 | 9508 | 9511 | 9512 | 9514 | 9515 | 9516 | 9517 |
| 9520 | 9521 | 9524 | 9530 | 9531 | 9534 | 9535 | 9537 | 9539 | 9547 | 9549 | 9551 |
| 9558 | 9559 | 9561 | 9563 | 9568 | 9569 | 9573 | 9574 | 9575 | 9576 | 9578 | 9580 |
| 9586 | 9587 | 9588 | 9589 | 9592 | 9594 | 9595 | 9598 | 9599 | 9602 | 9603 | 9604 |
| 9605 | 9611 | 9612 | 9613 | 9614 | 9619 | 9620 | 9624 | 9625 | 9627 | 9630 | 9632 |
| 9633 | 9635 | 9636 | 9645 | 9646 | 9649 | 9650 | 9652 | 9653 | 9658 | 9659 | 9669 |
| 9678 | 9679 | 9685 | 9689 | 9690 | 9701 | 9703 | 9704 | 9709 | 9710 | 9712 | 9713 |
| 9714 | 9715 | 9718 | 9725 | 9732 | 9734 | 9743 | 9745 | 9746 | 9747 | 9750 | 9751 |
| 9754 | 9758 | 9759 | 9765 | 9766 | 9771 | 9772 | 9773 | 9788 | 9789 | 9790 |
| 9798 | 9814 | 9815 | 9818 | 9826 | 9827 | 9828 | 9829 | 9830 | 9831 | 9832 | 9833 |
| 9834 | 9839 | 9840 | 9841 | 9852 | 9853 | 9855 | 9856 | 9858 | 9859 | 9860 | 9861 |
| 9862 | 9863 | 9864 | 9866 | 9868 | 9869 | 9874 | 9876 | 9877 | 9878 | 9879 | 9888 |
| 9891 | 9892 | 9893 | 9894 | 9897 | 9898 | 9902 | 9916 | 9922 | 9926 | 9927 | 9928 |
| 9929 | 9931 | 9934 | 9935 | 9936 | 9945 | 9946 | 9950 | 9958 | 9960 | 9963 | 9964 |
| 9970 | 9974 | 9976 | 9977 | 9981 | 9984 | 9987 | 9989 | 9991 | 9993 | 9995 | 9997 |
| 10002 | 10003 | 10004 | 10005 | 10007 | 10011 | 10019 | 10020 | 10021 | 10023 | 10026 | 10029 |
| 10034 | 10038 | 10044 | 10045 | 10047 | 10049 | 10050 | 10052 | 10053 | 10055 | 10059 | 10060 |
| 10061 | 10079 | 10084 | 10097 | 10098 | 10099 | 10100 | 10102 | 10104 | 10109 | 10114 | 10115 |
| 10121 | 10122 | 10132 | 10135 | 10136 | 10141 | 10142 | 10143 | 10144 | 10147 | 10151 | 10154 |
| 10158 | 10159 | 10163 | 10164 | 10165 | 10174 | 10175 | 10179 | 10181 | 10182 | 10185 | 10187 |
| 10190 | 10197 | 10198 | 10201 | 10204 | 10205 | 10207 | 10209 | 10210 | 10213 | 10214 | 10223 |
| 10225 | 10226 | 10227 | 10231 | 10232 | 10234 | 10235 | 10245 | 10248 | 10250 | 10253 | 10256 |

TABLE 13A-continued

Seed Oil Yield/Content

| | | | | | | | | | | | |
|---|---|---|---|---|---|---|---|---|---|---|---|
| 10259 | 10260 | 10261 | 10262 | 10263 | 10265 | 10266 | 10267 | 10268 | 10282 | 10283 | 10285 |
| 10293 | 10296 | 10301 | 10302 | 10303 | 10304 | 10305 | 10307 | 10309 | 10310 | 10311 | 10312 |
| 10318 | 10319 | 10322 | 10325 | 10327 | 10330 | 10336 | 10338 | 10339 | 10343 | 10346 | 10348 |
| 10351 | 10352 | 10354 | 10355 | 10357 | 10360 | 10361 | 10364 | 10365 | 10367 | 10368 | 10369 |
| 10370 | 10374 | 10375 | 10381 | 10382 | 10383 | 10384 | 10385 | 10386 | 10388 | 10395 | 10397 |
| 10399 | 10403 | 10404 | 10406 | 10410 | 10411 | 10412 | 10413 | 10415 | 10417 | 10418 | 10420 |
| 10424 | 10425 | 10427 | 10430 | 10431 | 10432 | 10433 | 10434 | 10435 | 10437 | 10438 | 10439 |
| 10442 | 10445 | 10453 | 10456 | 10457 | 10459 | 10462 | 10465 | 10468 | 10471 | 10473 | 10474 |
| 10476 | 10478 | 10479 | 10481 | 10484 | 10486 | 10487 | 10488 | 10489 | 10490 | 10493 | 10500 |
| 10501 | 10502 | 10503 | 10504 | 10505 | 10506 | 10509 | 10511 | 10514 | 10516 | 10520 | 10521 |
| 10522 | 10523 | 10524 | 10526 | 10528 | 10530 | 10531 | 10534 | 10537 | 10540 | 10541 | 10542 |
| 10543 | 10545 | 10546 | 10551 | 10555 | 10556 | 10557 | 10560 | 10564 | 10566 | 10567 | 10568 |
| 10569 | 10570 | 10571 | 10572 | 10574 | 10575 | 10577 | 10582 | 10589 | 10591 | 10593 | 10594 |
| 10596 | 10599 | 10600 | 10602 | 10603 | 10605 | 10607 | 10611 | 10612 | 10613 | 10615 | 10617 |
| 10619 | 10620 | 10622 | 10627 | 10628 | 10629 | 10630 | 10632 | 10638 | 10644 | 10646 | 10650 |
| 10651 | 10652 | 10654 | 10655 | 10657 | 10659 | 10660 | 10662 | 10663 | 10664 | 10667 | 10668 |
| 10671 | 10672 | 10674 | 10677 | 10679 | 10681 | 10683 | 10684 | 10685 | 10686 | 10687 | 10689 |
| 10690 | 10691 | 10694 | 10697 | 10698 | 10699 | 10700 | 10702 | 10705 | 10707 | 10708 | 10710 |
| 10711 | 10718 | 10721 | 10722 | 10723 | 10726 | 10729 | 10736 | 10739 | 10740 | 10744 | 10747 |
| 10748 | 10749 | 10750 | 10751 | 10752 | 10753 | 10754 | 10755 | 10757 | 10759 | 10760 | 10764 |
| 10765 | 10766 | 10774 | 10776 | 10781 | 10782 | 10783 | 10785 | 10786 | 10787 | 10788 | 10789 |
| 10796 | 10797 | 10798 | 10805 | 10807 | 10808 | 10810 | 10811 | 10813 | 10815 | 10816 | 10817 |
| 10818 | 10819 | 10820 | 10821 | 10824 | 10826 | 10828 | 10829 | 10830 | 10836 | 10838 | 10840 |
| 10841 | 10843 | 10844 | 10849 | 10850 | 10855 | 10859 | 10861 | 10866 | 10872 | 10879 | 10880 |
| 10881 | 10882 | 10888 | 10890 | 10891 | 10897 | 10898 | 10901 | 10902 | 10904 | 10907 | 10909 |
| 10910 | 10912 | 10913 | 10916 | 10920 | 10921 | 10926 | 10927 | 10928 | 10930 | 10931 | 10932 |
| 10933 | 10934 | 10935 | 10936 | 10937 | 10939 | 10940 | 10949 | 10950 | 10951 | 10952 | 10961 |
| 10962 | 10966 | 10968 | 10969 | 10970 | 10971 | 10977 | 10981 | 10982 | 10989 | 10990 | 10992 |
| 10995 | 10996 | 10997 | 10998 | 10999 | 11000 | 11001 | 11003 | 11004 | 11005 | 11008 | 11012 |
| 11013 | 11014 | 11017 | 11018 | 11021 | 11022 | 11028 | 11035 | 11036 | 11037 | 11041 | 11042 |
| 11045 | 11050 | 11051 | 11056 | 11057 | 11058 | 11061 | 11063 | 11064 | 11066 | 11073 | 11076 |
| 11079 | 11084 | 11085 | 11089 | 11090 | 11091 | 11093 | 11097 | 11102 | 11103 | 11105 | 11117 |
| 11119 | 11121 | 11136 | 11137 | 11153 | 11160 | 11163 | 11167 | 11169 | 11170 | 11174 | 11176 |
| 11180 | 11184 | 11185 | 11186 | 11188 | 11192 | 11195 | 11197 | 11216 | 11218 | 11219 | 11226 |
| 11233 | 11237 | 11240 | 11242 | 11245 | 11247 | 11248 | 11249 | 11251 | 11252 | 11253 | 11257 |
| 11259 | 11262 | 11274 | 11277 | 11285 | 11286 | 11297 | 11301 | 11303 | 11308 | 11309 | 11312 |
| 11317 | 11318 | 11320 | 11321 | 11327 | 11329 | 11332 | 11336 | 11338 | 11343 | 11344 | 11345 |
| 11349 | 11350 | 11353 | 11360 | 11362 | 11364 | 11369 | 11371 | 11373 | 11374 | 11376 | 11377 |
| 11381 | 11382 | 11384 | 11386 | 11387 | 11388 | 11394 | 11396 | 11397 | 11402 | 11407 | 11408 |
| 11413 | 11415 | 11416 | 11420 | 11422 | 11426 | 11427 | 11432 | 11433 | 11437 | 11439 | 11442 |
| 11443 | 11449 | 11450 | 11453 | 11455 | 11456 | 11463 | 11464 | 11465 | 11466 | 11467 | 11468 |
| 11469 | 11471 | 11472 | 11473 | 11474 | 11475 | 11478 | 11480 | 11485 | 11488 | 11490 | 11492 |
| 11493 | 11494 | 11495 | 11497 | 11498 | 11502 | 11503 | 11504 | 11506 | 11509 | 11511 | 11513 |
| 11514 | 11516 | 11517 | 11518 | 11520 | 11525 | 11526 | 11528 | 11531 | 11537 | 11538 | 11539 |
| 11540 | 11542 | 11546 | 11547 | 11548 | 11550 | 11551 | 11553 | 11554 | 11555 | 11558 | 11559 |
| 11562 | 11563 | 11564 | 11565 | 11566 | 11572 | 11578 | 11579 | 11583 | 11589 | 11591 | 11594 |
| 11595 | 11596 | 11597 | 11598 | 11602 | 11606 | 11608 | 11609 | 11610 | 11614 | 11615 | 11619 |
| 11623 | 11625 | 11628 | 11629 | 11630 | 11631 | 11633 | 11634 | 11635 | 11636 | 11637 | 11638 |
| 11639 | 11640 | 11641 | 11642 | 11643 | 11644 | 11645 | 11647 | 11649 | 11651 | 11652 | 11653 |
| 11655 | 11659 | 11661 | 11663 | 11665 | 11666 | 11667 | 11672 | 11673 | 11675 | 11676 | 11678 |
| 11679 | 11680 | 11688 | 11693 | 11694 | 11695 | 11696 | 11697 | 11698 | 11699 | 11701 | 11703 |
| 11705 | 11706 | 11707 | 11709 | 11717 | 11719 | 11721 | 11722 | 11723 | 11724 | 11725 | 11726 |
| 11730 | 11731 | 11735 | 11744 | 11745 | 11747 | 11749 | 11750 | 11754 | 11762 | 11766 | 11768 |
| 11769 | 11772 | 11773 | 11774 | 11779 | 11780 | 11782 | 11783 | 11786 | 11788 | 11793 | 11794 |
| 11795 | 11796 | 11799 | 11800 | 11803 | 11806 | 11808 | 11809 | 11810 | 11813 | 11814 | 11817 |
| 11819 | 11820 | 11821 | 11822 | 11824 | 11828 | 11829 | 11830 | 11833 | 11838 | 11839 | 11840 |
| 11842 | 11845 | 11847 | 11848 | 11850 | 11855 | 11856 | 11857 | 11859 | 11862 | 11863 | 11864 |
| 11866 | 11874 | 11875 | 11876 | 11880 | 11881 | 11883 | 11886 | 11887 | 11889 | 11895 | 11896 |
| 11897 | 11899 | 11900 | 11906 | 11907 | 11911 | 11915 | 11918 | 11919 | 11923 | 11924 | 11932 |
| 11936 | 11943 | 11945 | 11948 | 11949 | 11950 | 11951 | 11952 | 11956 | 11957 | 11958 | 11960 |
| 11961 | 11962 | 11963 | 11966 | 11969 | 11971 | 11977 | 11986 | 11988 | 11990 | 11993 | 11997 |
| 11998 | 11999 | 12000 | 12008 | 12010 | 12011 | 12012 | 12013 | 12014 | 12015 | 12017 | 12018 |
| 12019 | 12021 | 12027 | 12030 | 12031 | 12032 | 12033 | 12034 | 12040 | 12041 | 12044 | 12046 |
| 12052 | 12053 | 12055 | 12056 | 12058 | 12062 | 12068 | 12069 | 12070 | 12071 | 12072 | 12078 |
| 12079 | 12083 | 12086 | 12089 | 12091 | 12092 | 12096 | 12097 | 12098 | 12099 | 12100 | 12101 |
| 12102 | 12104 | 12106 | 12107 | 12109 | 12110 | 12111 | 12112 | 12116 | 12118 | 12119 | 12121 |
| 12124 | 12127 | 12128 | 12130 | 12135 | 12137 | 12138 | 12139 | 12140 | 12141 | 12142 | 12149 |
| 12151 | 12152 | 12154 | 12155 | 12159 | 12162 | 12163 | 12165 | 12167 | 12169 | 12172 | 12173 |
| 12176 | 12177 | 12178 | 12180 | 12186 | 12191 | 12192 | 12193 | 12195 | 12199 | 12200 | 12201 |
| 12206 | 12208 | 12212 | 12213 | 12214 | 12215 | 12218 | 12219 | 12225 | 12227 | 12228 | 12234 |
| 12237 | 12241 | 12242 | 12245 | 12247 | 12251 | 12253 | 12254 | 12255 | 12269 | 12270 | 12271 |
| 12272 | 12274 | 12275 | 12277 | 12278 | 12280 | 12282 | 12284 | 12286 | 12287 | 12293 | 12294 |
| 12297 | 12298 | 12299 | 12300 | 12302 | 12303 | 12304 | 12308 | 12310 | 12311 | 12312 | 12316 |
| 12319 | 12320 | 12321 | 12322 | 12324 | 12337 | 12338 | 12341 | 12343 | 12350 | 12351 | 12353 |
| 12358 | 12361 | 12363 | 12368 | 12373 | 12374 | 12376 | 12383 | 12387 | 12388 | 12394 | 12398 |
| 12400 | 12403 | 12404 | 12408 | 12418 | 12419 | 12425 | 12427 | 12428 | 12436 | 12437 | 12439 |
| 12440 | 12445 | 12446 | 12447 | 12448 | 12449 | 12450 | 12454 | 12455 | 12461 | 12471 | 12472 |

TABLE 13A-continued

Seed Oil Yield/Content

| | | | | | | | | | | | |
|---|---|---|---|---|---|---|---|---|---|---|---|
| 12473 | 12480 | 12481 | 12482 | 12483 | 12486 | 12488 | 12492 | 12494 | 12496 | 12500 | 12501 |
| 12509 | 12513 | 12517 | 12520 | 12524 | 12525 | 12526 | 12527 | 12535 | 12536 | 12537 | 12538 |
| 12541 | 12548 | 12553 | 12554 | 12558 | 12559 | 12566 | 12569 | 12572 | 12573 | 12575 | 12577 |
| 12589 | 12590 | 12592 | 12593 | 12596 | 12598 | 12600 | 12601 | 12602 | 12605 | 12610 | 12611 |
| 12614 | 12621 | 12623 | 12626 | 12629 | 12630 | 12638 | 12640 | 12644 | 12645 | 12652 | 12657 |
| 12661 | 12664 | 12666 | 12668 | 12671 | 12672 | 12673 | 12675 | 12678 | 12682 | 12688 | 12691 |
| 12692 | 12694 | 12695 | 12697 | 12698 | 12700 | 12703 | 12709 | 12712 | 12715 | 12720 | 12722 |
| 12723 | 12728 | 12730 | 12733 | 12734 | 12736 | 12738 | 12742 | 12743 | 12744 | 12751 | 12757 |
| 12762 | 12763 | 12764 | 12765 | 12768 | 12771 | 12772 | 12773 | 12774 | 12777 | 12783 | 12786 |
| 12791 | 12792 | 12793 | 12803 | 12806 | 12810 | 12812 | 12814 | 12817 | 12821 | 12824 | 12827 |
| 12829 | 12830 | 12835 | 12836 | 12840 | 12843 | 12845 | 12846 | 12848 | 12855 | 12868 | 12869 |
| 12876 | 12886 | 12889 | 12891 | 12897 | 12903 | 12908 | 12911 | 12912 | 12920 | 12922 | 12924 |
| 12925 | 12926 | 12932 | 12933 | 12936 | 12939 | 12941 | 12942 | 12943 | 12947 | 12949 | 12956 |
| 12957 | 12958 | 12962 | 12963 | 12968 | 12969 | 12976 | 12977 | 12978 | 12984 | 12986 | 12987 |
| 12989 | 12997 | 12999 | 13002 | 13013 | 13018 | 13020 | 13022 | 13023 | 13028 | 13029 | 13030 |
| 13033 | 13035 | 13037 | 13040 | 13042 | 13044 | 13045 | 13051 | 13053 | 13056 | 13063 | 13064 |
| 13065 | 13067 | 13068 | 13069 | 13073 | 13076 | 13078 | 13080 | 13086 | 13087 | 13090 | 13091 |
| 13098 | 13100 | 13103 | 13106 | 13108 | 13109 | 13111 | 13114 | 13119 | 13121 | 13124 | 13126 |
| 13128 | 13129 | 13136 | 13139 | 13142 | 13152 | 13154 | 13155 | 13159 | 13166 | 13168 | 13169 |
| 13171 | 13173 | 13177 | 13179 | 13185 | 13192 | 13195 | 13206 | 13212 | 13221 | 13222 | 13225 |
| 13229 | 13235 | 13241 | 13247 | 13249 | 13250 | 13251 | 13252 | 13253 | 13255 | 13257 | 13259 |
| 13260 | 13262 | 13263 | 13267 | 13274 | 13275 | 13276 | 13279 | 13281 | 13289 | 13291 | |
| 13295 | 13301 | 13303 | 13307 | 13308 | 13310 | 13313 | 13317 | 13319 | 13325 | 13328 | 13336 |
| 13340 | 13344 | 13346 | 13347 | 13348 | 13350 | 13351 | 13353 | 13354 | 13355 | 13357 | 13360 |
| 13366 | 13375 | 13380 | 13387 | 13395 | 13397 | 13401 | 13410 | 13416 | 13418 | 13422 | 13423 |
| 13424 | 13430 | 13433 | 13439 | 13441 | 13442 | 13444 | 13447 | 13453 | 13454 | 13455 | 13458 |
| 13459 | 13461 | 13462 | 13463 | 13464 | 13465 | 13466 | 13467 | 13470 | 13473 | 13476 | 13479 |
| 13480 | 13484 | 13485 | 13492 | 13493 | 13496 | 13497 | 13498 | 13499 | 13502 | 13505 | 13507 |
| 13509 | 13522 | 13523 | 13525 | 13527 | 13534 | 13535 | 13536 | 13538 | 13539 | 13543 | 13546 |
| 13547 | 13548 | 13550 | 13551 | 13554 | 13556 | 13557 | 13560 | 13561 | 13562 | 13563 | 13568 |
| 13570 | 13571 | 13573 | 13575 | 13578 | 13584 | 13585 | 13586 | 13588 | 13592 | 13593 | 13596 |
| 13597 | 13598 | 13599 | 13600 | 13605 | 13606 | 13607 | 13608 | 13610 | 13611 | 13612 | 13615 |
| 13617 | 13618 | 13619 | 13620 | 13621 | 13623 | 13624 | 13625 | 13627 | 13628 | 13630 | 13633 |
| 13636 | 13638 | 13640 | 13643 | 13645 | 13648 | 13650 | 13651 | 13653 | 13654 | 13655 | 13664 |
| 13667 | 13669 | 13671 | 13672 | 13673 | 13675 | 13676 | 13677 | 13678 | 13679 | 13685 | 13686 |
| 13688 | 13689 | 13692 | 13694 | 13695 | 13696 | 13697 | 13698 | 13700 | 13702 | 13703 | 13705 |
| 13706 | 13717 | 13718 | 13719 | 13720 | 13723 | 13724 | 13725 | 13726 | 13728 | 13733 | 13735 |
| 13736 | 13737 | 13738 | 13740 | 13741 | 13743 | 13747 | 13748 | 13749 | 13751 | 13752 | 13755 |
| 13757 | 13758 | 13761 | 13763 | 13769 | 13773 | 13774 | 13777 | 13778 | 13779 | 13781 | 13783 |
| 13784 | 13785 | 13786 | 13787 | 13788 | 13790 | 13791 | 13796 | 13797 | 13798 | 13801 | 13806 |
| 13810 | 13811 | 13813 | 13815 | 13817 | 13818 | 13822 | 13824 | 13828 | 13831 | 13837 | 13839 |
| 13841 | 13842 | 13845 | 13846 | 13848 | 13849 | 13851 | 13853 | 13856 | 13861 | 13862 | 13865 |
| 13866 | 13868 | 13869 | 13871 | 13873 | 13874 | 13877 | 13878 | 13880 | 13881 | 13885 | 13887 |
| 13889 | 13890 | 13892 | 13901 | 13903 | 13904 | 13906 | 13907 | 13912 | 13913 | 13915 | 13919 |
| 13920 | 13921 | 13925 | 13927 | 13928 | 13932 | 13934 | 13938 | 13939 | 13944 | 13945 | 13948 |
| 13949 | 13950 | 13953 | 13957 | 13962 | 13963 | 13966 | 13967 | 13969 | 13971 | 13974 | 13981 |
| 13982 | 13983 | 13984 | 13985 | 13986 | 13992 | 13996 | 14000 | 14005 | 14010 | 14014 | 14015 |
| 14017 | 14019 | 14030 | 14033 | 14034 | 14035 | 14036 | 14038 | 14039 | 14045 | 14046 | 14048 |
| 14049 | 14052 | 14053 | 14062 | 14064 | 14065 | 14067 | 14068 | 14071 | 14073 | 14078 | 14079 |
| 14082 | 14083 | 14084 | 14085 | 14086 | 14087 | 14088 | 14089 | 14092 | 14095 | 14096 | 14098 |
| 14101 | 14102 | 14103 | 14104 | 14105 | 14107 | 14113 | 14114 | 14120 | 14121 | 14132 | 14135 |
| 14143 | 14145 | 14149 | 14151 | 14152 | 14153 | 14157 | 14172 | 14173 | 14175 | 14177 | |
| 14181 | 14182 | 14184 | 14185 | 14195 | 14197 | 14199 | 14201 | 14202 | 14204 | 14205 | 14209 |
| 14211 | 14214 | 14216 | 14220 | 14221 | 14225 | 14230 | 14231 | 14232 | 14233 | 14234 | 14238 |
| 14242 | 14245 | 14246 | 14247 | 14248 | 14251 | 14252 | 14254 | 14255 | 14256 | 14257 | 14258 |
| 14259 | 14260 | 14261 | 14262 | 14266 | 14267 | 14268 | 14273 | 14274 | 14276 | 14277 | |
| 14279 | 14281 | 14283 | 14285 | 14286 | 14287 | 14288 | 14291 | 14293 | 14295 | 14296 | 14298 |
| 14299 | 14300 | 14304 | 14306 | 14308 | 14309 | 14312 | 14313 | 14317 | 14319 | 14320 | 14321 |
| 14322 | 14324 | 14327 | 14328 | 14331 | 14332 | 14333 | 14336 | 14337 | 14342 | 14343 | 14344 |
| 14346 | 14348 | 14349 | 14352 | 14354 | 14355 | 14356 | 14359 | 14364 | 14365 | 14369 | 14370 |
| 14374 | 14376 | 14377 | 14379 | 14381 | 14382 | 14383 | 14389 | 14392 | 14393 | 14394 | 14396 |
| 14398 | 14399 | 14400 | 14406 | 14410 | 14412 | 14413 | 14421 | 14423 | 14424 | 14425 | 14428 |
| 14430 | 14431 | 14432 | 14439 | 14444 | 14450 | 14452 | 14453 | 14454 | 14455 | 14456 | 14462 |
| 14469 | 14470 | 14472 | 14473 | 14474 | 14476 | 14478 | 14484 | 14486 | 14487 | 14488 | |
| 14491 | 14496 | 14498 | 14499 | 14501 | 14502 | 14506 | 14510 | 14517 | 14520 | 14522 | 14523 |
| 14524 | 14526 | 14528 | 14529 | 14530 | 14534 | 14535 | 14537 | 14538 | 14540 | 14542 | 14547 |
| 14551 | 14555 | 14560 | 14561 | 14563 | 14564 | 14565 | 14566 | 14568 | 14569 | 14571 | 14575 |
| 14576 | 14577 | 14578 | 14586 | 14588 | 14589 | 14591 | 14592 | 14594 | 14596 | 14598 | 14599 |
| 14603 | 14608 | 14613 | 14615 | 14616 | 14617 | 14618 | 14619 | 14620 | 14622 | 14623 | 14624 |
| 14628 | 14631 | 14633 | 14634 | 14636 | 14637 | 14638 | 14639 | 14643 | 14649 | 14650 | 14651 |
| 14652 | 14654 | 14657 | 14659 | 14662 | 14663 | 14664 | 14665 | 14667 | 14668 | 14678 | 14679 |
| 14681 | 14682 | 14683 | 14684 | 14685 | 14687 | 14688 | 14689 | 14691 | 14693 | 14694 | 14695 |
| 14697 | 14699 | 14700 | 14702 | 14704 | 14705 | 14706 | 14707 | 14708 | 14709 | 14710 | 14711 |
| 14712 | 14715 | 14717 | 14718 | 14719 | 14720 | 14723 | 14731 | 14733 | 14734 | 14736 | 14737 |
| 14738 | 14739 | 14740 | 14741 | 14743 | 14744 | 14746 | 14748 | 14749 | 14752 | 14753 | 14755 |
| 14757 | 14761 | 14762 | 14766 | 14774 | 14777 | 14778 | 14780 | 14781 | 14783 | 14790 | 14791 |
| 14795 | 14806 | 14807 | 14809 | 14810 | 14812 | 14814 | 14815 | 14816 | 14817 | 14820 | 14825 |

TABLE 13A-continued

Seed Oil Yield/Content

| | | | | | | | | | | | |
|---|---|---|---|---|---|---|---|---|---|---|---|
| 14829 | 14830 | 14831 | 14838 | 14840 | 14841 | 14842 | 14845 | 14847 | 14852 | 14858 | 14860 |
| 14861 | 14863 | 14864 | 14867 | 14869 | 14870 | 14871 | 14872 | 14873 | 14876 | 14879 | 14880 |
| 14882 | 14883 | 14885 | 14886 | 14888 | 14891 | 14892 | 14894 | 14895 | 14896 | 14901 | 14904 |
| 14905 | 14908 | 14909 | 14910 | 14920 | 14926 | 14931 | 14932 | 14934 | 14935 | 14938 | 14940 |
| 14943 | 14954 | 14955 | 14957 | 14958 | 14962 | 14963 | 14964 | 14968 | 14977 | 14978 | 14982 |
| 14983 | 14985 | 14986 | 14989 | 14990 | 14991 | 14994 | 14996 | 14999 | 15003 | 15006 | 15008 |
| 15011 | 15015 | 15016 | 15017 | 15018 | 15019 | 15022 | 15025 | 15026 | 15027 | 15029 | 15033 |
| 15036 | 15037 | 15047 | 15048 | 15051 | 15052 | 15055 | 15056 | 15058 | 15059 | 15060 | 15063 |
| 15064 | 15066 | 15067 | 15070 | 15071 | 15072 | 15073 | 15074 | 15075 | 15079 | 15081 | 15082 |
| 15084 | 15085 | 15088 | 15092 | 15093 | 15095 | 15096 | 15100 | 15101 | 15102 | 15103 | 15105 |
| 15107 | 15111 | 15115 | 15120 | 15123 | 15124 | 15125 | 15127 | 15131 | 15132 | 15136 | 15140 |
| 15141 | 15142 | 15143 | 15147 | 15151 | 15157 | 15158 | 15160 | 15162 | 15163 | 15164 | 15165 |
| 15166 | 15167 | 15168 | 15169 | 15170 | 15172 | 15174 | 15175 | 15176 | 15179 | 15180 | 15182 |
| 15183 | 15184 | 15187 | 15188 | 15189 | 15190 | 15191 | 15192 | 15193 | 15196 | 15198 | 15202 |
| 15211 | 15213 | 15214 | 15215 | 15216 | 15217 | 15219 | 15220 | 15221 | 15222 | 15223 | 15224 |
| 15226 | 15229 | 15232 | 15234 | 15236 | 15238 | 15239 | 15242 | 15256 | 15257 | 15268 | 15269 |
| 15271 | 15272 | 15273 | 15287 | 15288 | 15289 | 15292 | 15293 | 15295 | 15300 | 15301 | 15302 |
| 15305 | 15306 | 15310 | 15313 | 15316 | 15317 | 15322 | 15334 | 15335 | 15336 | 15337 | 15342 |
| 15343 | 15344 | 15350 | 15351 | 15357 | 15358 | 15360 | 15365 | 15366 | 15367 | 15370 | 15372 |
| 15375 | 15376 | 15377 | 15379 | 15380 | 15383 | 15388 | 15391 | 15392 | 15397 | 15398 | 15401 |
| 15406 | 15408 | 15409 | 15413 | 15415 | 15416 | 15417 | 15422 | 15423 | 15425 | 15426 | 15427 |
| 15428 | 15441 | 15442 | 15446 | 15448 | 15450 | 15454 | 15456 | 15459 | 15461 | 15462 | 15466 |
| 15467 | 15471 | 15480 | 15481 | 15482 | 15485 | 15490 | 15492 | 15498 | 15500 | 15510 | 15511 |
| 15512 | 15513 | 15518 | 15519 | 15521 | 15523 | 15525 | 15526 | 15530 | 15531 | 15532 | 15533 |
| 15534 | 15535 | 15536 | 15538 | 15541 | 15545 | 15546 | 15547 | 15548 | 15550 | 15551 | 15553 |
| 15555 | 15557 | 15558 | 15561 | 15562 | 15563 | 15564 | 15565 | 15567 | 15569 | 15570 | 15571 |
| 15575 | 15576 | 15577 | 15578 | 15582 | 15583 | 15585 | 15587 | 15593 | 15596 | 15601 | 15603 |
| 15607 | 15608 | 15609 | 15611 | 15612 | 15613 | 15614 | 15615 | 15616 | 15617 | 15621 | 15622 |
| 15623 | 15624 | 15625 | 15626 | 15629 | 15630 | 15633 | 15634 | 15639 | 15642 | 15646 | 15647 |
| 15648 | 15649 | 15650 | 15651 | 15652 | 15654 | 15655 | 15656 | 15657 | 15658 | 15659 | 15661 |
| 15666 | 15667 | 15668 | 15671 | 15672 | 15676 | 15679 | 15682 | 15683 | 15688 | 15702 | 15703 |
| 15704 | 15708 | 15709 | 15710 | 15711 | 15717 | 15718 | 15724 | 15725 | 15727 | 15732 | 15734 |
| 15737 | 15739 | 15742 | 15744 | 15745 | 15747 | 15748 | 15751 | 15756 | 15759 | 15760 | 15765 |
| 15766 | 15769 | 15774 | 15776 | 15777 | 15781 | 15783 | 15784 | 15785 | 15790 | 15791 | 15793 |
| 15794 | 15795 | 15796 | 15799 | 15808 | 15810 | 15811 | 15814 | 15816 | 15818 | 15822 | 15823 |
| 15824 | 15827 | 15829 | 15831 | 15836 | 15837 | 15841 | 15850 | 15852 | 15853 | 15856 | 15862 |
| 15863 | 15869 | 15871 | 15882 | 15883 | 15884 | 15885 | 15890 | 15891 | 15892 | 15894 | 15896 |
| 15897 | 15901 | 15902 | 15903 | 15904 | 15905 | 15906 | 15907 | 15909 | 15912 | 15917 | 15918 |
| 15919 | 15920 | 15923 | 15924 | 15926 | 15928 | 15930 | 15931 | 15934 | 15935 | 15936 | 15937 |
| 15938 | 15940 | 15942 | 15943 | 15944 | 15949 | 15951 | 15952 | 15953 | 15954 | 15958 | 15959 |
| 15961 | 15963 | 15969 | 15973 | 15978 | 15982 | 15983 | 15984 | 15985 | 15987 | 15988 | 15989 |
| 15990 | 15991 | 15992 | 15996 | 15997 | 15998 | 15999 | 16000 | 16001 | 16004 | 16005 | 16008 |
| 16009 | 16014 | 16017 | 16021 | 16023 | 16024 | 16025 | 16026 | 16028 | 16029 | 16030 | |
| 16031 | 16032 | 16033 | 16034 | 16035 | 16036 | 16037 | 16039 | 16041 | 16042 | 16045 | 16046 |
| 16047 | 16048 | 16049 | 16052 | 16056 | 16057 | 16058 | 16061 | 16062 | 16067 | 16069 | 16073 |
| 16074 | 16079 | 16092 | 16093 | 16094 | 16095 | 16098 | 16099 | 16105 | 16109 | 16110 | 16111 |
| 16117 | 16118 | 16122 | 16125 | 16127 | 16128 | 16129 | 16131 | 16132 | 16135 | 16138 | 16139 |
| 16143 | 16145 | 16149 | 16150 | 16153 | 16157 | 16160 | 16163 | 16164 | 16166 | 16167 | 16172 |
| 16173 | 16175 | 16176 | 16177 | 16178 | 16181 | 16189 | 16190 | 16192 | 16196 | 16198 | 16199 |
| 16203 | 16204 | 16205 | 16209 | 16210 | 16212 | 16218 | 16227 | 16228 | 16231 | 16233 | 16236 |
| 16238 | 16242 | 16246 | 16254 | 16256 | 16257 | 16258 | 16263 | 16264 | 16265 | 16267 | 16269 |
| 16272 | 16273 | 16274 | 16275 | 16276 | 16278 | 16280 | 16282 | 16284 | 16285 | 16289 | 16290 |
| 16291 | 16294 | 16295 | 16296 | 16298 | 16301 | 16302 | 16303 | 16304 | 16306 | 16308 | 16311 |
| 16312 | 16314 | 16315 | 16316 | 16317 | 16318 | 16322 | 16324 | 16328 | 16331 | 16335 | 16337 |
| 16341 | 16342 | 16344 | 16345 | 16346 | 16347 | 16348 | 16349 | 16351 | 16352 | 16353 | 16354 |
| 16356 | 16357 | 16359 | 16362 | 16363 | 16367 | 16370 | 16373 | 16376 | 16383 | 16385 | 16386 |
| 16388 | 16389 | 16391 | 16392 | 16402 | 16404 | 16407 | 16416 | 16418 | 16420 | 16421 | 16423 |
| 16428 | 16429 | 16430 | 16433 | 16434 | 16437 | 16441 | 16442 | 16445 | 16446 | 16449 | 16454 |
| 16457 | 16458 | 16463 | 16464 | 16465 | 16466 | 16470 | 16474 | 16476 | 16478 | 16480 | 16481 |
| 16483 | 16488 | 16489 | 16491 | 16494 | 16496 | 16497 | 16499 | 16506 | 16508 | 16512 | 16513 |
| 16514 | 16519 | 16521 | 16524 | 16525 | 16532 | 16533 | 16536 | 16537 | 16539 | 16545 | 16549 |
| 16550 | 16552 | 16555 | 16558 | 16560 | 16561 | 16563 | 16564 | 16571 | 16576 | 16580 | 16581 |
| 16583 | 16586 | 16590 | 16592 | 16594 | 16595 | 16596 | 16597 | 16598 | 16600 | 16601 | 16603 |
| 16604 | 16606 | 16608 | 16610 | 16612 | 16613 | 16614 | 16615 | 16619 | 16632 | 16639 | 16640 |
| 16641 | 16646 | 16647 | 16650 | 16662 | 16663 | 16664 | 16669 | 16670 | 16675 | 16677 | 16678 |
| 16679 | 16681 | 16687 | 16688 | 16690 | 16691 | 16692 | 16693 | 16694 | 16700 | 16702 | 16703 |
| 16704 | 16705 | 16706 | 16707 | 16708 | 16709 | 16720 | 16721 | 16726 | 16731 | 16734 | 16735 |
| 16736 | 16743 | 16747 | 16748 | 16749 | 16751 | 16752 | 16756 | 16757 | 16759 | 16760 | 16761 |
| 16763 | 16766 | 16773 | 16774 | 16776 | 16777 | 16778 | 16779 | 16783 | 16785 | 16787 | 16789 |
| 16792 | 16793 | 16794 | 16795 | 16799 | 16804 | 16805 | 16808 | 16809 | 16812 | 16815 | 16819 |
| 16821 | 16823 | 16824 | 16827 | 16828 | 16830 | 16835 | 16837 | 16839 | 16841 | 16844 | 16846 |
| 16850 | 16851 | 16854 | 16860 | 16863 | 16864 | 16865 | 16866 | 16867 | 16869 | 16870 | 16871 |
| 16873 | 16876 | 16878 | 16882 | 16883 | 16888 | 16890 | 16892 | 16893 | 16895 | 16897 | 16900 |
| 16901 | 16902 | 16905 | 16906 | 16907 | 16908 | 16909 | 16910 | 16911 | 16912 | 16913 | 16914 |
| 16915 | 16918 | 16920 | 16921 | 16922 | 16924 | 16926 | 16927 | 16928 | 16929 | 16932 | 16933 |
| 16935 | 16938 | 16939 | 16940 | 16941 | 16943 | 16944 | 16945 | 16946 | 16949 | 16950 | 16954 |
| 16955 | 16956 | 16959 | 16965 | 16968 | 16970 | 16972 | 16973 | 16975 | 16977 | 16980 | 16981 |

TABLE 13A-continued

Seed Oil Yield/Content

| | | | | | | | | | | | |
|---|---|---|---|---|---|---|---|---|---|---|---|
| 16983 | 16984 | 16985 | 16987 | 16991 | 16992 | 16995 | 16996 | 16997 | 16998 | 17000 | 17003 |
| 17009 | 17011 | 17012 | 17014 | 17015 | 17016 | 17017 | 17021 | 17023 | 17024 | 17027 | 17028 |
| 17031 | 17032 | 17037 | 17039 | 17040 | 17043 | 17044 | 17047 | 17050 | 17051 | 17053 | 17058 |
| 17059 | 17062 | 17063 | 17065 | 17067 | 17068 | 17069 | 17072 | 17073 | 17074 | 17085 | 17086 |
| 17088 | 17089 | 17093 | 17103 | 17104 | 17106 | 17109 | 17110 | 17111 | 17112 | 17113 | 17114 |
| 17115 | 17116 | 17123 | 17125 | 17126 | 17128 | 17129 | 17141 | 17144 | 17145 | 17146 |
| 17147 | 17152 | 17155 | 17156 | 17157 | 17158 | 17161 | 17164 | 17165 | 17169 | 17171 | 17176 |
| 17178 | 17180 | 17181 | 17182 | 17183 | 17184 | 17188 | 17190 | 17192 | 17196 | 17198 | 17201 |
| 17204 | 17206 | 17220 | 17225 | 17226 | 17228 | 17231 | 17234 | 17235 | 17237 | 17239 | 17240 |
| 17242 | 17244 | 17249 | 17251 | 17252 | 17253 | 17255 | 17256 | 17257 | 17258 | 17260 | 17261 |
| 17263 | 17264 | 17265 | 17268 | 17270 | 17272 | 17273 | 17276 | 17277 | 17278 | 17279 | 17281 |
| 17282 | 17284 | 17288 | 17290 | 17291 | 17292 | 17293 | 17296 | 17298 | 17299 | 17300 | 17301 |
| 17307 | 17308 | 17319 | 17321 | 17324 | 17325 | 17328 | 17330 | 17338 | 17340 | 17341 | 17343 |
| 17345 | 17347 | 17348 | 17351 | 17352 | 17353 | 17354 | 17355 | 17358 | 17359 | 17360 | 17361 |
| 17362 | 17364 | 17366 | 17367 | 17375 | 17388 | 17389 | 17391 | 17392 | 17394 | 17398 | 17399 |
| 17400 | 17403 | 17405 | 17407 | 17408 | 17409 | 17410 | 17411 | 17412 | 17413 | 17414 | 17422 |
| 17423 | 17426 | 17427 | 17429 | 17430 | 17431 | 17432 | 17433 | 17434 | 17435 | 17436 | 17437 |
| 17439 | 17440 | 17442 | 17447 | 17449 | 17450 | 17451 | 17454 | 17457 | 17459 | 17460 | 17461 |
| 17463 | 17466 | 17467 | 17470 | 17475 | 17476 | 17486 | 17487 | 17488 | 17489 | 17498 | 17502 |
| 17507 | 17509 | 17510 | 17511 | 17513 | 17515 | 17516 | 17518 | 17519 | 17522 | 17523 | 17525 |
| 17526 | 17528 | 17529 | 17530 | 17531 | 17536 | 17537 | 17538 | 17542 | 17545 | 17551 | 17552 |
| 17553 | 17554 | 17555 | 17556 | 17564 | 17565 | 17567 | 17568 | 17570 | 17571 | 17572 | 17573 |
| 17577 | 17578 | 17579 | 17580 | 17587 | 17594 | 17602 | 17605 | 17606 | 17607 | 17609 | 17610 |
| 17613 | 17614 | 17615 | 17616 | 17619 | 17622 | 17623 | 17625 | 17626 | 17632 | 17633 | 17635 |
| 17636 | 17645 | 17646 | 17647 | 17648 | 17650 | 17652 | 17653 | 17656 | 17658 | 17660 | 17661 |
| 17664 | 17665 | 17670 | 17671 | 17674 | 17675 | 17676 | 17678 | 17679 | 17680 | 17681 | 17694 |
| 17695 | 17696 | 17700 | 17701 | 17705 | 17711 | 17715 | 17716 | 17719 | 17720 | 17722 | 17724 |
| 17725 | 17729 | 17730 | 17731 | 17736 | 17738 | 17739 | 17741 | 17742 | 17745 | 17749 | 17762 |
| 17764 | 17770 | 17771 | 17779 | 17780 | 17783 | 17784 | 17786 | 17788 | 17790 | 17792 | 17795 |
| 17796 | 17798 | 17801 | 17807 | 17809 | 17813 | 17819 | 17820 | 17822 | 17832 | 17835 | 17837 |
| 17838 | 17840 | 17841 | 17846 | 17847 | 17848 | 17849 | 17850 | 17854 | 17860 | 17861 | 17863 |
| 17864 | 17865 | 17866 | 17867 | 17868 | 17869 | 17870 | 17872 | 17876 | 17881 | 17882 | 17884 |
| 17885 | 17886 | 17887 | 17888 | 17889 | 17892 | 17893 | 17898 | 17899 | 17901 | 17904 | 17909 |
| 17913 | 17914 | 17918 | 17921 | 17923 | 17926 | 17927 | 17929 | 17934 | 17935 | 17948 | 17949 |
| 17951 | 17955 | 17956 | 17958 | 17960 | 17961 | 17966 | 17968 | 17971 | 17974 | 17981 | 17982 |
| 17984 | 17985 | 17986 | 17987 | 17988 | 17989 | 17991 | 17993 | 17994 | 17995 | 17996 | 17997 |
| 17999 | 18002 | 18003 | 18006 | 18008 | 18010 | 18012 | 18013 | 18015 | 18018 | 18020 | 18021 |
| 18025 | 18026 | 18029 | 18030 | 18031 | 18034 | 18036 | 18039 | 18041 | 18043 | 18045 | 18049 |
| 18050 | 18051 | 18054 | 18055 | 18056 | 18059 | 18060 | 18062 | 18063 | 18066 | 18067 |
| 18069 | 18070 | 18071 | 18073 | 18074 | 18075 | 18076 | 18077 | 18078 | 18079 | 18080 | 18081 |
| 18082 | 18087 | 18089 | 18092 | 18099 | 18100 | 18101 | 18104 | 18105 | 18108 | 18113 | 18114 |
| 18116 | 18117 | 18119 | 18120 | 18121 | 18124 | 18125 | 18126 | 18127 | 18129 | 18130 | 18131 |
| 18133 | 18135 | 18138 | 18139 | 18140 | 18141 | 18143 | 18144 | 18148 | 18149 | 18151 |
| 18152 | 18154 | 18155 | 18156 | 18157 | 18158 | 18159 | 18170 | 18171 | 18173 | 18175 | 18176 |
| 18179 | 18180 | 18183 | 18185 | 18186 | 18187 | 18188 | 18189 | 18190 | 18191 | 18192 | 18193 |
| 18195 | 18199 | 18201 | 18204 | 18205 | 18209 | 18210 | 18211 | 18213 | 18219 | 18220 | 18221 |
| 18223 | 18226 | 18227 | 18228 | 18233 | 18235 | 18237 | 18241 | 18242 | 18245 | 18248 | 18259 |
| 18265 | 18266 | 18267 | 18270 | 18271 | 18274 | 18275 | 18276 | 18277 | 18278 | 18280 | 18281 |
| 18282 | 18285 | 18288 | 18293 | 18294 | 18295 | 18298 | 18299 | 18304 | 18308 | 18310 | 18311 |
| 18313 | 18314 | 18318 | 18322 | 18325 | 18327 | 18328 | 18329 | 18330 | 18338 | 18343 | 18344 |
| 18345 | 18349 | 18351 | 18356 | 18357 | 18359 | 18365 | 18367 | 18368 | 18369 | 18370 | 18371 |
| 18372 | 18373 | 18374 | 18377 | 18384 | 18390 | 18394 | 18395 | 18397 | 18401 | 18402 | 18403 |
| 18405 | 18410 | 18411 | 18417 | 18418 | 18419 | 18424 | 18425 | 18429 | 18430 | 18431 | 18432 |
| 18435 | 18442 | 18443 | 18444 | 18447 | 18449 | 18451 | 18453 | 18455 | 18464 | 18467 | 18468 |
| 18470 | 18473 | 18474 | 18475 | 18482 | 18484 | 18485 | 18486 | 18487 | 18489 | 18490 | 18491 |
| 18494 | 18500 | 18508 | 18512 | 18515 | 18516 | 18517 | 18519 | 18522 | 18528 | 18529 | 18535 |
| 18537 | 18544 | 18545 | 18548 | 18549 | 18550 | 18551 | 18556 | 18559 | 18569 | 18572 | 18573 |
| 18575 | 18576 | 18580 | 18581 | 18583 | 18588 | 18592 | 18593 | 18594 | 18595 | 18598 | 18600 |
| 18604 | 18608 | 18611 | 18612 | 18614 | 18616 | 18617 | 18618 | 18619 | 18621 | 18625 | 18630 |
| 18633 | 18634 | 18636 | 18640 | 18652 | 18655 | 18656 | 18658 | 18660 | 18661 | 18662 | 18668 |
| 18669 | 18672 | 18673 | 18681 | 18682 | 18683 | 18688 | 18692 | 18697 | 18699 | 18709 | 18710 |
| 18711 | 18718 | 18719 | 18726 | 18730 | 18731 | 18732 | 18733 | 18735 | 18740 | 18741 | 18743 |
| 18744 | 18748 | 18749 | 18751 | 18752 | 18759 | 18760 | 18761 | 18766 | 18767 | 18768 | 18771 |
| 18775 | 18779 | 18781 | 18782 | 18783 | 18785 | 18788 | 18790 | 18792 | 18802 | 18804 | 18822 |
| 18824 | 18825 | 18827 | 18828 | 18829 | 18834 | 18835 | 18837 | 18838 | 18839 | 18846 | 18858 |
| 18860 | 18861 | 18862 | 18863 | 18869 | 18879 | 18884 | 18896 | 18897 | 18904 | 18908 | 18910 |
| 18912 | 18915 | 18916 | 18920 | 18922 | 18924 | 18925 | 18926 | 18929 | 18930 | 18933 | 18937 |
| 18941 | 18945 | 18952 | 18953 | 18958 | 18959 | 18961 | 18964 | 18968 | 18977 | 18978 |
| 18980 | 18981 | 18986 | 18987 | 18990 | 18995 | 19000 | 19005 | 19007 | 19008 | 19009 | 19010 |
| 19019 | 19020 | 19022 | 19023 | 19026 | 19038 | 19042 | 19049 | 19051 | 19055 | 19059 | 19067 |
| 19069 | 19070 | 19073 | 19074 | 19075 | 19076 | 19077 | 19078 | 19080 | 19083 | 19084 | 19085 |
| 19088 | 19090 | 19091 | 19093 | 19099 | 19102 | 19104 | 19107 | 19115 | 19117 | 19118 | 19120 |
| 19122 | 19124 | 19127 | 19130 | 19131 | 19137 | 19139 | 19155 | 19156 | 19158 | 19160 | 19163 |
| 19169 | 19171 | 19173 | 19174 | 19176 | 19178 | 19181 | 19183 | 19184 | 19191 | 19195 | 19197 |
| 19198 | 19199 | 19200 | 19201 | 19202 | 19203 | 19205 | 19212 | 19214 | 19216 | 19221 | 19222 |
| 19228 | 19230 | 19231 | 19233 | 19234 | 19238 | 19239 | 19240 | 19242 | 19243 | 19245 | 19246 |
| 19250 | 19253 | 19255 | 19257 | 19258 | 19259 | 19260 | 19261 | 19262 | 19263 | 19264 | 19271 |

TABLE 13A-continued

Seed Oil Yield/Content

| | | | | | | | | | | | |
|---|---|---|---|---|---|---|---|---|---|---|---|
| 19273 | 19276 | 19277 | 19280 | 19282 | 19292 | 19294 | 19295 | 19300 | 19301 | 19306 | 19307 |
| 19309 | 19312 | 19316 | 19317 | 19325 | 19326 | 19330 | 19332 | 19333 | 19334 | 19338 | 19341 |
| 19342 | 19344 | 19346 | 19348 | 19351 | 19352 | 19355 | 19363 | 19364 | 19365 | 19366 | 19367 |
| 19368 | 19369 | 19370 | 19372 | 19376 | 19377 | 19378 | 19381 | 19387 | 19388 | 19389 | 19390 |
| 19391 | 19393 | 19394 | 19409 | 19412 | 19414 | 19416 | 19420 | 19422 | 19424 | 19433 | 19438 |
| 19441 | 19444 | 19445 | 19446 | 19447 | 19448 | 19449 | 19450 | 19461 | 19464 | 19465 | 19469 |
| 19470 | 19472 | 19477 | 19483 | 19486 | 19491 | 19493 | 19495 | 19496 | 19498 | 19501 | 19502 |
| 19503 | 19505 | 19511 | 19517 | 19522 | 19523 | 19524 | 19525 | 19528 | 19530 | 19532 | 19533 |
| 19534 | 19539 | 19540 | 19545 | 19549 | 19550 | 19552 | 19553 | 19554 | 19555 | 19557 | 19562 |
| 19566 | 19567 | 19572 | 19573 | 19574 | 19575 | 19578 | 19580 | 19581 | 19582 | 19583 | 19584 |
| 19585 | 19589 | 19590 | 19593 | 19594 | 19595 | 19597 | 19599 | 19612 | 19614 | 19615 | 19616 |
| 19617 | 19620 | 19623 | 19628 | 19633 | 19639 | 19644 | 19645 | 19649 | 19652 | 19655 | 19656 |
| 19658 | 19661 | 19663 | 19664 | 19666 | 19667 | 19671 | 19672 | 19681 | 19683 | 19684 | 19686 |
| 19688 | 19689 | 19690 | 19698 | 19699 | 19701 | 19702 | 19703 | 19704 | 19708 | 19711 | 19712 |
| 19713 | 19714 | 19715 | 19716 | 19717 | 19719 | 19735 | 19738 | 19739 | 19740 | 19741 | 19742 |
| 19743 | 19747 | 19751 | 19752 | 19754 | 19757 | 19763 | 19768 | 19769 | 19771 | 19772 | 19777 |
| 19781 | 19787 | 19791 | 19795 | 19796 | 19797 | 19799 | 19801 | 19802 | 19804 | 19806 | 19807 |
| 19808 | 19809 | 19810 | 19811 | 19812 | 19813 | 19814 | 19816 | 19817 | 19818 | 19820 | 19822 |
| 19825 | 19828 | 19831 | 19835 | 19838 | 19844 | 19846 | 19847 | 19848 | 19850 | 19852 | 19853 |
| 19854 | 19856 | 19857 | 19859 | 19860 | 19863 | 19866 | 19867 | 19876 | 19879 | 19881 | 19884 |
| 19889 | 19893 | 19900 | 19901 | 19905 | 19907 | 19908 | 19910 | 19912 | 19913 | 19915 | 19918 |
| 19919 | 19921 | 19922 | 19925 | 19926 | 19929 | 19930 | 19935 | 19946 | 19956 | 19957 | 19958 |
| 19966 | 19970 | 19973 | 19979 | 19981 | 19990 | 19997 | 19998 | 19999 | 20001 | 20007 | 20011 |
| 20014 | 20030 | 20032 | 20034 | 20035 | 20037 | 20039 | 20040 | 20041 | 20042 | 20043 | 20044 |
| 20045 | 20050 | 20051 | 20053 | 20054 | 20055 | 20056 | 20060 | 20068 | 20070 | 20071 | 20074 |
| 20076 | 20080 | 20082 | 20083 | 20086 | 20089 | 20090 | 20092 | 20093 | 20097 | 20099 | 20100 |
| 20101 | 20103 | 20106 | 20108 | 20109 | 20110 | 20118 | 20119 | 20121 | 20123 | 20126 | 20131 |
| 20133 | 20136 | 20140 | 20151 | 20152 | 20153 | 20154 | 20155 | 20156 | 20159 | 20160 | 20162 |
| 20169 | 20180 | 20181 | 20190 | 20191 | 20192 | 20195 | 20207 | 20216 | 20218 | 20220 | 20221 |
| 20222 | 20228 | 20229 | 20240 | 20241 | 20244 | 20245 | 20249 | 20253 | 20262 | 20263 | 20272 |
| 20275 | 20278 | 20280 | 20286 | 20290 | 20297 | 20298 | 20300 | 20301 | 20307 | 20308 | 20312 |
| 20313 | 20317 | 20319 | 20322 | 20326 | 20340 | 20342 | 20349 | 20350 | 20357 | 20358 | 20365 |
| 20369 | 20370 | 20374 | 20375 | 20377 | 20378 | 20386 | 20398 | 20400 | 20402 | 20404 | 20405 |
| 20409 | 20410 | 20412 | 20417 | 20418 | 20419 | 20420 | 20422 | 20423 | 20424 | 20425 | 20428 |
| 20429 | 20430 | 20437 | 20441 | 20444 | 20451 | 20452 | 20454 | 20457 | 20460 | 20461 | 20463 |
| 20464 | 20465 | 20466 | 20467 | 20468 | 20470 | 20473 | 20474 | 20476 | 20477 | 20480 | 20481 |
| 20482 | 20486 | 20489 | 20490 | 20491 | 20494 | 20495 | 20496 | 20500 | 20501 | 20503 | 20504 |
| 20505 | 20506 | 20508 | 20511 | 20512 | 20513 | 20515 | 20519 | 20523 | 20524 | 20525 | 20526 |
| 20529 | 20531 | 20532 | 20533 | 20534 | 20535 | 20536 | 20537 | 20539 | 20540 | 20543 | 20545 |
| 20548 | 20553 | 20554 | 20555 | 20556 | 20563 | 20564 | 20565 | 20567 | 20568 | 20570 | 20573 |
| 20576 | 20577 | 20578 | 20579 | 20580 | 20583 | 20584 | 20586 | 20588 | 20592 | 20593 | 20594 |
| 20598 | 20599 | 20600 | 20601 | 20602 | 20603 | 20605 | 20610 | 20612 | 20614 | 20615 | 20616 |
| 20617 | 20618 | 20619 | 20624 | 20627 | 20631 | 20636 | 20637 | 20639 | 20643 | 20646 | 20647 |
| 20648 | 20650 | 20655 | 20656 | 20661 | 20662 | 20663 | 20664 | 20665 | 20668 | 20670 | 20671 |
| 20673 | 20674 | 20677 | 20682 | 20688 | 20689 | 20690 | 20691 | 20692 | 20701 | 20703 | 20706 |
| 20707 | 20708 | 20709 | 20713 | 20715 | 20716 | 20718 | 20719 | 20720 | 20722 | 20725 | 20726 |
| 20730 | 20731 | 20736 | 20737 | 20739 | 20743 | 20744 | 20745 | 20746 | 20748 | 20749 | 20750 |
| 20752 | 20753 | 20757 | 20758 | 20761 | 20762 | 20765 | 20766 | 20768 | 20769 | 20771 | 20772 |
| 20773 | 20774 | 20775 | 20777 | 20778 | 20779 | 20780 | 20784 | 20785 | 20787 | 20789 | 20791 |
| 20797 | 20800 | 20801 | 20802 | 20803 | 20805 | 20806 | 20809 | 20811 | 20817 | 20821 | 20822 |
| 20826 | 20827 | 20828 | 20829 | 20831 | 20835 | 20836 | 20838 | 20839 | 20840 | 20848 | 20849 |
| 20850 | 20852 | 20854 | 20856 | 20857 | 20858 | 20859 | 20860 | 20865 | 20866 | 20868 | 20871 |
| 20874 | 20875 | 20876 | 20878 | 20886 | 20887 | 20889 | 20892 | 20893 | 20894 | 20895 | 20899 |
| 20903 | 20910 | 20912 | 20917 | 20919 | 20920 | 20921 | 20924 | 20928 | 20931 | 20936 | 20939 |
| 20942 | 20944 | 20946 | 20948 | 20951 | 20952 | 20959 | 20961 | 20963 | 20968 | 20970 | 20973 |
| 20980 | 20985 | 20987 | 20988 | 20989 | 20990 | 20991 | 20992 | 20993 | 20998 | 20999 | 21003 |
| 21004 | 21006 | 21008 | 21010 | 21017 | 21019 | 21021 | 21025 | 21026 | 21031 | 21032 | 21034 |
| 21035 | 21037 | 21042 | 21044 | 21045 | 21046 | 21054 | 21057 | 21059 | 21062 | 21063 | 21064 |
| 21068 | 21070 | 21071 | 21072 | 21073 | 21074 | 21075 | 21077 | 21084 | 21086 | 21091 | 21093 |
| 21101 | 21102 | 21103 | 21106 | 21111 | 21114 | 21119 | 21120 | 21124 | 21125 | 21129 | 21130 |
| 21131 | 21133 | 21134 | 21142 | 21143 | 21144 | 21147 | 21148 | 21149 | 21152 | 21154 | 21156 |
| 21159 | 21160 | 21161 | 21162 | 21164 | 21166 | 21167 | 21168 | 21170 | 21171 | 21173 | 21180 |
| 21183 | 21185 | 21186 | 21191 | 21193 | 21194 | 21196 | 21200 | 21204 | 21205 | 21206 | 21209 |
| 21210 | 21211 | 21214 | 21215 | 21216 | 21219 | 21220 | 21232 | 21235 | 21236 | 21243 | 21244 |
| 21245 | 21249 | 21252 | 21254 | 21256 | 21257 | 21260 | 21261 | 21263 | 21267 | 21271 | 21273 |
| 21280 | 21281 | 21283 | 21284 | 21285 | 21291 | 21293 | 21294 | 21295 | 21296 | 21297 | 21298 |
| 21301 | 21302 | 21304 | 21307 | 21312 | 21313 | 21314 | 21315 | 21320 | 21323 | 21324 | 21328 |
| 21329 | 21331 | 21332 | 21333 | 21334 | 21335 | 21338 | 21339 | 21340 | 21348 | 21349 | 21350 |
| 21354 | 21361 | 21363 | 21364 | 21366 | 21368 | 21371 | 21373 | 21374 | 21375 | 21376 | 21377 |
| 21379 | 21380 | 21381 | 21384 | 21387 | 21389 | 21395 | 21396 | 21398 | 21399 | 21400 | 21402 |
| 21403 | 21410 | 21411 | 21416 | 21417 | 21420 | 21421 | 21425 | 21426 | 21428 | 21430 | 21432 |
| 21434 | 21436 | 21441 | 21443 | 21445 | 21446 | 21447 | 21449 | 21459 | 21460 | 21462 | 21464 |
| 21466 | 21468 | 21470 | 21471 | 21479 | 21481 | 21483 | 21485 | 21489 | 21492 | 21503 | 21507 |
| 21512 | 21513 | 21521 | 21527 | 21532 | 21535 | 21546 | 21551 | 21552 | 21553 | 21557 | 21560 |
| 21562 | 21568 | 21569 | 21570 | 21571 | 21572 | 21574 | 21576 | 21582 | 21585 | 21586 | 21588 |
| 21590 | 21596 | 21597 | 21607 | 21608 | 21620 | 21624 | 21628 | 21631 | 21637 | 21639 | 21642 |
| 21646 | 21651 | 21655 | 21657 | 21661 | 21662 | 21664 | 21666 | 21670 | 21672 | 21674 | 21676 |

TABLE 13A-continued

Seed Oil Yield/Content

| | | | | | | | | | | | |
|---|---|---|---|---|---|---|---|---|---|---|---|
| 21677 | 21678 | 21680 | 21681 | 21682 | 21683 | 21686 | 21687 | 21689 | 21691 | 21692 | 21694 |
| 21695 | 21697 | 21700 | 21701 | 21702 | 21704 | 21705 | 21706 | 21707 | 21709 | 21710 | 21711 |
| 21712 | 21713 | 21714 | 21716 | 21717 | 21718 | 21720 | 21722 | 21723 | 21726 | 21729 | 21730 |
| 21731 | 21732 | 21733 | 21734 | 21735 | 21736 | 21737 | 21738 | 21739 | 21740 | 21741 | 21742 |
| 21745 | 21748 | 21749 | 21754 | 21757 | 21758 | 21759 | 21760 | 21763 | 21766 | 21768 | 21769 |
| 21774 | 21776 | 21778 | 21779 | 21781 | 21783 | 21784 | 21791 | 21794 | 21795 | 21800 | 21801 |
| 21803 | 21809 | 21813 | 21816 | 21817 | 21819 | 21820 | 21822 | 21824 | 21825 | 21828 | 21833 |
| 21835 | 21841 | 21844 | 21845 | 21847 | 21855 | 21860 | 21864 | 21872 | 21873 | 21883 | 21891 |
| 21893 | 21895 | 21896 | 21900 | 21908 | 21911 | 21929 | 21930 | 21937 | 21939 | 21941 | 21960 |
| 21963 | 21968 | 21972 | 21973 | 21975 | 21987 | 21988 | 21991 | 21992 | 21993 | 21994 | 21998 |
| 21999 | 22001 | 22006 | 22011 | 22012 | 22013 | 22014 | 22015 | 22017 | 22020 | 22021 | 22032 |
| 22033 | 22034 | 22035 | 22036 | 22038 | 22046 | 22047 | 22048 | 22053 | 22061 | 22066 | 22071 |
| 22072 | 22075 | 22078 | 22088 | 22094 | 22101 | 22102 | 22106 | 22107 | 22115 | 22116 | 22124 |
| 22125 | 22126 | 22127 | 22132 | 22134 | 22138 | 22146 | 22147 | 22163 | 22165 | 22170 | 22180 |
| 22186 | 22200 | 22205 | 22206 | 22210 | 22212 | 22213 | 22214 | 22215 | 22219 | 22220 | 22221 |
| 22222 | 22225 | 22231 | 22232 | 22238 | 22240 | 22245 | 22248 | 22253 | 22260 | 22261 | 22263 |
| 22269 | 22273 | 22275 | 22277 | 22279 | 22286 | 22290 | 22291 | 22295 | 22309 | 22313 | 22321 |
| 22325 | 22326 | 22327 | 22331 | 22332 | 22335 | 22345 | 22347 | 22366 | 22368 | 22370 | 22376 |
| 22378 | 22379 | 22386 | 22389 | 22391 | 22398 | 22402 | 22406 | 22417 | 22418 | 22419 | 22425 |
| 22428 | 22430 | 22431 | 22436 | 22438 | 22439 | 22440 | 22441 | 22442 | 22446 | 22447 | 22455 |
| 22458 | 22459 | 22464 | 22472 | 22492 | 22495 | 22499 | 22503 | 22509 | 22510 | 22522 | 22529 |
| 22533 | 22536 | 22538 | 22542 | 22544 | 22545 | 22549 | 22552 | 22565 | 22571 | 22572 | 22582 |
| 22583 | 22585 | 22593 | 22594 | 22598 | 22602 | 22608 | 22609 | 22610 | 22617 | 22630 | 22631 |
| 22632 | 22633 | 22635 | 22636 | 22642 | 22648 | 22653 | 22655 | 22666 | 22670 | 22675 | 22685 |
| 22700 | 22709 | 22717 | 22737 | 22738 | 22747 | 22748 | 22751 | 22753 | 22754 | 22756 | 22759 |
| 22765 | 22770 | 22773 | 22780 | 22782 | 22792 | 22796 | 22799 | 22801 | 22802 | 22817 | 22819 |
| 22822 | 22823 | 22824 | 22830 | 22831 | 22834 | 22837 | 22838 | 22839 | 22840 | 22843 | 22846 |
| 22850 | 22851 | 22852 | 22853 | 22854 | 22855 | 22859 | 22861 | 22862 | 22864 | 22865 | 22870 |
| 22872 | 22873 | 22879 | 22890 | 22892 | 22895 | 22896 | 22904 | 22905 | 22916 | 22917 | 22918 |
| 22920 | 22922 | 22928 | 22931 | 22934 | 22940 | 22945 | 22946 | 22947 | 22949 | 22952 | 22959 |
| 22962 | 22965 | 22967 | 22972 | 22974 | 22975 | 22976 | 22980 | 22981 | 22984 | 22991 | |
| 22993 | 22994 | 23000 | 23008 | 23013 | 23014 | 23015 | 23016 | 23019 | 23022 | 23023 | 23024 |
| 23026 | 23030 | 23031 | 23034 | 23035 | 23036 | 23039 | 23042 | 23052 | 23053 | 23057 | 23058 |
| 23059 | 23061 | 23063 | 23064 | 23067 | 23068 | 23070 | 23071 | 23073 | 23075 | 23080 | 23081 |
| 23084 | 23086 | 23087 | 23088 | 23091 | 23095 | 23096 | 23099 | 23103 | 23106 | 23107 | |
| 23109 | 23110 | 23112 | 23122 | 23123 | 23125 | 23126 | 23127 | 23133 | 23139 | 23140 | 23143 |
| 23144 | 23145 | 23146 | 23147 | 23148 | 23154 | 23156 | 23158 | 23161 | 23162 | 23164 | 23169 |
| 23170 | 23172 | 23174 | 23176 | 23177 | 23179 | 23181 | 23182 | 23183 | 23184 | 23185 | 23191 |
| 23192 | 23193 | 23196 | 23197 | 23198 | 23202 | 23203 | 23204 | 23208 | 23212 | 23213 | 23214 |
| 23217 | 23226 | 23227 | 23233 | 23235 | 23237 | 23240 | 23241 | 23242 | 23244 | 23247 | 23249 |
| 23251 | 23252 | 23253 | 23257 | 23258 | 23259 | 23260 | 23261 | 23263 | 23265 | 23267 | 23268 |
| 23269 | 23270 | 23271 | 23272 | 23273 | 23274 | 23276 | 23277 | 23282 | 23285 | 23286 | 23287 |
| 23289 | 23290 | 23291 | 23299 | 23300 | 23301 | 23302 | 23303 | 23304 | 23305 | 23310 | 23311 |
| 23312 | 23313 | 23318 | 23319 | 23321 | 23322 | 23324 | 23325 | 23326 | 23327 | 23328 | 23329 |
| 23333 | 23335 | 23337 | 23347 | 23348 | 23349 | 23350 | 23352 | 23354 | 23356 | 23358 | 23362 |
| 23363 | 23367 | 23369 | 23370 | 23371 | 23374 | 23376 | 23378 | 23382 | 23385 | 23388 | 23389 |
| 23390 | 23392 | 23393 | 23396 | 23399 | 23400 | 23401 | 23404 | 23408 | 23409 | 23412 | 23413 |
| 23421 | 23423 | 23426 | 23428 | 23433 | 23434 | 23442 | 23446 | 23447 | 23451 | 23455 | 23456 |
| 23457 | 23459 | 23462 | 23464 | 23466 | 23467 | 23468 | 23469 | 23474 | 23476 | 23477 | 23479 |
| 23480 | 23482 | 23484 | 23485 | 23490 | 23492 | 23495 | 23497 | 23498 | 23502 | 23505 | 23509 |
| 23510 | 23511 | 23513 | 23514 | 23516 | 23520 | 23524 | 23525 | 23526 | 23527 | 23529 | 23530 |
| 23531 | 23535 | 23536 | 23537 | 23538 | 23542 | 23546 | 23547 | 23551 | 23552 | 23557 | 23559 |
| 23562 | 23571 | 23572 | 23573 | 23574 | 23576 | 23577 | 23578 | 23579 | 23581 | 23582 | 23583 |
| 23584 | 23586 | 23587 | 23588 | 23595 | 23598 | 23601 | 23602 | 23603 | 23604 | 23605 | 23608 |
| 23609 | 23610 | 23612 | 23613 | 23616 | 23619 | 23621 | 23626 | 23627 | 23630 | 23631 | 23632 |
| 23635 | 23637 | 23638 | 23639 | 23640 | 23644 | 23646 | 23650 | 23651 | 23652 | 23653 | 23655 |
| 23656 | 23657 | 23658 | 23659 | 23663 | 23666 | 23667 | 23670 | 23671 | 23672 | 23673 | 23679 |
| 23684 | | | | | | | | | | | |

Table 13B SEQ ID NOs of Polynucleotides useful for improving Seed Oil Yield/Content

| | | | | | | | | | | | |
|---|---|---|---|---|---|---|---|---|---|---|---|
| 23688 | 23689 | 23691 | 23692 | 23693 | 23694 | 23695 | 23698 | 23699 | 23700 | 23704 | 23706 |
| 23713 | 23714 | 23718 | 23719 | 23721 | 23723 | 23724 | 23726 | 23737 | 23739 | 23742 | 23743 |
| 23747 | 23749 | 23750 | 23751 | 23760 | 23764 | 23768 | 23773 | 23775 | 23777 | 23778 | |
| 23786 | 23787 | 23788 | 23795 | 23796 | 23798 | 23799 | 23800 | 23801 | 23804 | 23805 | 23806 |
| 23807 | 23808 | 23809 | 23811 | 23812 | 23815 | 23818 | 23819 | 23820 | 23825 | 23832 | 23833 |
| 23834 | 23838 | 23840 | 23841 | 23843 | 23844 | 23847 | 23850 | 23856 | 23862 | 23865 | 23870 |
| 23871 | 23874 | 23875 | 23878 | 23879 | 23880 | 23881 | 23882 | 23884 | 23889 | 23891 | 23894 |
| 23895 | 23898 | 23899 | 23902 | 23910 | 23911 | 23912 | 23913 | 23914 | 23915 | 23917 | 23924 |
| 23925 | 23929 | 23931 | 23933 | 23934 | 23943 | 23944 | 23945 | 23953 | 23959 | 23960 | 23961 |
| 23962 | 23963 | 23964 | 23965 | 23966 | 23968 | 23969 | 23974 | 23976 | 23977 | 23978 | 23979 |
| 23982 | 23984 | 23989 | 23997 | 23998 | 24005 | 24007 | 24008 | 24012 | 24014 | 24016 | 24019 |
| 24022 | 24025 | 24027 | 24028 | 24029 | 24037 | 24043 | 24044 | 24050 | 24053 | 24054 | 24057 |
| 24058 | 24062 | 24063 | 24064 | 24065 | 24066 | 24071 | 24072 | 24075 | 24078 | 24079 | 24080 |
| 24082 | 24083 | 24085 | 24087 | 24090 | 24093 | 24097 | 24100 | 24105 | 24111 | 24114 | 24115 |
| 24119 | 24120 | 24123 | 24124 | 24126 | 24129 | 24130 | 24131 | 24132 | 24136 | 24143 | 24146 |
| 24147 | 24148 | 24150 | 24153 | 24161 | 24164 | 24165 | 24166 | 24167 | 24171 | 24177 | 24178 |

TABLE 13A-continued

Seed Oil Yield/Content

| | | | | | | | | | | | |
|---|---|---|---|---|---|---|---|---|---|---|---|
| 24180 | 24181 | 24182 | 24184 | 24185 | 24187 | 24188 | 24189 | 24191 | 24192 | 24195 | 24197 |
| 24202 | 24203 | 24206 | 24212 | 24213 | 24216 | 24218 | 24221 | 24222 | 24224 | 24225 | 24226 |
| 24228 | 24230 | 24231 | 24233 | 24235 | 24236 | 24239 | 24241 | 24242 | 24246 | 24247 | 24248 |
| 24249 | 24250 | 24257 | 24258 | 24259 | 24260 | 24261 | 24262 | 24263 | 24264 | 24266 | 24267 |
| 24268 | 24269 | 24270 | 24272 | 24274 | 24280 | 24286 | 24287 | 24289 | 24291 | 24292 | 24296 |
| 24300 | 24309 | 24310 | 24316 | 24317 | 24318 | 24319 | 24323 | 24324 | 24325 | 24326 | 24327 |
| 24328 | 24329 | 24330 | 24331 | 24333 | 24335 | 24349 | 24351 | 24352 | 24357 | 24358 | 24359 |
| 24360 | 24361 | 24362 | 24366 | 24368 | 24369 | 24371 | 24372 | 24380 | 24381 | 24382 | 24383 |
| 24387 | 24388 | 24390 | 24394 | 24400 | 24401 | 24407 | 24410 | 24412 | 24416 | 24419 | 24429 |
| 24431 | 24432 | 24433 | 24435 | 24436 | 24440 | 24443 | 24444 | 24446 | 24448 | 24449 | 24454 |
| 24468 | 24469 | 24470 | 24472 | 24474 | 24475 | 24479 | 24480 | 24481 | 24482 | 24483 | 24487 |
| 24499 | 24500 | 24502 | 24505 | 24506 | 24507 | 24510 | 24512 | 24513 | 24521 | 24522 | 24524 |
| 24526 | 24531 | 24532 | 24533 | 24534 | 24535 | 24536 | 24537 | 24538 | 24539 | 24540 | 24541 |
| 24542 | 24543 | 24546 | 24548 | 24550 | 24554 | 24557 | 24558 | 24559 | 24563 | 24566 | 24570 |
| 24572 | 24577 | 24581 | 24582 | 24584 | 24585 | 24586 | 24587 | 24589 | 24590 | 24591 | 24592 |
| 24593 | 24594 | 24595 | 24596 | 24607 | 24608 | 24609 | 24610 | 24611 | 24613 | 24615 | 24618 |
| 24620 | 24621 | 24622 | 24624 | 24625 | 24627 | 24628 | 24629 | 24630 | 24633 | 24635 | 24636 |
| 24637 | 24638 | 24640 | 24651 | 24652 | 24659 | 24661 | 24662 | 24663 | 24664 | 24666 | 24667 |
| 24670 | 24672 | 24674 | 24676 | 24678 | 24679 | 24680 | 24682 | 24684 | 24685 | 24690 | 24691 |
| 24692 | 24693 | 24694 | 24695 | 24698 | 24699 | 24700 | 24701 | 24702 | 24704 | 24707 | 24708 |
| 24711 | 24712 | 24714 | 24715 | 24716 | 24722 | 24723 | 24724 | 24725 | 24728 | 24730 | 24734 |
| 24739 | 24740 | 24742 | 24744 | 24747 | 24757 | 24760 | 24766 | 24768 | 24772 | 24773 | 24774 |
| 24780 | 24781 | 24786 | 24788 | 24792 | 24794 | 24800 | 24803 | 24809 | 24810 | 24814 | 24816 |
| 24817 | 24819 | 24820 | 24822 | 24823 | 24829 | 24832 | 24833 | 24836 | 24837 | 24842 | 24845 |
| 24847 | 24851 | 24853 | 24854 | 24860 | 24861 | 24870 | 24871 | 24872 | 24873 | 24875 | 24876 |
| 24881 | 24885 | 24886 | 24887 | 24890 | 24891 | 24894 | 24901 | 24904 | 24907 | 24916 | 24923 |
| 24927 | 24928 | 24932 | 24933 | 24937 | 24939 | 24942 | 24946 | 24961 | 24963 | 24970 | 24971 |
| 24978 | 24979 | 24986 | 24990 | 24991 | 24996 | 24997 | 24999 | 25000 | 25008 | 25019 | 25021 |
| 25024 | 25026 | 25028 | 25029 | 25033 | 25034 | 25036 | 25045 | 25048 | 25062 | 25084 | 25089 |
| 25090 | 25099 | 25104 | 25115 | 25121 | 25124 | 25125 | 25130 | 25131 | 25145 | 25146 | 25151 |
| 25152 | 25161 | 25164 | 25165 | 25169 | 25171 | 25176 | 25178 | 25179 | 25180 | 25181 | 25182 |
| 25184 | 25187 | 25188 | 25193 | 25194 | 25197 | 25200 | 25208 | 25212 | 25213 | 25228 | 25230 |
| 25239 | 25243 | 25251 | 25252 | 25261 | 25267 | 25269 | 25271 | 25276 | 25284 | 25291 | 25297 |
| 25302 | 25303 | 25304 | 25305 | 25314 | 25319 | 25322 | 25323 | 25328 | 25329 | 25332 | 25351 |
| 25357 | 25366 | 25367 | 25368 | 25372 | 25375 | 25376 | 25385 | 25386 | 25388 | 25389 | 25391 |
| 25393 | 25394 | 25398 | 25399 | 25406 | 25407 | 25408 | 25415 | 25418 | 25421 | 25423 | 25427 |
| 25429 | 25432 | 25433 | 25435 | 25436 | 25468 | 25470 | 25471 | 25472 | 25476 | 25482 | 25484 |
| 25503 | 25510 | 25511 | 25521 | 25525 | 25526 | 25528 | 25534 | 25537 | 25544 | 25552 | 25553 |
| 25554 | 25565 | 25570 | 25571 | 25577 | 25582 | 25583 | 25584 | 25586 | 25590 | 25591 | 25592 |
| 25599 | 25603 | 25604 | 25608 | 25615 | 25620 | 25621 | 25623 | 25633 | 25634 | 25635 | 25639 |
| 25640 | 25653 | 25658 | 25660 | 25662 | 25670 | 25679 | 25680 | 25681 | 25685 | 25693 | 25694 |
| 25695 | 25700 | 25701 | 25704 | 25706 | 25710 | 25713 | 25714 | 25715 | 25718 | 25729 | 25730 |
| 25731 | 25732 | 25738 | 25749 | 25750 | 25751 | 25753 | 25755 | 25771 | 25784 | 25791 |
| 25792 | 25794 | 25796 | 25797 | 25805 | 25806 | 25807 | 25809 | 25811 | 25817 | 25826 | 25827 |
| 25833 | 25834 | 25835 | 25842 | 25850 | 25861 | 25869 | 25871 | 25873 | 25878 | 25881 | 25885 |
| 25889 | 25890 | 25895 | 25899 | 25907 | 25912 | 25916 | 25917 | 25920 | 25941 | 25946 | 25950 |
| 25952 | 25954 | 25957 | 25967 | 25968 | 25970 | 25973 | 25981 | 25989 | 25990 | 25991 | 25992 |
| 25993 | 26002 | 26003 | 26006 | 26008 | 26009 | 26012 | 26014 | 26020 | 26037 | 26046 | 26051 |
| 26064 | 26081 | 26090 | 26100 | 26101 | 26105 | 26109 | 26112 | 26117 | 26125 | 26132 | 26137 |
| 26140 | 26142 | 26144 | 26153 | 26167 | 26172 | 26175 | 26176 | 26183 | 26184 | 26190 | 26191 |
| 26195 | 26204 | 26205 | 26211 | 26224 | 26233 | 26234 | 26238 | 26249 | 26253 | 26254 | 26255 |
| 26265 | 26267 | 26276 | 26279 | 26283 | 26286 | 26289 | 26293 | 26295 | 26296 | 26299 | 26309 |
| 26312 | 26313 | 26318 | 26319 | 26321 | 26326 | 26327 | 26329 | 26336 | 26338 | 26341 | 26345 |
| 26352 | 26353 | 26355 | 26359 | 26362 | 26363 | 26366 | 26374 | 26375 | 26376 | 26378 | 26379 |
| 26381 | 26382 | 26385 | 26390 | 26393 | 26395 | 26402 | 26406 | 26409 | 26413 | 26417 | 26418 |
| 26421 | 26424 | 26425 | 26426 | 26432 | 26433 | 26435 | 26436 | 26437 | 26439 | 26442 | 26443 |
| 26447 | 26448 | 26453 | 26454 | 26455 | 26458 | 26460 | 26461 | 26462 | 26467 | 26468 | 26469 |
| 26472 | 26474 | 26475 | 26477 | 26484 | 26494 | 26505 | 26509 | 26510 | 26511 | 26515 | 26519 |
| 26520 | 26522 | 26527 | 26529 | 26533 | 26534 | 26535 | 26538 | 26539 | 26540 | 26547 | 26550 |
| 26551 | 26557 | 26560 | 26565 | 26566 | 26569 | 26572 | 26574 | 26578 | 26579 | 26581 |
| 26582 | 26583 | 26585 | 26587 | 26591 | 26592 | 26594 | 26596 | 26597 | 26599 | 26603 | 26606 |
| 26609 | 26610 | 26612 | 26615 | 26616 | 26617 | 26618 | 26619 | 26621 | 26622 | 26623 | 26628 |
| 26629 | 26631 | 26632 | 26634 | 26646 | 26647 | 26648 | 26650 | 26651 | 26652 | 26653 | 26654 |
| 26655 | 26657 | 26658 | 26659 | 26660 | 26661 | 26664 | 26672 | 26674 | 26677 |
| 26678 | 26683 | 26689 | 26691 | 26692 | 26699 | 26703 | 26707 | 26708 | 26714 | 26717 | 26718 |
| 26719 | 26721 | 26722 | 26729 | 26730 | 26731 | 26732 | 26734 | 26739 | 26741 | 26744 | 26751 |
| 26753 | 26754 | 26756 | 26757 | 26762 | 26764 | 26774 | 26784 | 26787 | 26790 | 26794 | 26797 |
| 26800 | 26802 | 26811 | 26812 | 26817 | 26824 | 26825 | 26826 | 26832 | 26841 | 26843 | 26844 |
| 26852 | 26863 | 26865 | 26867 | 26871 | 26873 | 26875 | 26876 | 26885 | 26886 | 26887 | 26888 |
| 26893 | 26898 | 26906 | 26918 | 26919 | 26921 | 26922 | 26924 | 26927 | 26931 | 26933 | 26936 |
| 26937 | 26947 | 26957 | 26958 | 26963 | 26972 | 26973 | 26975 | 26977 | 26978 | 26982 | 26986 |
| 26988 | 26991 | 26992 | 26996 | 26998 | 27002 | 27005 | 27007 | 27009 | 27010 | 27011 | 27012 |
| 27013 | 27015 | 27018 | 27021 | 27025 | 27026 | 27030 | 27035 | 27044 | 27050 | 27053 | 27059 |
| 27068 | 27076 | 27079 | 27080 | 27082 | 27084 | 27098 | 27102 | 27106 | 27108 | 27110 | 27111 |
| 27123 | 27124 | 27127 | 27128 | 27129 | 27140 | 27142 | 27145 | 27153 | 27155 | 27156 | 27160 |
| 27161 | 27163 | 27165 | 27168 | 27169 | 27171 | 27172 | 27175 | 27177 | 27194 | 27198 | 27200 |
| 27201 | 27202 | 27205 | 27209 | 27216 | 27228 | 27231 | 27242 | 27246 | 27247 | 27250 | 27257 |

TABLE 13A-continued

Seed Oil Yield/Content

| | | | | | | | | | | | |
|---|---|---|---|---|---|---|---|---|---|---|---|
| 27258 | 27260 | 27262 | 27267 | 27277 | 27278 | 27279 | 27280 | 27284 | 27288 | 27292 | 27296 |
| 27303 | 27308 | 27310 | 27316 | 27322 | 27324 | 27326 | 27327 | 27334 | 27339 | 27341 | 27345 |
| 27349 | 27350 | 27354 | 27365 | 27369 | 27370 | 27373 | 27375 | 27376 | 27384 | 27385 | 27386 |
| 27387 | 27388 | 27389 | 27390 | 27392 | 27398 | 27400 | 27401 | 27402 | 27404 | 27409 | 27411 |
| 27412 | 27420 | 27422 | 27423 | 27426 | 27428 | 27432 | 27433 | 27434 | 27438 | 27444 | 27448 |
| 27449 | 27459 | 27461 | 27462 | 27464 | 27467 | 27479 | 27481 | 27487 | 27492 | 27498 |
| 27502 | 27506 | 27517 | 27521 | 27522 | 27523 | 27527 | 27532 | 27533 | 27537 | 27552 | 27553 |
| 27554 | 27558 | 27563 | 27565 | 27568 | 27571 | 27574 | 27575 | 27577 | 27579 | 27585 | 27591 |
| 27595 | 27602 | 27607 | 27611 | 27612 | 27618 | 27619 | 27624 | 27625 | 27635 | 27641 | 27643 |
| 27644 | 27645 | 27651 | 27653 | 27654 | 27655 | 27656 | 27663 | 27665 | 27669 | 27671 | 27673 |
| 27674 | 27682 | 27686 | 27690 | 27692 | 27693 | 27700 | 27706 | 27708 | 27709 | 27710 | 27712 |
| 27717 | 27720 | 27728 | 27731 | 27732 | 27734 | 27735 | 27739 | 27744 | 27748 | 27753 | 27761 |
| 27762 | 27763 | 27764 | 27765 | 27766 | 27767 | 27771 | 27780 | 27785 | 27787 | 27793 | 27797 |
| 27798 | 27804 | 27805 | 27809 | 27810 | 27813 | 27814 | 27818 | 27821 | 27824 | 27827 | 27829 |
| 27830 | 27832 | 27839 | 27841 | 27847 | 27851 | 27853 | 27855 | 27863 | 27865 | 27867 | 27868 |
| 27870 | 27873 | 27875 | 27876 | 27879 | 27882 | 27885 | 27887 | 27888 | 27889 | 27892 | 27905 |
| 27907 | 27909 | 27914 | 27919 | 27920 | 27921 | 27925 | 27929 | 27930 | 27935 | 27937 | 27938 |
| 27939 | 27941 | 27943 | 27945 | 27946 | 27948 | 27949 | 27950 | 27951 | 27952 | 27953 | 27958 |
| 27959 | 27961 | 27962 | 27964 | 27965 | 27966 | 27967 | 27969 | 27970 | 27971 | 27972 | 27974 |
| 27976 | 27977 | 27978 | 27980 | 27981 | 27982 | 27984 | 27988 | 27989 | 27991 | 27992 | 27993 |
| 27994 | 27995 | 27996 | 27998 | 27999 | 28000 | 28001 | 28002 | 28003 | 28005 | 28009 | 28013 |
| 28014 | 28017 | 28018 | 28019 | 28021 | 28025 | 28026 | 28028 | 28030 | 28031 | 28034 | 28037 |
| 28038 | 28039 | 28040 | 28041 | 28043 | 28045 | 28047 | 28049 | 28050 | 28052 | 28053 | 28054 |
| 28060 | 28063 | 28066 | 28067 | 28068 | 28070 | 28071 | 28074 | 28075 | 28077 | 28078 | 28085 |
| 28086 | 28087 | 28088 | 28092 | 28098 | 28103 | 28105 | 28109 | 28111 | 28112 | 28114 | 28115 |
| 28116 | 28117 | 28119 | 28120 | 28140 | 28141 | 28142 | 28147 | 28148 | 28149 | 28150 | 28151 |
| 28153 | 28154 | 28158 | 28161 | 28164 | 28166 | 28170 | 28171 | 28173 | 28174 | 28177 | 28178 |
| 28183 | 28184 | 28186 | 28187 | 28189 | 28190 | 28191 | 28192 | 28193 | 28194 | 28201 | 28208 |
| 28211 | 28213 | 28214 | 28215 | 28217 | 28221 | 28223 | 28226 | 28228 | 28229 | 28235 | 28236 |
| 28237 | 28240 | 28242 | 28243 | 28244 | 28245 | 28248 | 28249 | 28250 | 28254 | 28255 | 28256 |
| 28259 | 28263 | 28267 | 28268 | 28269 | 28271 | 28277 | 28278 | 28283 | 28286 | 28288 | 28289 |
| 28291 | 28292 | 28293 | 28294 | 28295 | 28296 | 28298 | 28301 | 28305 | 28306 | 28308 | 28309 |
| 28312 | 28313 | 28315 | 28316 | 28317 | 28318 | 28319 | 28320 | 28321 | 28322 | 28324 | 28325 |
| 28326 | 28328 | 28329 | 28332 | 28338 | 28341 | 28343 | 28344 | 28345 | 28354 | 28355 | 28361 |
| 28363 | 28368 | 28371 | 28373 | 28375 | 28377 | 28378 | 28383 | 28386 | 28387 | 28388 |
| 28389 | 28391 | 28392 | 28395 | 28396 | 28398 | 28399 | 28402 | 28403 | 28408 | 28412 | 28413 |
| 28414 | 28416 | 28418 | 28419 | 28420 | 28423 | 28426 | 28427 | 28429 | 28431 | 28432 | 28433 |
| 28434 | 28435 | 28436 | 28438 | 28439 | 28440 | 28442 | 28445 | 28449 | 28450 | 28456 | 28457 |
| 28458 | 28459 | 28460 | 28463 | 28464 | 28468 | 28470 | 28472 | 28474 | 28476 | 28479 | 28480 |
| 28481 | 28482 | 28485 | 28486 | 28489 | 28492 | 28493 | 28494 | 28496 | 28498 | 28499 | 28500 |
| 28502 | 28505 | 28508 | 28513 | 28516 | 28520 | 28521 | 28523 | 28524 | 28530 | 28532 | 28533 |
| 28534 | 28537 | 28541 | 28542 | 28547 | 28552 | 28553 | 28556 | 28557 | 28561 | 28565 | 28572 |
| 28573 | 28575 | 28576 | 28581 | 28582 | 28584 | 28585 | 28586 | 28588 | 28589 | 28590 | 28592 |
| 28594 | 28596 | 28597 | 28598 | 28599 | 28601 | 28604 | 28605 | 28607 | 28610 | 28611 | 28613 |
| 28616 | 28617 | 28620 | 28622 | 28626 | 28631 | 28633 | 28634 | 28635 | 28637 | 28638 | 28639 |
| 28641 | 28644 | 28645 | 28649 | 28656 | 28672 | 28674 | 28677 | 28678 | 28685 | 28689 | 28692 |
| 28693 | 28694 | 28699 | 28708 | 28709 | 28714 | 28720 | 28721 | 28722 | 28725 | 28732 | 28744 |
| 28747 | 28752 | 28765 | 28767 | 28770 | 28775 | 28776 | 28777 | 28780 | 28782 | 28784 | 28792 |
| 28802 | 28803 | 28804 | 28805 | 28807 | 28812 | 28822 | 28827 | 28834 | 28840 | 28841 | 28845 |
| 28848 | 28852 | 28857 | 28858 | 28859 | 28860 | 28867 | 28868 | 28870 | 28891 | 28895 | 28896 |
| 28899 | 28903 | 28913 | 28916 | 28917 | 28920 | 28925 | 28926 | 28927 | 28928 | 28934 | 28935 |
| 28936 | 28937 | 28938 | 28939 | 28941 | 28942 | 28944 | 28945 | 28946 | 28947 | 28950 | 28951 |
| 28952 | 28953 | 28955 | 28956 | 28957 | 28962 | 28965 | 28966 | 28968 | 28969 | 28970 | 28971 |
| 28985 | 28986 | 28993 | 28996 | 28997 | 28998 | 28999 | 29003 | 29005 | 29007 | 29009 | 29010 |
| 29013 | 29014 | 29016 | 29017 | 29018 | 29021 | 29023 | 29024 | 29032 | 29033 | 29050 | 29051 |
| 29057 | 29059 | 29060 | 29065 | 29066 | 29067 | 29074 | 29081 | 29084 | 29086 | 29089 | 29094 |
| 29095 | 29103 | 29110 | 29113 | 29115 | 29116 | 29120 | 29124 | 29126 | 29127 | 29128 | 29129 |
| 29131 | 29137 | 29138 | 29152 | 29155 | 29157 | 29167 | 29168 | 29172 | 29173 | 29174 | 29175 |
| 29180 | 29183 | 29184 | 29188 | 29194 | 29200 | 29203 | 29205 | 29214 | 29223 | 29224 | 29226 |
| 29228 | 29230 | 29231 | 29234 | 29235 | 29236 | 29237 | 29240 | 29254 | 29262 | 29265 | 29266 |
| 29271 | 29275 | 29276 | 29282 | 29286 | 29289 | 29291 | 29297 | 29299 | 29300 | 29301 | 29302 |
| 29303 | 29304 | 29305 | 29314 | 29318 | 29321 | 29325 | 29327 | 29329 | 29331 | 29333 | 29337 |
| 29339 | 29346 | 29347 | 29352 | 29356 | 29367 | 29373 | 29375 | 29380 | 29382 | 29385 | 29386 |
| 29387 | 29393 | 29396 | 29397 | 29400 | 29401 | 29402 | 29403 | 29404 | 29405 | 29410 | 29413 |
| 29414 | 29416 | 29421 | 29422 | 29423 | 29428 | 29432 | 29439 | 29445 | 29456 | 29457 | 29459 |
| 29460 | 29461 | 29464 | 29466 | 29471 | 29472 | 29474 | 29476 | 29482 | 29487 | 29490 | 29492 |
| 29499 | 29501 | 29504 | 29510 | 29512 | 29514 | 29515 | 29516 | 29517 | 29518 | 29521 | 29523 |
| 29531 | 29542 | 29544 | 29545 | 29553 | 29554 | 29558 | 29559 | 29560 | 29564 | 29571 | 29573 |
| 29598 | 29599 | 29601 | 29606 | 29609 | 29610 | 29619 | 29620 | 29621 | 29622 | 29623 | 29624 |
| 29625 | 29628 | 29634 | 29638 | 29645 | 29653 | 29655 | 29661 | 29663 | 29667 | 29669 | 29678 |
| 29679 | 29686 | 29687 | 29688 | 29689 | 29694 | 29697 | 29698 | 29704 | 29708 | 29709 | 29711 |
| 29715 | 29716 | 29719 | 29721 | 29723 | 29728 | 29729 | 29732 | 29739 | 29744 | 29745 |
| 29746 | 29753 | 29759 | 29760 | 29763 | 29764 | 29771 | 29772 | 29773 | 29776 | 29777 | 29780 |
| 29781 | 29782 | 29783 | 29785 | 29790 | 29791 | 29794 | 29795 | 29799 | 29800 | 29801 | 29802 |
| 29803 | 29807 | 29809 | 29810 | 29816 | 29817 | 29820 | 29821 | 29824 | 29825 | 29826 | 29827 |
| 29828 | 29831 | 29835 | 29836 | 29843 | 29845 | 29846 | 29847 | 29850 | 29855 | 29856 | 29860 |
| 29861 | 29862 | 29864 | 29875 | 29877 | 29878 | 29879 | 29880 | 29881 | 29883 | 29884 | 29887 |

TABLE 13A-continued

Seed Oil Yield/Content

| | | | | | | | | | | | |
|---|---|---|---|---|---|---|---|---|---|---|---|
| 29893 | 29894 | 29901 | 29906 | 29907 | 29908 | 29909 | 29910 | 29914 | 29918 | 29921 | 29922 |
| 29930 | 29931 | 29939 | 29943 | 29947 | 29949 | 29950 | 29955 | 29958 | 29959 | 29961 | 29966 |
| 29967 | 29968 | 29970 | 29974 | 29976 | 29986 | 29987 | 29997 | 29999 | 30001 | 30006 | 30007 |
| 30009 | 30020 | 30022 | 30025 | 30030 | 30034 | 30041 | 30042 | 30043 | 30044 | 30047 | 30048 |
| 30055 | 30056 | 30061 | 30063 | 30065 | 30068 | 30069 | 30073 | 30074 | 30093 | 30095 | 30097 |
| 30099 | 30100 | 30108 | 30115 | 30117 | 30118 | 30120 | 30122 | 30124 | 30128 | 30129 | 30130 |
| 30133 | 30136 | 30142 | 30143 | 30150 | 30151 | 30153 | 30154 | 30157 | 30162 | 30164 | 30171 |
| 30172 | 30173 | 30174 | 30178 | 30190 | 30191 | 30196 | 30197 | 30198 | 30202 | 30205 | 30207 |
| 30208 | 30209 | 30210 | 30211 | 30212 | 30218 | 30219 | 30222 | 30223 | 30224 | 30227 | 30228 |
| 30229 | 30231 | 30232 | 30233 | 30236 | 30237 | 30238 | 30244 | 30245 | 30248 | 30254 | 30261 |
| 30262 | 30265 | 30266 | 30267 | 30273 | 30281 | 30283 | 30285 | 30286 | 30289 | 30293 | 30302 |
| 30303 | 30304 | 30312 | 30317 | 30321 | 30323 | 30324 | 30333 | 30334 | 30335 | 30336 | 30341 |
| 30342 | 30343 | 30344 | 30345 | 30346 | 30347 | 30348 | 30349 | 30353 | 30355 | 30357 | 30358 |
| 30360 | 30361 | 30369 | 30370 | 30371 | 30372 | 30374 | 30377 | 30379 | 30380 | 30382 | |
| 30388 | 30389 | 30390 | 30391 | 30392 | 30393 | 30401 | 30402 | 30403 | 30406 | 30415 | 30417 |
| 30419 | 30420 | 30421 | 30423 | 30424 | 30426 | 30428 | 30434 | 30436 | 30437 | 30440 | 30443 |
| 30446 | 30447 | 30455 | 30458 | 30460 | 30463 | 30466 | 30467 | 30475 | 30484 | 30491 | 30493 |
| 30494 | 30501 | 30506 | 30507 | 30508 | 30513 | 30515 | 30516 | 30517 | 30523 | 30526 | 30532 |
| 30534 | 30536 | 30538 | 30541 | 30542 | 30549 | 30552 | 30557 | 30566 | 30567 | 30571 | 30572 |
| 30577 | 30580 | 30594 | 30604 | 30605 | 30606 | 30609 | 30614 | 30626 | 30648 | 30657 | 30658 |
| 30664 | 30672 | 30673 | 30678 | 30687 | 30688 | 30692 | 30695 | 30696 | 30705 | 30710 | 30712 |
| 30713 | 30714 | 30720 | 30721 | 30722 | 30724 | 30725 | 30726 | 30727 | 30730 | 30732 | 30733 |
| 30734 | 30736 | 30737 | 30738 | 30740 | 30744 | 30745 | 30748 | 30749 | 30750 | 30751 | 30752 |
| 30754 | 30755 | 30756 | 30757 | 30758 | 30759 | 30761 | 30763 | 30765 | 30770 | 30773 | 30774 |
| 30775 | 30777 | 30780 | 30781 | 30783 | 30785 | 30786 | 30789 | 30792 | 30793 | 30794 | 30795 |
| 30797 | 30799 | 30801 | 30803 | 30804 | 30806 | 30807 | 30808 | 30814 | 30817 | 30820 | 30821 |
| 30822 | 30823 | 30825 | 30826 | 30827 | 30829 | 30830 | 30832 | 30833 | 30840 | 30841 | 30842 |
| 30843 | 30845 | 30848 | 30854 | 30859 | 30861 | 30866 | 30869 | 30870 | 30872 | 30873 | 30874 |
| 30875 | 30877 | 30878 | 30880 | 30894 | 30900 | 30901 | 30907 | 30908 | 30909 | 30910 | 30911 |
| 30913 | 30914 | 30918 | 30920 | 30923 | 30925 | 30929 | 30930 | 30932 | 30933 | 30936 | 30937 |
| 30942 | 30943 | 30945 | 30946 | 30948 | 30949 | 30950 | 30951 | 30952 | 30953 | 30959 | 30967 |
| 30970 | 30971 | 30972 | 30973 | 30974 | 30975 | 30979 | 30981 | 30984 | 30986 | 30987 | 30991 |
| 30994 | 30997 | 30999 | 31000 | 31001 | 31002 | 31004 | 31006 | 31007 | 31008 | 31011 | 31012 |
| 31013 | 31016 | 31020 | 31024 | 31025 | 31026 | 31028 | 31034 | 31035 | 31040 | 31043 | 31045 |
| 31046 | 31048 | 31049 | 31050 | 31051 | 31052 | 31055 | 31057 | 31058 | 31062 | 31063 | 31066 |
| 31070 | 31071 | 31073 | 31074 | 31075 | 31076 | 31077 | 31078 | 31079 | 31080 | 31082 | 31083 |
| 31084 | 31086 | 31087 | 31090 | 31096 | 31097 | 31099 | 31101 | 31102 | 31104 | 31113 | 31114 |
| 31119 | 31120 | 31122 | 31127 | 31129 | 31130 | 31132 | 31134 | 31136 | 31137 | 31141 | 31144 |
| 31145 | 31146 | 31147 | 31149 | 31150 | 31154 | 31155 | 31159 | 31161 | 31162 | 31165 | 31167 |
| 31171 | 31172 | 31173 | 31175 | 31178 | 31179 | 31180 | 31182 | 31185 | 31186 | 31188 | 31189 |
| 31191 | 31192 | 31193 | 31194 | 31195 | 31197 | 31198 | 31199 | 31201 | 31204 | 31208 | 31210 |
| 31216 | 31217 | 31218 | 31219 | 31220 | 31223 | 31224 | 31228 | 31230 | 31232 | 31234 | 31236 |
| 31239 | 31240 | 31241 | 31242 | 31244 | 31245 | 31246 | 31248 | 31251 | 31252 | 31253 | 31255 |
| 31257 | 31258 | 31259 | 31261 | 31264 | 31267 | 31272 | 31275 | 31276 | 31279 | 31280 | 31282 |
| 31284 | 31289 | 31291 | 31292 | 31293 | 31296 | 31300 | 31301 | 31306 | 31311 | 31312 | 31316 |
| 31317 | 31321 | 31324 | 31330 | 31331 | 31333 | 31334 | 31339 | 31340 | 31342 | 31343 | 31344 |
| 31346 | 31347 | 31348 | 31350 | 31352 | 31354 | 31355 | 31356 | 31357 | 31359 | 31362 | 31363 |
| 31365 | 31368 | 31369 | 31371 | 31374 | 31375 | 31378 | 31382 | 31384 | 31389 | 31391 | 31392 |
| 31393 | 31395 | 31396 | 31397 | 31399 | 31402 | 31403 | 31407 | 31414 | 31416 | 31417 | 31420 |
| 31421 | 31424 | 31425 | 31430 | 31432 | 31434 | 31439 | 31440 | 31441 | 31442 | 31446 | 31447 |
| 31449 | 31451 | 31452 | 31453 | 31455 | 31456 | 31458 | 31459 | 31460 | 31464 | 31465 | 31469 |
| 31470 | 31471 | 31473 | 31476 | 31478 | 31481 | 31482 | 31492 | 31493 | 31494 | 31495 | 31496 |
| 31497 | 31500 | 31501 | 31502 | 31505 | 31509 | 31511 | 31514 | 31519 | 31520 | 31521 | 31523 |
| 31524 | 31526 | 31527 | 31531 | 31532 | 31533 | 31535 | 31539 | 31545 | 31546 | 31547 | 31555 |
| 31556 | 31557 | 31560 | 31562 | 31568 | 31569 | 31570 | 31571 | 31572 | 31579 | 31581 | 31583 |
| 31584 | 31592 | 31593 | 31599 | 31600 | 31606 | 31607 | 31609 | 31610 | 31612 | 31614 | 31616 |
| 31620 | 31623 | 31625 | 31626 | 31627 | 31631 | 31632 | 31633 | 31636 | 31638 | 31650 | 31651 |
| 31653 | 31654 | 31656 | 31657 | 31659 | 31660 | 31661 | 31663 | 31664 | 31666 | 31669 | 31672 |
| 31680 | 31682 | 31685 | 31688 | 31689 | 31690 | 31691 | 31694 | 31696 | 31698 | 31699 | 31700 |
| 31702 | 31704 | 31706 | 31711 | 31713 | 31714 | 31717 | 31718 | 31719 | 31725 | 31726 | 31728 |
| 31732 | 31733 | 31734 | 31735 | 31738 | 31740 | 31741 | 31742 | 31744 | 31745 | 31750 | 31757 |
| 31758 | 31759 | 31760 | 31761 | 31767 | 31770 | 31771 | 31773 | 31775 | 31779 | 31780 | 31784 |
| 31792 | 31794 | 31795 | 31796 | 31797 | 31798 | 31799 | 31801 | 31802 | 31804 | 31806 | 31809 |
| 31812 | 31815 | 31819 | 31820 | 31828 | 31830 | 31831 | 31832 | 31833 | 31835 | 31836 | 31837 |
| 31842 | 31843 | 31844 | 31846 | 31849 | 31850 | 31851 | 31854 | 31856 | 31857 | 31866 | 31867 |
| 31868 | 31869 | 31870 | 31871 | 31874 | 31875 | 31876 | 31881 | 31882 | 31883 | 31885 | 31889 |
| 31890 | 31893 | 31896 | 31897 | 31898 | 31900 | 31903 | 31905 | 31906 | 31907 | 31910 | 31911 |
| 31913 | 31914 | 31915 | 31921 | 31924 | 31925 | 31928 | 31930 | 31932 | 31935 | 31936 | 31937 |
| 31939 | 31940 | 31942 | 31943 | 31946 | 31948 | 31949 | 31950 | 31951 | 31952 | 31953 | 31956 |
| 31957 | 31958 | 31959 | 31961 | 31962 | 31963 | 31964 | 31966 | 31968 | 31969 | 31970 | 31973 |
| 31974 | 31975 | 31977 | 31978 | 31984 | 31985 | 31991 | 31992 | 31993 | 31994 | 31996 | 31999 |
| 32001 | 32006 | 32010 | 32011 | 32013 | 32015 | 32017 | 32025 | 32027 | 32029 | 32031 | 32032 |
| 32033 | 32036 | 32041 | 32042 | 32043 | 32048 | 32049 | 32051 | 32052 | 32057 | 32058 | 32059 |
| 32061 | 32062 | 32065 | 32069 | 32070 | 32071 | 32073 | 32074 | 32079 | 32081 | 32084 | 32085 |
| 32089 | 32091 | 32092 | 32093 | 32095 | 32097 | 32098 | 32100 | 32103 | 32104 | 32117 | 32118 |
| 32119 | 32125 | 32126 | 32127 | 32128 | 32129 | 32130 | 32131 | 32133 | 32134 | 32135 | 32136 |
| 32139 | 32140 | 32144 | 32145 | 32151 | 32153 | 32154 | 32155 | 32158 | 32159 | 32160 | 32166 |

TABLE 13A-continued

Seed Oil Yield/Content

| | | | | | | | | | | | |
|---|---|---|---|---|---|---|---|---|---|---|---|
| 32170 | 32171 | 32172 | 32175 | 32177 | 32180 | 32181 | 32183 | 32185 | 32186 | 32188 | 32189 |
| 32190 | 32196 | 32200 | 32201 | 32202 | 32203 | 32204 | 32205 | 32207 | 32208 | 32209 | 32210 |
| 32211 | 32212 | 32216 | 32217 | 32218 | 32219 | 32220 | 32221 | 32222 | 32224 | 32225 | 32226 |
| 32232 | 32238 | 32240 | 32243 | 32248 | 32249 | 32250 | 32251 | 32254 | 32255 | 32256 | 32258 |
| 32259 | 32263 | 32265 | 32266 | 32267 | 32268 | 32269 | 32271 | 32272 | 32273 | 32274 | 32275 |
| 32276 | 32277 | 32278 | 32279 | 32282 | 32287 | 32290 | 32291 | 32293 | 32294 | 32295 | 32296 |
| 32297 | 32298 | 32301 | 32308 | 32309 | 32312 | 32313 | 32314 | 32318 | 32332 | 32333 | 32335 |
| 32336 | 32337 | 32339 | 32340 | 32345 | 32346 | 32347 | 32350 | 32351 | 32352 | 32353 | 32354 |
| 32358 | 32359 | 32360 | 32361 | 32362 | 32363 | 32365 | 32367 | 32370 | 32372 | 32375 | 32378 |
| 32379 | 32382 | 32384 | 32385 | 32386 | 32388 | 32389 | 32393 | 32394 | 32397 | 32398 | 32399 |
| 32400 | 32404 | 32405 | 32406 | 32407 | 32408 | 32410 | 32411 | 32412 | 32413 | 32414 | 32415 |
| 32416 | 32417 | 32418 | 32425 | 32428 | 32429 | 32434 | 32435 | 32437 | 32442 | 32444 | 32446 |
| 32447 | 32450 | 32452 | 32453 | 32454 | 32455 | 32456 | 32457 | 32458 | 32461 | 32462 | 32464 |
| 32467 | 32468 | 32470 | 32473 | 32476 | 32480 | 32482 | 32483 | 32484 | 32487 | 32488 | 32490 |
| 32493 | 32494 | 32500 | 32501 | 32502 | 32503 | 32504 | 32509 | 32510 | 32513 | 32514 | 32515 |
| 32519 | 32520 | 32521 | 32522 | 32523 | 32526 | 32530 | 32531 | 32534 | 32539 | 32542 | 32543 |
| 32546 | 32547 | 32548 | 32549 | 32551 | 32552 | 32553 | 32555 | 32556 | 32559 | 32560 | 32563 |
| 32567 | 32572 | 32580 | 32581 | 32583 | 32586 | 32588 | 32590 | 32593 | 32596 | 32598 | 32600 |
| 32601 | 32603 | 32604 | 32605 | 32606 | 32608 | 32609 | 32610 | 32611 | 32614 | 32615 | 32620 |
| 32621 | 32623 | 32625 | 32626 | 32627 | 32632 | 32640 | 32645 | 32646 | 32647 | 32653 | 32657 |
| 32660 | 32661 | 32664 | 32667 | 32668 | 32671 | 32681 | 32685 | 32686 | 32687 | 32692 | 32693 |
| 32699 | 32700 | 32701 | 32702 | 32704 | 32705 | 32706 | 32707 | 32708 | 32709 | 32710 | 32713 |
| 32715 | 32716 | 32718 | 32722 | 32723 | 32724 | 32729 | 32732 | 32733 | 32735 | 32736 | 32738 |
| 32743 | 32748 | 32754 | 32755 | 32759 | 32760 | 32763 | 32767 | 32768 | 32769 | 32770 | 32773 |
| 32775 | 32776 | 32790 | 32791 | 32792 | 32793 | 32794 | 32795 | 32796 | 32797 | 32798 | 32801 |
| 32803 | 32805 | 32806 | 32810 | 32813 | 32814 | 32817 | 32819 | 32821 | 32822 | 32823 | 32829 |
| 32832 | 32835 | 32838 | 32840 | 32843 | 32851 | 32852 | 32854 | 32862 | 32869 | 32873 | 32876 |
| 32877 | 32879 | 32880 | 32881 | 32882 | 32884 | 32885 | 32888 | 32889 | 32899 | 32900 | 32903 |
| 32905 | 32907 | 32908 | 32909 | 32910 | 32914 | 32915 | 32922 | 32923 | 32926 | 32927 | 32928 |
| 32929 | 32930 | 32931 | 32932 | 32938 | 32940 | 32941 | 32942 | 32944 | 32951 | 32952 | 32953 |
| 32956 | 32957 | 32958 | 32960 | 32961 | 32963 | 32966 | 32969 | 32975 | 32976 | 32978 |
| 32979 | 32980 | 32981 | 32983 | 32987 | 32989 | 32990 | 32991 | 32997 | 33007 | 33008 | 33010 |
| 33011 | 33016 | 33017 | 33020 | 33021 | 33022 | 33023 | 33035 | 33039 | 33041 | 33045 | 33049 |
| 33051 | 33055 | 33056 | 33058 | 33059 | 33060 | 33063 | 33068 | 33070 | 33072 | 33073 | 33074 |
| 33076 | 33077 | 33082 | 33091 | 33092 | 33096 | 33106 | 33107 | 33110 | 33111 | 33112 | 33116 |
| 33122 | 33126 | 33127 | 33130 | 33140 | 33143 | 33144 | 33145 | 33147 | 33148 | 33149 | 33150 |
| 33151 | 33152 | 33155 | 33156 | 33157 | 33159 | 33162 | 33163 | 33164 | 33171 | 33172 | 33176 |
| 33177 | 33179 | 33185 | 33186 | 33194 | 33195 | 33198 | 33199 | 33201 | 33202 | 33203 | 33204 |
| 33207 | 33208 | 33211 | 33217 | 33218 | 33221 | 33222 | 33224 | 33234 | 33236 | 33238 |
| 33245 | 33246 | 33248 | 33250 | 33255 | 33256 | 33260 | 33261 | 33262 | 33263 | 33265 | 33267 |
| 33273 | 33274 | 33275 | 33276 | 33279 | 33281 | 33282 | 33285 | 33286 | 33289 | 33290 | 33291 |
| 33292 | 33298 | 33299 | 33300 | 33301 | 33306 | 33307 | 33311 | 33312 | 33314 | 33317 | 33319 |
| 33320 | 33322 | 33323 | 33332 | 33333 | 33336 | 33337 | 33339 | 33345 | 33346 | 33356 |
| 33365 | 33366 | 33372 | 33376 | 33377 | 33388 | 33390 | 33391 | 33396 | 33397 | 33399 | 33400 |
| 33401 | 33402 | 33405 | 33412 | 33419 | 33421 | 33430 | 33432 | 33433 | 33434 | 33437 | 33438 |
| 33441 | 33445 | 33446 | 33452 | 33453 | 33458 | 33459 | 33460 | 33461 | 33475 | 33476 | 33477 |
| 33485 | 33501 | 33502 | 33505 | 33513 | 33514 | 33515 | 33516 | 33517 | 33518 | 33519 | 33520 |
| 33521 | 33526 | 33527 | 33528 | 33539 | 33540 | 33542 | 33543 | 33545 | 33546 | 33547 | 33548 |
| 33549 | 33550 | 33551 | 33553 | 33555 | 33556 | 33561 | 33563 | 33564 | 33565 | 33566 | 33575 |
| 33578 | 33579 | 33580 | 33581 | 33584 | 33585 | 33589 | 33603 | 33609 | 33613 | 33614 | 33615 |
| 33616 | 33618 | 33621 | 33622 | 33623 | 33632 | 33633 | 33637 | 33645 | 33647 | 33650 | 33651 |
| 33657 | 33661 | 33663 | 33664 | 33668 | 33671 | 33674 | 33676 | 33678 | 33680 | 33682 | 33684 |
| 33689 | 33690 | 33691 | 33692 | 33694 | 33698 | 33706 | 33707 | 33708 | 33710 | 33713 | 33716 |
| 33721 | 33725 | 33731 | 33732 | 33734 | 33736 | 33737 | 33739 | 33740 | 33742 | 33746 | 33747 |
| 33748 | 33766 | 33771 | 33784 | 33785 | 33786 | 33787 | 33789 | 33791 | 33796 | 33801 | 33802 |
| 33808 | 33809 | 33819 | 33822 | 33823 | 33828 | 33829 | 33830 | 33831 | 33834 | 33838 | 33841 |
| 33845 | 33846 | 33850 | 33851 | 33852 | 33861 | 33862 | 33866 | 33868 | 33869 | 33872 | 33874 |
| 33877 | 33884 | 33885 | 33888 | 33891 | 33892 | 33894 | 33896 | 33897 | 33900 | 33901 | 33910 |
| 33912 | 33913 | 33914 | 33918 | 33919 | 33921 | 33922 | 33932 | 33935 | 33937 | 33940 | 33943 |
| 33946 | 33947 | 33948 | 33949 | 33950 | 33952 | 33953 | 33954 | 33955 | 33969 | 33970 | 33972 |
| 33980 | 33983 | 33988 | 33989 | 33990 | 33991 | 33992 | 33994 | 33996 | 33997 | 33998 | 33999 |
| 34005 | 34006 | 34009 | 34012 | 34014 | 34017 | 34023 | 34025 | 34026 | 34030 | 34033 | 34035 |
| 34038 | 34039 | 34041 | 34042 | 34044 | 34047 | 34048 | 34051 | 34052 | 34054 | 34055 | 34056 |
| 34057 | 34061 | 34062 | 34068 | 34069 | 34070 | 34071 | 34072 | 34073 | 34075 | 34082 | 34084 |
| 34086 | 34090 | 34091 | 34093 | 34097 | 34098 | 34099 | 34100 | 34102 | 34104 | 34105 | 34107 |
| 34111 | 34112 | 34114 | 34117 | 34118 | 34119 | 34120 | 34121 | 34122 | 34124 | 34125 | 34126 |
| 34129 | 34132 | 34140 | 34143 | 34144 | 34146 | 34149 | 34152 | 34155 | 34158 | 34160 | 34161 |
| 34163 | 34165 | 34166 | 34168 | 34171 | 34173 | 34174 | 34175 | 34177 | 34180 | 34187 |
| 34188 | 34189 | 34190 | 34191 | 34192 | 34193 | 34196 | 34198 | 34201 | 34203 | 34207 | 34208 |
| 34209 | 34210 | 34211 | 34213 | 34215 | 34217 | 34218 | 34221 | 34224 | 34227 | 34228 | 34229 |
| 34230 | 34232 | 34233 | 34238 | 34242 | 34243 | 34244 | 34247 | 34251 | 34253 | 34254 | 34255 |
| 34256 | 34257 | 34258 | 34259 | 34261 | 34262 | 34264 | 34269 | 34276 | 34278 | 34280 | 34281 |
| 34283 | 34286 | 34287 | 34289 | 34290 | 34292 | 34294 | 34298 | 34299 | 34300 | 34302 | 34304 |
| 34306 | 34307 | 34309 | 34314 | 34315 | 34316 | 34317 | 34319 | 34325 | 34331 | 34333 | 34337 |
| 34338 | 34339 | 34341 | 34342 | 34344 | 34346 | 34347 | 34349 | 34350 | 34351 | 34354 | 34355 |
| 34358 | 34359 | 34361 | 34364 | 34366 | 34368 | 34370 | 34371 | 34372 | 34373 | 34374 | 34376 |
| 34377 | 34378 | 34381 | 34384 | 34385 | 34386 | 34387 | 34389 | 34392 | 34394 | 34395 | 34397 |

TABLE 13A-continued

Seed Oil Yield/Content

| | | | | | | | | | | | |
|---|---|---|---|---|---|---|---|---|---|---|---|
| 34398 | 34405 | 34408 | 34409 | 34410 | 34413 | 34416 | 34423 | 34426 | 34427 | 34431 | 34434 |
| 34435 | 34436 | 34437 | 34438 | 34439 | 34440 | 34441 | 34442 | 34444 | 34446 | 34447 | 34451 |
| 34452 | 34453 | 34461 | 34463 | 34468 | 34469 | 34470 | 34472 | 34473 | 34474 | 34475 | 34476 |
| 34483 | 34484 | 34485 | 34492 | 34494 | 34495 | 34497 | 34498 | 34500 | 34502 | 34503 | 34504 |
| 34505 | 34506 | 34507 | 34508 | 34511 | 34513 | 34515 | 34516 | 34517 | 34523 | 34525 | 34527 |
| 34528 | 34530 | 34531 | 34536 | 34537 | 34542 | 34546 | 34548 | 34553 | 34559 | 34566 | 34567 |
| 34568 | 34569 | 34575 | 34577 | 34578 | 34584 | 34585 | 34588 | 34589 | 34591 | 34594 | 34596 |
| 34597 | 34599 | 34600 | 34603 | 34607 | 34608 | 34613 | 34614 | 34615 | 34617 | 34618 | 34619 |
| 34620 | 34621 | 34622 | 34623 | 34624 | 34626 | 34627 | 34636 | 34637 | 34638 | 34639 | 34648 |
| 34649 | 34653 | 34655 | 34656 | 34657 | 34658 | 34664 | 34668 | 34669 | 34676 | 34677 | 34679 |
| 34682 | 34683 | 34684 | 34685 | 34686 | 34687 | 34688 | 34690 | 34691 | 34692 | 34695 | 34699 |
| 34700 | 34701 | 34704 | 34705 | 34708 | 34709 | 34715 | 34722 | 34723 | 34724 | 34728 | 34729 |
| 34732 | 34737 | 34738 | 34743 | 34744 | 34745 | 34748 | 34750 | 34751 | 34753 | 34760 | 34763 |
| 34766 | 34771 | 34772 | 34776 | 34777 | 34778 | 34780 | 34784 | 34789 | 34790 | 34792 | 34804 |
| 34806 | 34808 | 34823 | 34824 | 34840 | 34847 | 34850 | 34854 | 34856 | 34857 | 34861 | 34863 |
| 34867 | 34871 | 34872 | 34873 | 34875 | 34879 | 34882 | 34884 | 34903 | 34905 | 34906 | 34913 |
| 34920 | 34924 | 34927 | 34929 | 34932 | 34934 | 34935 | 34936 | 34938 | 34939 | 34940 | 34944 |
| 34946 | 34949 | 34961 | 34964 | 34972 | 34973 | 34984 | 34990 | 34995 | 34996 | 34999 |
| 35004 | 35005 | 35007 | 35008 | 35014 | 35016 | 35019 | 35023 | 35025 | 35030 | 35031 | 35032 |
| 35036 | 35037 | 35040 | 35047 | 35049 | 35051 | 35056 | 35058 | 35060 | 35061 | 35063 | 35064 |
| 35068 | 35069 | 35071 | 35073 | 35074 | 35075 | 35081 | 35083 | 35084 | 35089 | 35094 | 35095 |
| 35100 | 35102 | 35103 | 35107 | 35109 | 35113 | 35114 | 35119 | 35120 | 35124 | 35126 | 35129 |
| 35130 | 35136 | 35137 | 35140 | 35142 | 35143 | 35150 | 35151 | 35152 | 35153 | 35154 | 35155 |
| 35156 | 35158 | 35159 | 35160 | 35161 | 35162 | 35165 | 35167 | 35172 | 35175 | 35177 | 35179 |
| 35180 | 35181 | 35182 | 35184 | 35185 | 35189 | 35190 | 35191 | 35193 | 35196 | 35198 | 35200 |
| 35201 | 35203 | 35204 | 35205 | 35207 | 35212 | 35213 | 35215 | 35218 | 35224 | 35225 | 35226 |
| 35227 | 35229 | 35233 | 35234 | 35235 | 35237 | 35238 | 35240 | 35241 | 35242 | 35245 | 35246 |
| 35249 | 35250 | 35251 | 35252 | 35253 | 35259 | 35265 | 35266 | 35270 | 35276 | 35278 | 35281 |
| 35282 | 35283 | 35284 | 35285 | 35289 | 35293 | 35295 | 35296 | 35297 | 35301 | 35302 | 35306 |
| 35310 | 35312 | 35315 | 35316 | 35317 | 35318 | 35320 | 35321 | 35322 | 35323 | 35324 | 35325 |
| 35326 | 35327 | 35328 | 35329 | 35330 | 35331 | 35332 | 35334 | 35336 | 35338 | 35339 | 35340 |
| 35342 | 35346 | 35348 | 35350 | 35352 | 35353 | 35354 | 35359 | 35360 | 35362 | 35363 | 35365 |
| 35366 | 35367 | 35375 | 35380 | 35381 | 35382 | 35383 | 35384 | 35385 | 35386 | 35388 | 35390 |
| 35392 | 35393 | 35394 | 35396 | 35404 | 35406 | 35408 | 35409 | 35410 | 35411 | 35412 | 35413 |
| 35417 | 35418 | 35422 | 35431 | 35432 | 35434 | 35436 | 35437 | 35441 | 35449 | 35453 | 35455 |
| 35456 | 35459 | 35460 | 35461 | 35466 | 35467 | 35469 | 35470 | 35473 | 35475 | 35480 | 35481 |
| 35482 | 35483 | 35486 | 35487 | 35490 | 35493 | 35495 | 35496 | 35497 | 35500 | 35501 | 35504 |
| 35506 | 35507 | 35508 | 35509 | 35511 | 35515 | 35516 | 35517 | 35520 | 35525 | 35526 | 35527 |
| 35529 | 35532 | 35534 | 35535 | 35537 | 35542 | 35543 | 35544 | 35549 | 35550 | 35551 |
| 35553 | 35561 | 35562 | 35563 | 35567 | 35568 | 35570 | 35573 | 35574 | 35576 | 35582 | 35583 |
| 35584 | 35586 | 35587 | 35593 | 35594 | 35598 | 35602 | 35605 | 35606 | 35610 | 35611 | 35619 |
| 35623 | 35630 | 35632 | 35635 | 35636 | 35637 | 35638 | 35639 | 35643 | 35644 | 35645 | 35647 |
| 35648 | 35649 | 35650 | 35653 | 35656 | 35658 | 35664 | 35673 | 35675 | 35677 | 35680 | 35684 |
| 35685 | 35686 | 35687 | 35695 | 35697 | 35698 | 35699 | 35700 | 35701 | 35702 | 35704 | 35705 |
| 35706 | 35708 | 35714 | 35717 | 35718 | 35719 | 35720 | 35721 | 35727 | 35728 | 35731 | 35733 |
| 35739 | 35740 | 35742 | 35743 | 35745 | 35749 | 35755 | 35756 | 35757 | 35758 | 35759 | 35765 |
| 35766 | 35770 | 35773 | 35776 | 35778 | 35779 | 35783 | 35784 | 35785 | 35786 | 35787 | 35788 |
| 35789 | 35791 | 35793 | 35794 | 35796 | 35797 | 35798 | 35799 | 35803 | 35805 | 35806 | 35808 |
| 35811 | 35814 | 35815 | 35817 | 35822 | 35824 | 35825 | 35826 | 35827 | 35828 | 35829 | 35836 |
| 35838 | 35839 | 35841 | 35842 | 35846 | 35849 | 35850 | 35852 | 35854 | 35856 | 35859 | 35860 |
| 35863 | 35864 | 35865 | 35867 | 35873 | 35878 | 35879 | 35880 | 35882 | 35886 | 35887 | 35888 |
| 35893 | 35895 | 35899 | 35900 | 35901 | 35902 | 35905 | 35906 | 35912 | 35914 | 35915 | 35921 |
| 35924 | 35928 | 35929 | 35932 | 35934 | 35938 | 35940 | 35941 | 35942 | 35956 | 35957 | 35958 |
| 35959 | 35961 | 35962 | 35964 | 35965 | 35967 | 35969 | 35971 | 35973 | 35974 | 35980 | 35981 |
| 35984 | 35985 | 35986 | 35987 | 35989 | 35990 | 35991 | 35995 | 35997 | 35998 | 35999 | 36003 |
| 36006 | 36007 | 36008 | 36009 | 36011 | 36024 | 36025 | 36028 | 36030 | 36037 | 36038 | 36040 |
| 36045 | 36048 | 36050 | 36055 | 36060 | 36061 | 36063 | 36070 | 36074 | 36075 | 36081 | 36085 |
| 36087 | 36090 | 36091 | 36095 | 36105 | 36106 | 36112 | 36114 | 36115 | 36123 | 36124 | 36126 |
| 36127 | 36132 | 36133 | 36134 | 36135 | 36136 | 36137 | 36141 | 36142 | 36148 | 36158 | 36159 |
| 36160 | 36167 | 36168 | 36169 | 36170 | 36173 | 36175 | 36179 | 36181 | 36183 | 36187 | 36188 |
| 36196 | 36200 | 36204 | 36207 | 36211 | 36212 | 36213 | 36214 | 36222 | 36223 | 36224 | 36225 |
| 36228 | 36235 | 36240 | 36241 | 36245 | 36246 | 36253 | 36256 | 36259 | 36260 | 36262 | 36264 |
| 36276 | 36277 | 36279 | 36280 | 36283 | 36285 | 36287 | 36288 | 36289 | 36292 | 36297 | 36298 |
| 36301 | 36308 | 36310 | 36313 | 36316 | 36317 | 36325 | 36327 | 36331 | 36332 | 36339 | 36344 |
| 36348 | 36351 | 36353 | 36355 | 36358 | 36359 | 36360 | 36362 | 36365 | 36369 | 36375 | 36378 |
| 36379 | 36381 | 36382 | 36384 | 36385 | 36387 | 36390 | 36396 | 36399 | 36402 | 36407 | 36409 |
| 36410 | 36415 | 36417 | 36420 | 36421 | 36423 | 36425 | 36429 | 36430 | 36431 | 36438 | 36444 |
| 36449 | 36450 | 36451 | 36452 | 36455 | 36458 | 36459 | 36460 | 36461 | 36464 | 36470 | 36473 |
| 36478 | 36479 | 36480 | 36490 | 36493 | 36497 | 36499 | 36501 | 36504 | 36508 | 36511 | 36514 |
| 36516 | 36517 | 36522 | 36523 | 36527 | 36530 | 36532 | 36533 | 36535 | 36542 | 36555 | 36556 |
| 36563 | 36573 | 36576 | 36578 | 36584 | 36590 | 36595 | 36598 | 36599 | 36607 | 36609 | 36611 |
| 36612 | 36613 | 36619 | 36620 | 36623 | 36626 | 36628 | 36629 | 36630 | 36634 | 36636 | 36643 |
| 36644 | 36645 | 36649 | 36650 | 36655 | 36656 | 36663 | 36664 | 36665 | 36671 | 36673 | 36674 |
| 36676 | 36684 | 36686 | 36689 | 36700 | 36705 | 36707 | 36709 | 36710 | 36715 | 36716 | 36717 |
| 36720 | 36722 | 36724 | 36727 | 36729 | 36731 | 36732 | 36738 | 36740 | 36743 | 36750 | 36751 |
| 36752 | 36754 | 36755 | 36756 | 36760 | 36763 | 36765 | 36767 | 36773 | 36774 | 36777 | 36778 |
| 36785 | 36787 | 36790 | 36793 | 36795 | 36796 | 36798 | 36801 | 36806 | 36808 | 36811 | 36813 |

TABLE 13A-continued

Seed Oil Yield/Content

| | | | | | | | | | | | |
|---|---|---|---|---|---|---|---|---|---|---|---|
| 36815 | 36816 | 36823 | 36826 | 36829 | 36839 | 36841 | 36842 | 36846 | 36853 | 36855 | 36856 |
| 36858 | 36860 | 36864 | 36866 | 36872 | 36879 | 36882 | 36893 | 36899 | 36908 | 36909 | 36912 |
| 36916 | 36922 | 36928 | 36934 | 36936 | 36937 | 36938 | 36939 | 36940 | 36942 | 36944 | 36946 |
| 36947 | 36949 | 36950 | 36954 | 36961 | 36962 | 36963 | 36966 | 36967 | 36968 | 36976 | 36978 |
| 36982 | 36988 | 36990 | 36994 | 36995 | 36997 | 37000 | 37004 | 37006 | 37012 | 37015 | 37023 |
| 37027 | 37031 | 37033 | 37034 | 37035 | 37037 | 37038 | 37040 | 37041 | 37042 | 37044 | 37047 |
| 37053 | 37062 | 37067 | 37074 | 37082 | 37084 | 37088 | 37097 | 37103 | 37105 | 37109 | 37110 |
| 37111 | 37117 | 37120 | 37126 | 37128 | 37129 | 37131 | 37134 | 37140 | 37141 | 37142 | 37145 |
| 37146 | 37148 | 37149 | 37150 | 37151 | 37152 | 37153 | 37154 | 37157 | 37160 | 37163 | 37166 |
| 37167 | 37171 | 37172 | 37179 | 37180 | 37183 | 37184 | 37185 | 37186 | 37189 | 37192 | 37194 |
| 37196 | 37209 | 37210 | 37212 | 37214 | 37221 | 37222 | 37223 | 37225 | 37226 | 37230 | 37233 |
| 37234 | 37235 | 37237 | 37238 | 37241 | 37243 | 37244 | 37247 | 37248 | 37249 | 37250 | 37255 |
| 37257 | 37258 | 37260 | 37262 | 37265 | 37271 | 37272 | 37273 | 37275 | 37279 | 37280 | 37283 |
| 37284 | 37285 | 37286 | 37287 | 37292 | 37293 | 37294 | 37295 | 37297 | 37298 | 37299 | 37302 |
| 37304 | 37305 | 37306 | 37307 | 37308 | 37310 | 37311 | 37312 | 37314 | 37315 | 37317 | 37320 |
| 37323 | 37325 | 37327 | 37330 | 37332 | 37335 | 37337 | 37338 | 37340 | 37341 | 37342 | 37351 |
| 37354 | 37356 | 37358 | 37359 | 37360 | 37362 | 37363 | 37364 | 37365 | 37366 | 37372 | 37373 |
| 37375 | 37376 | 37379 | 37381 | 37382 | 37383 | 37384 | 37385 | 37387 | 37389 | 37390 | 37392 |
| 37393 | 37404 | 37405 | 37406 | 37407 | 37410 | 37411 | 37412 | 37413 | 37415 | 37420 | 37422 |
| 37423 | 37424 | 37425 | 37427 | 37428 | 37430 | 37434 | 37435 | 37436 | 37438 | 37439 | 37442 |
| 37444 | 37445 | 37448 | 37450 | 37456 | 37460 | 37461 | 37464 | 37465 | 37466 | 37468 | 37470 |
| 37471 | 37472 | 37473 | 37474 | 37475 | 37477 | 37478 | 37483 | 37484 | 37485 | 37488 | 37493 |
| 37497 | 37498 | 37500 | 37502 | 37504 | 37505 | 37509 | 37511 | 37515 | 37518 | 37524 | 37526 |
| 37528 | 37529 | 37532 | 37533 | 37535 | 37536 | 37538 | 37540 | 37543 | 37548 | 37549 | 37552 |
| 37553 | 37555 | 37556 | 37558 | 37560 | 37561 | 37564 | 37565 | 37567 | 37568 | 37572 | 37574 |
| 37576 | 37577 | 37579 | 37588 | 37590 | 37591 | 37593 | 37594 | 37599 | 37600 | 37602 | 37606 |
| 37607 | 37608 | 37612 | 37614 | 37615 | 37619 | 37621 | 37625 | 37626 | 37631 | 37632 | 37635 |
| 37636 | 37637 | 37640 | 37644 | 37649 | 37650 | 37653 | 37654 | 37656 | 37658 | 37661 | 37668 |
| 37669 | 37670 | 37671 | 37672 | 37673 | 37679 | 37683 | 37687 | 37692 | 37697 | 37701 | 37702 |
| 37704 | 37706 | 37717 | 37720 | 37721 | 37722 | 37723 | 37725 | 37726 | 37732 | 37733 | 37735 |
| 37736 | 37739 | 37740 | 37749 | 37751 | 37752 | 37754 | 37755 | 37758 | 37760 | 37765 | 37766 |
| 37769 | 37770 | 37771 | 37772 | 37773 | 37774 | 37775 | 37776 | 37779 | 37782 | 37783 | 37785 |
| 37788 | 37789 | 37790 | 37791 | 37792 | 37794 | 37800 | 37801 | 37807 | 37808 | 37819 | 37822 |
| 37830 | 37832 | 37836 | 37838 | 37839 | 37840 | 37844 | 37852 | 37859 | 37860 | 37862 | 37864 |
| 37868 | 37869 | 37871 | 37872 | 37882 | 37884 | 37886 | 37888 | 37891 | 37892 | 37896 |
| 37898 | 37901 | 37903 | 37907 | 37908 | 37912 | 37917 | 37918 | 37919 | 37920 | 37921 | 37925 |
| 37929 | 37932 | 37933 | 37934 | 37935 | 37938 | 37939 | 37941 | 37942 | 37943 | 37944 | 37945 |
| 37946 | 37947 | 37948 | 37949 | 37953 | 37954 | 37955 | 37956 | 37960 | 37961 | 37963 | 37964 |
| 37966 | 37968 | 37970 | 37972 | 37973 | 37974 | 37975 | 37978 | 37980 | 37982 | 37983 | 37985 |
| 37986 | 37987 | 37991 | 37993 | 37995 | 37996 | 37999 | 38000 | 38004 | 38006 | 38007 | 38008 |
| 38009 | 38011 | 38014 | 38015 | 38018 | 38019 | 38020 | 38023 | 38024 | 38029 | 38030 | 38031 |
| 38033 | 38035 | 38036 | 38039 | 38041 | 38042 | 38043 | 38046 | 38051 | 38052 | 38056 | 38057 |
| 38061 | 38063 | 38064 | 38066 | 38068 | 38069 | 38070 | 38076 | 38079 | 38080 | 38081 | 38083 |
| 38085 | 38086 | 38087 | 38093 | 38097 | 38099 | 38100 | 38108 | 38110 | 38111 | 38112 | 38115 |
| 38117 | 38118 | 38119 | 38126 | 38131 | 38137 | 38139 | 38140 | 38141 | 38142 | 38143 | 38149 |
| 38156 | 38157 | 38159 | 38160 | 38161 | 38163 | 38165 | 38169 | 38171 | 38173 | 38174 | 38175 |
| 38178 | 38183 | 38185 | 38186 | 38188 | 38189 | 38193 | 38197 | 38204 | 38207 | 38209 | 38210 |
| 38211 | 38213 | 38215 | 38216 | 38217 | 38221 | 38222 | 38224 | 38225 | 38227 | 38229 | 38234 |
| 38238 | 38242 | 38247 | 38248 | 38250 | 38251 | 38252 | 38253 | 38255 | 38256 | 38258 | 38262 |
| 38263 | 38264 | 38265 | 38273 | 38275 | 38276 | 38278 | 38279 | 38281 | 38283 | 38285 | 38286 |
| 38290 | 38295 | 38300 | 38302 | 38303 | 38304 | 38305 | 38306 | 38309 | 38310 | 38311 |
| 38315 | 38318 | 38320 | 38321 | 38323 | 38324 | 38325 | 38326 | 38330 | 38336 | 38337 | 38338 |
| 38339 | 38341 | 38344 | 38346 | 38349 | 38350 | 38351 | 38352 | 38354 | 38355 | 38365 | 38366 |
| 38368 | 38369 | 38370 | 38371 | 38372 | 38374 | 38375 | 38376 | 38378 | 38380 | 38381 | 38382 |
| 38384 | 38386 | 38387 | 38389 | 38391 | 38392 | 38393 | 38394 | 38395 | 38396 | 38397 | 38398 |
| 38399 | 38402 | 38404 | 38405 | 38406 | 38407 | 38410 | 38418 | 38420 | 38421 | 38423 | 38424 |
| 38425 | 38426 | 38427 | 38428 | 38430 | 38431 | 38433 | 38435 | 38436 | 38439 | 38440 | 38442 |
| 38444 | 38448 | 38449 | 38453 | 38461 | 38464 | 38465 | 38467 | 38468 | 38470 | 38477 | 38478 |
| 38482 | 38493 | 38494 | 38496 | 38497 | 38499 | 38501 | 38502 | 38503 | 38504 | 38507 | 38512 |
| 38516 | 38517 | 38518 | 38525 | 38527 | 38528 | 38529 | 38532 | 38534 | 38539 | 38545 | 38547 |
| 38548 | 38550 | 38551 | 38554 | 38556 | 38557 | 38558 | 38559 | 38560 | 38563 | 38566 | 38567 |
| 38569 | 38570 | 38572 | 38573 | 38575 | 38578 | 38579 | 38581 | 38582 | 38583 | 38588 | 38591 |
| 38592 | 38595 | 38596 | 38597 | 38607 | 38613 | 38618 | 38619 | 38621 | 38622 | 38625 | 38627 |
| 38630 | 38641 | 38642 | 38644 | 38645 | 38649 | 38650 | 38651 | 38655 | 38664 | 38665 | 38669 |
| 38670 | 38672 | 38673 | 38676 | 38677 | 38678 | 38681 | 38683 | 38686 | 38690 | 38693 | 38695 |
| 38698 | 38702 | 38703 | 38704 | 38705 | 38706 | 38709 | 38712 | 38713 | 38714 | 38716 | 38720 |
| 38723 | 38724 | 38734 | 38735 | 38738 | 38739 | 38742 | 38743 | 38745 | 38746 | 38747 | 38750 |
| 38751 | 38753 | 38754 | 38757 | 38758 | 38759 | 38760 | 38761 | 38762 | 38766 | 38768 | 38769 |
| 38771 | 38772 | 38775 | 38779 | 38780 | 38782 | 38783 | 38787 | 38788 | 38789 | 38790 | 38792 |
| 38794 | 38798 | 38802 | 38807 | 38810 | 38811 | 38812 | 38814 | 38818 | 38819 | 38823 | 38827 |
| 38828 | 38829 | 38830 | 38834 | 38838 | 38844 | 38845 | 38847 | 38849 | 38850 | 38851 | 38852 |
| 38853 | 38854 | 38855 | 38856 | 38857 | 38859 | 38861 | 38862 | 38863 | 38866 | 38867 | 38869 |
| 38870 | 38871 | 38874 | 38875 | 38876 | 38877 | 38878 | 38879 | 38880 | 38883 | 38885 | 38889 |
| 38898 | 38900 | 38901 | 38902 | 38903 | 38904 | 38906 | 38907 | 38908 | 38909 | 38910 | 38911 |
| 38913 | 38916 | 38919 | 38921 | 38923 | 38925 | 38926 | 38929 | 38943 | 38944 | 38955 | 38956 |
| 38958 | 38959 | 38960 | 38974 | 38975 | 38976 | 38979 | 38980 | 38982 | 38987 | 38988 | 38989 |
| 38992 | 38993 | 38997 | 39000 | 39003 | 39004 | 39009 | 39021 | 39022 | 39023 | 39024 | 39029 |

TABLE 13A-continued

Seed Oil Yield/Content

| | | | | | | | | | | | |
|---|---|---|---|---|---|---|---|---|---|---|---|
| 39030 | 39031 | 39037 | 39038 | 39044 | 39045 | 39047 | 39052 | 39053 | 39054 | 39057 | 39059 |
| 39062 | 39063 | 39064 | 39066 | 39067 | 39070 | 39075 | 39078 | 39079 | 39084 | 39085 | 39088 |
| 39093 | 39095 | 39096 | 39100 | 39102 | 39103 | 39104 | 39109 | 39110 | 39112 | 39113 | 39114 |
| 39115 | 39128 | 39129 | 39133 | 39135 | 39137 | 39141 | 39143 | 39146 | 39148 | 39149 | 39153 |
| 39154 | 39158 | 39167 | 39168 | 39169 | 39172 | 39177 | 39179 | 39185 | 39187 | 39197 | 39198 |
| 39199 | 39200 | 39205 | 39206 | 39208 | 39210 | 39212 | 39213 | 39217 | 39218 | 39219 | 39220 |
| 39221 | 39222 | 39223 | 39225 | 39228 | 39232 | 39233 | 39234 | 39235 | 39237 | 39238 | 39240 |
| 39242 | 39244 | 39245 | 39248 | 39249 | 39250 | 39251 | 39252 | 39254 | 39256 | 39257 | 39258 |
| 39262 | 39263 | 39264 | 39265 | 39269 | 39270 | 39272 | 39274 | 39280 | 39283 | 39288 | 39290 |
| 39294 | 39295 | 39296 | 39298 | 39299 | 39300 | 39301 | 39302 | 39303 | 39304 | 39308 | 39309 |
| 39310 | 39311 | 39312 | 39313 | 39316 | 39317 | 39320 | 39321 | 39326 | 39329 | 39333 | 39334 |
| 39335 | 39336 | 39337 | 39338 | 39339 | 39341 | 39342 | 39343 | 39344 | 39345 | 39346 | 39348 |
| 39353 | 39354 | 39355 | 39358 | 39359 | 39363 | 39366 | 39369 | 39370 | 39375 | 39389 | 39390 |
| 39391 | 39395 | 39396 | 39397 | 39398 | 39404 | 39405 | 39411 | 39412 | 39414 | 39419 | 39421 |
| 39424 | 39426 | 39429 | 39431 | 39432 | 39434 | 39435 | 39438 | 39443 | 39446 | 39447 | 39452 |
| 39453 | 39456 | 39461 | 39463 | 39464 | 39468 | 39470 | 39471 | 39472 | 39477 | 39478 | 39480 |
| 39481 | 39482 | 39483 | 39486 | 39495 | 39497 | 39498 | 39501 | 39503 | 39505 | 39509 | 39510 |
| 39511 | 39514 | 39516 | 39518 | 39523 | 39524 | 39528 | 39537 | 39539 | 39540 | 39543 | 39549 |
| 39550 | 39556 | 39558 | 39569 | 39570 | 39571 | 39572 | 39577 | 39578 | 39579 | 39581 | 39583 |
| 39584 | 39588 | 39589 | 39590 | 39591 | 39592 | 39593 | 39594 | 39596 | 39599 | 39604 | 39605 |
| 39606 | 39607 | 39610 | 39611 | 39613 | 39615 | 39617 | 39618 | 39621 | 39622 | 39623 | 39624 |
| 39625 | 39627 | 39629 | 39630 | 39631 | 39636 | 39638 | 39639 | 39640 | 39641 | 39645 | 39646 |
| 39648 | 39650 | 39656 | 39660 | 39665 | 39669 | 39670 | 39671 | 39672 | 39674 | 39675 | 39676 |
| 39677 | 39678 | 39679 | 39683 | 39684 | 39685 | 39686 | 39687 | 39688 | 39691 | 39692 | 39695 |
| 39696 | 39701 | 39704 | 39708 | 39710 | 39711 | 39712 | 39713 | 39714 | 39715 | 39716 | 39717 |
| 39718 | 39719 | 39720 | 39721 | 39722 | 39723 | 39724 | 39726 | 39728 | 39729 | 39732 | 39733 |
| 39734 | 39735 | 39736 | 39739 | 39743 | 39744 | 39745 | 39748 | 39749 | 39754 | 39756 | 39760 |
| 39761 | 39766 | 39779 | 39780 | 39781 | 39782 | 39785 | 39786 | 39792 | 39796 | 39797 | 39798 |
| 39804 | 39805 | 39809 | 39812 | 39814 | 39815 | 39816 | 39818 | 39819 | 39822 | 39825 | 39826 |
| 39830 | 39832 | 39836 | 39837 | 39840 | 39844 | 39847 | 39850 | 39851 | 39853 | 39854 | 39859 |
| 39860 | 39862 | 39863 | 39864 | 39865 | 39868 | 39876 | 39879 | 39883 | 39885 | 39886 |
| 39890 | 39891 | 39892 | 39896 | 39897 | 39899 | 39905 | 39914 | 39915 | 39918 | 39920 | 39923 |
| 39925 | 39929 | 39933 | 39941 | 39943 | 39944 | 39945 | 39950 | 39951 | 39952 | 39954 | 39956 |
| 39959 | 39960 | 39961 | 39962 | 39963 | 39965 | 39967 | 39969 | 39971 | 39972 | 39976 | 39977 |
| 39978 | 39981 | 39982 | 39983 | 39985 | 39988 | 39989 | 39990 | 39991 | 39993 | 39995 | 39998 |
| 39999 | 40001 | 40002 | 40003 | 40004 | 40005 | 40009 | 40011 | 40015 | 40018 | 40022 | 40024 |
| 40028 | 40029 | 40031 | 40032 | 40033 | 40034 | 40035 | 40036 | 40038 | 40039 | 40040 | 40041 |
| 40043 | 40044 | 40046 | 40049 | 40050 | 40054 | 40057 | 40060 | 40063 | 40070 | 40072 | 40073 |
| 40075 | 40076 | 40078 | 40079 | 40089 | 40091 | 40094 | 40103 | 40105 | 40107 | 40108 | 40110 |
| 40115 | 40116 | 40117 | 40120 | 40121 | 40124 | 40128 | 40129 | 40132 | 40133 | 40136 | 40141 |
| 40144 | 40145 | 40150 | 40151 | 40152 | 40153 | 40157 | 40161 | 40163 | 40165 | 40167 | 40168 |
| 40170 | 40175 | 40176 | 40178 | 40181 | 40183 | 40184 | 40186 | 40193 | 40195 | 40199 | 40200 |
| 40201 | 40206 | 40208 | 40211 | 40212 | 40219 | 40220 | 40223 | 40224 | 40226 | 40232 | 40236 |
| 40237 | 40239 | 40242 | 40245 | 40247 | 40248 | 40250 | 40251 | 40258 | 40263 | 40267 | 40268 |
| 40270 | 40273 | 40277 | 40279 | 40281 | 40282 | 40283 | 40284 | 40285 | 40287 | 40288 | 40290 |
| 40291 | 40293 | 40295 | 40297 | 40299 | 40300 | 40301 | 40302 | 40303 | 40319 | 40326 | 40327 |
| 40328 | 40333 | 40334 | 40337 | 40349 | 40350 | 40351 | 40356 | 40357 | 40362 | 40364 | 40365 |
| 40366 | 40368 | 40374 | 40375 | 40377 | 40378 | 40379 | 40380 | 40381 | 40387 | 40389 | 40390 |
| 40391 | 40392 | 40393 | 40394 | 40395 | 40396 | 40407 | 40408 | 40413 | 40418 | 40421 | 40422 |
| 40423 | 40430 | 40434 | 40435 | 40436 | 40438 | 40439 | 40443 | 40444 | 40446 | 40447 | 40448 |
| 40450 | 40453 | 40460 | 40461 | 40463 | 40464 | 40465 | 40466 | 40470 | 40472 | 40474 | 40476 |
| 40479 | 40480 | 40481 | 40482 | 40486 | 40491 | 40492 | 40495 | 40496 | 40499 | 40502 | 40506 |
| 40508 | 40510 | 40511 | 40514 | 40515 | 40517 | 40522 | 40524 | 40526 | 40528 | 40531 | 40533 |
| 40537 | 40538 | 40541 | 40547 | 40550 | 40551 | 40552 | 40553 | 40554 | 40556 | 40557 | 40558 |
| 40560 | 40563 | 40565 | 40569 | 40570 | 40575 | 40577 | 40579 | 40580 | 40582 | 40584 | 40587 |
| 40588 | 40589 | 40592 | 40593 | 40594 | 40595 | 40596 | 40598 | 40599 | 40600 | 40601 |
| 40602 | 40605 | 40607 | 40608 | 40609 | 40611 | 40613 | 40614 | 40615 | 40616 | 40619 | 40620 |
| 40622 | 40625 | 40626 | 40627 | 40628 | 40630 | 40631 | 40632 | 40633 | 40636 | 40637 | 40641 |
| 40642 | 40643 | 40646 | 40652 | 40655 | 40657 | 40659 | 40660 | 40662 | 40664 | 40667 | 40668 |
| 40670 | 40671 | 40672 | 40674 | 40678 | 40679 | 40682 | 40683 | 40684 | 40685 | 40687 | 40690 |
| 40696 | 40698 | 40699 | 40701 | 40702 | 40703 | 40704 | 40708 | 40710 | 40711 | 40714 | 40715 |
| 40718 | 40719 | 40724 | 40726 | 40727 | 40730 | 40731 | 40734 | 40737 | 40738 | 40740 | 40745 |
| 40746 | 40749 | 40750 | 40752 | 40754 | 40755 | 40756 | 40759 | 40760 | 40761 | 40772 | 40773 |
| 40775 | 40776 | 40780 | 40790 | 40791 | 40793 | 40796 | 40797 | 40798 | 40799 | 40800 | 40801 |
| 40802 | 40803 | 40810 | 40812 | 40813 | 40815 | 40816 | 40827 | 40828 | 40831 | 40832 | 40833 |
| 40834 | 40839 | 40842 | 40843 | 40844 | 40845 | 40848 | 40851 | 40852 | 40856 | 40858 | 40863 |
| 40865 | 40867 | 40868 | 40869 | 40870 | 40871 | 40875 | 40877 | 40879 | 40883 | 40885 | 40888 |
| 40891 | 40893 | 40907 | 40912 | 40913 | 40915 | 40918 | 40921 | 40924 | 40926 | 40927 |
| 40929 | 40931 | 40936 | 40938 | 40939 | 40940 | 40942 | 40943 | 40944 | 40945 | 40947 | 40948 |
| 40950 | 40951 | 40952 | 40955 | 40957 | 40959 | 40960 | 40963 | 40964 | 40965 | 40966 | 40968 |
| 40969 | 40971 | 40975 | 40977 | 40978 | 40979 | 40980 | 40983 | 40985 | 40986 | 40987 | 40988 |
| 40994 | 40995 | 41006 | 41008 | 41011 | 41012 | 41015 | 41017 | 41025 | 41027 | 41028 | 41030 |
| 41032 | 41034 | 41035 | 41038 | 41039 | 41040 | 41041 | 41042 | 41045 | 41046 | 41047 | 41048 |
| 41049 | 41051 | 41053 | 41054 | 41062 | 41075 | 41076 | 41078 | 41079 | 41081 | 41085 | 41086 |
| 41087 | 41090 | 41092 | 41094 | 41095 | 41096 | 41097 | 41098 | 41099 | 41100 | 41101 | 41109 |
| 41110 | 41113 | 41114 | 41116 | 41117 | 41118 | 41119 | 41120 | 41121 | 41122 | 41123 | 41124 |
| 41126 | 41127 | 41129 | 41134 | 41136 | 41137 | 41138 | 41141 | 41144 | 41146 | 41147 | 41148 |

TABLE 13A-continued

Seed Oil Yield/Content

| | | | | | | | | | | | |
|---|---|---|---|---|---|---|---|---|---|---|---|
| 41150 | 41153 | 41154 | 41157 | 41162 | 41163 | 41173 | 41174 | 41175 | 41176 | 41185 | 41189 |
| 41194 | 41196 | 41197 | 41198 | 41200 | 41202 | 41203 | 41205 | 41206 | 41209 | 41210 | 41212 |
| 41213 | 41215 | 41216 | 41217 | 41218 | 41223 | 41224 | 41225 | 41229 | 41232 | 41238 | 41239 |
| 41240 | 41241 | 41242 | 41243 | 41251 | 41252 | 41254 | 41255 | 41257 | 41258 | 41259 | 41260 |
| 41264 | 41265 | 41266 | 41267 | 41274 | 41281 | 41289 | 41292 | 41293 | 41294 | 41296 | 41297 |
| 41300 | 41301 | 41302 | 41303 | 41306 | 41309 | 41310 | 41312 | 41313 | 41319 | 41320 | 41322 |
| 41323 | 41332 | 41333 | 41334 | 41335 | 41337 | 41339 | 41340 | 41343 | 41345 | 41347 | 41348 |
| 41351 | 41352 | 41357 | 41358 | 41361 | 41362 | 41363 | 41365 | 41366 | 41367 | 41368 | 41381 |
| 41382 | 41383 | 41387 | 41388 | 41392 | 41398 | 41402 | 41403 | 41406 | 41407 | 41409 | 41411 |
| 41412 | 41416 | 41417 | 41418 | 41423 | 41425 | 41426 | 41428 | 41429 | 41432 | 41436 | 41449 |
| 41451 | 41457 | 41458 | 41466 | 41467 | 41470 | 41471 | 41473 | 41475 | 41477 | 41479 | 41482 |
| 41483 | 41485 | 41488 | 41494 | 41496 | 41500 | 41506 | 41507 | 41509 | 41519 | 41522 | 41524 |
| 41525 | 41527 | 41528 | 41533 | 41534 | 41535 | 41536 | 41537 | 41541 | 41547 | 41548 | 41550 |
| 41551 | 41552 | 41553 | 41554 | 41555 | 41556 | 41557 | 41563 | 41568 | 41569 | 41571 |
| 41572 | 41573 | 41574 | 41575 | 41576 | 41579 | 41580 | 41585 | 41586 | 41588 | 41591 | 41596 |
| 41600 | 41601 | 41605 | 41608 | 41610 | 41613 | 41614 | 41616 | 41621 | 41622 | 41635 | 41636 |
| 41638 | 41642 | 41643 | 41645 | 41647 | 41648 | 41653 | 41655 | 41658 | 41661 | 41668 | 41669 |
| 41671 | 41672 | 41673 | 41674 | 41675 | 41676 | 41678 | 41680 | 41681 | 41682 | 41683 | 41684 |
| 41686 | 41689 | 41690 | 41693 | 41695 | 41697 | 41699 | 41700 | 41702 | 41705 | 41707 | 41708 |
| 41712 | 41713 | 41716 | 41717 | 41718 | 41721 | 41723 | 41726 | 41728 | 41730 | 41732 | 41736 |
| 41737 | 41738 | 41741 | 41742 | 41743 | 41746 | 41747 | 41748 | 41749 | 41750 | 41753 | 41754 |
| 41756 | 41757 | 41758 | 41760 | 41761 | 41762 | 41763 | 41764 | 41765 | 41766 | 41767 | 41768 |
| 41769 | 41774 | 41776 | 41779 | 41786 | 41787 | 41788 | 41791 | 41792 | 41795 | 41800 | 41801 |
| 41803 | 41804 | 41806 | 41807 | 41808 | 41811 | 41812 | 41813 | 41814 | 41816 | 41817 | 41818 |
| 41820 | 41822 | 41825 | 41826 | 41827 | 41828 | 41830 | 41831 | 41832 | 41835 | 41836 | 41838 |
| 41839 | 41841 | 41842 | 41843 | 41844 | 41845 | 41846 | 41857 | 41858 | 41860 | 41862 | 41863 |
| 41866 | 41867 | 41870 | 41872 | 41873 | 41874 | 41875 | 41876 | 41877 | 41878 | 41879 | 41880 |
| 41882 | 41886 | 41888 | 41891 | 41892 | 41896 | 41897 | 41898 | 41900 | 41906 | 41907 | 41908 |
| 41910 | 41913 | 41914 | 41915 | 41920 | 41922 | 41924 | 41928 | 41929 | 41932 | 41935 | 41946 |
| 41952 | 41953 | 41954 | 41957 | 41958 | 41961 | 41962 | 41963 | 41964 | 41965 | 41967 | 41968 |
| 41969 | 41972 | 41975 | 41980 | 41981 | 41982 | 41985 | 41986 | 41991 | 41995 | 41997 | 41998 |
| 42000 | 42001 | 42005 | 42009 | 42012 | 42014 | 42015 | 42016 | 42017 | 42025 | 42030 | 42031 |
| 42032 | 42036 | 42038 | 42043 | 42044 | 42046 | 42052 | 42054 | 42055 | 42056 | 42057 | 42058 |
| 42059 | 42060 | 42061 | 42064 | 42071 | 42077 | 42081 | 42082 | 42084 | 42088 | 42089 | 42090 |
| 42092 | 42097 | 42098 | 42104 | 42105 | 42106 | 42111 | 42112 | 42116 | 42117 | 42118 | 42119 |
| 42122 | 42129 | 42130 | 42131 | 42134 | 42136 | 42138 | 42140 | 42142 | 42151 | 42154 | 42155 |
| 42157 | 42160 | 42161 | 42162 | 42169 | 42171 | 42172 | 42173 | 42174 | 42176 | 42177 | 42178 |
| 42181 | 42187 | 42195 | 42199 | 42202 | 42203 | 42204 | 42206 | 42209 | 42215 | 42216 | 42222 |
| 42224 | 42231 | 42232 | 42235 | 42236 | 42237 | 42238 | 42243 | 42246 | 42256 | 42259 | 42260 |
| 42262 | 42263 | 42267 | 42268 | 42270 | 42275 | 42279 | 42280 | 42281 | 42282 | 42285 | 42287 |
| 42291 | 42295 | 42298 | 42299 | 42301 | 42303 | 42304 | 42305 | 42306 | 42308 | 42312 | 42317 |
| 42320 | 42321 | 42323 | 42327 | 42339 | 42342 | 42343 | 42345 | 42347 | 42348 | 42349 | 42355 |
| 42356 | 42359 | 42360 | 42368 | 42369 | 42370 | 42375 | 42379 | 42384 | 42386 | 42396 | 42397 |
| 42398 | 42405 | 42406 | 42413 | 42417 | 42418 | 42419 | 42420 | 42422 | 42427 | 42428 | 42430 |
| 42431 | 42435 | 42436 | 42438 | 42439 | 42446 | 42447 | 42448 | 42453 | 42454 | 42455 | 42458 |
| 42462 | 42465 | 42468 | 42469 | 42470 | 42472 | 42475 | 42477 | 42479 | 42489 | 42491 | 42509 |
| 42511 | 42512 | 42514 | 42515 | 42516 | 42521 | 42522 | 42524 | 42525 | 42526 | 42533 | 42545 |
| 42547 | 42548 | 42549 | 42550 | 42556 | 42566 | 42571 | 42583 | 42584 | 42591 | 42595 | 42597 |
| 42599 | 42602 | 42603 | 42607 | 42609 | 42611 | 42612 | 42613 | 42616 | 42617 | 42620 | 42624 |
| 42628 | 42632 | 42639 | 42640 | 42645 | 42646 | 42648 | 42650 | 42651 | 42655 | 42664 | 42665 |
| 42667 | 42668 | 42673 | 42674 | 42677 | 42682 | 42687 | 42692 | 42694 | 42695 | 42696 | 42697 |
| 42706 | 42707 | 42709 | 42710 | 42713 | 42725 | 42729 | 42736 | 42738 | 42742 | 42746 | 42754 |
| 42756 | 42757 | 42760 | 42761 | 42762 | 42763 | 42764 | 42765 | 42767 | 42770 | 42771 | 42772 |
| 42775 | 42777 | 42778 | 42780 | 42786 | 42789 | 42791 | 42794 | 42802 | 42804 | 42805 | 42807 |
| 42809 | 42811 | 42814 | 42817 | 42818 | 42824 | 42826 | 42842 | 42843 | 42845 | 42847 | 42850 |
| 42856 | 42858 | 42860 | 42861 | 42863 | 42865 | 42868 | 42870 | 42871 | 42878 | 42882 | 42884 |
| 42885 | 42886 | 42887 | 42888 | 42889 | 42890 | 42892 | 42899 | 42901 | 42903 | 42908 | 42909 |
| 42915 | 42917 | 42918 | 42920 | 42921 | 42925 | 42926 | 42927 | 42929 | 42930 | 42932 | 42933 |
| 42937 | 42940 | 42942 | 42944 | 42945 | 42946 | 42947 | 42948 | 42949 | 42950 | 42951 | 42958 |
| 42960 | 42963 | 42964 | 42967 | 42969 | 42979 | 42981 | 42987 | 42988 | 42993 | 42994 |
| 42996 | 42999 | 43003 | 43004 | 43012 | 43013 | 43017 | 43019 | 43020 | 43021 | 43025 | 43028 |
| 43029 | 43031 | 43033 | 43035 | 43038 | 43039 | 43042 | 43050 | 43051 | 43052 | 43053 | 43054 |
| 43055 | 43056 | 43057 | 43059 | 43063 | 43064 | 43065 | 43068 | 43074 | 43075 | 43076 | 43077 |
| 43078 | 43080 | 43081 | 43096 | 43099 | 43101 | 43103 | 43107 | 43109 | 43111 | 43120 | 43125 |
| 43128 | 43131 | 43132 | 43133 | 43134 | 43135 | 43136 | 43137 | 43148 | 43151 | 43152 | 43156 |
| 43157 | 43159 | 43164 | 43170 | 43173 | 43178 | 43180 | 43182 | 43183 | 43185 | 43188 | 43189 |
| 43190 | 43192 | 43198 | 43204 | 43209 | 43210 | 43211 | 43212 | 43215 | 43217 | 43219 | 43220 |
| 43221 | 43226 | 43227 | 43232 | 43236 | 43237 | 43239 | 43240 | 43241 | 43242 | 43244 | 43249 |
| 43253 | 43254 | 43259 | 43260 | 43261 | 43262 | 43265 | 43267 | 43268 | 43269 | 43270 | 43271 |
| 43272 | 43276 | 43277 | 43280 | 43281 | 43282 | 43284 | 43286 | 43299 | 43301 | 43302 | 43303 |
| 43304 | 43307 | 43310 | 43315 | 43320 | 43326 | 43331 | 43332 | 43336 | 43339 | 43342 | 43343 |
| 43345 | 43348 | 43350 | 43351 | 43353 | 43354 | 43358 | 43359 | 43368 | 43370 | 43371 | 43373 |
| 43375 | 43376 | 43377 | 43385 | 43386 | 43388 | 43389 | 43390 | 43391 | 43395 | 43398 | 43399 |
| 43400 | 43401 | 43402 | 43403 | 43404 | 43406 | 43422 | 43425 | 43426 | 43427 | 43428 | 43429 |
| 43430 | 43434 | 43438 | 43439 | 43441 | 43444 | 43450 | 43455 | 43456 | 43458 | 43459 | 43464 |
| 43468 | 43474 | 43478 | 43482 | 43483 | 43484 | 43486 | 43488 | 43489 | 43491 | 43493 | 43494 |
| 43495 | 43496 | 43497 | 43498 | 43499 | 43500 | 43501 | 43503 | 43504 | 43505 | 43507 | 43509 |

TABLE 13A-continued

Seed Oil Yield/Content

| | | | | | | | | | | | |
|---|---|---|---|---|---|---|---|---|---|---|---|
| 43512 | 43515 | 43518 | 43522 | 43525 | 43531 | 43533 | 43534 | 43535 | 43537 | 43539 | 43540 |
| 43541 | 43543 | 43544 | 43546 | 43547 | 43550 | 43553 | 43554 | 43563 | 43566 | 43568 | 43571 |
| 43576 | 43580 | 43587 | 43588 | 43592 | 43594 | 43595 | 43597 | 43599 | 43600 | 43602 | 43605 |
| 43606 | 43608 | 43609 | 43612 | 43613 | 43616 | 43617 | 43622 | 43633 | 43643 | 43644 | 43645 |
| 43653 | 43657 | 43660 | 43666 | 43668 | 43677 | 43684 | 43685 | 43686 | 43688 | 43694 | 43698 |
| 43701 | 43717 | 43719 | 43721 | 43722 | 43724 | 43726 | 43727 | 43728 | 43729 | 43730 | 43731 |
| 43732 | 43737 | 43738 | 43740 | 43741 | 43742 | 43743 | 43747 | 43755 | 43757 | 43758 | 43761 |
| 43763 | 43767 | 43769 | 43770 | 43773 | 43776 | 43777 | 43779 | 43780 | 43784 | 43786 | 43787 |
| 43788 | 43790 | 43793 | 43795 | 43796 | 43797 | 43805 | 43806 | 43808 | 43810 | 43813 | 43818 |
| 43820 | 43823 | 43827 | 43838 | 43839 | 43840 | 43841 | 43842 | 43843 | 43846 | 43847 | 43849 |
| 43856 | 43867 | 43868 | 43877 | 43878 | 43879 | 43882 | 43894 | 43903 | 43905 | 43907 | 43908 |
| 43909 | 43915 | 43916 | 43927 | 43928 | 43931 | 43932 | 43936 | 43940 | 43949 | 43950 | 43959 |
| 43962 | 43965 | 43967 | 43973 | 43977 | 43984 | 43985 | 43987 | 43988 | 43994 | 43995 | 43999 |
| 44000 | 44004 | 44006 | 44009 | 44013 | 44027 | 44029 | 44036 | 44037 | 44044 | 44045 | 44052 |
| 44056 | 44057 | 44061 | 44062 | 44064 | 44065 | 44073 | 44085 | 44087 | 44089 | 44091 | 44092 |
| 44096 | 44097 | 44099 | 44104 | 44105 | 44106 | 44107 | 44109 | 44110 | 44111 | 44112 | 44115 |
| 44116 | 44117 | 44124 | 44128 | 44131 | 44138 | 44139 | 44141 | 44144 | 44147 | 44148 | 44150 |
| 44151 | 44152 | 44153 | 44154 | 44155 | 44157 | 44160 | 44163 | 44164 | 44167 | 44168 | |
| 44169 | 44173 | 44176 | 44177 | 44178 | 44181 | 44182 | 44183 | 44187 | 44188 | 44190 | 44191 |
| 44192 | 44193 | 44195 | 44198 | 44199 | 44200 | 44202 | 44206 | 44210 | 44211 | 44212 | 44213 |
| 44216 | 44218 | 44219 | 44220 | 44221 | 44222 | 44223 | 44224 | 44226 | 44227 | 44230 | 44232 |
| 44235 | 44240 | 44241 | 44242 | 44243 | 44250 | 44251 | 44252 | 44254 | 44255 | 44257 | 44260 |
| 44263 | 44264 | 44265 | 44266 | 44267 | 44270 | 44271 | 44273 | 44275 | 44279 | 44280 | 44281 |
| 44285 | 44286 | 44287 | 44288 | 44289 | 44290 | 44292 | 44297 | 44299 | 44301 | 44302 | 44303 |
| 44304 | 44305 | 44306 | 44311 | 44314 | 44318 | 44323 | 44324 | 44326 | 44330 | 44333 | 44334 |
| 44335 | 44337 | 44342 | 44343 | 44348 | 44349 | 44350 | 44351 | 44352 | 44355 | 44357 | 44358 |
| 44360 | 44361 | 44364 | 44369 | 44375 | 44376 | 44377 | 44378 | 44379 | 44388 | 44390 | 44393 |
| 44394 | 44395 | 44396 | 44400 | 44402 | 44403 | 44405 | 44406 | 44407 | 44409 | 44412 | 44413 |
| 44417 | 44418 | 44423 | 44424 | 44426 | 44430 | 44431 | 44432 | 44433 | 44435 | 44436 | 44437 |
| 44439 | 44440 | 44444 | 44445 | 44448 | 44449 | 44452 | 44453 | 44455 | 44456 | 44458 | 44459 |
| 44460 | 44461 | 44462 | 44464 | 44465 | 44466 | 44467 | 44471 | 44472 | 44474 | 44476 | 44478 |
| 44484 | 44487 | 44488 | 44489 | 44490 | 44492 | 44493 | 44496 | 44498 | 44504 | 44508 | 44509 |
| 44513 | 44514 | 44515 | 44516 | 44518 | 44522 | 44523 | 44525 | 44526 | 44527 | 44535 | 44536 |
| 44537 | 44539 | 44541 | 44543 | 44544 | 44545 | 44546 | 44547 | 44552 | 44553 | 44555 | 44558 |
| 44561 | 44562 | 44563 | 44565 | 44573 | 44574 | 44576 | 44579 | 44580 | 44581 | 44582 | 44586 |
| 44590 | 44597 | 44599 | 44604 | 44606 | 44607 | 44608 | 44611 | 44615 | 44618 | 44623 | 44626 |
| 44629 | 44631 | 44633 | 44635 | 44638 | 44639 | 44646 | 44648 | 44650 | 44655 | 44657 | 44660 |
| 44667 | 44672 | 44674 | 44675 | 44676 | 44677 | 44678 | 44679 | 44680 | 44685 | 44686 | 44690 |
| 44691 | 44693 | 44695 | 44697 | 44704 | 44706 | 44708 | 44712 | 44713 | 44718 | 44719 | 44721 |
| 44722 | 44724 | 44729 | 44731 | 44732 | 44733 | 44741 | 44744 | 44746 | 44749 | 44750 | 44751 |
| 44755 | 44757 | 44758 | 44759 | 44760 | 44761 | 44762 | 44764 | 44771 | 44773 | 44778 | 44780 |
| 44788 | 44789 | 44790 | 44793 | 44798 | 44801 | 44806 | 44807 | 44811 | 44812 | 44816 | 44817 |
| 44818 | 44820 | 44821 | 44829 | 44830 | 44831 | 44834 | 44835 | 44836 | 44839 | 44841 | 44843 |
| 44846 | 44847 | 44848 | 44849 | 44851 | 44853 | 44854 | 44855 | 44857 | 44858 | 44860 | 44867 |
| 44870 | 44872 | 44873 | 44878 | 44880 | 44881 | 44883 | 44887 | 44891 | 44892 | 44893 | 44896 |
| 44897 | 44898 | 44901 | 44902 | 44903 | 44906 | 44907 | 44919 | 44922 | 44923 | 44930 | 44931 |
| 44932 | 44936 | 44939 | 44941 | 44943 | 44944 | 44947 | 44950 | 44954 | 44958 | 44960 | |
| 44967 | 44968 | 44970 | 44971 | 44972 | 44978 | 44980 | 44981 | 44982 | 44983 | 44984 | 44985 |
| 44988 | 44989 | 44991 | 44994 | 44999 | 45000 | 45001 | 45002 | 45007 | 45010 | 45011 | 45015 |
| 45016 | 45018 | 45019 | 45020 | 45021 | 45022 | 45025 | 45026 | 45027 | 45035 | 45036 | 45037 |
| 45041 | 45048 | 45050 | 45051 | 45053 | 45055 | 45058 | 45060 | 45061 | 45062 | 45063 | 45064 |
| 45066 | 45067 | 45068 | 45071 | 45074 | 45076 | 45082 | 45083 | 45085 | 45086 | 45087 | 45089 |
| 45090 | 45097 | 45098 | 45103 | 45104 | 45107 | 45108 | 45112 | 45113 | 45115 | 45117 | 45119 |
| 45121 | 45123 | 45128 | 45130 | 45132 | 45133 | 45134 | 45136 | 45146 | 45147 | 45149 | 45151 |
| 45153 | 45155 | 45157 | 45158 | 45166 | 45168 | 45170 | 45172 | 45176 | 45179 | 45190 | 45194 |
| 45199 | 45200 | 45208 | 45214 | 45219 | 45222 | 45233 | 45238 | 45239 | 45240 | 45244 | 45247 |
| 45249 | 45255 | 45256 | 45257 | 45258 | 45259 | 45261 | 45263 | 45269 | 45272 | 45273 | 45275 |
| 45277 | 45283 | 45284 | 45294 | 45295 | 45307 | 45311 | 45315 | 45318 | 45324 | 45326 | 45329 |
| 45333 | 45338 | 45342 | 45344 | 45348 | 45349 | 45351 | 45353 | 45357 | 45359 | 45361 | 45363 |
| 45364 | 45365 | 45368 | 45369 | 45370 | 45373 | 45374 | 45376 | 45378 | 45379 | 45381 | |
| 45382 | 45384 | 45387 | 45388 | 45389 | 45391 | 45392 | 45393 | 45394 | 45396 | 45397 | 45398 |
| 45399 | 45400 | 45401 | 45403 | 45404 | 45405 | 45407 | 45409 | 45410 | 45413 | 45416 | 45417 |
| 45418 | 45419 | 45420 | 45421 | 45422 | 45423 | 45424 | 45425 | 45426 | 45427 | 45428 | 45429 |
| 45432 | 45435 | 45436 | 45441 | 45444 | 45445 | 45446 | 45447 | 45450 | 45453 | 45455 | 45456 |
| 45461 | 45463 | 45465 | 45466 | 45468 | 45470 | 45471 | 45478 | 45481 | 45482 | 45487 | 45488 |
| 45490 | 45496 | 45500 | 45503 | 45504 | 45506 | 45507 | 45509 | 45511 | 45512 | 45515 | 45520 |
| 45522 | 45528 | 45531 | 45532 | 45534 | 45542 | 45547 | 45551 | 45559 | 45560 | 45570 | 45578 |
| 45580 | 45582 | 45583 | 45587 | 45595 | 45598 | 45616 | 45617 | 45624 | 45626 | 45628 | 45647 |
| 45650 | 45655 | 45659 | 45660 | 45662 | 45674 | 45675 | 45678 | 45679 | 45680 | 45681 | 45685 |
| 45686 | 45688 | 45693 | 45698 | 45699 | 45700 | 45701 | 45702 | 45704 | 45707 | 45708 | 45719 |
| 45720 | 45721 | 45722 | 45723 | 45725 | 45733 | 45734 | 45735 | 45740 | 45748 | 45753 | 45758 |
| 45759 | 45762 | 45765 | 45775 | 45781 | 45788 | 45789 | 45794 | 45802 | 45803 | 45811 | |
| 45812 | 45813 | 45814 | 45819 | 45821 | 45825 | 45833 | 45834 | 45850 | 45852 | 45857 | 45867 |
| 45873 | 45887 | 45892 | 45893 | 45897 | 45899 | 45900 | 45901 | 45902 | 45906 | 45907 | 45908 |
| 45909 | 45912 | 45918 | 45919 | 45925 | 45927 | 45932 | 45935 | 45940 | 45947 | 45948 | 45950 |
| 45956 | 45960 | 45962 | 45964 | 45966 | 45973 | 45977 | 45978 | 45982 | 45996 | 46000 | 46008 |
| 46012 | 46013 | 46014 | 46018 | 46019 | 46022 | 46032 | 46034 | 46053 | 46055 | 46057 | 46063 |

TABLE 13A-continued

Seed Oil Yield/Content

| | | | | | | | | | | | |
|---|---|---|---|---|---|---|---|---|---|---|---|
| 46065 | 46066 | 46073 | 46076 | 46078 | 46085 | 46089 | 46093 | 46104 | 46105 | 46106 | 46112 |
| 46115 | 46117 | 46118 | 46123 | 46125 | 46126 | 46127 | 46128 | 46129 | 46133 | 46134 | 46142 |
| 46145 | 46146 | 46151 | 46159 | 46179 | 46182 | 46186 | 46190 | 46196 | 46197 | 46209 | 46216 |
| 46220 | 46223 | 46225 | 46229 | 46231 | 46232 | 46236 | 46239 | 46252 | 46258 | 46259 | 46269 |
| 46270 | 46272 | 46280 | 46281 | 46285 | 46289 | 46295 | 46296 | 46297 | 46304 | 46317 | 46318 |
| 46319 | 46320 | 46322 | 46323 | 46329 | 46335 | 46340 | 46342 | 46353 | 46357 | 46362 | 46372 |
| 46387 | 46396 | 46404 | 46424 | 46425 | 46434 | 46435 | 46438 | 46440 | 46441 | 46443 | 46446 |
| 46452 | 46457 | 46460 | 46467 | 46469 | 46479 | 46483 | 46486 | 46488 | 46489 | 46504 | 46506 |
| 46509 | 46510 | 46511 | 46517 | 46518 | 46521 | 46524 | 46525 | 46526 | 46527 | 46530 | 46533 |
| 46537 | 46538 | 46539 | 46540 | 46541 | 46542 | 46546 | 46548 | 46549 | 46551 | 46552 | 46557 |
| 46559 | 46560 | 46566 | 46577 | 46579 | 46582 | 46583 | 46591 | 46592 | 46603 | 46604 | 46605 |
| 46607 | 46609 | 46615 | 46618 | 46621 | 46627 | 46632 | 46633 | 46634 | 46636 | 46639 | 46646 |
| 46649 | 46652 | 46654 | 46659 | 46661 | 46662 | 46663 | 46665 | 46667 | 46668 | 46671 | 46678 |
| 46680 | 46681 | 46687 | 46695 | 46700 | 46701 | 46702 | 46703 | 46706 | 46709 | 46710 | 46711 |
| 46713 | 46717 | 46718 | 46721 | 46722 | 46723 | 46726 | 46729 | 46739 | 46740 | 46744 | 46745 |
| 46746 | 46748 | 46750 | 46751 | 46754 | 46755 | 46757 | 46758 | 46760 | 46762 | 46767 | 46768 |
| 46771 | 46773 | 46774 | 46775 | 46778 | 46782 | 46783 | 46784 | 46786 | 46790 | 46793 | 46794 |
| 46796 | 46797 | 46799 | 46809 | 46810 | 46812 | 46813 | 46814 | 46820 | 46826 | 46827 | 46830 |
| 46831 | 46832 | 46833 | 46834 | 46835 | 46841 | 46843 | 46845 | 46848 | 46849 | 46851 | 46856 |
| 46857 | 46859 | 46861 | 46863 | 46864 | 46866 | 46868 | 46869 | 46870 | 46871 | 46872 | 46878 |
| 46879 | 46880 | 46883 | 46884 | 46885 | 46889 | 46890 | 46891 | 46895 | 46899 | 46900 | 46901 |
| 46904 | 46913 | 46914 | 46920 | 46922 | 46924 | 46927 | 46928 | 46929 | 46931 | 46934 | 46936 |
| 46938 | 46939 | 46940 | 46944 | 46945 | 46946 | 46947 | 46948 | 46950 | 46952 | 46954 | 46955 |
| 46956 | 46957 | 46958 | 46959 | 46960 | 46961 | 46963 | 46964 | 46969 | 46972 | 46973 | 46974 |
| 46976 | 46977 | 46978 | 46986 | 46987 | 46988 | 46989 | 46990 | 46991 | 46992 | 46997 | 46998 |
| 46999 | 47000 | 47005 | 47006 | 47008 | 47009 | 47011 | 47012 | 47013 | 47014 | 47015 | 47016 |
| 47020 | 47022 | 47024 | 47034 | 47035 | 47036 | 47037 | 47039 | 47041 | 47043 | 47045 | 47049 |
| 47050 | 47054 | 47056 | 47057 | 47058 | 47061 | 47063 | 47065 | 47069 | 47072 | 47075 | 47076 |
| 47077 | 47079 | 47080 | 47083 | 47086 | 47087 | 47088 | 47091 | 47095 | 47096 | 47099 | 47100 |
| 47108 | 47110 | 47113 | 47115 | 47120 | 47121 | 47129 | 47133 | 47134 | 47138 | 47142 | 47143 |
| 47144 | 47146 | 47149 | 47151 | 47153 | 47154 | 47155 | 47161 | 47163 | 47164 | 47165 | 47166 |
| 47167 | 47169 | 47171 | 47172 | 47177 | 47179 | 47182 | 47184 | 47185 | 47189 | 47192 | 47196 |
| 47197 | 47198 | 47200 | 47201 | 47203 | 47207 | 47211 | 47212 | 47213 | 47214 | 47216 | 47217 |
| 47218 | 47222 | 47223 | 47224 | 47225 | 47229 | 47233 | 47234 | 47238 | 47239 | 47244 | 47246 |
| 47249 | 47258 | 47259 | 47260 | 47261 | 47263 | 47264 | 47265 | 47266 | 47268 | 47269 | 47270 |
| 47271 | 47273 | 47274 | 47275 | 47282 | 47285 | 47288 | 47289 | 47291 | 47292 | 47295 |
| 47296 | 47297 | 47299 | 47300 | 47303 | 47306 | 47308 | 47313 | 47314 | 47317 | 47318 | 47319 |
| 47322 | 47324 | 47325 | 47326 | 47327 | 47331 | 47333 | 47337 | 47338 | 47339 | 47340 | 47342 |
| 47343 | 47344 | 47345 | 47346 | 47350 | 47353 | 47354 | 47357 | 47358 | 47359 | 47360 | 47366 |
| 47371 | | | | | | | | | | | |

TABLE 14

Seed Protein Yield/Content

Table 14A SEQ ID NOs of Polypeptides useful for improving Seed Protein Yield/Content

| | | | | | | | | | | | |
|---|---|---|---|---|---|---|---|---|---|---|---|
| 8 | 20 | 52 | 55 | 63 | 66 | 67 | 79 | 80 | 85 | 87 | 88 |
| 91 | 98 | 100 | 102 | 126 | 129 | 140 | 141 | 142 | 143 | 157 | 168 |
| 176 | 189 | 191 | 193 | 221 | 227 | 239 | 242 | 245 | 264 | 273 | 282 |
| 298 | 304 | 308 | 309 | 312 | 315 | 320 | 330 | 334 | 337 | 342 | 347 |
| 348 | 351 | 357 | 361 | 365 | 367 | 373 | 383 | 397 | 406 | 414 | 419 |
| 430 | 445 | 452 | 463 | 475 | 476 | 480 | 488 | 500 | 503 | 509 | 516 |
| 519 | 542 | 545 | 555 | 556 | 558 | 559 | 566 | 578 | 584 | 592 | 611 |
| 621 | 623 | 631 | 633 | 645 | 647 | 657 | 675 | 677 | 686 | 690 | 695 |
| 700 | 714 | 716 | 729 | 732 | 734 | 745 | 753 | 758 | 777 | 819 | 826 |
| 838 | 853 | 861 | 898 | 905 | 935 | 936 | 943 | 948 | 955 | 956 | 957 |
| 978 | 981 | 985 | 998 | 999 | 1000 | 1001 | 1012 | 1017 | 1028 | 1029 | 1041 |
| 1045 | 1048 | 1050 | 1054 | 1060 | 1084 | 1090 | 1101 | 1137 | 1145 | 1146 | 1157 |
| 1161 | 1169 | 1170 | 1171 | 1172 | 1195 | 1205 | 1208 | 1216 | 1217 | 1253 | 1265 |
| 1267 | 1275 | 1276 | 1277 | 1278 | 1291 | 1299 | 1300 | 1311 | 1333 | 1358 | 1393 |
| 1411 | 1417 | 1418 | 1419 | 1421 | 1423 | 1427 | 1441 | 1443 | 1444 | 1447 | 1450 |
| 1458 | 1459 | 1465 | 1469 | 1482 | 1495 | 1497 | 1504 | 1506 | 1508 | 1513 | 1538 |
| 1543 | 1549 | 1565 | 1571 | 1573 | 1574 | 1599 | 1601 | 1616 | 1623 | 1636 | 1639 |
| 1643 | 1645 | 1665 | 1679 | 1680 | 1681 | 1685 | 1689 | 1691 | 1698 | 1699 | 1701 |
| 1704 | 1706 | 1707 | 1721 | 1725 | 1730 | 1732 | 1739 | 1741 | 1742 | 1751 | 1753 |
| 1754 | 1756 | 1759 | 1769 | 1772 | 1783 | 1785 | 1805 | 1815 | 1816 | 1826 | 1827 |
| 1841 | 1846 | 1867 | 1872 | 1876 | 1880 | 1892 | 1893 | 1895 | 1898 | 1899 | 1910 |
| 1916 | 1926 | 1929 | 1931 | 1936 | 1946 | 1947 | 1953 | 1960 | 1962 | 1987 | 1994 |
| 2006 | 2008 | 2014 | 2019 | 2028 | 2051 | 2057 | 2059 | 2067 | 2071 | 2079 | 2082 |
| 2083 | 2086 | 2089 | 2095 | 2117 | 2126 | 2131 | 2140 | 2146 | 2152 | 2165 | 2182 |
| 2184 | 2203 | 2207 | 2226 | 2230 | 2233 | 2243 | 2244 | 2249 | 2262 | 2265 | 2269 |
| 2279 | 2286 | 2294 | 2301 | 2306 | 2308 | 2314 | 2316 | 2320 | 2322 | 2333 | 2340 |
| 2345 | 2352 | 2358 | 2369 | 2373 | 2374 | 2384 | 2387 | 2392 | 2402 | 2406 | 2414 |

TABLE 14-continued

Seed Protein Yield/Content

| | | | | | | | | | | | |
|---|---|---|---|---|---|---|---|---|---|---|---|
| 2422 | 2441 | 2455 | 2457 | 2461 | 2464 | 2476 | 2480 | 2481 | 2482 | 2483 | 2503 |
| 2504 | 2517 | 2518 | 2531 | 2536 | 2538 | 2553 | 2554 | 2566 | 2569 | 2570 | 2575 |
| 2580 | 2589 | 2597 | 2602 | 2605 | 2608 | 2619 | 2622 | 2632 | 2636 | 2638 | 2653 |
| 2683 | 2702 | 2747 | 2750 | 2757 | 2762 | 2769 | 2770 | 2785 | 2791 | 2798 | 2806 |
| 2811 | 2853 | 2857 | 2858 | 2859 | 2862 | 2865 | 2866 | 2876 | 2878 | 2898 | 2902 |
| 2953 | 2958 | 2965 | 2978 | 3015 | 3017 | 3026 | 3035 | 3036 | 3037 | 3038 | 3039 |
| 3040 | 3045 | 3050 | 3052 | 3070 | 3074 | 3088 | 3096 | 3100 | 3105 | 3110 | 3113 |
| 3120 | 3121 | 3122 | 3124 | 3125 | 3126 | 3129 | 3150 | 3154 | 3156 | 3157 | 3166 |
| 3173 | 3175 | 3182 | 3185 | 3186 | 3188 | 3199 | 3216 | 3217 | 3219 | 3226 | 3231 |
| 3235 | 3238 | 3240 | 3244 | 3250 | 3257 | 3266 | 3273 | 3277 | 3284 | 3288 | 3290 |
| 3298 | 3307 | 3309 | 3311 | 3315 | 3324 | 3327 | 3330 | 3339 | 3344 | 3350 | 3353 |
| 3355 | 3360 | 3365 | 3379 | 3381 | 3386 | 3389 | 3392 | 3393 | 3394 | 3404 | 3410 |
| 3421 | 3422 | 3426 | 3427 | 3428 | 3430 | 3431 | 3436 | 3440 | 3445 | 3451 | 3453 |
| 3455 | 3461 | 3466 | 3471 | 3488 | 3489 | 3495 | 3514 | 3520 | 3527 | 3528 | |
| 3529 | 3542 | 3543 | 3558 | 3560 | 3563 | 3583 | 3597 | 3599 | 3611 | 3616 | 3618 |
| 3619 | 3625 | 3627 | 3630 | 3634 | 3635 | 3640 | 3654 | 3655 | 3658 | 3661 | 3694 |
| 3697 | 3699 | 3700 | 3702 | 3703 | 3714 | 3715 | 3722 | 3733 | 3735 | 3766 | 3770 |
| 3776 | 3783 | 3785 | 3788 | 3793 | 3798 | 3803 | 3808 | 3819 | 3836 | 3843 | 3850 |
| 3865 | 3867 | 3868 | 3872 | 3877 | 3878 | 3879 | 3885 | 3886 | 3907 | 3911 | 3912 |
| 3913 | 3915 | 3920 | 3924 | 3934 | 3938 | 3943 | 3954 | 3956 | 3957 | 3966 | 3970 |
| 3979 | 3982 | 3983 | 3990 | 3993 | 3998 | 4001 | 4002 | 4013 | 4015 | 4016 | 4018 |
| 4023 | 4030 | 4032 | 4041 | 4043 | 4044 | 4052 | 4057 | 4074 | 4075 | 4078 | 4080 |
| 4081 | 4083 | 4097 | 4098 | 4100 | 4106 | 4118 | 4121 | 4123 | 4127 | 4130 | 4140 |
| 4154 | 4161 | 4162 | 4168 | 4169 | 4176 | 4192 | 4200 | 4201 | 4209 | 4213 | 4217 |
| 4225 | 4233 | 4240 | 4250 | 4257 | 4270 | 4275 | 4297 | 4319 | 4322 | 4337 | 4350 |
| 4361 | 4368 | 4369 | 4370 | 4391 | 4397 | 4399 | 4413 | 4416 | 4421 | 4422 | 4432 |
| 4444 | 4447 | 4450 | 4459 | 4494 | 4508 | 4520 | 4521 | 4542 | 4544 | 4548 | 4600 |
| 4619 | 4663 | 4664 | 4670 | 4671 | 4675 | 4677 | 4687 | 4708 | 4726 | 4740 | 4751 |
| 4754 | 4761 | 4772 | 4792 | 4804 | 4807 | 4828 | 4833 | 4837 | 4845 | 4853 | 4854 |
| 4858 | 4860 | 4874 | 4881 | 4885 | 4895 | 4896 | 4897 | 4901 | 4904 | 4909 | 4910 |
| 4915 | 4955 | 4975 | 4976 | 4985 | 4989 | 5007 | 5008 | 5012 | 5015 | 5033 | 5035 |
| 5040 | 5045 | 5050 | 5062 | 5065 | 5067 | 5069 | 5070 | 5071 | 5072 | 5073 | 5074 |
| 5088 | 5093 | 5098 | 5103 | 5105 | 5116 | 5117 | 5118 | 5126 | 5134 | 5140 | 5153 |
| 5154 | 5155 | 5157 | 5165 | 5176 | 5177 | 5185 | 5198 | 5202 | 5204 | 5208 | 5213 |
| 5217 | 5225 | 5228 | 5230 | 5238 | 5239 | 5240 | 5241 | 5244 | 5245 | 5247 | 5248 |
| 5249 | 5250 | 5251 | 5252 | 5275 | 5277 | 5286 | 5296 | 5297 | 5300 | 5302 | 5306 |
| 5313 | 5314 | 5316 | 5317 | 5318 | 5321 | 5327 | 5332 | 5333 | 5335 | 5340 | 5343 |
| 5344 | 5346 | 5348 | 5349 | 5350 | 5351 | 5352 | 5353 | 5354 | 5355 | 5358 | 5361 |
| 5371 | 5373 | 5374 | 5376 | 5377 | 5382 | 5390 | 5397 | 5398 | 5408 | 5411 | 5419 |
| 5423 | 5426 | 5428 | 5436 | 5442 | 5446 | 5450 | 5451 | 5452 | 5458 | 5472 | 5473 |
| 5481 | 5486 | 5487 | 5510 | 5515 | 5518 | 5527 | 5535 | 5541 | 5542 | 5545 | 5546 |
| 5550 | 5551 | 5578 | 5583 | 5586 | 5587 | 5590 | 5595 | 5611 | 5621 | 5625 | 5626 |
| 5627 | 5638 | 5652 | 5657 | 5658 | 5659 | 5660 | 5665 | 5688 | 5695 | 5698 | 5699 |
| 5700 | 5709 | 5714 | 5716 | 5717 | 5725 | 5738 | 5749 | 5753 | 5756 | 5775 | 5777 |
| 5784 | 5785 | 5787 | 5789 | 5795 | 5799 | 5808 | 5809 | 5814 | 5823 | 5827 | 5829 |
| 5830 | 5834 | 5836 | 5850 | 5855 | 5857 | 5864 | 5865 | 5866 | 5871 | 5872 | 5873 |
| 5879 | 5903 | 5911 | 5912 | 5919 | 5947 | 5951 | 5965 | 5968 | 5978 | 5980 | 5991 |
| 5998 | 6000 | 6001 | 6007 | 6008 | 6011 | 6013 | 6016 | 6029 | 6036 | 6038 | 6041 |
| 6044 | 6045 | 6046 | 6068 | 6072 | 6073 | 6084 | 6085 | 6088 | 6089 | 6090 | 6095 |
| 6096 | 6098 | 6103 | 6115 | 6116 | 6122 | 6124 | 6126 | 6129 | 6130 | 6137 | 6138 |
| 6140 | 6142 | 6144 | 6148 | 6149 | 6160 | 6163 | 6168 | 6169 | 6196 | 6197 | 6198 |
| 6220 | 6221 | 6222 | 6223 | 6235 | 6253 | 6254 | 6256 | 6257 | 6258 | 6259 | 6260 |
| 6262 | 6263 | 6279 | 6280 | 6281 | 6283 | 6285 | 6286 | 6287 | 6299 | 6300 | 6310 |
| 6314 | 6319 | 6320 | 6329 | 6333 | 6334 | 6335 | 6336 | 6337 | 6341 | 6342 | 6343 |
| 6358 | 6359 | 6363 | 6368 | 6374 | 6376 | 6381 | 6384 | 6385 | 6386 | 6398 | 6399 |
| 6402 | 6403 | 6404 | 6405 | 6406 | 6412 | 6416 | 6417 | 6421 | 6427 | 6428 | 6430 |
| 6436 | 6442 | 6443 | 6446 | 6451 | 6452 | 6455 | 6456 | 6459 | 6463 | 6464 | 6476 |
| 6486 | 6490 | 6491 | 6506 | 6509 | 6510 | 6512 | 6514 | 6515 | 6517 | 6520 | 6521 |
| 6524 | 6526 | 6531 | 6532 | 6533 | 6534 | 6535 | 6536 | 6537 | 6538 | 6539 | 6543 |
| 6546 | 6548 | 6549 | 6560 | 6561 | 6580 | 6593 | 6595 | 6606 | 6609 | 6610 | 6611 |
| 6615 | 6619 | 6622 | 6623 | 6629 | 6634 | 6643 | 6645 | 6663 | 6664 | 6666 | 6670 |
| 6672 | 6673 | 6674 | 6675 | 6680 | 6681 | 6685 | 6701 | 6702 | 6703 | 6706 | 6716 |
| 6728 | 6734 | 6739 | 6741 | 6747 | 6771 | 6773 | 6776 | 6777 | 6778 | 6780 | 6795 |
| 6797 | 6798 | 6799 | 6802 | 6806 | 6807 | 6810 | 6826 | 6828 | 6836 | 6842 | 6849 |
| 6850 | 6851 | 6854 | 6855 | 6862 | 6869 | 6870 | 6879 | 6880 | 6885 | 6886 | 6890 |
| 6913 | 6927 | 6939 | 6945 | 6959 | 6960 | 6962 | 6970 | 6977 | 6981 | 6982 | 6985 |
| 6991 | 6992 | 7000 | 7002 | 7003 | 7004 | 7006 | 7009 | 7011 | 7024 | 7026 | 7053 |
| 7075 | 7078 | 7092 | 7105 | 7111 | 7115 | 7122 | 7123 | 7124 | 7146 | 7152 | 7154 |
| 7169 | 7172 | 7177 | 7179 | 7190 | 7203 | 7206 | 7210 | 7219 | 7253 | 7266 | 7279 |
| 7280 | 7300 | 7302 | 7357 | 7376 | 7422 | 7423 | 7429 | 7430 | 7434 | 7436 | 7446 |
| 7467 | 7485 | 7499 | 7510 | 7513 | 7520 | 7522 | 7532 | 7552 | 7563 | 7566 | 7587 |
| 7592 | 7597 | 7604 | 7612 | 7613 | 7617 | 7619 | 7634 | 7639 | 7643 | 7653 | 7654 |
| 7655 | 7659 | 7662 | 7667 | 7668 | 7673 | 7713 | 7740 | 7793 | 7798 | 7799 | 7813 |
| 7829 | 7831 | 7834 | 7836 | 7847 | 7855 | 7858 | 7862 | 7866 | 7867 | 7874 | 7894 |
| 7899 | 7908 | 7929 | 7932 | 7951 | 7959 | 7981 | 7986 | 7988 | 7992 | 8000 | 8016 |
| 8025 | 8039 | 8070 | 8074 | 8082 | 8091 | 8096 | 8106 | 8120 | 8138 | 8151 | 8152 |
| 8156 | 8177 | 8195 | 8205 | 8209 | 8219 | 8224 | 8225 | 8230 | 8240 | 8258 | 8259 |

TABLE 14-continued

Seed Protein Yield/Content

| | | | | | | | | | | | |
|---|---|---|---|---|---|---|---|---|---|---|---|
| 8289 | 8292 | 8308 | 8310 | 8311 | 8318 | 8334 | 8343 | 8346 | 8366 | 8375 | 8376 |
| 8381 | 8400 | 8418 | 8422 | 8434 | 8435 | 8445 | 8448 | 8453 | 8455 | 8462 | 8478 |
| 8491 | 8501 | 8503 | 8505 | 8506 | 8510 | 8511 | 8527 | 8535 | 8536 | 8537 | 8564 |
| 8575 | 8577 | 8578 | 8580 | 8585 | 8587 | 8592 | 8600 | 8615 | 8624 | 8640 | 8658 |
| 8660 | 8663 | 8665 | 8677 | 8695 | 8698 | 8699 | 8704 | 8705 | 8707 | 8716 | 8746 |
| 8747 | 8756 | 8791 | 8792 | 8805 | 8813 | 8815 | 8816 | 8837 | 8879 | 8897 | 8902 |
| 8907 | 8915 | 8922 | 8932 | 8946 | 8963 | 8972 | 8988 | 8997 | 9004 | 9006 | 9018 |
| 9030 | 9047 | 9064 | 9066 | 9083 | 9092 | 9093 | 9094 | 9103 | 9112 | 9124 | 9135 |
| 9140 | 9160 | 9161 | 9165 | 9166 | 9174 | 9189 | 9190 | 9191 | 9196 | 9203 | 9204 |
| 9205 | 9218 | 9230 | 9234 | 9248 | 9258 | 9268 | 9270 | 9282 | 9283 | 9286 | 9289 |
| 9290 | 9316 | 9323 | 9324 | 9328 | 9336 | 9343 | 9347 | 9350 | 9353 | 9357 | 9361 |
| 9374 | 9384 | 9416 | 9417 | 9427 | 9436 | 9438 | 9440 | 9445 | 9451 | 9459 | 9468 |
| 9489 | 9490 | 9493 | 9506 | 9507 | 9508 | 9512 | 9513 | 9522 | 9524 | 9525 | 9528 |
| 9529 | 9539 | 9546 | 9550 | 9551 | 9553 | 9580 | 9593 | 9616 | 9630 | 9645 | 9646 |
| 9654 | 9656 | 9684 | 9696 | 9700 | 9710 | 9717 | 9734 | 9744 | 9753 | 9761 | 9766 |
| 9773 | 9785 | 9794 | 9802 | 9803 | 9804 | 9805 | 9806 | 9822 | 9827 | 9832 | 9858 |
| 9881 | 9886 | 9925 | 9928 | 9942 | 9961 | 9966 | 9975 | 9981 | 9982 | 9983 | 10001 |
| 10024 | 10026 | 10027 | 10058 | 10088 | 10109 | 10110 | 10136 | 10150 | 10157 | 10159 | 10167 |
| 10169 | 10171 | 10172 | 10183 | 10187 | 10190 | 10238 | 10239 | 10240 | 10244 | 10252 | 10268 |
| 10293 | 10297 | 10306 | 10319 | 10333 | 10334 | 10341 | 10352 | 10366 | 10368 | 10372 | 10381 |
| 10382 | 10385 | 10398 | 10402 | 10404 | 10407 | 10413 | 10418 | 10426 | 10429 | 10440 | 10443 |
| 10446 | 10448 | 10467 | 10480 | 10511 | 10514 | 10521 | 10525 | 10545 | 10547 | 10563 | 10602 |
| 10604 | 10608 | 10610 | 10617 | 10623 | 10625 | 10632 | 10646 | 10666 | 10667 | 10669 | 10670 |
| 10676 | 10677 | 10687 | 10743 | 10745 | 10793 | 10797 | 10800 | 10802 | 10817 | 10825 | 10827 |
| 10845 | 10847 | 10854 | 10864 | 10866 | 10867 | 10871 | 10882 | 10894 | 10899 | 10905 | 10916 |
| 10922 | 10923 | 10924 | 10929 | 10930 | 10931 | 10938 | 10942 | 10953 | 10961 | 10966 | 10975 |
| 10979 | 10985 | 10992 | 11005 | 11008 | 11011 | 11013 | 11014 | 11025 | 11026 | 11027 | 11032 |
| 11038 | 11041 | 11047 | 11048 | 11093 | 11118 | 11119 | 11136 | 11143 | 11145 | 11146 | 11150 |
| 11154 | 11163 | 11167 | 11178 | 11185 | 11200 | 11213 | 11215 | 11222 | 11229 | 11277 | 11282 |
| 11313 | 11339 | 11340 | 11346 | 11347 | 11363 | 11364 | 11371 | 11378 | 11391 | 11393 | 11414 |
| 11438 | 11447 | 11449 | 11483 | 11498 | 11499 | 11502 | 11512 | 11536 | 11539 | 11548 |
| 11566 | 11577 | 11586 | 11587 | 11590 | 11593 | 11594 | 11597 | 11600 | 11602 | 11612 | 11623 |
| 11625 | 11629 | 11659 | 11663 | 11664 | 11669 | 11681 | 11682 | 11683 | 11691 | 11704 | 11710 |
| 11712 | 11714 | 11715 | 11725 | 11731 | 11732 | 11739 | 11748 | 11763 | 11772 | 11775 | 11783 |
| 11790 | 11795 | 11796 | 11818 | 11834 | 11839 | 11851 | 11854 | 11857 | 11885 | 11887 | 11890 |
| 11897 | 11920 | 11951 | 11973 | 11978 | 11982 | 11984 | 11986 | 11988 | 12006 | 12014 | 12023 |
| 12028 | 12029 | 12042 | 12057 | 12061 | 12062 | 12065 | 12073 | 12075 | 12081 | 12086 | 12149 |
| 12158 | 12177 | 12195 | 12196 | 12198 | 12201 | 12203 | 12234 | 12236 | 12272 | 12275 | 12282 |
| 12284 | 12291 | 12314 | 12316 | 12326 | 12332 | 12333 | 12347 | 12348 | 12349 | 12353 | 12358 |
| 12368 | 12373 | 12374 | 12376 | 12383 | 12386 | 12390 | 12393 | 12401 | 12408 | 12410 | 12422 |
| 12425 | 12427 | 12430 | 12436 | 12445 | 12446 | 12450 | 12451 | 12453 | 12454 | 12468 | 12471 |
| 12477 | 12483 | 12486 | 12488 | 12496 | 12500 | 12503 | 12509 | 12525 | 12530 | 12537 | 12539 |
| 12546 | 12556 | 12562 | 12563 | 12566 | 12572 | 12598 | 12600 | 12601 | 12602 | 12612 | 12613 |
| 12621 | 12623 | 12624 | 12635 | 12638 | 12643 | 12644 | 12650 | 12652 | 12653 | 12659 | 12666 |
| 12668 | 12672 | 12675 | 12678 | 12688 | 12689 | 12693 | 12700 | 12708 | 12713 | 12715 | 12717 |
| 12730 | 12742 | 12744 | 12750 | 12751 | 12757 | 12762 | 12778 | 12792 | 12793 | 12800 | 12802 |
| 12806 | 12808 | 12810 | 12827 | 12828 | 12829 | 12834 | 12838 | 12840 | 12846 | 12857 | 12869 |
| 12870 | 12883 | 12894 | 12902 | 12912 | 12916 | 12936 | 12938 | 12941 | 12947 | 12975 | 12976 |
| 12986 | 12990 | 12995 | 13004 | 13018 | 13020 | 13022 | 13028 | 13033 | 13040 | 13057 | 13059 |
| 13068 | 13070 | 13072 | 13075 | 13080 | 13090 | 13091 | 13092 | 13098 | 13102 | 13106 | 13108 |
| 13109 | 13124 | 13127 | 13128 | 13136 | 13139 | 13146 | 13152 | 13164 | 13167 | 13179 | 13180 |
| 13188 | 13190 | 13193 | 13195 | 13197 | 13199 | 13200 | 13203 | 13204 | 13212 | 13221 | 13225 |
| 13230 | 13233 | 13235 | 13239 | 13240 | 13242 | 13244 | 13247 | 13258 | 13259 | 13262 | 13276 |
| 13277 | 13286 | 13294 | 13295 | 13303 | 13304 | 13306 | 13307 | 13310 | 13319 | 13324 | 13325 |
| 13327 | 13328 | 13335 | 13338 | 13339 | 13340 | 13350 | 13351 | 13354 | 13357 | 13360 | 13365 |
| 13366 | 13371 | 13375 | 13387 | 13392 | 13393 | 13395 | 13397 | 13400 | 13406 | 13418 | 13421 |
| 13423 | 13429 | 13430 | 13432 | 13434 | 13435 | 13436 | 13441 | 13447 | 13465 | 13469 | 13470 |
| 13481 | 13488 | 13491 | 13497 | 13526 | 13540 | 13543 | 13546 | 13554 | 13558 | 13566 | 13573 |
| 13575 | 13578 | 13584 | 13601 | 13614 | 13621 | 13627 | 13652 | 13653 | 13659 | 13662 | 13666 |
| 13671 | 13688 | 13694 | 13703 | 13709 | 13711 | 13712 | 13722 | 13724 | 13738 | 13739 | 13744 |
| 13749 | 13750 | 13770 | 13781 | 13788 | 13795 | 13810 | 13811 | 13821 | 13872 | 13880 | 13888 |
| 13897 | 13899 | 13906 | 13913 | 13916 | 13946 | 13956 | 13962 | 13971 | 13972 | 13974 | 13980 |
| 13991 | 13994 | 13999 | 14009 | 14028 | 14029 | 14031 | 14037 | 14045 | 14046 | 14047 | 14054 |
| 14055 | 14063 | 14065 | 14066 | 14067 | 14091 | 14092 | 14127 | 14131 | 14145 | 14163 |
| 14183 | 14194 | 14200 | 14214 | 14223 | 14228 | 14241 | 14242 | 14246 | 14265 | 14270 | 14283 |
| 14293 | 14295 | 14301 | 14313 | 14323 | 14339 | 14341 | 14343 | 14350 | 14354 | 14358 | 14385 |
| 14386 | 14413 | 14415 | 14426 | 14431 | 14438 | 14449 | 14456 | 14458 | 14467 | 14472 | 14474 |
| 14481 | 14482 | 14492 | 14494 | 14501 | 14508 | 14513 | 14519 | 14522 | 14529 | 14533 | 14534 |
| 14536 | 14540 | 14542 | 14543 | 14547 | 14579 | 14581 | 14615 | 14629 | 14638 | 14644 | 14664 |
| 14669 | 14676 | 14696 | 14710 | 14720 | 14721 | 14747 | 14748 | 14769 | 14785 | 14786 | 14795 |
| 14797 | 14798 | 14799 | 14801 | 14810 | 14811 | 14816 | 14846 | 14847 | 14856 | 14857 | 14866 |
| 14867 | 14877 | 14884 | 14894 | 14905 | 14912 | 14913 | 14914 | 14918 | 14946 | 14949 | 14958 |
| 14962 | 14967 | 14970 | 14972 | 14973 | 14980 | 14983 | 14984 | 14986 | 15003 | 15037 | 15042 |
| 15045 | 15047 | 15052 | 15058 | 15060 | 15062 | 15069 | 15079 | 15081 | 15087 | 15092 | 15101 |
| 15103 | 15109 | 15115 | 15142 | 15149 | 15156 | 15177 | 15199 | 15200 | 15225 | 15247 | 15292 |
| 15294 | 15295 | 15301 | 15302 | 15310 | 15339 | 15345 | 15364 | 15365 | 15367 | 15386 | 15387 |
| 15389 | 15405 | 15409 | 15418 | 15428 | 15431 | 15433 | 15439 | 15440 | 15445 | 15446 | 15447 |

TABLE 14-continued

Seed Protein Yield/Content

| | | | | | | | | | | | |
|---|---|---|---|---|---|---|---|---|---|---|---|
| 15449 | 15450 | 15451 | 15452 | 15453 | 15462 | 15465 | 15473 | 15480 | 15484 | 15491 | 15499 |
| 15501 | 15502 | 15507 | 15508 | 15509 | 15510 | 15514 | 15517 | 15524 | 15539 | 15543 | 15557 |
| 15562 | 15569 | 15591 | 15592 | 15599 | 15600 | 15601 | 15605 | 15631 | 15642 | 15644 | 15647 |
| 15648 | 15649 | 15650 | 15651 | 15652 | 15654 | 15655 | 15656 | 15657 | 15659 | 15660 | 15661 |
| 15667 | 15668 | 15676 | 15706 | 15712 | 15731 | 15732 | 15734 | 15754 | 15755 | 15757 | 15773 |
| 15777 | 15786 | 15796 | 15800 | 15801 | 15807 | 15808 | 15809 | 15813 | 15814 | 15815 | 15817 |
| 15818 | 15819 | 15820 | 15821 | 15831 | 15834 | 15843 | 15850 | 15855 | 15870 | 15873 | 15874 |
| 15879 | 15880 | 15881 | 15882 | 15886 | 15889 | 15895 | 15910 | 15915 | 15930 | 15935 | 15942 |
| 15967 | 15968 | 15976 | 15977 | 15980 | 16006 | 16017 | 16019 | 16023 | 16024 | 16025 | 16026 |
| 16027 | 16028 | 16029 | 16030 | 16031 | 16033 | 16034 | 16035 | 16036 | 16037 | 16039 | 16041 |
| 16042 | 16045 | 16046 | 16047 | 16051 | 16052 | 16057 | 16058 | 16067 | 16096 | 16101 | 16116 |
| 16117 | 16118 | 16138 | 16140 | 16141 | 16156 | 16168 | 16178 | 16182 | 16183 | 16188 | 16189 |
| 16191 | 16195 | 16196 | 16197 | 16199 | 16200 | 16201 | 16202 | 16212 | 16216 | 16222 | 16228 |
| 16230 | 16237 | 16245 | 16248 | 16249 | 16252 | 16253 | 16254 | 16260 | 16261 | 16268 | 16286 |
| 16298 | 16303 | 16308 | 16329 | 16330 | 16333 | 16334 | 16340 | 16360 | 16370 | 16398 | 16405 |
| 16415 | 16422 | 16424 | 16426 | 16429 | 16433 | 16435 | 16443 | 16450 | 16452 | 16453 | 16455 |
| 16463 | 16479 | 16483 | 16496 | 16516 | 16527 | 16530 | 16534 | 16535 | 16546 | 16547 | 16549 |
| 16555 | 16578 | 16579 | 16606 | 16608 | 16615 | 16619 | 16622 | 16635 | 16636 | 16671 | 16684 |
| 16685 | 16686 | 16687 | 16707 | 16708 | 16719 | 16726 | 16736 | 16756 | 16775 | 16778 | 16784 |
| 16787 | 16794 | 16801 | 16815 | 16821 | 16827 | 16828 | 16832 | 16834 | 16842 | 16853 | 16860 |
| 16862 | 16866 | 16881 | 16886 | 16887 | 16920 | 16934 | 16943 | 16948 | 16953 | 16959 | 16962 |
| 16990 | 17035 | 17042 | 17054 | 17064 | 17066 | 17070 | 17081 | 17082 | 17100 | 17101 | 17112 |
| 17121 | 17123 | 17130 | 17151 | 17183 | 17203 | 17215 | 17216 | 17217 | 17218 | 17219 | 17220 |
| 17226 | 17232 | 17233 | 17236 | 17243 | 17246 | 17247 | 17248 | 17250 | 17276 | 17290 | 17291 |
| 17294 | 17297 | 17302 | 17304 | 17315 | 17316 | 17317 | 17318 | 17328 | 17335 | 17358 | 17386 |
| 17390 | 17410 | 17420 | 17421 | 17424 | 17425 | 17426 | 17431 | 17461 | 17463 | 17480 | 17491 |
| 17492 | 17514 | 17515 | 17516 | 17521 | 17526 | 17527 | 17540 | 17544 | 17545 | 17558 | 17562 |
| 17569 | 17576 | 17586 | 17589 | 17593 | 17596 | 17597 | 17598 | 17603 | 17622 | 17624 | 17627 |
| 17632 | 17633 | 17640 | 17652 | 17661 | 17665 | 17675 | 17682 | 17684 | 17685 | 17686 | 17698 |
| 17699 | 17708 | 17710 | 17724 | 17726 | 17763 | 17773 | 17782 | 17784 | 17797 | 17802 | 17809 |
| 17815 | 17816 | 17820 | 17826 | 17828 | 17833 | 17836 | 17856 | 17862 | 17863 | 17874 |
| 17875 | 17879 | 17880 | 17889 | 17894 | 17912 | 17915 | 17918 | 17919 | 17923 | 17925 | 17930 |
| 17937 | 17940 | 17945 | 17948 | 17949 | 17951 | 17953 | 17969 | 17971 | 17976 | 17981 | 17982 |
| 18001 | 18002 | 18010 | 18020 | 18030 | 18031 | 18035 | 18049 | 18058 | 18067 | 18070 | 18071 |
| 18073 | 18074 | 18075 | 18076 | 18077 | 18078 | 18079 | 18080 | 18089 | 18096 | 18121 | 18127 |
| 18134 | 18138 | 18142 | 18150 | 18154 | 18158 | 18162 | 18172 | 18174 | 18180 | 18183 | 18185 |
| 18186 | 18187 | 18191 | 18195 | 18200 | 18203 | 18219 | 18247 | 18250 | 18259 | 18260 | 18261 |
| 18270 | 18271 | 18272 | 18290 | 18296 | 18298 | 18306 | 18319 | 18327 | 18328 | 18329 | 18341 |
| 18348 | 18366 | 18375 | 18384 | 18391 | 18407 | 18417 | 18420 | 18424 | 18434 | 18443 | 18448 |
| 18454 | 18465 | 18466 | 18492 | 18494 | 18500 | 18502 | 18519 | 18540 | 18552 | 18562 | 18575 |
| 18582 | 18590 | 18606 | 18609 | 18610 | 18619 | 18626 | 18628 | 18629 | 18633 | 18641 | 18643 |
| 18665 | 18667 | 18674 | 18698 | 18700 | 18701 | 18703 | 18717 | 18719 | 18752 | 18758 | 18759 |
| 18771 | 18772 | 18773 | 18788 | 18794 | 18795 | 18796 | 18854 | 18881 | 18886 | 18892 |
| 18899 | 18913 | 18923 | 18935 | 18936 | 18946 | 18963 | 18985 | 18992 | 18993 | 18999 | 19024 |
| 19025 | 19045 | 19047 | 19052 | 19108 | 19109 | 19111 | 19132 | 19135 | 19137 | 19140 | 19141 |
| 19150 | 19151 | 19152 | 19153 | 19162 | 19170 | 19186 | 19191 | 19192 | 19195 | 19196 | 19207 |
| 19209 | 19210 | 19217 | 19237 | 19241 | 19254 | 19264 | 19266 | 19267 | 19270 | 19284 | 19287 |
| 19296 | 19297 | 19298 | 19299 | 19304 | 19306 | 19308 | 19318 | 19320 | 19321 | 19322 | 19323 |
| 19324 | 19335 | 19345 | 19347 | 19349 | 19353 | 19366 | 19374 | 19375 | 19381 | 19382 | 19387 |
| 19389 | 19390 | 19402 | 19403 | 19413 | 19430 | 19432 | 19434 | 19443 | 19452 | 19453 | 19459 |
| 19462 | 19467 | 19475 | 19490 | 19496 | 19515 | 19520 | 19532 | 19535 | 19537 | 19553 | 19568 |
| 19591 | 19596 | 19605 | 19607 | 19612 | 19613 | 19616 | 19618 | 19619 | 19622 | 19625 | 19626 |
| 19629 | 19648 | 19656 | 19660 | 19679 | 19696 | 19703 | 19707 | 19710 | 19725 | 19734 | 19736 |
| 19758 | 19761 | 19762 | 19763 | 19772 | 19779 | 19780 | 19786 | 19789 | 19790 | 19791 | 19795 |
| 19831 | 19852 | 19878 | 19887 | 19915 | 19920 | 19922 | 19923 | 19939 | 19989 | 20013 | 20033 |
| 20036 | 20039 | 20047 | 20068 | 20069 | 20085 | 20086 | 20087 | 20106 | 20114 | 20115 | 20117 |
| 20125 | 20139 | 20171 | 20182 | 20192 | 20211 | 20216 | 20217 | 20221 | 20232 | 20263 | 20264 |
| 20273 | 20274 | 20291 | 20294 | 20320 | 20331 | 20333 | 20341 | 20342 | 20343 | 20344 | 20357 |
| 20365 | 20366 | 20376 | 20397 | 20426 | 20441 | 20458 | 20475 | 20488 | 20516 | 20517 | 20521 |
| 20531 | 20561 | 20563 | 20565 | 20569 | 20589 | 20601 | 20607 | 20627 | 20642 | 20643 | 20645 |
| 20653 | 20654 | 20672 | 20676 | 20679 | 20681 | 20683 | 20689 | 20695 | 20696 | 20698 | 20699 |
| 20700 | 20724 | 20732 | 20740 | 20741 | 20751 | 20772 | 20777 | 20783 | 20785 | 20787 | 20797 |
| 20812 | 20819 | 20828 | 20842 | 20872 | 20888 | 20890 | 20893 | 20896 | 20901 | 20906 | 20910 |
| 20911 | 20918 | 20921 | 20935 | 20938 | 20942 | 20947 | 20953 | 20957 | 20988 | 21000 | 21005 |
| 21027 | 21028 | 21029 | 21051 | 21052 | 21061 | 21068 | 21076 | 21082 | 21090 | 21093 | 21098 |
| 21121 | 21144 | 21148 | 21157 | 21173 | 21181 | 21182 | 21184 | 21192 | 21195 | 21201 | 21207 |
| 21212 | 21215 | 21218 | 21220 | 21222 | 21223 | 21230 | 21235 | 21241 | 21261 | 21268 | 21274 |
| 21278 | 21286 | 21288 | 21292 | 21294 | 21310 | 21325 | 21326 | 21329 | 21331 | 21332 | 21338 |
| 21347 | 21351 | 21362 | 21372 | 21394 | 21395 | 21398 | 21399 | 21406 | 21420 | 21422 | 21434 |
| 21444 | 21450 | 21461 | 21474 | 21475 | 21492 | 21528 | 21547 | 21549 | 21561 | 21579 | 21587 |
| 21600 | 21608 | 21613 | 21614 | 21615 | 21619 | 21625 | 21626 | 21627 | 21631 | 21632 | 21640 |
| 21641 | 21648 | 21660 | 21737 | 21744 | 21775 | 21785 | 21787 | 21798 | 21804 | 21807 | 21817 |
| 21821 | 21823 | 21825 | 21826 | 21834 | 21843 | 21846 | 21847 | 21852 | 21855 | 21873 | 21879 |
| 21880 | 21881 | 21886 | 21891 | 21892 | 21894 | 21898 | 21909 | 21914 | 21925 | 21929 | 21930 |
| 21943 | 21951 | 21961 | 21968 | 21975 | 21982 | 21991 | 21994 | 22000 | 22003 | 22012 | 22014 |
| 22020 | 22026 | 22028 | 22029 | 22034 | 22037 | 22046 | 22047 | 22048 | 22051 | 22055 | 22064 |
| 22066 | 22072 | 22077 | 22078 | 22086 | 22088 | 22089 | 22091 | 22111 | 22113 | 22116 | 22119 |

TABLE 14-continued

Seed Protein Yield/Content

| | | | | | | | | | | | |
|---|---|---|---|---|---|---|---|---|---|---|---|
| 22123 | 22125 | 22127 | 22131 | 22137 | 22146 | 22152 | 22176 | 22181 | 22196 | 22200 | 22202 |
| 22206 | 22207 | 22208 | 22210 | 22220 | 22221 | 22229 | 22233 | 22236 | 22240 | 22267 | 22275 |
| 22277 | 22282 | 22287 | 22290 | 22296 | 22297 | 22313 | 22322 | 22323 | 22328 | 22332 | 22338 |
| 22340 | 22345 | 22368 | 22371 | 22374 | 22376 | 22381 | 22397 | 22398 | 22404 | 22406 | 22407 |
| 22408 | 22417 | 22431 | 22433 | 22436 | 22442 | 22447 | 22470 | 22472 | 22493 | 22504 | 22510 |
| 22512 | 22522 | 22527 | 22532 | 22533 | 22539 | 22545 | 22546 | 22555 | 22560 | 22563 | 22571 |
| 22574 | 22590 | 22594 | 22599 | 22602 | 22603 | 22606 | 22619 | 22630 | 22631 | 22642 | 22644 |
| 22645 | 22646 | 22657 | 22658 | 22678 | 22681 | 22682 | 22688 | 22689 | 22710 | 22720 | 22724 |
| 22729 | 22738 | 22753 | 22754 | 22755 | 22759 | 22765 | 22769 | 22775 | 22782 | 22791 | 22792 |
| 22793 | 22797 | 22803 | 22805 | 22816 | 22848 | 22868 | 22871 | 22876 | 22877 | 22880 | 22881 |
| 22883 | 22894 | 22897 | 22904 | 22920 | 22936 | 22938 | 22941 | 22966 | 22972 | 22973 | 22988 |
| 22989 | 23012 | 23018 | 23020 | 23021 | 23036 | 23043 | 23049 | 23050 | 23057 | 23058 | 23059 |
| 23063 | 23064 | 23066 | 23068 | 23072 | 23078 | 23087 | 23091 | 23097 | 23099 | 23106 | 23118 |
| 23119 | 23120 | 23129 | 23130 | 23131 | 23132 | 23148 | 23165 | 23173 | 23180 | 23185 | 23197 |
| 23201 | 23213 | 23215 | 23224 | 23228 | 23258 | 23259 | 23278 | 23280 | 23290 | 23304 | 23305 |
| 23324 | 23348 | 23367 | 23371 | 23382 | 23385 | 23406 | 23410 | 23416 | 23430 | 23431 | 23438 |
| 23439 | 23440 | 23451 | 23460 | 23463 | 23481 | 23496 | 23499 | 23504 | 23508 | 23513 | 23521 |
| 23522 | 23529 | 23533 | 23535 | 23536 | 23544 | 23551 | 23552 | 23556 | 23562 | 23567 | 23568 |
| 23570 | 23576 | 23583 | 23589 | 23593 | 23595 | 23621 | 23624 | 23628 | 23633 | 23641 | 23642 |
| 23654 | 23656 | 23659 | 23661 | 23670 | 23671 | 23679 | 23683 | 23684 | | | |

Table 14B SEQ ID NOs of Polynucleotides useful for improving Seed Protein Yield/Content

| | | | | | | | | | | | |
|---|---|---|---|---|---|---|---|---|---|---|---|
| 23695 | 23707 | 23739 | 23742 | 23750 | 23753 | 23754 | 23766 | 23767 | 23772 | 23774 | 23775 |
| 23778 | 23785 | 23787 | 23789 | 23813 | 23816 | 23827 | 23828 | 23829 | 23830 | 23844 | 23855 |
| 23863 | 23876 | 23878 | 23880 | 23908 | 23914 | 23926 | 23929 | 23932 | 23951 | 23960 | 23969 |
| 23985 | 23991 | 23995 | 23996 | 23999 | 24002 | 24007 | 24017 | 24021 | 24024 | 24029 | 24034 |
| 24035 | 24038 | 24044 | 24048 | 24052 | 24054 | 24060 | 24070 | 24084 | 24093 | 24101 | 24106 |
| 24117 | 24132 | 24139 | 24150 | 24162 | 24163 | 24167 | 24175 | 24187 | 24190 | 24196 | 24203 |
| 24206 | 24229 | 24232 | 24242 | 24243 | 24245 | 24246 | 24253 | 24265 | 24271 | 24279 | 24298 |
| 24308 | 24310 | 24318 | 24320 | 24332 | 24334 | 24344 | 24362 | 24364 | 24373 | 24377 | 24382 |
| 24387 | 24401 | 24403 | 24416 | 24419 | 24421 | 24432 | 24440 | 24445 | 24464 | 24506 | 24513 |
| 24525 | 24540 | 24548 | 24585 | 24592 | 24622 | 24623 | 24630 | 24635 | 24642 | 24643 | 24644 |
| 24665 | 24668 | 24672 | 24685 | 24686 | 24687 | 24688 | 24699 | 24704 | 24715 | 24716 | 24728 |
| 24732 | 24735 | 24737 | 24741 | 24747 | 24771 | 24777 | 24788 | 24824 | 24832 | 24833 | 24844 |
| 24848 | 24856 | 24857 | 24858 | 24859 | 24882 | 24892 | 24895 | 24903 | 24904 | 24940 | 24952 |
| 24954 | 24962 | 24963 | 24964 | 24965 | 24978 | 24986 | 24987 | 24998 | 25020 | 25045 | 25080 |
| 25098 | 25104 | 25105 | 25106 | 25108 | 25110 | 25114 | 25128 | 25130 | 25131 | 25134 | 25137 |
| 25145 | 25146 | 25152 | 25156 | 25169 | 25182 | 25184 | 25191 | 25193 | 25195 | 25200 | 25225 |
| 25230 | 25236 | 25252 | 25258 | 25260 | 25261 | 25286 | 25288 | 25303 | 25310 | 25323 | 25326 |
| 25330 | 25332 | 25352 | 25366 | 25367 | 25368 | 25372 | 25376 | 25378 | 25385 | 25386 | 25388 |
| 25391 | 25393 | 25394 | 25408 | 25412 | 25417 | 25419 | 25426 | 25428 | 25429 | 25438 | 25440 |
| 25441 | 25443 | 25446 | 25456 | 25459 | 25470 | 25472 | 25492 | 25502 | 25503 | 25513 | 25514 |
| 25528 | 25533 | 25554 | 25559 | 25563 | 25567 | 25579 | 25580 | 25582 | 25585 | 25586 | 25597 |
| 25603 | 25613 | 25616 | 25618 | 25623 | 25633 | 25634 | 25640 | 25647 | 25649 | 25674 | 25681 |
| 25693 | 25695 | 25701 | 25706 | 25715 | 25738 | 25744 | 25746 | 25754 | 25758 | 25766 | 25769 |
| 25770 | 25773 | 25776 | 25782 | 25804 | 25813 | 25818 | 25827 | 25833 | 25839 | 25852 | 25869 |
| 25871 | 25890 | 25894 | 25913 | 25917 | 25920 | 25930 | 25931 | 25936 | 25949 | 25952 | 25956 |
| 25966 | 25973 | 25981 | 25988 | 25993 | 25995 | 26001 | 26003 | 26007 | 26009 | 26020 | 26027 |
| 26032 | 26039 | 26045 | 26056 | 26060 | 26061 | 26071 | 26074 | 26079 | 26089 | 26093 | 26101 |
| 26109 | 26128 | 26142 | 26144 | 26148 | 26151 | 26163 | 26167 | 26168 | 26169 | 26170 | 26190 |
| 26191 | 26204 | 26205 | 26218 | 26223 | 26225 | 26240 | 26241 | 26253 | 26256 | 26257 | 26262 |
| 26267 | 26276 | 26284 | 26289 | 26292 | 26295 | 26306 | 26309 | 26319 | 26323 | 26325 | 26340 |
| 26370 | 26389 | 26434 | 26437 | 26444 | 26449 | 26456 | 26457 | 26472 | 26478 | 26485 | 26493 |
| 26498 | 26540 | 26544 | 26545 | 26546 | 26549 | 26552 | 26553 | 26563 | 26565 | 26585 | 26589 |
| 26640 | 26645 | 26652 | 26665 | 26702 | 26704 | 26713 | 26722 | 26723 | 26724 | 26725 | 26726 |
| 26727 | 26732 | 26737 | 26739 | 26757 | 26761 | 26775 | 26783 | 26787 | 26792 | 26797 | 26800 |
| 26807 | 26808 | 26809 | 26811 | 26812 | 26813 | 26816 | 26837 | 26841 | 26843 | 26844 | 26853 |
| 26860 | 26862 | 26869 | 26872 | 26873 | 26875 | 26886 | 26903 | 26904 | 26906 | 26913 | 26918 |
| 26922 | 26925 | 26927 | 26931 | 26937 | 26944 | 26953 | 26960 | 26964 | 26971 | 26975 | 26977 |
| 26985 | 26994 | 26996 | 26998 | 27002 | 27011 | 27014 | 27017 | 27026 | 27031 | 27037 | 27040 |
| 27042 | 27047 | 27052 | 27066 | 27068 | 27073 | 27076 | 27079 | 27080 | 27081 | 27091 | 27097 |
| 27108 | 27109 | 27113 | 27114 | 27115 | 27117 | 27118 | 27123 | 27127 | 27132 | 27138 | 27140 |
| 27142 | 27148 | 27153 | 27158 | 27175 | 27176 | 27182 | 27188 | 27201 | 27207 | 27214 | 27215 |
| 27216 | 27229 | 27230 | 27245 | 27247 | 27250 | 27270 | 27284 | 27286 | 27298 | 27303 | 27305 |
| 27306 | 27312 | 27314 | 27317 | 27321 | 27322 | 27327 | 27341 | 27342 | 27345 | 27348 | 27381 |
| 27384 | 27386 | 27387 | 27389 | 27390 | 27401 | 27402 | 27409 | 27420 | 27422 | 27453 | 27457 |
| 27463 | 27470 | 27472 | 27475 | 27480 | 27485 | 27490 | 27495 | 27506 | 27523 | 27530 | 27537 |
| 27552 | 27554 | 27555 | 27559 | 27564 | 27565 | 27566 | 27572 | 27573 | 27594 | 27598 | 27599 |
| 27600 | 27602 | 27607 | 27611 | 27621 | 27625 | 27630 | 27641 | 27643 | 27644 | 27653 | 27657 |
| 27666 | 27669 | 27670 | 27677 | 27680 | 27685 | 27688 | 27689 | 27700 | 27702 | 27703 | 27705 |
| 27710 | 27717 | 27719 | 27728 | 27730 | 27731 | 27739 | 27744 | 27761 | 27762 | 27765 | 27767 |
| 27768 | 27770 | 27784 | 27785 | 27787 | 27793 | 27805 | 27808 | 27810 | 27814 | 27817 | 27827 |
| 27841 | 27848 | 27849 | 27855 | 27856 | 27863 | 27879 | 27887 | 27888 | 27896 | 27900 | 27904 |
| 27912 | 27920 | 27927 | 27937 | 27944 | 27957 | 27962 | 27984 | 28006 | 28009 | 28024 | 28037 |
| 28048 | 28055 | 28056 | 28057 | 28078 | 28084 | 28086 | 28100 | 28103 | 28108 | 28109 | 28119 |
| 28131 | 28134 | 28137 | 28146 | 28181 | 28195 | 28207 | 28208 | 28229 | 28231 | 28235 | 28287 |
| 28306 | 28350 | 28351 | 28357 | 28358 | 28362 | 28364 | 28374 | 28395 | 28413 | 28427 | 28438 |

TABLE 14-continued

Seed Protein Yield/Content

| | | | | | | | | | | | |
|---|---|---|---|---|---|---|---|---|---|---|---|
| 28441 | 28448 | 28459 | 28479 | 28491 | 28494 | 28515 | 28520 | 28524 | 28532 | 28540 | 28541 |
| 28545 | 28547 | 28561 | 28568 | 28572 | 28582 | 28583 | 28584 | 28588 | 28591 | 28596 | 28597 |
| 28602 | 28642 | 28662 | 28663 | 28672 | 28676 | 28694 | 28695 | 28699 | 28702 | 28720 | 28722 |
| 28727 | 28732 | 28737 | 28749 | 28752 | 28754 | 28756 | 28757 | 28758 | 28759 | 28760 | 28761 |
| 28775 | 28780 | 28785 | 28790 | 28792 | 28803 | 28804 | 28805 | 28813 | 28821 | 28827 | 28840 |
| 28841 | 28842 | 28844 | 28852 | 28863 | 28864 | 28872 | 28885 | 28889 | 28891 | 28895 | 28900 |
| 28904 | 28912 | 28915 | 28917 | 28925 | 28926 | 28927 | 28928 | 28931 | 28932 | 28934 | 28935 |
| 28936 | 28937 | 28938 | 28939 | 28962 | 28964 | 28973 | 28983 | 28984 | 28987 | 28989 | 28993 |
| 29000 | 29001 | 29003 | 29004 | 29005 | 29008 | 29014 | 29019 | 29020 | 29022 | 29027 | 29030 |
| 29031 | 29033 | 29035 | 29036 | 29037 | 29038 | 29039 | 29040 | 29041 | 29042 | 29045 | 29048 |
| 29058 | 29060 | 29061 | 29063 | 29064 | 29069 | 29077 | 29084 | 29085 | 29095 | 29098 | 29106 |
| 29110 | 29113 | 29115 | 29123 | 29129 | 29133 | 29137 | 29138 | 29139 | 29145 | 29159 | 29160 |
| 29168 | 29173 | 29174 | 29197 | 29202 | 29205 | 29214 | 29222 | 29228 | 29229 | 29232 | 29233 |
| 29237 | 29238 | 29265 | 29270 | 29273 | 29274 | 29277 | 29282 | 29298 | 29308 | 29312 | 29313 |
| 29314 | 29325 | 29339 | 29344 | 29345 | 29346 | 29347 | 29352 | 29375 | 29382 | 29385 | 29386 |
| 29387 | 29396 | 29401 | 29403 | 29404 | 29412 | 29425 | 29436 | 29440 | 29443 | 29462 | 29464 |
| 29471 | 29472 | 29474 | 29476 | 29482 | 29486 | 29495 | 29496 | 29501 | 29510 | 29514 | 29516 |
| 29517 | 29521 | 29523 | 29537 | 29542 | 29544 | 29551 | 29552 | 29553 | 29558 | 29559 | 29560 |
| 29566 | 29590 | 29598 | 29599 | 29606 | 29634 | 29638 | 29652 | 29655 | 29665 | 29667 | 29678 |
| 29685 | 29687 | 29688 | 29694 | 29695 | 29698 | 29700 | 29703 | 29716 | 29723 | 29725 | 29728 |
| 29731 | 29732 | 29733 | 29755 | 29759 | 29760 | 29771 | 29772 | 29775 | 29776 | 29777 | 29782 |
| 29783 | 29785 | 29790 | 29802 | 29803 | 29809 | 29811 | 29813 | 29816 | 29817 | 29824 | 29825 |
| 29827 | 29829 | 29831 | 29835 | 29836 | 29847 | 29850 | 29855 | 29856 | 29883 | 29884 | 29885 |
| 29907 | 29908 | 29909 | 29910 | 29922 | 29940 | 29941 | 29943 | 29944 | 29945 | 29946 | 29947 |
| 29949 | 29950 | 29966 | 29967 | 29968 | 29970 | 29972 | 29973 | 29974 | 29986 | 29987 | 29997 |
| 30001 | 30006 | 30007 | 30016 | 30020 | 30021 | 30022 | 30023 | 30024 | 30028 | 30029 | 30030 |
| 30045 | 30046 | 30050 | 30055 | 30061 | 30063 | 30068 | 30071 | 30072 | 30073 | 30085 | 30086 |
| 30089 | 30090 | 30091 | 30092 | 30093 | 30099 | 30103 | 30104 | 30108 | 30114 | 30115 | 30117 |
| 30123 | 30129 | 30130 | 30133 | 30138 | 30139 | 30142 | 30143 | 30146 | 30150 | 30151 | 30163 |
| 30173 | 30177 | 30178 | 30193 | 30196 | 30197 | 30199 | 30201 | 30202 | 30204 | 30207 | 30208 |
| 30211 | 30213 | 30218 | 30219 | 30220 | 30221 | 30222 | 30223 | 30224 | 30225 | 30226 | 30230 |
| 30233 | 30235 | 30236 | 30247 | 30248 | 30267 | 30280 | 30282 | 30293 | 30296 | 30297 | 30298 |
| 30302 | 30306 | 30309 | 30310 | 30316 | 30321 | 30330 | 30332 | 30350 | 30351 | 30353 | 30357 |
| 30359 | 30360 | 30361 | 30362 | 30367 | 30368 | 30372 | 30388 | 30389 | 30390 | 30393 | 30403 |
| 30415 | 30421 | 30426 | 30428 | 30434 | 30458 | 30460 | 30463 | 30464 | 30465 | 30467 | 30482 |
| 30484 | 30485 | 30486 | 30489 | 30493 | 30494 | 30497 | 30513 | 30515 | 30523 | 30529 | 30536 |
| 30537 | 30538 | 30541 | 30542 | 30549 | 30556 | 30557 | 30566 | 30567 | 30572 | 30573 | 30577 |
| 30600 | 30614 | 30626 | 30632 | 30646 | 30647 | 30649 | 30657 | 30664 | 30668 | 30669 | 30672 |
| 30678 | 30679 | 30687 | 30689 | 30690 | 30691 | 30693 | 30696 | 30698 | 30711 | 30713 | 30740 |
| 30762 | 30765 | 30779 | 30792 | 30798 | 30802 | 30809 | 30810 | 30811 | 30833 | 30839 | 30841 |
| 30856 | 30859 | 30864 | 30866 | 30877 | 30890 | 30893 | 30897 | 30906 | 30940 | 30953 | 30966 |
| 30967 | 30987 | 30989 | 31044 | 31063 | 31109 | 31110 | 31116 | 31117 | 31121 | 31123 | 31133 |
| 31154 | 31172 | 31186 | 31197 | 31200 | 31207 | 31209 | 31219 | 31239 | 31250 | 31253 | 31274 |
| 31279 | 31284 | 31291 | 31299 | 31300 | 31304 | 31306 | 31321 | 31326 | 31330 | 31340 | 31341 |
| 31342 | 31346 | 31349 | 31354 | 31355 | 31360 | 31400 | 31427 | 31480 | 31485 | 31486 | 31500 |
| 31516 | 31518 | 31521 | 31523 | 31534 | 31542 | 31545 | 31549 | 31553 | 31554 | 31561 | 31581 |
| 31586 | 31595 | 31616 | 31619 | 31638 | 31646 | 31668 | 31673 | 31675 | 31679 | 31687 | 31703 |
| 31712 | 31726 | 31757 | 31761 | 31769 | 31778 | 31783 | 31793 | 31807 | 31825 | 31838 | 31839 |
| 31843 | 31864 | 31882 | 31892 | 31896 | 31906 | 31911 | 31912 | 31917 | 31927 | 31945 | 31946 |
| 31976 | 31979 | 31995 | 31997 | 31998 | 32005 | 32021 | 32030 | 32033 | 32053 | 32062 | 32063 |
| 32068 | 32087 | 32105 | 32109 | 32121 | 32122 | 32132 | 32135 | 32140 | 32142 | 32149 | 32165 |
| 32178 | 32188 | 32190 | 32192 | 32193 | 32197 | 32198 | 32214 | 32222 | 32223 | 32224 | 32251 |
| 32262 | 32264 | 32265 | 32267 | 32272 | 32274 | 32279 | 32287 | 32302 | 32311 | 32327 | 32345 |
| 32347 | 32350 | 32352 | 32364 | 32382 | 32385 | 32386 | 32391 | 32392 | 32394 | 32403 | 32433 |
| 32434 | 32443 | 32478 | 32479 | 32492 | 32500 | 32502 | 32503 | 32524 | 32566 | 32584 | 32589 |
| 32594 | 32602 | 32609 | 32619 | 32633 | 32650 | 32659 | 32675 | 32684 | 32691 | 32693 | 32705 |
| 32717 | 32734 | 32751 | 32753 | 32770 | 32779 | 32780 | 32781 | 32790 | 32799 | 32811 | 32822 |
| 32827 | 32847 | 32848 | 32852 | 32853 | 32861 | 32876 | 32877 | 32878 | 32883 | 32890 | 32891 |
| 32892 | 32905 | 32917 | 32921 | 32935 | 32945 | 32955 | 32957 | 32969 | 32970 | 32973 | 32976 |
| 32977 | 33003 | 33010 | 33011 | 33015 | 33023 | 33030 | 33034 | 33037 | 33040 | 33044 | 33048 |
| 33061 | 33071 | 33103 | 33104 | 33114 | 33123 | 33125 | 33127 | 33132 | 33138 | 33146 | 33155 |
| 33176 | 33177 | 33180 | 33193 | 33194 | 33195 | 33199 | 33200 | 33209 | 33211 | 33212 | 33215 |
| 33216 | 33226 | 33233 | 33237 | 33238 | 33240 | 33267 | 33280 | 33303 | 33317 | 33332 | 33333 |
| 33341 | 33343 | 33371 | 33383 | 33387 | 33397 | 33404 | 33421 | 33440 | 33448 | 33453 |
| 33460 | 33472 | 33481 | 33489 | 33490 | 33491 | 33492 | 33493 | 33509 | 33514 | 33519 | 33545 |
| 33568 | 33573 | 33612 | 33615 | 33629 | 33648 | 33653 | 33662 | 33668 | 33669 | 33670 | 33688 |
| 33711 | 33713 | 33714 | 33745 | 33775 | 33796 | 33797 | 33823 | 33837 | 33844 | 33846 | 33854 |
| 33856 | 33858 | 33859 | 33870 | 33874 | 33877 | 33925 | 33926 | 33931 | 33939 | 33955 |
| 33980 | 33984 | 33993 | 34006 | 34020 | 34021 | 34028 | 34039 | 34053 | 34055 | 34059 | 34068 |
| 34069 | 34072 | 34085 | 34089 | 34091 | 34094 | 34100 | 34105 | 34113 | 34116 | 34127 | 34130 |
| 34133 | 34135 | 34154 | 34167 | 34198 | 34201 | 34208 | 34212 | 34232 | 34234 | 34250 | 34289 |
| 34291 | 34295 | 34297 | 34304 | 34310 | 34312 | 34319 | 34333 | 34353 | 34354 | 34356 | 34357 |
| 34363 | 34364 | 34374 | 34430 | 34432 | 34480 | 34484 | 34487 | 34489 | 34504 | 34512 | 34514 |
| 34532 | 34534 | 34541 | 34551 | 34553 | 34554 | 34558 | 34569 | 34581 | 34586 | 34592 | 34603 |
| 34609 | 34610 | 34611 | 34616 | 34617 | 34618 | 34625 | 34629 | 34640 | 34648 | 34653 | 34662 |
| 34666 | 34672 | 34679 | 34692 | 34695 | 34698 | 34700 | 34701 | 34712 | 34713 | 34714 | 34719 |
| 34725 | 34728 | 34734 | 34735 | 34780 | 34805 | 34806 | 34823 | 34830 | 34832 | 34833 | 34837 |

TABLE 14-continued

Seed Protein Yield/Content

| | | | | | | | | | | | |
|---|---|---|---|---|---|---|---|---|---|---|---|
| 34841 | 34850 | 34854 | 34865 | 34872 | 34887 | 34900 | 34902 | 34909 | 34916 | 34964 | 34969 |
| 35000 | 35026 | 35027 | 35033 | 35034 | 35050 | 35051 | 35058 | 35065 | 35078 | 35080 | 35101 |
| 35125 | 35134 | 35136 | 35170 | 35185 | 35186 | 35189 | 35193 | 35199 | 35223 | 35226 | 35235 |
| 35253 | 35264 | 35273 | 35274 | 35277 | 35280 | 35281 | 35284 | 35287 | 35289 | 35299 | 35310 |
| 35312 | 35316 | 35346 | 35350 | 35351 | 35356 | 35368 | 35369 | 35370 | 35378 | 35391 | 35397 |
| 35399 | 35401 | 35402 | 35412 | 35418 | 35419 | 35426 | 35435 | 35450 | 35459 | 35462 | 35470 |
| 35477 | 35482 | 35483 | 35505 | 35521 | 35526 | 35538 | 35541 | 35544 | 35572 | 35574 | 35577 |
| 35584 | 35607 | 35638 | 35660 | 35665 | 35669 | 35671 | 35673 | 35675 | 35693 | 35701 | 35710 |
| 35715 | 35716 | 35729 | 35744 | 35748 | 35749 | 35752 | 35760 | 35762 | 35768 | 35773 | 35836 |
| 35845 | 35864 | 35882 | 35883 | 35885 | 35888 | 35890 | 35921 | 35923 | 35959 | 35962 | 35969 |
| 35971 | 35978 | 36001 | 36003 | 36013 | 36019 | 36020 | 36034 | 36035 | 36036 | 36040 | 36045 |
| 36055 | 36060 | 36061 | 36063 | 36070 | 36073 | 36077 | 36080 | 36088 | 36095 | 36097 | 36109 |
| 36112 | 36114 | 36117 | 36123 | 36132 | 36133 | 36137 | 36138 | 36140 | 36141 | 36155 | 36158 |
| 36164 | 36170 | 36173 | 36175 | 36183 | 36187 | 36190 | 36196 | 36212 | 36217 | 36224 | 36226 |
| 36233 | 36243 | 36249 | 36250 | 36253 | 36259 | 36285 | 36287 | 36288 | 36289 | 36299 | 36300 |
| 36308 | 36310 | 36311 | 36322 | 36325 | 36330 | 36331 | 36337 | 36339 | 36340 | 36346 | 36353 |
| 36355 | 36359 | 36362 | 36365 | 36375 | 36376 | 36380 | 36387 | 36395 | 36400 | 36402 | 36404 |
| 36417 | 36429 | 36431 | 36437 | 36438 | 36444 | 36449 | 36465 | 36479 | 36480 | 36487 | 36489 |
| 36493 | 36495 | 36497 | 36514 | 36515 | 36516 | 36521 | 36525 | 36527 | 36533 | 36544 | 36556 |
| 36557 | 36570 | 36581 | 36589 | 36599 | 36603 | 36623 | 36625 | 36628 | 36634 | 36662 | 36663 |
| 36673 | 36677 | 36682 | 36691 | 36705 | 36707 | 36709 | 36715 | 36720 | 36727 | 36744 | 36746 |
| 36755 | 36757 | 36759 | 36762 | 36767 | 36777 | 36778 | 36779 | 36785 | 36789 | 36793 | 36795 |
| 36796 | 36811 | 36814 | 36815 | 36823 | 36826 | 36833 | 36839 | 36851 | 36854 | 36866 | 36867 |
| 36875 | 36877 | 36880 | 36882 | 36884 | 36886 | 36887 | 36890 | 36891 | 36899 | 36908 | 36912 |
| 36917 | 36920 | 36922 | 36926 | 36927 | 36929 | 36931 | 36934 | 36945 | 36946 | 36949 | 36963 |
| 36964 | 36973 | 36981 | 36982 | 36990 | 36991 | 36993 | 36994 | 36997 | 37006 | 37011 | 37012 |
| 37014 | 37015 | 37022 | 37025 | 37026 | 37027 | 37037 | 37038 | 37041 | 37044 | 37047 | 37052 |
| 37053 | 37058 | 37062 | 37074 | 37079 | 37080 | 37082 | 37084 | 37087 | 37093 | 37105 | 37108 |
| 37110 | 37116 | 37117 | 37119 | 37121 | 37122 | 37123 | 37128 | 37134 | 37152 | 37156 | 37157 |
| 37168 | 37175 | 37178 | 37184 | 37213 | 37227 | 37230 | 37233 | 37241 | 37245 | 37253 | 37260 |
| 37262 | 37265 | 37271 | 37288 | 37301 | 37308 | 37314 | 37339 | 37340 | 37346 | 37349 | 37353 |
| 37358 | 37375 | 37381 | 37390 | 37396 | 37398 | 37399 | 37409 | 37411 | 37425 | 37426 | 37431 |
| 37436 | 37437 | 37457 | 37468 | 37475 | 37482 | 37497 | 37498 | 37508 | 37559 | 37567 | 37575 |
| 37584 | 37586 | 37593 | 37600 | 37603 | 37633 | 37643 | 37649 | 37658 | 37659 | 37661 | 37667 |
| 37678 | 37681 | 37686 | 37696 | 37715 | 37716 | 37718 | 37724 | 37733 | 37734 | 37741 |
| 37742 | 37750 | 37752 | 37753 | 37754 | 37778 | 37779 | 37781 | 37814 | 37818 | 37832 | 37850 |
| 37870 | 37881 | 37887 | 37901 | 37910 | 37915 | 37928 | 37929 | 37933 | 37952 | 37957 | 37970 |
| 37980 | 37982 | 37988 | 38000 | 38010 | 38026 | 38028 | 38030 | 38037 | 38041 | 38045 | 38072 |
| 38073 | 38100 | 38102 | 38113 | 38118 | 38125 | 38136 | 38143 | 38145 | 38154 | 38159 | 38161 |
| 38168 | 38169 | 38179 | 38181 | 38188 | 38195 | 38200 | 38206 | 38209 | 38216 | 38220 | 38221 |
| 38223 | 38227 | 38229 | 38230 | 38234 | 38266 | 38268 | 38302 | 38316 | 38325 | 38331 | 38351 |
| 38356 | 38363 | 38383 | 38397 | 38407 | 38408 | 38434 | 38435 | 38456 | 38472 | 38473 | 38482 |
| 38484 | 38485 | 38486 | 38488 | 38497 | 38498 | 38503 | 38533 | 38534 | 38543 | 38544 | 38553 |
| 38554 | 38564 | 38571 | 38581 | 38592 | 38599 | 38600 | 38601 | 38605 | 38633 | 38636 | 38645 |
| 38649 | 38654 | 38657 | 38659 | 38660 | 38667 | 38670 | 38671 | 38673 | 38690 | 38724 | 38729 |
| 38732 | 38734 | 38739 | 38745 | 38747 | 38749 | 38756 | 38766 | 38768 | 38774 | 38779 | 38788 |
| 38790 | 38796 | 38802 | 38829 | 38836 | 38843 | 38864 | 38886 | 38887 | 38912 | 38934 | 38979 |
| 38981 | 38982 | 38988 | 38989 | 38997 | 39026 | 39032 | 39051 | 39052 | 39054 | 39073 | 39074 |
| 39076 | 39092 | 39096 | 39105 | 39115 | 39118 | 39120 | 39126 | 39127 | 39132 | 39133 | 39134 |
| 39136 | 39137 | 39138 | 39139 | 39140 | 39149 | 39152 | 39160 | 39167 | 39171 | 39178 | 39186 |
| 39188 | 39189 | 39194 | 39195 | 39196 | 39197 | 39201 | 39204 | 39211 | 39226 | 39230 | 39244 |
| 39249 | 39256 | 39278 | 39279 | 39286 | 39287 | 39288 | 39292 | 39318 | 39329 | 39331 | 39334 |
| 39335 | 39336 | 39337 | 39338 | 39339 | 39341 | 39342 | 39343 | 39344 | 39346 | 39347 | 39348 |
| 39354 | 39355 | 39363 | 39393 | 39399 | 39418 | 39419 | 39421 | 39441 | 39442 | 39444 | 39460 |
| 39464 | 39473 | 39483 | 39487 | 39488 | 39494 | 39495 | 39496 | 39500 | 39501 | 39502 | 39504 |
| 39505 | 39506 | 39507 | 39508 | 39518 | 39521 | 39530 | 39537 | 39542 | 39557 | 39560 | 39561 |
| 39566 | 39567 | 39568 | 39569 | 39573 | 39576 | 39582 | 39597 | 39602 | 39617 | 39622 | 39629 |
| 39654 | 39655 | 39663 | 39664 | 39667 | 39693 | 39704 | 39706 | 39710 | 39711 | 39712 | 39713 |
| 39714 | 39715 | 39716 | 39717 | 39718 | 39720 | 39721 | 39722 | 39723 | 39724 | 39726 | 39728 |
| 39729 | 39732 | 39733 | 39734 | 39738 | 39739 | 39744 | 39754 | 39783 | 39788 | 39803 |
| 39804 | 39805 | 39825 | 39827 | 39828 | 39843 | 39855 | 39865 | 39869 | 39870 | 39875 | 39876 |
| 39878 | 39882 | 39883 | 39884 | 39886 | 39887 | 39888 | 39889 | 39899 | 39903 | 39909 | 39915 |
| 39917 | 39924 | 39932 | 39935 | 39936 | 39939 | 39940 | 39941 | 39947 | 39948 | 39955 | 39973 |
| 39985 | 39990 | 39995 | 40016 | 40017 | 40020 | 40021 | 40027 | 40047 | 40057 | 40085 | 40092 |
| 40102 | 40109 | 40111 | 40113 | 40116 | 40120 | 40122 | 40130 | 40137 | 40139 | 40140 | 40142 |
| 40150 | 40166 | 40170 | 40183 | 40203 | 40214 | 40217 | 40221 | 40222 | 40233 | 40234 | 40236 |
| 40242 | 40265 | 40266 | 40293 | 40295 | 40302 | 40306 | 40309 | 40322 | 40323 | 40358 | 40371 |
| 40372 | 40373 | 40374 | 40394 | 40395 | 40406 | 40413 | 40423 | 40443 | 40462 | 40465 | 40471 |
| 40474 | 40481 | 40488 | 40502 | 40508 | 40514 | 40515 | 40519 | 40521 | 40529 | 40540 | 40547 |
| 40549 | 40553 | 40568 | 40573 | 40574 | 40607 | 40621 | 40630 | 40635 | 40640 | 40646 | 40649 |
| 40677 | 40722 | 40729 | 40741 | 40751 | 40753 | 40757 | 40768 | 40769 | 40787 | 40788 | 40799 |
| 40808 | 40810 | 40817 | 40838 | 40870 | 40890 | 40902 | 40903 | 40904 | 40905 | 40906 | 40907 |
| 40913 | 40919 | 40920 | 40923 | 40930 | 40933 | 40934 | 40935 | 40937 | 40963 | 40977 | 40978 |
| 40981 | 40984 | 40989 | 40991 | 41002 | 41003 | 41004 | 41005 | 41015 | 41022 | 41045 | 41073 |
| 41077 | 41097 | 41107 | 41108 | 41111 | 41112 | 41113 | 41118 | 41148 | 41150 | 41167 | 41178 |
| 41179 | 41201 | 41202 | 41203 | 41208 | 41213 | 41214 | 41227 | 41231 | 41232 | 41245 | 41249 |
| 41256 | 41263 | 41273 | 41276 | 41280 | 41283 | 41284 | 41285 | 41290 | 41309 | 41311 | 41314 |

TABLE 14-continued

Seed Protein Yield/Content

| | | | | | | | | | | |
|---|---|---|---|---|---|---|---|---|---|---|
| 41319 | 41320 | 41327 | 41339 | 41348 | 41352 | 41362 | 41369 | 41371 | 41372 | 41373 | 41385 |
| 41386 | 41395 | 41397 | 41411 | 41413 | 41450 | 41460 | 41469 | 41471 | 41484 | 41489 | 41496 |
| 41502 | 41503 | 41507 | 41513 | 41515 | 41520 | 41523 | 41531 | 41543 | 41549 | 41550 | 41561 |
| 41562 | 41566 | 41567 | 41576 | 41581 | 41599 | 41602 | 41605 | 41606 | 41610 | 41612 | 41617 |
| 41624 | 41627 | 41632 | 41635 | 41636 | 41638 | 41640 | 41656 | 41658 | 41663 | 41668 | 41669 |
| 41688 | 41689 | 41697 | 41707 | 41717 | 41718 | 41722 | 41736 | 41745 | 41754 | 41757 | 41758 |
| 41760 | 41761 | 41762 | 41763 | 41764 | 41765 | 41766 | 41767 | 41776 | 41783 | 41808 | 41814 |
| 41821 | 41825 | 41829 | 41837 | 41841 | 41845 | 41849 | 41859 | 41861 | 41867 | 41870 | 41872 |
| 41873 | 41874 | 41878 | 41882 | 41887 | 41890 | 41906 | 41934 | 41937 | 41946 | 41947 | 41948 |
| 41957 | 41958 | 41959 | 41977 | 41983 | 41985 | 41993 | 42006 | 42014 | 42015 | 42016 | 42028 |
| 42035 | 42053 | 42062 | 42071 | 42078 | 42094 | 42104 | 42107 | 42111 | 42121 | 42130 | 42135 |
| 42141 | 42152 | 42153 | 42179 | 42181 | 42187 | 42189 | 42206 | 42227 | 42239 | 42249 | 42262 |
| 42269 | 42277 | 42293 | 42296 | 42297 | 42306 | 42313 | 42315 | 42316 | 42320 | 42328 | 42330 |
| 42352 | 42354 | 42361 | 42385 | 42387 | 42388 | 42390 | 42404 | 42406 | 42439 | 42445 | 42446 |
| 42458 | 42459 | 42460 | 42475 | 42481 | 42482 | 42483 | 42487 | 42541 | 42568 | 42573 | 42579 |
| 42586 | 42600 | 42610 | 42622 | 42623 | 42633 | 42650 | 42672 | 42679 | 42680 | 42686 | 42711 |
| 42712 | 42732 | 42734 | 42739 | 42795 | 42796 | 42798 | 42819 | 42822 | 42824 | 42827 | 42828 |
| 42837 | 42838 | 42839 | 42840 | 42849 | 42857 | 42873 | 42878 | 42879 | 42882 | 42883 | 42894 |
| 42896 | 42897 | 42904 | 42924 | 42928 | 42941 | 42951 | 42953 | 42954 | 42957 | 42971 | 42974 |
| 42983 | 42984 | 42985 | 42986 | 42991 | 42993 | 42995 | 43005 | 43007 | 43008 | 43009 | 43010 |
| 43011 | 43022 | 43032 | 43034 | 43036 | 43040 | 43053 | 43061 | 43062 | 43068 | 43069 | 43074 |
| 43076 | 43077 | 43089 | 43090 | 43100 | 43117 | 43119 | 43121 | 43130 | 43139 | 43140 | 43146 |
| 43149 | 43154 | 43162 | 43177 | 43183 | 43202 | 43207 | 43219 | 43222 | 43224 | 43240 | 43255 |
| 43278 | 43283 | 43292 | 43294 | 43299 | 43300 | 43303 | 43305 | 43306 | 43309 | 43312 | 43313 |
| 43316 | 43335 | 43343 | 43347 | 43366 | 43383 | 43390 | 43394 | 43397 | 43412 | 43421 | 43423 |
| 43445 | 43448 | 43449 | 43450 | 43459 | 43466 | 43467 | 43473 | 43476 | 43477 | 43478 | 43482 |
| 43518 | 43539 | 43565 | 43574 | 43602 | 43607 | 43609 | 43610 | 43626 | 43676 | 43700 | 43720 |
| 43723 | 43726 | 43734 | 43755 | 43756 | 43772 | 43773 | 43774 | 43793 | 43801 | 43802 | 43804 |
| 43812 | 43826 | 43858 | 43869 | 43879 | 43898 | 43903 | 43904 | 43908 | 43919 | 43950 | 43951 |
| 43960 | 43961 | 43978 | 43981 | 44007 | 44018 | 44020 | 44028 | 44029 | 44030 | 44031 | 44044 |
| 44052 | 44053 | 44063 | 44084 | 44113 | 44128 | 44145 | 44162 | 44175 | 44203 | 44204 | 44208 |
| 44218 | 44248 | 44250 | 44252 | 44256 | 44276 | 44288 | 44294 | 44314 | 44329 | 44330 | 44332 |
| 44340 | 44341 | 44359 | 44363 | 44366 | 44368 | 44370 | 44376 | 44382 | 44383 | 44385 | 44386 |
| 44387 | 44411 | 44419 | 44427 | 44428 | 44438 | 44459 | 44464 | 44470 | 44472 | 44474 | 44484 |
| 44499 | 44506 | 44515 | 44529 | 44559 | 44575 | 44577 | 44580 | 44583 | 44588 | 44593 | 44597 |
| 44598 | 44605 | 44608 | 44622 | 44625 | 44629 | 44634 | 44640 | 44644 | 44675 | 44687 | 44692 |
| 44714 | 44715 | 44716 | 44738 | 44739 | 44748 | 44755 | 44763 | 44769 | 44777 | 44780 | 44785 |
| 44808 | 44831 | 44835 | 44844 | 44860 | 44868 | 44869 | 44871 | 44879 | 44882 | 44888 | 44894 |
| 44899 | 44902 | 44905 | 44907 | 44909 | 44910 | 44917 | 44922 | 44928 | 44948 | 44955 | 44961 |
| 44965 | 44973 | 44975 | 44979 | 44981 | 44997 | 45012 | 45013 | 45016 | 45018 | 45019 | 45025 |
| 45034 | 45038 | 45049 | 45059 | 45081 | 45082 | 45085 | 45086 | 45093 | 45107 | 45109 | 45121 |
| 45131 | 45137 | 45148 | 45161 | 45162 | 45179 | 45215 | 45234 | 45236 | 45248 | 45266 | 45274 |
| 45287 | 45295 | 45300 | 45301 | 45302 | 45306 | 45312 | 45313 | 45314 | 45318 | 45319 | 45327 |
| 45328 | 45335 | 45347 | 45424 | 45431 | 45462 | 45472 | 45474 | 45485 | 45491 | 45494 | 45504 |
| 45508 | 45510 | 45512 | 45513 | 45521 | 45530 | 45533 | 45534 | 45539 | 45542 | 45560 | 45566 |
| 45567 | 45568 | 45573 | 45578 | 45579 | 45581 | 45585 | 45596 | 45601 | 45612 | 45616 | 45617 |
| 45630 | 45638 | 45648 | 45655 | 45662 | 45669 | 45678 | 45681 | 45687 | 45690 | 45699 | 45701 |
| 45707 | 45713 | 45715 | 45716 | 45721 | 45724 | 45733 | 45734 | 45735 | 45738 | 45742 | 45751 |
| 45753 | 45759 | 45764 | 45765 | 45773 | 45775 | 45776 | 45778 | 45798 | 45800 | 45803 | 45806 |
| 45810 | 45812 | 45814 | 45818 | 45824 | 45833 | 45839 | 45863 | 45868 | 45883 | 45887 | 45889 |
| 45893 | 45894 | 45895 | 45897 | 45907 | 45908 | 45916 | 45920 | 45923 | 45927 | 45954 | 45962 |
| 45964 | 45969 | 45974 | 45977 | 45983 | 45984 | 46000 | 46009 | 46010 | 46015 | 46019 | 46025 |
| 46027 | 46032 | 46055 | 46058 | 46061 | 46063 | 46068 | 46084 | 46085 | 46091 | 46093 | 46094 |
| 46095 | 46104 | 46118 | 46120 | 46123 | 46129 | 46134 | 46157 | 46159 | 46180 | 46191 | 46197 |
| 46199 | 46209 | 46214 | 46219 | 46220 | 46226 | 46232 | 46233 | 46242 | 46247 | 46250 | 46258 |
| 46261 | 46277 | 46281 | 46286 | 46289 | 46290 | 46293 | 46306 | 46317 | 46318 | 46329 | 46331 |
| 46332 | 46333 | 46344 | 46345 | 46365 | 46368 | 46369 | 46375 | 46376 | 46397 | 46407 | 46411 |
| 46416 | 46425 | 46440 | 46441 | 46442 | 46446 | 46452 | 46456 | 46462 | 46469 | 46478 | 46479 |
| 46480 | 46484 | 46490 | 46492 | 46503 | 46535 | 46555 | 46558 | 46563 | 46564 | 46567 | 46568 |
| 46570 | 46581 | 46584 | 46591 | 46607 | 46623 | 46625 | 46628 | 46653 | 46659 | 46660 | 46675 |
| 46676 | 46699 | 46705 | 46707 | 46708 | 46723 | 46730 | 46736 | 46737 | 46744 | 46745 | 46746 |
| 46750 | 46751 | 46753 | 46755 | 46759 | 46765 | 46774 | 46778 | 46784 | 46786 | 46793 | 46805 |
| 46806 | 46807 | 46816 | 46817 | 46818 | 46819 | 46835 | 46852 | 46860 | 46867 | 46872 | 46884 |
| 46888 | 46900 | 46902 | 46911 | 46915 | 46945 | 46946 | 46965 | 46967 | 46977 | 46991 | 46992 |
| 47011 | 47035 | 47054 | 47058 | 47069 | 47072 | 47093 | 47097 | 47103 | 47117 | 47118 | 47125 |
| 47126 | 47127 | 47138 | 47147 | 47150 | 47168 | 47183 | 47186 | 47191 | 47195 | 47200 | 47208 |
| 47209 | 47216 | 47220 | 47222 | 47223 | 47231 | 47238 | 47239 | 47243 | 47249 | 47254 | 47255 |
| 47257 | 47263 | 47270 | 47276 | 47280 | 47282 | 47308 | 47311 | 47315 | 47320 | 47328 | 47329 |
| 47341 | 47343 | 47346 | 47348 | 47357 | 47358 | 47366 | 47370 | 47371 | | | |

TABLE 15

Yield: Carbohydrate

Table 15A SEQ ID NOs of Polypeptides useful for improving Yield: Carbohydrate

| | | | | | | | | | | | |
|---|---|---|---|---|---|---|---|---|---|---|---|
| 4 | 7 | 12 | 17 | 21 | 27 | 31 | 32 | 33 | 34 | 36 | 37 |
| 39 | 44 | 49 | 50 | 53 | 56 | 62 | 68 | 73 | 74 | 77 | 81 |
| 82 | 88 | 95 | 99 | 101 | 104 | 108 | 110 | 111 | 112 | 114 | 119 |
| 120 | 121 | 124 | 125 | 127 | 128 | 131 | 132 | 133 | 136 | 138 | 139 |
| 145 | 160 | 163 | 169 | 175 | 180 | 183 | 184 | 187 | 188 | 191 | 194 |
| 195 | 197 | 199 | 207 | 208 | 209 | 210 | 211 | 212 | 213 | 214 | 215 |
| 216 | 220 | 222 | 224 | 225 | 226 | 236 | 237 | 244 | 248 | 249 | 253 |
| 257 | 258 | 262 | 266 | 276 | 279 | 281 | 289 | 290 | 291 | 293 | 303 |
| 306 | 311 | 313 | 314 | 318 | 328 | 329 | 335 | 338 | 340 | 341 | 342 |
| 345 | 350 | 362 | 363 | 364 | 366 | 378 | 379 | 384 | 385 | 388 | 390 |
| 391 | 392 | 394 | 395 | 396 | 397 | 398 | 399 | 400 | 401 | 403 | 405 |
| 407 | 410 | 411 | 413 | 427 | 432 | 433 | 444 | 449 | 456 | 457 | 459 |
| 460 | 461 | 462 | 464 | 465 | 466 | 469 | 474 | 477 | 478 | 479 | 484 |
| 485 | 487 | 489 | 490 | 494 | 495 | 497 | 498 | 499 | 501 | 502 | 504 |
| 505 | 512 | 515 | 516 | 524 | 528 | 529 | 530 | 537 | 538 | 548 | 549 |
| 552 | 555 | 557 | 560 | 561 | 562 | 571 | 575 | 576 | 579 | 581 | 582 |
| 583 | 585 | 593 | 597 | 600 | 603 | 607 | 608 | 609 | 612 | 613 | 618 |
| 620 | 622 | 625 | 626 | 630 | 632 | 634 | 636 | 637 | 638 | 639 | 640 |
| 641 | 642 | 643 | 644 | 648 | 651 | 663 | 664 | 670 | 671 | 676 | 679 |
| 680 | 683 | 684 | 685 | 687 | 695 | 696 | 698 | 699 | 701 | 702 | 707 |
| 709 | 710 | 718 | 720 | 722 | 723 | 724 | 729 | 730 | 742 | 746 | 747 |
| 749 | 752 | 753 | 755 | 756 | 757 | 758 | 759 | 760 | 761 | 763 | 765 |
| 767 | 768 | 769 | 781 | 792 | 793 | 794 | 795 | 796 | 798 | 799 | 809 |
| 810 | 811 | 812 | 813 | 818 | 820 | 821 | 823 | 825 | 834 | 835 | 837 |
| 839 | 841 | 842 | 843 | 844 | 848 | 849 | 851 | 856 | 861 | 862 | 863 |
| 864 | 865 | 867 | 868 | 869 | 870 | 871 | 872 | 874 | 875 | 879 | 885 |
| 886 | 887 | 888 | 889 | 890 | 891 | 894 | 899 | 900 | 902 | 906 | 908 |
| 921 | 923 | 926 | 931 | 934 | 937 | 938 | 941 | 942 | 943 | 945 | 946 |
| 951 | 952 | 964 | 968 | 970 | 974 | 975 | 976 | 979 | 986 | 989 | 992 |
| 993 | 994 | 1005 | 1014 | 1018 | 1021 | 1032 | 1036 | 1042 | 1043 | 1046 | 1052 |
| 1053 | 1055 | 1064 | 1073 | 1085 | 1086 | 1089 | 1091 | 1092 | 1093 | 1099 | 1112 |
| 1113 | 1116 | 1130 | 1134 | 1136 | 1142 | 1149 | 1153 | 1155 | 1166 | 1167 | 1174 |
| 1188 | 1194 | 1198 | 1199 | 1203 | 1204 | 1219 | 1224 | 1225 | 1229 | 1231 | 1234 |
| 1236 | 1241 | 1243 | 1246 | 1263 | 1264 | 1270 | 1274 | 1281 | 1282 | 1284 | 1303 |
| 1313 | 1316 | 1321 | 1326 | 1329 | 1332 | 1339 | 1341 | 1342 | 1361 | 1372 | 1375 |
| 1414 | 1415 | 1426 | 1428 | 1429 | 1430 | 1431 | 1432 | 1435 | 1458 | 1463 | 1473 |
| 1474 | 1484 | 1489 | 1491 | 1492 | 1494 | 1497 | 1506 | 1507 | 1510 | 1515 | 1518 |
| 1521 | 1526 | 1541 | 1543 | 1554 | 1555 | 1565 | 1568 | 1572 | 1575 | 1576 | 1578 |
| 1580 | 1582 | 1584 | 1588 | 1589 | 1590 | 1591 | 1597 | 1598 | 1603 | 1605 | 1608 |
| 1618 | 1624 | 1625 | 1632 | 1641 | 1642 | 1651 | 1661 | 1669 | 1679 | 1680 | 1681 |
| 1683 | 1684 | 1688 | 1689 | 1696 | 1698 | 1699 | 1702 | 1704 | 1705 | 1706 | 1712 |
| 1719 | 1720 | 1728 | 1737 | 1745 | 1746 | 1749 | 1768 | 1781 | 1785 | 1797 | 1802 |
| 1806 | 1812 | 1814 | 1818 | 1824 | 1834 | 1838 | 1839 | 1841 | 1844 | 1847 | 1854 |
| 1856 | 1860 | 1867 | 1882 | 1883 | 1884 | 1887 | 1896 | 1897 | 1903 | 1904 | 1905 |
| 1908 | 1912 | 1917 | 1918 | 1920 | 1930 | 1933 | 1936 | 1939 | 1952 | 1958 | 1971 |
| 1973 | 2006 | 2006 | 2007 | 2008 | 2013 | 2015 | 2019 | 2027 | 2028 | 2038 | 2055 |
| 2062 | 2068 | 2104 | 2111 | 2115 | 2119 | 2122 | 2123 | 2130 | 2140 | 2147 | 2148 |
| 2154 | 2157 | 2159 | 2164 | 2166 | 2167 | 2168 | 2186 | 2194 | 2202 | 2208 | 2209 |
| 2213 | 2223 | 2229 | 2245 | 2246 | 2251 | 2252 | 2255 | 2260 | 2267 | 2268 | 2283 |
| 2284 | 2285 | 2292 | 2299 | 2311 | 2314 | 2315 | 2319 | 2320 | 2321 | 2322 |
| 2325 | 2327 | 2328 | 2330 | 2359 | 2364 | 2376 | 2427 | 2428 | 2434 | 2438 | 2440 |
| 2443 | 2444 | 2446 | 2453 | 2454 | 2461 | 2470 | 2475 | 2488 | 2489 | 2490 | 2497 |
| 2504 | 2507 | 2510 | 2524 | 2533 | 2546 | 2547 | 2550 | 2551 | 2560 | 2562 | 2564 |
| 2574 | 2578 | 2588 | 2589 | 2598 | 2603 | 2606 | 2615 | 2621 | 2624 | 2625 |
| 2626 | 2627 | 2632 | 2633 | 2635 | 2639 | 2640 | 2644 | 2658 | 2665 | 2666 | 2676 |
| 2679 | 2680 | 2685 | 2687 | 2688 | 2689 | 2691 | 2692 | 2694 | 2695 | 2696 | 2698 |
| 2700 | 2703 | 2706 | 2708 | 2711 | 2715 | 2719 | 2722 | 2725 | 2726 | 2727 | 2728 |
| 2734 | 2735 | 2737 | 2738 | 2745 | 2750 | 2751 | 2752 | 2755 | 2756 | 2759 | 2760 |
| 2761 | 2766 | 2767 | 2771 | 2774 | 2775 | 2777 | 2778 | 2780 | 2781 | 2783 | 2785 |
| 2790 | 2792 | 2795 | 2797 | 2801 | 2803 | 2807 | 2822 | 2823 | 2825 | 2828 | 2833 |
| 2840 | 2842 | 2847 | 2848 | 2852 | 2854 | 2863 | 2864 | 2873 | 2874 | 2879 | 2885 |
| 2889 | 2890 | 2894 | 2901 | 2904 | 2905 | 2909 | 2910 | 2912 | 2913 | 2914 | 2915 |
| 2916 | 2919 | 2920 | 2922 | 2923 | 2924 | 2925 | 2926 | 2928 | 2936 | 2938 | 2943 |
| 2944 | 2945 | 2946 | 2954 | 2959 | 2960 | 2961 | 2963 | 2964 | 2968 | 2970 | 2971 |
| 2972 | 2976 | 2977 | 2979 | 2980 | 2984 | 2985 | 2986 | 2995 | 3002 | 3003 | 3004 |
| 3007 | 3008 | 3009 | 3010 | 3012 | 3020 | 3023 | 3030 | 3031 | 3041 | 3045 | 3052 |
| 3054 | 3055 | 3065 | 3066 | 3067 | 3068 | 3069 | 3080 | 3087 | 3089 | 3100 | 3101 |
| 3103 | 3104 | 3107 | 3109 | 3113 | 3115 | 3124 | 3130 | 3132 | 3136 | 3145 | 3152 |
| 3154 | 3156 | 3176 | 3178 | 3181 | 3186 | 3187 | 3188 | 3189 | 3191 | 3194 | 3197 |
| 3200 | 3201 | 3206 | 3212 | 3213 | 3219 | 3232 | 3233 | 3236 | 3246 | 3248 | 3249 |
| 3251 | 3252 | 3254 | 3265 | 3270 | 3275 | 3285 | 3286 | 3290 | 3299 | 3301 | 3304 |
| 3305 | 3308 | 3309 | 3315 | 3318 | 3319 | 3324 | 3328 | 3334 | 3335 | 3343 | 3345 |
| 3348 | 3351 | 3352 | 3357 | 3358 | 3362 | 3363 | 3381 | 3385 | 3389 | 3392 | 3395 |
| 3396 | 3397 | 3398 | 3399 | 3409 | 3411 | 3414 | 3415 | 3418 | 3419 | 3421 | 3425 |
| 3434 | 3436 | 3438 | 3440 | 3442 | 3454 | 3458 | 3473 | 3478 | 3480 | 3481 | 3487 |

TABLE 15-continued

Yield: Carbohydrate

| | | | | | | | | | | | |
|---|---|---|---|---|---|---|---|---|---|---|---|
| 3490 | 3491 | 3500 | 3515 | 3526 | 3529 | 3531 | 3544 | 3555 | 3560 | 3569 | 3571 |
| 3573 | 3580 | 3588 | 3590 | 3591 | 3600 | 3605 | 3610 | 3621 | 3624 | 3629 | 3636 |
| 3637 | 3639 | 3640 | 3641 | 3643 | 3646 | 3654 | 3657 | 3658 | 3662 | 3665 | 3667 |
| 3671 | 3677 | 3680 | 3682 | 3686 | 3688 | 3695 | 3698 | 3703 | 3709 | 3711 | 3713 |
| 3714 | 3719 | 3724 | 3725 | 3733 | 3738 | 3739 | 3745 | 3746 | 3747 | 3748 | 3750 |
| 3758 | 3762 | 3764 | 3772 | 3774 | 3778 | 3780 | 3784 | 3792 | 3793 | 3794 | 3800 |
| 3805 | 3810 | 3811 | 3815 | 3819 | 3824 | 3834 | 3835 | 3837 | 3846 | 3847 | 3853 |
| 3864 | 3865 | 3866 | 3869 | 3871 | 3876 | 3887 | 3894 | 3895 | 3904 | 3918 | 3920 |
| 3924 | 3929 | 3937 | 3950 | 3951 | 3953 | 3966 | 3967 | 3969 | 3970 | 3973 | 3976 |
| 3978 | 3982 | 3984 | 3986 | 3987 | 4004 | 4006 | 4011 | 4019 | 4022 | 4033 | 4035 |
| 4037 | 4041 | 4044 | 4045 | 4047 | 4048 | 4056 | 4061 | 4077 | 4108 | 4111 | 4113 |
| 4114 | 4115 | 4117 | 4118 | 4123 | 4126 | 4128 | 4129 | 4134 | 4136 | 4137 | 4141 |
| 4142 | 4143 | 4152 | 4153 | 4164 | 4166 | 4168 | 4173 | 4176 | 4178 | 4179 | 4180 |
| 4183 | 4184 | 4186 | 4193 | 4204 | 4206 | 4211 | 4215 | 4218 | 4222 | 4227 | 4228 |
| 4229 | 4233 | 4238 | 4241 | 4242 | 4243 | 4244 | 4246 | 4249 | 4251 | 4252 | 4254 |
| 4255 | 4256 | 4259 | 4261 | 4262 | 4263 | 4266 | 4269 | 4271 | 4276 | 4277 | 4278 |
| 4279 | 4280 | 4282 | 4284 | 4285 | 4286 | 4287 | 4289 | 4291 | 4292 | 4293 | 4294 |
| 4295 | 4296 | 4299 | 4304 | 4305 | 4306 | 4307 | 4308 | 4309 | 4311 | 4314 | 4316 |
| 4318 | 4320 | 4321 | 4325 | 4326 | 4327 | 4329 | 4330 | 4332 | 4336 | 4338 | 4340 |
| 4344 | 4349 | 4355 | 4356 | 4357 | 4358 | 4360 | 4362 | 4363 | 4364 | 4366 | 4367 |
| 4368 | 4373 | 4375 | 4377 | 4379 | 4380 | 4381 | 4382 | 4383 | 4387 | 4390 | 4392 |
| 4401 | 4403 | 4404 | 4405 | 4406 | 4410 | 4411 | 4412 | 4414 | 4424 | 4425 | 4427 |
| 4428 | 4429 | 4437 | 4438 | 4441 | 4446 | 4448 | 4451 | 4452 | 4453 | 4455 | 4457 |
| 4460 | 4461 | 4464 | 4465 | 4466 | 4467 | 4471 | 4473 | 4474 | 4475 | 4479 | 4481 |
| 4483 | 4484 | 4485 | 4486 | 4490 | 4499 | 4502 | 4503 | 4504 | 4505 | 4506 | 4512 |
| 4514 | 4515 | 4517 | 4521 | 4526 | 4530 | 4531 | 4532 | 4534 | 4535 | 4536 | 4541 |
| 4543 | 4546 | 4549 | 4552 | 4553 | 4555 | 4557 | 4558 | 4561 | 4565 | 4568 | 4570 |
| 4572 | 4577 | 4578 | 4581 | 4582 | 4586 | 4594 | 4596 | 4601 | 4603 | 4604 | 4605 |
| 4606 | 4608 | 4609 | 4610 | 4611 | 4612 | 4613 | 4614 | 4618 | 4621 | 4622 | 4624 |
| 4625 | 4626 | 4632 | 4634 | 4635 | 4637 | 4638 | 4639 | 4640 | 4643 | 4644 | 4646 |
| 4647 | 4648 | 4651 | 4652 | 4653 | 4654 | 4656 | 4672 | 4673 | 4674 | 4678 | |
| 4679 | 4681 | 4688 | 4691 | 4693 | 4696 | 4697 | 4699 | 4700 | 4702 | 4704 | 4705 |
| 4706 | 4707 | 4711 | 4712 | 4714 | 4716 | 4719 | 4725 | 4727 | 4731 | 4732 | 4733 |
| 4734 | 4736 | 4739 | 4742 | 4745 | 4746 | 4747 | 4749 | 4750 | 4757 | 4758 | 4762 |
| 4763 | 4766 | 4767 | 4768 | 4771 | 4773 | 4775 | 4776 | 4780 | 4781 | 4785 | 4787 |
| 4788 | 4789 | 4790 | 4793 | 4796 | 4797 | 4799 | 4800 | 4802 | 4803 | 4806 | 4807 |
| 4810 | 4811 | 4812 | 4813 | 4814 | 4818 | 4822 | 4823 | 4830 | 4831 | 4832 | 4834 |
| 4835 | 4836 | 4840 | 4841 | 4842 | 4846 | 4847 | 4848 | 4855 | 4857 | 4860 | 4863 |
| 4865 | 4866 | 4868 | 4869 | 4871 | 4872 | 4875 | 4883 | 4886 | 4887 | 4888 | 4889 |
| 4892 | 4894 | 4899 | 4902 | 4903 | 4907 | 4911 | 4912 | 4913 | 4914 | 4917 | 4923 |
| 4924 | 4928 | 4931 | 4933 | 4935 | 4939 | 4943 | 4944 | 4945 | 4946 | 4947 | 4950 |
| 4951 | 4952 | 4954 | 4958 | 4960 | 4962 | 4964 | 4965 | 4972 | 4977 | 4981 | 4988 |
| 4992 | 4995 | 5003 | 5005 | 5023 | 5027 | 5038 | 5068 | 5081 | 5083 | 5088 | 5090 |
| 5104 | 5116 | 5117 | 5118 | 5120 | 5125 | 5152 | 5153 | 5158 | 5159 | 5172 | 5173 |
| 5180 | 5209 | 5226 | 5233 | 5234 | 5237 | 5257 | 5268 | 5271 | 5281 | 5282 | 5283 |
| 5284 | 5292 | 5293 | 5298 | 5316 | 5318 | 5326 | 5330 | 5334 | 5336 | 5338 | 5339 |
| 5346 | 5363 | 5378 | 5379 | 5394 | 5433 | 5434 | 5437 | 5439 | 5440 | 5441 | 5442 |
| 5453 | 5465 | 5470 | 5471 | 5474 | 5481 | 5490 | 5495 | 5507 | 5516 | 5520 | 5521 |
| 5522 | 5523 | 5524 | 5525 | 5533 | 5534 | 5539 | 5540 | 5543 | 5549 | 5552 | 5566 |
| 5584 | 5588 | 5589 | 5600 | 5602 | 5604 | 5609 | 5610 | 5631 | 5640 | 5646 | 5650 |
| 5656 | 5662 | 5665 | 5669 | 5680 | 5682 | 5692 | 5693 | 5701 | 5706 | 5711 | 5715 |
| 5716 | 5734 | 5735 | 5743 | 5745 | 5752 | 5773 | 5774 | 5780 | 5783 | 5788 | 5791 |
| 5794 | 5796 | 5803 | 5805 | 5806 | 5812 | 5817 | 5838 | 5844 | 5862 | 5863 | 5867 |
| 5868 | 5876 | 5886 | 5901 | 5902 | 5904 | 5910 | 5914 | 5920 | 5922 | 5923 | 5932 |
| 5933 | 5934 | 5946 | 5958 | 5975 | 5978 | 5990 | 5992 | 5993 | 6000 | 6001 | 6002 |
| 6010 | 6011 | 6012 | 6015 | 6023 | 6024 | 6026 | 6027 | 6032 | 6033 | 6034 | 6052 |
| 6062 | 6081 | 6084 | 6089 | 6090 | 6093 | 6104 | 6107 | 6108 | 6112 | 6115 | 6116 |
| 6133 | 6134 | 6143 | 6152 | 6153 | 6154 | 6156 | 6158 | 6159 | 6166 | 6175 | 6177 |
| 6187 | 6189 | 6191 | 6192 | 6197 | 6200 | 6210 | 6214 | 6220 | 6224 | 6231 | 6234 |
| 6239 | 6240 | 6241 | 6244 | 6251 | 6252 | 6263 | 6268 | 6269 | 6271 | 6272 | 6274 |
| 6280 | 6305 | 6353 | 6354 | 6355 | 6356 | 6360 | 6361 | 6369 | 6394 | 6397 | 6413 |
| 6433 | 6435 | 6437 | 6438 | 6441 | 6446 | 6450 | 6458 | 6466 | 6470 | 6471 | 6472 |
| 6473 | 6475 | 6477 | 6479 | 6484 | 6485 | 6489 | 6497 | 6502 | 6503 | 6504 | 6511 |
| 6515 | 6520 | 6524 | 6525 | 6526 | 6542 | 6547 | 6550 | 6551 | 6558 | 6561 | 6562 |
| 6563 | 6567 | 6578 | 6579 | 6581 | 6582 | 6583 | 6594 | 6597 | 6598 | 6606 | 6620 |
| 6625 | 6636 | 6640 | 6641 | 6673 | 6674 | 6693 | 6695 | 6701 | 6714 | 6715 | 6718 |
| 6720 | 6730 | 6732 | 6733 | 6739 | 6743 | 6749 | 6759 | 6768 | 6770 | 6771 | 6780 |
| 6788 | 6806 | 6809 | 6815 | 6819 | 6821 | 6822 | 6823 | 6826 | 6829 | 6830 | 6845 |
| 6870 | 6876 | 6877 | 6902 | 6907 | 6910 | 6912 | 6927 | 6939 | 6970 | 6971 | 6972 |
| 6985 | 6986 | 6990 | 7001 | 7018 | 7026 | 7033 | 7034 | 7035 | 7037 | 7039 | 7040 |
| 7041 | 7043 | 7045 | 7047 | 7048 | 7049 | 7050 | 7051 | 7052 | 7053 | 7055 | 7060 |
| 7061 | 7062 | 7063 | 7064 | 7065 | 7067 | 7070 | 7072 | 7074 | 7076 | 7077 | 7081 |
| 7082 | 7083 | 7085 | 7086 | 7088 | 7093 | 7095 | 7099 | 7102 | 7104 | 7109 | 7110 |
| 7111 | 7112 | 7114 | 7116 | 7117 | 7118 | 7120 | 7121 | 7122 | 7127 | 7129 | 7131 |
| 7133 | 7134 | 7135 | 7137 | 7138 | 7140 | 7142 | 7145 | 7147 | 7156 | 7158 | 7159 |
| 7160 | 7162 | 7166 | 7167 | 7168 | 7170 | 7182 | 7183 | 7185 | 7186 | 7187 | 7193 |
| 7196 | 7197 | 7200 | 7205 | 7207 | 7211 | 7212 | 7213 | 7217 | 7220 | 7221 | 7224 |

TABLE 15-continued

Yield: Carbohydrate

| | | | | | | | | | | | |
|---|---|---|---|---|---|---|---|---|---|---|---|
| 7225 | 7226 | 7227 | 7231 | 7233 | 7234 | 7238 | 7240 | 7242 | 7243 | 7244 | 7245 |
| 7249 | 7258 | 7261 | 7262 | 7263 | 7264 | 7270 | 7272 | 7274 | 7276 | 7280 | 7285 |
| 7288 | 7289 | 7290 | 7292 | 7293 | 7294 | 7299 | 7301 | 7304 | 7309 | 7310 | 7312 |
| 7314 | 7315 | 7319 | 7323 | 7325 | 7327 | 7329 | 7334 | 7335 | 7338 | 7339 | 7343 |
| 7351 | 7353 | 7358 | 7360 | 7361 | 7362 | 7363 | 7365 | 7366 | 7367 | 7368 | 7369 |
| 7370 | 7371 | 7375 | 7379 | 7382 | 7383 | 7384 | 7389 | 7390 | 7392 | 7393 | 7395 |
| 7396 | 7397 | 7398 | 7401 | 7402 | 7404 | 7405 | 7406 | 7409 | 7410 | 7411 | 7412 |
| 7414 | 7417 | 7431 | 7432 | 7433 | 7437 | 7438 | 7440 | 7447 | 7450 | 7454 | 7455 |
| 7457 | 7458 | 7460 | 7462 | 7463 | 7465 | 7466 | 7470 | 7471 | 7472 | 7475 | 7478 |
| 7484 | 7485 | 7486 | 7491 | 7492 | 7493 | 7494 | 7495 | 7498 | 7502 | 7505 | 7506 |
| 7507 | 7509 | 7516 | 7517 | 7521 | 7523 | 7526 | 7527 | 7528 | 7531 | 7533 | 7535 |
| 7536 | 7540 | 7541 | 7545 | 7547 | 7548 | 7549 | 7550 | 7553 | 7556 | 7558 | 7559 |
| 7561 | 7562 | 7565 | 7566 | 7569 | 7570 | 7571 | 7572 | 7573 | 7577 | 7581 | 7582 |
| 7589 | 7590 | 7591 | 7593 | 7594 | 7595 | 7599 | 7600 | 7601 | 7605 | 7606 | 7607 |
| 7614 | 7616 | 7619 | 7622 | 7624 | 7625 | 7627 | 7628 | 7629 | 7631 | 7632 | 7635 |
| 7641 | 7644 | 7645 | 7646 | 7647 | 7650 | 7652 | 7657 | 7660 | 7661 | 7665 | 7669 |
| 7670 | 7671 | 7672 | 7675 | 7681 | 7682 | 7686 | 7689 | 7691 | 7693 | 7697 | 7701 |
| 7702 | 7703 | 7704 | 7705 | 7708 | 7709 | 7710 | 7712 | 7718 | 7720 | 7722 | |
| 7723 | 7729 | 7730 | 7732 | 7738 | 7745 | 7752 | 7753 | 7754 | 7755 | 7758 | 7759 |
| 7760 | 7762 | 7764 | 7765 | 7766 | 7768 | 7769 | 7773 | 7775 | 7778 | 7781 | 7783 |
| 7784 | 7787 | 7788 | 7791 | 7794 | 7796 | 7806 | 7809 | 7810 | 7813 | 7817 | 7818 |
| 7822 | 7824 | 7825 | 7833 | 7835 | 7836 | 7837 | 7838 | 7839 | 7843 | 7844 | 7846 |
| 7852 | 7859 | 7863 | 7864 | 7869 | 7870 | 7875 | 7877 | 7879 | 7881 | 7882 | 7883 |
| 7884 | 7885 | 7897 | 7901 | 7904 | 7905 | 7906 | 7909 | 7918 | 7920 | 7923 | 7925 |
| 7927 | 7928 | 7930 | 7933 | 7934 | 7935 | 7936 | 7937 | 7938 | 7940 | 7942 | 7943 |
| 7945 | 7946 | 7947 | 7948 | 7952 | 7956 | 7957 | 7962 | 7963 | 7969 | 7970 | 7972 |
| 7973 | 7974 | 7975 | 7976 | 7977 | 7984 | 7985 | 7991 | 7994 | 7995 | 8001 | 8002 |
| 8003 | 8004 | 8005 | 8008 | 8009 | 8011 | 8012 | 8013 | 8014 | 8015 | 8016 | 8017 |
| 8018 | 8021 | 8022 | 8024 | 8026 | 8027 | 8030 | 8031 | 8032 | 8034 | 8036 | 8037 |
| 8039 | 8041 | 8045 | 8049 | 8052 | 8054 | 8055 | 8056 | 8063 | 8068 | 8071 | 8072 |
| 8078 | 8084 | 8085 | 8088 | 8092 | 8098 | 8108 | 8109 | 8111 | 8112 | 8113 | 8114 |
| 8115 | 8117 | 8119 | 8120 | 8122 | 8123 | 8124 | 8126 | 8127 | 8128 | 8129 | 8139 |
| 8144 | 8145 | 8147 | 8150 | 8157 | 8158 | 8159 | 8160 | 8162 | 8166 | 8167 | 8170 |
| 8175 | 8180 | 8181 | 8182 | 8183 | 8184 | 8186 | 8187 | 8188 | 8189 | 8195 | 8206 |
| 8207 | 8208 | 8209 | 8212 | 8218 | 8219 | 8222 | 8228 | 8232 | 8235 | 8238 | 8241 |
| 8243 | 8244 | 8245 | 8247 | 8250 | 8251 | 8253 | 8254 | 8262 | 8263 | 8265 | 8268 |
| 8270 | 8271 | 8272 | 8273 | 8274 | 8276 | 8277 | 8283 | 8286 | 8287 | 8290 | 8294 |
| 8295 | 8296 | 8299 | 8305 | 8306 | 8307 | 8309 | 8312 | 8314 | 8321 | 8324 | 8326 |
| 8328 | 8335 | 8337 | 8340 | 8341 | 8342 | 8344 | 8345 | 8346 | 8347 | 8354 | 8355 |
| 8356 | 8357 | 8359 | 8361 | 8365 | 8368 | 8370 | 8371 | 8372 | 8377 | 8379 | 8383 |
| 8384 | 8385 | 8387 | 8391 | 8392 | 8394 | 8396 | 8398 | 8401 | 8404 | 8406 | 8407 |
| 8408 | 8409 | 8411 | 8412 | 8413 | 8414 | 8416 | 8417 | 8425 | 8426 | 8430 | 8432 |
| 8438 | 8442 | 8443 | 8444 | 8446 | 8449 | 8452 | 8458 | 8464 | 8466 | 8467 | 8468 |
| 8469 | 8471 | 8472 | 8483 | 8484 | 8485 | 8486 | 8492 | 8493 | 8494 | 8498 | 8499 |
| 8500 | 8508 | 8512 | 8513 | 8514 | 8515 | 8516 | 8517 | 8521 | 8522 | 8523 | 8524 |
| 8526 | 8528 | 8531 | 8534 | 8539 | 8546 | 8551 | 8552 | 8556 | 8557 | 8564 | 8566 |
| 8567 | 8569 | 8571 | 8572 | 8573 | 8574 | 8578 | 8579 | 8586 | 8587 | 8588 | 8593 |
| 8595 | 8612 | 8614 | 8616 | 8618 | 8619 | 8621 | 8625 | 8627 | 8633 | 8634 | 8645 |
| 8646 | 8651 | 8652 | 8653 | 8654 | 8655 | 8664 | 8667 | 8672 | 8679 | 8683 | 8686 |
| 8688 | 8691 | 8692 | 8693 | 8701 | 8702 | 8706 | 8707 | 8708 | 8712 | 8715 | 8718 |
| 8720 | 8723 | 8728 | 8729 | 8730 | 8731 | 8732 | 8733 | 8734 | 8738 | 8741 | 8742 |
| 8747 | 8748 | 8752 | 8755 | 8762 | 8763 | 8765 | 8766 | 8767 | 8768 | 8769 | 8770 |
| 8774 | 8777 | 8780 | 8781 | 8782 | 8783 | 8793 | 8795 | 8796 | 8802 | 8803 | 8814 |
| 8816 | 8817 | 8819 | 8821 | 8827 | 8828 | 8830 | 8831 | 8832 | 8833 | 8834 | 8847 |
| 8848 | 8850 | 8853 | 8855 | 8860 | 8861 | 8862 | 8864 | 8866 | 8870 | 8871 | 8875 |
| 8876 | 8882 | 8885 | 8890 | 8893 | 8894 | 8895 | 8896 | 8899 | 8900 | 8901 | 8909 |
| 8910 | 8916 | 8917 | 8919 | 8921 | 8923 | 8924 | 8925 | 8927 | 8928 | 8929 | 8931 |
| 8933 | 8934 | 8938 | 8939 | 8940 | 8943 | 8947 | 8958 | 8960 | 8964 | 8965 | 8966 |
| 8973 | 8974 | 8980 | 8981 | 8983 | 8984 | 8985 | 8987 | 8998 | 8999 | 9000 | 9001 |
| 9002 | 9006 | 9012 | 9013 | 9014 | 9015 | 9016 | 9017 | 9018 | 9019 | 9021 | 9022 |
| 9027 | 9028 | 9029 | 9031 | 9035 | 9041 | 9045 | 9046 | 9047 | 9048 | 9051 | 9056 |
| 9058 | 9059 | 9062 | 9063 | 9068 | 9069 | 9072 | 9073 | 9076 | 9078 | 9080 | 9089 |
| 9096 | 9097 | 9104 | 9105 | 9106 | 9109 | 9110 | 9111 | 9114 | 9116 | 9118 | 9132 |
| 9133 | 9136 | 9139 | 9145 | 9147 | 9148 | 9149 | 9151 | 9153 | 9154 | 9156 | |
| 9163 | 9164 | 9165 | 9167 | 9170 | 9171 | 9173 | 9176 | 9177 | 9179 | 9186 | 9192 |
| 9200 | 9201 | 9208 | 9216 | 9218 | 9220 | 9225 | 9229 | 9233 | 9234 | 9235 | 9236 |
| 9238 | 9242 | 9243 | 9244 | 9245 | 9249 | 9254 | 9255 | 9262 | 9264 | 9265 | 9266 |
| 9267 | 9269 | 9270 | 9271 | 9273 | 9274 | 9291 | 9292 | 9293 | 9294 | 9295 | 9296 |
| 9300 | 9304 | 9308 | 9312 | 9323 | 9324 | 9325 | 9326 | 9330 | 9332 | 9333 | 9335 |
| 9348 | 9349 | 9358 | 9361 | 9363 | 9364 | 9368 | 9369 | 9372 | 9373 | 9376 | 9377 |
| 9381 | 9383 | 9387 | 9396 | 9401 | 9405 | 9406 | 9408 | 9410 | 9413 | 9414 | 9418 |
| 9423 | 9424 | 9425 | 9429 | 9434 | 9437 | 9439 | 9440 | 9454 | 9456 | 9463 | 9465 |
| 9466 | 9469 | 9473 | 9475 | 9476 | 9477 | 9483 | 9485 | 9487 | 9489 | 9490 | 9491 |
| 9492 | 9494 | 9495 | 9501 | 9511 | 9514 | 9515 | 9516 | 9517 | 9519 | 9531 | 9542 |
| 9544 | 9547 | 9549 | 9551 | 9554 | 9556 | 9560 | 9563 | 9565 | 9566 | 9569 | 9570 |
| 9574 | 9576 | 9578 | 9579 | 9582 | 9589 | 9592 | 9594 | 9595 | 9598 | 9602 | 9603 |
| 9608 | 9613 | 9614 | 9615 | 9619 | 9620 | 9624 | 9625 | 9627 | 9631 | 9632 | 9633 |

TABLE 15-continued

Yield: Carbohydrate

| | | | | | | | | | | |
|---|---|---|---|---|---|---|---|---|---|---|
| 9636 | 9645 | 9649 | 9650 | 9652 | 9653 | 9669 | 9671 | 9675 | 9681 | 9685 | 9704 |
| 9709 | 9712 | 9713 | 9715 | 9720 | 9725 | 9736 | 9737 | 9738 | 9743 | 9748 | 9759 |
| 9764 | 9766 | 9772 | 9774 | 9776 | 9787 | 9788 | 9789 | 9790 | 9829 | 9831 | 9840 |
| 9851 | 9858 | 9861 | 9863 | 9864 | 9865 | 9866 | 9868 | 9869 | 9876 | 9884 | 9888 |
| 9891 | 9892 | 9893 | 9894 | 9895 | 9896 | 9897 | 9898 | 9909 | 9910 | 9916 | 9920 |
| 9922 | 9926 | 9927 | 9929 | 9935 | 9936 | 9945 | 9946 | 9950 | 9958 | 9960 | 9965 |
| 9968 | 9969 | 9970 | 9976 | 9984 | 9985 | 9987 | 9988 | 9989 | 9990 | 9991 | 9993 |
| 9994 | 9995 | 10002 | 10003 | 10004 | 10005 | 10007 | 10009 | 10010 | 10016 | 10017 | 10019 |
| 10020 | 10021 | 10022 | 10023 | 10024 | 10034 | 10035 | 10037 | 10038 | 10039 | 10042 | 10045 |
| 10047 | 10050 | 10052 | 10053 | 10059 | 10060 | 10061 | 10064 | 10079 | 10084 | 10100 | 10104 |
| 10132 | 10133 | 10136 | 10141 | 10142 | 10144 | 10154 | 10158 | 10164 | 10165 | 10175 | 10179 |
| 10181 | 10182 | 10194 | 10195 | 10197 | 10198 | 10199 | 10200 | 10203 | 10204 | 10205 | 10209 |
| 10214 | 10216 | 10224 | 10225 | 10227 | 10230 | 10231 | 10232 | 10233 | 10234 | 10235 | 10237 |
| 10241 | 10245 | 10246 | 10248 | 10250 | 10253 | 10257 | 10259 | 10260 | 10261 | 10263 | 10264 |
| 10267 | 10268 | 10272 | 10273 | 10279 | 10281 | 10282 | 10283 | 10285 | 10293 | 10296 | 10307 |
| 10309 | 10310 | 10312 | 10325 | 10327 | 10331 | 10337 | 10342 | 10343 | 10344 | 10346 | 10350 |
| 10354 | 10355 | 10361 | 10367 | 10369 | 10374 | 10375 | 10382 | 10384 | 10386 | 10388 | 10395 |
| 10397 | 10399 | 10401 | 10405 | 10406 | 10407 | 10409 | 10410 | 10411 | 10413 | 10415 | 10420 |
| 10422 | 10424 | 10425 | 10427 | 10430 | 10434 | 10435 | 10451 | 10453 | 10460 | 10463 | 10465 |
| 10466 | 10468 | 10469 | 10473 | 10474 | 10477 | 10481 | 10486 | 10488 | 10494 | 10497 | 10499 |
| 10500 | 10501 | 10503 | 10505 | 10509 | 10510 | 10511 | 10516 | 10517 | 10519 | 10520 | 10522 |
| 10523 | 10524 | 10525 | 10526 | 10527 | 10528 | 10531 | 10536 | 10538 | 10540 | 10541 | 10542 |
| 10546 | 10548 | 10551 | 10552 | 10553 | 10556 | 10557 | 10560 | 10561 | 10565 | 10569 | 10571 |
| 10572 | 10573 | 10574 | 10575 | 10577 | 10578 | 10580 | 10581 | 10584 | 10587 | 10588 | 10589 |
| 10590 | 10592 | 10594 | 10596 | 10597 | 10601 | 10602 | 10603 | 10605 | 10611 | 10612 | 10614 |
| 10615 | 10616 | 10627 | 10628 | 10629 | 10630 | 10632 | 10636 | 10641 | 10642 | 10651 | 10652 |
| 10653 | 10654 | 10655 | 10656 | 10657 | 10658 | 10659 | 10660 | 10661 | 10662 | 10663 | 10664 |
| 10665 | 10667 | 10668 | 10674 | 10679 | 10681 | 10682 | 10683 | 10684 | 10689 | 10694 | 10695 |
| 10697 | 10698 | 10700 | 10703 | 10709 | 10710 | 10711 | 10712 | 10713 | 10714 | 10716 | 10718 |
| 10719 | 10720 | 10721 | 10722 | 10723 | 10725 | 10726 | 10727 | 10728 | 10729 | 10731 | 10732 |
| 10733 | 10736 | 10737 | 10738 | 10739 | 10740 | 10742 | 10744 | 10747 | 10748 | 10749 | 10751 |
| 10752 | 10753 | 10758 | 10759 | 10760 | 10761 | 10762 | 10764 | 10765 | 10766 | 10770 | 10771 |
| 10772 | 10774 | 10775 | 10777 | 10784 | 10787 | 10797 | 10798 | 10807 | 10810 | 10811 | 10812 |
| 10815 | 10819 | 10821 | 10823 | 10824 | 10826 | 10828 | 10829 | 10830 | 10831 | 10836 | 10837 |
| 10841 | 10842 | 10844 | 10849 | 10851 | 10852 | 10855 | 10857 | 10859 | 10861 | 10869 | 10882 |
| 10886 | 10888 | 10889 | 10890 | 10895 | 10897 | 10898 | 10900 | 10901 | 10902 | 10906 | 10908 |
| 10913 | 10915 | 10916 | 10920 | 10921 | 10925 | 10927 | 10928 | 10930 | 10931 | 10932 | 10933 |
| 10944 | 10949 | 10950 | 10951 | 10956 | 10957 | 10962 | 10967 | 10968 | 10969 | 10970 | 10971 |
| 10972 | 10974 | 10977 | 10981 | 10982 | 10984 | 10992 | 10993 | 10994 | 10995 | 10997 | 10998 |
| 11000 | 11002 | 11003 | 11004 | 11009 | 11010 | 11012 | 11013 | 11017 | 11021 | 11034 | 11035 |
| 11036 | 11037 | 11041 | 11053 | 11054 | 11057 | 11061 | 11064 | 11065 | 11072 | 11075 | 11079 |
| 11084 | 11085 | 11091 | 11097 | 11099 | 11121 | 11122 | 11124 | 11130 | 11134 | 11135 | 11147 |
| 11157 | 11162 | 11169 | 11172 | 11174 | 11184 | 11186 | 11188 | 11190 | 11192 | 11194 |
| 11195 | 11201 | 11217 | 11218 | 11219 | 11223 | 11225 | 11234 | 11240 | 11242 | 11247 | 11248 |
| 11249 | 11259 | 11264 | 11265 | 11273 | 11281 | 11288 | 11298 | 11301 | 11304 | 11309 | 11312 |
| 11317 | 11318 | 11331 | 11332 | 11336 | 11337 | 11338 | 11344 | 11349 | 11350 | 11357 | 11360 |
| 11362 | 11369 | 11372 | 11373 | 11374 | 11375 | 11376 | 11377 | 11378 | 11381 | 11382 | 11384 |
| 11385 | 11387 | 11388 | 11394 | 11396 | 11397 | 11399 | 11400 | 11401 | 11402 | 11404 | 11406 |
| 11407 | 11409 | 11420 | 11422 | 11424 | 11427 | 11428 | 11429 | 11436 | 11437 | 11438 | 11439 |
| 11440 | 11441 | 11442 | 11443 | 11446 | 11450 | 11452 | 11453 | 11455 | 11456 | 11458 | 11462 |
| 11467 | 11471 | 11474 | 11475 | 11477 | 11478 | 11482 | 11484 | 11486 | 11489 | 11491 | 11492 |
| 11493 | 11494 | 11496 | 11497 | 11501 | 11502 | 11503 | 11504 | 11507 | 11514 | 11516 | 11519 |
| 11520 | 11521 | 11522 | 11523 | 11524 | 11525 | 11526 | 11528 | 11531 | 11532 | 11537 | 11546 |
| 11547 | 11548 | 11550 | 11551 | 11557 | 11558 | 11559 | 11560 | 11564 | 11572 | 11578 | 11579 |
| 11583 | 11585 | 11589 | 11591 | 11594 | 11595 | 11597 | 11598 | 11599 | 11601 | 11603 | 11606 |
| 11608 | 11609 | 11610 | 11613 | 11617 | 11620 | 11626 | 11628 | 11629 | 11631 | 11633 | 11635 |
| 11637 | 11639 | 11640 | 11641 | 11642 | 11643 | 11649 | 11650 | 11651 | 11655 | 11657 | 11661 |
| 11665 | 11666 | 11668 | 11670 | 11671 | 11672 | 11673 | 11674 | 11675 | 11676 | 11677 | 11679 |
| 11680 | 11686 | 11687 | 11692 | 11693 | 11694 | 11695 | 11696 | 11698 | 11701 | 11702 | 11703 |
| 11705 | 11707 | 11711 | 11717 | 11721 | 11723 | 11724 | 11725 | 11726 | 11727 | 11728 | 11731 |
| 11735 | 11737 | 11740 | 11741 | 11744 | 11745 | 11750 | 11751 | 11755 | 11757 | 11761 | 11767 |
| 11768 | 11773 | 11779 | 11780 | 11782 | 11783 | 11788 | 11793 | 11794 | 11799 | 11803 | 11809 |
| 11817 | 11819 | 11820 | 11821 | 11822 | 11823 | 11826 | 11828 | 11832 | 11833 | 11836 | 11837 |
| 11838 | 11839 | 11842 | 11847 | 11855 | 11856 | 11862 | 11863 | 11864 | 11874 | 11875 | 11880 |
| 11881 | 11882 | 11886 | 11888 | 11889 | 11893 | 11895 | 11896 | 11898 | 11900 | 11901 | 11902 |
| 11906 | 11907 | 11909 | 11912 | 11913 | 11915 | 11918 | 11919 | 11923 | 11927 | 11928 | 11931 |
| 11942 | 11943 | 11944 | 11945 | 11948 | 11952 | 11955 | 11957 | 11958 | 11961 | 11962 | 11964 |
| 11965 | 11966 | 11969 | 11971 | 11977 | 11979 | 11981 | 11990 | 11992 | 11995 | 11997 | 11998 |
| 11999 | 12000 | 12001 | 12010 | 12011 | 12012 | 12015 | 12017 | 12018 | 12019 | 12022 | 12027 |
| 12030 | 12031 | 12032 | 12037 | 12038 | 12039 | 12040 | 12041 | 12043 | 12044 | 12047 | 12048 |
| 12049 | 12052 | 12053 | 12054 | 12055 | 12056 | 12057 | 12058 | 12059 | 12060 | 12063 | 12067 |
| 12068 | 12069 | 12070 | 12082 | 12085 | 12091 | 12092 | 12096 | 12097 | 12098 | 12101 | 12106 |
| 12111 | 12112 | 12119 | 12120 | 12121 | 12122 | 12124 | 12125 | 12126 | 12127 | 12128 | 12137 |
| 12139 | 12142 | 12148 | 12149 | 12151 | 12152 | 12155 | 12162 | 12165 | 12168 | 12169 | 12172 |
| 12173 | 12176 | 12178 | 12180 | 12181 | 12191 | 12192 | 12193 | 12195 | 12199 | 12213 | 12214 |
| 12215 | 12218 | 12219 | 12223 | 12225 | 12227 | 12229 | 12237 | 12238 | 12240 | 12242 | 12245 |
| 12251 | 12252 | 12253 | 12254 | 12255 | 12258 | 12267 | 12268 | 12269 | 12270 | 12271 | 12275 |

TABLE 15-continued

Yield: Carbohydrate

| | | | | | | | | | | | |
|---|---|---|---|---|---|---|---|---|---|---|---|
| 12276 | 12277 | 12280 | 12281 | 12285 | 12287 | 12288 | 12293 | 12294 | 12295 | 12297 | 12298 |
| 12299 | 12300 | 12301 | 12302 | 12303 | 12304 | 12305 | 12308 | 12309 | 12310 | 12318 | 12319 |
| 12320 | 12321 | 12322 | 12323 | 12327 | 12328 | 12341 | 12343 | 12350 | 12351 | 12352 | 12356 |
| 12368 | 12370 | 12373 | 12375 | 12376 | 12382 | 12384 | 12388 | 12395 | 12398 | 12402 | 12403 |
| 12404 | 12413 | 12416 | 12417 | 12418 | 12427 | 12428 | 12433 | 12435 | 12436 | 12437 | 12438 |
| 12439 | 12440 | 12446 | 12448 | 12449 | 12450 | 12454 | 12457 | 12458 | 12461 | 12463 | 12467 |
| 12469 | 12471 | 12472 | 12478 | 12480 | 12483 | 12484 | 12486 | 12491 | 12499 | 12500 | 12501 |
| 12517 | 12522 | 12524 | 12526 | 12528 | 12529 | 12532 | 12533 | 12535 | 12536 | 12538 | 12541 |
| 12542 | 12548 | 12554 | 12558 | 12559 | 12565 | 12567 | 12569 | 12570 | 12574 | 12575 | 12577 |
| 12581 | 12590 | 12592 | 12593 | 12597 | 12599 | 12602 | 12607 | 12609 | 12614 | 12618 | 12620 |
| 12626 | 12627 | 12629 | 12630 | 12640 | 12645 | 12657 | 12658 | 12661 | 12666 | 12672 | 12673 |
| 12677 | 12678 | 12682 | 12686 | 12688 | 12695 | 12697 | 12698 | 12700 | 12703 | 12704 | 12706 |
| 12711 | 12712 | 12716 | 12720 | 12722 | 12723 | 12725 | 12730 | 12738 | 12742 | 12743 | 12744 |
| 12751 | 12753 | 12754 | 12755 | 12761 | 12763 | 12765 | 12766 | 12769 | 12773 | 12774 | 12780 |
| 12783 | 12786 | 12788 | 12789 | 12793 | 12797 | 12803 | 12804 | 12806 | 12807 | 12810 | 12812 |
| 12817 | 12821 | 12824 | 12825 | 12830 | 12833 | 12840 | 12845 | 12846 | 12850 | 12854 | 12855 |
| 12860 | 12868 | 12869 | 12872 | 12879 | 12889 | 12890 | 12904 | 12908 | 12910 | 12914 | 12915 |
| 12918 | 12922 | 12923 | 12925 | 12928 | 12931 | 12932 | 12935 | 12939 | 12942 | 12945 | 12946 |
| 12947 | 12949 | 12951 | 12956 | 12957 | 12959 | 12960 | 12963 | 12966 | 12968 | 12971 | 12976 |
| 12977 | 12978 | 12980 | 12984 | 12986 | 12987 | 12992 | 12997 | 12999 | 13000 | 13002 | 13006 |
| 13007 | 13008 | 13018 | 13020 | 13022 | 13023 | 13027 | 13028 | 13030 | 13031 | 13033 | 13035 |
| 13036 | 13042 | 13044 | 13045 | 13047 | 13048 | 13050 | 13051 | 13056 | 13059 | 13065 | 13067 |
| 13069 | 13078 | 13086 | 13089 | 13091 | 13094 | 13103 | 13105 | 13107 | 13109 | 13122 | 13123 |
| 13128 | 13129 | 13139 | 13140 | 13141 | 13144 | 13154 | 13155 | 13163 | 13168 | 13173 | 13178 |
| 13185 | 13187 | 13201 | 13206 | 13210 | 13221 | 13222 | 13226 | 13234 | 13237 | 13249 | 13251 |
| 13252 | 13253 | 13255 | 13259 | 13262 | 13263 | 13279 | 13281 | 13284 | 13302 | 13303 | 13307 |
| 13308 | 13311 | 13321 | 13325 | 13329 | 13330 | 13336 | 13340 | 13347 | 13350 | 13351 | 13352 |
| 13353 | 13354 | 13355 | 13359 | 13361 | 13366 | 13370 | 13391 | 13395 | 13405 | 13422 | 13423 |
| 13424 | 13426 | 13430 | 13431 | 13433 | 13437 | 13438 | 13440 | 13443 | 13444 | 13447 | 13456 |
| 13458 | 13460 | 13461 | 13462 | 13463 | 13464 | 13465 | 13466 | 13467 | 13471 | 13472 | 13473 |
| 13474 | 13475 | 13478 | 13480 | 13484 | 13485 | 13493 | 13497 | 13502 | 13508 | 13509 | 13515 |
| 13516 | 13522 | 13523 | 13525 | 13530 | 13531 | 13535 | 13536 | 13550 | 13551 | 13560 | 13561 |
| 13569 | 13570 | 13571 | 13575 | 13577 | 13579 | 13585 | 13592 | 13593 | 13594 | 13599 | 13603 |
| 13604 | 13606 | 13607 | 13610 | 13615 | 13617 | 13622 | 13626 | 13627 | 13629 | 13634 | 13636 |
| 13639 | 13640 | 13642 | 13646 | 13648 | 13654 | 13655 | 13663 | 13664 | 13665 | 13667 | 13672 |
| 13673 | 13674 | 13675 | 13676 | 13677 | 13678 | 13685 | 13686 | 13689 | 13692 | 13695 | 13696 |
| 13702 | 13705 | 13706 | 13716 | 13718 | 13721 | 13725 | 13726 | 13733 | 13734 | 13736 | 13738 |
| 13740 | 13743 | 13745 | 13746 | 13747 | 13748 | 13751 | 13752 | 13755 | 13761 | 13769 | 13772 |
| 13773 | 13777 | 13779 | 13783 | 13784 | 13785 | 13790 | 13793 | 13794 | 13796 | 13799 | 13800 |
| 13807 | 13812 | 13815 | 13818 | 13819 | 13824 | 13826 | 13827 | 13828 | 13831 | 13832 | 13841 |
| 13848 | 13849 | 13856 | 13860 | 13861 | 13862 | 13864 | 13865 | 13868 | 13869 | 13870 | 13871 |
| 13872 | 13873 | 13874 | 13875 | 13876 | 13877 | 13878 | 13880 | 13885 | 13886 | 13887 | 13890 |
| 13892 | 13893 | 13894 | 13895 | 13900 | 13903 | 13904 | 13905 | 13909 | 13912 | 13915 | 13917 |
| 13919 | 13921 | 13922 | 13925 | 13928 | 13929 | 13931 | 13935 | 13942 | 13944 | 13951 | 13952 |
| 13953 | 13957 | 13960 | 13963 | 13964 | 13968 | 13970 | 13973 | 13975 | 13984 | 13985 | 13986 |
| 13993 | 14000 | 14005 | 14008 | 14010 | 14011 | 14014 | 14017 | 14019 | 14022 | 14032 | 14033 |
| 14034 | 14035 | 14036 | 14038 | 14039 | 14041 | 14044 | 14051 | 14058 | 14067 | 14068 | 14073 |
| 14078 | 14079 | 14081 | 14083 | 14084 | 14085 | 14086 | 14089 | 14093 | 14095 | 14101 | 14102 |
| 14103 | 14104 | 14107 | 14110 | 14113 | 14114 | 14115 | 14116 | 14119 | 14120 | 14121 | 14122 |
| 14128 | 14129 | 14130 | 14132 | 14136 | 14137 | 14139 | 14140 | 14142 | 14143 | 14144 | 14150 |
| 14151 | 14157 | 14158 | 14159 | 14160 | 14164 | 14165 | 14167 | 14173 | 14174 | 14180 | 14182 |
| 14185 | 14189 | 14192 | 14193 | 14196 | 14197 | 14199 | 14201 | 14204 | 14205 | 14209 | 14210 |
| 14211 | 14214 | 14215 | 14219 | 14220 | 14221 | 14222 | 14225 | 14226 | 14230 | 14231 | 14232 |
| 14236 | 14245 | 14251 | 14254 | 14256 | 14257 | 14258 | 14260 | 14262 | 14264 | 14266 | 14268 |
| 14269 | 14273 | 14276 | 14280 | 14281 | 14284 | 14285 | 14286 | 14287 | 14289 | 14291 | 14297 |
| 14298 | 14299 | 14300 | 14302 | 14303 | 14304 | 14306 | 14308 | 14310 | 14312 | 14314 | 14316 |
| 14321 | 14322 | 14324 | 14325 | 14326 | 14327 | 14328 | 14329 | 14338 | 14343 | 14344 | 14345 |
| 14349 | 14352 | 14355 | 14356 | 14357 | 14359 | 14361 | 14364 | 14365 | 14366 | 14369 | 14370 |
| 14375 | 14376 | 14382 | 14386 | 14389 | 14394 | 14398 | 14399 | 14401 | 14405 | 14406 | 14408 |
| 14410 | 14412 | 14413 | 14416 | 14417 | 14422 | 14423 | 14424 | 14427 | 14428 | 14429 | 14432 |
| 14437 | 14439 | 14440 | 14444 | 14445 | 14447 | 14450 | 14454 | 14455 | 14463 | 14468 | 14469 |
| 14476 | 14478 | 14480 | 14485 | 14486 | 14488 | 14489 | 14490 | 14491 | 14492 | 14496 | 14497 |
| 14500 | 14502 | 14503 | 14509 | 14510 | 14512 | 14525 | 14526 | 14527 | 14530 | 14533 | 14534 |
| 14535 | 14538 | 14545 | 14549 | 14551 | 14555 | 14559 | 14560 | 14562 | 14563 | 14564 | 14565 |
| 14569 | 14571 | 14573 | 14576 | 14577 | 14584 | 14585 | 14586 | 14587 | 14588 | 14589 | 14591 |
| 14592 | 14597 | 14604 | 14608 | 14611 | 14612 | 14613 | 14614 | 14617 | 14618 | 14619 | 14620 |
| 14624 | 14626 | 14630 | 14631 | 14633 | 14634 | 14636 | 14637 | 14638 | 14639 | 14640 | 14641 |
| 14642 | 14643 | 14646 | 14651 | 14654 | 14658 | 14660 | 14662 | 14665 | 14667 | 14680 |
| 14681 | 14682 | 14683 | 14684 | 14688 | 14691 | 14692 | 14694 | 14695 | 14697 | 14698 | 14702 |
| 14703 | 14705 | 14706 | 14709 | 14712 | 14715 | 14716 | 14717 | 14719 | 14720 | 14724 | 14728 |
| 14731 | 14733 | 14734 | 14735 | 14736 | 14737 | 14738 | 14739 | 14741 | 14743 | 14744 | 14748 |
| 14755 | 14757 | 14765 | 14766 | 14770 | 14773 | 14777 | 14778 | 14779 | 14780 | 14781 | 14782 |
| 14783 | 14784 | 14790 | 14791 | 14793 | 14802 | 14803 | 14806 | 14808 | 14809 | 14814 | 14817 |
| 14819 | 14820 | 14821 | 14823 | 14825 | 14826 | 14827 | 14828 | 14829 | 14831 | 14833 | 14834 |
| 14835 | 14836 | 14837 | 14838 | 14839 | 14842 | 14843 | 14845 | 14852 | 14855 | 14858 | 14859 |
| 14860 | 14861 | 14865 | 14870 | 14872 | 14873 | 14874 | 14875 | 14876 | 14877 | 14878 | 14880 |
| 14882 | 14886 | 14888 | 14889 | 14893 | 14895 | 14896 | 14898 | 14900 | 14904 | 14908 | 14915 |

TABLE 15-continued

Yield: Carbohydrate

| | | | | | | | | | | | |
|---|---|---|---|---|---|---|---|---|---|---|---|
| 14920 | 14927 | 14930 | 14931 | 14932 | 14933 | 14934 | 14935 | 14936 | 14937 | 14938 | 14939 |
| 14940 | 14941 | 14942 | 14943 | 14944 | 14952 | 14955 | 14957 | 14958 | 14959 | 14971 | 14976 |
| 14979 | 14982 | 14985 | 14988 | 14994 | 14997 | 15001 | 15002 | 15005 | 15006 | 15008 | 15009 |
| 15010 | 15011 | 15012 | 15015 | 15016 | 15017 | 15019 | 15022 | 15023 | 15024 | 15027 | 15028 |
| 15030 | 15033 | 15036 | 15044 | 15048 | 15049 | 15050 | 15051 | 15052 | 15055 | 15056 | 15057 |
| 15058 | 15059 | 15063 | 15065 | 15066 | 15067 | 15070 | 15073 | 15075 | 15077 | 15082 | 15083 |
| 15088 | 15091 | 15095 | 15096 | 15098 | 15099 | 15100 | 15101 | 15102 | 15104 | 15105 | 15107 |
| 15111 | 15114 | 15117 | 15120 | 15127 | 15131 | 15135 | 15137 | 15139 | 15140 | 15142 | 15143 |
| 15147 | 15148 | 15158 | 15161 | 15163 | 15165 | 15166 | 15167 | 15168 | 15169 | 15174 | 15176 |
| 15178 | 15179 | 15180 | 15181 | 15184 | 15186 | 15188 | 15189 | 15192 | 15196 | 15197 | 15198 |
| 15200 | 15201 | 15204 | 15208 | 15211 | 15213 | 15214 | 15215 | 15218 | 15219 | 15220 | 15221 |
| 15222 | 15223 | 15226 | 15231 | 15234 | 15236 | 15241 | 15242 | 15256 | 15257 | 15258 | 15260 |
| 15261 | 15268 | 15269 | 15270 | 15271 | 15272 | 15273 | 15276 | 15287 | 15291 | 15295 | 15301 |
| 15302 | 15306 | 15307 | 15308 | 15314 | 15329 | 15332 | 15334 | 15335 | 15336 | 15337 | 15341 |
| 15342 | 15343 | 15350 | 15351 | 15353 | 15357 | 15358 | 15359 | 15361 | 15362 | 15363 | 15366 |
| 15368 | 15370 | 15373 | 15374 | 15375 | 15379 | 15382 | 15385 | 15390 | 15394 | 15395 | 15397 |
| 15399 | 15400 | 15402 | 15417 | 15420 | 15426 | 15427 | 15428 | 15434 | 15435 | 15442 | 15444 |
| 15446 | 15448 | 15454 | 15455 | 15456 | 15459 | 15461 | 15466 | 15469 | 15470 | 15472 | 15478 |
| 15479 | 15481 | 15482 | 15483 | 15484 | 15485 | 15486 | 15493 | 15494 | 15495 | 15497 | 15498 |
| 15511 | 15512 | 15513 | 15521 | 15523 | 15525 | 15527 | 15533 | 15535 | 15538 | 15541 | 15548 |
| 15551 | 15553 | 15555 | 15560 | 15561 | 15562 | 15563 | 15564 | 15566 | 15567 | 15570 | 15571 |
| 15572 | 15574 | 15576 | 15577 | 15579 | 15580 | 15581 | 15583 | 15586 | 15590 | 15595 | 15597 |
| 15598 | 15604 | 15607 | 15608 | 15611 | 15612 | 15613 | 15614 | 15615 | 15616 | 15618 | 15621 |
| 15622 | 15623 | 15640 | 15641 | 15646 | 15661 | 15667 | 15668 | 15672 | 15673 | 15674 | 15680 |
| 15696 | 15699 | 15701 | 15702 | 15703 | 15704 | 15709 | 15710 | 15717 | 15718 | 15720 | 15724 |
| 15725 | 15726 | 15728 | 15729 | 15730 | 15733 | 15735 | 15737 | 15740 | 15741 | 15742 | 15743 |
| 15747 | 15750 | 15753 | 15758 | 15762 | 15763 | 15765 | 15767 | 15768 | 15770 | 15785 | 15788 |
| 15794 | 15795 | 15796 | 15802 | 15803 | 15811 | 15812 | 15814 | 15816 | 15822 | 15823 | 15824 |
| 15827 | 15829 | 15836 | 15839 | 15840 | 15842 | 15848 | 15849 | 15851 | 15852 | 15853 | 15854 |
| 15855 | 15856 | 15857 | 15864 | 15865 | 15866 | 15868 | 15869 | 15883 | 15884 | 15885 | 15892 |
| 15894 | 15896 | 15898 | 15904 | 15906 | 15909 | 15912 | 15914 | 15920 | 15924 | 15926 | 15928 |
| 15933 | 15934 | 15935 | 15936 | 15937 | 15939 | 15940 | 15943 | 15944 | 15945 | 15947 | 15951 |
| 15952 | 15953 | 15955 | 15956 | 15957 | 15959 | 15962 | 15966 | 15972 | 15974 | 15975 | 15979 |
| 15982 | 15983 | 15985 | 15987 | 15988 | 15989 | 15990 | 15991 | 15993 | 15996 | 15997 | 15998 |
| 16015 | 16016 | 16021 | 16048 | 16050 | 16052 | 16057 | 16058 | 16062 | 16063 | 16064 | 16071 |
| 16087 | 16090 | 16092 | 16093 | 16094 | 16095 | 16099 | 16100 | 16105 | 16106 | 16109 | 16110 |
| 16112 | 16113 | 16114 | 16115 | 16119 | 16120 | 16122 | 16123 | 16126 | 16127 | 16131 | 16134 |
| 16137 | 16142 | 16146 | 16147 | 16149 | 16151 | 16152 | 16154 | 16167 | 16170 | 16176 | 16177 |
| 16178 | 16184 | 16185 | 16190 | 16194 | 16196 | 16198 | 16203 | 16204 | 16205 | 16209 | 16210 |
| 16218 | 16219 | 16220 | 16221 | 16227 | 16229 | 16230 | 16231 | 16232 | 16233 | 16234 | 16239 |
| 16241 | 16242 | 16244 | 16256 | 16257 | 16258 | 16265 | 16267 | 16272 | 16276 | 16277 | 16280 |
| 16282 | 16289 | 16291 | 16294 | 16295 | 16300 | 16301 | 16302 | 16303 | 16305 | 16306 | 16310 |
| 16311 | 16312 | 16313 | 16315 | 16316 | 16317 | 16319 | 16320 | 16321 | 16322 | 16327 | 16332 |
| 16336 | 16338 | 16341 | 16344 | 16345 | 16346 | 16347 | 16348 | 16349 | 16357 | 16368 | 16369 |
| 16377 | 16378 | 16379 | 16380 | 16384 | 16385 | 16386 | 16387 | 16391 | 16394 | 16400 | 16402 |
| 16403 | 16404 | 16410 | 16416 | 16418 | 16420 | 16421 | 16423 | 16425 | 16427 | 16429 | 16430 |
| 16434 | 16438 | 16440 | 16441 | 16442 | 16445 | 16451 | 16454 | 16457 | 16460 | 16462 | 16464 |
| 16465 | 16466 | 16470 | 16474 | 16478 | 16480 | 16482 | 16488 | 16505 | 16508 | 16512 | 16513 |
| 16514 | 16517 | 16518 | 16525 | 16531 | 16532 | 16533 | 16536 | 16537 | 16542 | 16544 | 16545 |
| 16556 | 16558 | 16559 | 16560 | 16561 | 16564 | 16569 | 16571 | 16580 | 16581 | 16583 | 16585 |
| 16587 | 16588 | 16589 | 16592 | 16595 | 16596 | 16597 | 16600 | 16601 | 16603 | 16604 | 16605 |
| 16606 | 16612 | 16616 | 16617 | 16628 | 16629 | 16632 | 16634 | 16642 | 16643 | 16644 |
| 16646 | 16647 | 16650 | 16651 | 16663 | 16664 | 16675 | 16676 | 16677 | 16678 | 16679 | 16681 |
| 16692 | 16693 | 16694 | 16698 | 16700 | 16703 | 16705 | 16707 | 16708 | 16718 | 16719 | 16720 |
| 16721 | 16723 | 16727 | 16730 | 16731 | 16734 | 16735 | 16746 | 16748 | 16749 | 16751 | 16756 |
| 16759 | 16761 | 16762 | 16763 | 16764 | 16766 | 16771 | 16773 | 16774 | 16779 | 16782 | 16783 |
| 16784 | 16785 | 16786 | 16789 | 16790 | 16792 | 16793 | 16794 | 16797 | 16808 | 16811 | 16812 |
| 16816 | 16823 | 16824 | 16827 | 16829 | 16830 | 16835 | 16839 | 16844 | 16846 | 16851 | 16855 |
| 16856 | 16860 | 16863 | 16865 | 16869 | 16870 | 16878 | 16882 | 16885 | 16888 | 16890 | 16892 |
| 16893 | 16897 | 16900 | 16902 | 16903 | 16905 | 16906 | 16907 | 16908 | 16911 | 16912 | 16913 |
| 16914 | 16915 | 16917 | 16924 | 16926 | 16928 | 16929 | 16931 | 16932 | 16940 | 16941 | 16945 |
| 16947 | 16949 | 16951 | 16954 | 16956 | 16966 | 16967 | 16968 | 16969 | 16970 | 16971 | 16974 |
| 16978 | 16979 | 16980 | 16981 | 16982 | 16983 | 16985 | 16996 | 17003 | 17005 | 17011 | 17012 |
| 17018 | 17021 | 17028 | 17031 | 17032 | 17036 | 17043 | 17044 | 17045 | 17050 | 17051 | 17052 |
| 17056 | 17063 | 17067 | 17068 | 17072 | 17073 | 17075 | 17077 | 17078 | 17079 | 17080 | 17085 |
| 17086 | 17111 | 17113 | 17114 | 17115 | 17116 | 17117 | 17118 | 17120 | 17127 | 17129 | 17133 |
| 17140 | 17141 | 17142 | 17144 | 17145 | 17146 | 17147 | 17148 | 17150 | 17152 | 17156 | 17157 |
| 17158 | 17162 | 17164 | 17165 | 17169 | 17171 | 17176 | 17177 | 17178 | 17179 | 17180 | 17181 |
| 17182 | 17183 | 17184 | 17185 | 17190 | 17192 | 17201 | 17212 | 17213 | 17214 | 17223 | 17224 |
| 17225 | 17249 | 17251 | 17252 | 17253 | 17254 | 17255 | 17256 | 17257 | 17258 | 17260 | 17261 |
| 17262 | 17264 | 17266 | 17267 | 17268 | 17269 | 17270 | 17272 | 17277 | 17279 | 17280 | 17281 |
| 17282 | 17285 | 17286 | 17287 | 17288 | 17289 | 17290 | 17291 | 17296 | 17297 | 17298 | 17301 |
| 17306 | 17307 | 17308 | 17314 | 17321 | 17322 | 17324 | 17325 | 17338 | 17339 | 17340 | 17341 |
| 17342 | 17344 | 17345 | 17349 | 17350 | 17351 | 17352 | 17353 | 17354 | 17355 | 17356 | 17360 |
| 17361 | 17364 | 17366 | 17367 | 17375 | 17376 | 17388 | 17389 | 17392 | 17394 | 17395 | 17396 |
| 17397 | 17398 | 17399 | 17400 | 17403 | 17405 | 17408 | 17410 | 17411 | 17412 | 17413 | 17417 |
| 17418 | 17427 | 17430 | 17433 | 17434 | 17435 | 17436 | 17437 | 17442 | 17444 | 17445 | 17446 |

TABLE 15-continued

Yield: Carbohydrate

| | | | | | | | | | | | |
|---|---|---|---|---|---|---|---|---|---|---|---|
| 17447 | 17448 | 17449 | 17450 | 17451 | 17458 | 17464 | 17465 | 17467 | 17470 | 17472 | 17473 |
| 17474 | 17475 | 17489 | 17495 | 17496 | 17498 | 17502 | 17505 | 17506 | 17508 | 17509 | 17511 |
| 17512 | 17513 | 17515 | 17516 | 17518 | 17528 | 17529 | 17530 | 17531 | 17534 | 17536 | 17537 |
| 17538 | 17539 | 17541 | 17542 | 17543 | 17553 | 17554 | 17555 | 17556 | 17568 | 17572 | 17573 |
| 17578 | 17594 | 17595 | 17601 | 17602 | 17603 | 17604 | 17605 | 17606 | 17610 | 17611 | 17613 |
| 17616 | 17618 | 17619 | 17625 | 17630 | 17631 | 17632 | 17633 | 17645 | 17646 | 17647 | 17648 |
| 17649 | 17652 | 17653 | 17658 | 17660 | 17661 | 17662 | 17663 | 17664 | 17665 | 17666 | 17674 |
| 17677 | 17678 | 17680 | 17681 | 17694 | 17695 | 17696 | 17700 | 17705 | 17711 | 17715 | 17719 |
| 17720 | 17721 | 17722 | 17724 | 17725 | 17740 | 17741 | 17742 | 17747 | 17754 | 17756 | 17761 |
| 17764 | 17768 | 17769 | 17770 | 17776 | 17777 | 17778 | 17780 | 17781 | 17783 | 17784 | 17785 |
| 17791 | 17795 | 17796 | 17803 | 17804 | 17808 | 17813 | 17818 | 17819 | 17825 | 17827 | 17831 |
| 17832 | 17834 | 17835 | 17836 | 17837 | 17838 | 17839 | 17840 | 17841 | 17846 | 17848 | 17853 |
| 17854 | 17860 | 17863 | 17864 | 17865 | 17866 | 17867 | 17868 | 17869 | 17872 | 17876 | 17877 |
| 17878 | 17881 | 17883 | 17884 | 17885 | 17886 | 17887 | 17900 | 17901 | 17903 | 17905 | 17906 |
| 17909 | 17916 | 17926 | 17929 | 17931 | 17932 | 17935 | 17942 | 17943 | 17947 | 17949 | 17950 |
| 17951 | 17955 | 17956 | 17958 | 17964 | 17966 | 17968 | 17980 | 17982 | 17983 | 17989 | 17991 |
| 17996 | 17997 | 17998 | 17999 | 18002 | 18004 | 18006 | 18007 | 18009 | 18011 | 18012 | 18013 |
| 18015 | 18016 | 18020 | 18021 | 18024 | 18028 | 18029 | 18034 | 18036 | 18041 | 18042 | 18043 |
| 18045 | 18048 | 18049 | 18050 | 18051 | 18054 | 18061 | 18062 | 18063 | 18064 | 18066 | 18068 |
| 18084 | 18086 | 18098 | 18099 | 18101 | 18102 | 18104 | 18107 | 18108 | 18111 | 18112 | 18114 |
| 18116 | 18120 | 18121 | 18122 | 18131 | 18133 | 18138 | 18139 | 18147 | 18148 | 18151 | 18152 |
| 18154 | 18155 | 18164 | 18165 | 18170 | 18171 | 18173 | 18183 | 18185 | 18188 | 18189 | 18190 |
| 18191 | 18193 | 18199 | 18201 | 18209 | 18210 | 18211 | 18212 | 18220 | 18226 | 18227 | 18236 |
| 18237 | 18241 | 18242 | 18254 | 18255 | 18259 | 18263 | 18265 | 18266 | 18267 | 18270 | 18271 |
| 18273 | 18274 | 18275 | 18276 | 18277 | 18278 | 18282 | 18288 | 18292 | 18293 | 18294 | 18295 |
| 18298 | 18303 | 18305 | 18307 | 18312 | 18313 | 18317 | 18318 | 18323 | 18324 | 18330 | 18336 |
| 18337 | 18342 | 18343 | 18344 | 18346 | 18349 | 18351 | 18352 | 18353 | 18354 | 18356 | 18357 |
| 18358 | 18359 | 18360 | 18367 | 18368 | 18370 | 18371 | 18372 | 18373 | 18374 | 18377 | 18386 |
| 18388 | 18394 | 18395 | 18396 | 18401 | 18402 | 18403 | 18405 | 18413 | 18414 | 18416 | 18417 |
| 18418 | 18425 | 18429 | 18430 | 18431 | 18432 | 18433 | 18441 | 18442 | 18443 | 18444 | 18449 |
| 18464 | 18467 | 18468 | 18471 | 18473 | 18474 | 18475 | 18476 | 18480 | 18489 | 18490 | 18497 |
| 18500 | 18501 | 18503 | 18505 | 18506 | 18512 | 18513 | 18517 | 18518 | 18522 | 18524 | 18528 |
| 18529 | 18530 | 18531 | 18534 | 18535 | 18544 | 18545 | 18553 | 18555 | 18559 | 18565 | 18576 |
| 18580 | 18583 | 18584 | 18585 | 18593 | 18594 | 18598 | 18599 | 18604 | 18614 | 18617 | 18618 |
| 18621 | 18622 | 18634 | 18635 | 18636 | 18652 | 18653 | 18655 | 18656 | 18658 | 18660 | 18668 |
| 18669 | 18675 | 18680 | 18681 | 18682 | 18683 | 18684 | 18690 | 18697 | 18704 | 18711 | 18712 |
| 18713 | 18715 | 18719 | 18723 | 18735 | 18743 | 18744 | 18749 | 18759 | 18760 | 18761 | 18765 |
| 18766 | 18767 | 18768 | 18775 | 18776 | 18777 | 18778 | 18781 | 18782 | 18783 | 18801 | 18802 |
| 18804 | 18809 | 18811 | 18822 | 18824 | 18825 | 18828 | 18829 | 18837 | 18839 | 18846 | 18856 |
| 18858 | 18863 | 18876 | 18879 | 18896 | 18897 | 18898 | 18912 | 18915 | 18918 | 18922 | 18928 |
| 18933 | 18937 | 18940 | 18950 | 18953 | 18958 | 18959 | 18964 | 18966 | 18971 | 18972 | 18973 |
| 18977 | 18978 | 18980 | 18981 | 18986 | 18995 | 18996 | 19000 | 19009 | 19010 | 19011 | 19017 |
| 19020 | 19023 | 19026 | 19030 | 19038 | 19040 | 19043 | 19049 | 19062 | 19066 | 19067 |
| 19070 | 19074 | 19075 | 19076 | 19077 | 19080 | 19084 | 19085 | 19089 | 19094 | 19097 | 19100 |
| 19101 | 19102 | 19107 | 19115 | 19122 | 19125 | 19127 | 19129 | 19137 | 19145 | 19155 | 19156 |
| 19163 | 19164 | 19171 | 19173 | 19174 | 19176 | 19178 | 19180 | 19182 | 19183 | 19187 | 19193 |
| 19197 | 19198 | 19200 | 19201 | 19202 | 19203 | 19205 | 19214 | 19216 | 19221 | 19222 | 19223 |
| 19231 | 19234 | 19238 | 19239 | 19240 | 19242 | 19243 | 19246 | 19250 | 19253 | 19255 | 19258 |
| 19259 | 19261 | 19262 | 19269 | 19271 | 19273 | 19282 | 19283 | 19289 | 19292 | 19293 | 19295 |
| 19307 | 19309 | 19311 | 19312 | 19316 | 19330 | 19331 | 19333 | 19334 | 19339 | 19341 | 19342 |
| 19346 | 19347 | 19348 | 19351 | 19352 | 19355 | 19361 | 19365 | 19368 | 19369 | 19370 | 19372 |
| 19373 | 19376 | 19377 | 19378 | 19379 | 19383 | 19390 | 19394 | 19396 | 19397 | 19398 | 19401 |
| 19408 | 19414 | 19415 | 19416 | 19417 | 19418 | 19419 | 19422 | 19425 | 19429 | 19441 | 19442 |
| 19444 | 19445 | 19446 | 19447 | 19448 | 19449 | 19450 | 19451 | 19456 | 19472 | 19477 | 19478 |
| 19479 | 19484 | 19488 | 19491 | 19493 | 19494 | 19495 | 19497 | 19498 | 19499 | 19501 | 19502 |
| 19504 | 19517 | 19523 | 19524 | 19528 | 19530 | 19534 | 19538 | 19539 | 19540 | 19546 | 19551 |
| 19552 | 19554 | 19555 | 19556 | 19566 | 19567 | 19570 | 19574 | 19581 | 19584 | 19585 | 19587 |
| 19589 | 19590 | 19593 | 19594 | 19597 | 19614 | 19620 | 19621 | 19622 | 19623 | 19630 | 19632 |
| 19635 | 19638 | 19639 | 19661 | 19663 | 19664 | 19667 | 19668 | 19671 | 19672 | 19682 | 19688 |
| 19689 | 19690 | 19691 | 19695 | 19702 | 19703 | 19705 | 19706 | 19712 | 19715 | 19716 | 19717 |
| 19718 | 19719 | 19721 | 19723 | 19735 | 19739 | 19740 | 19741 | 19742 | 19743 | 19745 | 19751 |
| 19752 | 19753 | 19760 | 19763 | 19769 | 19770 | 19771 | 19776 | 19777 | 19781 | 19787 | 19793 |
| 19797 | 19799 | 19801 | 19802 | 19804 | 19806 | 19807 | 19808 | 19809 | 19810 | 19812 | 19814 |
| 19817 | 19820 | 19822 | 19825 | 19828 | 19835 | 19838 | 19840 | 19844 | 19845 | 19848 |
| 19849 | 19850 | 19854 | 19858 | 19859 | 19862 | 19866 | 19867 | 19871 | 19872 | 19873 | 19874 |
| 19881 | 19882 | 19884 | 19888 | 19889 | 19893 | 19894 | 19897 | 19901 | 19904 | 19906 | 19907 |
| 19908 | 19913 | 19925 | 19927 | 19935 | 19940 | 19948 | 19949 | 19951 | 19957 | 19958 | 19959 |
| 19960 | 19965 | 19966 | 19970 | 19973 | 19978 | 19979 | 19990 | 19992 | 19995 | 19996 |
| 19999 | 20010 | 20011 | 20014 | 20016 | 20018 | 20020 | 20026 | 20030 | 20032 | 20034 | 20043 |
| 20044 | 20045 | 20049 | 20051 | 20054 | 20056 | 20060 | 20062 | 20063 | 20070 | 20071 | 20074 |
| 20076 | 20077 | 20080 | 20083 | 20086 | 20093 | 20097 | 20099 | 20100 | 20105 | 20106 | 20107 |
| 20109 | 20116 | 20128 | 20132 | 20133 | 20136 | 20138 | 20146 | 20153 | 20154 | 20159 | 20160 |
| 20161 | 20162 | 20163 | 20165 | 20170 | 20177 | 20182 | 20190 | 20193 | 20195 | 20202 | 20218 |
| 20222 | 20228 | 20235 | 20244 | 20245 | 20249 | 20250 | 20251 | 20258 | 20267 | 20271 | 20275 |
| 20279 | 20280 | 20282 | 20284 | 20286 | 20298 | 20302 | 20303 | 20304 | 20306 | 20307 | 20310 |
| 20313 | 20329 | 20330 | 20336 | 20340 | 20347 | 20348 | 20350 | 20369 | 20378 | 20381 | 20386 |
| 20391 | 20393 | 20396 | 20402 | 20404 | 20405 | 20415 | 20416 | 20417 | 20420 | 20423 | 20424 |

TABLE 15-continued

Yield: Carbohydrate

| | | | | | | | | | | | |
|---|---|---|---|---|---|---|---|---|---|---|---|
| 20425 | 20430 | 20431 | 20433 | 20452 | 20454 | 20456 | 20457 | 20463 | 20464 | 20465 | 20466 |
| 20467 | 20468 | 20470 | 20471 | 20473 | 20476 | 20481 | 20482 | 20489 | 20490 | 20491 | 20493 |
| 20496 | 20497 | 20498 | 20502 | 20503 | 20505 | 20506 | 20508 | 20509 | 20513 | 20518 | 20519 |
| 20522 | 20523 | 20525 | 20528 | 20531 | 20532 | 20533 | 20537 | 20540 | 20541 | 20542 | 20544 |
| 20545 | 20553 | 20555 | 20559 | 20563 | 20564 | 20567 | 20568 | 20570 | 20574 | 20577 | 20579 |
| 20583 | 20584 | 20585 | 20588 | 20592 | 20593 | 20594 | 20602 | 20603 | 20604 | 20606 | 20608 |
| 20612 | 20615 | 20616 | 20622 | 20624 | 20626 | 20631 | 20636 | 20637 | 20640 | 20647 | 20649 |
| 20656 | 20657 | 20661 | 20662 | 20663 | 20664 | 20665 | 20666 | 20670 | 20673 | 20674 | 20682 |
| 20688 | 20692 | 20693 | 20701 | 20705 | 20706 | 20707 | 20708 | 20710 | 20712 | 20713 | 20714 |
| 20716 | 20722 | 20725 | 20726 | 20729 | 20742 | 20744 | 20745 | 20746 | 20747 | 20748 | 20749 |
| 20750 | 20751 | 20752 | 20753 | 20754 | 20760 | 20761 | 20762 | 20769 | 20773 | 20780 | 20784 |
| 20789 | 20792 | 20793 | 20797 | 20800 | 20801 | 20804 | 20807 | 20809 | 20816 | 20817 | 20821 |
| 20823 | 20824 | 20825 | 20826 | 20827 | 20828 | 20836 | 20837 | 20838 | 20839 | 20844 | 20845 |
| 20846 | 20848 | 20849 | 20850 | 20854 | 20856 | 20859 | 20865 | 20866 | 20867 | 20874 | 20875 |
| 20876 | 20878 | 20883 | 20884 | 20886 | 20887 | 20889 | 20895 | 20897 | 20898 | 20899 | 20903 |
| 20916 | 20920 | 20924 | 20931 | 20932 | 20939 | 20943 | 20946 | 20951 | 20959 | 20960 | 20968 |
| 20971 | 20973 | 20977 | 20980 | 20986 | 20987 | 20988 | 20989 | 20990 | 20991 | 20998 | 20999 |
| 21003 | 21006 | 21021 | 21025 | 21031 | 21034 | 21035 | 21037 | 21038 | 21042 | 21044 | 21046 |
| 21047 | 21048 | 21049 | 21054 | 21057 | 21062 | 21064 | 21066 | 21068 | 21070 | 21071 | 21072 |
| 21074 | 21075 | 21077 | 21084 | 21086 | 21087 | 21091 | 21092 | 21094 | 21097 | 21101 | 21103 |
| 21104 | 21107 | 21111 | 21114 | 21124 | 21127 | 21130 | 21132 | 21133 | 21135 | 21142 | 21143 |
| 21146 | 21147 | 21149 | 21156 | 21162 | 21164 | 21166 | 21167 | 21168 | 21172 | 21175 | 21180 |
| 21183 | 21184 | 21185 | 21186 | 21187 | 21189 | 21190 | 21191 | 21193 | 21194 | 21200 | 21204 |
| 21205 | 21206 | 21209 | 21210 | 21211 | 21214 | 21219 | 21220 | 21245 | 21246 | 21248 | 21249 |
| 21252 | 21253 | 21262 | 21263 | 21267 | 21271 | 21277 | 21283 | 21291 | 21295 | 21298 | 21302 |
| 21303 | 21304 | 21311 | 21312 | 21313 | 21314 | 21317 | 21318 | 21324 | 21331 | 21333 | 21334 |
| 21335 | 21339 | 21348 | 21354 | 21355 | 21363 | 21364 | 21365 | 21373 | 21375 | 21377 | 21379 |
| 21381 | 21385 | 21389 | 21391 | 21402 | 21410 | 21411 | 21412 | 21416 | 21428 | 21430 | 21432 |
| 21436 | 21445 | 21449 | 21458 | 21459 | 21462 | 21466 | 21467 | 21471 | 21479 | 21483 | 21487 |
| 21501 | 21507 | 21512 | 21518 | 21520 | 21521 | 21525 | 21530 | 21533 | 21534 | 21535 | 21536 |
| 21539 | 21540 | 21546 | 21551 | 21552 | 21557 | 21560 | 21562 | 21563 | 21564 | 21576 | 21579 |
| 21582 | 21585 | 21597 | 21617 | 21618 | 21620 | 21624 | 21630 | 21637 | 21638 | 21639 | 21642 |
| 21644 | 21657 | 21658 | 21659 | 21661 | 21662 | 21666 | 21671 | 21675 | 21676 | 21681 | 21682 |
| 21686 | 21687 | 21695 | 21697 | 21700 | 21701 | 21702 | 21705 | 21706 | 21707 | 21711 | 21712 |
| 21713 | 21714 | 21715 | 21716 | 21717 | 21718 | 21720 | 21721 | 21723 | 21726 | 21730 | 21731 |
| 21732 | 21733 | 21734 | 21735 | 21736 | 21737 | 21738 | 21740 | 21741 | 21742 | 21745 | 21754 |
| 21758 | 21759 | 21760 | 21761 | 21762 | 21766 | 21768 | 21769 | 21776 | 21779 | 21781 | 21783 |
| 21789 | 21793 | 21800 | 21801 | 21806 | 21813 | 21816 | 21819 | 21820 | 21824 | 21825 | 21831 |
| 21833 | 21841 | 21844 | 21845 | 21847 | 21856 | 21857 | 21860 | 21861 | 21862 | 21864 | 21870 |
| 21873 | 21883 | 21893 | 21896 | 21906 | 21908 | 21920 | 21930 | 21939 | 21946 | 21947 | 21952 |
| 21962 | 21966 | 21972 | 21975 | 21992 | 21996 | 21998 | 21999 | 22001 | 22002 | 22011 | 22012 |
| 22013 | 22015 | 22017 | 22020 | 22032 | 22033 | 22035 | 22036 | 22044 | 22046 | 22047 | 22048 |
| 22049 | 22053 | 22061 | 22062 | 22066 | 22071 | 22072 | 22074 | 22075 | 22078 | 22079 | 22088 |
| 22091 | 22096 | 22097 | 22102 | 22106 | 22107 | 22108 | 22115 | 22116 | 22121 | 22122 | 22124 |
| 22125 | 22126 | 22127 | 22130 | 22134 | 22135 | 22163 | 22165 | 22180 | 22194 | 22200 | 22201 |
| 22206 | 22209 | 22210 | 22212 | 22213 | 22219 | 22230 | 22231 | 22232 | 22234 | 22235 | 22238 |
| 22239 | 22248 | 22254 | 22259 | 22260 | 22261 | 22269 | 22277 | 22286 | 22295 | 22309 | 22313 |
| 22325 | 22326 | 22327 | 22329 | 22331 | 22332 | 22335 | 22337 | 22346 | 22348 | 22361 | 22372 |
| 22377 | 22378 | 22384 | 22401 | 22402 | 22414 | 22417 | 22418 | 22419 | 22430 | 22438 | 22440 |
| 22441 | 22448 | 22451 | 22463 | 22491 | 22495 | 22500 | 22502 | 22503 | 22506 | 22508 | 22510 |
| 22514 | 22520 | 22533 | 22536 | 22549 | 22572 | 22578 | 22585 | 22586 | 22593 | 22594 | 22595 |
| 22598 | 22614 | 22623 | 22630 | 22631 | 22632 | 22633 | 22635 | 22640 | 22648 | 22655 | |
| 22663 | 22669 | 22677 | 22679 | 22700 | 22709 | 22723 | 22736 | 22747 | 22749 | 22759 | 22764 |
| 22766 | 22770 | 22780 | 22786 | 22787 | 22801 | 22819 | 22822 | 22823 | 22830 | 22831 | 22833 |
| 22836 | 22837 | 22845 | 22846 | 22855 | 22856 | 22858 | 22859 | 22861 | 22862 | 22864 | 22865 |
| 22872 | 22873 | 22890 | 22892 | 22893 | 22899 | 22909 | 22911 | 22914 | 22915 | 22916 | 22917 |
| 22919 | 22922 | 22924 | 22931 | 22933 | 22945 | 22946 | 22954 | 22963 | 22965 | 22967 | 22974 |
| 22975 | 22978 | 22984 | 22985 | 22991 | 22998 | 22999 | 23000 | 23006 | 23008 | 23009 | 23015 |
| 23026 | 23027 | 23031 | 23032 | 23034 | 23039 | 23055 | 23058 | 23067 | 23069 | 23070 | 23071 |
| 23073 | 23075 | 23077 | 23080 | 23081 | 23082 | 23084 | 23086 | 23092 | 23096 | 23097 | 23102 |
| 23104 | 23105 | 23106 | 23107 | 23109 | 23110 | 23112 | 23122 | 23123 | 23125 | 23126 | 23133 |
| 23138 | 23139 | 23140 | 23143 | 23144 | 23147 | 23148 | 23150 | 23151 | 23152 | 23154 | 23162 |
| 23164 | 23165 | 23169 | 23170 | 23186 | 23187 | 23189 | 23190 | 23191 | 23192 | 23193 | 23194 |
| 23195 | 23203 | 23209 | 23210 | 23212 | 23217 | 23225 | 23226 | 23227 | 23229 | 23231 | 23232 |
| 23233 | 23234 | 23235 | 23236 | 23237 | 23238 | 23239 | 23240 | 23241 | 23242 | 23244 | 23247 |
| 23249 | 23252 | 23253 | 23259 | 23260 | 23261 | 23262 | 23263 | 23264 | 23265 | 23266 | 23267 |
| 23268 | 23270 | 23272 | 23275 | 23276 | 23277 | 23282 | 23286 | 23287 | 23288 | 23289 | 23291 |
| 23292 | 23296 | 23299 | 23300 | 23301 | 23302 | 23303 | 23304 | 23307 | 23309 | 23310 | 23311 |
| 23313 | 23314 | 23321 | 23322 | 23323 | 23324 | 23325 | 23326 | 23327 | 23333 | 23336 | 23345 |
| 23347 | 23349 | 23351 | 23352 | 23353 | 23354 | 23355 | 23361 | 23362 | 23367 | 23368 | 23369 |
| 23370 | 23371 | 23373 | 23374 | 23375 | 23376 | 23377 | 23379 | 23385 | 23388 | 23389 | 23390 |
| 23396 | 23399 | 23400 | 23408 | 23409 | 23410 | 23413 | 23419 | 23423 | 23432 | 23433 | 23434 |
| 23442 | 23443 | 23444 | 23445 | 23446 | 23447 | 23450 | 23456 | 23457 | 23462 | 23464 | 23468 |
| 23469 | 23471 | 23479 | 23482 | 23484 | 23485 | 23490 | 23493 | 23501 | 23505 | 23507 | 23511 |
| 23513 | 23516 | 23517 | 23518 | 23525 | 23527 | 23531 | 23536 | 23537 | 23538 | 23541 | 23542 |
| 23545 | 23546 | 23547 | 23551 | 23552 | 23554 | 23555 | 23558 | 23559 | 23561 | 23563 | 23566 |
| 23571 | 23572 | 23577 | 23578 | 23581 | 23582 | 23583 | 23584 | 23585 | 23586 | 23587 | 23588 |

TABLE 15-continued

Yield: Carbohydrate

| | | | | | | | | | | | |
|---|---|---|---|---|---|---|---|---|---|---|---|
| 23594 | 23596 | 23598 | 23599 | 23601 | 23602 | 23605 | 23608 | 23610 | 23616 | 23619 | 23620 |
| 23630 | 23631 | 23635 | 23638 | 23639 | 23640 | 23646 | 23650 | 23655 | 23656 | 23658 | 23665 |
| 23666 | 23667 | 23672 | 23673 | 23677 | 23679 | 23687 | | | | | |

Table 15B SEQ ID NOs of Polynucleotides useful for improving Yield: Carbohydrate

| | | | | | | | | | | | |
|---|---|---|---|---|---|---|---|---|---|---|---|
| 23691 | 23694 | 23699 | 23704 | 23708 | 23714 | 23718 | 23719 | 23720 | 23721 | 23723 | 23724 |
| 23726 | 23731 | 23736 | 23737 | 23740 | 23743 | 23749 | 23755 | 23760 | 23761 | 23764 | 23768 |
| 23769 | 23775 | 23782 | 23786 | 23788 | 23791 | 23795 | 23797 | 23798 | 23799 | 23801 | 23806 |
| 23807 | 23808 | 23811 | 23812 | 23814 | 23815 | 23818 | 23819 | 23820 | 23823 | 23825 | 23826 |
| 23832 | 23847 | 23850 | 23856 | 23862 | 23867 | 23870 | 23871 | 23874 | 23875 | 23878 | 23881 |
| 23882 | 23884 | 23886 | 23894 | 23895 | 23896 | 23897 | 23898 | 23899 | 23900 | 23901 | 23902 |
| 23903 | 23907 | 23909 | 23911 | 23912 | 23913 | 23923 | 23924 | 23931 | 23935 | 23936 | 23940 |
| 23944 | 23945 | 23949 | 23953 | 23963 | 23966 | 23968 | 23976 | 23977 | 23978 | 23980 | 23990 |
| 23993 | 23998 | 24000 | 24001 | 24005 | 24015 | 24016 | 24022 | 24025 | 24027 | 24028 | 24029 |
| 24032 | 24037 | 24049 | 24050 | 24051 | 24053 | 24065 | 24066 | 24071 | 24072 | 24075 | 24077 |
| 24078 | 24079 | 24081 | 24082 | 24083 | 24084 | 24085 | 24086 | 24087 | 24088 | 24090 | 24092 |
| 24094 | 24097 | 24098 | 24100 | 24114 | 24119 | 24120 | 24131 | 24136 | 24143 | 24144 | 24146 |
| 24147 | 24148 | 24149 | 24151 | 24152 | 24153 | 24156 | 24161 | 24164 | 24165 | 24166 | 24171 |
| 24172 | 24174 | 24176 | 24177 | 24181 | 24182 | 24184 | 24185 | 24186 | 24188 | 24189 | 24191 |
| 24192 | 24199 | 24202 | 24203 | 24211 | 24215 | 24216 | 24217 | 24224 | 24225 | 24235 | 24236 |
| 24239 | 24242 | 24244 | 24247 | 24248 | 24249 | 24258 | 24262 | 24263 | 24266 | 24268 | 24269 |
| 24270 | 24272 | 24280 | 24284 | 24287 | 24290 | 24294 | 24295 | 24296 | 24299 | 24300 | 24305 |
| 24307 | 24309 | 24312 | 24313 | 24317 | 24319 | 24321 | 24323 | 24324 | 24325 | 24326 | 24327 |
| 24328 | 24329 | 24330 | 24331 | 24335 | 24338 | 24350 | 24351 | 24357 | 24358 | 24363 | 24366 |
| 24367 | 24370 | 24371 | 24372 | 24374 | 24382 | 24383 | 24385 | 24386 | 24388 | 24389 | 24394 |
| 24396 | 24397 | 24405 | 24407 | 24409 | 24410 | 24411 | 24416 | 24417 | 24429 | 24433 | 24434 |
| 24436 | 24439 | 24440 | 24442 | 24443 | 24444 | 24445 | 24446 | 24447 | 24448 | 24450 | 24452 |
| 24454 | 24455 | 24456 | 24468 | 24479 | 24480 | 24481 | 24482 | 24483 | 24485 | 24486 | 24496 |
| 24497 | 24498 | 24499 | 24500 | 24505 | 24507 | 24508 | 24510 | 24512 | 24521 | 24522 | 24524 |
| 24526 | 24528 | 24529 | 24530 | 24531 | 24535 | 24536 | 24538 | 24543 | 24548 | 24549 | 24550 |
| 24551 | 24552 | 24554 | 24555 | 24556 | 24557 | 24558 | 24559 | 24561 | 24562 | 24566 | 24572 |
| 24573 | 24574 | 24575 | 24576 | 24577 | 24578 | 24581 | 24586 | 24587 | 24589 | 24593 | 24595 |
| 24608 | 24610 | 24613 | 24618 | 24621 | 24624 | 24625 | 24628 | 24629 | 24630 | 24632 | 24633 |
| 24638 | 24639 | 24651 | 24655 | 24657 | 24661 | 24662 | 24663 | 24666 | 24673 | 24676 | 24679 |
| 24680 | 24681 | 24692 | 24701 | 24705 | 24708 | 24719 | 24723 | 24729 | 24730 | 24733 | 24739 |
| 24740 | 24742 | 24751 | 24760 | 24772 | 24773 | 24776 | 24778 | 24779 | 24780 | 24786 | 24799 |
| 24800 | 24803 | 24817 | 24821 | 24823 | 24829 | 24836 | 24840 | 24842 | 24853 | 24854 | 24861 |
| 24875 | 24881 | 24885 | 24886 | 24890 | 24891 | 24906 | 24911 | 24912 | 24916 | 24918 | 24921 |
| 24923 | 24928 | 24930 | 24933 | 24950 | 24951 | 24957 | 24968 | 24969 | 24971 | 24990 |
| 25000 | 25003 | 25008 | 25013 | 25016 | 25019 | 25026 | 25028 | 25029 | 25048 | 25059 | 25062 |
| 25101 | 25102 | 25113 | 25115 | 25116 | 25117 | 25118 | 25119 | 25122 | 25145 | 25150 | 25160 |
| 25161 | 25171 | 25176 | 25178 | 25179 | 25181 | 25184 | 25193 | 25194 | 25197 | 25202 | 25205 |
| 25208 | 25213 | 25228 | 25230 | 25241 | 25242 | 25252 | 25255 | 25259 | 25262 | 25263 | 25265 |
| 25267 | 25269 | 25271 | 25275 | 25276 | 25277 | 25278 | 25284 | 25285 | 25290 | 25292 | 25295 |
| 25305 | 25311 | 25312 | 25319 | 25328 | 25329 | 25338 | 25348 | 25356 | 25366 | 25367 | 25368 |
| 25370 | 25371 | 25375 | 25376 | 25383 | 25385 | 25386 | 25389 | 25391 | 25392 | 25393 | 25399 |
| 25406 | 25407 | 25415 | 25424 | 25432 | 25433 | 25436 | 25455 | 25468 | 25472 | 25484 | 25489 |
| 25493 | 25499 | 25501 | 25505 | 25511 | 25521 | 25525 | 25526 | 25528 | 25531 | 25534 | 25541 |
| 25543 | 25547 | 25554 | 25569 | 25570 | 25571 | 25574 | 25583 | 25584 | 25590 | 25591 | 25592 |
| 25595 | 25599 | 25604 | 25605 | 25607 | 25617 | 25620 | 25623 | 25626 | 25639 | 25645 | 25658 |
| 25660 | 25693 | 25693 | 25694 | 25695 | 25700 | 25702 | 25706 | 25714 | 25715 | 25725 | 25742 |
| 25749 | 25755 | 25791 | 25798 | 25802 | 25806 | 25809 | 25810 | 25817 | 25827 | 25834 | 25835 |
| 25841 | 25844 | 25846 | 25851 | 25853 | 25854 | 25855 | 25873 | 25881 | 25889 | 25895 | 25896 |
| 25900 | 25910 | 25916 | 25932 | 25933 | 25938 | 25939 | 25942 | 25947 | 25954 | 25955 | 25970 |
| 25971 | 25972 | 25979 | 25986 | 25998 | 26001 | 26002 | 26003 | 26006 | 26007 | 26008 | 26009 |
| 26012 | 26014 | 26015 | 26017 | 26046 | 26051 | 26063 | 26114 | 26121 | 26125 | 26127 |
| 26130 | 26131 | 26133 | 26140 | 26141 | 26148 | 26157 | 26162 | 26175 | 26176 | 26177 | 26184 |
| 26191 | 26194 | 26197 | 26211 | 26220 | 26233 | 26234 | 26237 | 26238 | 26247 | 26249 | 26251 |
| 26261 | 26265 | 26275 | 26276 | 26285 | 26290 | 26293 | 26296 | 26302 | 26308 | 26311 | 26312 |
| 26313 | 26314 | 26319 | 26320 | 26322 | 26326 | 26327 | 26331 | 26345 | 26352 | 26353 | 26363 |
| 26366 | 26367 | 26372 | 26374 | 26375 | 26376 | 26378 | 26379 | 26381 | 26382 | 26383 | 26385 |
| 26387 | 26390 | 26393 | 26395 | 26398 | 26402 | 26406 | 26409 | 26412 | 26413 | 26414 | 26415 |
| 26421 | 26422 | 26424 | 26425 | 26432 | 26437 | 26438 | 26439 | 26442 | 26443 | 26446 | 26447 |
| 26448 | 26453 | 26454 | 26458 | 26461 | 26462 | 26464 | 26465 | 26467 | 26468 | 26470 | 26472 |
| 26477 | 26479 | 26482 | 26484 | 26488 | 26490 | 26494 | 26509 | 26510 | 26512 | 26515 | 26520 |
| 26527 | 26529 | 26534 | 26535 | 26539 | 26541 | 26550 | 26551 | 26560 | 26561 | 26566 | 26572 |
| 26576 | 26577 | 26581 | 26588 | 26591 | 26592 | 26596 | 26597 | 26599 | 26600 | 26601 | 26602 |
| 26603 | 26606 | 26607 | 26609 | 26610 | 26611 | 26612 | 26613 | 26615 | 26623 | 26625 | 26630 |
| 26631 | 26632 | 26633 | 26641 | 26646 | 26647 | 26648 | 26650 | 26651 | 26655 | 26657 | 26658 |
| 26659 | 26663 | 26664 | 26666 | 26667 | 26671 | 26672 | 26673 | 26682 | 26689 | 26690 | 26691 |
| 26694 | 26695 | 26696 | 26697 | 26699 | 26707 | 26710 | 26717 | 26718 | 26728 | 26732 | 26739 |
| 26741 | 26742 | 26752 | 26753 | 26754 | 26755 | 26756 | 26767 | 26774 | 26776 | 26787 | 26788 |
| 26790 | 26791 | 26794 | 26796 | 26800 | 26802 | 26811 | 26817 | 26819 | 26823 | 26832 | 26839 |
| 26841 | 26843 | 26863 | 26865 | 26868 | 26873 | 26874 | 26875 | 26876 | 26878 | 26881 | 26884 |
| 26887 | 26888 | 26893 | 26899 | 26900 | 26906 | 26919 | 26920 | 26923 | 26933 | 26935 | 26936 |
| 26938 | 26939 | 26941 | 26952 | 26957 | 26962 | 26972 | 26973 | 26977 | 26986 | 26988 | 26991 |
| 26992 | 26995 | 26996 | 27002 | 27005 | 27006 | 27011 | 27015 | 27021 | 27022 | 27030 | 27032 |

TABLE 15-continued

Yield: Carbohydrate

| | | | | | | | | | | | |
|---|---|---|---|---|---|---|---|---|---|---|---|
| 27035 | 27038 | 27039 | 27044 | 27045 | 27049 | 27050 | 27068 | 27072 | 27076 | 27079 | 27082 |
| 27083 | 27084 | 27085 | 27086 | 27096 | 27098 | 27101 | 27102 | 27105 | 27106 | 27108 | 27112 |
| 27121 | 27123 | 27125 | 27127 | 27129 | 27141 | 27145 | 27160 | 27165 | 27167 | 27168 | 27174 |
| 27177 | 27178 | 27187 | 27202 | 27213 | 27216 | 27218 | 27231 | 27242 | 27247 | 27256 | 27258 |
| 27260 | 27267 | 27275 | 27277 | 27278 | 27287 | 27292 | 27297 | 27308 | 27311 | 27316 | 27323 |
| 27324 | 27326 | 27327 | 27328 | 27330 | 27333 | 27341 | 27344 | 27345 | 27349 | 27352 | 27354 |
| 27358 | 27364 | 27367 | 27369 | 27373 | 27375 | 27382 | 27385 | 27390 | 27396 | 27398 | 27400 |
| 27401 | 27406 | 27411 | 27412 | 27420 | 27425 | 27426 | 27432 | 27433 | 27434 | 27435 | 27437 |
| 27445 | 27449 | 27451 | 27459 | 27461 | 27465 | 27467 | 27471 | 27479 | 27480 | 27481 | 27487 |
| 27492 | 27497 | 27498 | 27502 | 27506 | 27511 | 27521 | 27522 | 27524 | 27533 | 27534 | 27540 |
| 27551 | 27552 | 27553 | 27556 | 27558 | 27563 | 27574 | 27581 | 27582 | 27591 | 27605 | 27607 |
| 27611 | 27616 | 27624 | 27637 | 27638 | 27640 | 27653 | 27654 | 27656 | 27657 | 27660 | 27663 |
| 27665 | 27669 | 27671 | 27673 | 27674 | 27691 | 27693 | 27698 | 27706 | 27709 | 27720 | 27722 |
| 27724 | 27728 | 27731 | 27732 | 27734 | 27735 | 27743 | 27748 | 27764 | 27795 | 27798 | 27800 |
| 27801 | 27802 | 27804 | 27805 | 27810 | 27813 | 27815 | 27816 | 27821 | 27823 | 27824 | 27828 |
| 27829 | 27830 | 27839 | 27840 | 27851 | 27853 | 27855 | 27860 | 27863 | 27865 | 27866 | 27867 |
| 27870 | 27871 | 27873 | 27880 | 27891 | 27893 | 27898 | 27902 | 27905 | 27909 | 27914 | 27915 |
| 27916 | 27920 | 27925 | 27928 | 27929 | 27930 | 27931 | 27933 | 27936 | 27938 | 27939 | 27941 |
| 27942 | 27943 | 27946 | 27948 | 27949 | 27950 | 27953 | 27956 | 27958 | 27963 | 27964 | 27965 |
| 27966 | 27967 | 27969 | 27971 | 27972 | 27973 | 27974 | 27976 | 27978 | 27979 | 27980 | 27981 |
| 27982 | 27983 | 27986 | 27991 | 27992 | 27993 | 27994 | 27995 | 27996 | 27998 | 28001 | 28003 |
| 28005 | 28007 | 28008 | 28012 | 28013 | 28014 | 28016 | 28017 | 28019 | 28023 | 28025 | 28027 |
| 28031 | 28036 | 28042 | 28043 | 28044 | 28045 | 28047 | 28049 | 28050 | 28051 | 28053 | 28054 |
| 28055 | 28060 | 28062 | 28064 | 28066 | 28067 | 28068 | 28069 | 28070 | 28074 | 28077 | 28079 |
| 28088 | 28090 | 28091 | 28092 | 28093 | 28097 | 28098 | 28099 | 28101 | 28111 | 28112 | 28114 |
| 28115 | 28116 | 28124 | 28125 | 28128 | 28133 | 28135 | 28138 | 28139 | 28140 | 28142 | 28144 |
| 28147 | 28148 | 28151 | 28152 | 28153 | 28154 | 28158 | 28160 | 28161 | 28162 | 28166 | 28168 |
| 28170 | 28171 | 28172 | 28173 | 28177 | 28186 | 28189 | 28190 | 28191 | 28192 | 28193 | 28199 |
| 28201 | 28202 | 28204 | 28208 | 28213 | 28217 | 28218 | 28219 | 28221 | 28222 | 28223 | 28228 |
| 28230 | 28233 | 28236 | 28239 | 28240 | 28242 | 28244 | 28245 | 28248 | 28252 | 28255 | 28257 |
| 28259 | 28264 | 28265 | 28268 | 28269 | 28273 | 28281 | 28283 | 28288 | 28290 | 28291 | 28292 |
| 28293 | 28295 | 28296 | 28297 | 28298 | 28299 | 28300 | 28301 | 28305 | 28308 | 28309 | 28311 |
| 28312 | 28313 | 28319 | 28321 | 28322 | 28324 | 28325 | 28326 | 28327 | 28330 | 28331 | 28333 |
| 28334 | 28335 | 28338 | 28339 | 28340 | 28341 | 28343 | 28345 | 28359 | 28360 | 28361 | 28365 |
| 28366 | 28368 | 28375 | 28378 | 28380 | 28383 | 28384 | 28386 | 28387 | 28389 | 28391 | 28392 |
| 28393 | 28394 | 28398 | 28399 | 28401 | 28403 | 28406 | 28412 | 28414 | 28418 | 28419 | 28420 |
| 28421 | 28423 | 28426 | 28429 | 28432 | 28433 | 28434 | 28436 | 28437 | 28444 | 28445 | 28449 |
| 28450 | 28453 | 28454 | 28455 | 28458 | 28460 | 28462 | 28463 | 28467 | 28468 | 28472 | 28474 |
| 28475 | 28476 | 28477 | 28480 | 28483 | 28484 | 28486 | 28487 | 28489 | 28490 | 28493 | 28494 |
| 28497 | 28498 | 28499 | 28500 | 28501 | 28505 | 28509 | 28510 | 28517 | 28518 | 28519 | 28521 |
| 28522 | 28523 | 28527 | 28528 | 28529 | 28533 | 28534 | 28535 | 28542 | 28544 | 28547 | 28550 |
| 28552 | 28553 | 28555 | 28556 | 28558 | 28559 | 28562 | 28570 | 28573 | 28574 | 28575 | 28576 |
| 28579 | 28581 | 28586 | 28589 | 28590 | 28594 | 28598 | 28599 | 28600 | 28601 | 28604 | 28610 |
| 28611 | 28615 | 28618 | 28620 | 28622 | 28626 | 28630 | 28631 | 28632 | 28633 | 28634 | 28637 |
| 28638 | 28639 | 28641 | 28645 | 28647 | 28649 | 28651 | 28652 | 28659 | 28664 | 28668 | 28675 |
| 28679 | 28682 | 28690 | 28692 | 28710 | 28714 | 28725 | 28755 | 28768 | 28770 | 28775 | 28777 |
| 28791 | 28803 | 28804 | 28805 | 28807 | 28812 | 28839 | 28840 | 28845 | 28846 | 28859 | 28860 |
| 28867 | 28896 | 28913 | 28920 | 28921 | 28924 | 28944 | 28955 | 28958 | 28968 | 28969 | 28970 |
| 28971 | 28979 | 28980 | 28985 | 29003 | 29005 | 29013 | 29017 | 29021 | 29023 | 29025 | 29026 |
| 29033 | 29050 | 29065 | 29066 | 29081 | 29120 | 29121 | 29124 | 29126 | 29127 | 29128 | 29129 |
| 29140 | 29152 | 29157 | 29158 | 29161 | 29168 | 29177 | 29182 | 29194 | 29203 | 29207 | 29208 |
| 29209 | 29210 | 29211 | 29212 | 29220 | 29221 | 29226 | 29227 | 29230 | 29236 | 29239 | 29253 |
| 29271 | 29275 | 29276 | 29287 | 29289 | 29291 | 29296 | 29297 | 29318 | 29327 | 29333 | 29337 |
| 29343 | 29349 | 29352 | 29356 | 29367 | 29369 | 29379 | 29380 | 29388 | 29393 | 29398 | 29402 |
| 29403 | 29421 | 29422 | 29430 | 29432 | 29439 | 29460 | 29461 | 29467 | 29470 | 29475 | 29478 |
| 29481 | 29483 | 29490 | 29492 | 29493 | 29499 | 29504 | 29525 | 29531 | 29549 | 29550 | 29554 |
| 29555 | 29563 | 29573 | 29588 | 29589 | 29591 | 29597 | 29601 | 29607 | 29609 | 29610 | 29619 |
| 29620 | 29621 | 29633 | 29645 | 29662 | 29665 | 29677 | 29679 | 29680 | 29687 | 29688 | 29689 |
| 29697 | 29698 | 29699 | 29702 | 29710 | 29711 | 29713 | 29714 | 29719 | 29720 | 29721 | 29739 |
| 29749 | 29768 | 29771 | 29776 | 29777 | 29780 | 29791 | 29794 | 29795 | 29799 | 29802 | 29803 |
| 29820 | 29821 | 29830 | 29839 | 29840 | 29841 | 29843 | 29845 | 29846 | 29853 | 29862 | 29864 |
| 29874 | 29876 | 29878 | 29879 | 29884 | 29887 | 29897 | 29901 | 29907 | 29911 | 29918 | 29921 |
| 29926 | 29927 | 29928 | 29931 | 29938 | 29939 | 29950 | 29955 | 29956 | 29958 | 29959 | 29961 |
| 29967 | 29992 | 30040 | 30041 | 30042 | 30043 | 30047 | 30048 | 30081 | 30084 | 30100 |
| 30120 | 30122 | 30124 | 30125 | 30128 | 30133 | 30137 | 30145 | 30153 | 30157 | 30158 | 30159 |
| 30160 | 30162 | 30164 | 30166 | 30171 | 30172 | 30176 | 30184 | 30189 | 30190 | 30191 | 30198 |
| 30202 | 30207 | 30211 | 30212 | 30213 | 30229 | 30234 | 30237 | 30238 | 30245 | 30248 | 30249 |
| 30250 | 30254 | 30265 | 30266 | 30268 | 30269 | 30270 | 30281 | 30284 | 30285 | 30293 | 30307 |
| 30312 | 30323 | 30327 | 30328 | 30360 | 30361 | 30380 | 30382 | 30388 | 30401 | 30402 | 30405 |
| 30407 | 30417 | 30419 | 30420 | 30426 | 30430 | 30436 | 30446 | 30455 | 30457 | 30458 | 30467 |
| 30475 | 30493 | 30496 | 30502 | 30506 | 30508 | 30509 | 30510 | 30513 | 30516 | 30517 | 30532 |
| 30557 | 30563 | 30564 | 30589 | 30594 | 30597 | 30599 | 30614 | 30626 | 30657 | 30658 | 30659 |
| 30672 | 30673 | 30677 | 30688 | 30705 | 30713 | 30720 | 30721 | 30722 | 30724 | 30726 | 30727 |
| 30728 | 30730 | 30732 | 30734 | 30735 | 30736 | 30737 | 30738 | 30739 | 30740 | 30742 | 30747 |
| 30748 | 30749 | 30750 | 30751 | 30752 | 30754 | 30757 | 30759 | 30761 | 30763 | 30764 | 30768 |
| 30769 | 30770 | 30772 | 30773 | 30775 | 30780 | 30782 | 30786 | 30789 | 30791 | 30796 | 30797 |
| 30798 | 30799 | 30801 | 30803 | 30804 | 30805 | 30807 | 30808 | 30809 | 30814 | 30816 | 30818 |

TABLE 15-continued

Yield: Carbohydrate

| | | | | | | | | | | | |
|---|---|---|---|---|---|---|---|---|---|---|---|
| 30820 | 30821 | 30822 | 30824 | 30825 | 30827 | 30829 | 30832 | 30834 | 30843 | 30845 | 30846 |
| 30847 | 30849 | 30853 | 30854 | 30855 | 30857 | 30869 | 30870 | 30872 | 30873 | 30874 | 30880 |
| 30883 | 30884 | 30887 | 30892 | 30894 | 30898 | 30899 | 30900 | 30904 | 30907 | 30908 | 30911 |
| 30912 | 30913 | 30914 | 30918 | 30920 | 30921 | 30925 | 30927 | 30929 | 30930 | 30931 | 30932 |
| 30936 | 30945 | 30948 | 30949 | 30950 | 30951 | 30957 | 30959 | 30961 | 30963 | 30967 | 30972 |
| 30975 | 30976 | 30977 | 30979 | 30980 | 30981 | 30986 | 30988 | 30991 | 30996 | 30997 | 30999 |
| 31001 | 31002 | 31006 | 31010 | 31012 | 31014 | 31016 | 31021 | 31022 | 31025 | 31026 | 31030 |
| 31038 | 31040 | 31045 | 31047 | 31048 | 31049 | 31050 | 31052 | 31053 | 31054 | 31055 | 31056 |
| 31057 | 31058 | 31062 | 31066 | 31069 | 31070 | 31071 | 31076 | 31077 | 31079 | 31080 | 31082 |
| 31083 | 31084 | 31085 | 31088 | 31089 | 31091 | 31092 | 31093 | 31096 | 31097 | 31098 | 31099 |
| 31101 | 31104 | 31118 | 31119 | 31120 | 31124 | 31125 | 31127 | 31134 | 31137 | 31141 | 31142 |
| 31144 | 31145 | 31147 | 31149 | 31150 | 31152 | 31153 | 31157 | 31158 | 31159 | 31162 | 31165 |
| 31171 | 31172 | 31173 | 31178 | 31179 | 31180 | 31181 | 31182 | 31185 | 31189 | 31192 | 31193 |
| 31194 | 31196 | 31203 | 31204 | 31208 | 31210 | 31213 | 31214 | 31215 | 31218 | 31220 | 31222 |
| 31223 | 31227 | 31228 | 31232 | 31234 | 31235 | 31236 | 31237 | 31240 | 31243 | 31245 | 31246 |
| 31248 | 31249 | 31252 | 31253 | 31256 | 31257 | 31258 | 31259 | 31260 | 31264 | 31268 | 31269 |
| 31276 | 31277 | 31278 | 31280 | 31281 | 31282 | 31286 | 31287 | 31288 | 31292 | 31293 | 31294 |
| 31301 | 31303 | 31306 | 31309 | 31311 | 31312 | 31314 | 31315 | 31318 | 31319 | 31322 |
| 31328 | 31331 | 31332 | 31333 | 31334 | 31337 | 31339 | 31344 | 31347 | 31348 | 31352 | 31356 |
| 31357 | 31358 | 31359 | 31362 | 31368 | 31369 | 31373 | 31376 | 31378 | 31380 | 31384 | 31388 |
| 31389 | 31390 | 31391 | 31392 | 31395 | 31396 | 31397 | 31399 | 31403 | 31405 | 31407 | 31409 |
| 31410 | 31416 | 31417 | 31419 | 31425 | 31432 | 31439 | 31440 | 31442 | 31445 | 31446 |
| 31447 | 31449 | 31451 | 31452 | 31453 | 31455 | 31456 | 31460 | 31462 | 31465 | 31468 | 31470 |
| 31471 | 31474 | 31475 | 31478 | 31481 | 31483 | 31493 | 31496 | 31497 | 31500 | 31504 | 31505 |
| 31509 | 31511 | 31512 | 31520 | 31522 | 31523 | 31524 | 31525 | 31526 | 31530 | 31531 | 31533 |
| 31539 | 31546 | 31550 | 31551 | 31556 | 31557 | 31562 | 31564 | 31566 | 31568 | 31569 | 31570 |
| 31571 | 31572 | 31584 | 31588 | 31591 | 31592 | 31593 | 31596 | 31605 | 31607 | 31610 | 31612 |
| 31614 | 31615 | 31617 | 31620 | 31621 | 31622 | 31623 | 31624 | 31625 | 31627 | 31629 | 31630 |
| 31632 | 31633 | 31634 | 31635 | 31639 | 31643 | 31644 | 31649 | 31650 | 31656 | 31657 | 31659 |
| 31660 | 31661 | 31662 | 31663 | 31664 | 31671 | 31672 | 31678 | 31681 | 31682 | 31688 | 31689 |
| 31690 | 31691 | 31692 | 31695 | 31696 | 31698 | 31699 | 31700 | 31701 | 31702 | 31703 | 31704 |
| 31705 | 31708 | 31709 | 31711 | 31713 | 31714 | 31717 | 31718 | 31719 | 31721 | 31723 | 31724 |
| 31726 | 31728 | 31732 | 31736 | 31739 | 31741 | 31742 | 31743 | 31750 | 31755 | 31758 | 31759 |
| 31765 | 31771 | 31772 | 31775 | 31779 | 31785 | 31795 | 31796 | 31798 | 31799 | 31800 | 31801 |
| 31802 | 31804 | 31806 | 31807 | 31809 | 31810 | 31811 | 31813 | 31814 | 31815 | 31816 | 31826 |
| 31831 | 31832 | 31834 | 31837 | 31844 | 31845 | 31846 | 31847 | 31849 | 31853 | 31854 | 31857 |
| 31862 | 31867 | 31868 | 31869 | 31870 | 31871 | 31873 | 31874 | 31875 | 31876 | 31882 | 31893 |
| 31894 | 31895 | 31896 | 31899 | 31905 | 31906 | 31909 | 31915 | 31919 | 31922 | 31925 | 31928 |
| 31930 | 31931 | 31932 | 31934 | 31937 | 31938 | 31940 | 31941 | 31949 | 31950 | 31952 | 31955 |
| 31957 | 31958 | 31959 | 31960 | 31961 | 31963 | 31964 | 31970 | 31973 | 31974 | 31977 | 31981 |
| 31982 | 31983 | 31986 | 31992 | 31993 | 31994 | 31996 | 31999 | 32001 | 32008 | 32011 | 32013 |
| 32015 | 32022 | 32024 | 32027 | 32028 | 32029 | 32031 | 32032 | 32033 | 32034 | 32041 | 32042 |
| 32043 | 32044 | 32046 | 32048 | 32052 | 32055 | 32057 | 32058 | 32059 | 32064 | 32066 | 32070 |
| 32071 | 32072 | 32074 | 32078 | 32079 | 32081 | 32083 | 32085 | 32088 | 32091 | 32093 | 32094 |
| 32095 | 32096 | 32098 | 32099 | 32100 | 32101 | 32103 | 32104 | 32112 | 32113 | 32117 | 32119 |
| 32125 | 32129 | 32130 | 32131 | 32133 | 32136 | 32139 | 32145 | 32151 | 32153 | 32154 | 32155 |
| 32156 | 32158 | 32159 | 32170 | 32171 | 32172 | 32173 | 32179 | 32180 | 32181 | 32185 | 32186 |
| 32187 | 32195 | 32199 | 32200 | 32201 | 32202 | 32203 | 32204 | 32208 | 32209 | 32210 | 32211 |
| 32213 | 32215 | 32218 | 32221 | 32226 | 32233 | 32238 | 32239 | 32243 | 32244 | 32251 | 32253 |
| 32254 | 32256 | 32258 | 32259 | 32260 | 32261 | 32265 | 32266 | 32273 | 32274 | 32275 | 32280 |
| 32282 | 32299 | 32301 | 32303 | 32305 | 32306 | 32308 | 32312 | 32314 | 32320 | 32321 | 32332 |
| 32333 | 32338 | 32339 | 32340 | 32341 | 32342 | 32351 | 32354 | 32366 | 32370 | 32373 |
| 32375 | 32378 | 32379 | 32380 | 32388 | 32389 | 32393 | 32394 | 32395 | 32399 | 32402 | 32405 |
| 32407 | 32410 | 32415 | 32416 | 32417 | 32418 | 32419 | 32420 | 32421 | 32425 | 32428 | 32429 |
| 32434 | 32435 | 32439 | 32442 | 32449 | 32450 | 32452 | 32453 | 32454 | 32455 | 32456 | 32457 |
| 32461 | 32464 | 32467 | 32468 | 32469 | 32470 | 32480 | 32482 | 32483 | 32489 | 32490 | 32501 |
| 32503 | 32504 | 32506 | 32508 | 32514 | 32515 | 32517 | 32518 | 32519 | 32520 | 32521 | 32534 |
| 32535 | 32537 | 32540 | 32542 | 32547 | 32548 | 32549 | 32551 | 32553 | 32557 | 32558 | 32562 |
| 32563 | 32569 | 32572 | 32577 | 32580 | 32581 | 32582 | 32583 | 32586 | 32587 | 32588 | 32596 |
| 32597 | 32603 | 32604 | 32606 | 32608 | 32610 | 32611 | 32612 | 32614 | 32615 | 32616 | 32618 |
| 32620 | 32621 | 32625 | 32626 | 32627 | 32630 | 32634 | 32645 | 32647 | 32651 | 32652 | 32653 |
| 32660 | 32661 | 32667 | 32668 | 32670 | 32671 | 32672 | 32674 | 32685 | 32686 | 32687 | 32688 |
| 32689 | 32693 | 32699 | 32700 | 32701 | 32702 | 32703 | 32704 | 32705 | 32706 | 32708 | 32709 |
| 32714 | 32715 | 32716 | 32718 | 32722 | 32728 | 32732 | 32734 | 32735 | 32738 | 32743 |
| 32745 | 32746 | 32749 | 32750 | 32755 | 32756 | 32759 | 32760 | 32763 | 32765 | 32767 | 32776 |
| 32783 | 32784 | 32791 | 32792 | 32793 | 32796 | 32791 | 32798 | 32801 | 32803 | 32805 | 32819 |
| 32820 | 32823 | 32826 | 32832 | 32834 | 32835 | 32836 | 32837 | 32838 | 32840 | 32841 | 32843 |
| 32850 | 32851 | 32852 | 32854 | 32857 | 32858 | 32860 | 32863 | 32864 | 32866 | 32873 | 32879 |
| 32887 | 32888 | 32895 | 32903 | 32905 | 32907 | 32912 | 32916 | 32920 | 32921 | 32922 | 32923 |
| 32925 | 32929 | 32930 | 32931 | 32932 | 32936 | 32941 | 32942 | 32949 | 32951 | 32952 | 32953 |
| 32954 | 32956 | 32957 | 32958 | 32960 | 32961 | 32978 | 32979 | 32980 | 32981 | 32982 | 32983 |
| 32987 | 32991 | 32995 | 32999 | 33010 | 33011 | 33012 | 33013 | 33017 | 33019 | 33020 | 33022 |
| 33035 | 33036 | 33045 | 33048 | 33050 | 33051 | 33055 | 33056 | 33059 | 33060 | 33063 | 33064 |
| 33068 | 33070 | 33074 | 33083 | 33088 | 33092 | 33093 | 33095 | 33097 | 33100 | 33101 | 33105 |
| 33110 | 33111 | 33112 | 33116 | 33121 | 33124 | 33126 | 33127 | 33141 | 33143 | 33150 | 33152 |
| 33153 | 33156 | 33160 | 33162 | 33163 | 33164 | 33170 | 33172 | 33174 | 33176 | 33177 | 33178 |
| 33179 | 33181 | 33182 | 33188 | 33198 | 33201 | 33202 | 33203 | 33204 | 33206 | 33218 | 33229 |

TABLE 15-continued

Yield: Carbohydrate

| | | | | | | | | | | | |
|---|---|---|---|---|---|---|---|---|---|---|---|
| 33231 | 33234 | 33236 | 33238 | 33241 | 33243 | 33247 | 33250 | 33252 | 33253 | 33256 | 33257 |
| 33261 | 33263 | 33265 | 33266 | 33269 | 33276 | 33279 | 33281 | 33282 | 33285 | 33289 | 33290 |
| 33295 | 33300 | 33301 | 33302 | 33306 | 33307 | 33311 | 33312 | 33314 | 33318 | 33319 | 33320 |
| 33323 | 33332 | 33336 | 33337 | 33339 | 33340 | 33356 | 33358 | 33362 | 33368 | 33372 | 33391 |
| 33396 | 33399 | 33400 | 33402 | 33407 | 33412 | 33423 | 33424 | 33425 | 33430 | 33435 | 33446 |
| 33451 | 33453 | 33459 | 33461 | 33463 | 33474 | 33475 | 33476 | 33477 | 33516 | 33518 | 33527 |
| 33538 | 33545 | 33548 | 33550 | 33551 | 33552 | 33553 | 33555 | 33556 | 33563 | 33571 | 33575 |
| 33578 | 33579 | 33580 | 33581 | 33582 | 33583 | 33584 | 33585 | 33596 | 33597 | 33603 | 33607 |
| 33609 | 33613 | 33614 | 33616 | 33622 | 33623 | 33632 | 33633 | 33637 | 33645 | 33647 | 33652 |
| 33655 | 33656 | 33657 | 33663 | 33671 | 33672 | 33674 | 33675 | 33676 | 33677 | 33678 | 33680 |
| 33681 | 33682 | 33689 | 33690 | 33691 | 33692 | 33694 | 33696 | 33697 | 33703 | 33704 | 33706 |
| 33707 | 33708 | 33709 | 33710 | 33711 | 33721 | 33722 | 33724 | 33725 | 33726 | 33729 | 33732 |
| 33734 | 33737 | 33739 | 33740 | 33746 | 33747 | 33748 | 33751 | 33766 | 33771 | 33787 | 33791 |
| 33819 | 33820 | 33823 | 33828 | 33829 | 33831 | 33841 | 33845 | 33851 | 33852 | 33862 | 33866 |
| 33868 | 33869 | 33881 | 33882 | 33884 | 33885 | 33886 | 33887 | 33890 | 33891 | 33892 | 33896 |
| 33901 | 33903 | 33911 | 33912 | 33914 | 33917 | 33918 | 33919 | 33920 | 33921 | 33922 | 33924 |
| 33928 | 33932 | 33933 | 33935 | 33937 | 33940 | 33944 | 33946 | 33947 | 33948 | 33950 | 33951 |
| 33954 | 33955 | 33959 | 33960 | 33966 | 33968 | 33969 | 33970 | 33972 | 33980 | 33983 | 33994 |
| 33996 | 33997 | 33999 | 34012 | 34014 | 34018 | 34024 | 34029 | 34030 | 34031 | 34033 | 34037 |
| 34041 | 34042 | 34048 | 34054 | 34056 | 34061 | 34062 | 34069 | 34071 | 34073 | 34075 | 34082 |
| 34084 | 34086 | 34088 | 34092 | 34093 | 34094 | 34096 | 34097 | 34098 | 34100 | 34102 | 34107 |
| 34109 | 34111 | 34112 | 34114 | 34117 | 34121 | 34122 | 34138 | 34140 | 34147 | 34150 | 34152 |
| 34153 | 34155 | 34156 | 34160 | 34161 | 34164 | 34168 | 34173 | 34175 | 34181 | 34184 | 34186 |
| 34187 | 34188 | 34190 | 34192 | 34196 | 34197 | 34198 | 34203 | 34204 | 34206 | 34207 | 34209 |
| 34210 | 34211 | 34212 | 34213 | 34214 | 34215 | 34218 | 34223 | 34225 | 34227 | 34228 | 34229 |
| 34233 | 34235 | 34238 | 34239 | 34240 | 34243 | 34244 | 34247 | 34248 | 34252 | 34256 | 34258 |
| 34259 | 34260 | 34261 | 34262 | 34264 | 34265 | 34267 | 34268 | 34274 | 34275 | 34276 | |
| 34277 | 34279 | 34281 | 34283 | 34284 | 34288 | 34289 | 34290 | 34292 | 34298 | 34299 | 34301 |
| 34302 | 34303 | 34314 | 34315 | 34316 | 34317 | 34319 | 34323 | 34328 | 34329 | 34338 | 34339 |
| 34340 | 34341 | 34342 | 34343 | 34344 | 34345 | 34346 | 34347 | 34348 | 34349 | 34350 | 34351 |
| 34352 | 34354 | 34355 | 34361 | 34366 | 34368 | 34369 | 34370 | 34371 | 34376 | 34381 | 34382 |
| 34384 | 34385 | 34387 | 34390 | 34396 | 34397 | 34398 | 34399 | 34400 | 34401 | 34403 | 34405 |
| 34406 | 34407 | 34408 | 34409 | 34410 | 34412 | 34413 | 34414 | 34415 | 34416 | 34418 | 34419 |
| 34420 | 34423 | 34424 | 34425 | 34426 | 34427 | 34429 | 34431 | 34434 | 34435 | 34436 | 34438 |
| 34439 | 34440 | 34445 | 34446 | 34447 | 34448 | 34449 | 34451 | 34452 | 34453 | 34457 | 34458 |
| 34459 | 34461 | 34462 | 34464 | 34471 | 34474 | 34484 | 34485 | 34494 | 34497 | 34498 | 34499 |
| 34502 | 34506 | 34508 | 34510 | 34511 | 34513 | 34515 | 34516 | 34517 | 34518 | 34523 | 34524 |
| 34528 | 34529 | 34531 | 34536 | 34538 | 34539 | 34542 | 34544 | 34546 | 34548 | 34556 | 34569 |
| 34573 | 34575 | 34576 | 34577 | 34582 | 34584 | 34585 | 34587 | 34588 | 34589 | 34593 | 34595 |
| 34600 | 34602 | 34603 | 34607 | 34608 | 34612 | 34614 | 34615 | 34617 | 34618 | 34619 | 34620 |
| 34631 | 34636 | 34637 | 34638 | 34643 | 34644 | 34649 | 34654 | 34655 | 34656 | 34657 | 34658 |
| 34659 | 34661 | 34664 | 34668 | 34669 | 34671 | 34679 | 34680 | 34681 | 34682 | 34684 | 34685 |
| 34687 | 34689 | 34690 | 34691 | 34696 | 34697 | 34699 | 34700 | 34704 | 34708 | 34721 | 34722 |
| 34723 | 34724 | 34728 | 34740 | 34741 | 34744 | 34748 | 34751 | 34752 | 34759 | 34762 | 34766 |
| 34771 | 34772 | 34778 | 34784 | 34786 | 34808 | 34809 | 34811 | 34817 | 34821 | 34822 | 34834 |
| 34844 | 34849 | 34856 | 34859 | 34861 | 34871 | 34873 | 34875 | 34876 | 34877 | 34879 | 34881 |
| 34882 | 34888 | 34904 | 34905 | 34906 | 34910 | 34912 | 34921 | 34927 | 34929 | 34934 | 34935 |
| 34936 | 34946 | 34951 | 34952 | 34960 | 34968 | 34975 | 34985 | 34988 | 34991 | 34996 | 34999 |
| 35004 | 35005 | 35018 | 35019 | 35023 | 35024 | 35025 | 35031 | 35036 | 35037 | 35044 | 35047 |
| 35049 | 35056 | 35059 | 35060 | 35061 | 35062 | 35063 | 35064 | 35065 | 35068 | 35069 | 35071 |
| 35072 | 35074 | 35075 | 35081 | 35083 | 35084 | 35086 | 35087 | 35088 | 35089 | 35091 | 35093 |
| 35094 | 35096 | 35107 | 35109 | 35111 | 35114 | 35115 | 35116 | 35123 | 35124 | 35125 | 35126 |
| 35127 | 35128 | 35129 | 35130 | 35133 | 35137 | 35139 | 35140 | 35142 | 35143 | 35145 | 35149 |
| 35154 | 35158 | 35161 | 35162 | 35164 | 35165 | 35169 | 35171 | 35173 | 35176 | 35178 | 35179 |
| 35180 | 35181 | 35183 | 35184 | 35188 | 35189 | 35190 | 35191 | 35194 | 35201 | 35203 | 35206 |
| 35207 | 35208 | 35210 | 35211 | 35212 | 35213 | 35215 | 35218 | 35219 | 35224 | 35233 | |
| 35234 | 35235 | 35237 | 35238 | 35244 | 35245 | 35246 | 35247 | 35251 | 35259 | 35265 | 35266 |
| 35270 | 35272 | 35276 | 35278 | 35281 | 35282 | 35284 | 35285 | 35286 | 35288 | 35290 | 35293 |
| 35295 | 35296 | 35297 | 35300 | 35304 | 35307 | 35313 | 35315 | 35316 | 35318 | 35320 | 35322 |
| 35324 | 35326 | 35327 | 35328 | 35329 | 35330 | 35336 | 35337 | 35338 | 35342 | 35344 | 35348 |
| 35352 | 35353 | 35355 | 35357 | 35358 | 35359 | 35360 | 35361 | 35362 | 35363 | 35364 | 35366 |
| 35367 | 35373 | 35374 | 35379 | 35380 | 35381 | 35382 | 35383 | 35385 | 35388 | 35389 | 35390 |
| 35392 | 35394 | 35398 | 35404 | 35408 | 35410 | 35411 | 35412 | 35413 | 35414 | 35415 | 35418 |
| 35422 | 35424 | 35427 | 35428 | 35431 | 35432 | 35437 | 35438 | 35442 | 35444 | 35448 | 35454 |
| 35455 | 35460 | 35466 | 35467 | 35469 | 35470 | 35475 | 35480 | 35481 | 35486 | 35490 | 35496 |
| 35504 | 35506 | 35507 | 35508 | 35509 | 35510 | 35513 | 35515 | 35519 | 35520 | 35523 | 35524 |
| 35525 | 35526 | 35529 | 35534 | 35542 | 35543 | 35549 | 35550 | 35551 | 35561 | 35562 | 35567 |
| 35568 | 35569 | 35573 | 35575 | 35576 | 35580 | 35582 | 35583 | 35585 | 35587 | 35588 | 35589 |
| 35593 | 35594 | 35596 | 35599 | 35600 | 35602 | 35605 | 35606 | 35610 | 35614 | 35615 | 35618 |
| 35629 | 35630 | 35631 | 35632 | 35635 | 35639 | 35642 | 35644 | 35645 | 35648 | 35649 | 35651 |
| 35652 | 35653 | 35656 | 35658 | 35664 | 35666 | 35668 | 35677 | 35679 | 35682 | 35684 | 35685 |
| 35686 | 35687 | 35688 | 35697 | 35698 | 35699 | 35702 | 35704 | 35705 | 35706 | 35709 | 35714 |
| 35717 | 35718 | 35719 | 35724 | 35725 | 35726 | 35727 | 35728 | 35730 | 35731 | 35734 | 35735 |
| 35736 | 35739 | 35740 | 35741 | 35742 | 35743 | 35744 | 35745 | 35746 | 35747 | 35750 | 35754 |
| 35755 | 35756 | 35757 | 35769 | 35772 | 35778 | 35779 | 35783 | 35784 | 35785 | 35788 | 35793 |
| 35798 | 35799 | 35806 | 35807 | 35808 | 35809 | 35811 | 35812 | 35813 | 35814 | 35815 | 35824 |
| 35826 | 35829 | 35835 | 35836 | 35838 | 35839 | 35842 | 35849 | 35852 | 35855 | 35856 | 35859 |

TABLE 15-continued

Yield: Carbohydrate

| | | | | | | | | | | | |
|---|---|---|---|---|---|---|---|---|---|---|---|
| 35860 | 35863 | 35865 | 35867 | 35868 | 35878 | 35879 | 35880 | 35882 | 35886 | 35900 | 35901 |
| 35902 | 35905 | 35906 | 35910 | 35912 | 35914 | 35916 | 35924 | 35925 | 35927 | 35929 | 35932 |
| 35938 | 35939 | 35940 | 35941 | 35942 | 35945 | 35954 | 35955 | 35956 | 35957 | 35958 | 35962 |
| 35963 | 35964 | 35967 | 35968 | 35972 | 35974 | 35975 | 35980 | 35981 | 35982 | 35984 | 35985 |
| 35986 | 35987 | 35988 | 35989 | 35990 | 35991 | 35992 | 35995 | 35996 | 35997 | 36005 | 36006 |
| 36007 | 36008 | 36009 | 36010 | 36014 | 36015 | 36028 | 36030 | 36037 | 36038 | 36039 | 36043 |
| 36055 | 36057 | 36060 | 36062 | 36063 | 36069 | 36071 | 36075 | 36082 | 36085 | 36089 | 36090 |
| 36091 | 36100 | 36103 | 36104 | 36105 | 36114 | 36115 | 36120 | 36122 | 36123 | 36124 | 36125 |
| 36126 | 36127 | 36133 | 36135 | 36136 | 36137 | 36141 | 36144 | 36145 | 36148 | 36150 | 36154 |
| 36156 | 36158 | 36159 | 36165 | 36167 | 36170 | 36171 | 36173 | 36178 | 36186 | 36187 | 36188 |
| 36204 | 36209 | 36211 | 36213 | 36215 | 36216 | 36219 | 36220 | 36222 | 36223 | 36225 | 36228 |
| 36229 | 36235 | 36241 | 36245 | 36246 | 36252 | 36254 | 36256 | 36257 | 36261 | 36262 | 36264 |
| 36268 | 36277 | 36279 | 36280 | 36284 | 36286 | 36289 | 36294 | 36296 | 36301 | 36305 | 36307 |
| 36313 | 36314 | 36316 | 36317 | 36327 | 36332 | 36344 | 36345 | 36348 | 36353 | 36359 | 36360 |
| 36364 | 36365 | 36369 | 36373 | 36375 | 36382 | 36384 | 36385 | 36387 | 36390 | 36391 | 36393 |
| 36398 | 36399 | 36403 | 36407 | 36409 | 36410 | 36412 | 36417 | 36425 | 36429 | 36430 | 36431 |
| 36438 | 36440 | 36441 | 36442 | 36448 | 36450 | 36452 | 36453 | 36456 | 36460 | 36461 | 36467 |
| 36470 | 36473 | 36475 | 36476 | 36480 | 36484 | 36490 | 36491 | 36493 | 36494 | 36497 | 36499 |
| 36504 | 36508 | 36511 | 36512 | 36517 | 36520 | 36527 | 36532 | 36533 | 36537 | 36541 | 36542 |
| 36547 | 36555 | 36556 | 36559 | 36566 | 36576 | 36577 | 36591 | 36595 | 36597 | 36601 | 36602 |
| 36605 | 36609 | 36610 | 36612 | 36615 | 36618 | 36619 | 36622 | 36626 | 36629 | 36632 | 36633 |
| 36634 | 36636 | 36638 | 36643 | 36644 | 36646 | 36647 | 36650 | 36653 | 36655 | 36658 | 36663 |
| 36664 | 36665 | 36667 | 36671 | 36673 | 36674 | 36679 | 36684 | 36686 | 36687 | 36689 | 36693 |
| 36694 | 36695 | 36705 | 36707 | 36709 | 36710 | 36714 | 36715 | 36717 | 36718 | 36720 | 36722 |
| 36723 | 36729 | 36731 | 36732 | 36734 | 36735 | 36737 | 36738 | 36743 | 36746 | 36752 | 36754 |
| 36756 | 36765 | 36773 | 36776 | 36778 | 36781 | 36790 | 36792 | 36794 | 36796 | 36809 | 36810 |
| 36815 | 36816 | 36826 | 36827 | 36828 | 36831 | 36841 | 36842 | 36850 | 36855 | 36860 | 36865 |
| 36872 | 36874 | 36888 | 36893 | 36897 | 36908 | 36909 | 36913 | 36921 | 36924 | 36936 | 36938 |
| 36939 | 36940 | 36942 | 36946 | 36949 | 36950 | 36966 | 36968 | 36971 | 36989 | 36990 | 36994 |
| 36995 | 36998 | 37008 | 37012 | 37016 | 37017 | 37023 | 37027 | 37034 | 37037 | 37038 | 37039 |
| 37040 | 37041 | 37042 | 37046 | 37048 | 37053 | 37057 | 37078 | 37082 | 37092 | 37109 | 37110 |
| 37111 | 37113 | 37117 | 37118 | 37120 | 37124 | 37125 | 37127 | 37130 | 37131 | 37134 | 37143 |
| 37145 | 37147 | 37148 | 37149 | 37150 | 37151 | 37152 | 37153 | 37154 | 37158 | 37159 | 37160 |
| 37161 | 37162 | 37165 | 37167 | 37171 | 37172 | 37180 | 37184 | 37189 | 37195 | 37196 | 37202 |
| 37203 | 37209 | 37210 | 37212 | 37217 | 37218 | 37222 | 37223 | 37237 | 37238 | 37247 | 37248 |
| 37256 | 37257 | 37258 | 37262 | 37264 | 37266 | 37272 | 37279 | 37280 | 37281 | 37286 | 37290 |
| 37291 | 37293 | 37294 | 37297 | 37302 | 37304 | 37309 | 37313 | 37314 | 37316 | 37321 | 37323 |
| 37326 | 37327 | 37329 | 37333 | 37335 | 37341 | 37342 | 37350 | 37351 | 37352 | 37354 | 37359 |
| 37360 | 37361 | 37362 | 37364 | 37365 | 37372 | 37373 | 37376 | 37379 | 37382 | 37383 | |
| 37389 | 37392 | 37393 | 37403 | 37405 | 37408 | 37412 | 37413 | 37420 | 37421 | 37423 | 37425 |
| 37427 | 37430 | 37432 | 37433 | 37434 | 37435 | 37438 | 37439 | 37442 | 37448 | 37456 | 37459 |
| 37460 | 37464 | 37466 | 37470 | 37471 | 37472 | 37477 | 37480 | 37481 | 37483 | 37486 | 37487 |
| 37494 | 37499 | 37502 | 37505 | 37506 | 37511 | 37513 | 37514 | 37515 | 37518 | 37519 | 37528 |
| 37535 | 37536 | 37543 | 37547 | 37548 | 37549 | 37551 | 37552 | 37555 | 37556 | 37557 | 37558 |
| 37559 | 37560 | 37561 | 37562 | 37563 | 37564 | 37565 | 37567 | 37572 | 37573 | 37574 | 37577 |
| 37579 | 37580 | 37581 | 37582 | 37587 | 37590 | 37591 | 37592 | 37596 | 37599 | 37602 | 37604 |
| 37606 | 37608 | 37609 | 37612 | 37615 | 37616 | 37618 | 37622 | 37629 | 37631 | 37638 | 37639 |
| 37640 | 37644 | 37647 | 37650 | 37651 | 37655 | 37657 | 37660 | 37662 | 37671 | 37672 | 37673 |
| 37680 | 37687 | 37692 | 37695 | 37697 | 37698 | 37701 | 37704 | 37706 | 37709 | 37719 | 37720 |
| 37721 | 37722 | 37723 | 37725 | 37726 | 37728 | 37731 | 37738 | 37745 | 37754 | 37755 | 37760 |
| 37765 | 37766 | 37768 | 37770 | 37771 | 37772 | 37773 | 37776 | 37780 | 37782 | 37788 | 37789 |
| 37790 | 37791 | 37794 | 37797 | 37800 | 37801 | 37802 | 37806 | 37807 | 37808 | 37809 | |
| 37815 | 37816 | 37817 | 37819 | 37823 | 37824 | 37826 | 37827 | 37829 | 37830 | 37831 | 37837 |
| 37838 | 37844 | 37845 | 37846 | 37847 | 37851 | 37852 | 37854 | 37860 | 37861 | 37867 | 37869 |
| 37872 | 37876 | 37879 | 37880 | 37883 | 37884 | 37886 | 37888 | 37891 | 37892 | 37896 | 37897 |
| 37898 | 37901 | 37902 | 37906 | 37907 | 37908 | 37909 | 37912 | 37913 | 37917 | 37918 | 37919 |
| 37923 | 37932 | 37938 | 37941 | 37943 | 37944 | 37945 | 37947 | 37949 | 37951 | 37953 | 37955 |
| 37956 | 37960 | 37963 | 37967 | 37968 | 37971 | 37972 | 37973 | 37974 | 37976 | 37978 | 37984 |
| 37985 | 37986 | 37987 | 37989 | 37990 | 37991 | 37993 | 37995 | 37997 | 37999 | 38001 | 38003 |
| 38008 | 38009 | 38011 | 38012 | 38013 | 38014 | 38015 | 38016 | 38025 | 38030 | 38031 | 38032 |
| 38036 | 38039 | 38042 | 38043 | 38044 | 38046 | 38048 | 38051 | 38052 | 38053 | 38056 | 38057 |
| 38062 | 38063 | 38069 | 38073 | 38076 | 38081 | 38085 | 38086 | 38088 | 38092 | 38093 | 38095 |
| 38097 | 38099 | 38100 | 38103 | 38104 | 38109 | 38110 | 38111 | 38114 | 38115 | 38116 | 38119 |
| 38124 | 38126 | 38127 | 38131 | 38132 | 38134 | 38137 | 38141 | 38150 | 38155 | 38156 | |
| 38163 | 38165 | 38167 | 38172 | 38173 | 38175 | 38176 | 38177 | 38178 | 38179 | 38183 | 38184 |
| 38187 | 38189 | 38190 | 38196 | 38197 | 38199 | 38212 | 38213 | 38214 | 38217 | 38220 | 38221 |
| 38222 | 38225 | 38232 | 38236 | 38238 | 38242 | 38246 | 38247 | 38249 | 38250 | 38251 | 38252 |
| 38256 | 38258 | 38260 | 38263 | 38264 | 38271 | 38272 | 38273 | 38274 | 38275 | 38276 | 38278 |
| 38279 | 38284 | 38291 | 38295 | 38298 | 38299 | 38300 | 38301 | 38304 | 38305 | 38306 | 38307 |
| 38311 | 38313 | 38317 | 38318 | 38320 | 38321 | 38323 | 38324 | 38325 | 38326 | 38327 | 38328 |
| 38329 | 38330 | 38333 | 38338 | 38341 | 38345 | 38347 | 38349 | 38351 | 38352 | 38354 | 38367 |
| 38368 | 38369 | 38370 | 38371 | 38375 | 38378 | 38379 | 38381 | 38382 | 38384 | 38385 | 38389 |
| 38390 | 38392 | 38393 | 38396 | 38399 | 38402 | 38403 | 38404 | 38406 | 38407 | 38411 | 38415 |
| 38418 | 38420 | 38421 | 38422 | 38423 | 38424 | 38425 | 38426 | 38428 | 38430 | 38431 | 38435 |
| 38442 | 38444 | 38452 | 38453 | 38457 | 38460 | 38464 | 38465 | 38466 | 38467 | 38468 | 38469 |
| 38470 | 38471 | 38477 | 38478 | 38480 | 38489 | 38490 | 38493 | 38495 | 38496 | 38501 | 38504 |
| 38506 | 38507 | 38508 | 38510 | 38512 | 38513 | 38514 | 38515 | 38516 | 38518 | 38520 | 38521 |

TABLE 15-continued

Yield: Carbohydrate

| | | | | | | | | | | | |
|---|---|---|---|---|---|---|---|---|---|---|---|
| 38522 | 38523 | 38524 | 38525 | 38526 | 38529 | 38530 | 38532 | 38539 | 38542 | 38545 | 38546 |
| 38547 | 38548 | 38552 | 38557 | 38559 | 38560 | 38561 | 38562 | 38563 | 38564 | 38565 | 38567 |
| 38569 | 38573 | 38575 | 38576 | 38580 | 38582 | 38583 | 38585 | 38587 | 38591 | 38595 | 38602 |
| 38607 | 38614 | 38617 | 38618 | 38619 | 38620 | 38621 | 38622 | 38623 | 38624 | 38625 | 38626 |
| 38627 | 38628 | 38629 | 38630 | 38631 | 38639 | 38642 | 38644 | 38645 | 38646 | 38658 | 38663 |
| 38666 | 38669 | 38672 | 38675 | 38681 | 38684 | 38688 | 38689 | 38692 | 38693 | 38695 | 38696 |
| 38697 | 38698 | 38699 | 38702 | 38703 | 38704 | 38706 | 38709 | 38710 | 38711 | 38714 | 38715 |
| 38717 | 38720 | 38723 | 38731 | 38735 | 38736 | 38737 | 38738 | 38739 | 38742 | 38743 | 38744 |
| 38745 | 38746 | 38750 | 38752 | 38753 | 38754 | 38757 | 38760 | 38762 | 38764 | 38769 | 38770 |
| 38775 | 38778 | 38782 | 38783 | 38785 | 38786 | 38787 | 38788 | 38789 | 38791 | 38792 | 38794 |
| 38798 | 38801 | 38804 | 38807 | 38814 | 38818 | 38822 | 38824 | 38826 | 38827 | 38829 | 38830 |
| 38834 | 38835 | 38845 | 38848 | 38850 | 38852 | 38853 | 38854 | 38855 | 38856 | 38861 | 38863 |
| 38865 | 38866 | 38867 | 38868 | 38871 | 38873 | 38875 | 38876 | 38879 | 38883 | 38884 | 38885 |
| 38887 | 38888 | 38891 | 38895 | 38898 | 38900 | 38901 | 38902 | 38905 | 38906 | 38907 | 38908 |
| 38909 | 38910 | 38913 | 38918 | 38921 | 38923 | 38928 | 38929 | 38943 | 38944 | 38945 | 38947 |
| 38948 | 38955 | 38956 | 38957 | 38958 | 38959 | 38960 | 38963 | 38974 | 38978 | 38982 | 38988 |
| 38989 | 38993 | 38994 | 38995 | 39001 | 39016 | 39019 | 39021 | 39022 | 39023 | 39024 | 39028 |
| 39029 | 39030 | 39037 | 39038 | 39040 | 39044 | 39045 | 39046 | 39048 | 39049 | 39050 | 39053 |
| 39055 | 39057 | 39060 | 39061 | 39062 | 39066 | 39069 | 39072 | 39077 | 39081 | 39082 | 39084 |
| 39086 | 39087 | 39089 | 39104 | 39107 | 39113 | 39114 | 39115 | 39121 | 39122 | 39129 | 39131 |
| 39133 | 39135 | 39141 | 39142 | 39143 | 39146 | 39148 | 39153 | 39156 | 39157 | 39159 | 39165 |
| 39166 | 39168 | 39169 | 39170 | 39171 | 39172 | 39173 | 39180 | 39181 | 39182 | 39184 | 39185 |
| 39198 | 39199 | 39200 | 39208 | 39210 | 39212 | 39214 | 39220 | 39222 | 39225 | 39228 | 39235 |
| 39238 | 39240 | 39242 | 39247 | 39248 | 39249 | 39250 | 39251 | 39253 | 39254 | 39257 | 39258 |
| 39259 | 39261 | 39263 | 39264 | 39266 | 39267 | 39268 | 39270 | 39273 | 39277 | 39282 | 39284 |
| 39285 | 39291 | 39294 | 39295 | 39298 | 39299 | 39300 | 39301 | 39302 | 39303 | 39305 | 39308 |
| 39309 | 39310 | 39327 | 39328 | 39333 | 39348 | 39354 | 39355 | 39359 | 39360 | 39361 | 39367 |
| 39383 | 39386 | 39388 | 39389 | 39390 | 39391 | 39396 | 39397 | 39404 | 39405 | 39407 | 39411 |
| 39412 | 39413 | 39415 | 39416 | 39417 | 39420 | 39422 | 39424 | 39427 | 39428 | 39429 | 39430 |
| 39434 | 39437 | 39440 | 39445 | 39449 | 39450 | 39452 | 39454 | 39455 | 39457 | 39472 | 39475 |
| 39481 | 39482 | 39483 | 39489 | 39490 | 39498 | 39499 | 39501 | 39503 | 39509 | 39510 | 39511 |
| 39514 | 39516 | 39523 | 39526 | 39527 | 39529 | 39535 | 39536 | 39538 | 39539 | 39540 | 39541 |
| 39542 | 39543 | 39544 | 39551 | 39552 | 39553 | 39555 | 39556 | 39570 | 39571 | 39572 | 39579 |
| 39581 | 39583 | 39585 | 39591 | 39593 | 39596 | 39599 | 39601 | 39607 | 39611 | 39613 | 39615 |
| 39620 | 39621 | 39622 | 39623 | 39624 | 39626 | 39627 | 39630 | 39631 | 39632 | 39634 | 39638 |
| 39639 | 39640 | 39642 | 39643 | 39644 | 39646 | 39649 | 39653 | 39659 | 39661 | 39662 | 39666 |
| 39669 | 39670 | 39672 | 39674 | 39675 | 39676 | 39677 | 39678 | 39680 | 39683 | 39684 | 39685 |
| 39702 | 39703 | 39708 | 39735 | 39737 | 39739 | 39744 | 39745 | 39749 | 39750 | 39751 | 39758 |
| 39774 | 39777 | 39779 | 39780 | 39781 | 39782 | 39786 | 39789 | 39793 | 39796 | 39797 | |
| 39799 | 39800 | 39801 | 39802 | 39806 | 39807 | 39809 | 39810 | 39813 | 39814 | 39818 | 39821 |
| 39824 | 39829 | 39833 | 39834 | 39836 | 39838 | 39839 | 39841 | 39854 | 39857 | 39863 | 39864 |
| 39865 | 39871 | 39872 | 39877 | 39881 | 39883 | 39885 | 39890 | 39891 | 39892 | 39896 | 39897 |
| 39905 | 39906 | 39907 | 39908 | 39914 | 39916 | 39917 | 39918 | 39919 | 39920 | 39921 | 39926 |
| 39928 | 39929 | 39931 | 39943 | 39944 | 39945 | 39952 | 39954 | 39959 | 39963 | 39964 | 39967 |
| 39969 | 39976 | 39978 | 39981 | 39982 | 39987 | 39988 | 39989 | 39990 | 39992 | 39993 | 39997 |
| 39998 | 39999 | 40000 | 40002 | 40003 | 40004 | 40006 | 40007 | 40008 | 40009 | 40014 | 40019 |
| 40023 | 40025 | 40028 | 40031 | 40032 | 40033 | 40034 | 40036 | 40044 | 40055 | 40056 | |
| 40064 | 40065 | 40066 | 40067 | 40071 | 40072 | 40073 | 40074 | 40078 | 40081 | 40087 | 40089 |
| 40090 | 40091 | 40097 | 40103 | 40105 | 40107 | 40108 | 40110 | 40112 | 40114 | 40116 | 40117 |
| 40121 | 40125 | 40127 | 40128 | 40129 | 40132 | 40138 | 40141 | 40144 | 40147 | 40149 | 40151 |
| 40152 | 40153 | 40157 | 40161 | 40165 | 40167 | 40169 | 40175 | 40192 | 40195 | 40199 | 40200 |
| 40201 | 40204 | 40205 | 40212 | 40218 | 40219 | 40220 | 40223 | 40224 | 40229 | 40231 | 40232 |
| 40243 | 40245 | 40246 | 40247 | 40248 | 40251 | 40256 | 40258 | 40267 | 40268 | 40270 | 40272 |
| 40274 | 40275 | 40276 | 40279 | 40282 | 40283 | 40284 | 40287 | 40288 | 40290 | 40291 | 40292 |
| 40293 | 40299 | 40303 | 40304 | 40315 | 40316 | 40319 | 40321 | 40328 | 40329 | 40330 | 40331 |
| 40333 | 40334 | 40337 | 40338 | 40350 | 40351 | 40362 | 40363 | 40365 | 40366 | 40368 | |
| 40379 | 40380 | 40381 | 40385 | 40387 | 40390 | 40392 | 40394 | 40395 | 40405 | 40406 | 40407 |
| 40408 | 40410 | 40414 | 40417 | 40418 | 40421 | 40422 | 40433 | 40435 | 40436 | 40438 | 40443 |
| 40446 | 40448 | 40449 | 40450 | 40451 | 40453 | 40458 | 40460 | 40461 | 40466 | 40469 | 40470 |
| 40471 | 40472 | 40473 | 40476 | 40477 | 40479 | 40480 | 40481 | 40484 | 40495 | 40498 | 40499 |
| 40503 | 40510 | 40511 | 40514 | 40516 | 40517 | 40522 | 40526 | 40531 | 40533 | 40538 | 40542 |
| 40543 | 40547 | 40550 | 40552 | 40556 | 40557 | 40565 | 40569 | 40572 | 40575 | 40577 | 40579 |
| 40580 | 40584 | 40587 | 40589 | 40590 | 40592 | 40593 | 40594 | 40595 | 40598 | 40599 | 40600 |
| 40601 | 40602 | 40604 | 40611 | 40613 | 40615 | 40616 | 40618 | 40627 | 40628 | 40632 | |
| 40634 | 40636 | 40638 | 40641 | 40643 | 40653 | 40654 | 40655 | 40656 | 40657 | 40658 | 40661 |
| 40665 | 40666 | 40667 | 40668 | 40669 | 40670 | 40672 | 40683 | 40690 | 40692 | 40698 | 40699 |
| 40705 | 40708 | 40715 | 40718 | 40719 | 40723 | 40730 | 40731 | 40732 | 40737 | 40738 | 40739 |
| 40743 | 40750 | 40754 | 40755 | 40759 | 40760 | 40762 | 40764 | 40765 | 40766 | 40767 | 40772 |
| 40773 | 40798 | 40800 | 40801 | 40802 | 40803 | 40804 | 40805 | 40807 | 40814 | 40816 | 40820 |
| 40827 | 40828 | 40829 | 40831 | 40832 | 40833 | 40834 | 40835 | 40837 | 40839 | 40843 | 40844 |
| 40845 | 40849 | 40851 | 40852 | 40856 | 40858 | 40863 | 40864 | 40865 | 40866 | 40867 | 40868 |
| 40869 | 40870 | 40871 | 40872 | 40877 | 40879 | 40888 | 40899 | 40900 | 40901 | 40910 | 40911 |
| 40912 | 40936 | 40938 | 40939 | 40940 | 40941 | 40942 | 40943 | 40944 | 40945 | 40947 | 40948 |
| 40949 | 40951 | 40953 | 40954 | 40955 | 40956 | 40957 | 40959 | 40964 | 40966 | 40967 | 40968 |
| 40969 | 40972 | 40973 | 40974 | 40975 | 40976 | 40977 | 40978 | 40983 | 40984 | 40985 | 40988 |
| 40993 | 40994 | 40995 | 41001 | 41008 | 41009 | 41011 | 41012 | 41025 | 41026 | 41027 | 41028 |
| 41029 | 41031 | 41032 | 41036 | 41037 | 41038 | 41039 | 41040 | 41041 | 41042 | 41043 | 41047 |

TABLE 15-continued

Yield: Carbohydrate

| | | | | | | | | | | | |
|---|---|---|---|---|---|---|---|---|---|---|---|
| 41048 | 41051 | 41053 | 41054 | 41062 | 41063 | 41075 | 41076 | 41079 | 41081 | 41082 | 41083 |
| 41084 | 41085 | 41086 | 41087 | 41090 | 41092 | 41095 | 41097 | 41098 | 41099 | 41100 | 41104 |
| 41105 | 41114 | 41117 | 41120 | 41121 | 41122 | 41123 | 41124 | 41129 | 41131 | 41132 | 41133 |
| 41134 | 41135 | 41136 | 41137 | 41138 | 41145 | 41151 | 41152 | 41154 | 41157 | 41159 | 41160 |
| 41161 | 41162 | 41176 | 41182 | 41183 | 41185 | 41189 | 41192 | 41193 | 41195 | 41196 | 41198 |
| 41199 | 41200 | 41202 | 41203 | 41205 | 41215 | 41216 | 41217 | 41218 | 41221 | 41223 | 41224 |
| 41225 | 41226 | 41228 | 41229 | 41230 | 41240 | 41241 | 41242 | 41243 | 41255 | 41259 | 41260 |
| 41265 | 41281 | 41282 | 41288 | 41289 | 41290 | 41291 | 41292 | 41293 | 41297 | 41298 | 41300 |
| 41303 | 41305 | 41306 | 41312 | 41317 | 41318 | 41319 | 41320 | 41332 | 41333 | 41334 | 41335 |
| 41336 | 41339 | 41340 | 41345 | 41347 | 41348 | 41349 | 41350 | 41351 | 41352 | 41353 | 41361 |
| 41364 | 41365 | 41367 | 41368 | 41381 | 41382 | 41383 | 41387 | 41392 | 41398 | 41402 | 41406 |
| 41407 | 41408 | 41409 | 41411 | 41412 | 41427 | 41428 | 41429 | 41434 | 41441 | 41443 | 41448 |
| 41451 | 41455 | 41456 | 41457 | 41463 | 41464 | 41465 | 41467 | 41468 | 41470 | 41471 | 41472 |
| 41478 | 41482 | 41483 | 41490 | 41491 | 41495 | 41500 | 41505 | 41506 | 41512 | 41514 | 41518 |
| 41519 | 41521 | 41522 | 41523 | 41524 | 41525 | 41526 | 41527 | 41528 | 41533 | 41535 | 41540 |
| 41541 | 41547 | 41550 | 41551 | 41552 | 41553 | 41554 | 41555 | 41556 | 41559 | 41563 | 41564 |
| 41565 | 41568 | 41570 | 41571 | 41572 | 41573 | 41574 | 41575 | 41587 | 41590 | 41592 | 41593 |
| 41596 | 41603 | 41613 | 41616 | 41618 | 41619 | 41622 | 41629 | 41630 | 41634 | 41636 | 41637 |
| 41638 | 41642 | 41643 | 41645 | 41651 | 41653 | 41655 | 41667 | 41669 | 41670 | 41676 | 41678 |
| 41683 | 41684 | 41685 | 41686 | 41689 | 41691 | 41693 | 41694 | 41696 | 41698 | 41699 | 41700 |
| 41702 | 41703 | 41707 | 41708 | 41711 | 41715 | 41716 | 41721 | 41723 | 41728 | 41729 | 41730 |
| 41732 | 41735 | 41736 | 41737 | 41738 | 41741 | 41748 | 41749 | 41750 | 41751 | 41753 | 41755 |
| 41771 | 41773 | 41785 | 41786 | 41788 | 41789 | 41791 | 41794 | 41795 | 41798 | 41799 | 41801 |
| 41803 | 41807 | 41808 | 41809 | 41818 | 41820 | 41825 | 41826 | 41834 | 41835 | 41838 | 41839 |
| 41841 | 41842 | 41851 | 41852 | 41857 | 41858 | 41860 | 41870 | 41872 | 41875 | 41876 | 41877 |
| 41878 | 41880 | 41886 | 41888 | 41896 | 41897 | 41898 | 41899 | 41907 | 41913 | 41914 | 41923 |
| 41924 | 41928 | 41929 | 41941 | 41942 | 41946 | 41950 | 41952 | 41953 | 41954 | 41957 | 41958 |
| 41960 | 41961 | 41962 | 41963 | 41964 | 41965 | 41969 | 41975 | 41979 | 41980 | 41981 | 41982 |
| 41985 | 41990 | 41992 | 41994 | 41999 | 42000 | 42004 | 42005 | 42010 | 42011 | 42017 | 42023 |
| 42024 | 42029 | 42030 | 42031 | 42033 | 42036 | 42038 | 42039 | 42040 | 42041 | 42043 | 42044 |
| 42045 | 42046 | 42047 | 42054 | 42055 | 42057 | 42058 | 42059 | 42060 | 42061 | 42064 | 42073 |
| 42075 | 42081 | 42082 | 42083 | 42088 | 42089 | 42090 | 42092 | 42100 | 42101 | 42103 | 42104 |
| 42105 | 42112 | 42116 | 42117 | 42118 | 42119 | 42120 | 42128 | 42129 | 42130 | 42131 | 42136 |
| 42151 | 42154 | 42155 | 42158 | 42160 | 42161 | 42162 | 42163 | 42167 | 42176 | 42177 | 42184 |
| 42187 | 42188 | 42190 | 42192 | 42193 | 42199 | 42200 | 42204 | 42205 | 42209 | 42211 | 42215 |
| 42216 | 42217 | 42218 | 42221 | 42222 | 42231 | 42232 | 42240 | 42242 | 42246 | 42252 | 42263 |
| 42267 | 42270 | 42271 | 42272 | 42280 | 42281 | 42285 | 42286 | 42291 | 42301 | 42304 | 42305 |
| 42308 | 42309 | 42321 | 42322 | 42323 | 42339 | 42340 | 42342 | 42343 | 42345 | 42347 | 42355 |
| 42356 | 42362 | 42367 | 42368 | 42369 | 42370 | 42371 | 42377 | 42384 | 42391 | 42398 | 42399 |
| 42400 | 42402 | 42406 | 42410 | 42422 | 42430 | 42431 | 42436 | 42446 | 42447 | 42448 | 42452 |
| 42453 | 42454 | 42455 | 42462 | 42463 | 42464 | 42465 | 42468 | 42469 | 42470 | 42488 | 42489 |
| 42491 | 42496 | 42498 | 42509 | 42511 | 42512 | 42515 | 42516 | 42524 | 42526 | 42533 | 42543 |
| 42545 | 42550 | 42563 | 42566 | 42583 | 42584 | 42585 | 42599 | 42602 | 42605 | 42609 | 42615 |
| 42620 | 42624 | 42627 | 42637 | 42640 | 42645 | 42646 | 42651 | 42653 | 42658 | 42659 | 42660 |
| 42664 | 42665 | 42667 | 42668 | 42673 | 42682 | 42683 | 42687 | 42696 | 42697 | 42698 | 42704 |
| 42707 | 42710 | 42713 | 42717 | 42725 | 42727 | 42730 | 42736 | 42743 | 42749 | 42753 | 42754 |
| 42757 | 42761 | 42762 | 42763 | 42764 | 42767 | 42771 | 42772 | 42781 | 42784 | 42787 |
| 42788 | 42789 | 42794 | 42802 | 42809 | 42812 | 42814 | 42816 | 42824 | 42832 | 42842 | 42843 |
| 42850 | 42851 | 42858 | 42860 | 42861 | 42863 | 42865 | 42867 | 42869 | 42870 | 42874 | 42880 |
| 42884 | 42885 | 42887 | 42888 | 42889 | 42890 | 42892 | 42901 | 42903 | 42908 | 42909 | 42910 |
| 42918 | 42921 | 42925 | 42926 | 42927 | 42929 | 42930 | 42933 | 42937 | 42940 | 42942 | 42945 |
| 42946 | 42948 | 42949 | 42956 | 42958 | 42960 | 42969 | 42976 | 42979 | 42980 | 42982 |
| 42994 | 42996 | 42998 | 42999 | 43003 | 43017 | 43018 | 43020 | 43021 | 43026 | 43028 | 43029 |
| 43033 | 43034 | 43035 | 43038 | 43039 | 43042 | 43048 | 43052 | 43055 | 43056 | 43057 | 43059 |
| 43060 | 43063 | 43064 | 43065 | 43066 | 43070 | 43077 | 43081 | 43083 | 43084 | 43085 | 43088 |
| 43095 | 43101 | 43102 | 43103 | 43104 | 43105 | 43106 | 43109 | 43112 | 43116 | 43128 | 43129 |
| 43131 | 43132 | 43133 | 43134 | 43135 | 43136 | 43137 | 43138 | 43143 | 43159 | 43164 | 43165 |
| 43166 | 43171 | 43175 | 43178 | 43180 | 43181 | 43182 | 43184 | 43185 | 43186 | 43188 | 43189 |
| 43191 | 43204 | 43210 | 43211 | 43215 | 43217 | 43221 | 43225 | 43226 | 43227 | 43233 | 43238 |
| 43239 | 43241 | 43242 | 43243 | 43253 | 43254 | 43257 | 43267 | 43268 | 43271 | 43272 | 43274 |
| 43276 | 43277 | 43280 | 43281 | 43284 | 43301 | 43307 | 43308 | 43309 | 43310 | 43317 | 43319 |
| 43322 | 43325 | 43326 | 43348 | 43350 | 43351 | 43354 | 43355 | 43358 | 43359 | 43369 | 43375 |
| 43376 | 43377 | 43378 | 43382 | 43389 | 43390 | 43392 | 43393 | 43399 | 43402 | 43403 | 43404 |
| 43405 | 43406 | 43408 | 43410 | 43422 | 43426 | 43427 | 43428 | 43429 | 43430 | 43432 | 43438 |
| 43439 | 43440 | 43447 | 43450 | 43456 | 43457 | 43458 | 43463 | 43464 | 43468 | 43474 | 43480 |
| 43484 | 43486 | 43488 | 43489 | 43491 | 43493 | 43494 | 43495 | 43496 | 43497 | 43499 | 43501 |
| 43504 | 43507 | 43509 | 43512 | 43515 | 43522 | 43525 | 43527 | 43528 | 43531 | 43532 | 43535 |
| 43536 | 43537 | 43541 | 43545 | 43546 | 43549 | 43553 | 43554 | 43558 | 43559 | 43560 | 43561 |
| 43568 | 43569 | 43571 | 43575 | 43576 | 43580 | 43581 | 43584 | 43588 | 43591 | 43593 | 43594 |
| 43595 | 43600 | 43612 | 43614 | 43622 | 43627 | 43635 | 43636 | 43638 | 43644 | 43645 | 43646 |
| 43647 | 43652 | 43653 | 43657 | 43660 | 43665 | 43666 | 43667 | 43677 | 43679 | 43682 | 43683 |
| 43686 | 43697 | 43698 | 43701 | 43703 | 43705 | 43707 | 43713 | 43717 | 43719 | 43721 | 43730 |
| 43731 | 43732 | 43736 | 43738 | 43741 | 43743 | 43747 | 43749 | 43750 | 43757 | 43758 | 43761 |
| 43763 | 43764 | 43767 | 43770 | 43773 | 43780 | 43784 | 43786 | 43787 | 43792 | 43793 | 43794 |
| 43796 | 43803 | 43815 | 43819 | 43820 | 43823 | 43825 | 43833 | 43840 | 43841 | 43846 | 43847 |
| 43848 | 43849 | 43850 | 43852 | 43857 | 43864 | 43869 | 43877 | 43880 | 43882 | 43889 | 43905 |
| 43909 | 43915 | 43922 | 43931 | 43932 | 43936 | 43937 | 43938 | 43945 | 43954 | 43958 | 43962 |

TABLE 15-continued

Yield: Carbohydrate

| | | | | | | | | | | |
|---|---|---|---|---|---|---|---|---|---|---|
| 43966 | 43967 | 43969 | 43971 | 43973 | 43985 | 43989 | 43990 | 43991 | 43993 | 43994 | 43997 |
| 44000 | 44016 | 44017 | 44023 | 44027 | 44034 | 44035 | 44037 | 44056 | 44065 | 44068 | 44073 |
| 44078 | 44080 | 44083 | 44089 | 44091 | 44092 | 44102 | 44103 | 44104 | 44107 | 44110 | 44111 |
| 44112 | 44117 | 44118 | 44120 | 44139 | 44141 | 44143 | 44144 | 44150 | 44151 | 44152 | 44153 |
| 44154 | 44155 | 44157 | 44158 | 44160 | 44163 | 44168 | 44169 | 44176 | 44177 | 44178 | 44180 |
| 44183 | 44184 | 44185 | 44189 | 44190 | 44192 | 44193 | 44195 | 44196 | 44200 | 44205 | 44206 |
| 44209 | 44210 | 44212 | 44215 | 44218 | 44219 | 44220 | 44224 | 44227 | 44228 | 44229 | 44231 |
| 44232 | 44240 | 44242 | 44246 | 44250 | 44251 | 44254 | 44255 | 44257 | 44261 | 44264 | 44266 |
| 44270 | 44271 | 44272 | 44275 | 44279 | 44280 | 44281 | 44289 | 44290 | 44291 | 44293 | 44295 |
| 44299 | 44302 | 44303 | 44309 | 44311 | 44313 | 44318 | 44323 | 44324 | 44327 | 44334 | 44336 |
| 44343 | 44344 | 44348 | 44349 | 44350 | 44351 | 44352 | 44353 | 44357 | 44360 | 44361 | 44369 |
| 44375 | 44379 | 44380 | 44388 | 44392 | 44393 | 44394 | 44395 | 44397 | 44399 | 44400 | 44401 |
| 44403 | 44409 | 44412 | 44413 | 44416 | 44429 | 44431 | 44432 | 44433 | 44434 | 44435 | 44436 |
| 44437 | 44438 | 44439 | 44440 | 44441 | 44447 | 44448 | 44449 | 44456 | 44460 | 44467 | 44471 |
| 44476 | 44479 | 44480 | 44484 | 44487 | 44488 | 44491 | 44494 | 44496 | 44503 | 44504 | 44508 |
| 44510 | 44511 | 44512 | 44513 | 44514 | 44515 | 44523 | 44524 | 44525 | 44526 | 44531 | 44532 |
| 44533 | 44535 | 44536 | 44537 | 44541 | 44543 | 44546 | 44552 | 44553 | 44554 | 44561 | 44562 |
| 44563 | 44565 | 44570 | 44571 | 44573 | 44574 | 44576 | 44582 | 44584 | 44585 | 44586 | 44590 |
| 44603 | 44607 | 44611 | 44618 | 44619 | 44626 | 44630 | 44633 | 44638 | 44646 | 44647 | 44655 |
| 44658 | 44660 | 44664 | 44667 | 44673 | 44674 | 44675 | 44676 | 44677 | 44678 | 44685 | 44686 |
| 44690 | 44693 | 44708 | 44712 | 44718 | 44721 | 44722 | 44724 | 44725 | 44729 | 44731 | 44733 |
| 44734 | 44735 | 44736 | 44741 | 44744 | 44749 | 44751 | 44753 | 44755 | 44757 | 44758 | 44759 |
| 44761 | 44762 | 44764 | 44771 | 44773 | 44774 | 44778 | 44779 | 44781 | 44784 | 44788 | 44790 |
| 44791 | 44794 | 44798 | 44801 | 44811 | 44814 | 44817 | 44819 | 44820 | 44822 | 44829 | 44830 |
| 44833 | 44834 | 44836 | 44843 | 44849 | 44851 | 44853 | 44854 | 44855 | 44859 | 44862 | 44867 |
| 44870 | 44871 | 44872 | 44873 | 44874 | 44876 | 44877 | 44878 | 44880 | 44881 | 44887 | 44891 |
| 44892 | 44893 | 44896 | 44897 | 44898 | 44901 | 44906 | 44907 | 44932 | 44933 | 44935 | 44936 |
| 44939 | 44940 | 44949 | 44950 | 44954 | 44958 | 44964 | 44970 | 44978 | 44982 | 44985 | 44989 |
| 44990 | 44991 | 44998 | 44999 | 45000 | 45001 | 45004 | 45005 | 45011 | 45018 | 45020 | 45021 |
| 45022 | 45026 | 45035 | 45041 | 45042 | 45050 | 45051 | 45052 | 45060 | 45062 | 45064 | 45066 |
| 45068 | 45072 | 45076 | 45078 | 45089 | 45097 | 45098 | 45099 | 45103 | 45115 | 45117 | 45119 |
| 45123 | 45132 | 45136 | 45145 | 45146 | 45149 | 45153 | 45154 | 45158 | 45166 | 45170 | 45174 |
| 45188 | 45194 | 45199 | 45205 | 45207 | 45208 | 45212 | 45217 | 45220 | 45221 | 45222 | 45223 |
| 45226 | 45227 | 45233 | 45238 | 45239 | 45244 | 45247 | 45249 | 45250 | 45251 | 45263 | 45266 |
| 45269 | 45272 | 45284 | 45304 | 45305 | 45307 | 45311 | 45317 | 45324 | 45325 | 45326 | 45329 |
| 45331 | 45344 | 45345 | 45346 | 45348 | 45349 | 45353 | 45358 | 45362 | 45363 | 45368 | 45369 |
| 45373 | 45374 | 45382 | 45384 | 45387 | 45388 | 45389 | 45392 | 45393 | 45394 | 45398 | 45399 |
| 45400 | 45401 | 45402 | 45403 | 45404 | 45405 | 45407 | 45408 | 45410 | 45413 | 45417 | 45418 |
| 45419 | 45420 | 45421 | 45422 | 45423 | 45424 | 45425 | 45427 | 45428 | 45429 | 45432 | 45441 |
| 45445 | 45446 | 45447 | 45448 | 45449 | 45453 | 45455 | 45456 | 45463 | 45466 | 45468 | 45470 |
| 45476 | 45480 | 45487 | 45488 | 45493 | 45500 | 45503 | 45506 | 45507 | 45511 | 45512 | 45518 |
| 45520 | 45528 | 45531 | 45532 | 45534 | 45543 | 45544 | 45547 | 45548 | 45549 | 45551 | 45557 |
| 45560 | 45570 | 45580 | 45583 | 45593 | 45595 | 45607 | 45626 | 45633 | 45634 | 45639 |
| 45649 | 45653 | 45659 | 45662 | 45679 | 45683 | 45685 | 45686 | 45688 | 45689 | 45698 | 45699 |
| 45700 | 45702 | 45704 | 45707 | 45719 | 45720 | 45722 | 45723 | 45731 | 45733 | 45734 | 45735 |
| 45736 | 45740 | 45748 | 45749 | 45753 | 45758 | 45759 | 45761 | 45762 | 45765 | 45766 | 45775 |
| 45778 | 45783 | 45784 | 45789 | 45793 | 45794 | 45795 | 45803 | 45808 | 45809 | 45811 |
| 45812 | 45813 | 45814 | 45817 | 45821 | 45822 | 45850 | 45852 | 45867 | 45881 | 45887 | 45888 |
| 45893 | 45896 | 45897 | 45899 | 45900 | 45906 | 45917 | 45918 | 45919 | 45921 | 45922 | 45925 |
| 45926 | 45935 | 45941 | 45946 | 45947 | 45948 | 45956 | 45964 | 45973 | 45982 | 45996 | 46000 |
| 46012 | 46013 | 46014 | 46016 | 46018 | 46019 | 46022 | 46024 | 46033 | 46035 | 46048 | 46059 |
| 46064 | 46065 | 46071 | 46088 | 46089 | 46101 | 46104 | 46105 | 46106 | 46117 | 46125 | 46127 |
| 46128 | 46135 | 46138 | 46150 | 46178 | 46182 | 46187 | 46189 | 46190 | 46193 | 46195 | 46197 |
| 46201 | 46207 | 46220 | 46223 | 46236 | 46259 | 46265 | 46272 | 46273 | 46280 | 46281 | 46282 |
| 46285 | 46301 | 46310 | 46317 | 46318 | 46319 | 46320 | 46322 | 46323 | 46327 | 46335 | 46342 |
| 46350 | 46356 | 46364 | 46366 | 46387 | 46396 | 46410 | 46423 | 46434 | 46436 | 46446 | 46451 |
| 46453 | 46457 | 46467 | 46473 | 46474 | 46488 | 46506 | 46509 | 46510 | 46517 | 46518 | 46520 |
| 46523 | 46524 | 46532 | 46533 | 46542 | 46543 | 46545 | 46546 | 46548 | 46549 | 46551 | 46552 |
| 46559 | 46560 | 46577 | 46579 | 46580 | 46586 | 46596 | 46598 | 46601 | 46602 | 46603 | 46604 |
| 46606 | 46609 | 46611 | 46618 | 46620 | 46632 | 46633 | 46641 | 46650 | 46652 | 46654 | 46661 |
| 46662 | 46665 | 46671 | 46672 | 46678 | 46685 | 46686 | 46687 | 46693 | 46695 | 46696 | 46702 |
| 46713 | 46714 | 46718 | 46719 | 46721 | 46726 | 46742 | 46745 | 46754 | 46756 | 46757 | 46758 |
| 46760 | 46762 | 46764 | 46767 | 46768 | 46769 | 46771 | 46773 | 46779 | 46783 | 46784 | 46789 |
| 46791 | 46792 | 46793 | 46794 | 46796 | 46797 | 46799 | 46809 | 46810 | 46812 | 46813 | 46820 |
| 46825 | 46826 | 46827 | 46830 | 46831 | 46834 | 46835 | 46837 | 46838 | 46839 | 46841 | 46849 |
| 46851 | 46852 | 46856 | 46857 | 46873 | 46874 | 46876 | 46877 | 46878 | 46879 | 46880 | 46881 |
| 46882 | 46890 | 46896 | 46897 | 46899 | 46904 | 46912 | 46913 | 46914 | 46916 | 46918 | 46919 |
| 46920 | 46921 | 46922 | 46923 | 46924 | 46925 | 46926 | 46927 | 46928 | 46929 | 46931 | 46934 |
| 46936 | 46939 | 46940 | 46946 | 46947 | 46948 | 46949 | 46950 | 46951 | 46952 | 46953 | 46954 |
| 46955 | 46957 | 46959 | 46962 | 46963 | 46964 | 46969 | 46973 | 46974 | 46975 | 46976 | 46978 |
| 46979 | 46983 | 46986 | 46987 | 46988 | 46989 | 46990 | 46991 | 46994 | 46996 | 46997 | 46998 |
| 47000 | 47001 | 47008 | 47009 | 47010 | 47011 | 47012 | 47013 | 47014 | 47020 | 47023 | 47032 |
| 47034 | 47036 | 47038 | 47039 | 47040 | 47041 | 47042 | 47048 | 47049 | 47054 | 47055 | 47056 |
| 47057 | 47058 | 47060 | 47061 | 47062 | 47063 | 47064 | 47066 | 47072 | 47075 | 47076 | 47077 |
| 47083 | 47086 | 47087 | 47095 | 47096 | 47097 | 47100 | 47106 | 47110 | 47119 | 47120 | 47121 |
| 47129 | 47130 | 47131 | 47132 | 47133 | 47134 | 47137 | 47143 | 47144 | 47149 | 47151 | 47155 |
| 47156 | 47158 | 47166 | 47169 | 47171 | 47172 | 47177 | 47180 | 47188 | 47192 | 47194 | 47198 |

TABLE 15-continued

Yield: Carbohydrate

| | | | | | | | | | | |
|---|---|---|---|---|---|---|---|---|---|---|
| 47200 | 47203 | 47204 | 47205 | 47212 | 47214 | 47218 | 47223 | 47224 | 47225 | 47228 | 47229 |
| 47232 | 47233 | 47234 | 47238 | 47239 | 47241 | 47242 | 47245 | 47246 | 47248 | 47250 | 47253 |
| 47258 | 47259 | 47264 | 47265 | 47268 | 47269 | 47270 | 47271 | 47272 | 47273 | 47274 | 47275 |
| 47281 | 47283 | 47285 | 47286 | 47288 | 47289 | 47292 | 47295 | 47297 | 47303 | 47306 | 47307 |
| 47317 | 47318 | 47322 | 47325 | 47326 | 47327 | 47333 | 47337 | 47342 | 47343 | 47345 | 47352 |
| 47353 | 47354 | 47359 | 47360 | 47364 | 47366 | 47374 | | | | | |

TABLE 16

Yield: Nitrogen

Table 16A SEQ ID NOs of Polypeptides useful for improving Yield: Nitrogen

| | | | | | | | | | | |
|---|---|---|---|---|---|---|---|---|---|---|
| 9 | 18 | 21 | 68 | 71 | 76 | 93 | 94 | 110 | 129 | 139 | 209 |
| 231 | 261 | 262 | 264 | 287 | 295 | 333 | 345 | 350 | 353 | 362 | 364 |
| 443 | 447 | 455 | 508 | 603 | 612 | 616 | 618 | 625 | 626 | 681 | 699 |
| 722 | 755 | 768 | 780 | 785 | 789 | 798 | 805 | 806 | 807 | 808 | 811 |
| 815 | 827 | 828 | 829 | 830 | 831 | 832 | 840 | 852 | 859 | 869 | 873 |
| 901 | 918 | 919 | 968 | 970 | 1022 | 1032 | 1089 | 1110 | 1112 | 1224 | 1225 |
| 1295 | 1296 | 1312 | 1326 | 1354 | 1518 | 1584 | 1592 | 1747 | 1753 | 1806 | 1877 |
| 1988 | 1993 | 1995 | 2082 | 2124 | 2126 | 2129 | 2152 | 2160 | 2166 | 2199 | 2209 |
| 2246 | 2251 | 2341 | 2398 | 2407 | 2409 | 2411 | 2470 | 2550 | 2624 | 2629 | 2684 |
| 2727 | 2741 | 2820 | 2846 | 2899 | 2920 | 2954 | 2983 | 2987 | 3002 | 3005 | 3012 |
| 3017 | 3061 | 3132 | 3169 | 3171 | 3181 | 3194 | 3233 | 3259 | 3264 | 3316 | 3334 |
| 3348 | 3368 | 3379 | 3409 | 3500 | 3516 | 3611 | 3674 | 3675 | 3684 | 3685 | 3710 |
| 3771 | 3810 | 3828 | 4000 | 4046 | 4076 | 4128 | 4194 | 4229 | 4269 | 4299 | 4303 |
| 4355 | 4377 | 4407 | 4409 | 4420 | 4451 | 4481 | 4493 | 4505 | 4565 | 4569 | 4653 |
| 4678 | 4717 | 4738 | 4748 | 4762 | 4805 | 4817 | 4827 | 4828 | 4850 | 4862 | 4873 |
| 4890 | 4919 | 4940 | 4943 | 4964 | 5020 | 5152 | 5211 | 5214 | 5215 | 5279 | 5480 |
| 5510 | 5701 | 5737 | 5771 | 5778 | 5788 | 5801 | 5859 | 5868 | 5924 | 5925 | 5926 |
| 6069 | 6093 | 6105 | 6194 | 6232 | 6505 | 6717 | 6793 | 6871 | 6907 | 6912 | 6990 |
| 7055 | 7059 | 7109 | 7131 | 7163 | 7165 | 7176 | 7211 | 7240 | 7252 | 7263 | 7323 |
| 7326 | 7411 | 7437 | 7476 | 7497 | 7508 | 7521 | 7564 | 7576 | 7586 | 7587 | 7609 |
| 7621 | 7633 | 7648 | 7677 | 7698 | 7701 | 7722 | 7787 | 7788 | 7795 | 7805 | 7811 |
| 7854 | 7859 | 7863 | 7864 | 7868 | 7873 | 7898 | 7937 | 7939 | 7952 | 7994 | 8032 |
| 8057 | 8066 | 8100 | 8121 | 8160 | 8204 | 8215 | 8265 | 8274 | 8304 | 8332 | 8359 |
| 8367 | 8374 | 8415 | 8422 | 8424 | 8425 | 8445 | 8456 | 8477 | 8489 | 8504 | 8528 |
| 8544 | 8574 | 8605 | 8616 | 8635 | 8636 | 8637 | 8638 | 8659 | 8680 | 8685 | 8686 |
| 8715 | 8819 | 8880 | 8931 | 8943 | 8949 | 8952 | 8969 | 9010 | 9039 | 9059 | 9060 |
| 9074 | 9091 | 9153 | 9193 | 9200 | 9222 | 9225 | 9231 | 9268 | 9308 | 9332 | 9340 |
| 9401 | 9410 | 9412 | 9413 | 9438 | 9458 | 9462 | 9480 | 9519 | 9575 | 9583 | 9629 |
| 9643 | 9657 | 9662 | 9663 | 9670 | 9682 | 9687 | 9693 | 9698 | 9699 | 9702 | 9707 |
| 9709 | 9728 | 9729 | 9730 | 9736 | 9741 | 9752 | 9756 | 9757 | 9758 | 9760 | 9763 |
| 9783 | 9784 | 9796 | 9797 | 9801 | 9810 | 9816 | 9817 | 9823 | 9824 | 9825 | 9839 |
| 9842 | 9843 | 9844 | 9845 | 9846 | 9847 | 9848 | 9849 | 9850 | 9871 | 9872 | 9873 |
| 9882 | 9883 | 9885 | 9887 | 9906 | 9911 | 9914 | 9915 | 9917 | 9918 | 9919 | 9921 |
| 9941 | 9947 | 9948 | 9954 | 9955 | 9965 | 9998 | 9999 | 10018 | 10065 | 10104 | 10192 |
| 10222 | 10237 | 10253 | 10296 | 10337 | 10347 | 10402 | 10428 | 10444 | 10463 | 10515 | 10516 |
| 10530 | 10585 | 10607 | 10621 | 10634 | 10641 | 10742 | 10792 | 10804 | 10831 | 10856 | 10857 |
| 10909 | 10949 | 10957 | 10974 | 10986 | 10994 | 11053 | 11054 | 11072 | 11105 | 11138 | 11160 |
| 11193 | 11202 | 11227 | 11249 | 11264 | 11265 | 11281 | 11288 | 11309 | 11314 | 11413 | 11446 |
| 11458 | 11459 | 11481 | 11546 | 11582 | 11592 | 11632 | 11650 | 11661 | 11690 | 11720 | 11747 |
| 11749 | 11802 | 11803 | 11804 | 11815 | 11824 | 11840 | 11878 | 11947 | 11974 | 11985 | 11997 |
| 12026 | 12063 | 12083 | 12094 | 12135 | 12138 | 12153 | 12171 | 12196 | 12252 | 12375 | 12458 |
| 12507 | 12528 | 12529 | 12558 | 12605 | 12620 | 12676 | 12683 | 12686 | 12716 | 12761 | 12770 |
| 12797 | 12800 | 12823 | 12849 | 12996 | 13000 | 13055 | 13156 | 13163 | 13313 | 13323 | 13333 |
| 13334 | 13396 | 13446 | 13471 | 13472 | 13478 | 13479 | 13537 | 13538 | 13539 | 13556 | 13707 |
| 13716 | 13721 | 13723 | 13729 | 13793 | 13794 | 13797 | 13875 | 13926 | 13989 | 14012 | 14024 |
| 14025 | 14041 | 14066 | 14070 | 14106 | 14123 | 14192 | 14199 | 14208 | 14216 | 14232 | 14235 |
| 14248 | 14250 | 14275 | 14353 | 14383 | 14384 | 14487 | 14507 | 14518 | 14551 | 14625 | 14657 |
| 14698 | 14713 | 14715 | 14724 | 14725 | 14746 | 14754 | 14832 | 14871 | 14911 | 14966 | 15002 |
| 15020 | 15076 | 15120 | 15132 | 15181 | 15194 | 15196 | 15204 | 15206 | 15224 | 15233 | 15260 |
| 15388 | 15390 | 15399 | 15400 | 15442 | 15460 | 15471 | 15478 | 15479 | 15515 | 15529 | 15627 |
| 15694 | 15756 | 15758 | 15767 | 15768 | 15811 | 15828 | 15841 | 15848 | 15849 | 15887 | 15900 |
| 16002 | 16085 | 16139 | 16142 | 16151 | 16152 | 16190 | 16208 | 16262 | 16271 | 16355 | 16380 |
| 16417 | 16452 | 16481 | 16517 | 16565 | 16566 | 16567 | 16568 | 16595 | 16598 | 16642 | 16643 |
| 16660 | 16662 | 16683 | 16709 | 16715 | 16771 | 16791 | 16801 | 16814 | 16852 | 16896 | 16946 |
| 16996 | 17020 | 17080 | 17121 | 17134 | 17135 | 17155 | 17177 | 17231 | 17284 | 17329 | 17336 |
| 17348 | 17365 | 17373 | 17380 | 17396 | 17397 | 17466 | 17476 | 17487 | 17508 | 17572 | 17599 |
| 17658 | 17663 | 17688 | 17701 | 17708 | 17726 | 17747 | 17764 | 17765 | 17766 | 17785 | 17859 |
| 17936 | 18027 | 18054 | 18088 | 18098 | 18099 | 18107 | 18149 | 18176 | 18177 | 18192 | 18205 |
| 18338 | 18352 | 18353 | 18354 | 18367 | 18379 | 18406 | 18413 | 18414 | 18420 | 18537 | 18569 |
| 18586 | 18587 | 18612 | 18653 | 18713 | 18763 | 18804 | 18851 | 18852 | 18882 | 18914 | 18971 |
| 18978 | 19022 | 19037 | 19055 | 19072 | 19073 | 19082 | 19106 | 19182 | 19185 | 19187 | 19216 |

TABLE 16-continued

Yield: Nitrogen

| | | | | | | | | | | |
|---|---|---|---|---|---|---|---|---|---|---|
| 19256 | 19431 | 19433 | 19461 | 19464 | 19466 | 19478 | 19522 | 19572 | 19579 | 19605 | 19630 |
| 19680 | 19706 | 19709 | 19745 | 19782 | 19783 | 19784 | 19826 | 19847 | 19849 | 19916 | 19978 |
| 20008 | 20016 | 20035 | 20050 | 20133 | 20229 | 20233 | 20241 | 20270 | 20361 | 20362 | 20377 |
| 20391 | 20423 | 20469 | 20480 | 20485 | 20497 | 20548 | 20562 | 20580 | 20657 | 20695 | 20742 |
| 20747 | 20764 | 20801 | 20813 | 20814 | 20815 | 20855 | 20897 | 20919 | 20925 | 20927 | 21007 |
| 21015 | 21016 | 21038 | 21094 | 21125 | 21132 | 21147 | 21154 | 21158 | 21246 | 21281 | 21288 |
| 21327 | 21336 | 21337 | 21355 | 21391 | 21412 | 21429 | 21442 | 21467 | 21487 | 21513 | 21516 |
| 21525 | 21563 | 21564 | 21586 | 21603 | 21604 | 21658 | 21659 | 21669 | 21701 | 21706 | 21722 |
| 21743 | 21752 | 21757 | 21786 | 21803 | 21831 | 21835 | 21850 | 21952 | 22023 | 22097 | 22130 |
| 22152 | 22161 | 22197 | 22241 | 22307 | 22331 | 22377 | 22403 | 22439 | 22508 | 22516 | 22519 |
| 22553 | 22715 | 22814 | 22858 | 22887 | 22888 | 22889 | 22895 | 22909 | 22919 | 22932 | 22938 |
| 22969 | 23003 | 23017 | 23040 | 23076 | 23150 | 23159 | 23183 | 23195 | 23214 | 23218 | 23225 |
| 23238 | 23239 | 23293 | 23312 | 23315 | 23339 | 23340 | 23341 | 23342 | 23350 | 23387 | 23418 |
| 23422 | 23437 | 23479 | 23516 | 23523 | 23597 | 23610 | 23628 | 23636 | 23657 | 23660 | |

Table 16B SEQ ID NOs of Polynucleotides useful for improving Yield: Nitrogen

| | | | | | | | | | | |
|---|---|---|---|---|---|---|---|---|---|---|
| 23696 | 23705 | 23708 | 23755 | 23758 | 23763 | 23780 | 23781 | 23797 | 23816 | 23826 | 23896 |
| 23918 | 23948 | 23949 | 23951 | 23974 | 23982 | 24020 | 24032 | 24037 | 24040 | 24049 | 24051 |
| 24130 | 24134 | 24142 | 24195 | 24290 | 24299 | 24303 | 24305 | 24312 | 24313 | 24368 | 24386 |
| 24409 | 24442 | 24455 | 24467 | 24472 | 24476 | 24485 | 24492 | 24493 | 24494 | 24495 | 24498 |
| 24502 | 24514 | 24515 | 24516 | 24517 | 24518 | 24519 | 24527 | 24539 | 24546 | 24556 | 24560 |
| 24588 | 24605 | 24606 | 24655 | 24657 | 24709 | 24719 | 24776 | 24797 | 24799 | 24911 | 24912 |
| 24982 | 24983 | 24999 | 25013 | 25041 | 25205 | 25271 | 25279 | 25434 | 25440 | 25493 | 25564 |
| 25675 | 25680 | 25682 | 25769 | 25811 | 25813 | 25816 | 25839 | 25847 | 25853 | 25886 | 25896 |
| 25933 | 25938 | 26028 | 26085 | 26094 | 26096 | 26098 | 26157 | 26237 | 26311 | 26316 | 26371 |
| 26414 | 26428 | 26507 | 26533 | 26586 | 26607 | 26641 | 26670 | 26674 | 26689 | 26692 | 26699 |
| 26704 | 26748 | 26819 | 26856 | 26858 | 26868 | 26881 | 26920 | 26946 | 26951 | 27003 | 27021 |
| 27035 | 27055 | 27066 | 27096 | 27187 | 27203 | 27298 | 27361 | 27362 | 27371 | 27372 | 27397 |
| 27458 | 27497 | 27515 | 27687 | 27733 | 27763 | 27815 | 27881 | 27916 | 27956 | 27986 | 27990 |
| 28042 | 28064 | 28094 | 28096 | 28107 | 28138 | 28168 | 28180 | 28192 | 28252 | 28256 | 28340 |
| 28365 | 28404 | 28425 | 28435 | 28449 | 28492 | 28504 | 28514 | 28515 | 28537 | 28549 | 28560 |
| 28577 | 28606 | 28627 | 28630 | 28651 | 28707 | 28839 | 28898 | 28901 | 28902 | 28966 | 29167 |
| 29197 | 29388 | 29424 | 29458 | 29465 | 29475 | 29488 | 29546 | 29555 | 29611 | 29612 | 29613 |
| 29756 | 29780 | 29792 | 29881 | 29919 | 30192 | 30404 | 30480 | 30558 | 30594 | 30599 | 30677 |
| 30742 | 30746 | 30796 | 30818 | 30850 | 30852 | 30863 | 30898 | 30927 | 30939 | 30950 | 31010 |
| 31013 | 31098 | 31124 | 31163 | 31184 | 31195 | 31208 | 31251 | 31263 | 31273 | 31274 | 31296 |
| 31308 | 31320 | 31335 | 31364 | 31385 | 31388 | 31409 | 31474 | 31475 | 31482 | 31492 | 31498 |
| 31541 | 31546 | 31550 | 31551 | 31555 | 31560 | 31585 | 31624 | 31626 | 31639 | 31681 | 31719 |
| 31744 | 31753 | 31787 | 31808 | 31847 | 31891 | 31902 | 31952 | 31961 | 31991 | 32019 | 32046 |
| 32054 | 32061 | 32102 | 32109 | 32111 | 32112 | 32132 | 32143 | 32164 | 32176 | 32191 | 32215 |
| 32231 | 32261 | 32292 | 32303 | 32322 | 32323 | 32324 | 32325 | 32346 | 32367 | 32372 | 32373 |
| 32402 | 32506 | 32567 | 32618 | 32630 | 32636 | 32639 | 32656 | 32697 | 32726 | 32746 | 32747 |
| 32761 | 32778 | 32840 | 32880 | 32887 | 32909 | 32912 | 32955 | 32995 | 33019 | 33027 | |
| 33088 | 33097 | 33099 | 33100 | 33125 | 33145 | 33149 | 33167 | 33206 | 33262 | 33270 | 33316 |
| 33330 | 33344 | 33349 | 33350 | 33357 | 33369 | 33374 | 33380 | 33385 | 33386 | 33389 | 33394 |
| 33396 | 33415 | 33416 | 33417 | 33423 | 33428 | 33439 | 33443 | 33444 | 33445 | 33447 | 33450 |
| 33470 | 33471 | 33483 | 33484 | 33488 | 33497 | 33503 | 33504 | 33511 | 33512 | 33526 | |
| 33529 | 33530 | 33531 | 33532 | 33533 | 33534 | 33535 | 33536 | 33537 | 33558 | 33559 | 33560 |
| 33569 | 33570 | 33572 | 33574 | 33593 | 33598 | 33601 | 33602 | 33604 | 33605 | 33606 | 33608 |
| 33628 | 33634 | 33635 | 33641 | 33642 | 33652 | 33685 | 33686 | 33705 | 33752 | 33791 | 33879 |
| 33909 | 33924 | 33940 | 33983 | 34024 | 34034 | 34089 | 34115 | 34131 | 34150 | 34202 | 34203 |
| 34217 | 34272 | 34294 | 34308 | 34321 | 34328 | 34429 | 34479 | 34491 | 34518 | 34543 | 34544 |
| 34596 | 34636 | 34644 | 34661 | 34673 | 34681 | 34740 | 34741 | 34759 | 34792 | 34825 | 34847 |
| 34880 | 34889 | 34914 | 34936 | 34951 | 34952 | 34968 | 34975 | 34996 | 35001 | 35100 | 35133 |
| 35145 | 35146 | 35168 | 35233 | 35269 | 35279 | 35319 | 35337 | 35348 | 35377 | 35407 | 35434 |
| 35436 | 35489 | 35490 | 35491 | 35502 | 35511 | 35527 | 35565 | 35634 | 35661 | 35672 | 35684 |
| 35713 | 35750 | 35770 | 35781 | 35822 | 35825 | 35840 | 35858 | 35883 | 35939 | 36062 | 36145 |
| 36194 | 36215 | 36216 | 36245 | 36292 | 36307 | 36363 | 36370 | 36373 | 36403 | 36448 | 36457 |
| 36484 | 36487 | 36510 | 36536 | 36683 | 36687 | 36742 | 36843 | 36850 | 37000 | 37010 | 37020 |
| 37021 | 37083 | 37133 | 37158 | 37159 | 37165 | 37166 | 37224 | 37225 | 37226 | 37243 | 37394 |
| 37403 | 37408 | 37410 | 37416 | 37480 | 37481 | 37484 | 37562 | 37613 | 37676 | 37699 | 37711 |
| 37712 | 37728 | 37753 | 37757 | 37793 | 37810 | 37879 | 37886 | 37895 | 37903 | 37919 | 37922 |
| 37935 | 37937 | 37962 | 38040 | 38070 | 38071 | 38174 | 38194 | 38205 | 38238 | 38312 | 38344 |
| 38385 | 38400 | 38402 | 38411 | 38412 | 38433 | 38441 | 38463 | 38558 | 38598 | 38653 | 38689 |
| 38707 | 38763 | 38807 | 38819 | 38868 | 38881 | 38883 | 38891 | 38893 | 38911 | 38920 | 38947 |
| 39075 | 39077 | 39086 | 39087 | 39129 | 39147 | 39158 | 39165 | 39166 | 39202 | 39216 | 39314 |
| 39381 | 39443 | 39445 | 39454 | 39455 | 39498 | 39515 | 39528 | 39535 | 39536 | 39574 | 39587 |
| 39689 | 39772 | 39826 | 39829 | 39838 | 39839 | 39877 | 39895 | 39949 | 39958 | 40042 | 40067 |
| 40104 | 40139 | 40168 | 40204 | 40252 | 40253 | 40254 | 40255 | 40282 | 40285 | 40329 | 40330 |
| 40347 | 40349 | 40370 | 40396 | 40402 | 40458 | 40478 | 40488 | 40501 | 40539 | 40583 | 40633 |
| 40683 | 40707 | 40767 | 40808 | 40821 | 40822 | 40842 | 40864 | 40918 | 40971 | 41016 | 41023 |
| 41035 | 41052 | 41060 | 41067 | 41083 | 41084 | 41153 | 41174 | 41195 | 41259 | 41286 | |
| 41345 | 41350 | 41375 | 41388 | 41395 | 41413 | 41434 | 41451 | 41452 | 41453 | 41472 | 41546 |
| 41623 | 41714 | 41741 | 41775 | 41785 | 41786 | 41794 | 41836 | 41863 | 41864 | 41879 | 41892 |
| 42025 | 42039 | 42040 | 42041 | 42054 | 42066 | 42093 | 42100 | 42101 | 42107 | 42224 | 42256 |
| 42273 | 42274 | 42299 | 42340 | 42400 | 42450 | 42491 | 42538 | 42539 | 42569 | 42601 | 42658 |
| 42665 | 42709 | 42724 | 42742 | 42759 | 42760 | 42769 | 42793 | 42869 | 42872 | 42874 | 42903 |

TABLE 16-continued

Yield: Nitrogen

| | | | | | | | | | | | |
|---|---|---|---|---|---|---|---|---|---|---|---|
| 42943 | 43118 | 43120 | 43148 | 43151 | 43153 | 43165 | 43209 | 43259 | 43266 | 43292 | 43317 |
| 43367 | 43393 | 43396 | 43432 | 43469 | 43470 | 43471 | 43513 | 43534 | 43536 | 43603 | 43665 |
| 43695 | 43703 | 43722 | 43737 | 43820 | 43916 | 43920 | 43928 | 43957 | 44048 | 44049 | 44064 |
| 44078 | 44110 | 44156 | 44167 | 44172 | 44184 | 44235 | 44249 | 44267 | 44344 | 44382 | 44429 |
| 44434 | 44451 | 44488 | 44500 | 44501 | 44502 | 44542 | 44584 | 44606 | 44612 | 44614 | 44694 |
| 44702 | 44703 | 44725 | 44781 | 44812 | 44819 | 44834 | 44841 | 44845 | 44933 | 44968 | 44975 |
| 45014 | 45023 | 45024 | 45042 | 45078 | 45099 | 45116 | 45129 | 45154 | 45174 | 45200 | 45203 |
| 45212 | 45250 | 45251 | 45273 | 45290 | 45291 | 45345 | 45346 | 45356 | 45388 | 45393 | 45409 |
| 45430 | 45439 | 45444 | 45473 | 45490 | 45518 | 45522 | 45537 | 45639 | 45710 | 45784 | 45817 |
| 45839 | 45848 | 45884 | 45928 | 45994 | 46018 | 46064 | 46090 | 46126 | 46195 | 46203 | 46206 |
| 46240 | 46402 | 46501 | 46545 | 46574 | 46575 | 46576 | 46582 | 46596 | 46606 | 46619 | 46625 |
| 46656 | 46690 | 46704 | 46727 | 46763 | 46837 | 46846 | 46870 | 46882 | 46901 | 46905 | 46912 |
| 46925 | 46926 | 46980 | 46999 | 47002 | 47026 | 47027 | 47028 | 47029 | 47037 | 47074 | 47105 |
| 47109 | 47124 | 47166 | 47203 | 47210 | 47284 | 47297 | 47315 | 47323 | 47344 | 47347 | |

TABLE 17

Yield: Phosphorus

Table 17A SEQ ID NOs of Polypeptides useful for improving Yield: Phosphorus

| | | | | | | | | | | | |
|---|---|---|---|---|---|---|---|---|---|---|---|
| 24 | 304 | 438 | 695 | 861 | 982 | 1023 | 1074 | 1109 | 1177 | 1187 | 1396 |
| 1401 | 1403 | 1421 | 1424 | 1453 | 1454 | 1475 | 1482 | 1486 | 1488 | 1498 | 1514 |
| 1532 | 1538 | 1549 | 1560 | 1574 | 1576 | 1578 | 1581 | 1595 | 1596 | 1600 | 1619 |
| 1696 | 1697 | 1700 | 1721 | 1742 | 1766 | 1767 | 1795 | 1820 | 1841 | 1842 | 1864 |
| 1874 | 1879 | 1891 | 1895 | 1908 | 1924 | 1938 | 1940 | 1967 | 1968 | 1989 | 1991 |
| 2000 | 2012 | 2016 | 2039 | 2049 | 2069 | 2076 | 2085 | 2088 | 2092 | 2103 | 2108 |
| 2159 | 2161 | 2177 | 2187 | 2188 | 2212 | 2236 | 2248 | 2280 | 2299 | 2314 | 2320 |
| 2338 | 2349 | 2355 | 2371 | 2376 | 2385 | 2395 | 2414 | 2422 | 2434 | 2451 | 2454 |
| 2462 | 2494 | 2499 | 2503 | 2511 | 2515 | 2525 | 2533 | 2549 | 2557 | 2565 | 2571 |
| 2577 | 2581 | 2589 | 2611 | 2897 | 3045 | 3079 | 3091 | 3101 | 3110 | 3112 | 3147 |
| 3204 | 3205 | 3211 | 3221 | 3225 | 3229 | 3257 | 3269 | 3275 | 3282 | 3287 | 3303 |
| 3312 | 3329 | 3416 | 3428 | 3434 | 3438 | 3451 | 3452 | 3477 | 3483 | 3485 | 3514 |
| 3528 | 3552 | 3560 | 3569 | 3574 | 3596 | 3613 | 3635 | 3697 | 3718 | 3719 | 3738 |
| 3744 | 3752 | 3796 | 3848 | 3859 | 3860 | 3864 | 3880 | 3898 | 3944 | 3956 | 3957 |
| 3991 | 4007 | 4014 | 4015 | 4017 | 4023 | 4063 | 4090 | 4106 | 4120 | 4121 | 4132 |
| 4162 | 4163 | 4170 | 4193 | 4257 | 4459 | 4708 | 4782 | 4845 | 4904 | 4977 | 4979 |
| 4995 | 5032 | 5056 | 5060 | 5086 | 5133 | 5137 | 5138 | 5153 | 5156 | 5159 | 5186 |
| 5198 | 5227 | 5234 | 5235 | 5236 | 5237 | 5271 | 5309 | 5310 | 5311 | 5312 | 5321 |
| 5376 | 5388 | 5394 | 5422 | 5424 | 5475 | 5481 | 5500 | 5517 | 5554 | 5555 | 5566 |
| 5572 | 5573 | 5582 | 5645 | 5653 | 5655 | 5662 | 5685 | 5689 | 5692 | 5739 | 5763 |
| 5806 | 5808 | 5809 | 5810 | 5811 | 5838 | 5839 | 5849 | 5857 | 5877 | 5920 | 5930 |
| 5935 | 5936 | 5937 | 5950 | 5955 | 5956 | 5964 | 5997 | 6037 | 6038 | 6063 | 6064 |
| 6070 | 6074 | 6075 | 6117 | 6118 | 6119 | 6136 | 6137 | 6138 | 6155 | 6168 | 6169 |
| 6170 | 6181 | 6187 | 6203 | 6217 | 6267 | 6347 | 6401 | 6479 | 6482 | 6483 | 6518 |
| 6537 | 6603 | 6606 | 6696 | 6753 | 6770 | 6791 | 6806 | 6854 | 6872 | 6913 | 6928 |
| 6929 | 6973 | 6974 | 6975 | 6998 | 7009 | 7012 | 7027 | 7111 | 7219 | 7467 | 7542 |
| 7662 | 7763 | 7915 | 8221 | 8491 | 8778 | 8820 | 8937 | 8971 | 9070 | 9210 | 9402 |
| 9680 | 9886 | 9940 | 9973 | 9979 | 10025 | 10030 | 10068 | 10116 | 10123 | 10137 | 10177 |
| 10180 | 10458 | 10529 | 10905 | 10916 | 10930 | 10931 | 10938 | 10992 | 11027 | 11038 | 11041 |
| 11191 | 11502 | 11543 | 11577 | 11846 | 12090 | 12204 | 12230 | 12410 | 12474 | 12485 | 12509 |
| 12518 | 12539 | 12552 | 12557 | 12564 | 12567 | 12582 | 12609 | 12615 | 12616 | 12653 | 12677 |
| 12689 | 12691 | 12731 | 12752 | 12754 | 12755 | 12758 | 12816 | 12834 | 12871 | 12880 | 12887 |
| 12915 | 12936 | 12945 | 12951 | 12952 | 12966 | 12981 | 13070 | 13141 | 13162 | 13164 | 13178 |
| 13183 | 13194 | 13208 | 13224 | 13231 | 13245 | 13302 | 13306 | 13329 | 13360 | 13374 | 13447 |
| 13465 | 13497 | 13575 | 13816 | 13847 | 14075 | 14243 | 14438 | 14505 | 14676 | 14720 | 14906 |
| 15156 | 15200 | 15424 | 15792 | 16174 | 16415 | 16699 | 16765 | 16836 | 17119 | 17493 | 18047 |
| 18083 | 18089 | 18138 | 18259 | 18270 | 18271 | 18272 | 18398 | 18527 | 18948 | 19095 | 19219 |
| 19251 | 19399 | 19415 | 19480 | 19598 | 19933 | 19982 | 20023 | 20293 | 20449 | 20678 | 20734 |
| 21036 | 21137 | 21242 | 21448 | 21477 | 21548 | 21882 | 21919 | 21949 | 21964 | 21974 | 22007 |
| 22019 | 22030 | 22056 | 22065 | 22070 | 22082 | 22088 | 22108 | 22138 | 22144 | 22148 | |
| 22151 | 22154 | 22174 | 22196 | 22225 | 22228 | 22235 | 22242 | 22243 | 22255 | 22277 | 22281 |
| 22300 | 22319 | 22346 | 22360 | 22364 | 22367 | 22400 | 22401 | 22409 | 22432 | 22459 | 22460 |
| 22461 | 22471 | 22498 | 22500 | 22502 | 22520 | 22522 | 22528 | 22537 | 22575 | 22588 | 22624 |
| 22625 | 22653 | 22669 | 22678 | 22702 | 22712 | 22739 | 22741 | 22744 | 22764 | 22882 | 23056 |
| 23072 | 23411 | 23460 | 23611 | 23661 | | | | | | | |

Table 17B SEQ ID NOs of Polynucleotides useful for improving Yield: Phosphorus

| | | | | | | | | | | | |
|---|---|---|---|---|---|---|---|---|---|---|---|
| 23711 | 23991 | 24125 | 24382 | 24548 | 24669 | 24710 | 24761 | 24796 | 24864 | 24874 | 25083 |
| 25088 | 25090 | 25108 | 25111 | 25140 | 25141 | 25162 | 25169 | 25173 | 25175 | 25185 | 25201 |
| 25219 | 25225 | 25236 | 25247 | 25261 | 25263 | 25265 | 25268 | 25282 | 25283 | 25287 | 25306 |
| 25383 | 25384 | 25387 | 25408 | 25429 | 25453 | 25454 | 25482 | 25507 | 25528 | 25529 | 25551 |
| 25561 | 25566 | 25578 | 25582 | 25595 | 25611 | 25625 | 25627 | 25654 | 25655 | 25676 | 25678 |
| 25687 | 25699 | 25703 | 25726 | 25736 | 25756 | 25763 | 25772 | 25775 | 25779 | 25790 | 25795 |

TABLE 17-continued

Yield: Phosphorus

| | | | | | | | | | | | |
|---|---|---|---|---|---|---|---|---|---|---|---|
| 25846 | 25848 | 25864 | 25874 | 25875 | 25899 | 25923 | 25935 | 25967 | 25986 | 26001 | 26007 |
| 26025 | 26036 | 26042 | 26058 | 26063 | 26072 | 26082 | 26101 | 26109 | 26121 | 26138 | 26141 |
| 26149 | 26181 | 26186 | 26190 | 26198 | 26202 | 26212 | 26220 | 26236 | 26244 | 26252 | 26258 |
| 26264 | 26268 | 26276 | 26298 | 26584 | 26732 | 26766 | 26778 | 26788 | 26797 | 26799 | 26834 |
| 26891 | 26892 | 26898 | 26908 | 26912 | 26916 | 26944 | 26956 | 26962 | 26969 | 26974 | 26990 |
| 26999 | 27016 | 27103 | 27115 | 27121 | 27125 | 27138 | 27139 | 27164 | 27170 | 27172 | 27201 |
| 27215 | 27239 | 27247 | 27256 | 27261 | 27283 | 27300 | 27322 | 27384 | 27405 | 27406 | 27425 |
| 27431 | 27439 | 27483 | 27535 | 27546 | 27547 | 27551 | 27567 | 27585 | 27631 | 27643 | 27644 |
| 27678 | 27694 | 27701 | 27702 | 27704 | 27710 | 27750 | 27777 | 27793 | 27807 | 27808 | 27819 |
| 27849 | 27850 | 27857 | 27880 | 27944 | 28146 | 28395 | 28469 | 28532 | 28591 | 28664 | 28666 |
| 28682 | 28719 | 28743 | 28747 | 28773 | 28820 | 28824 | 28825 | 28840 | 28843 | 28846 | 28873 |
| 28885 | 28914 | 28921 | 28922 | 28923 | 28924 | 28958 | 28996 | 28997 | 28998 | 28999 | 29008 |
| 29063 | 29075 | 29081 | 29109 | 29111 | 29162 | 29168 | 29187 | 29204 | 29241 | 29242 | 29253 |
| 29259 | 29260 | 29269 | 29332 | 29340 | 29342 | 29349 | 29372 | 29376 | 29379 | 29426 | 29450 |
| 29493 | 29495 | 29496 | 29497 | 29498 | 29525 | 29526 | 29536 | 29544 | 29564 | 29607 | 29617 |
| 29622 | 29623 | 29624 | 29637 | 29642 | 29643 | 29651 | 29684 | 29724 | 29725 | 29750 | 29751 |
| 29757 | 29761 | 29762 | 29804 | 29805 | 29806 | 29823 | 29824 | 29825 | 29842 | 29855 | 29856 |
| 29857 | 29868 | 29874 | 29880 | 29904 | 29954 | 30034 | 30088 | 30166 | 30169 | 30170 | 30205 |
| 30224 | 30290 | 30293 | 30383 | 30440 | 30457 | 30478 | 30493 | 30541 | 30559 | 30600 | 30615 |
| 30616 | 30660 | 30661 | 30662 | 30685 | 30696 | 30699 | 30714 | 30798 | 30906 | 31154 | 31229 |
| 31349 | 31450 | 31602 | 31908 | 32178 | 32465 | 32507 | 32624 | 32658 | 32757 | 32897 | 33089 |
| 33367 | 33573 | 33627 | 33660 | 33666 | 33712 | 33717 | 33755 | 33810 | 33824 | 33864 |
| 33867 | 34145 | 34216 | 34592 | 34603 | 34617 | 34618 | 34625 | 34679 | 34714 | 34725 | 34728 |
| 34878 | 35189 | 35230 | 35264 | 35533 | 35777 | 35891 | 35917 | 36097 | 36161 | 36172 | 36196 |
| 36205 | 36226 | 36239 | 36244 | 36251 | 36254 | 36269 | 36296 | 36302 | 36303 | 36340 | 36364 |
| 36376 | 36378 | 36418 | 36439 | 36441 | 36442 | 36445 | 36503 | 36521 | 36558 | 36567 | 36574 |
| 36602 | 36623 | 36632 | 36638 | 36639 | 36653 | 36668 | 36757 | 36828 | 36849 | 36851 | 36865 |
| 36870 | 36881 | 36895 | 36911 | 36918 | 36932 | 36989 | 36993 | 37016 | 37047 | 37061 | 37134 |
| 37152 | 37184 | 37262 | 37503 | 37534 | 37762 | 37930 | 38125 | 38192 | 38363 | 38407 | 38593 |
| 38843 | 38887 | 39111 | 39479 | 39861 | 40102 | 40386 | 40452 | 40523 | 40806 | 41180 | 41734 |
| 41770 | 41776 | 41825 | 41946 | 41957 | 41958 | 41959 | 42085 | 42214 | 42635 | 42782 | 42906 |
| 42938 | 43086 | 43102 | 43167 | 43285 | 43620 | 43669 | 43710 | 43980 | 44136 | 44365 | 44421 |
| 44723 | 44824 | 44929 | 45135 | 45164 | 45235 | 45569 | 45606 | 45636 | 45651 | 45661 | 45694 |
| 45706 | 45717 | 45743 | 45752 | 45757 | 45769 | 45775 | 45795 | 45803 | 45825 | 45831 | 45835 |
| 45838 | 45841 | 45861 | 45883 | 45912 | 45915 | 45922 | 45929 | 45930 | 45942 | 45964 | 45968 |
| 45987 | 46006 | 46033 | 46047 | 46051 | 46054 | 46087 | 46088 | 46096 | 46119 | 46146 | 46147 |
| 46148 | 46158 | 46185 | 46187 | 46189 | 46207 | 46209 | 46215 | 46224 | 46262 | 46275 | 46311 |
| 46312 | 46340 | 46356 | 46365 | 46389 | 46399 | 46426 | 46428 | 46431 | 46451 | 46569 | 46743 |
| 46759 | 47098 | 47147 | 47298 | 47348 | | | | | | | |

TABLE 18

Yield: Photosynthesis

Table 18A SEQ ID NOs of Polypeptides useful for improving Yield: Photosynthesis

| | | | | | | | | | | | |
|---|---|---|---|---|---|---|---|---|---|---|---|
| 2809 | 3161 | 5960 | 6291 | 6292 | 6293 | 6294 | 6295 | 6296 | 6873 | 6874 | 6875 |
| 13792 | 15950 | 19004 | 19036 | 19834 | 20200 | 20459 | | | | | |

Table 18B SEQ ID NOs of Polynucleotides useful for improving Yield: Photosynthesis

| | | | | | | | | | | | |
|---|---|---|---|---|---|---|---|---|---|---|---|
| 26496 | 26848 | 29647 | 29978 | 29979 | 29980 | 29981 | 29982 | 29983 | 30560 | 30561 | 30562 |
| 37479 | 39637 | 42691 | 42723 | 43521 | 43887 | 44146 | | | | | |

TABLE 19

Yield: Stress Tolerance

Table 19A SEQ ID NOs of Polypeptides useful for improving Yield: Stress Tolerance

| | | | | | | | | | | | |
|---|---|---|---|---|---|---|---|---|---|---|---|
| 3 | 4 | 6 | 8 | 11 | 12 | 14 | 15 | 16 | 17 | 19 | 22 |
| 26 | 28 | 29 | 31 | 36 | 39 | 40 | 41 | 42 | 43 | 46 | 48 |
| 51 | 52 | 54 | 55 | 56 | 58 | 59 | 63 | 67 | 69 | 71 | 72 |
| 73 | 78 | 80 | 81 | 84 | 88 | 89 | 90 | 91 | 92 | 96 | 97 |
| 99 | 100 | 103 | 106 | 107 | 109 | 115 | 117 | 118 | 120 | 121 | 122 |
| 128 | 130 | 137 | 144 | 145 | 146 | 147 | 150 | 151 | 153 | 154 | 155 |
| 156 | 157 | 159 | 161 | 162 | 164 | 170 | 171 | 172 | 174 | 177 | 178 |
| 182 | 184 | 185 | 186 | 190 | 191 | 194 | 195 | 196 | 198 | 200 | 203 |
| 204 | 212 | 217 | 218 | 221 | 224 | 230 | 232 | 233 | 234 | 235 | 238 |
| 240 | 247 | 250 | 252 | 254 | 255 | 257 | 258 | 260 | 265 | 266 | 267 |
| 272 | 274 | 275 | 280 | 282 | 283 | 285 | 288 | 293 | 294 | 295 | 296 |
| 299 | 301 | 305 | 307 | 310 | 316 | 317 | 318 | 319 | 320 | 321 | 329 |
| 331 | 332 | 338 | 339 | 341 | 342 | 343 | 344 | 346 | 349 | 350 | 352 |

TABLE 19-continued

Yield: Stress Tolerance

| | | | | | | | | | | | |
|---|---|---|---|---|---|---|---|---|---|---|---|
| 354 | 356 | 357 | 358 | 359 | 360 | 363 | 366 | 368 | 369 | 372 | 374 |
| 378 | 379 | 380 | 381 | 382 | 383 | 387 | 389 | 391 | 393 | 395 | 396 |
| 399 | 400 | 401 | 402 | 403 | 404 | 405 | 408 | 409 | 412 | 416 | 418 |
| 421 | 422 | 423 | 425 | 426 | 429 | 434 | 435 | 436 | 437 | 440 | 443 |
| 446 | 449 | 450 | 451 | 453 | 454 | 456 | 458 | 459 | 462 | 466 | 467 |
| 468 | 470 | 471 | 472 | 473 | 477 | 479 | 480 | 482 | 484 | 486 | 487 |
| 491 | 498 | 500 | 501 | 502 | 505 | 506 | 508 | 510 | 511 | 515 | 516 |
| 517 | 518 | 519 | 520 | 521 | 522 | 523 | 525 | 526 | 527 | 536 | 537 |
| 539 | 540 | 541 | 543 | 544 | 547 | 548 | 549 | 550 | 551 | 555 | 556 |
| 560 | 564 | 568 | 569 | 570 | 571 | 575 | 576 | 582 | 585 | 587 | 589 |
| 590 | 593 | 596 | 599 | 601 | 606 | 609 | 614 | 616 | 623 | 624 | 631 |
| 635 | 636 | 643 | 646 | 648 | 649 | 650 | 653 | 655 | 656 | 659 | 660 |
| 664 | 665 | 666 | 667 | 668 | 671 | 672 | 673 | 675 | 678 | 680 | 681 |
| 682 | 684 | 685 | 688 | 691 | 692 | 693 | 695 | 696 | 705 | 706 | 708 |
| 709 | 712 | 715 | 717 | 719 | 720 | 725 | 726 | 727 | 732 | 735 | 736 |
| 738 | 739 | 740 | 741 | 744 | 746 | 750 | 751 | 754 | 756 | 757 | 760 |
| 761 | 764 | 766 | 770 | 771 | 772 | 773 | 774 | 776 | 778 | 779 | 782 |
| 784 | 787 | 788 | 791 | 803 | 804 | 813 | 814 | 815 | 816 | 818 | 820 |
| 822 | 823 | 824 | 835 | 836 | 837 | 844 | 848 | 849 | 852 | 853 | 854 |
| 856 | 857 | 859 | 862 | 868 | 870 | 871 | 872 | 878 | 885 | 890 | 893 |
| 895 | 896 | 897 | 902 | 903 | 904 | 906 | 909 | 910 | 912 | 913 | 914 |
| 915 | 916 | 920 | 923 | 927 | 930 | 931 | 934 | 937 | 943 | 954 | 955 |
| 956 | 957 | 959 | 964 | 969 | 973 | 975 | 976 | 977 | 979 | 980 | 983 |
| 985 | 988 | 989 | 990 | 993 | 995 | 996 | 997 | 998 | 1002 | 1006 | 1010 |
| 1014 | 1015 | 1016 | 1019 | 1021 | 1022 | 1023 | 1024 | 1025 | 1026 | 1030 | 1031 |
| 1033 | 1034 | 1035 | 1036 | 1039 | 1040 | 1041 | 1047 | 1048 | 1050 | 1054 | 1055 |
| 1057 | 1058 | 1059 | 1060 | 1061 | 1062 | 1063 | 1065 | 1067 | 1068 | 1069 | 1070 |
| 1072 | 1073 | 1075 | 1077 | 1078 | 1082 | 1083 | 1084 | 1086 | 1088 | 1094 | 1095 |
| 1100 | 1101 | 1102 | 1105 | 1106 | 1108 | 1110 | 1111 | 1113 | 1114 | 1119 | 1120 |
| 1121 | 1123 | 1126 | 1128 | 1130 | 1131 | 1132 | 1135 | 1138 | 1139 | 1140 | 1141 |
| 1143 | 1144 | 1145 | 1147 | 1148 | 1149 | 1152 | 1155 | 1156 | 1157 | 1159 | 1161 |
| 1162 | 1167 | 1168 | 1173 | 1174 | 1175 | 1176 | 1178 | 1179 | 1181 | 1182 | 1183 |
| 1184 | 1185 | 1186 | 1187 | 1188 | 1190 | 1191 | 1192 | 1193 | 1196 | 1198 | 1199 |
| 1200 | 1201 | 1202 | 1205 | 1207 | 1209 | 1211 | 1214 | 1217 | 1218 | 1221 | 1222 |
| 1226 | 1228 | 1229 | 1235 | 1237 | 1239 | 1241 | 1243 | 1245 | 1246 | 1247 | 1250 |
| 1252 | 1253 | 1254 | 1255 | 1256 | 1257 | 1258 | 1261 | 1262 | 1266 | 1268 | 1269 |
| 1271 | 1276 | 1284 | 1285 | 1289 | 1290 | 1291 | 1292 | 1297 | 1299 | 1300 | 1302 |
| 1307 | 1308 | 1309 | 1310 | 1311 | 1312 | 1313 | 1315 | 1318 | 1319 | 1323 | 1324 |
| 1325 | 1327 | 1328 | 1330 | 1331 | 1333 | 1336 | 1337 | 1344 | 1345 | 1346 | 1347 |
| 1348 | 1349 | 1358 | 1365 | 1372 | 1375 | 1377 | 1388 | 1391 | 1394 | 1396 | 1402 |
| 1403 | 1404 | 1406 | 1408 | 1409 | 1415 | 1416 | 1417 | 1419 | 1421 | 1422 | 1424 |
| 1425 | 1427 | 1428 | 1431 | 1433 | 1434 | 1437 | 1438 | 1439 | 1446 | 1447 | 1448 |
| 1449 | 1450 | 1451 | 1458 | 1459 | 1460 | 1461 | 1462 | 1464 | 1470 | 1471 | 1473 |
| 1475 | 1476 | 1477 | 1479 | 1480 | 1481 | 1482 | 1483 | 1486 | 1487 | 1488 | 1490 |
| 1493 | 1495 | 1496 | 1497 | 1499 | 1502 | 1503 | 1504 | 1505 | 1506 | 1507 | 1510 |
| 1514 | 1517 | 1520 | 1521 | 1523 | 1527 | 1529 | 1531 | 1532 | 1535 | 1543 | 1546 |
| 1548 | 1550 | 1551 | 1552 | 1556 | 1559 | 1560 | 1564 | 1565 | 1566 | 1567 | 1568 |
| 1571 | 1572 | 1574 | 1576 | 1578 | 1579 | 1581 | 1583 | 1585 | 1590 | 1591 | 1593 |
| 1595 | 1597 | 1600 | 1601 | 1602 | 1604 | 1606 | 1607 | 1608 | 1611 | 1612 | 1613 |
| 1614 | 1615 | 1617 | 1619 | 1621 | 1622 | 1625 | 1626 | 1627 | 1628 | 1630 | 1631 |
| 1632 | 1634 | 1636 | 1637 | 1641 | 1650 | 1653 | 1654 | 1657 | 1659 | 1660 | 1662 |
| 1663 | 1664 | 1667 | 1668 | 1671 | 1673 | 1674 | 1675 | 1679 | 1680 | 1681 | 1683 |
| 1685 | 1686 | 1687 | 1689 | 1691 | 1692 | 1695 | 1696 | 1697 | 1698 | 1699 | 1700 |
| 1702 | 1703 | 1704 | 1706 | 1709 | 1710 | 1712 | 1713 | 1715 | 1716 | 1717 | 1718 |
| 1721 | 1722 | 1724 | 1725 | 1726 | 1727 | 1728 | 1730 | 1731 | 1733 | 1738 | 1740 |
| 1742 | 1747 | 1748 | 1749 | 1750 | 1752 | 1754 | 1755 | 1760 | 1762 | 1764 | 1765 |
| 1766 | 1767 | 1768 | 1771 | 1773 | 1774 | 1775 | 1776 | 1778 | 1779 | 1780 | 1785 |
| 1786 | 1787 | 1788 | 1792 | 1793 | 1795 | 1796 | 1797 | 1798 | 1799 | 1800 | 1801 |
| 1803 | 1804 | 1808 | 1809 | 1810 | 1814 | 1816 | 1817 | 1819 | 1820 | 1821 | 1822 |
| 1825 | 1827 | 1828 | 1829 | 1830 | 1831 | 1832 | 1833 | 1834 | 1835 | 1836 | 1837 |
| 1841 | 1842 | 1846 | 1848 | 1849 | 1851 | 1852 | 1853 | 1855 | 1862 | 1863 | 1864 |
| 1867 | 1868 | 1870 | 1874 | 1876 | 1877 | 1878 | 1880 | 1882 | 1885 | 1886 | 1888 |
| 1890 | 1891 | 1894 | 1895 | 1896 | 1897 | 1899 | 1902 | 1903 | 1906 | 1908 | 1909 |
| 1914 | 1916 | 1922 | 1923 | 1924 | 1927 | 1928 | 1930 | 1931 | 1934 | 1935 | 1936 |
| 1938 | 1940 | 1941 | 1943 | 1944 | 1945 | 1949 | 1950 | 1951 | 1952 | 1953 | 1955 |
| 1963 | 1964 | 1966 | 1967 | 1968 | 1969 | 1970 | 1971 | 1974 | 1977 | 1978 | 1979 |
| 1985 | 1986 | 1989 | 1991 | 1994 | 1997 | 1999 | 2000 | 2001 | 2002 | 2003 | 2004 |
| 2005 | 2006 | 2007 | 2008 | 2010 | 2012 | 2014 | 2016 | 2017 | 2018 | 2019 | 2020 |
| 2021 | 2023 | 2024 | 2025 | 2028 | 2029 | 2032 | 2034 | 2036 | 2039 | 2040 | 2041 |
| 2042 | 2044 | 2046 | 2047 | 2048 | 2049 | 2050 | 2051 | 2053 | 2057 | 2058 | 2059 |
| 2065 | 2069 | 2075 | 2076 | 2077 | 2078 | 2080 | 2084 | 2085 | 2087 | 2088 | 2089 |
| 2090 | 2091 | 2092 | 2094 | 2096 | 2097 | 2098 | 2100 | 2102 | 2103 | 2104 | 2105 |
| 2106 | 2107 | 2108 | 2112 | 2118 | 2119 | 2121 | 2124 | 2125 | 2126 | 2127 | 2128 |
| 2131 | 2132 | 2133 | 2134 | 2137 | 2139 | 2140 | 2143 | 2144 | 2146 | 2147 | 2148 |
| 2150 | 2151 | 2154 | 2156 | 2157 | 2158 | 2159 | 2161 | 2162 | 2163 | 2164 | 2169 |
| 2171 | 2172 | 2173 | 2174 | 2175 | 2176 | 2177 | 2179 | 2180 | 2181 | 2182 | 2183 |
| 2184 | 2186 | 2187 | 2188 | 2192 | 2194 | 2195 | 2198 | 2199 | 2200 | 2201 | 2202 |

TABLE 19-continued

Yield: Stress Tolerance

| | | | | | | | | | | | |
|---|---|---|---|---|---|---|---|---|---|---|---|
| 2203 | 2204 | 2205 | 2206 | 2208 | 2210 | 2211 | 2212 | 2213 | 2214 | 2216 | 2218 |
| 2220 | 2222 | 2226 | 2228 | 2230 | 2231 | 2232 | 2233 | 2235 | 2236 | 2237 | 2238 |
| 2240 | 2241 | 2247 | 2248 | 2250 | 2252 | 2253 | 2254 | 2259 | 2263 | 2264 | 2265 |
| 2270 | 2271 | 2272 | 2273 | 2274 | 2276 | 2277 | 2278 | 2280 | 2282 | 2285 | 2286 |
| 2287 | 2288 | 2289 | 2290 | 2291 | 2292 | 2293 | 2294 | 2297 | 2298 | 2299 | 2300 |
| 2302 | 2303 | 2306 | 2307 | 2310 | 2312 | 2313 | 2315 | 2316 | 2317 | 2321 | 2322 |
| 2323 | 2331 | 2332 | 2333 | 2334 | 2336 | 2338 | 2339 | 2341 | 2343 | 2345 | 2346 |
| 2349 | 2351 | 2352 | 2354 | 2356 | 2357 | 2360 | 2362 | 2363 | 2365 | 2366 | 2367 |
| 2368 | 2370 | 2371 | 2373 | 2374 | 2376 | 2377 | 2378 | 2380 | 2381 | 2383 | 2385 |
| 2386 | 2388 | 2389 | 2390 | 2393 | 2394 | 2395 | 2397 | 2404 | 2405 | 2406 | 2411 |
| 2413 | 2414 | 2415 | 2419 | 2420 | 2421 | 2422 | 2423 | 2424 | 2425 | 2426 | 2429 |
| 2430 | 2431 | 2432 | 2433 | 2434 | 2436 | 2437 | 2439 | 2440 | 2441 | 2442 | 2443 |
| 2444 | 2445 | 2447 | 2448 | 2450 | 2451 | 2454 | 2455 | 2457 | 2458 | 2460 | 2462 |
| 2463 | 2464 | 2466 | 2472 | 2474 | 2477 | 2478 | 2480 | 2483 | 2485 | 2486 | 2490 |
| 2491 | 2492 | 2495 | 2497 | 2498 | 2499 | 2500 | 2503 | 2504 | 2506 | 2508 | 2510 |
| 2513 | 2514 | 2516 | 2517 | 2518 | 2519 | 2521 | 2522 | 2523 | 2525 | 2527 | 2528 |
| 2529 | 2530 | 2533 | 2534 | 2537 | 2540 | 2548 | 2549 | 2552 | 2561 | 2565 | 2566 |
| 2567 | 2568 | 2570 | 2571 | 2572 | 2574 | 2576 | 2577 | 2579 | 2581 | 2586 | 2588 |
| 2589 | 2597 | 2599 | 2600 | 2601 | 2602 | 2604 | 2608 | 2610 | 2612 | 2613 | 2614 |
| 2616 | 2617 | 2622 | 2623 | 2625 | 2626 | 2628 | 2632 | 2634 | 2638 | 2641 | 2642 |
| 2646 | 2648 | 2650 | 2651 | 2652 | 2653 | 2655 | 2656 | 2657 | 2659 | 2661 | 2662 |
| 2663 | 2667 | 2669 | 2670 | 2671 | 2674 | 2678 | 2682 | 2683 | 2686 | 2687 | 2688 |
| 2690 | 2691 | 2692 | 2697 | 2699 | 2701 | 2704 | 2705 | 2706 | 2707 | 2708 | 2710 |
| 2714 | 2718 | 2720 | 2723 | 2729 | 2731 | 2733 | 2736 | 2741 | 2742 | 2743 | 2744 |
| 2746 | 2747 | 2750 | 2752 | 2754 | 2755 | 2759 | 2763 | 2765 | 2767 | 2768 | 2773 |
| 2776 | 2779 | 2781 | 2784 | 2785 | 2786 | 2788 | 2793 | 2798 | 2800 | 2804 | 2805 |
| 2808 | 2813 | 2814 | 2815 | 2816 | 2818 | 2819 | 2821 | 2826 | 2827 | 2828 | 2829 |
| 2830 | 2831 | 2833 | 2836 | 2837 | 2839 | 2840 | 2841 | 2843 | 2844 | 2845 | 2846 |
| 2847 | 2850 | 2851 | 2853 | 2855 | 2860 | 2861 | 2864 | 2867 | 2868 | 2869 | 2871 |
| 2872 | 2875 | 2877 | 2878 | 2881 | 2882 | 2884 | 2887 | 2888 | 2893 | 2894 | 2895 |
| 2896 | 2898 | 2900 | 2904 | 2905 | 2907 | 2916 | 2917 | 2918 | 2919 | 2921 | 2927 |
| 2929 | 2936 | 2937 | 2939 | 2945 | 2946 | 2947 | 2948 | 2951 | 2955 | 2956 | 2957 |
| 2958 | 2959 | 2960 | 2964 | 2965 | 2969 | 2982 | 2984 | 2986 | 2987 | 2988 | 2994 |
| 2997 | 2998 | 2999 | 3000 | 3005 | 3006 | 3007 | 3011 | 3012 | 3014 | 3018 | 3019 |
| 3022 | 3029 | 3031 | 3035 | 3043 | 3044 | 3046 | 3047 | 3048 | 3051 | 3052 | 3055 |
| 3057 | 3059 | 3060 | 3061 | 3062 | 3063 | 3066 | 3069 | 3070 | 3071 | 3072 | 3073 |
| 3075 | 3077 | 3078 | 3081 | 3082 | 3083 | 3085 | 3086 | 3087 | 3090 | 3091 | 3093 |
| 3094 | 3095 | 3100 | 3101 | 3106 | 3108 | 3109 | 3110 | 3112 | 3113 | 3124 | 3126 |
| 3127 | 3128 | 3131 | 3136 | 3137 | 3138 | 3139 | 3141 | 3143 | 3144 | 3146 | 3147 |
| 3148 | 3154 | 3155 | 3156 | 3158 | 3159 | 3160 | 3163 | 3165 | 3168 | 3170 | 3172 |
| 3175 | 3177 | 3179 | 3180 | 3184 | 3186 | 3188 | 3190 | 3193 | 3195 | 3196 | 3198 |
| 3200 | 3201 | 3202 | 3203 | 3204 | 3205 | 3206 | 3207 | 3208 | 3211 | 3219 | 3220 |
| 3224 | 3227 | 3228 | 3231 | 3234 | 3236 | 3238 | 3240 | 3241 | 3242 | 3245 | 3249 |
| 3253 | 3254 | 3255 | 3258 | 3259 | 3261 | 3262 | 3263 | 3265 | 3266 | 3267 | 3269 |
| 3271 | 3274 | 3275 | 3278 | 3280 | 3281 | 3282 | 3283 | 3285 | 3287 | 3288 | 3289 |
| 3290 | 3291 | 3292 | 3297 | 3300 | 3302 | 3303 | 3305 | 3306 | 3309 | 3310 | 3311 |
| 3312 | 3313 | 3315 | 3318 | 3319 | 3320 | 3321 | 3322 | 3324 | 3329 | 3331 | 3332 |
| 3333 | 3334 | 3337 | 3339 | 3340 | 3342 | 3343 | 3345 | 3346 | 3347 | 3350 | 3356 |
| 3357 | 3359 | 3361 | 3362 | 3363 | 3364 | 3365 | 3366 | 3371 | 3373 | 3375 | 3376 |
| 3378 | 3380 | 3381 | 3382 | 3383 | 3384 | 3389 | 3390 | 3391 | 3392 | 3395 | 3396 |
| 3400 | 3401 | 3402 | 3405 | 3407 | 3413 | 3415 | 3416 | 3419 | 3420 | 3421 | 3426 |
| 3427 | 3429 | 3432 | 3434 | 3436 | 3437 | 3438 | 3440 | 3442 | 3443 | 3444 | 3446 |
| 3447 | 3450 | 3452 | 3453 | 3457 | 3458 | 3460 | 3461 | 3463 | 3464 | 3468 | 3469 |
| 3470 | 3471 | 3473 | 3477 | 3479 | 3481 | 3482 | 3483 | 3485 | 3486 | 3487 | 3488 |
| 3491 | 3493 | 3496 | 3498 | 3502 | 3503 | 3504 | 3505 | 3506 | 3508 | 3510 | 3512 |
| 3513 | 3514 | 3517 | 3518 | 3521 | 3522 | 3523 | 3524 | 3525 | 3526 | 3529 | 3530 |
| 3532 | 3533 | 3534 | 3535 | 3538 | 3539 | 3540 | 3542 | 3545 | 3547 | 3548 | 3549 |
| 3550 | 3552 | 3553 | 3554 | 3555 | 3557 | 3559 | 3560 | 3562 | 3563 | 3568 | 3569 |
| 3570 | 3573 | 3574 | 3575 | 3581 | 3589 | 3590 | 3591 | 3592 | 3594 | 3595 | 3596 |
| 3597 | 3598 | 3602 | 3603 | 3607 | 3608 | 3609 | 3613 | 3621 | 3628 | 3629 | 3630 |
| 3632 | 3635 | 3636 | 3640 | 3642 | 3644 | 3645 | 3650 | 3654 | 3655 | 3656 | 3658 |
| 3659 | 3660 | 3661 | 3662 | 3663 | 3666 | 3669 | 3670 | 3672 | 3673 | 3681 | 3682 |
| 3683 | 3687 | 3688 | 3689 | 3690 | 3691 | 3692 | 3693 | 3695 | 3696 | 3697 | 3700 |
| 3703 | 3704 | 3705 | 3706 | 3708 | 3714 | 3715 | 3718 | 3719 | 3720 | 3721 | 3722 |
| 3723 | 3724 | 3726 | 3727 | 3728 | 3730 | 3731 | 3733 | 3734 | 3735 | 3736 | 3737 |
| 3738 | 3739 | 3740 | 3741 | 3742 | 3744 | 3747 | 3749 | 3751 | 3752 | 3754 | 3755 |
| 3757 | 3758 | 3759 | 3760 | 3765 | 3769 | 3771 | 3773 | 3775 | 3776 | 3777 | 3780 |
| 3781 | 3784 | 3786 | 3787 | 3790 | 3793 | 3794 | 3796 | 3797 | 3799 | 3801 | 3804 |
| 3806 | 3808 | 3809 | 3813 | 3816 | 3817 | 3818 | 3819 | 3820 | 3821 | 3825 | 3826 |
| 3827 | 3833 | 3838 | 3839 | 3840 | 3842 | 3843 | 3844 | 3845 | 3846 | 3847 | 3848 |
| 3851 | 3852 | 3854 | 3855 | 3856 | 3857 | 3859 | 3860 | 3861 | 3864 | 3865 | 3869 |
| 3875 | 3877 | 3878 | 3880 | 3883 | 3885 | 3888 | 3889 | 3891 | 3892 | 3893 | 3896 |
| 3897 | 3898 | 3899 | 3900 | 3901 | 3902 | 3905 | 3906 | 3914 | 3915 | 3917 | 3919 |
| 3920 | 3923 | 3924 | 3927 | 3928 | 3930 | 3931 | 3932 | 3936 | 3937 | 3938 | 3939 |
| 3940 | 3944 | 3946 | 3947 | 3950 | 3954 | 3955 | 3956 | 3957 | 3958 | 3959 | 3960 |
| 3966 | 3968 | 3974 | 3976 | 3977 | 3978 | 3980 | 3981 | 3982 | 3983 | 3985 | 3987 |
| 3991 | 3994 | 3995 | 3996 | 3997 | 3999 | 4002 | 4006 | 4007 | 4008 | 4009 | 4012 |

TABLE 19-continued

Yield: Stress Tolerance

| | | | | | | | | | | | |
|---|---|---|---|---|---|---|---|---|---|---|---|
| 4013 | 4014 | 4016 | 4020 | 4021 | 4023 | 4024 | 4025 | 4028 | 4029 | 4030 | 4031 |
| 4034 | 4038 | 4040 | 4041 | 4044 | 4045 | 4047 | 4049 | 4052 | 4054 | 4056 | 4057 |
| 4058 | 4059 | 4060 | 4063 | 4064 | 4065 | 4067 | 4068 | 4070 | 4073 | 4075 | 4076 |
| 4078 | 4079 | 4082 | 4085 | 4088 | 4090 | 4091 | 4092 | 4093 | 4094 | 4095 | 4096 |
| 4098 | 4100 | 4101 | 4103 | 4104 | 4105 | 4106 | 4107 | 4110 | 4112 | 4113 | 4116 |
| 4117 | 4118 | 4120 | 4121 | 4122 | 4123 | 4124 | 4125 | 4127 | 4132 | 4133 | 4135 |
| 4139 | 4140 | 4142 | 4145 | 4146 | 4149 | 4150 | 4151 | 4152 | 4153 | 4154 | 4157 |
| 4158 | 4159 | 4160 | 4163 | 4168 | 4169 | 4170 | 4171 | 4172 | 4174 | 4176 | 4177 |
| 4178 | 4179 | 4182 | 4185 | 4187 | 4189 | 4193 | 4195 | 4197 | 4198 | 4200 | 4201 |
| 4202 | 4203 | 4205 | 4207 | 4208 | 4216 | 4217 | 4219 | 4223 | 4224 | 4225 | 4228 |
| 4230 | 4233 | 4234 | 4235 | 4239 | 4240 | 4242 | 4243 | 4245 | 4251 | 4252 | 4253 |
| 4254 | 4255 | 4256 | 4260 | 4261 | 4267 | 4268 | 4272 | 4277 | 4280 | 4282 | 4283 |
| 4285 | 4288 | 4290 | 4291 | 4293 | 4294 | 4295 | 4297 | 4301 | 4302 | 4310 | 4311 |
| 4312 | 4313 | 4314 | 4316 | 4317 | 4320 | 4324 | 4326 | 4327 | 4328 | 4330 | 4334 |
| 4335 | 4342 | 4345 | 4346 | 4347 | 4356 | 4359 | 4360 | 4362 | 4363 | 4366 | 4372 |
| 4373 | 4381 | 4385 | 4386 | 4388 | 4390 | 4391 | 4393 | 4394 | 4395 | 4398 | 4401 |
| 4402 | 4405 | 4411 | 4415 | 4416 | 4419 | 4423 | 4426 | 4429 | 4431 | 4433 | 4434 |
| 4436 | 4439 | 4440 | 4442 | 4443 | 4444 | 4445 | 4448 | 4449 | 4450 | 4453 | 4455 |
| 4458 | 4464 | 4466 | 4468 | 4469 | 4470 | 4472 | 4476 | 4478 | 4480 | 4482 | 4487 |
| 4488 | 4489 | 4490 | 4491 | 4493 | 4494 | 4496 | 4497 | 4501 | 4502 | 4505 | 4506 |
| 4507 | 4509 | 4513 | 4514 | 4515 | 4519 | 4521 | 4522 | 4523 | 4525 | 4529 | 4533 |
| 4537 | 4540 | 4542 | 4548 | 4551 | 4552 | 4553 | 4554 | 4555 | 4557 | 4559 | 4560 |
| 4562 | 4564 | 4566 | 4568 | 4569 | 4571 | 4574 | 4575 | 4579 | 4580 | 4582 | 4583 |
| 4585 | 4587 | 4593 | 4595 | 4596 | 4597 | 4598 | 4599 | 4603 | 4608 | 4609 | 4611 |
| 4614 | 4615 | 4617 | 4618 | 4619 | 4620 | 4621 | 4622 | 4626 | 4627 | 4631 | 4634 |
| 4635 | 4636 | 4642 | 4649 | 4650 | 4652 | 4654 | 4655 | 4657 | 4660 | 4661 | 4662 |
| 4664 | 4665 | 4666 | 4670 | 4676 | 4681 | 4683 | 4685 | 4686 | 4691 | 4693 | 4695 |
| 4698 | 4701 | 4702 | 4705 | 4708 | 4709 | 4710 | 4711 | 4713 | 4716 | 4718 | 4721 |
| 4723 | 4724 | 4727 | 4728 | 4729 | 4737 | 4740 | 4741 | 4743 | 4748 | 4751 | 4756 |
| 4759 | 4760 | 4762 | 4763 | 4764 | 4765 | 4769 | 4771 | 4774 | 4778 | 4781 | 4783 |
| 4784 | 4785 | 4786 | 4787 | 4791 | 4793 | 4801 | 4805 | 4806 | 4807 | 4808 | 4810 |
| 4811 | 4812 | 4813 | 4815 | 4816 | 4818 | 4819 | 4820 | 4824 | 4826 | 4829 | 4833 |
| 4837 | 4845 | 4846 | 4849 | 4850 | 4851 | 4852 | 4854 | 4861 | 4864 | 4865 | 4866 |
| 4869 | 4874 | 4876 | 4879 | 4880 | 4882 | 4884 | 4885 | 4886 | 4888 | 4891 | 4893 |
| 4894 | 4895 | 4897 | 4898 | 4899 | 4901 | 4907 | 4908 | 4911 | 4912 | 4914 | 4916 |
| 4917 | 4920 | 4922 | 4923 | 4925 | 4926 | 4927 | 4935 | 4936 | 4937 | 4938 | 4939 |
| 4942 | 4944 | 4946 | 4947 | 4953 | 4954 | 4956 | 4961 | 4962 | 4963 | 4965 | 4966 |
| 4968 | 4971 | 4973 | 4977 | 4978 | 4979 | 4982 | 4983 | 4984 | 4985 | 4986 | 4988 |
| 4990 | 4991 | 4992 | 4993 | 4995 | 4996 | 4997 | 5000 | 5001 | 5002 | 5003 | 5005 |
| 5007 | 5008 | 5009 | 5010 | 5011 | 5012 | 5013 | 5016 | 5017 | 5022 | 5023 | 5024 |
| 5025 | 5026 | 5028 | 5029 | 5030 | 5031 | 5032 | 5033 | 5035 | 5036 | 5037 | 5038 |
| 5039 | 5040 | 5041 | 5042 | 5044 | 5045 | 5046 | 5049 | 5050 | 5051 | 5052 | 5054 |
| 5055 | 5056 | 5057 | 5058 | 5059 | 5060 | 5061 | 5063 | 5064 | 5065 | 5066 | 5067 |
| 5068 | 5075 | 5076 | 5077 | 5079 | 5084 | 5085 | 5086 | 5087 | 5088 | 5089 | 5091 |
| 5092 | 5093 | 5096 | 5097 | 5099 | 5100 | 5104 | 5105 | 5107 | 5108 | 5112 | 5114 |
| 5115 | 5116 | 5117 | 5118 | 5119 | 5121 | 5122 | 5125 | 5127 | 5131 | 5132 | 5133 |
| 5134 | 5137 | 5138 | 5139 | 5140 | 5141 | 5142 | 5143 | 5144 | 5145 | 5147 | 5148 |
| 5149 | 5150 | 5151 | 5153 | 5154 | 5156 | 5157 | 5158 | 5159 | 5164 | 5165 | 5166 |
| 5167 | 5168 | 5169 | 5172 | 5173 | 5174 | 5175 | 5178 | 5179 | 5180 | 5181 | 5182 |
| 5183 | 5184 | 5186 | 5187 | 5188 | 5189 | 5194 | 5195 | 5196 | 5197 | 5199 | 5200 |
| 5201 | 5203 | 5204 | 5205 | 5206 | 5208 | 5210 | 5211 | 5212 | 5214 | 5215 | 5216 |
| 5217 | 5218 | 5219 | 5220 | 5221 | 5222 | 5223 | 5224 | 5226 | 5227 | 5230 | 5231 |
| 5232 | 5233 | 5234 | 5235 | 5236 | 5237 | 5238 | 5239 | 5240 | 5241 | 5242 | 5243 |
| 5247 | 5248 | 5249 | 5250 | 5251 | 5252 | 5254 | 5255 | 5256 | 5257 | 5262 | 5267 |
| 5271 | 5272 | 5273 | 5274 | 5275 | 5276 | 5278 | 5279 | 5280 | 5285 | 5287 | 5288 |
| 5289 | 5290 | 5291 | 5294 | 5295 | 5298 | 5299 | 5301 | 5304 | 5305 | 5306 | 5309 |
| 5310 | 5311 | 5312 | 5315 | 5317 | 5319 | 5320 | 5324 | 5325 | 5327 | 5328 | 5338 |
| 5339 | 5347 | 5356 | 5359 | 5362 | 5363 | 5364 | 5365 | 5367 | 5368 | 5369 | 5372 |
| 5373 | 5375 | 5380 | 5381 | 5382 | 5383 | 5384 | 5385 | 5386 | 5387 | 5388 | 5389 |
| 5391 | 5392 | 5393 | 5394 | 5395 | 5396 | 5397 | 5399 | 5401 | 5408 | 5409 | 5410 |
| 5412 | 5413 | 5414 | 5415 | 5417 | 5418 | 5421 | 5422 | 5423 | 5424 | 5425 | 5426 |
| 5428 | 5430 | 5431 | 5432 | 5437 | 5439 | 5440 | 5441 | 5442 | 5443 | 5445 | 5448 |
| 5449 | 5450 | 5451 | 5453 | 5454 | 5456 | 5462 | 5463 | 5464 | 5466 | 5467 | 5468 |
| 5469 | 5471 | 5472 | 5473 | 5475 | 5476 | 5477 | 5479 | 5480 | 5481 | 5483 | 5484 |
| 5485 | 5486 | 5487 | 5488 | 5489 | 5491 | 5492 | 5493 | 5494 | 5496 | 5498 | 5499 |
| 5500 | 5501 | 5502 | 5503 | 5504 | 5508 | 5509 | 5512 | 5513 | 5514 | 5516 | 5517 |
| 5518 | 5527 | 5528 | 5533 | 5534 | 5540 | 5541 | 5542 | 5544 | 5547 | 5550 | 5551 |
| 5552 | 5553 | 5554 | 5555 | 5556 | 5557 | 5559 | 5560 | 5561 | 5562 | 5564 | 5565 |
| 5566 | 5567 | 5568 | 5569 | 5570 | 5572 | 5573 | 5578 | 5580 | 5581 | 5588 | 5589 |
| 5591 | 5592 | 5593 | 5594 | 5595 | 5598 | 5601 | 5603 | 5604 | 5605 | 5606 | 5608 |
| 5609 | 5610 | 5612 | 5613 | 5614 | 5615 | 5616 | 5617 | 5618 | 5619 | 5622 | 5623 |
| 5624 | 5627 | 5628 | 5629 | 5630 | 5632 | 5633 | 5634 | 5635 | 5636 | 5637 | 5638 |
| 5640 | 5641 | 5643 | 5644 | 5645 | 5646 | 5647 | 5650 | 5651 | 5653 | 5654 | 5655 |
| 5658 | 5659 | 5660 | 5661 | 5662 | 5663 | 5665 | 5666 | 5667 | 5668 | 5669 | 5670 |
| 5673 | 5674 | 5675 | 5677 | 5678 | 5679 | 5681 | 5683 | 5684 | 5685 | 5686 | 5687 |
| 5688 | 5689 | 5690 | 5692 | 5693 | 5694 | 5695 | 5698 | 5699 | 5700 | 5702 | 5703 |
| 5704 | 5707 | 5708 | 5709 | 5710 | 5712 | 5713 | 5714 | 5716 | 5717 | 5718 | 5722 |

TABLE 19-continued

| Yield: Stress Tolerance | | | | | | | | | | | |
|---|---|---|---|---|---|---|---|---|---|---|---|
| 5723 | 5724 | 5726 | 5727 | 5728 | 5729 | 5730 | 5731 | 5732 | 5734 | 5736 | 5739 |
| 5740 | 5742 | 5743 | 5745 | 5747 | 5748 | 5749 | 5750 | 5751 | 5754 | 5755 | 5757 |
| 5759 | 5761 | 5762 | 5763 | 5764 | 5765 | 5766 | 5768 | 5769 | 5772 | 5777 | 5778 |
| 5779 | 5780 | 5782 | 5784 | 5785 | 5786 | 5787 | 5789 | 5790 | 5791 | 5792 | 5794 |
| 5795 | 5796 | 5797 | 5798 | 5802 | 5803 | 5804 | 5805 | 5806 | 5807 | 5810 | 5811 |
| 5812 | 5813 | 5814 | 5815 | 5816 | 5818 | 5819 | 5820 | 5821 | 5823 | 5824 | 5826 |
| 5827 | 5828 | 5829 | 5830 | 5832 | 5833 | 5834 | 5835 | 5837 | 5838 | 5839 | 5841 |
| 5842 | 5843 | 5845 | 5848 | 5849 | 5851 | 5852 | 5853 | 5854 | 5855 | 5856 | 5857 |
| 5858 | 5860 | 5862 | 5863 | 5866 | 5871 | 5872 | 5873 | 5877 | 5878 | 5879 | 5880 |
| 5882 | 5883 | 5885 | 5888 | 5889 | 5890 | 5892 | 5893 | 5894 | 5895 | 5896 | 5898 |
| 5899 | 5900 | 5901 | 5902 | 5903 | 5904 | 5905 | 5906 | 5907 | 5908 | 5909 | 5911 |
| 5912 | 5914 | 5915 | 5916 | 5917 | 5918 | 5919 | 5920 | 5921 | 5927 | 5930 | 5935 |
| 5936 | 5937 | 5939 | 5940 | 5941 | 5942 | 5944 | 5945 | 5947 | 5948 | 5950 | 5951 |
| 5952 | 5953 | 5954 | 5955 | 5956 | 5957 | 5959 | 5961 | 5962 | 5964 | 5966 | 5968 |
| 5969 | 5970 | 5971 | 5973 | 5974 | 5975 | 5976 | 5977 | 5980 | 5981 | 5983 | 5984 |
| 5985 | 5986 | 5987 | 5988 | 5989 | 5990 | 5991 | 5993 | 5995 | 5996 | 5997 | 6000 |
| 6001 | 6002 | 6003 | 6007 | 6009 | 6011 | 6012 | 6017 | 6019 | 6020 | 6024 | 6026 |
| 6027 | 6028 | 6029 | 6030 | 6031 | 6035 | 6036 | 6037 | 6038 | 6039 | 6040 | 6041 |
| 6042 | 6043 | 6045 | 6047 | 6048 | 6049 | 6050 | 6051 | 6052 | 6053 | 6055 | 6057 |
| 6059 | 6060 | 6061 | 6062 | 6063 | 6064 | 6065 | 6067 | 6070 | 6071 | 6072 | 6073 |
| 6074 | 6075 | 6078 | 6080 | 6081 | 6082 | 6083 | 6084 | 6085 | 6086 | 6087 | 6089 |
| 6090 | 6091 | 6095 | 6096 | 6097 | 6099 | 6100 | 6101 | 6102 | 6103 | 6104 | 6109 |
| 6110 | 6111 | 6115 | 6116 | 6117 | 6118 | 6119 | 6121 | 6122 | 6123 | 6124 | 6125 |
| 6126 | 6127 | 6128 | 6132 | 6135 | 6136 | 6137 | 6138 | 6139 | 6140 | 6143 | 6144 |
| 6145 | 6146 | 6148 | 6149 | 6151 | 6152 | 6155 | 6156 | 6158 | 6159 | 6160 | 6161 |
| 6162 | 6163 | 6164 | 6165 | 6167 | 6168 | 6169 | 6170 | 6171 | 6172 | 6173 | 6174 |
| 6176 | 6177 | 6178 | 6179 | 6180 | 6182 | 6183 | 6184 | 6186 | 6187 | 6188 | 6189 |
| 6193 | 6194 | 6196 | 6197 | 6199 | 6200 | 6202 | 6203 | 6204 | 6205 | 6208 | 6209 |
| 6210 | 6211 | 6213 | 6215 | 6216 | 6217 | 6218 | 6219 | 6220 | 6221 | 6222 | 6223 |
| 6225 | 6226 | 6227 | 6228 | 6229 | 6230 | 6231 | 6233 | 6235 | 6236 | 6237 | 6238 |
| 6240 | 6241 | 6245 | 6246 | 6248 | 6249 | 6250 | 6255 | 6256 | 6260 | 6261 | 6263 |
| 6264 | 6265 | 6266 | 6267 | 6268 | 6271 | 6273 | 6274 | 6275 | 6276 | 6277 | 6278 |
| 6279 | 6280 | 6281 | 6282 | 6283 | 6284 | 6287 | 6288 | 6289 | 6290 | 6297 | 6299 |
| 6300 | 6302 | 6304 | 6305 | 6306 | 6307 | 6308 | 6309 | 6310 | 6311 | 6312 | 6313 |
| 6314 | 6319 | 6320 | 6321 | 6322 | 6323 | 6329 | 6331 | 6332 | 6333 | 6335 | 6338 |
| 6339 | 6340 | 6341 | 6343 | 6344 | 6345 | 6347 | 6354 | 6360 | 6361 | 6368 | 6370 |
| 6371 | 6372 | 6373 | 6374 | 6375 | 6376 | 6377 | 6379 | 6380 | 6381 | 6383 | 6386 |
| 6389 | 6392 | 6393 | 6394 | 6396 | 6397 | 6401 | 6406 | 6407 | 6408 | 6409 | 6411 |
| 6412 | 6413 | 6414 | 6415 | 6418 | 6419 | 6420 | 6421 | 6426 | 6428 | 6429 | 6430 |
| 6431 | 6433 | 6434 | 6435 | 6438 | 6439 | 6442 | 6443 | 6444 | 6445 | 6446 | 6447 |
| 6448 | 6449 | 6454 | 6455 | 6456 | 6457 | 6458 | 6461 | 6462 | 6463 | 6464 | 6465 |
| 6467 | 6468 | 6469 | 6470 | 6471 | 6472 | 6473 | 6476 | 6479 | 6480 | 6481 | 6482 |
| 6483 | 6484 | 6485 | 6486 | 6487 | 6488 | 6491 | 6492 | 6493 | 6494 | 6495 | 6496 |
| 6500 | 6509 | 6510 | 6511 | 6514 | 6515 | 6518 | 6520 | 6521 | 6524 | 6528 | 6529 |
| 6531 | 6532 | 6535 | 6536 | 6537 | 6540 | 6541 | 6544 | 6545 | 6546 | 6547 | 6549 |
| 6552 | 6553 | 6554 | 6555 | 6556 | 6557 | 6558 | 6559 | 6561 | 6562 | 6563 | 6565 |
| 6566 | 6568 | 6569 | 6570 | 6571 | 6572 | 6576 | 6577 | 6578 | 6579 | 6580 | 6584 |
| 6585 | 6586 | 6595 | 6596 | 6597 | 6599 | 6602 | 6603 | 6605 | 6606 | 6607 | 6608 |
| 6612 | 6613 | 6614 | 6615 | 6617 | 6618 | 6624 | 6625 | 6626 | 6627 | 6628 | 6630 |
| 6632 | 6633 | 6634 | 6635 | 6636 | 6637 | 6638 | 6642 | 6644 | 6650 | 6651 | 6652 |
| 6653 | 6654 | 6666 | 6667 | 6669 | 6670 | 6673 | 6674 | 6677 | 6682 | 6685 | 6686 |
| 6688 | 6692 | 6696 | 6697 | 6698 | 6699 | 6701 | 6703 | 6706 | 6707 | 6709 |
| 6710 | 6711 | 6712 | 6713 | 6716 | 6719 | 6721 | 6722 | 6723 | 6725 | 6726 | 6728 |
| 6730 | 6731 | 6734 | 6735 | 6738 | 6739 | 6740 | 6741 | 6742 | 6746 | 6747 | 6748 |
| 6749 | 6750 | 6753 | 6754 | 6755 | 6756 | 6757 | 6758 | 6759 | 6761 | 6762 | 6763 |
| 6764 | 6765 | 6767 | 6768 | 6769 | 6770 | 6771 | 6772 | 6773 | 6774 | 6775 | 6776 |
| 6780 | 6781 | 6782 | 6783 | 6784 | 6785 | 6786 | 6787 | 6789 | 6790 | 6791 | 6792 |
| 6794 | 6795 | 6797 | 6800 | 6801 | 6803 | 6804 | 6805 | 6806 | 6807 | 6808 | 6811 |
| 6812 | 6813 | 6815 | 6816 | 6817 | 6818 | 6819 | 6820 | 6821 | 6822 | 6823 | 6824 |
| 6825 | 6826 | 6827 | 6828 | 6829 | 6831 | 6833 | 6834 | 6835 | 6836 | 6837 | 6838 |
| 6839 | 6841 | 6843 | 6845 | 6847 | 6848 | 6849 | 6851 | 6852 | 6853 | 6854 | 6856 |
| 6857 | 6858 | 6859 | 6860 | 6861 | 6862 | 6863 | 6864 | 6866 | 6867 | 6868 | 6870 |
| 6871 | 6872 | 6876 | 6877 | 6878 | 6879 | 6880 | 6883 | 6885 | 6887 | 6889 | 6890 |
| 6891 | 6892 | 6894 | 6895 | 6896 | 6897 | 6898 | 6899 | 6901 | 6902 | 6903 |
| 6904 | 6906 | 6911 | 6914 | 6915 | 6916 | 6920 | 6921 | 6922 | 6923 | 6927 | 6928 |
| 6929 | 6930 | 6931 | 6933 | 6934 | 6935 | 6936 | 6937 | 6938 | 6939 | 6940 | 6941 |
| 6944 | 6946 | 6947 | 6948 | 6949 | 6950 | 6951 | 6952 | 6953 | 6954 | 6955 | 6956 |
| 6957 | 6958 | 6961 | 6965 | 6969 | 6970 | 6973 | 6974 | 6975 | 6976 | 6977 | 6980 |
| 6984 | 6985 | 6988 | 6989 | 6991 | 6992 | 6994 | 6996 | 6997 | 6998 | 6999 | 7000 |
| 7001 | 7007 | 7008 | 7009 | 7010 | 7012 | 7013 | 7014 | 7015 | 7019 | 7020 | 7021 |
| 7022 | 7026 | 7027 | 7032 | 7035 | 7037 | 7038 | 7040 | 7044 | 7046 | 7047 | 7049 |
| 7050 | 7051 | 7053 | 7057 | 7058 | 7066 | 7067 | 7068 | 7069 | 7070 | 7072 | 7073 |
| 7076 | 7080 | 7082 | 7083 | 7084 | 7086 | 7090 | 7091 | 7097 | 7100 | 7101 | 7102 |
| 7110 | 7113 | 7114 | 7116 | 7117 | 7120 | 7126 | 7127 | 7135 | 7136 | 7140 | 7141 |
| 7143 | 7145 | 7146 | 7148 | 7149 | 7150 | 7153 | 7156 | 7157 | 7161 | 7167 | 7171 |
| 7172 | 7175 | 7180 | 7181 | 7184 | 7187 | 7189 | 7191 | 7192 | 7195 | 7198 | 7199 |
| 7201 | 7202 | 7203 | 7204 | 7207 | 7208 | 7209 | 7210 | 7213 | 7215 | 7218 | 7224 |

TABLE 19-continued

Yield: Stress Tolerance

| | | | | | | | | | | | |
|---|---|---|---|---|---|---|---|---|---|---|---|
| 7226 | 7228 | 7229 | 7230 | 7232 | 7235 | 7237 | 7239 | 7241 | 7246 | 7247 | 7248 |
| 7249 | 7250 | 7252 | 7253 | 7255 | 7256 | 7260 | 7261 | 7263 | 7264 | 7265 | 7266 |
| 7267 | 7271 | 7272 | 7273 | 7274 | 7278 | 7280 | 7281 | 7282 | 7291 | 7295 | 7298 |
| 7300 | 7306 | 7308 | 7309 | 7310 | 7311 | 7312 | 7314 | 7316 | 7318 | 7320 | 7325 |
| 7326 | 7328 | 7331 | 7332 | 7336 | 7337 | 7339 | 7340 | 7342 | 7344 | 7350 | 7352 |
| 7353 | 7354 | 7355 | 7356 | 7360 | 7365 | 7366 | 7368 | 7371 | 7372 | 7374 | 7375 |
| 7376 | 7377 | 7378 | 7379 | 7380 | 7384 | 7385 | 7389 | 7392 | 7393 | 7394 | 7400 |
| 7407 | 7408 | 7410 | 7412 | 7413 | 7415 | 7419 | 7420 | 7421 | 7423 | 7424 | 7425 |
| 7429 | 7432 | 7435 | 7440 | 7442 | 7444 | 7445 | 7450 | 7451 | 7452 | 7453 | 7456 |
| 7459 | 7460 | 7463 | 7464 | 7467 | 7468 | 7469 | 7471 | 7473 | 7475 | 7477 | 7480 |
| 7482 | 7483 | 7486 | 7487 | 7488 | 7496 | 7499 | 7500 | 7503 | 7508 | 7510 | 7515 |
| 7518 | 7519 | 7521 | 7523 | 7524 | 7525 | 7529 | 7531 | 7534 | 7538 | 7541 | 7543 |
| 7544 | 7545 | 7546 | 7547 | 7551 | 7553 | 7560 | 7564 | 7565 | 7566 | 7567 | 7569 |
| 7570 | 7571 | 7572 | 7574 | 7575 | 7577 | 7578 | 7579 | 7583 | 7585 | 7588 | 7592 |
| 7596 | 7597 | 7604 | 7605 | 7608 | 7609 | 7610 | 7611 | 7613 | 7620 | 7623 | 7624 |
| 7625 | 7629 | 7634 | 7638 | 7640 | 7642 | 7643 | 7644 | 7646 | 7649 | 7651 | 7652 |
| 7653 | 7655 | 7656 | 7657 | 7659 | 7665 | 7666 | 7669 | 7670 | 7672 | 7674 | 7675 |
| 7678 | 7680 | 7683 | 7684 | 7685 | 7693 | 7694 | 7695 | 7696 | 7697 | 7700 | 7702 |
| 7704 | 7705 | 7711 | 7712 | 7714 | 7719 | 7720 | 7721 | 7723 | 7724 | 7726 | 7728 |
| 7731 | 7735 | 7736 | 7737 | 7739 | 7742 | 7743 | 7746 | 7749 | 7750 | 7756 | 7757 |
| 7764 | 7767 | 7770 | 7771 | 7772 | 7773 | 7774 | 7776 | 7777 | 7782 | 7784 | 7785 |
| 7789 | 7790 | 7791 | 7792 | 7794 | 7795 | 7801 | 7802 | 7803 | 7805 | 7807 | 7808 |
| 7809 | 7810 | 7812 | 7813 | 7815 | 7816 | 7819 | 7820 | 7822 | 7823 | 7826 | 7836 |
| 7837 | 7839 | 7840 | 7841 | 7842 | 7846 | 7850 | 7852 | 7856 | 7858 | 7860 | 7861 |
| 7862 | 7865 | 7869 | 7871 | 7872 | 7873 | 7878 | 7880 | 7885 | 7886 | 7890 | 7891 |
| 7892 | 7894 | 7895 | 7896 | 7900 | 7902 | 7903 | 7905 | 7910 | 7911 | 7912 | 7913 |
| 7917 | 7918 | 7920 | 7921 | 7922 | 7923 | 7924 | 7926 | 7933 | 7938 | 7939 | 7941 |
| 7944 | 7951 | 7953 | 7954 | 7955 | 7958 | 7960 | 7961 | 7964 | 7965 | 7971 | 7977 |
| 7978 | 7979 | 7980 | 7983 | 7987 | 7989 | 7993 | 7996 | 7997 | 8001 | 8006 | 8007 |
| 8009 | 8010 | 8011 | 8012 | 8014 | 8015 | 8019 | 8020 | 8023 | 8024 | 8028 | 8033 |
| 8035 | 8039 | 8040 | 8041 | 8043 | 8044 | 8047 | 8050 | 8051 | 8054 | 8057 | 8060 |
| 8061 | 8062 | 8063 | 8064 | 8066 | 8070 | 8072 | 8074 | 8075 | 8076 | 8077 | 8079 |
| 8080 | 8081 | 8082 | 8083 | 8084 | 8089 | 8093 | 8094 | 8099 | 8100 | 8101 | 8102 |
| 8103 | 8104 | 8105 | 8106 | 8108 | 8111 | 8112 | 8114 | 8115 | 8116 | 8130 | 8132 |
| 8133 | 8134 | 8135 | 8136 | 8137 | 8140 | 8141 | 8142 | 8143 | 8145 | 8150 | 8153 |
| 8154 | 8157 | 8159 | 8161 | 8162 | 8168 | 8171 | 8172 | 8174 | 8175 | 8176 | 8178 |
| 8191 | 8192 | 8193 | 8194 | 8195 | 8206 | 8207 | 8209 | 8210 | 8214 | 8217 | 8218 |
| 8219 | 8220 | 8224 | 8225 | 8226 | 8229 | 8231 | 8239 | 8241 | 8243 | 8245 | 8248 |
| 8249 | 8255 | 8256 | 8257 | 8259 | 8261 | 8262 | 8263 | 8265 | 8266 | 8270 | 8275 |
| 8276 | 8277 | 8280 | 8284 | 8285 | 8288 | 8290 | 8291 | 8292 | 8296 | 8297 | 8298 |
| 8300 | 8303 | 8304 | 8309 | 8312 | 8313 | 8314 | 8315 | 8316 | 8317 | 8319 | 8320 |
| 8322 | 8323 | 8324 | 8327 | 8328 | 8329 | 8331 | 8333 | 8342 | 8345 | 8350 | 8351 |
| 8352 | 8353 | 8358 | 8361 | 8362 | 8363 | 8369 | 8373 | 8374 | 8375 | 8379 | 8380 |
| 8388 | 8389 | 8390 | 8393 | 8395 | 8399 | 8404 | 8406 | 8410 | 8412 | 8414 | 8416 |
| 8421 | 8423 | 8427 | 8428 | 8429 | 8433 | 8436 | 8437 | 8446 | 8449 | 8451 | 8454 |
| 8457 | 8459 | 8460 | 8461 | 8465 | 8471 | 8474 | 8475 | 8476 | 8479 | 8482 | 8484 |
| 8485 | 8487 | 8488 | 8489 | 8493 | 8495 | 8496 | 8499 | 8501 | 8502 | 8503 | 8506 |
| 8511 | 8513 | 8519 | 8520 | 8530 | 8531 | 8535 | 8537 | 8539 | 8540 | 8541 | 8542 |
| 8545 | 8548 | 8549 | 8551 | 8554 | 8555 | 8560 | 8562 | 8564 | 8565 | 8567 | 8576 |
| 8578 | 8579 | 8580 | 8581 | 8582 | 8586 | 8588 | 8589 | 8590 | 8592 | 8594 | 8595 |
| 8596 | 8597 | 8598 | 8599 | 8601 | 8602 | 8604 | 8606 | 8609 | 8610 | 8611 | 8612 |
| 8613 | 8617 | 8620 | 8623 | 8625 | 8626 | 8628 | 8629 | 8631 | 8632 | 8639 | 8641 |
| 8642 | 8643 | 8644 | 8646 | 8650 | 8652 | 8657 | 8661 | 8662 | 8663 | 8667 | 8668 |
| 8672 | 8676 | 8678 | 8680 | 8683 | 8684 | 8685 | 8687 | 8688 | 8689 | 8690 | 8691 |
| 8692 | 8694 | 8695 | 8698 | 8699 | 8702 | 8703 | 8707 | 8709 | 8710 | 8712 | 8714 |
| 8723 | 8729 | 8735 | 8736 | 8737 | 8739 | 8740 | 8741 | 8742 | 8743 | 8744 | 8747 |
| 8748 | 8749 | 8750 | 8751 | 8753 | 8754 | 8755 | 8757 | 8762 | 8763 | 8764 | 8767 |
| 8773 | 8778 | 8779 | 8783 | 8785 | 8787 | 8788 | 8789 | 8790 | 8793 | 8796 | 8798 |
| 8799 | 8803 | 8804 | 8806 | 8809 | 8810 | 8811 | 8812 | 8813 | 8817 | 8818 | 8825 |
| 8828 | 8829 | 8832 | 8838 | 8840 | 8841 | 8842 | 8843 | 8844 | 8845 | 8846 | 8847 |
| 8852 | 8854 | 8855 | 8857 | 8858 | 8859 | 8863 | 8867 | 8872 | 8876 | 8877 | 8880 |
| 8881 | 8884 | 8886 | 8887 | 8888 | 8889 | 8891 | 8892 | 8894 | 8897 | 8898 | 8899 |
| 8901 | 8904 | 8906 | 8907 | 8908 | 8912 | 8913 | 8914 | 8920 | 8922 | 8928 | 8933 |
| 8935 | 8939 | 8941 | 8944 | 8946 | 8948 | 8950 | 8951 | 8954 | 8956 | 8958 | 8966 |
| 8968 | 8969 | 8971 | 8975 | 8976 | 8977 | 8978 | 8979 | 8984 | 8986 | 8989 | 8990 |
| 8991 | 8992 | 8993 | 8995 | 9005 | 9006 | 9008 | 9010 | 9011 | 9017 | 9018 | 9019 |
| 9022 | 9023 | 9024 | 9025 | 9029 | 9031 | 9032 | 9034 | 9040 | 9042 | 9043 | 9049 |
| 9050 | 9053 | 9054 | 9055 | 9056 | 9057 | 9067 | 9070 | 9072 | 9077 | 9079 | 9083 |
| 9084 | 9088 | 9090 | 9092 | 9095 | 9098 | 9099 | 9100 | 9101 | 9102 | 9103 | 9105 |
| 9108 | 9113 | 9114 | 9116 | 9119 | 9120 | 9121 | 9122 | 9123 | 9128 | 9129 | 9132 |
| 9134 | 9135 | 9136 | 9138 | 9143 | 9144 | 9146 | 9148 | 9152 | 9153 | 9156 | 9157 |
| 9158 | 9159 | 9162 | 9165 | 9167 | 9168 | 9169 | 9172 | 9175 | 9178 | 9180 | 9181 |
| 9183 | 9186 | 9189 | 9190 | 9192 | 9193 | 9194 | 9195 | 9197 | 9198 | 9204 | 9206 |
| 9209 | 9212 | 9215 | 9217 | 9219 | 9224 | 9226 | 9227 | 9228 | 9232 | 9236 | 9237 |
| 9239 | 9240 | 9241 | 9243 | 9244 | 9245 | 9246 | 9252 | 9255 | 9256 | 9257 | 9260 |
| 9261 | 9263 | 9264 | 9265 | 9269 | 9270 | 9273 | 9274 | 9275 | 9276 | 9277 | 9278 |
| 9279 | 9280 | 9282 | 9284 | 9285 | 9287 | 9289 | 9290 | 9298 | 9299 | 9303 | 9304 |

TABLE 19-continued

Yield: Stress Tolerance

| | | | | | | | | | | | |
|---|---|---|---|---|---|---|---|---|---|---|---|
| 9306 | 9311 | 9315 | 9327 | 9329 | 9331 | 9334 | 9336 | 9337 | 9338 | 9339 | 9340 |
| 9341 | 9342 | 9343 | 9344 | 9346 | 9351 | 9352 | 9355 | 9356 | 9363 | 9365 | 9366 |
| 9368 | 9369 | 9370 | 9371 | 9372 | 9380 | 9382 | 9385 | 9386 | 9393 | 9397 | 9400 |
| 9403 | 9404 | 9407 | 9409 | 9411 | 9415 | 9419 | 9420 | 9422 | 9423 | 9424 | 9425 |
| 9428 | 9431 | 9432 | 9433 | 9435 | 9439 | 9440 | 9441 | 9442 | 9444 | 9447 | 9448 |
| 9450 | 9451 | 9453 | 9455 | 9460 | 9461 | 9462 | 9463 | 9467 | 9468 | 9471 | 9474 |
| 9475 | 9476 | 9478 | 9479 | 9480 | 9481 | 9482 | 9484 | 9488 | 9490 | 9496 | 9497 |
| 9498 | 9500 | 9502 | 9503 | 9504 | 9507 | 9508 | 9511 | 9512 | 9513 | 9518 | 9520 |
| 9521 | 9523 | 9524 | 9526 | 9527 | 9530 | 9532 | 9533 | 9539 | 9540 | 9542 | 9545 |
| 9546 | 9550 | 9555 | 9558 | 9562 | 9564 | 9567 | 9569 | 9574 | 9575 | 9576 | 9577 |
| 9581 | 9584 | 9585 | 9586 | 9588 | 9589 | 9590 | 9600 | 9601 | 9604 | 9606 | 9607 |
| 9609 | 9610 | 9612 | 9614 | 9621 | 9623 | 9625 | 9626 | 9628 | 9630 | 9634 | 9635 |
| 9636 | 9637 | 9638 | 9639 | 9640 | 9644 | 9645 | 9646 | 9648 | 9649 | 9650 | 9652 |
| 9661 | 9664 | 9665 | 9666 | 9667 | 9668 | 9669 | 9672 | 9673 | 9674 | 9676 | 9677 |
| 9683 | 9695 | 9697 | 9700 | 9701 | 9705 | 9706 | 9707 | 9708 | 9710 | 9712 | 9713 |
| 9715 | 9716 | 9721 | 9722 | 9723 | 9724 | 9725 | 9726 | 9727 | 9732 | 9735 | 9742 |
| 9743 | 9747 | 9750 | 9751 | 9754 | 9755 | 9758 | 9759 | 9762 | 9766 | 9769 | 9770 |
| 9772 | 9774 | 9775 | 9777 | 9778 | 9779 | 9780 | 9781 | 9782 | 9786 | 9788 | 9791 |
| 9792 | 9793 | 9795 | 9798 | 9799 | 9800 | 9807 | 9808 | 9809 | 9811 | 9812 | 9813 |
| 9814 | 9820 | 9821 | 9829 | 9831 | 9833 | 9835 | 9836 | 9837 | 9838 | 9839 | 9853 |
| 9854 | 9856 | 9857 | 9858 | 9861 | 9864 | 9865 | 9866 | 9869 | 9874 | 9875 | 9876 |
| 9879 | 9881 | 9889 | 9890 | 9892 | 9900 | 9901 | 9902 | 9903 | 9907 | 9908 | 9912 |
| 9913 | 9923 | 9924 | 9927 | 9928 | 9930 | 9937 | 9938 | 9939 | 9940 | 9946 | 9949 |
| 9950 | 9953 | 9958 | 9959 | 9960 | 9963 | 9973 | 9977 | 9978 | 9979 | 9980 | 9981 |
| 9985 | 9986 | 9989 | 9993 | 9994 | 9995 | 9996 | 9997 | 10006 | 10014 | 10018 | 10025 |
| 10026 | 10030 | 10031 | 10032 | 10033 | 10034 | 10038 | 10040 | 10041 | 10049 | 10053 | 10055 |
| 10059 | 10061 | 10063 | 10067 | 10068 | 10069 | 10070 | 10073 | 10075 | 10083 | 10086 | 10088 |
| 10089 | 10091 | 10092 | 10098 | 10099 | 10100 | 10102 | 10103 | 10104 | 10105 | 10106 | 10107 |
| 10108 | 10109 | 10112 | 10113 | 10114 | 10115 | 10118 | 10119 | 10120 | 10121 | 10123 | 10125 |
| 10130 | 10131 | 10132 | 10134 | 10135 | 10136 | 10137 | 10143 | 10145 | 10147 | 10148 | 10149 |
| 10151 | 10153 | 10155 | 10156 | 10158 | 10159 | 10160 | 10161 | 10162 | 10163 | 10168 | 10170 |
| 10173 | 10174 | 10177 | 10178 | 10180 | 10181 | 10182 | 10183 | 10184 | 10185 | 10187 | 10190 |
| 10191 | 10193 | 10196 | 10204 | 10206 | 10208 | 10211 | 10212 | 10213 | 10217 | 10223 | 10228 |
| 10229 | 10232 | 10235 | 10236 | 10242 | 10243 | 10249 | 10255 | 10258 | 10259 | 10262 | 10265 |
| 10266 | 10268 | 10269 | 10270 | 10274 | 10275 | 10276 | 10277 | 10278 | 10279 | 10284 | 10285 |
| 10286 | 10288 | 10289 | 10291 | 10292 | 10295 | 10296 | 10298 | 10299 | 10300 | 10304 | 10305 |
| 10308 | 10311 | 10312 | 10313 | 10314 | 10315 | 10316 | 10318 | 10319 | 10320 | 10324 | 10326 |
| 10328 | 10329 | 10330 | 10332 | 10335 | 10336 | 10341 | 10344 | 10345 | 10348 | 10349 | 10356 |
| 10357 | 10358 | 10359 | 10363 | 10364 | 10365 | 10366 | 10368 | 10369 | 10370 | 10373 | 10374 |
| 10375 | 10376 | 10378 | 10379 | 10381 | 10384 | 10389 | 10390 | 10392 | 10393 | 10394 | 10396 |
| 10400 | 10403 | 10404 | 10408 | 10410 | 10411 | 10413 | 10416 | 10417 | 10418 | 10421 | 10423 |
| 10424 | 10431 | 10434 | 10436 | 10438 | 10439 | 10445 | 10446 | 10447 | 10449 | 10450 | 10451 |
| 10452 | 10461 | 10470 | 10471 | 10473 | 10474 | 10475 | 10478 | 10479 | 10482 | 10483 | 10485 |
| 10487 | 10490 | 10496 | 10498 | 10505 | 10507 | 10508 | 10509 | 10512 | 10513 | 10514 | 10515 |
| 10518 | 10520 | 10521 | 10524 | 10530 | 10531 | 10532 | 10533 | 10534 | 10535 | 10539 | 10543 |
| 10544 | 10545 | 10550 | 10558 | 10559 | 10567 | 10575 | 10576 | 10579 | 10580 | 10586 | 10589 |
| 10591 | 10595 | 10596 | 10597 | 10598 | 10599 | 10600 | 10602 | 10603 | 10606 | 10607 | 10609 |
| 10615 | 10617 | 10618 | 10619 | 10622 | 10624 | 10625 | 10626 | 10629 | 10630 | 10631 | 10632 |
| 10633 | 10635 | 10638 | 10640 | 10643 | 10644 | 10646 | 10647 | 10649 | 10664 | 10671 | 10672 |
| 10675 | 10676 | 10678 | 10679 | 10680 | 10681 | 10682 | 10687 | 10688 | 10690 | 10691 | 10692 |
| 10693 | 10694 | 10696 | 10697 | 10701 | 10704 | 10705 | 10708 | 10710 | 10711 | 10715 | 10722 |
| 10729 | 10730 | 10734 | 10735 | 10736 | 10740 | 10741 | 10747 | 10748 | 10749 | 10750 | 10755 |
| 10756 | 10765 | 10768 | 10769 | 10773 | 10776 | 10778 | 10779 | 10782 | 10791 | 10794 | 10795 |
| 10797 | 10798 | 10799 | 10800 | 10801 | 10805 | 10807 | 10809 | 10810 | 10811 | 10816 | 10818 |
| 10819 | 10821 | 10822 | 10826 | 10828 | 10829 | 10830 | 10832 | 10839 | 10841 | 10850 | 10855 |
| 10858 | 10859 | 10860 | 10862 | 10866 | 10868 | 10872 | 10873 | 10875 | 10876 | 10877 | 10879 |
| 10880 | 10882 | 10883 | 10885 | 10890 | 10893 | 10894 | 10896 | 10898 | 10909 | 10910 | 10911 |
| 10913 | 10917 | 10918 | 10919 | 10920 | 10928 | 10930 | 10931 | 10932 | 10933 | 10941 | 10943 |
| 10945 | 10946 | 10947 | 10952 | 10954 | 10955 | 10960 | 10961 | 10964 | 10968 | 10969 | 10970 |
| 10971 | 10972 | 10973 | 10976 | 10978 | 10980 | 10985 | 10996 | 10998 | 11000 | 11003 | 11005 |
| 11006 | 11007 | 11013 | 11014 | 11017 | 11018 | 11019 | 11020 | 11024 | 11026 | 11028 | 11029 |
| 11030 | 11032 | 11033 | 11039 | 11041 | 11043 | 11045 | 11046 | 11047 | 11049 | 11050 | 11051 |
| 11052 | 11055 | 11058 | 11060 | 11061 | 11062 | 11064 | 11066 | 11067 | 11068 | 11069 | 11070 |
| 11071 | 11073 | 11074 | 11076 | 11077 | 11078 | 11079 | 11081 | 11085 | 11086 | 11088 | 11091 |
| 11092 | 11094 | 11095 | 11096 | 11098 | 11100 | 11101 | 11102 | 11103 | 11105 | 11106 | 11109 |
| 11110 | 11111 | 11112 | 11113 | 11115 | 11116 | 11117 | 11119 | 11120 | 11122 | 11123 | 11125 |
| 11126 | 11127 | 11128 | 11129 | 11131 | 11132 | 11133 | 11135 | 11136 | 11137 | 11139 | 11140 |
| 11141 | 11142 | 11143 | 11145 | 11146 | 11149 | 11150 | 11152 | 11155 | 11156 | 11158 |  |
| 11159 | 11160 | 11161 | 11163 | 11165 | 11166 | 11167 | 11168 | 11171 | 11174 | 11181 | 11182 |
| 11183 | 11184 | 11185 | 11187 | 11188 | 11195 | 11196 | 11197 | 11200 | 11202 | 11203 | 11204 |
| 11205 | 11206 | 11207 | 11208 | 11209 | 11210 | 11211 | 11212 | 11214 | 11216 | 11221 | 11222 |
| 11228 | 11230 | 11236 | 11237 | 11238 | 11241 | 11242 | 11244 | 11245 | 11246 | 11248 | 11249 |
| 11250 | 11251 | 11254 | 11255 | 11257 | 11258 | 11260 | 11263 | 11266 | 11268 | 11269 | 11270 |
| 11271 | 11272 | 11277 | 11282 | 11283 | 11284 | 11285 | 11286 | 11287 | 11289 | 11290 | 11293 |
| 11294 | 11296 | 11297 | 11298 | 11299 | 11300 | 11307 | 11308 | 11309 | 11310 | 11311 | 11312 |
| 11313 | 11316 | 11319 | 11320 | 11324 | 11325 | 11326 | 11327 | 11328 | 11329 | 11332 | 11334 |
| 11336 | 11338 | 11345 | 11347 | 11348 | 11349 | 11350 | 11351 | 11356 | 11358 | 11360 | 11361 |

TABLE 19-continued

Yield: Stress Tolerance

| | | | | | | | | | | | |
|---|---|---|---|---|---|---|---|---|---|---|---|
| 11362 | 11364 | 11365 | 11366 | 11367 | 11368 | 11370 | 11371 | 11377 | 11380 | 11381 | 11383 |
| 11387 | 11388 | 11389 | 11390 | 11392 | 11396 | 11398 | 11402 | 11403 | 11405 | 11407 | 11410 |
| 11412 | 11413 | 11417 | 11419 | 11420 | 11423 | 11425 | 11427 | 11431 | 11432 | 11433 | 11434 |
| 11435 | 11439 | 11440 | 11442 | 11443 | 11444 | 11445 | 11448 | 11449 | 11451 | 11453 | 11455 |
| 11457 | 11460 | 11463 | 11465 | 11466 | 11470 | 11471 | 11475 | 11476 | 11478 | 11479 | 11485 |
| 11489 | 11490 | 11493 | 11494 | 11498 | 11500 | 11502 | 11506 | 11515 | 11516 | 11518 | 11523 |
| 11526 | 11529 | 11530 | 11533 | 11534 | 11537 | 11538 | 11539 | 11540 | 11542 | 11544 | 11545 |
| 11550 | 11552 | 11554 | 11555 | 11557 | 11559 | 11561 | 11564 | 11565 | 11566 | 11567 | 11568 |
| 11570 | 11572 | 11574 | 11575 | 11576 | 11578 | 11581 | 11584 | 11588 | 11593 | 11594 | 11595 |
| 11597 | 11598 | 11604 | 11605 | 11606 | 11607 | 11609 | 11612 | 11614 | 11616 | 11623 | 11624 |
| 11627 | 11629 | 11632 | 11633 | 11637 | 11646 | 11648 | 11649 | 11651 | 11653 | 11656 | 11658 |
| 11659 | 11661 | 11663 | 11667 | 11685 | 11691 | 11697 | 11708 | 11709 | 11713 | 11714 | 11716 |
| 11718 | 11719 | 11722 | 11729 | 11731 | 11734 | 11736 | 11738 | 11740 | 11742 | 11743 | 11744 |
| 11746 | 11747 | 11749 | 11756 | 11760 | 11763 | 11766 | 11768 | 11769 | 11770 | 11773 | 11774 |
| 11776 | 11777 | 11778 | 11781 | 11783 | 11786 | 11788 | 11789 | 11791 | 11795 | 11796 | 11797 |
| 11800 | 11801 | 11805 | 11807 | 11811 | 11812 | 11813 | 11816 | 11825 | 11827 | 11829 | 11830 |
| 11831 | 11835 | 11838 | 11839 | 11840 | 11843 | 11844 | 11848 | 11850 | 11853 | 11855 | 11859 |
| 11861 | 11863 | 11867 | 11868 | 11870 | 11871 | 11874 | 11875 | 11876 | 11877 | 11879 | 11881 |
| 11884 | 11887 | 11888 | 11889 | 11891 | 11892 | 11894 | 11897 | 11899 | 11902 | 11903 | 11904 |
| 11905 | 11907 | 11908 | 11911 | 11912 | 11914 | 11915 | 11919 | 11922 | 11925 | 11926 | 11929 |
| 11932 | 11935 | 11936 | 11939 | 11940 | 11941 | 11946 | 11948 | 11950 | 11951 | 11953 | 11954 |
| 11957 | 11959 | 11961 | 11967 | 11970 | 11972 | 11975 | 11976 | 11977 | 11983 | 11985 | 11987 |
| 11988 | 11996 | 11997 | 12002 | 12004 | 12005 | 12007 | 12011 | 12013 | 12014 | 12017 | 12018 |
| 12020 | 12021 | 12023 | 12025 | 12030 | 12031 | 12033 | 12034 | 12035 | 12036 | 12044 | 12045 |
| 12050 | 12052 | 12053 | 12058 | 12059 | 12062 | 12064 | 12066 | 12071 | 12074 | 12077 | 12078 |
| 12079 | 12080 | 12083 | 12084 | 12086 | 12088 | 12089 | 12092 | 12093 | 12095 | 12096 | 12099 |
| 12103 | 12106 | 12109 | 12110 | 12112 | 12113 | 12117 | 12119 | 12123 | 12124 | 12128 | 12129 |
| 12131 | 12132 | 12135 | 12136 | 12137 | 12138 | 12140 | 12143 | 12144 | 12145 | 12146 | 12147 |
| 12149 | 12155 | 12156 | 12157 | 12159 | 12160 | 12161 | 12162 | 12167 | 12169 | 12170 | 12174 |
| 12175 | 12176 | 12177 | 12178 | 12179 | 12183 | 12186 | 12187 | 12188 | 12189 | 12190 | 12192 |
| 12193 | 12194 | 12195 | 12197 | 12200 | 12201 | 12202 | 12205 | 12211 | 12212 | 12213 | |
| 12216 | 12217 | 12218 | 12221 | 12222 | 12224 | 12226 | 12228 | 12231 | 12232 | 12233 | 12235 |
| 12239 | 12241 | 12242 | 12244 | 12245 | 12246 | 12247 | 12248 | 12250 | 12251 | 12253 | 12256 |
| 12260 | 12261 | 12262 | 12264 | 12265 | 12266 | 12269 | 12272 | 12273 | 12274 | 12275 | 12279 |
| 12282 | 12284 | 12292 | 12296 | 12298 | 12304 | 12305 | 12306 | 12307 | 12308 | 12312 | 12315 |
| 12316 | 12317 | 12324 | 12325 | 12330 | 12335 | 12339 | 12340 | 12341 | 12342 | 12344 | 12345 |
| 12346 | 12357 | 12358 | 12360 | 12362 | 12363 | 12364 | 12366 | 12368 | 12371 | 12372 | 12373 |
| 12376 | 12377 | 12378 | 12379 | 12380 | 12381 | 12385 | 12387 | 12389 | 12391 | 12395 | 12396 |
| 12397 | 12398 | 12399 | 12400 | 12407 | 12408 | 12409 | 12412 | 12418 | 12420 | 12423 | 12426 |
| 12427 | 12431 | 12433 | 12434 | 12436 | 12441 | 12444 | 12446 | 12450 | 12451 | 12452 | 12454 |
| 12456 | 12459 | 12460 | 12461 | 12462 | 12464 | 12465 | 12466 | 12470 | 12471 | 12472 | 12474 |
| 12475 | 12479 | 12482 | 12483 | 12484 | 12485 | 12486 | 12487 | 12488 | 12489 | 12492 | 12493 |
| 12494 | 12495 | 12496 | 12498 | 12500 | 12502 | 12504 | 12505 | 12507 | 12509 | 12513 | 12514 |
| 12515 | 12516 | 12517 | 12518 | 12521 | 12524 | 12525 | 12527 | 12530 | 12531 | 12539 | 12540 |
| 12547 | 12551 | 12552 | 12554 | 12556 | 12557 | 12564 | 12566 | 12567 | 12568 | 12571 | 12575 |
| 12576 | 12579 | 12580 | 12581 | 12582 | 12583 | 12585 | 12586 | 12589 | 12593 | 12594 | 12595 |
| 12596 | 12598 | 12600 | 12602 | 12604 | 12605 | 12608 | 12609 | 12611 | 12615 | 12616 | 12617 |
| 12622 | 12624 | 12625 | 12626 | 12627 | 12628 | 12629 | 12630 | 12633 | 12634 | 12636 | 12638 |
| 12639 | 12642 | 12643 | 12644 | 12645 | 12646 | 12647 | 12648 | 12649 | 12653 | 12655 | 12662 |
| 12664 | 12665 | 12666 | 12668 | 12672 | 12673 | 12677 | 12678 | 12679 | 12688 | 12689 | 12690 |
| 12691 | 12692 | 12694 | 12695 | 12696 | 12699 | 12700 | 12702 | 12703 | 12707 | 12709 | 12710 |
| 12717 | 12720 | 12721 | 12722 | 12723 | 12726 | 12727 | 12728 | 12730 | 12731 | 12733 | |
| 12734 | 12736 | 12737 | 12739 | 12741 | 12742 | 12745 | 12746 | 12747 | 12748 | 12751 | 12752 |
| 12754 | 12755 | 12758 | 12760 | 12764 | 12765 | 12767 | 12768 | 12771 | 12774 | 12777 | 12778 |
| 12779 | 12781 | 12782 | 12784 | 12788 | 12790 | 12793 | 12794 | 12801 | 12806 | 12808 | 12810 |
| 12813 | 12815 | 12816 | 12819 | 12820 | 12822 | 12825 | 12827 | 12832 | 12835 | 12836 | 12837 |
| 12838 | 12840 | 12841 | 12842 | 12844 | 12846 | 12847 | 12851 | 12853 | 12854 | 12859 | 12861 |
| 12862 | 12863 | 12864 | 12865 | 12866 | 12869 | 12874 | 12876 | 12877 | 12879 | 12880 | 12882 |
| 12886 | 12889 | 12891 | 12892 | 12893 | 12895 | 12898 | 12899 | 12900 | 12901 | 12903 | 12906 |
| 12907 | 12911 | 12912 | 12913 | 12915 | 12916 | 12918 | 12921 | 12924 | 12925 | 12926 | 12927 |
| 12929 | 12931 | 12932 | 12934 | 12936 | 12937 | 12939 | 12941 | 12943 | 12944 | 12945 | 12947 |
| 12949 | 12951 | 12952 | 12953 | 12964 | 12966 | 12967 | 12969 | 12976 | 12977 | 12979 | 12981 |
| 12983 | 12984 | 12985 | 12986 | 12987 | 12989 | 12991 | 12992 | 12993 | 12994 | 12998 | 13001 |
| 13003 | 13006 | 13007 | 13010 | 13011 | 13014 | 13018 | 13019 | 13020 | 13022 | 13023 | 13025 |
| 13026 | 13028 | 13029 | 13032 | 13033 | 13038 | 13039 | 13040 | 13041 | 13043 | 13044 | 13046 |
| 13049 | 13051 | 13052 | 13054 | 13061 | 13062 | 13064 | 13071 | 13072 | 13073 | 13074 | 13076 |
| 13078 | 13079 | 13080 | 13081 | 13082 | 13085 | 13088 | 13090 | 13091 | 13093 | 13095 | 13096 |
| 13098 | 13100 | 13101 | 13104 | 13106 | 13108 | 13109 | 13111 | 13112 | 13113 | 13114 | 13115 |
| 13119 | 13120 | 13121 | 13122 | 13125 | 13126 | 13128 | 13130 | 13131 | 13134 | 13136 | 13137 |
| 13139 | 13141 | 13144 | 13145 | 13147 | 13148 | 13149 | 13150 | 13151 | 13152 | 13155 | 13156 |
| 13158 | 13159 | 13160 | 13161 | 13162 | 13165 | 13166 | 13169 | 13170 | 13171 | 13178 | 13179 |
| 13182 | 13183 | 13184 | 13188 | 13189 | 13191 | 13192 | 13193 | 13194 | 13195 | 13197 | 13198 |
| 13201 | 13202 | 13205 | 13208 | 13209 | 13211 | 13212 | 13213 | 13214 | 13215 | 13216 | 13217 |
| 13219 | 13221 | 13223 | 13224 | 13225 | 13228 | 13231 | 13236 | 13239 | 13242 | 13246 | 13247 |
| 13249 | 13252 | 13253 | 13254 | 13256 | 13257 | 13259 | 13261 | 13262 | 13263 | 13264 | 13265 |
| 13266 | 13269 | 13270 | 13271 | 13272 | 13277 | 13278 | 13280 | 13282 | 13283 | 13284 | 13287 |
| 13292 | 13293 | 13295 | 13296 | 13297 | 13298 | 13300 | 13302 | 13303 | 13306 | 13307 | 13310 |

TABLE 19-continued

Yield: Stress Tolerance

| | | | | | | | | | | | |
|---|---|---|---|---|---|---|---|---|---|---|---|
| 13312 | 13313 | 13314 | 13315 | 13316 | 13317 | 13318 | 13319 | 13320 | 13322 | 13325 | 13326 |
| 13329 | 13330 | 13331 | 13333 | 13335 | 13337 | 13338 | 13339 | 13341 | 13343 | 13344 | 13345 |
| 13347 | 13349 | 13350 | 13351 | 13354 | 13355 | 13356 | 13358 | 13360 | 13362 | 13365 | 13366 |
| 13369 | 13371 | 13373 | 13374 | 13375 | 13376 | 13377 | 13379 | 13381 | 13384 | 13385 | 13386 |
| 13387 | 13389 | 13390 | 13394 | 13395 | 13400 | 13401 | 13403 | 13408 | 13409 | 13410 | 13418 |
| 13419 | 13420 | 13421 | 13422 | 13423 | 13424 | 13425 | 13427 | 13428 | 13429 | 13430 | 13434 |
| 13437 | 13441 | 13445 | 13447 | 13449 | 13450 | 13451 | 13453 | 13454 | 13459 | 13467 | 13470 |
| 13473 | 13477 | 13479 | 13480 | 13481 | 13483 | 13484 | 13485 | 13486 | 13488 | 13491 | 13493 |
| 13494 | 13499 | 13506 | 13509 | 13510 | 13511 | 13514 | 13517 | 13518 | 13519 | 13520 | 13521 |
| 13522 | 13524 | 13528 | 13529 | 13534 | 13535 | 13536 | 13538 | 13539 | 13541 | 13542 | 13543 |
| 13544 | 13549 | 13552 | 13553 | 13554 | 13555 | 13556 | 13557 | 13558 | 13559 | 13562 | 13564 |
| 13567 | 13568 | 13570 | 13571 | 13572 | 13574 | 13575 | 13576 | 13577 | 13578 | 13582 | 13587 |
| 13591 | 13592 | 13595 | 13596 | 13598 | 13606 | 13610 | 13612 | 13613 | 13616 | 13617 | 13620 |
| 13627 | 13631 | 13632 | 13633 | 13637 | 13640 | 13641 | 13643 | 13644 | 13647 | 13648 | 13649 |
| 13650 | 13653 | 13656 | 13657 | 13660 | 13661 | 13662 | 13668 | 13670 | 13671 | 13675 | 13679 |
| 13680 | 13682 | 13688 | 13690 | 13691 | 13693 | 13694 | 13699 | 13702 | 13703 | 13704 | 13706 |
| 13707 | 13710 | 13713 | 13714 | 13715 | 13717 | 13719 | 13720 | 13727 | 13728 | 13731 | 13732 |
| 13736 | 13737 | 13738 | 13740 | 13742 | 13749 | 13751 | 13752 | 13754 | 13755 | 13756 | 13758 |
| 13759 | 13764 | 13767 | 13768 | 13769 | 13773 | 13775 | 13776 | 13780 | 13781 | 13783 | 13784 |
| 13789 | 13797 | 13798 | 13802 | 13803 | 13804 | 13805 | 13806 | 13807 | 13809 | 13810 | 13811 |
| 13813 | 13816 | 13817 | 13818 | 13820 | 13825 | 13829 | 13830 | 13833 | 13834 | 13835 | 13836 |
| 13837 | 13839 | 13841 | 13843 | 13844 | 13845 | 13846 | 13851 | 13855 | 13859 | 13863 | 13865 |
| 13866 | 13867 | 13868 | 13869 | 13873 | 13874 | 13877 | 13880 | 13881 | 13882 | 13884 | 13887 |
| 13890 | 13896 | 13898 | 13901 | 13902 | 13903 | 13904 | 13905 | 13906 | 13908 | 13910 | 13911 |
| 13912 | 13913 | 13914 | 13917 | 13918 | 13920 | 13924 | 13927 | 13928 | 13930 | 13932 | 13936 |
| 13939 | 13941 | 13943 | 13946 | 13948 | 13951 | 13955 | 13957 | 13958 | 13959 | 13961 | 13970 |
| 13971 | 13973 | 13974 | 13979 | 13987 | 13988 | 13990 | 13995 | 13997 | 13999 | 14000 | 14001 |
| 14002 | 14004 | 14005 | 14006 | 14007 | 14016 | 14017 | 14018 | 14020 | 14021 | 14022 | 14026 |
| 14027 | 14030 | 14033 | 14034 | 14035 | 14036 | 14039 | 14040 | 14043 | 14045 | 14048 | 14049 |
| 14050 | 14051 | 14053 | 14057 | 14060 | 14061 | 14062 | 14067 | 14068 | 14069 | 14072 | 14075 |
| 14077 | 14078 | 14086 | 14090 | 14092 | 14097 | 14098 | 14108 | 14109 | 14113 | 14117 | 14124 |
| 14125 | 14126 | 14134 | 14138 | 14141 | 14143 | 14145 | 14147 | 14149 | 14150 | 14151 | 14152 |
| 14154 | 14155 | 14161 | 14162 | 14166 | 14168 | 14170 | 14175 | 14176 | 14178 | 14181 | 14183 |
| 14186 | 14187 | 14191 | 14195 | 14197 | 14198 | 14204 | 14212 | 14213 | 14216 | 14218 | 14224 |
| 14225 | 14227 | 14228 | 14232 | 14233 | 14234 | 14236 | 14238 | 14239 | 14240 | 14242 | 14244 |
| 14246 | 14247 | 14248 | 14249 | 14253 | 14255 | 14257 | 14259 | 14260 | 14263 | 14266 | 14271 |
| 14272 | 14277 | 14278 | 14283 | 14284 | 14290 | 14293 | 14294 | 14296 | 14305 | 14307 | 14308 |
| 14309 | 14313 | 14314 | 14320 | 14322 | 14324 | 14325 | 14328 | 14330 | 14333 | 14334 | 14335 |
| 14338 | 14340 | 14346 | 14348 | 14351 | 14355 | 14356 | 14359 | 14360 | 14363 | 14364 | 14365 |
| 14367 | 14368 | 14371 | 14372 | 14381 | 14383 | 14384 | 14388 | 14391 | 14392 | 14395 | 14397 |
| 14399 | 14400 | 14402 | 14403 | 14404 | 14407 | 14409 | 14411 | 14412 | 14413 | 14418 | 14421 |
| 14424 | 14431 | 14433 | 14434 | 14436 | 14441 | 14443 | 14444 | 14446 | 14448 | 14452 | 14453 |
| 14457 | 14460 | 14461 | 14464 | 14465 | 14466 | 14471 | 14472 | 14473 | 14474 | 14475 | 14476 |
| 14477 | 14479 | 14482 | 14483 | 14484 | 14487 | 14488 | 14490 | 14491 | 14493 | 14501 | 14504 |
| 14508 | 14510 | 14514 | 14515 | 14516 | 14517 | 14519 | 14521 | 14522 | 14523 | 14525 | 14526 |
| 14528 | 14529 | 14531 | 14534 | 14535 | 14540 | 14541 | 14544 | 14547 | 14548 | 14550 | 14551 |
| 14556 | 14558 | 14560 | 14563 | 14564 | 14565 | 14567 | 14570 | 14574 | 14575 | 14580 | |
| 14582 | 14586 | 14588 | 14590 | 14594 | 14597 | 14598 | 14600 | 14607 | 14610 | 14613 | 14615 |
| 14616 | 14621 | 14624 | 14626 | 14632 | 14634 | 14645 | 14647 | 14648 | 14652 | 14653 | 14656 |
| 14657 | 14659 | 14662 | 14663 | 14664 | 14666 | 14669 | 14673 | 14674 | 14675 | 14677 | 14678 |
| 14686 | 14697 | 14700 | 14701 | 14705 | 14706 | 14707 | 14708 | 14711 | 14714 | 14717 | |
| 14720 | 14722 | 14723 | 14726 | 14729 | 14730 | 14731 | 14732 | 14734 | 14740 | 14745 | 14746 |
| 14748 | 14750 | 14752 | 14757 | 14758 | 14760 | 14763 | 14764 | 14771 | 14772 | 14777 | 14788 |
| 14791 | 14792 | 14794 | 14795 | 14796 | 14799 | 14800 | 14804 | 14805 | 14806 | 14810 | 14813 |
| 14816 | 14818 | 14820 | 14822 | 14824 | 14825 | 14832 | 14835 | 14840 | 14842 | 14843 | 14844 |
| 14845 | 14847 | 14848 | 14849 | 14850 | 14851 | 14853 | 14854 | 14864 | 14867 | 14868 | |
| 14869 | 14871 | 14873 | 14875 | 14876 | 14880 | 14881 | 14882 | 14885 | 14890 | 14894 | 14901 |
| 14902 | 14903 | 14907 | 14912 | 14916 | 14917 | 14920 | 14923 | 14924 | 14925 | 14931 | 14938 |
| 14943 | 14945 | 14947 | 14950 | 14951 | 14955 | 14956 | 14960 | 14962 | 14963 | 14964 | 14965 |
| 14967 | 14973 | 14974 | 14975 | 14978 | 14979 | 14981 | 14983 | 14985 | 14986 | 14987 | 14991 |
| 14992 | 14995 | 14997 | 15003 | 15004 | 15008 | 15013 | 15014 | 15015 | 15016 | 15020 | 15021 |
| 15025 | 15027 | 15029 | 15030 | 15031 | 15032 | 15034 | 15035 | 15036 | 15037 | 15038 | 15039 |
| 15040 | 15043 | 15046 | 15047 | 15051 | 15053 | 15058 | 15059 | 15060 | 15061 | 15064 | 15068 |
| 15075 | 15079 | 15080 | 15083 | 15089 | 15090 | 15092 | 15093 | 15094 | 15096 | 15103 | 15106 |
| 15107 | 15110 | 15112 | 15113 | 15115 | 15116 | 15118 | 15119 | 15120 | 15122 | 15125 | 15126 |
| 15130 | 15132 | 15133 | 15136 | 15140 | 15141 | 15142 | 15144 | 15145 | 15146 | 15149 | 15153 |
| 15154 | 15155 | 15158 | 15159 | 15160 | 15171 | 15179 | 15180 | 15183 | 15185 | 15188 | 15189 |
| 15190 | 15191 | 15192 | 15193 | 15195 | 15198 | 15202 | 15203 | 15207 | 15209 | 15210 | 15211 |
| 15212 | 15214 | 15216 | 15224 | 15227 | 15228 | 15229 | 15236 | 15237 | 15240 | 15243 | 15244 |
| 15251 | 15252 | 15259 | 15263 | 15265 | 15268 | 15274 | 15275 | 15283 | 15285 | 15286 | 15287 |
| 15289 | 15292 | 15293 | 15295 | 15296 | 15297 | 15303 | 15310 | 15321 | 15322 | 15325 | 15326 |
| 15327 | 15328 | 15334 | 15335 | 15336 | 15338 | 15340 | 15342 | 15346 | 15348 | 15349 | 15353 |
| 15354 | 15356 | 15358 | 15360 | 15365 | 15369 | 15371 | 15374 | 15376 | 15377 | 15378 | 15379 |
| 15380 | 15388 | 15392 | 15393 | 15396 | 15398 | 15401 | 15403 | 15406 | 15407 | 15409 | 15410 |
| 15411 | 15414 | 15415 | 15416 | 15419 | 15421 | 15422 | 15423 | 15428 | 15429 | 15430 | 15431 |
| 15436 | 15437 | 15438 | 15440 | 15442 | 15443 | 15449 | 15450 | 15454 | 15455 | 15457 | 15458 |
| 15459 | 15463 | 15471 | 15474 | 15475 | 15477 | 15480 | 15482 | 15488 | 15489 | 15490 | 15492 |

TABLE 19-continued

Yield: Stress Tolerance

| | | | | | | | | | | | |
|---|---|---|---|---|---|---|---|---|---|---|---|
| 15496 | 15500 | 15506 | 15510 | 15511 | 15512 | 15516 | 15518 | 15519 | 15520 | 15522 | 15525 |
| 15526 | 15530 | 15533 | 15534 | 15535 | 15538 | 15544 | 15545 | 15551 | 15552 | 15553 | 15556 |
| 15560 | 15561 | 15562 | 15563 | 15566 | 15569 | 15573 | 15575 | 15580 | 15582 | 15583 | 15584 |
| 15585 | 15587 | 15601 | 15602 | 15606 | 15609 | 15610 | 15611 | 15617 | 15619 | 15620 | 15624 |
| 15630 | 15632 | 15634 | 15636 | 15637 | 15638 | 15639 | 15642 | 15643 | 15646 | 15647 | 15648 |
| 15649 | 15650 | 15651 | 15652 | 15654 | 15655 | 15656 | 15657 | 15658 | 15659 | 15661 | 15662 |
| 15663 | 15669 | 15676 | 15687 | 15688 | 15691 | 15692 | 15693 | 15694 | 15695 | 15702 | 15703 |
| 15705 | 15707 | 15708 | 15709 | 15713 | 15715 | 15716 | 15721 | 15723 | 15725 | 15727 | 15732 |
| 15736 | 15738 | 15741 | 15744 | 15745 | 15746 | 15747 | 15748 | 15756 | 15760 | 15761 | 15764 |
| 15766 | 15769 | 15771 | 15774 | 15775 | 15777 | 15778 | 15779 | 15782 | 15783 | 15784 | 15787 |
| 15789 | 15790 | 15791 | 15796 | 15797 | 15798 | 15799 | 15800 | 15804 | 15805 | 15806 | 15808 |
| 15809 | 15811 | 15817 | 15818 | 15822 | 15823 | 15825 | 15826 | 15827 | 15830 | 15832 | 15835 |
| 15841 | 15844 | 15845 | 15847 | 15850 | 15853 | 15854 | 15858 | 15860 | 15861 | 15862 | 15863 |
| 15867 | 15871 | 15878 | 15882 | 15883 | 15884 | 15888 | 15890 | 15891 | 15893 | 15896 | 15897 |
| 15901 | 15904 | 15905 | 15906 | 15909 | 15916 | 15917 | 15924 | 15925 | 15926 | 15929 | 15933 |
| 15934 | 15935 | 15936 | 15939 | 15942 | 15946 | 15949 | 15951 | 15956 | 15958 | 15959 | 15960 |
| 15961 | 15963 | 15981 | 15984 | 15985 | 15986 | 15992 | 15994 | 15995 | 15999 | 16005 | 16007 |
| 16009 | 16011 | 16012 | 16013 | 16014 | 16017 | 16018 | 16021 | 16023 | 16024 | 16025 | 16026 |
| 16027 | 16028 | 16029 | 16030 | 16031 | 16033 | 16034 | 16035 | 16036 | 16037 | 16039 | 16041 |
| 16042 | 16045 | 16046 | 16047 | 16048 | 16049 | 16052 | 16053 | 16059 | 16067 | 16070 | 16078 |
| 16079 | 16080 | 16083 | 16084 | 16085 | 16086 | 16092 | 16093 | 16094 | 16097 | 16099 | 16102 |
| 16103 | 16104 | 16107 | 16108 | 16110 | 16111 | 16117 | 16121 | 16124 | 16126 | 16128 | 16129 |
| 16130 | 16131 | 16132 | 16138 | 16139 | 16143 | 16144 | 16148 | 16150 | 16153 | 16157 | 16158 |
| 16159 | 16161 | 16162 | 16164 | 16165 | 16166 | 16169 | 16171 | 16172 | 16173 | 16178 | 16179 |
| 16180 | 16181 | 16182 | 16186 | 16187 | 16189 | 16190 | 16191 | 16193 | 16199 | 16200 | 16204 |
| 16205 | 16206 | 16207 | 16210 | 16211 | 16214 | 16215 | 16223 | 16224 | 16226 | 16228 | 16233 |
| 16234 | 16235 | 16236 | 16238 | 16240 | 16243 | 16246 | 16254 | 16255 | 16256 | 16257 | 16259 |
| 16263 | 16264 | 16266 | 16269 | 16272 | 16273 | 16276 | 16277 | 16280 | 16284 | 16291 | 16292 |
| 16294 | 16297 | 16300 | 16301 | 16302 | 16303 | 16305 | 16308 | 16309 | 16314 | 16315 | 16319 |
| 16322 | 16323 | 16324 | 16328 | 16339 | 16342 | 16344 | 16350 | 16351 | 16352 | 16359 | 16361 |
| 16363 | 16365 | 16366 | 16367 | 16370 | 16371 | 16373 | 16374 | 16375 | 16376 | 16381 | 16382 |
| 16383 | 16386 | 16388 | 16389 | 16391 | 16395 | 16396 | 16397 | 16406 | 16407 | 16408 | 16409 |
| 16411 | 16412 | 16413 | 16414 | 16419 | 16420 | 16421 | 16428 | 16429 | 16430 | 16432 | 16433 |
| 16436 | 16437 | 16444 | 16445 | 16446 | 16447 | 16448 | 16451 | 16454 | 16456 | 16457 | 16459 |
| 16462 | 16463 | 16467 | 16468 | 16469 | 16471 | 16472 | 16475 | 16477 | 16478 | 16480 | 16481 |
| 16483 | 16484 | 16485 | 16486 | 16487 | 16490 | 16495 | 16496 | 16497 | 16501 | 16502 | 16503 |
| 16510 | 16511 | 16512 | 16514 | 16519 | 16520 | 16522 | 16524 | 16525 | 16529 | 16536 | 16540 |
| 16549 | 16550 | 16551 | 16552 | 16553 | 16554 | 16555 | 16558 | 16560 | 16561 | 16562 | 16570 |
| 16571 | 16574 | 16575 | 16576 | 16577 | 16580 | 16590 | 16591 | 16592 | 16593 | 16595 | 16597 |
| 16598 | 16599 | 16603 | 16605 | 16607 | 16609 | 16610 | 16611 | 16616 | 16618 | 16620 | 16621 |
| 16624 | 16625 | 16626 | 16630 | 16631 | 16633 | 16637 | 16646 | 16647 | 16649 | 16653 | 16654 |
| 16655 | 16656 | 16657 | 16658 | 16659 | 16661 | 16662 | 16664 | 16666 | 16667 | 16668 | 16669 |
| 16670 | 16674 | 16675 | 16679 | 16680 | 16681 | 16682 | 16687 | 16689 | 16692 | 16693 | 16695 |
| 16696 | 16697 | 16701 | 16702 | 16703 | 16705 | 16707 | 16709 | 16710 | 16711 | 16712 | 16713 |
| 16714 | 16715 | 16716 | 16717 | 16721 | 16722 | 16726 | 16728 | 16729 | 16732 | 16735 | 16737 |
| 16738 | 16740 | 16744 | 16749 | 16753 | 16756 | 16757 | 16758 | 16759 | 16767 | 16769 | 16770 |
| 16772 | 16776 | 16777 | 16778 | 16779 | 16780 | 16781 | 16782 | 16783 | 16787 | 16788 | 16790 |
| 16793 | 16798 | 16799 | 16803 | 16804 | 16805 | 16806 | 16807 | 16809 | 16810 | 16812 | 16813 |
| 16815 | 16817 | 16823 | 16826 | 16827 | 16828 | 16830 | 16831 | 16833 | 16835 | 16836 | 16837 |
| 16838 | 16840 | 16841 | 16843 | 16844 | 16849 | 16851 | 16854 | 16857 | 16858 | 16859 | 16861 |
| 16863 | 16864 | 16865 | 16866 | 16868 | 16870 | 16872 | 16873 | 16875 | 16877 | 16879 | 16884 |
| 16889 | 16891 | 16894 | 16895 | 16898 | 16899 | 16901 | 16904 | 16909 | 16915 | 16916 | 16917 |
| 16919 | 16920 | 16923 | 16925 | 16926 | 16930 | 16933 | 16935 | 16940 | 16941 | 16943 | 16946 |
| 16948 | 16949 | 16952 | 16957 | 16958 | 16959 | 16963 | 16964 | 16968 | 16970 | 16980 | 16981 |
| 16983 | 16984 | 16985 | 16986 | 16987 | 16988 | 16993 | 16995 | 17002 | 17006 | 17009 | 17010 |
| 17011 | 17015 | 17017 | 17020 | 17024 | 17026 | 17029 | 17030 | 17031 | 17032 | 17033 | 17037 |
| 17040 | 17042 | 17044 | 17046 | 17049 | 17055 | 17057 | 17058 | 17059 | 17060 | 17061 | 17063 |
| 17065 | 17067 | 17068 | 17069 | 17071 | 17072 | 17092 | 17093 | 17094 | 17095 | 17100 | 17102 |
| 17103 | 17105 | 17111 | 17113 | 17122 | 17123 | 17125 | 17126 | 17129 | 17131 | 17136 | 17137 |
| 17138 | 17139 | 17140 | 17143 | 17149 | 17153 | 17154 | 17155 | 17157 | 17158 | 17159 | 17163 |
| 17166 | 17167 | 17168 | 17169 | 17170 | 17171 | 17172 | 17174 | 17178 | 17182 | 17183 | 17185 |
| 17186 | 17187 | 17189 | 17193 | 17194 | 17195 | 17196 | 17197 | 17198 | 17199 | 17200 | 17201 |
| 17204 | 17205 | 17207 | 17208 | 17210 | 17211 | 17217 | 17220 | 17221 | 17222 | 17226 | 17230 |
| 17231 | 17234 | 17235 | 17236 | 17237 | 17240 | 17249 | 17259 | 17265 | 17270 | 17273 | 17274 |
| 17275 | 17277 | 17278 | 17279 | 17281 | 17283 | 17284 | 17289 | 17301 | 17303 | 17307 | 17309 |
| 17310 | 17313 | 17319 | 17321 | 17322 | 17323 | 17326 | 17327 | 17328 | 17330 | 17331 | 17332 |
| 17333 | 17337 | 17345 | 17348 | 17352 | 17358 | 17359 | 17363 | 17368 | 17369 | 17370 | 17371 |
| 17372 | 17373 | 17374 | 17375 | 17377 | 17378 | 17379 | 17381 | 17382 | 17383 | 17384 | 17385 |
| 17387 | 17388 | 17389 | 17391 | 17392 | 17398 | 17399 | 17401 | 17402 | 17403 | 17404 | 17410 |
| 17412 | 17415 | 17418 | 17419 | 17421 | 17426 | 17427 | 17430 | 17436 | 17443 | 17447 | 17453 |
| 17454 | 17455 | 17456 | 17462 | 17463 | 17464 | 17466 | 17467 | 17468 | 17469 | 17471 | 17476 |
| 17477 | 17478 | 17481 | 17483 | 17484 | 17485 | 17490 | 17491 | 17494 | 17500 | 17501 | 17504 |
| 17507 | 17510 | 17515 | 17517 | 17519 | 17520 | 17522 | 17523 | 17524 | 17526 | 17527 | 17535 |
| 17536 | 17537 | 17545 | 17546 | 17547 | 17548 | 17549 | 17550 | 17551 | 17552 | 17554 | 17555 |
| 17556 | 17557 | 17559 | 17560 | 17564 | 17565 | 17566 | 17568 | 17570 | 17571 | 17572 | 17573 |
| 17574 | 17575 | 17579 | 17582 | 17583 | 17584 | 17587 | 17588 | 17589 | 17590 | 17592 | 17600 |
| 17605 | 17608 | 17614 | 17615 | 17617 | 17619 | 17622 | 17623 | 17626 | 17629 | 17641 | 17651 |

TABLE 19-continued

Yield: Stress Tolerance

| | | | | | | | | | | | |
|---|---|---|---|---|---|---|---|---|---|---|---|
| 17652 | 17654 | 17655 | 17656 | 17657 | 17658 | 17659 | 17660 | 17661 | 17667 | 17668 | 17669 |
| 17670 | 17671 | 17672 | 17673 | 17675 | 17676 | 17678 | 17679 | 17683 | 17685 | 17687 | 17688 |
| 17689 | 17690 | 17691 | 17692 | 17693 | 17697 | 17701 | 17702 | 17706 | 17707 | 17712 | 17713 |
| 17718 | 17722 | 17723 | 17724 | 17725 | 17727 | 17728 | 17731 | 17732 | 17733 | 17737 | 17738 |
| 17739 | 17741 | 17742 | 17743 | 17744 | 17745 | 17746 | 17749 | 17752 | 17753 | 17755 | 17757 |
| 17758 | 17759 | 17760 | 17762 | 17765 | 17767 | 17770 | 17772 | 17774 | 17775 | 17776 | 17786 |
| 17788 | 17789 | 17790 | 17791 | 17793 | 17805 | 17806 | 17807 | 17809 | 17810 | 17811 | 17814 |
| 17817 | 17820 | 17821 | 17822 | 17823 | 17824 | 17830 | 17837 | 17840 | 17843 | 17849 | 17851 |
| 17852 | 17856 | 17857 | 17858 | 17860 | 17863 | 17868 | 17869 | 17870 | 17873 | 17888 | 17889 |
| 17890 | 17891 | 17895 | 17896 | 17897 | 17898 | 17899 | 17901 | 17902 | 17906 | 17913 | 17914 |
| 17917 | 17918 | 17920 | 17921 | 17922 | 17924 | 17925 | 17926 | 17927 | 17928 | 17930 | 17933 |
| 17934 | 17938 | 17939 | 17941 | 17944 | 17946 | 17948 | 17949 | 17951 | 17954 | 17955 | 17958 |
| 17959 | 17963 | 17965 | 17966 | 17968 | 17970 | 17971 | 17973 | 17979 | 17981 | 17982 | 17984 |
| 17985 | 17990 | 17992 | 17993 | 17995 | 18008 | 18009 | 18010 | 18012 | 18013 | 18017 | 18022 |
| 18025 | 18026 | 18030 | 18031 | 18032 | 18034 | 18036 | 18037 | 18038 | 18041 | 18043 | 18045 |
| 18046 | 18049 | 18050 | 18051 | 18052 | 18054 | 18055 | 18058 | 18060 | 18063 | 18065 | 18066 |
| 18067 | 18069 | 18070 | 18071 | 18073 | 18074 | 18075 | 18076 | 18077 | 18078 | 18079 | 18080 |
| 18081 | 18082 | 18086 | 18089 | 18091 | 18094 | 18095 | 18101 | 18103 | 18106 | 18113 | 18115 |
| 18118 | 18121 | 18123 | 18128 | 18131 | 18132 | 18135 | 18136 | 18143 | 18145 | 18146 | 18147 |
| 18149 | 18150 | 18151 | 18153 | 18154 | 18156 | 18160 | 18163 | 18166 | 18167 | 18168 | 18169 |
| 18170 | 18172 | 18176 | 18178 | 18180 | 18181 | 18182 | 18184 | 18186 | 18187 | 18191 | 18192 |
| 18194 | 18195 | 18196 | 18197 | 18198 | 18199 | 18203 | 18204 | 18205 | 18206 | 18208 | 18211 |
| 18213 | 18217 | 18222 | 18226 | 18227 | 18228 | 18230 | 18232 | 18234 | 18237 | 18239 | 18241 |
| 18245 | 18249 | 18251 | 18260 | 18261 | 18264 | 18265 | 18266 | 18267 | 18269 | 18270 | 18271 |
| 18278 | 18281 | 18284 | 18286 | 18290 | 18297 | 18300 | 18301 | 18302 | 18306 | 18308 | 18309 |
| 18311 | 18313 | 18315 | 18316 | 18317 | 18320 | 18321 | 18323 | 18326 | 18330 | 18332 | 18333 |
| 18334 | 18335 | 18338 | 18345 | 18350 | 18355 | 18359 | 18361 | 18362 | 18364 | 18365 | 18367 |
| 18378 | 18379 | 18380 | 18381 | 18382 | 18383 | 18387 | 18389 | 18390 | 18391 | 18397 | 18399 |
| 18400 | 18401 | 18402 | 18405 | 18416 | 18417 | 18418 | 18421 | 18422 | 18423 | 18424 | 18426 |
| 18427 | 18430 | 18431 | 18432 | 18434 | 18435 | 18436 | 18437 | 18438 | 18442 | 18443 | 18444 |
| 18446 | 18447 | 18451 | 18452 | 18456 | 18457 | 18458 | 18459 | 18460 | 18461 | 18462 | 18464 |
| 18469 | 18473 | 18474 | 18475 | 18477 | 18478 | 18479 | 18486 | 18487 | 18488 | 18489 | 18491 |
| 18496 | 18497 | 18498 | 18499 | 18500 | 18504 | 18506 | 18507 | 18509 | 18510 | 18511 | 18514 |
| 18517 | 18522 | 18525 | 18526 | 18529 | 18532 | 18533 | 18537 | 18538 | 18540 | 18544 | 18545 |
| 18546 | 18551 | 18554 | 18555 | 18557 | 18558 | 18561 | 18562 | 18563 | 18568 | 18569 | 18571 |
| 18574 | 18577 | 18578 | 18580 | 18583 | 18592 | 18593 | 18594 | 18595 | 18597 | 18598 | 18600 |
| 18601 | 18602 | 18605 | 18606 | 18607 | 18608 | 18612 | 18613 | 18614 | 18617 | 18618 | 18620 |
| 18624 | 18625 | 18628 | 18629 | 18631 | 18632 | 18633 | 18635 | 18636 | 18637 | 18639 | 18640 |
| 18641 | 18642 | 18643 | 18644 | 18646 | 18647 | 18648 | 18649 | 18650 | 18651 | 18654 | 18655 |
| 18657 | 18660 | 18665 | 18667 | 18668 | 18671 | 18672 | 18673 | 18674 | 18676 | 18678 | 18688 |
| 18691 | 18693 | 18694 | 18695 | 18696 | 18697 | 18699 | 18705 | 18706 | 18707 | 18710 | 18711 |
| 18716 | 18718 | 18719 | 18720 | 18722 | 18724 | 18725 | 18728 | 18729 | 18731 | 18733 | 18736 |
| 18737 | 18739 | 18740 | 18741 | 18742 | 18745 | 18751 | 18752 | 18754 | 18755 | 18756 | 18759 |
| 18760 | 18761 | 18762 | 18764 | 18768 | 18769 | 18771 | 18774 | 18775 | 18779 | 18780 | 18781 |
| 18786 | 18788 | 18789 | 18791 | 18793 | 18795 | 18798 | 18801 | 18804 | 18805 | 18807 | 18808 |
| 18812 | 18814 | 18815 | 18816 | 18817 | 18819 | 18820 | 18821 | 18824 | 18828 | 18830 | 18831 |
| 18832 | 18836 | 18840 | 18844 | 18845 | 18846 | 18847 | 18848 | 18850 | 18855 | 18858 | 18859 |
| 18861 | 18862 | 18863 | 18864 | 18865 | 18866 | 18867 | 18869 | 18870 | 18871 | 18872 | 18873 |
| 18874 | 18877 | 18878 | 18882 | 18884 | 18885 | 18886 | 18887 | 18888 | 18889 | 18890 | 18893 |
| 18895 | 18897 | 18901 | 18902 | 18904 | 18905 | 18906 | 18907 | 18912 | 18914 | 18916 | 18917 |
| 18919 | 18921 | 18923 | 18925 | 18926 | 18930 | 18934 | 18935 | 18936 | 18937 | 18938 | 18941 |
| 18942 | 18943 | 18944 | 18949 | 18952 | 18953 | 18954 | 18955 | 18956 | 18957 | 18960 | 18961 |
| 18962 | 18963 | 18967 | 18970 | 18974 | 18975 | 18976 | 18978 | 18979 | 18982 | 18983 | 18989 |
| 18991 | 18996 | 18998 | 18999 | 19002 | 19007 | 19008 | 19012 | 19013 | 19015 | 19016 | 19018 |
| 19021 | 19022 | 19023 | 19026 | 19028 | 19029 | 19031 | 19034 | 19035 | 19039 | 19048 | 19054 |
| 19055 | 19057 | 19058 | 19059 | 19060 | 19063 | 19065 | 19069 | 19071 | 19073 | 19079 | 19081 |
| 19086 | 19087 | 19092 | 19095 | 19098 | 19103 | 19105 | 19109 | 19112 | 19114 | 19115 | 19116 |
| 19118 | 19119 | 19120 | 19121 | 19123 | 19128 | 19133 | 19134 | 19136 | 19137 | 19138 | 19139 |
| 19142 | 19143 | 19144 | 19148 | 19154 | 19156 | 19157 | 19158 | 19159 | 19160 | 19165 | 19172 |
| 19175 | 19177 | 19179 | 19191 | 19194 | 19195 | 19198 | 19199 | 19200 | 19201 | 19202 | 19203 |
| 19204 | 19205 | 19206 | 19208 | 19211 | 19213 | 19214 | 19216 | 19218 | 19220 | 19221 | 19224 |
| 19225 | 19229 | 19231 | 19232 | 19233 | 19235 | 19239 | 19240 | 19242 | 19243 | 19244 | 19247 |
| 19248 | 19249 | 19252 | 19257 | 19260 | 19261 | 19264 | 19265 | 19268 | 19271 | 19272 | 19274 |
| 19275 | 19276 | 19277 | 19278 | 19280 | 19281 | 19284 | 19288 | 19291 | 19294 | 19295 |
| 19300 | 19301 | 19302 | 19303 | 19305 | 19306 | 19309 | 19314 | 19315 | 19317 | 19328 | 19330 |
| 19333 | 19334 | 19336 | 19337 | 19338 | 19340 | 19343 | 19350 | 19351 | 19358 | 19359 | 19360 |
| 19363 | 19364 | 19365 | 19366 | 19371 | 19372 | 19380 | 19381 | 19385 | 19386 | 19389 | 19390 |
| 19391 | 19392 | 19394 | 19395 | 19396 | 19399 | 19402 | 19404 | 19405 | 19406 | 19407 | 19410 |
| 19411 | 19414 | 19415 | 19416 | 19420 | 19423 | 19426 | 19427 | 19428 | 19433 | 19434 | 19435 |
| 19436 | 19439 | 19440 | 19441 | 19455 | 19456 | 19457 | 19458 | 19461 | 19463 | 19464 | 19465 |
| 19467 | 19471 | 19472 | 19473 | 19474 | 19476 | 19480 | 19481 | 19482 | 19483 | 19485 | 19486 |
| 19487 | 19492 | 19493 | 19500 | 19502 | 19506 | 19508 | 19509 | 19510 | 19511 | 19512 | 19513 |
| 19516 | 19518 | 19519 | 19520 | 19521 | 19522 | 19523 | 19526 | 19531 | 19532 | 19541 | 19542 |
| 19543 | 19544 | 19547 | 19549 | 19550 | 19553 | 19557 | 19558 | 19559 | 19560 | 19563 | 19564 |
| 19569 | 19571 | 19572 | 19573 | 19575 | 19577 | 19578 | 19579 | 19580 | 19583 | 19585 | 19588 |
| 19593 | 19594 | 19595 | 19599 | 19600 | 19601 | 19602 | 19603 | 19604 | 19606 | 19608 | 19610 |
| 19611 | 19612 | 19614 | 19616 | 19617 | 19618 | 19620 | 19624 | 19627 | 19628 | 19631 | 19634 |

TABLE 19-continued

Yield: Stress Tolerance

| | | | | | | | | | | | |
|---|---|---|---|---|---|---|---|---|---|---|---|
| 19637 | 19639 | 19641 | 19642 | 19644 | 19645 | 19647 | 19653 | 19654 | 19656 | 19657 | 19659 |
| 19664 | 19665 | 19666 | 19669 | 19670 | 19671 | 19672 | 19676 | 19684 | 19686 | 19689 | 19690 |
| 19693 | 19696 | 19703 | 19704 | 19708 | 19711 | 19714 | 19716 | 19719 | 19720 | 19722 | 19724 |
| 19727 | 19728 | 19729 | 19730 | 19731 | 19732 | 19733 | 19735 | 19737 | 19739 | 19746 | 19748 |
| 19749 | 19754 | 19755 | 19759 | 19761 | 19763 | 19765 | 19766 | 19767 | 19772 | 19774 | 19776 |
| 19778 | 19779 | 19785 | 19788 | 19790 | 19791 | 19795 | 19799 | 19800 | 19802 | 19803 | 19805 |
| 19808 | 19819 | 19820 | 19821 | 19823 | 19824 | 19826 | 19829 | 19831 | 19833 | 19838 | 19839 |
| 19840 | 19841 | 19842 | 19846 | 19847 | 19850 | 19852 | 19853 | 19854 | 19855 | 19857 | 19859 |
| 19860 | 19861 | 19865 | 19868 | 19869 | 19870 | 19875 | 19877 | 19878 | 19880 | 19884 | 19885 |
| 19891 | 19892 | 19895 | 19896 | 19897 | 19902 | 19903 | 19909 | 19911 | 19914 | 19915 | 19916 |
| 19917 | 19918 | 19921 | 19922 | 19924 | 19928 | 19929 | 19930 | 19931 | 19932 | 19933 | 19935 |
| 19936 | 19937 | 19938 | 19942 | 19943 | 19945 | 19946 | 19948 | 19950 | 19954 | 19955 | 19956 |
| 19958 | 19961 | 19962 | 19964 | 19968 | 19969 | 19975 | 19977 | 19985 | 19986 | 19988 | 19990 |
| 19991 | 19994 | 20000 | 20003 | 20005 | 20006 | 20009 | 20011 | 20012 | 20013 | 20019 | 20021 |
| 20022 | 20023 | 20024 | 20025 | 20027 | 20028 | 20031 | 20032 | 20033 | 20035 | 20038 | 20042 |
| 20046 | 20048 | 20050 | 20056 | 20057 | 20058 | 20060 | 20065 | 20066 | 20067 | 20068 | 20074 |
| 20075 | 20078 | 20079 | 20084 | 20086 | 20088 | 20089 | 20103 | 20104 | 20106 | 20108 | 20111 |
| 20112 | 20113 | 20118 | 20119 | 20120 | 20122 | 20126 | 20127 | 20129 | 20130 | 20133 | 20134 |
| 20135 | 20137 | 20140 | 20141 | 20143 | 20144 | 20147 | 20148 | 20149 | 20150 | 20155 | 20157 |
| 20158 | 20162 | 20167 | 20172 | 20173 | 20174 | 20178 | 20185 | 20186 | 20192 | 20194 | 20195 |
| 20197 | 20198 | 20199 | 20201 | 20203 | 20204 | 20205 | 20207 | 20208 | 20212 | 20213 | 20214 |
| 20215 | 20216 | 20219 | 20220 | 20221 | 20223 | 20225 | 20226 | 20227 | 20229 | 20230 | 20236 |
| 20237 | 20238 | 20241 | 20242 | 20243 | 20246 | 20247 | 20248 | 20249 | 20252 | 20253 | 20255 |
| 20257 | 20259 | 20260 | 20261 | 20262 | 20263 | 20264 | 20266 | 20268 | 20269 | 20275 | 20276 |
| 20277 | 20278 | 20280 | 20282 | 20285 | 20287 | 20289 | 20291 | 20296 | 20297 | 20298 | 20299 |
| 20301 | 20304 | 20309 | 20312 | 20313 | 20314 | 20317 | 20319 | 20320 | 20321 | 20322 | 20323 |
| 20324 | 20325 | 20328 | 20332 | 20334 | 20335 | 20337 | 20342 | 20350 | 20351 | 20355 | 20356 |
| 20357 | 20358 | 20363 | 20365 | 20366 | 20368 | 20372 | 20373 | 20374 | 20375 | 20376 | 20377 |
| 20378 | 20380 | 20383 | 20384 | 20388 | 20389 | 20390 | 20392 | 20394 | 20395 | 20397 | 20400 |
| 20407 | 20408 | 20409 | 20410 | 20411 | 20412 | 20413 | 20414 | 20417 | 20418 | 20419 | 20421 |
| 20428 | 20432 | 20434 | 20435 | 20436 | 20437 | 20438 | 20439 | 20440 | 20441 | 20442 | 20443 |
| 20445 | 20446 | 20447 | 20448 | 20449 | 20450 | 20452 | 20453 | 20454 | 20455 | 20460 | 20461 |
| 20472 | 20474 | 20480 | 20484 | 20486 | 20492 | 20493 | 20494 | 20503 | 20504 | 20506 | 20507 |
| 20514 | 20515 | 20520 | 20530 | 20531 | 20535 | 20536 | 20539 | 20543 | 20546 | 20547 | 20548 |
| 20550 | 20551 | 20553 | 20554 | 20557 | 20558 | 20560 | 20562 | 20564 | 20565 | 20566 | 20568 |
| 20569 | 20570 | 20575 | 20577 | 20578 | 20580 | 20586 | 20591 | 20593 | 20597 | 20600 | 20601 |
| 20603 | 20607 | 20615 | 20619 | 20621 | 20623 | 20624 | 20625 | 20627 | 20628 | 20629 | 20630 |
| 20632 | 20633 | 20634 | 20635 | 20641 | 20643 | 20644 | 20646 | 20647 | 20648 | 20651 | 20652 |
| 20655 | 20658 | 20659 | 20660 | 20668 | 20669 | 20670 | 20675 | 20680 | 20685 | 20686 | 20687 |
| 20689 | 20694 | 20701 | 20702 | 20704 | 20706 | 20707 | 20709 | 20713 | 20714 | 20715 | 20717 |
| 20723 | 20728 | 20731 | 20733 | 20734 | 20739 | 20743 | 20744 | 20745 | 20749 | 20750 | 20755 |
| 20756 | 20757 | 20758 | 20759 | 20761 | 20765 | 20770 | 20772 | 20773 | 20774 | 20776 | 20777 |
| 20781 | 20782 | 20784 | 20786 | 20787 | 20788 | 20789 | 20795 | 20797 | 20798 | 20800 | 20801 |
| 20802 | 20805 | 20806 | 20807 | 20808 | 20809 | 20810 | 20811 | 20817 | 20819 | 20820 | 20827 |
| 20828 | 20829 | 20830 | 20832 | 20833 | 20834 | 20835 | 20836 | 20840 | 20847 | 20848 | 20852 |
| 20853 | 20854 | 20859 | 20860 | 20861 | 20862 | 20863 | 20865 | 20869 | 20870 | 20871 | 20873 |
| 20877 | 20878 | 20880 | 20881 | 20882 | 20885 | 20886 | 20891 | 20892 | 20893 | 20894 | 20895 |
| 20902 | 20904 | 20905 | 20907 | 20908 | 20909 | 20910 | 20913 | 20915 | 20918 | 20919 | 20921 |
| 20922 | 20923 | 20929 | 20930 | 20933 | 20935 | 20937 | 20940 | 20941 | 20942 | 20946 | 20947 |
| 20949 | 20950 | 20952 | 20955 | 20956 | 20957 | 20962 | 20964 | 20965 | 20966 | 20967 | 20969 |
| 20972 | 20974 | 20975 | 20978 | 20979 | 20982 | 20983 | 20984 | 20987 | 20988 | 20989 | 20990 |
| 20991 | 20992 | 20993 | 20995 | 20997 | 21002 | 21003 | 21004 | 21007 | 21008 | 21009 | 21011 |
| 21012 | 21013 | 21014 | 21020 | 21023 | 21032 | 21037 | 21039 | 21040 | 21041 | 21042 | 21043 |
| 21047 | 21050 | 21051 | 21052 | 21055 | 21058 | 21059 | 21060 | 21065 | 21067 | 21068 | 21069 |
| 21073 | 21075 | 21077 | 21080 | 21081 | 21085 | 21088 | 21089 | 21091 | 21092 | 21095 | 21096 |
| 21098 | 21103 | 21105 | 21108 | 21109 | 21110 | 21111 | 21112 | 21113 | 21115 | 21116 | 21117 |
| 21118 | 21119 | 21122 | 21123 | 21124 | 21128 | 21129 | 21130 | 21136 | 21137 | 21140 | 21141 |
| 21143 | 21144 | 21147 | 21149 | 21150 | 21151 | 21153 | 21161 | 21163 | 21164 | 21165 | 21167 |
| 21170 | 21173 | 21176 | 21177 | 21178 | 21179 | 21185 | 21186 | 21188 | 21195 | 21196 | 21198 |
| 21199 | 21200 | 21202 | 21203 | 21204 | 21206 | 21208 | 21209 | 21210 | 21213 | 21219 | 21220 |
| 21224 | 21226 | 21227 | 21228 | 21229 | 21231 | 21233 | 21235 | 21238 | 21240 | 21243 | 21244 |
| 21245 | 21249 | 21250 | 21251 | 21260 | 21263 | 21264 | 21265 | 21266 | 21270 | 21271 | 21272 |
| 21275 | 21276 | 21277 | 21280 | 21281 | 21282 | 21283 | 21284 | 21285 | 21287 | 21290 | 21291 |
| 21296 | 21300 | 21304 | 21306 | 21308 | 21309 | 21313 | 21314 | 21316 | 21321 | 21323 | 21324 |
| 21328 | 21330 | 21331 | 21332 | 21333 | 21335 | 21340 | 21341 | 21342 | 21343 | 21344 | 21345 |
| 21346 | 21347 | 21348 | 21351 | 21353 | 21354 | 21356 | 21357 | 21359 | 21363 | 21364 | 21365 |
| 21366 | 21367 | 21368 | 21369 | 21371 | 21372 | 21373 | 21378 | 21379 | 21381 | 21383 | 21384 |
| 21386 | 21387 | 21389 | 21390 | 21392 | 21393 | 21394 | 21395 | 21396 | 21398 | 21402 | 21404 |
| 21405 | 21406 | 21409 | 21410 | 21411 | 21414 | 21415 | 21416 | 21418 | 21419 | 21422 | 21423 |
| 21424 | 21425 | 21428 | 21430 | 21432 | 21433 | 21434 | 21435 | 21436 | 21439 | 21441 | 21442 |
| 21443 | 21445 | 21446 | 21447 | 21448 | 21455 | 21456 | 21457 | 21462 | 21463 | 21464 | 21465 |
| 21466 | 21472 | 21473 | 21475 | 21476 | 21478 | 21479 | 21480 | 21481 | 21484 | 21486 | 21488 |
| 21491 | 21492 | 21494 | 21495 | 21496 | 21497 | 21498 | 21499 | 21502 | 21504 | 21505 | 21506 |
| 21507 | 21509 | 21510 | 21511 | 21513 | 21514 | 21515 | 21522 | 21526 | 21527 | 21528 | 21538 |
| 21541 | 21543 | 21545 | 21547 | 21549 | 21552 | 21555 | 21556 | 21557 | 21558 | 21559 | 21561 |
| 21565 | 21566 | 21567 | 21574 | 21578 | 21580 | 21583 | 21585 | 21586 | 21587 | 21588 | 21589 |
| 21590 | 21591 | 21592 | 21593 | 21598 | 21600 | 21602 | 21607 | 21608 | 21611 | 21612 | 21615 |

TABLE 19-continued

Yield: Stress Tolerance

| | | | | | | | | | | | |
|---|---|---|---|---|---|---|---|---|---|---|---|
| 21616 | 21622 | 21623 | 21624 | 21629 | 21631 | 21637 | 21639 | 21640 | 21643 | 21645 | 21647 |
| 21649 | 21652 | 21653 | 21654 | 21655 | 21656 | 21660 | 21664 | 21666 | 21668 | 21670 | 21673 |
| 21677 | 21679 | 21680 | 21682 | 21683 | 21684 | 21689 | 21690 | 21691 | 21692 | 21693 | 21694 |
| 21696 | 21698 | 21699 | 21701 | 21702 | 21703 | 21704 | 21711 | 21712 | 21722 | 21724 | 21726 |
| 21728 | 21729 | 21731 | 21741 | 21745 | 21746 | 21747 | 21750 | 21751 | 21753 | 21756 | 21757 |
| 21758 | 21760 | 21763 | 21765 | 21770 | 21771 | 21772 | 21777 | 21778 | 21779 | 21780 | 21781 |
| 21788 | 21790 | 21791 | 21792 | 21794 | 21795 | 21796 | 21797 | 21801 | 21802 | 21803 | 21809 |
| 21810 | 21811 | 21812 | 21813 | 21814 | 21815 | 21816 | 21817 | 21818 | 21819 | 21821 | 21822 |
| 21823 | 21824 | 21825 | 21827 | 21832 | 21836 | 21837 | 21838 | 21839 | 21840 | 21841 | 21842 |
| 21844 | 21845 | 21847 | 21848 | 21850 | 21851 | 21853 | 21854 | 21858 | 21859 | 21865 | 21866 |
| 21867 | 21869 | 21873 | 21875 | 21876 | 21878 | 21882 | 21883 | 21885 | 21887 | 21889 | 21890 |
| 21891 | 21896 | 21897 | 21900 | 21902 | 21905 | 21910 | 21911 | 21912 | 21915 | 21916 | 21917 |
| 21918 | 21919 | 21921 | 21926 | 21929 | 21930 | 21934 | 21937 | 21938 | 21940 | 21942 | 21943 |
| 21945 | 21948 | 21949 | 21950 | 21953 | 21954 | 21956 | 21958 | 21959 | 21960 | 21961 | 21962 |
| 21964 | 21965 | 21969 | 21971 | 21973 | 21974 | 21975 | 21980 | 21981 | 21982 | 21983 | 21984 |
| 21985 | 21986 | 21987 | 21988 | 21989 | 21999 | 22000 | 22006 | 22007 | 22009 | 22010 | 22011 |
| 22012 | 22013 | 22015 | 22016 | 22019 | 22020 | 22021 | 22022 | 22024 | 22027 | 22030 | 22031 |
| 22033 | 22034 | 22038 | 22039 | 22040 | 22041 | 22043 | 22044 | 22045 | 22046 | 22047 | 22048 |
| 22049 | 22050 | 22053 | 22054 | 22056 | 22058 | 22060 | 22063 | 22066 | 22067 | 22071 | 22072 |
| 22075 | 22076 | 22078 | 22081 | 22082 | 22083 | 22088 | 22090 | 22093 | 22094 | 22096 | 22098 |
| 22101 | 22104 | 22107 | 22108 | 22109 | 22110 | 22114 | 22116 | 22120 | 22124 | 22125 | 22126 |
| 22127 | 22128 | 22133 | 22135 | 22137 | 22138 | 22139 | 22140 | 22141 | 22143 | 22144 | 22145 |
| 22146 | 22147 | 22148 | 22150 | 22151 | 22153 | 22154 | 22155 | 22156 | 22158 | 22160 | 22161 |
| 22164 | 22165 | 22166 | 22167 | 22168 | 22170 | 22171 | 22174 | 22175 | 22176 | 22177 | 22181 |
| 22183 | 22184 | 22185 | 22186 | 22187 | 22190 | 22191 | 22192 | 22193 | 22195 | 22198 | 22200 |
| 22201 | 22204 | 22205 | 22206 | 22207 | 22210 | 22214 | 22216 | 22217 | 22218 | 22220 | 22221 |
| 22224 | 22225 | 22226 | 22227 | 22228 | 22232 | 22233 | 22235 | 22237 | 22239 | 22240 | 22243 |
| 22244 | 22246 | 22249 | 22251 | 22252 | 22253 | 22255 | 22257 | 22264 | 22265 | 22266 | 22268 |
| 22269 | 22270 | 22271 | 22272 | 22277 | 22279 | 22280 | 22281 | 22282 | 22283 | 22284 | 22289 |
| 22291 | 22293 | 22294 | 22295 | 22296 | 22298 | 22299 | 22300 | 22301 | 22302 | 22303 | 22306 |
| 22308 | 22310 | 22313 | 22314 | 22315 | 22316 | 22319 | 22320 | 22325 | 22332 | 22333 | 22335 |
| 22336 | 22340 | 22341 | 22342 | 22346 | 22350 | 22351 | 22352 | 22353 | 22354 | 22357 | 22359 |
| 22360 | 22362 | 22364 | 22365 | 22366 | 22367 | 22368 | 22369 | 22370 | 22371 | 22372 | 22373 |
| 22375 | 22376 | 22378 | 22379 | 22380 | 22382 | 22384 | 22386 | 22387 | 22390 | 22391 | 22392 |
| 22393 | 22394 | 22396 | 22398 | 22399 | 22400 | 22401 | 22402 | 22405 | 22406 | 22407 | 22409 |
| 22410 | 22413 | 22415 | 22416 | 22417 | 22420 | 22424 | 22425 | 22427 | 22428 | 22430 | 22432 |
| 22433 | 22436 | 22438 | 22439 | 22443 | 22444 | 22446 | 22452 | 22454 | 22458 | 22459 | 22460 |
| 22461 | 22463 | 22468 | 22471 | 22472 | 22480 | 22482 | 22484 | 22487 | 22490 | 22492 | 22494 |
| 22495 | 22496 | 22497 | 22498 | 22499 | 22500 | 22501 | 22502 | 22503 | 22507 | 22509 | 22510 |
| 22511 | 22512 | 22515 | 22517 | 22520 | 22522 | 22525 | 22528 | 22533 | 22536 | 22537 | 22538 |
| 22540 | 22543 | 22544 | 22545 | 22547 | 22548 | 22550 | 22551 | 22554 | 22558 | 22564 | 22565 |
| 22568 | 22569 | 22570 | 22571 | 22573 | 22575 | 22577 | 22578 | 22579 | 22581 | 22582 | 22583 |
| 22584 | 22585 | 22588 | 22590 | 22591 | 22592 | 22593 | 22594 | 22595 | 22596 | 22597 | 22601 |
| 22605 | 22606 | 22607 | 22609 | 22610 | 22611 | 22612 | 22613 | 22616 | 22617 | 22620 | 22621 |
| 22622 | 22624 | 22625 | 22626 | 22628 | 22630 | 22631 | 22632 | 22634 | 22638 | 22641 | 22642 |
| 22646 | 22649 | 22652 | 22653 | 22654 | 22660 | 22667 | 22669 | 22672 | 22674 | 22675 | 22680 |
| 22683 | 22685 | 22687 | 22691 | 22693 | 22694 | 22696 | 22698 | 22701 | 22702 | 22703 | 22704 |
| 22705 | 22706 | 22707 | 22708 | 22712 | 22713 | 22722 | 22725 | 22726 | 22727 | 22728 | 22730 |
| 22732 | 22733 | 22737 | 22739 | 22740 | 22741 | 22742 | 22743 | 22744 | 22746 | 22748 | 22750 |
| 22752 | 22753 | 22754 | 22755 | 22757 | 22759 | 22760 | 22762 | 22763 | 22764 | 22765 | 22767 |
| 22768 | 22769 | 22771 | 22772 | 22775 | 22776 | 22777 | 22780 | 22781 | 22782 | 22786 | 22788 |
| 22789 | 22790 | 22791 | 22794 | 22798 | 22799 | 22801 | 22802 | 22804 | 22806 | 22807 | 22808 |
| 22809 | 22810 | 22811 | 22813 | 22815 | 22817 | 22821 | 22823 | 22825 | 22828 | 22831 | 22832 |
| 22834 | 22835 | 22838 | 22839 | 22840 | 22843 | 22844 | 22846 | 22848 | 22854 | 22859 | 22862 |
| 22863 | 22864 | 22865 | 22868 | 22870 | 22872 | 22873 | 22875 | 22878 | 22881 | 22885 | 22886 |
| 22890 | 22891 | 22894 | 22895 | 22897 | 22898 | 22900 | 22901 | 22903 | 22905 | 22906 | |
| 22907 | 22910 | 22911 | 22912 | 22913 | 22920 | 22921 | 22922 | 22924 | 22925 | 22927 | 22928 |
| 22930 | 22931 | 22933 | 22935 | 22936 | 22939 | 22946 | 22948 | 22953 | 22955 | 22956 | 22957 |
| 22958 | 22962 | 22964 | 22966 | 22968 | 22971 | 22972 | 22980 | 22982 | 22983 | 22986 | 22987 |
| 22989 | 22992 | 22995 | 22996 | 22997 | 22999 | 23000 | 23001 | 23003 | 23004 | 23005 | 23007 |
| 23008 | 23011 | 23013 | 23015 | 23025 | 23026 | 23028 | 23029 | 23030 | 23033 | 23037 | 23038 |
| 23044 | 23049 | 23051 | 23052 | 23054 | 23059 | 23060 | 23062 | 23063 | 23065 | 23067 | 23068 |
| 23071 | 23073 | 23075 | 23079 | 23080 | 23083 | 23087 | 23089 | 23090 | 23095 | 23097 | 23100 |
| 23101 | 23107 | 23108 | 23110 | 23111 | 23113 | 23115 | 23116 | 23117 | 23119 | 23120 | 23121 |
| 23124 | 23125 | 23126 | 23127 | 23135 | 23141 | 23142 | 23145 | 23146 | 23147 | 23148 | 23155 |
| 23157 | 23158 | 23162 | 23163 | 23166 | 23167 | 23176 | 23179 | 23180 | 23181 | 23182 | 23183 |
| 23185 | 23188 | 23198 | 23201 | 23202 | 23205 | 23207 | 23214 | 23217 | 23219 | 23220 | 23221 |
| 23222 | 23223 | 23226 | 23227 | 23230 | 23233 | 23236 | 23240 | 23241 | 23243 | 23245 | 23246 |
| 23247 | 23254 | 23255 | 23256 | 23259 | 23261 | 23263 | 23265 | 23270 | 23271 | 23272 | 23276 |
| 23281 | 23283 | 23286 | 23290 | 23292 | 23294 | 23295 | 23297 | 23298 | 23302 | 23304 | 23306 |
| 23312 | 23313 | 23316 | 23322 | 23324 | 23326 | 23329 | 23330 | 23331 | 23332 | 23334 | 23338 |
| 23343 | 23344 | 23349 | 23350 | 23352 | 23355 | 23358 | 23359 | 23360 | 23363 | 23364 | 23365 |
| 23366 | 23370 | 23371 | 23372 | 23376 | 23380 | 23381 | 23383 | 23384 | 23385 | 23391 | 23392 |
| 23394 | 23395 | 23397 | 23398 | 23401 | 23402 | 23403 | 23405 | 23407 | 23413 | 23414 | 23415 |
| 23423 | 23425 | 23426 | 23427 | 23429 | 23430 | 23434 | 23436 | 23440 | 23441 | 23446 | 23448 |
| 23449 | 23450 | 23452 | 23453 | 23457 | 23459 | 23463 | 23464 | 23465 | 23467 | 23468 | 23469 |
| 23470 | 23474 | 23479 | 23480 | 23484 | 23487 | 23488 | 23489 | 23491 | 23497 | 23498 | 23500 |

TABLE 19-continued

| Yield: Stress Tolerance | | | | | | | | | | | |
|---|---|---|---|---|---|---|---|---|---|---|---|
| 23502 | 23503 | 23505 | 23511 | 23512 | 23514 | 23515 | 23516 | 23520 | 23524 | 23526 | 23529 |
| 23531 | 23532 | 23534 | 23535 | 23536 | 23538 | 23539 | 23540 | 23546 | 23549 | 23550 | 23551 |
| 23552 | 23553 | 23560 | 23562 | 23565 | 23567 | 23568 | 23575 | 23582 | 23583 | 23584 | 23590 |
| 23591 | 23592 | 23595 | 23598 | 23601 | 23602 | 23604 | 23607 | 23610 | 23612 | 23613 | 23614 |
| 23615 | 23617 | 23618 | 23619 | 23622 | 23623 | 23625 | 23631 | 23634 | 23638 | 23640 | 23645 |
| 23647 | 23648 | 23649 | 23650 | 23651 | 23652 | 23653 | 23656 | 23658 | 23659 | 23662 | 23664 |
| 23666 | 23667 | 23668 | 23669 | 23671 | 23673 | 23674 | 23675 | 23676 | 23678 | 23681 | 23684 |
| 23686 | | | | | | | | | | | |

Table 19B SEQ ID NOs of Polynucleotides useful for improving Yield: Stress Tolerance

| | | | | | | | | | | | |
|---|---|---|---|---|---|---|---|---|---|---|---|
| 23690 | 23691 | 23693 | 23695 | 23698 | 23699 | 23701 | 23702 | 23703 | 23704 | 23706 | 23709 |
| 23713 | 23715 | 23716 | 23718 | 23723 | 23726 | 23727 | 23728 | 23729 | 23730 | 23733 | 23735 |
| 23738 | 23739 | 23741 | 23742 | 23743 | 23745 | 23746 | 23750 | 23754 | 23756 | 23758 | 23759 |
| 23760 | 23765 | 23767 | 23768 | 23771 | 23775 | 23776 | 23777 | 23778 | 23779 | 23783 | 23784 |
| 23786 | 23787 | 23790 | 23793 | 23794 | 23796 | 23802 | 23804 | 23805 | 23807 | 23808 | 23809 |
| 23815 | 23817 | 23824 | 23831 | 23832 | 23833 | 23834 | 23837 | 23838 | 23840 | 23841 | 23842 |
| 23843 | 23844 | 23846 | 23848 | 23849 | 23851 | 23857 | 23858 | 23859 | 23861 | 23864 | 23865 |
| 23869 | 23871 | 23872 | 23873 | 23877 | 23878 | 23881 | 23882 | 23883 | 23885 | 23887 | 23890 |
| 23891 | 23899 | 23904 | 23905 | 23908 | 23911 | 23917 | 23919 | 23920 | 23921 | 23922 | 23925 |
| 23927 | 23934 | 23937 | 23939 | 23941 | 23942 | 23944 | 23945 | 23947 | 23952 | 23953 | 23954 |
| 23959 | 23961 | 23962 | 23967 | 23969 | 23970 | 23972 | 23975 | 23980 | 23981 | 23982 | 23983 |
| 23986 | 23988 | 23992 | 23994 | 23997 | 24003 | 24004 | 24005 | 24006 | 24007 | 24008 | 24016 |
| 24018 | 24019 | 24025 | 24026 | 24028 | 24029 | 24030 | 24031 | 24033 | 24036 | 24037 | 24039 |
| 24041 | 24043 | 24044 | 24045 | 24046 | 24047 | 24050 | 24053 | 24055 | 24056 | 24059 | 24061 |
| 24065 | 24066 | 24067 | 24068 | 24069 | 24070 | 24074 | 24076 | 24078 | 24080 | 24082 | 24083 |
| 24086 | 24087 | 24088 | 24089 | 24090 | 24091 | 24092 | 24095 | 24096 | 24099 | 24103 | 24105 |
| 24108 | 24109 | 24110 | 24112 | 24113 | 24116 | 24121 | 24122 | 24123 | 24124 | 24127 | 24130 |
| 24133 | 24136 | 24137 | 24138 | 24140 | 24141 | 24143 | 24145 | 24146 | 24149 | 24153 | 24154 |
| 24155 | 24157 | 24158 | 24159 | 24160 | 24164 | 24166 | 24167 | 24169 | 24171 | 24173 | 24174 |
| 24178 | 24185 | 24187 | 24188 | 24189 | 24192 | 24193 | 24195 | 24197 | 24198 | 24202 | 24203 |
| 24204 | 24205 | 24206 | 24207 | 24208 | 24209 | 24210 | 24212 | 24213 | 24214 | 24223 | 24224 |
| 24226 | 24227 | 24228 | 24230 | 24231 | 24234 | 24235 | 24236 | 24237 | 24238 | 24242 | 24243 |
| 24247 | 24251 | 24255 | 24256 | 24257 | 24258 | 24262 | 24263 | 24269 | 24272 | 24274 | 24276 |
| 24277 | 24280 | 24283 | 24286 | 24288 | 24293 | 24296 | 24301 | 24303 | 24310 | 24311 | 24318 |
| 24322 | 24323 | 24330 | 24333 | 24335 | 24336 | 24337 | 24340 | 24342 | 24343 | 24346 | 24347 |
| 24351 | 24352 | 24353 | 24354 | 24355 | 24358 | 24359 | 24360 | 24362 | 24365 | 24367 | 24368 |
| 24369 | 24371 | 24372 | 24375 | 24378 | 24379 | 24380 | 24382 | 24383 | 24392 | 24393 | 24395 |
| 24396 | 24399 | 24402 | 24404 | 24406 | 24407 | 24412 | 24413 | 24414 | 24419 | 24422 | 24423 |
| 24425 | 24426 | 24427 | 24428 | 24431 | 24433 | 24437 | 24438 | 24441 | 24443 | 24444 | 24447 |
| 24448 | 24451 | 24453 | 24457 | 24458 | 24459 | 24460 | 24461 | 24463 | 24465 | 24466 | 24469 |
| 24471 | 24474 | 24475 | 24478 | 24490 | 24491 | 24500 | 24501 | 24502 | 24503 | 24505 | 24507 |
| 24509 | 24510 | 24511 | 24522 | 24523 | 24524 | 24531 | 24535 | 24536 | 24539 | 24540 | 24541 |
| 24543 | 24544 | 24546 | 24549 | 24555 | 24557 | 24558 | 24559 | 24565 | 24572 | 24577 | 24580 |
| 24582 | 24583 | 24584 | 24589 | 24590 | 24591 | 24593 | 24596 | 24597 | 24599 | 24600 | 24601 |
| 24602 | 24603 | 24607 | 24610 | 24614 | 24617 | 24618 | 24621 | 24624 | 24630 | 24641 | 24642 |
| 24643 | 24644 | 24646 | 24651 | 24656 | 24660 | 24662 | 24663 | 24664 | 24666 | 24667 | 24670 |
| 24672 | 24675 | 24676 | 24677 | 24680 | 24682 | 24683 | 24684 | 24685 | 24689 | 24693 | 24697 |
| 24701 | 24702 | 24703 | 24706 | 24708 | 24709 | 24710 | 24711 | 24712 | 24713 | 24717 | 24718 |
| 24720 | 24721 | 24722 | 24723 | 24726 | 24727 | 24728 | 24734 | 24735 | 24737 | 24741 | 24742 |
| 24744 | 24745 | 24746 | 24747 | 24748 | 24749 | 24750 | 24752 | 24754 | 24755 | 24756 | 24757 |
| 24759 | 24760 | 24762 | 24764 | 24765 | 24769 | 24770 | 24771 | 24773 | 24775 | 24781 | 24782 |
| 24787 | 24788 | 24789 | 24792 | 24793 | 24795 | 24797 | 24798 | 24801 | 24806 | 24807 | |
| 24808 | 24810 | 24813 | 24815 | 24817 | 24818 | 24819 | 24822 | 24825 | 24826 | 24827 | 24828 |
| 24830 | 24831 | 24832 | 24834 | 24835 | 24836 | 24839 | 24842 | 24843 | 24844 | 24846 | 24848 |
| 24849 | 24854 | 24855 | 24860 | 24861 | 24862 | 24863 | 24865 | 24866 | 24868 | 24869 | 24870 |
| 24871 | 24872 | 24873 | 24874 | 24875 | 24877 | 24878 | 24879 | 24880 | 24883 | 24885 | 24886 |
| 24887 | 24888 | 24889 | 24892 | 24894 | 24896 | 24898 | 24901 | 24904 | 24905 | 24908 | 24909 |
| 24913 | 24915 | 24916 | 24922 | 24924 | 24926 | 24928 | 24930 | 24932 | 24933 | 24934 | 24937 |
| 24939 | 24940 | 24941 | 24942 | 24943 | 24944 | 24945 | 24948 | 24949 | 24953 | 24955 | 24956 |
| 24958 | 24963 | 24971 | 24972 | 24976 | 24977 | 24978 | 24979 | 24984 | 24986 | 24987 | 24989 |
| 24994 | 24995 | 24996 | 24997 | 24998 | 24999 | 25000 | 25002 | 25005 | 25006 | 25010 | 25011 |
| 25012 | 25014 | 25015 | 25017 | 25018 | 25020 | 25023 | 25024 | 25031 | 25032 | 25033 | 25034 |
| 25035 | 25036 | 25045 | 25052 | 25059 | 25062 | 25064 | 25075 | 25078 | 25081 | 25083 | 25089 |
| 25090 | 25091 | 25093 | 25095 | 25096 | 25102 | 25103 | 25104 | 25106 | 25108 | 25109 | 25111 |
| 25112 | 25114 | 25115 | 25118 | 25120 | 25121 | 25124 | 25125 | 25126 | 25133 | 25134 | 25135 |
| 25136 | 25137 | 25138 | 25145 | 25146 | 25147 | 25148 | 25149 | 25151 | 25157 | 25158 | 25160 |
| 25162 | 25163 | 25164 | 25166 | 25167 | 25168 | 25169 | 25170 | 25173 | 25174 | 25175 | 25177 |
| 25180 | 25182 | 25183 | 25184 | 25186 | 25189 | 25190 | 25191 | 25192 | 25193 | 25194 | 25197 |
| 25201 | 25204 | 25207 | 25208 | 25210 | 25214 | 25216 | 25218 | 25219 | 25222 | 25230 | 25233 |
| 25235 | 25237 | 25238 | 25239 | 25243 | 25246 | 25247 | 25251 | 25252 | 25253 | 25254 | 25255 |
| 25258 | 25259 | 25261 | 25263 | 25265 | 25266 | 25268 | 25270 | 25272 | 25277 | 25278 | 25280 |
| 25282 | 25284 | 25287 | 25288 | 25289 | 25291 | 25293 | 25294 | 25295 | 25298 | 25299 | 25300 |
| 25301 | 25302 | 25304 | 25306 | 25308 | 25309 | 25312 | 25313 | 25314 | 25315 | 25317 | 25318 |
| 25319 | 25321 | 25323 | 25324 | 25328 | 25337 | 25340 | 25341 | 25344 | 25346 | 25347 | 25349 |
| 25350 | 25351 | 25354 | 25355 | 25358 | 25360 | 25361 | 25362 | 25366 | 25367 | 25368 | 25370 |
| 25372 | 25373 | 25374 | 25376 | 25378 | 25379 | 25382 | 25383 | 25384 | 25385 | 25386 | 25387 |
| 25389 | 25390 | 25391 | 25393 | 25396 | 25397 | 25399 | 25400 | 25402 | 25403 | 25404 | 25405 |

TABLE 19-continued

Yield: Stress Tolerance

| | | | | | | | | | | | |
|---|---|---|---|---|---|---|---|---|---|---|---|
| 25408 | 25409 | 25411 | 25412 | 25413 | 25414 | 25415 | 25417 | 25418 | 25420 | 25425 | 25427 |
| 25429 | 25434 | 25435 | 25436 | 25437 | 25439 | 25441 | 25442 | 25447 | 25449 | 25451 | 25452 |
| 25453 | 25454 | 25455 | 25458 | 25460 | 25461 | 25462 | 25463 | 25465 | 25466 | 25467 | 25472 |
| 25473 | 25474 | 25475 | 25479 | 25480 | 25482 | 25483 | 25484 | 25485 | 25486 | 25487 | 25488 |
| 25490 | 25491 | 25495 | 25496 | 25497 | 25501 | 25503 | 25504 | 25506 | 25507 | 25508 | 25509 |
| 25512 | 25514 | 25515 | 25516 | 25517 | 25518 | 25519 | 25520 | 25521 | 25522 | 25523 | 25524 |
| 25528 | 25529 | 25533 | 25535 | 25536 | 25538 | 25539 | 25540 | 25542 | 25549 | 25550 | 25551 |
| 25554 | 25555 | 25557 | 25561 | 25563 | 25564 | 25565 | 25567 | 25569 | 25572 | 25573 | 25575 |
| 25577 | 25578 | 25581 | 25582 | 25583 | 25584 | 25586 | 25589 | 25590 | 25593 | 25595 | 25596 |
| 25601 | 25603 | 25609 | 25610 | 25611 | 25614 | 25615 | 25617 | 25618 | 25621 | 25622 | 25623 |
| 25625 | 25627 | 25628 | 25630 | 25631 | 25632 | 25636 | 25637 | 25638 | 25639 | 25640 | 25642 |
| 25650 | 25651 | 25653 | 25654 | 25655 | 25656 | 25657 | 25658 | 25661 | 25664 | 25665 | 25666 |
| 25672 | 25673 | 25676 | 25678 | 25681 | 25684 | 25686 | 25687 | 25688 | 25689 | 25690 | 25691 |
| 25692 | 25693 | 25694 | 25695 | 25697 | 25699 | 25701 | 25703 | 25704 | 25705 | 25706 | 25707 |
| 25708 | 25710 | 25711 | 25712 | 25715 | 25716 | 25719 | 25721 | 25723 | 25726 | 25727 | 25728 |
| 25729 | 25731 | 25733 | 25734 | 25735 | 25736 | 25737 | 25738 | 25740 | 25744 | 25745 | 25746 |
| 25752 | 25756 | 25762 | 25763 | 25764 | 25765 | 25767 | 25771 | 25772 | 25774 | 25775 | 25776 |
| 25777 | 25778 | 25779 | 25781 | 25783 | 25784 | 25785 | 25787 | 25789 | 25790 | 25791 | 25792 |
| 25793 | 25794 | 25795 | 25799 | 25805 | 25806 | 25808 | 25811 | 25812 | 25813 | 25814 | 25815 |
| 25818 | 25819 | 25820 | 25821 | 25824 | 25826 | 25827 | 25830 | 25831 | 25833 | 25834 | 25835 |
| 25837 | 25838 | 25841 | 25843 | 25844 | 25845 | 25846 | 25848 | 25849 | 25850 | 25851 | 25856 |
| 25858 | 25859 | 25860 | 25861 | 25862 | 25863 | 25864 | 25866 | 25867 | 25868 | 25869 | 25870 |
| 25871 | 25873 | 25874 | 25875 | 25879 | 25881 | 25882 | 25885 | 25886 | 25887 | 25888 | 25889 |
| 25890 | 25891 | 25892 | 25893 | 25895 | 25897 | 25898 | 25899 | 25900 | 25901 | 25903 | 25905 |
| 25907 | 25909 | 25913 | 25915 | 25917 | 25918 | 25919 | 25920 | 25922 | 25923 | 25924 | 25925 |
| 25927 | 25928 | 25934 | 25935 | 25937 | 25939 | 25940 | 25941 | 25946 | 25950 | 25951 | 25952 |
| 25957 | 25958 | 25959 | 25960 | 25961 | 25963 | 25964 | 25965 | 25967 | 25969 | 25972 | 25973 |
| 25974 | 25975 | 25976 | 25977 | 25978 | 25979 | 25980 | 25981 | 25984 | 25985 | 25986 | 25987 |
| 25989 | 25990 | 25993 | 25994 | 25997 | 25999 | 26000 | 26002 | 26003 | 26004 | 26008 | 26009 |
| 26010 | 26018 | 26019 | 26020 | 26021 | 26023 | 26025 | 26026 | 26028 | 26030 | 26032 | 26033 |
| 26036 | 26038 | 26039 | 26041 | 26043 | 26044 | 26047 | 26049 | 26050 | 26052 | 26053 | 26054 |
| 26055 | 26057 | 26058 | 26060 | 26061 | 26063 | 26064 | 26065 | 26067 | 26068 | 26070 | 26072 |
| 26073 | 26075 | 26076 | 26077 | 26080 | 26081 | 26082 | 26084 | 26091 | 26092 | 26093 | 26098 |
| 26100 | 26101 | 26102 | 26106 | 26107 | 26108 | 26109 | 26110 | 26111 | 26112 | 26113 | 26116 |
| 26117 | 26118 | 26119 | 26120 | 26121 | 26123 | 26124 | 26126 | 26127 | 26128 | 26129 | 26130 |
| 26131 | 26132 | 26134 | 26135 | 26137 | 26138 | 26141 | 26142 | 26144 | 26145 | 26147 | 26149 |
| 26150 | 26151 | 26153 | 26159 | 26161 | 26164 | 26165 | 26167 | 26170 | 26172 | 26173 | 26177 |
| 26178 | 26179 | 26182 | 26184 | 26185 | 26186 | 26187 | 26190 | 26191 | 26193 | 26195 | 26197 |
| 26200 | 26201 | 26203 | 26204 | 26205 | 26206 | 26208 | 26209 | 26212 | 26214 | 26215 |
| 26216 | 26217 | 26220 | 26221 | 26224 | 26227 | 26235 | 26236 | 26239 | 26248 | 26252 | 26253 |
| 26254 | 26255 | 26257 | 26258 | 26259 | 26261 | 26263 | 26264 | 26266 | 26268 | 26273 | 26275 |
| 26276 | 26284 | 26286 | 26287 | 26288 | 26289 | 26291 | 26295 | 26297 | 26299 | 26300 | 26301 |
| 26303 | 26304 | 26309 | 26310 | 26312 | 26313 | 26315 | 26319 | 26321 | 26325 | 26328 | 26329 |
| 26333 | 26335 | 26337 | 26338 | 26339 | 26340 | 26342 | 26343 | 26344 | 26346 | 26348 | 26349 |
| 26350 | 26354 | 26356 | 26357 | 26358 | 26361 | 26365 | 26369 | 26370 | 26373 | 26374 | 26375 |
| 26377 | 26378 | 26379 | 26384 | 26386 | 26388 | 26391 | 26392 | 26393 | 26394 | 26395 | 26397 |
| 26401 | 26405 | 26407 | 26410 | 26416 | 26418 | 26420 | 26423 | 26428 | 26429 | 26430 | 26431 |
| 26433 | 26434 | 26437 | 26439 | 26441 | 26442 | 26446 | 26450 | 26452 | 26454 | 26455 | 26460 |
| 26463 | 26466 | 26468 | 26471 | 26472 | 26473 | 26475 | 26480 | 26485 | 26487 | 26491 | 26492 |
| 26495 | 26500 | 26501 | 26502 | 26503 | 26505 | 26506 | 26508 | 26513 | 26514 | 26515 | 26516 |
| 26517 | 26518 | 26520 | 26523 | 26524 | 26526 | 26527 | 26528 | 26530 | 26531 | 26532 | 26533 |
| 26534 | 26537 | 26538 | 26540 | 26542 | 26547 | 26548 | 26551 | 26554 | 26555 | 26556 | 26558 |
| 26559 | 26562 | 26564 | 26565 | 26568 | 26569 | 26571 | 26574 | 26575 | 26580 | 26581 | 26582 |
| 26583 | 26585 | 26587 | 26591 | 26592 | 26594 | 26603 | 26604 | 26605 | 26606 | 26608 | 26614 |
| 26616 | 26623 | 26624 | 26626 | 26632 | 26633 | 26634 | 26635 | 26638 | 26642 | 26643 | 26644 |
| 26645 | 26646 | 26647 | 26651 | 26652 | 26656 | 26669 | 26671 | 26674 | 26675 | 26681 |
| 26684 | 26685 | 26686 | 26687 | 26692 | 26693 | 26694 | 26698 | 26699 | 26701 | 26705 | 26706 |
| 26709 | 26716 | 26718 | 26722 | 26730 | 26731 | 26733 | 26734 | 26735 | 26738 | 26739 | 26742 |
| 26744 | 26746 | 26747 | 26748 | 26749 | 26750 | 26753 | 26756 | 26757 | 26758 | 26759 | 26760 |
| 26762 | 26764 | 26765 | 26768 | 26769 | 26770 | 26772 | 26774 | 26777 | 26778 | 26780 |
| 26781 | 26782 | 26787 | 26788 | 26793 | 26795 | 26796 | 26797 | 26799 | 26800 | 26811 | 26813 |
| 26814 | 26815 | 26818 | 26823 | 26824 | 26825 | 26826 | 26828 | 26830 | 26831 | 26833 | 26834 |
| 26835 | 26841 | 26842 | 26843 | 26845 | 26846 | 26847 | 26850 | 26852 | 26855 | 26857 | 26859 |
| 26862 | 26864 | 26866 | 26867 | 26871 | 26873 | 26875 | 26877 | 26880 | 26882 | 26883 | 26885 |
| 26887 | 26888 | 26889 | 26890 | 26891 | 26892 | 26893 | 26894 | 26895 | 26898 | 26906 | 26907 |
| 26911 | 26914 | 26915 | 26918 | 26921 | 26923 | 26925 | 26927 | 26928 | 26929 | 26932 | 26936 |
| 26940 | 26941 | 26942 | 26945 | 26946 | 26948 | 26949 | 26950 | 26952 | 26953 | 26954 | 26956 |
| 26958 | 26961 | 26962 | 26965 | 26967 | 26968 | 26969 | 26970 | 26972 | 26974 | 26975 | 26976 |
| 26977 | 26978 | 26979 | 26984 | 26987 | 26989 | 26990 | 26992 | 26993 | 26996 | 26997 | 26998 |
| 26999 | 27000 | 27002 | 27005 | 27006 | 27007 | 27008 | 27009 | 27011 | 27016 | 27018 | 27019 |
| 27020 | 27021 | 27024 | 27026 | 27027 | 27029 | 27030 | 27032 | 27033 | 27034 | 27037 | 27043 |
| 27044 | 27046 | 27048 | 27049 | 27050 | 27051 | 27052 | 27053 | 27058 | 27060 | 27062 | 27063 |
| 27065 | 27067 | 27068 | 27069 | 27070 | 27071 | 27076 | 27077 | 27078 | 27079 | 27082 | 27083 |
| 27087 | 27088 | 27089 | 27092 | 27094 | 27100 | 27102 | 27103 | 27106 | 27107 | 27108 | 27113 |
| 27114 | 27116 | 27119 | 27121 | 27123 | 27124 | 27125 | 27127 | 27129 | 27130 | 27131 | 27133 |
| 27134 | 27137 | 27139 | 27140 | 27144 | 27145 | 27147 | 27148 | 27150 | 27151 | 27155 | 27156 |
| 27157 | 27158 | 27160 | 27164 | 27166 | 27168 | 27169 | 27170 | 27172 | 27173 | 27174 | 27175 |

TABLE 19-continued

Yield: Stress Tolerance

| | | | | | | | | | | | |
|---|---|---|---|---|---|---|---|---|---|---|---|
| 27178 | 27180 | 27183 | 27185 | 27189 | 27190 | 27191 | 27192 | 27193 | 27195 | 27197 | 27199 |
| 27200 | 27201 | 27204 | 27205 | 27208 | 27209 | 27210 | 27211 | 27212 | 27213 | 27216 | 27217 |
| 27219 | 27220 | 27221 | 27222 | 27225 | 27226 | 27227 | 27229 | 27232 | 27234 | 27235 | 27236 |
| 27237 | 27239 | 27240 | 27241 | 27242 | 27244 | 27246 | 27247 | 27249 | 27250 | 27255 | 27256 |
| 27257 | 27260 | 27261 | 27262 | 27268 | 27276 | 27277 | 27278 | 27279 | 27281 | 27282 | 27283 |
| 27284 | 27285 | 27289 | 27290 | 27294 | 27295 | 27296 | 27300 | 27308 | 27315 | 27316 | 27317 |
| 27319 | 27322 | 27323 | 27327 | 27329 | 27331 | 27332 | 27337 | 27341 | 27342 | 27343 | 27345 |
| 27346 | 27347 | 27348 | 27349 | 27350 | 27353 | 27356 | 27357 | 27359 | 27360 | 27368 | 27369 |
| 27370 | 27374 | 27375 | 27376 | 27377 | 27378 | 27379 | 27380 | 27382 | 27383 | 27384 | 27387 |
| 27390 | 27391 | 27392 | 27393 | 27395 | 27401 | 27402 | 27405 | 27406 | 27407 | 27408 | 27409 |
| 27410 | 27411 | 27413 | 27414 | 27415 | 27417 | 27418 | 27420 | 27421 | 27422 | 27423 | 27424 |
| 27425 | 27426 | 27427 | 27428 | 27429 | 27431 | 27434 | 27436 | 27438 | 27439 | 27441 | 27442 |
| 27444 | 27445 | 27446 | 27447 | 27452 | 27456 | 27458 | 27460 | 27462 | 27463 | 27464 | 27467 |
| 27468 | 27471 | 27473 | 27474 | 27477 | 27480 | 27481 | 27483 | 27484 | 27486 | 27488 | 27491 |
| 27493 | 27495 | 27496 | 27500 | 27503 | 27504 | 27505 | 27506 | 27507 | 27508 | 27512 | 27513 |
| 27514 | 27520 | 27525 | 27526 | 27527 | 27529 | 27530 | 27531 | 27532 | 27533 | 27534 | 27535 |
| 27538 | 27539 | 27541 | 27542 | 27543 | 27544 | 27546 | 27547 | 27548 | 27551 | 27552 | 27556 |
| 27562 | 27564 | 27565 | 27567 | 27570 | 27572 | 27575 | 27576 | 27578 | 27579 | 27580 | 27583 |
| 27584 | 27585 | 27586 | 27587 | 27588 | 27589 | 27592 | 27593 | 27601 | 27602 | 27604 | 27606 |
| 27607 | 27610 | 27611 | 27614 | 27615 | 27617 | 27618 | 27619 | 27623 | 27624 | 27625 | 27626 |
| 27627 | 27631 | 27633 | 27634 | 27637 | 27641 | 27642 | 27643 | 27644 | 27645 | 27646 | 27647 |
| 27653 | 27655 | 27661 | 27663 | 27664 | 27665 | 27667 | 27668 | 27669 | 27670 | 27672 | 27674 |
| 27678 | 27681 | 27682 | 27683 | 27684 | 27686 | 27689 | 27693 | 27694 | 27695 | 27696 | 27699 |
| 27700 | 27701 | 27703 | 27707 | 27708 | 27710 | 27711 | 27712 | 27715 | 27716 | 27717 | 27718 |
| 27721 | 27725 | 27727 | 27728 | 27731 | 27732 | 27734 | 27736 | 27739 | 27741 | 27743 | 27744 |
| 27745 | 27746 | 27747 | 27750 | 27751 | 27752 | 27754 | 27755 | 27757 | 27760 | 27762 | 27763 |
| 27765 | 27766 | 27769 | 27772 | 27775 | 27777 | 27778 | 27779 | 27780 | 27781 | 27782 | 27783 |
| 27785 | 27787 | 27788 | 27790 | 27791 | 27792 | 27793 | 27794 | 27797 | 27799 | 27800 | 27803 |
| 27804 | 27805 | 27807 | 27808 | 27809 | 27810 | 27811 | 27812 | 27814 | 27819 | 27820 | 27822 |
| 27826 | 27827 | 27829 | 27832 | 27833 | 27836 | 27837 | 27838 | 27839 | 27840 | 27841 | 27844 |
| 27845 | 27846 | 27847 | 27850 | 27855 | 27856 | 27857 | 27858 | 27859 | 27861 | 27863 | 27864 |
| 27865 | 27866 | 27869 | 27872 | 27874 | 27876 | 27880 | 27882 | 27884 | 27885 | 27887 | 27888 |
| 27889 | 27890 | 27892 | 27894 | 27895 | 27903 | 27904 | 27906 | 27910 | 27911 | 27912 | 27915 |
| 27917 | 27920 | 27921 | 27922 | 27926 | 27927 | 27929 | 27930 | 27932 | 27938 | 27939 | 27940 |
| 27941 | 27942 | 27943 | 27947 | 27948 | 27954 | 27955 | 27959 | 27964 | 27967 | 27969 | 27970 |
| 27972 | 27975 | 27977 | 27978 | 27980 | 27981 | 27982 | 27984 | 27988 | 27989 | 27997 | 27998 |
| 27999 | 28000 | 28001 | 28003 | 28004 | 28007 | 28011 | 28013 | 28014 | 28015 | 28017 | 28021 |
| 28022 | 28029 | 28032 | 28033 | 28034 | 28043 | 28046 | 28047 | 28049 | 28050 | 28053 | 28059 |
| 28060 | 28068 | 28072 | 28073 | 28075 | 28077 | 28078 | 28080 | 28081 | 28082 | 28085 | 28088 |
| 28089 | 28092 | 28098 | 28102 | 28103 | 28106 | 28110 | 28113 | 28116 | 28118 | 28120 | 28121 |
| 28123 | 28126 | 28127 | 28129 | 28130 | 28131 | 28132 | 28135 | 28136 | 28137 | 28140 | 28142 |
| 28145 | 28151 | 28153 | 28155 | 28156 | 28157 | 28159 | 28163 | 28165 | 28167 | 28169 | 28174 |
| 28175 | 28176 | 28177 | 28178 | 28180 | 28181 | 28183 | 28189 | 28184 | 28189 | 28192 | 28193 |
| 28194 | 28196 | 28200 | 28201 | 28202 | 28206 | 28208 | 28209 | 28210 | 28212 | 28216 | 28220 |
| 28224 | 28227 | 28229 | 28235 | 28238 | 28239 | 28240 | 28241 | 28242 | 28244 | 28246 | 28247 |
| 28249 | 28251 | 28253 | 28255 | 28256 | 28258 | 28261 | 28262 | 28266 | 28267 | 28269 | 28270 |
| 28272 | 28274 | 28280 | 28282 | 28283 | 28284 | 28285 | 28286 | 28290 | 28295 | 28296 | 28298 |
| 28301 | 28302 | 28304 | 28305 | 28306 | 28307 | 28308 | 28309 | 28313 | 28314 | 28318 | 28321 |
| 28322 | 28323 | 28329 | 28336 | 28337 | 28339 | 28341 | 28342 | 28344 | 28347 | 28348 | 28349 |
| 28351 | 28352 | 28353 | 28357 | 28363 | 28368 | 28370 | 28372 | 28373 | 28378 | 28380 | 28382 |
| 28385 | 28388 | 28389 | 28392 | 28395 | 28396 | 28397 | 28398 | 28400 | 28403 | 28405 | 28408 |
| 28410 | 28411 | 28414 | 28415 | 28416 | 28424 | 28427 | 28428 | 28430 | 28435 | 28438 | 28443 |
| 28446 | 28447 | 28449 | 28450 | 28451 | 28452 | 28456 | 28458 | 28461 | 28465 | 28468 | 28470 |
| 28471 | 28472 | 28473 | 28474 | 28478 | 28480 | 28488 | 28492 | 28493 | 28494 | 28495 | 28497 |
| 28498 | 28499 | 28500 | 28502 | 28503 | 28505 | 28506 | 28507 | 28511 | 28513 | 28516 | 28520 |
| 28524 | 28532 | 28533 | 28536 | 28537 | 28538 | 28539 | 28548 | 28551 | 28552 | 28553 |
| 28556 | 28561 | 28563 | 28566 | 28567 | 28569 | 28571 | 28572 | 28573 | 28575 | 28578 | 28580 |
| 28581 | 28582 | 28584 | 28585 | 28586 | 28588 | 28594 | 28595 | 28598 | 28599 | 28601 | 28603 |
| 28604 | 28607 | 28609 | 28610 | 28612 | 28613 | 28614 | 28622 | 28623 | 28624 | 28625 | 28626 |
| 28629 | 28631 | 28633 | 28634 | 28640 | 28641 | 28643 | 28648 | 28649 | 28650 | 28652 | 28653 |
| 28655 | 28658 | 28660 | 28664 | 28665 | 28666 | 28669 | 28670 | 28671 | 28672 | 28673 | 28675 |
| 28677 | 28678 | 28679 | 28680 | 28682 | 28683 | 28684 | 28687 | 28688 | 28689 | 28690 | 28692 |
| 28694 | 28695 | 28696 | 28697 | 28698 | 28699 | 28700 | 28703 | 28704 | 28709 | 28710 | 28711 |
| 28712 | 28713 | 28715 | 28716 | 28717 | 28718 | 28719 | 28720 | 28722 | 28723 | 28724 | 28725 |
| 28726 | 28727 | 28728 | 28729 | 28731 | 28732 | 28733 | 28736 | 28737 | 28738 | 28739 | 28741 |
| 28742 | 28743 | 28744 | 28745 | 28746 | 28747 | 28748 | 28750 | 28751 | 28752 | 28753 | 28754 |
| 28755 | 28762 | 28763 | 28764 | 28766 | 28771 | 28772 | 28773 | 28774 | 28775 | 28776 | 28778 |
| 28779 | 28780 | 28783 | 28784 | 28786 | 28787 | 28791 | 28792 | 28794 | 28795 | 28799 | 28801 |
| 28802 | 28803 | 28804 | 28805 | 28806 | 28808 | 28809 | 28812 | 28814 | 28818 | 28819 | 28820 |
| 28821 | 28824 | 28825 | 28826 | 28827 | 28828 | 28829 | 28830 | 28831 | 28832 | 28834 | 28835 |
| 28836 | 28837 | 28838 | 28840 | 28841 | 28843 | 28844 | 28845 | 28846 | 28851 | 28852 | 28853 |
| 28854 | 28855 | 28856 | 28859 | 28860 | 28861 | 28862 | 28865 | 28867 | 28868 | 28869 |
| 28870 | 28871 | 28873 | 28874 | 28875 | 28876 | 28881 | 28882 | 28883 | 28884 | 28886 | 28887 |
| 28888 | 28890 | 28891 | 28892 | 28893 | 28895 | 28897 | 28898 | 28899 | 28901 | 28902 | 28903 |
| 28904 | 28905 | 28906 | 28907 | 28908 | 28909 | 28910 | 28911 | 28913 | 28914 | 28917 | 28918 |
| 28919 | 28920 | 28921 | 28922 | 28923 | 28924 | 28925 | 28926 | 28927 | 28928 | 28929 | 28930 |
| 28934 | 28935 | 28936 | 28937 | 28938 | 28939 | 28941 | 28942 | 28943 | 28944 | 28949 | 28954 |

TABLE 19-continued

Yield: Stress Tolerance

| | | | | | | | | | | | |
|---|---|---|---|---|---|---|---|---|---|---|---|
| 28958 | 28959 | 28960 | 28961 | 28962 | 28963 | 28965 | 28966 | 28967 | 28972 | 28974 | 28975 |
| 28976 | 28977 | 28978 | 28981 | 28982 | 28985 | 28986 | 28988 | 28991 | 28992 | 28993 | 28996 |
| 28997 | 28998 | 28999 | 29002 | 29004 | 29006 | 29007 | 29011 | 29012 | 29014 | 29015 | 29025 |
| 29026 | 29034 | 29043 | 29046 | 29049 | 29050 | 29051 | 29052 | 29054 | 29055 | 29056 | 29059 |
| 29060 | 29062 | 29067 | 29068 | 29069 | 29070 | 29071 | 29072 | 29073 | 29074 | 29075 | 29076 |
| 29078 | 29079 | 29080 | 29081 | 29082 | 29083 | 29084 | 29086 | 29088 | 29095 | 29096 | 29097 |
| 29099 | 29100 | 29101 | 29102 | 29104 | 29105 | 29108 | 29109 | 29110 | 29111 | 29112 | 29113 |
| 29115 | 29117 | 29118 | 29119 | 29124 | 29126 | 29127 | 29128 | 29129 | 29130 | 29132 | 29135 |
| 29136 | 29137 | 29138 | 29140 | 29141 | 29143 | 29149 | 29150 | 29151 | 29153 | 29154 | 29155 |
| 29156 | 29158 | 29159 | 29160 | 29162 | 29163 | 29164 | 29166 | 29167 | 29168 | 29170 | 29171 |
| 29172 | 29173 | 29174 | 29175 | 29176 | 29178 | 29179 | 29180 | 29181 | 29183 | 29185 | 29186 |
| 29187 | 29188 | 29189 | 29190 | 29191 | 29195 | 29196 | 29199 | 29200 | 29201 | 29203 | 29204 |
| 29205 | 29214 | 29215 | 29220 | 29221 | 29227 | 29228 | 29229 | 29231 | 29234 | 29237 | 29238 |
| 29239 | 29240 | 29241 | 29242 | 29243 | 29244 | 29246 | 29247 | 29248 | 29249 | 29251 | 29252 |
| 29253 | 29254 | 29255 | 29256 | 29257 | 29259 | 29260 | 29265 | 29267 | 29268 | 29275 | 29276 |
| 29278 | 29279 | 29280 | 29281 | 29282 | 29285 | 29288 | 29290 | 29291 | 29292 | 29293 | 29295 |
| 29296 | 29297 | 29299 | 29300 | 29301 | 29302 | 29303 | 29304 | 29305 | 29306 | 29309 | 29310 |
| 29311 | 29314 | 29315 | 29316 | 29317 | 29319 | 29320 | 29321 | 29322 | 29323 | 29324 | 29325 |
| 29327 | 29328 | 29330 | 29331 | 29332 | 29333 | 29334 | 29337 | 29338 | 29340 | 29341 | 29342 |
| 29345 | 29346 | 29347 | 29348 | 29349 | 29350 | 29352 | 29353 | 29354 | 29355 | 29356 | 29357 |
| 29360 | 29361 | 29362 | 29364 | 29365 | 29366 | 29368 | 29370 | 29371 | 29372 | 29373 | 29374 |
| 29375 | 29376 | 29377 | 29379 | 29380 | 29381 | 29382 | 29385 | 29386 | 29387 | 29389 | 29390 |
| 29391 | 29394 | 29395 | 29396 | 29397 | 29399 | 29400 | 29401 | 29403 | 29404 | 29405 | 29409 |
| 29410 | 29411 | 29413 | 29414 | 29415 | 29416 | 29417 | 29418 | 29419 | 29421 | 29423 | 29426 |
| 29427 | 29429 | 29430 | 29432 | 29434 | 29435 | 29436 | 29437 | 29438 | 29441 | 29442 | 29444 |
| 29446 | 29448 | 29449 | 29450 | 29451 | 29452 | 29453 | 29455 | 29456 | 29459 | 29464 | 29465 |
| 29466 | 29467 | 29469 | 29471 | 29472 | 29473 | 29474 | 29476 | 29477 | 29478 | 29479 | 29481 |
| 29482 | 29483 | 29484 | 29485 | 29489 | 29490 | 29491 | 29492 | 29493 | 29494 | 29497 | 29498 |
| 29499 | 29500 | 29501 | 29502 | 29503 | 29505 | 29506 | 29507 | 29508 | 29510 | 29511 | 29513 |
| 29514 | 29515 | 29516 | 29517 | 29519 | 29520 | 29521 | 29522 | 29524 | 29525 | 29526 | 29528 |
| 29529 | 29530 | 29532 | 29535 | 29536 | 29538 | 29539 | 29540 | 29541 | 29542 | 29543 | 29544 |
| 29545 | 29547 | 29549 | 29550 | 29553 | 29558 | 29559 | 29560 | 29564 | 29565 | 29566 | 29567 |
| 29569 | 29570 | 29572 | 29575 | 29576 | 29577 | 29579 | 29580 | 29581 | 29582 | 29583 | 29585 |
| 29586 | 29587 | 29588 | 29589 | 29590 | 29591 | 29592 | 29593 | 29594 | 29595 | 29596 | 29598 |
| 29599 | 29601 | 29602 | 29603 | 29604 | 29605 | 29606 | 29607 | 29608 | 29614 | 29617 | 29622 |
| 29623 | 29624 | 29626 | 29627 | 29628 | 29629 | 29631 | 29632 | 29634 | 29635 | 29637 | 29638 |
| 29639 | 29640 | 29641 | 29642 | 29643 | 29644 | 29646 | 29648 | 29649 | 29651 | 29653 | 29655 |
| 29656 | 29657 | 29658 | 29660 | 29661 | 29662 | 29663 | 29664 | 29667 | 29668 | 29670 | 29671 |
| 29672 | 29673 | 29674 | 29675 | 29676 | 29677 | 29678 | 29680 | 29682 | 29683 | 29684 | 29687 |
| 29688 | 29689 | 29690 | 29694 | 29696 | 29698 | 29699 | 29704 | 29706 | 29707 | 29711 | 29713 |
| 29714 | 29715 | 29716 | 29717 | 29718 | 29722 | 29723 | 29724 | 29725 | 29726 | 29727 | 29728 |
| 29729 | 29730 | 29732 | 29734 | 29735 | 29736 | 29737 | 29738 | 29739 | 29740 | 29742 | 29744 |
| 29746 | 29747 | 29748 | 29749 | 29750 | 29751 | 29752 | 29754 | 29757 | 29758 | 29759 | 29760 |
| 29761 | 29762 | 29765 | 29767 | 29768 | 29769 | 29770 | 29771 | 29772 | 29773 | 29774 | 29776 |
| 29777 | 29778 | 29782 | 29783 | 29784 | 29786 | 29787 | 29788 | 29789 | 29790 | 29791 | 29796 |
| 29797 | 29798 | 29802 | 29803 | 29804 | 29805 | 29806 | 29808 | 29809 | 29810 | 29811 | 29812 |
| 29813 | 29814 | 29815 | 29819 | 29822 | 29823 | 29824 | 29825 | 29826 | 29827 | 29830 | 29831 |
| 29832 | 29833 | 29835 | 29836 | 29838 | 29839 | 29842 | 29843 | 29845 | 29846 | 29847 | 29848 |
| 29849 | 29850 | 29851 | 29852 | 29854 | 29855 | 29856 | 29857 | 29858 | 29859 | 29860 | 29861 |
| 29863 | 29864 | 29865 | 29866 | 29867 | 29869 | 29870 | 29871 | 29873 | 29874 | 29875 | 29876 |
| 29880 | 29881 | 29883 | 29884 | 29886 | 29887 | 29889 | 29890 | 29891 | 29892 | 29895 | 29896 |
| 29897 | 29898 | 29900 | 29902 | 29903 | 29904 | 29905 | 29906 | 29907 | 29908 | 29909 | 29910 |
| 29912 | 29913 | 29914 | 29915 | 29916 | 29917 | 29918 | 29920 | 29922 | 29923 | 29924 | 29925 |
| 29927 | 29928 | 29932 | 29933 | 29935 | 29936 | 29937 | 29942 | 29943 | 29947 | 29948 | 29950 |
| 29951 | 29952 | 29953 | 29954 | 29955 | 29958 | 29960 | 29961 | 29962 | 29963 | 29964 | 29965 |
| 29966 | 29967 | 29968 | 29969 | 29970 | 29971 | 29974 | 29975 | 29976 | 29977 | 29984 | 29986 |
| 29987 | 29989 | 29991 | 29992 | 29993 | 29994 | 29995 | 29996 | 29997 | 29998 | 29999 | 30000 |
| 30001 | 30006 | 30007 | 30008 | 30009 | 30010 | 30016 | 30018 | 30019 | 30020 | 30022 | 30025 |
| 30026 | 30027 | 30028 | 30030 | 30031 | 30032 | 30034 | 30041 | 30047 | 30048 | 30055 | 30057 |
| 30058 | 30059 | 30060 | 30061 | 30062 | 30063 | 30064 | 30067 | 30068 | 30070 | 30073 | |
| 30076 | 30079 | 30080 | 30081 | 30083 | 30084 | 30088 | 30093 | 30094 | 30095 | 30096 | 30098 |
| 30099 | 30100 | 30101 | 30102 | 30105 | 30106 | 30107 | 30108 | 30113 | 30115 | 30116 | 30117 |
| 30118 | 30120 | 30121 | 30122 | 30125 | 30126 | 30129 | 30130 | 30131 | 30132 | 30133 | 30134 |
| 30135 | 30136 | 30141 | 30142 | 30143 | 30144 | 30145 | 30148 | 30149 | 30150 | 30151 | 30152 |
| 30154 | 30155 | 30156 | 30157 | 30158 | 30159 | 30160 | 30163 | 30166 | 30167 | 30168 | 30169 |
| 30170 | 30171 | 30172 | 30173 | 30174 | 30175 | 30178 | 30179 | 30180 | 30181 | 30182 | 30183 |
| 30187 | 30196 | 30197 | 30198 | 30201 | 30202 | 30205 | 30207 | 30208 | 30211 | 30215 | 30216 |
| 30218 | 30219 | 30222 | 30223 | 30224 | 30227 | 30228 | 30231 | 30232 | 30233 | 30234 | 30236 |
| 30239 | 30240 | 30241 | 30242 | 30243 | 30244 | 30245 | 30246 | 30248 | 30249 | 30250 | 30252 |
| 30253 | 30255 | 30256 | 30257 | 30258 | 30259 | 30263 | 30264 | 30265 | 30266 | 30267 | 30271 |
| 30272 | 30273 | 30282 | 30283 | 30284 | 30286 | 30289 | 30290 | 30292 | 30293 | 30294 | 30295 |
| 30299 | 30300 | 30301 | 30302 | 30304 | 30305 | 30311 | 30312 | 30313 | 30314 | 30315 | 30317 |
| 30319 | 30320 | 30321 | 30322 | 30323 | 30324 | 30325 | 30329 | 30331 | 30337 | 30338 | 30339 |
| 30340 | 30341 | 30353 | 30354 | 30356 | 30357 | 30360 | 30361 | 30364 | 30369 | 30372 | 30373 |
| 30375 | 30379 | 30383 | 30384 | 30385 | 30386 | 30388 | 30389 | 30390 | 30393 | 30394 | 30396 |
| 30397 | 30398 | 30399 | 30400 | 30403 | 30406 | 30408 | 30409 | 30410 | 30412 | 30413 | 30415 |
| 30417 | 30418 | 30421 | 30422 | 30425 | 30426 | 30427 | 30428 | 30429 | 30433 | 30434 | 30435 |

TABLE 19-continued

Yield: Stress Tolerance

| | | | | | | | | | | | |
|---|---|---|---|---|---|---|---|---|---|---|---|
| 30436 | 30437 | 30440 | 30441 | 30442 | 30443 | 30444 | 30445 | 30446 | 30448 | 30449 | 30450 |
| 30451 | 30452 | 30454 | 30455 | 30456 | 30457 | 30458 | 30459 | 30460 | 30461 | 30462 | 30463 |
| 30467 | 30468 | 30469 | 30470 | 30471 | 30472 | 30473 | 30474 | 30476 | 30477 | 30478 | 30479 |
| 30481 | 30482 | 30484 | 30487 | 30488 | 30490 | 30491 | 30492 | 30493 | 30494 | 30495 | 30498 |
| 30499 | 30500 | 30502 | 30503 | 30504 | 30505 | 30506 | 30507 | 30508 | 30509 | 30510 | 30511 |
| 30512 | 30513 | 30514 | 30515 | 30516 | 30518 | 30520 | 30521 | 30522 | 30523 | 30524 | 30525 |
| 30526 | 30528 | 30530 | 30532 | 30534 | 30535 | 30536 | 30538 | 30539 | 30540 | 30541 | 30543 |
| 30544 | 30545 | 30546 | 30547 | 30548 | 30549 | 30550 | 30551 | 30553 | 30554 | 30555 | 30557 |
| 30558 | 30559 | 30563 | 30564 | 30565 | 30566 | 30567 | 30570 | 30572 | 30574 | 30576 | 30577 |
| 30578 | 30579 | 30581 | 30582 | 30583 | 30584 | 30585 | 30586 | 30587 | 30588 | 30589 | 30590 |
| 30591 | 30593 | 30598 | 30601 | 30602 | 30603 | 30607 | 30608 | 30609 | 30610 | 30614 | 30615 |
| 30616 | 30617 | 30618 | 30620 | 30621 | 30622 | 30623 | 30624 | 30625 | 30626 | 30627 | 30628 |
| 30631 | 30633 | 30634 | 30635 | 30636 | 30637 | 30638 | 30639 | 30640 | 30641 | 30642 | 30643 |
| 30644 | 30645 | 30648 | 30652 | 30656 | 30657 | 30660 | 30661 | 30662 | 30663 | 30664 | 30667 |
| 30671 | 30672 | 30675 | 30676 | 30678 | 30679 | 30681 | 30683 | 30684 | 30685 | 30686 | 30687 |
| 30688 | 30694 | 30695 | 30696 | 30697 | 30699 | 30700 | 30701 | 30702 | 30706 | 30707 | 30708 |
| 30709 | 30713 | 30714 | 30719 | 30722 | 30724 | 30725 | 30727 | 30731 | 30733 | 30734 | 30736 |
| 30737 | 30738 | 30740 | 30744 | 30745 | 30753 | 30754 | 30755 | 30756 | 30757 | 30759 | 30760 |
| 30763 | 30767 | 30769 | 30770 | 30771 | 30773 | 30777 | 30778 | 30784 | 30787 | 30788 | 30789 |
| 30797 | 30800 | 30801 | 30803 | 30804 | 30807 | 30813 | 30814 | 30822 | 30823 | 30827 | 30828 |
| 30830 | 30832 | 30833 | 30835 | 30836 | 30837 | 30840 | 30843 | 30844 | 30848 | 30854 | 30858 |
| 30859 | 30862 | 30867 | 30868 | 30871 | 30874 | 30876 | 30878 | 30879 | 30882 | 30885 | 30886 |
| 30888 | 30889 | 30890 | 30891 | 30894 | 30895 | 30896 | 30897 | 30900 | 30902 | 30905 | 30911 |
| 30913 | 30915 | 30916 | 30917 | 30919 | 30922 | 30924 | 30926 | 30928 | 30933 | 30934 | 30935 |
| 30936 | 30937 | 30939 | 30940 | 30942 | 30943 | 30947 | 30948 | 30950 | 30951 | 30952 | 30953 |
| 30954 | 30958 | 30959 | 30960 | 30961 | 30965 | 30967 | 30968 | 30969 | 30978 | 30982 | 30985 |
| 30987 | 30993 | 30995 | 30996 | 30997 | 30998 | 30999 | 31001 | 31003 | 31005 | 31007 | 31012 |
| 31013 | 31015 | 31018 | 31019 | 31023 | 31024 | 31026 | 31027 | 31029 | 31031 | 31037 | 31039 |
| 31040 | 31041 | 31042 | 31043 | 31047 | 31052 | 31053 | 31055 | 31058 | 31059 | 31061 | 31062 |
| 31063 | 31064 | 31065 | 31066 | 31067 | 31071 | 31072 | 31076 | 31079 | 31080 | 31081 | 31087 |
| 31094 | 31095 | 31097 | 31099 | 31100 | 31102 | 31106 | 31107 | 31108 | 31110 | 31111 | 31112 |
| 31116 | 31119 | 31122 | 31127 | 31129 | 31131 | 31132 | 31137 | 31138 | 31139 | 31140 | 31143 |
| 31146 | 31147 | 31150 | 31151 | 31154 | 31155 | 31156 | 31158 | 31160 | 31162 | 31164 | 31167 |
| 31169 | 31170 | 31173 | 31174 | 31175 | 31183 | 31186 | 31187 | 31190 | 31195 | 31197 | 31202 |
| 31205 | 31206 | 31208 | 31210 | 31211 | 31212 | 31216 | 31218 | 31221 | 31225 | 31228 | 31230 |
| 31231 | 31232 | 31233 | 31234 | 31238 | 31240 | 31247 | 31251 | 31252 | 31253 | 31254 | 31256 |
| 31257 | 31258 | 31259 | 31261 | 31262 | 31264 | 31265 | 31266 | 31270 | 31272 | 31275 | 31279 |
| 31283 | 31284 | 31291 | 31292 | 31295 | 31296 | 31297 | 31298 | 31300 | 31307 | 31310 | 31311 |
| 31312 | 31316 | 31321 | 31325 | 31327 | 31329 | 31330 | 31331 | 31333 | 31336 | 31338 | 31339 |
| 31340 | 31342 | 31343 | 31344 | 31346 | 31352 | 31353 | 31356 | 31357 | 31359 | 31361 | 31362 |
| 31365 | 31367 | 31370 | 31371 | 31372 | 31380 | 31381 | 31382 | 31383 | 31384 | 31387 | 31389 |
| 31391 | 31392 | 31398 | 31399 | 31401 | 31406 | 31407 | 31408 | 31410 | 31411 | 31413 | 31415 |
| 31418 | 31422 | 31423 | 31424 | 31426 | 31429 | 31430 | 31433 | 31436 | 31437 | 31443 | 31444 |
| 31451 | 31454 | 31457 | 31458 | 31459 | 31460 | 31461 | 31463 | 31464 | 31469 | 31471 | 31472 |
| 31476 | 31477 | 31478 | 31479 | 31481 | 31482 | 31488 | 31489 | 31490 | 31492 | 31494 | 31495 |
| 31496 | 31497 | 31499 | 31500 | 31502 | 31503 | 31506 | 31507 | 31509 | 31510 | 31513 | 31523 |
| 31524 | 31526 | 31527 | 31528 | 31529 | 31533 | 31537 | 31539 | 31543 | 31545 | 31547 | 31548 |
| 31549 | 31552 | 31556 | 31558 | 31559 | 31560 | 31565 | 31567 | 31572 | 31573 | 31577 | 31578 |
| 31579 | 31581 | 31582 | 31583 | 31587 | 31589 | 31590 | 31592 | 31597 | 31598 | 31599 | 31600 |
| 31604 | 31605 | 31607 | 31608 | 31609 | 31610 | 31611 | 31613 | 31620 | 31625 | 31626 | 31628 |
| 31631 | 31638 | 31640 | 31641 | 31642 | 31645 | 31647 | 31648 | 31651 | 31652 | 31658 | 31664 |
| 31665 | 31666 | 31667 | 31670 | 31674 | 31676 | 31680 | 31683 | 31684 | 31688 | 31693 | 31694 |
| 31696 | 31697 | 31698 | 31699 | 31701 | 31702 | 31706 | 31707 | 31710 | 31711 | 31715 | 31720 |
| 31722 | 31726 | 31727 | 31728 | 31730 | 31731 | 31734 | 31737 | 31738 | 31741 | 31744 | 31747 |
| 31748 | 31749 | 31750 | 31751 | 31753 | 31757 | 31759 | 31761 | 31762 | 31763 | 31764 | 31766 |
| 31767 | 31768 | 31769 | 31770 | 31771 | 31776 | 31780 | 31781 | 31786 | 31787 | 31788 | 31789 |
| 31790 | 31791 | 31792 | 31793 | 31795 | 31798 | 31799 | 31801 | 31802 | 31803 | 31817 | 31819 |
| 31820 | 31821 | 31822 | 31823 | 31824 | 31827 | 31828 | 31829 | 31830 | 31832 | 31837 | 31840 |
| 31841 | 31844 | 31846 | 31848 | 31849 | 31855 | 31858 | 31859 | 31861 | 31862 | 31863 | 31865 |
| 31878 | 31879 | 31880 | 31881 | 31882 | 31893 | 31894 | 31897 | 31901 | 31904 | 31905 |
| 31906 | 31907 | 31911 | 31912 | 31913 | 31916 | 31918 | 31926 | 31928 | 31930 | 31932 | 31935 |
| 31936 | 31942 | 31943 | 31944 | 31946 | 31948 | 31949 | 31950 | 31952 | 31953 | 31957 | 31962 |
| 31963 | 31964 | 31967 | 31971 | 31972 | 31975 | 31977 | 31978 | 31979 | 31983 | 31984 | 31985 |
| 31987 | 31990 | 31991 | 31996 | 31999 | 32000 | 32001 | 32002 | 32003 | 32004 | 32006 | 32007 |
| 32009 | 32010 | 32011 | 32014 | 32015 | 32016 | 32018 | 32020 | 32029 | 32032 | 32037 | 32038 |
| 32039 | 32040 | 32045 | 32048 | 32049 | 32050 | 32056 | 32060 | 32061 | 32062 | 32066 | 32067 |
| 32075 | 32076 | 32077 | 32080 | 32082 | 32086 | 32091 | 32093 | 32097 | 32099 | 32101 | 32103 |
| 32108 | 32110 | 32114 | 32115 | 32116 | 32120 | 32123 | 32124 | 32133 | 32136 | 32138 | 32141 |
| 32144 | 32146 | 32147 | 32148 | 32152 | 32158 | 32161 | 32162 | 32163 | 32166 | 32169 | 32171 |
| 32172 | 32174 | 32175 | 32176 | 32180 | 32182 | 32183 | 32186 | 32188 | 32189 | 32190 | 32193 |
| 32198 | 32200 | 32206 | 32207 | 32217 | 32218 | 32222 | 32224 | 32226 | 32227 | 32228 | 32229 |
| 32232 | 32235 | 32236 | 32238 | 32241 | 32242 | 32247 | 32249 | 32251 | 32252 | 32254 | 32263 |
| 32265 | 32266 | 32267 | 32268 | 32269 | 32273 | 32275 | 32276 | 32277 | 32279 | 32281 | 32282 |
| 32283 | 32284 | 32285 | 32286 | 32288 | 32289 | 32291 | 32293 | 32296 | 32297 | 32298 | 32299 |
| 32300 | 32304 | 32307 | 32310 | 32312 | 32313 | 32315 | 32316 | 32318 | 32319 | 32326 | 32328 |
| 32329 | 32330 | 32331 | 32333 | 32337 | 32339 | 32344 | 32348 | 32349 | 32350 | 32354 | 32355 |
| 32359 | 32363 | 32365 | 32367 | 32370 | 32371 | 32372 | 32374 | 32375 | 32376 | 32377 | 32378 |

TABLE 19-continued

Yield: Stress Tolerance

| | | | | | | | | | | | |
|---|---|---|---|---|---|---|---|---|---|---|---|
| 32379 | 32381 | 32382 | 32385 | 32386 | 32389 | 32390 | 32394 | 32396 | 32397 | 32399 | 32401 |
| 32410 | 32416 | 32422 | 32423 | 32424 | 32426 | 32427 | 32428 | 32429 | 32430 | 32431 | 32434 |
| 32435 | 32436 | 32437 | 32438 | 32440 | 32441 | 32442 | 32444 | 32449 | 32450 | 32451 | 32454 |
| 32460 | 32465 | 32466 | 32470 | 32472 | 32474 | 32475 | 32476 | 32477 | 32480 | 32483 | 32485 |
| 32486 | 32490 | 32491 | 32493 | 32496 | 32497 | 32498 | 32499 | 32500 | 32504 | 32505 | 32512 |
| 32515 | 32516 | 32519 | 32525 | 32527 | 32528 | 32529 | 32530 | 32531 | 32532 | 32533 | 32534 |
| 32539 | 32541 | 32542 | 32544 | 32545 | 32546 | 32550 | 32554 | 32559 | 32563 | 32564 | 32567 |
| 32568 | 32571 | 32573 | 32574 | 32575 | 32576 | 32578 | 32579 | 32581 | 32584 | 32585 | 32586 |
| 32588 | 32591 | 32593 | 32594 | 32595 | 32599 | 32600 | 32601 | 32607 | 32609 | 32615 | 32620 |
| 32622 | 32626 | 32628 | 32631 | 32633 | 32635 | 32637 | 32638 | 32641 | 32643 | 32645 | 32653 |
| 32655 | 32656 | 32658 | 32662 | 32663 | 32664 | 32665 | 32666 | 32671 | 32673 | 32676 | 32677 |
| 32678 | 32679 | 32680 | 32682 | 32692 | 32693 | 32695 | 32697 | 32698 | 32704 | 32705 | 32706 |
| 32709 | 32710 | 32711 | 32712 | 32716 | 32718 | 32719 | 32721 | 32727 | 32729 | 32730 | 32736 |
| 32737 | 32740 | 32741 | 32742 | 32743 | 32744 | 32754 | 32757 | 32759 | 32764 | 32766 | 32770 |
| 32771 | 32775 | 32777 | 32779 | 32782 | 32785 | 32786 | 32787 | 32788 | 32789 | 32790 | 32792 |
| 32795 | 32800 | 32801 | 32803 | 32806 | 32807 | 32808 | 32809 | 32810 | 32815 | 32816 | 32819 |
| 32821 | 32822 | 32823 | 32825 | 32830 | 32831 | 32833 | 32835 | 32839 | 32840 | 32843 | 32844 |
| 32845 | 32846 | 32849 | 32852 | 32854 | 32855 | 32856 | 32859 | 32862 | 32865 | 32867 | 32868 |
| 32870 | 32873 | 32876 | 32877 | 32879 | 32880 | 32881 | 32882 | 32884 | 32885 | 32891 | 32893 |
| 32896 | 32899 | 32902 | 32904 | 32906 | 32911 | 32913 | 32914 | 32915 | 32919 | 32923 | 32924 |
| 32926 | 32927 | 32928 | 32930 | 32931 | 32932 | 32933 | 32939 | 32942 | 32943 | 32944 | 32947 |
| 32948 | 32950 | 32951 | 32952 | 32956 | 32957 | 32960 | 32961 | 32962 | 32963 | 32964 | 32965 |
| 32966 | 32967 | 32969 | 32971 | 32972 | 32974 | 32976 | 32977 | 32985 | 32986 | 32990 | 32991 |
| 32993 | 32998 | 33002 | 33014 | 33016 | 33018 | 33021 | 33023 | 33024 | 33025 | 33026 | 33027 |
| 33028 | 33029 | 33030 | 33031 | 33033 | 33038 | 33039 | 33042 | 33043 | 33050 | 33052 | 33053 |
| 33055 | 33056 | 33057 | 33058 | 33059 | 33067 | 33069 | 33072 | 33073 | 33080 | 33084 | 33087 |
| 33090 | 33091 | 33094 | 33096 | 33098 | 33102 | 33106 | 33107 | 33109 | 33110 | 33111 | 33112 |
| 33115 | 33118 | 33119 | 33120 | 33122 | 33126 | 33127 | 33128 | 33129 | 33131 | 33134 | 33135 |
| 33137 | 33138 | 33140 | 33142 | 33147 | 33148 | 33149 | 33150 | 33154 | 33155 | 33158 | 33161 |
| 33162 | 33163 | 33165 | 33166 | 33167 | 33168 | 33169 | 33171 | 33175 | 33177 | 33183 | 33184 |
| 33185 | 33187 | 33189 | 33190 | 33191 | 33194 | 33195 | 33198 | 33199 | 33200 | 33205 | 33207 |
| 33208 | 33210 | 33211 | 33213 | 33214 | 33217 | 33219 | 33220 | 33226 | 33227 | 33229 | 33232 |
| 33233 | 33237 | 33242 | 33245 | 33249 | 33251 | 33254 | 33256 | 33261 | 33262 | 33263 | 33264 |
| 33268 | 33271 | 33272 | 33273 | 33275 | 33276 | 33277 | 33287 | 33288 | 33291 | 33293 | 33294 |
| 33296 | 33297 | 33299 | 33301 | 33308 | 33310 | 33312 | 33313 | 33315 | 33317 | 33321 | 33322 |
| 33323 | 33324 | 33325 | 33326 | 33327 | 33331 | 33332 | 33333 | 33335 | 33336 | 33337 | 33339 |
| 33348 | 33351 | 33352 | 33353 | 33354 | 33355 | 33356 | 33359 | 33360 | 33361 | 33363 | 33364 |
| 33370 | 33382 | 33384 | 33387 | 33388 | 33392 | 33393 | 33394 | 33395 | 33397 | 33399 | 33400 |
| 33402 | 33403 | 33408 | 33409 | 33410 | 33411 | 33412 | 33413 | 33414 | 33419 | 33422 | 33429 |
| 33430 | 33434 | 33437 | 33438 | 33441 | 33442 | 33445 | 33446 | 33449 | 33453 | 33456 | 33457 |
| 33459 | 33461 | 33462 | 33464 | 33465 | 33466 | 33467 | 33468 | 33469 | 33473 | 33475 | 33478 |
| 33479 | 33480 | 33482 | 33485 | 33486 | 33487 | 33494 | 33495 | 33496 | 33498 | 33499 | 33500 |
| 33501 | 33507 | 33508 | 33516 | 33518 | 33520 | 33522 | 33523 | 33524 | 33525 | 33526 | 33540 |
| 33541 | 33543 | 33544 | 33545 | 33548 | 33551 | 33552 | 33553 | 33556 | 33561 | 33562 | 33563 |
| 33566 | 33568 | 33576 | 33577 | 33579 | 33587 | 33588 | 33589 | 33590 | 33594 | 33595 | 33599 |
| 33600 | 33610 | 33611 | 33614 | 33615 | 33617 | 33624 | 33625 | 33626 | 33627 | 33633 | 33636 |
| 33637 | 33640 | 33645 | 33646 | 33647 | 33650 | 33660 | 33664 | 33665 | 33666 | 33667 | 33668 |
| 33672 | 33673 | 33676 | 33680 | 33681 | 33682 | 33683 | 33684 | 33693 | 33701 | 33705 | 33712 |
| 33713 | 33717 | 33718 | 33719 | 33720 | 33721 | 33725 | 33727 | 33728 | 33736 | 33740 | 33742 |
| 33746 | 33748 | 33750 | 33754 | 33755 | 33756 | 33757 | 33760 | 33762 | 33770 | 33773 | 33775 |
| 33776 | 33778 | 33779 | 33785 | 33786 | 33787 | 33789 | 33790 | 33791 | 33792 | 33793 | 33794 |
| 33795 | 33796 | 33799 | 33800 | 33801 | 33802 | 33805 | 33806 | 33807 | 33808 | 33810 | 33812 |
| 33817 | 33818 | 33819 | 33821 | 33822 | 33823 | 33824 | 33830 | 33832 | 33834 | 33835 | 33836 |
| 33838 | 33840 | 33842 | 33843 | 33845 | 33846 | 33847 | 33848 | 33849 | 33850 | 33855 | 33857 |
| 33860 | 33861 | 33864 | 33865 | 33867 | 33868 | 33869 | 33870 | 33871 | 33872 | 33874 | 33877 |
| 33878 | 33880 | 33883 | 33891 | 33893 | 33895 | 33898 | 33899 | 33904 | 33910 | 33915 |
| 33916 | 33919 | 33922 | 33923 | 33929 | 33930 | 33936 | 33942 | 33945 | 33946 | 33949 | 33952 |
| 33953 | 33955 | 33956 | 33957 | 33961 | 33962 | 33963 | 33964 | 33965 | 33966 | 33971 | 33972 |
| 33973 | 33975 | 33976 | 33978 | 33979 | 33982 | 33983 | 33985 | 33986 | 33987 | 33991 | 33992 |
| 33995 | 33998 | 33999 | 34000 | 34001 | 34002 | 34003 | 34005 | 34006 | 34007 | 34011 | 34013 |
| 34015 | 34016 | 34017 | 34019 | 34022 | 34023 | 34028 | 34031 | 34032 | 34035 | 34036 | 34043 |
| 34044 | 34045 | 34046 | 34050 | 34051 | 34052 | 34053 | 34055 | 34056 | 34057 | 34060 | 34061 |
| 34062 | 34063 | 34065 | 34066 | 34068 | 34071 | 34076 | 34077 | 34079 | 34080 | 34081 | 34083 |
| 34087 | 34090 | 34095 | 34097 | 34098 | 34100 | 34103 | 34104 | 34105 | 34108 | 34110 |
| 34111 | 34118 | 34121 | 34123 | 34125 | 34126 | 34132 | 34133 | 34134 | 34136 | 34137 | 34138 |
| 34139 | 34148 | 34157 | 34158 | 34160 | 34161 | 34162 | 34165 | 34166 | 34169 | 34170 | 34172 |
| 34174 | 34177 | 34183 | 34185 | 34192 | 34194 | 34195 | 34196 | 34199 | 34200 | 34201 | 34202 |
| 34205 | 34207 | 34208 | 34211 | 34217 | 34218 | 34219 | 34220 | 34221 | 34222 | 34226 | 34230 |
| 34231 | 34232 | 34237 | 34245 | 34246 | 34254 | 34262 | 34263 | 34266 | 34267 | 34273 | 34276 |
| 34278 | 34282 | 34283 | 34284 | 34285 | 34286 | 34287 | 34289 | 34290 | 34293 | 34294 | 34296 |
| 34302 | 34304 | 34305 | 34306 | 34309 | 34311 | 34312 | 34313 | 34316 | 34317 | 34318 | 34319 |
| 34320 | 34322 | 34325 | 34327 | 34330 | 34331 | 34333 | 34334 | 34336 | 34351 | 34358 | 34359 |
| 34362 | 34363 | 34365 | 34366 | 34367 | 34368 | 34369 | 34374 | 34375 | 34377 | 34378 | 34379 |
| 34380 | 34381 | 34383 | 34384 | 34388 | 34391 | 34392 | 34395 | 34397 | 34398 | 34402 | 34409 |
| 34416 | 34417 | 34421 | 34422 | 34423 | 34427 | 34428 | 34434 | 34435 | 34436 | 34437 | 34442 |
| 34443 | 34452 | 34455 | 34456 | 34460 | 34463 | 34465 | 34466 | 34469 | 34478 | 34481 | 34482 |
| 34484 | 34485 | 34486 | 34487 | 34488 | 34492 | 34494 | 34496 | 34497 | 34498 | 34503 | 34505 |

TABLE 19-continued

Yield: Stress Tolerance

| | | | | | | | | | | | |
|---|---|---|---|---|---|---|---|---|---|---|---|
| 34506 | 34508 | 34509 | 34513 | 34515 | 34516 | 34517 | 34519 | 34526 | 34528 | 34537 | 34542 |
| 34545 | 34546 | 34547 | 34549 | 34553 | 34555 | 34559 | 34560 | 34562 | 34563 | 34564 | 34566 |
| 34567 | 34569 | 34570 | 34572 | 34577 | 34580 | 34581 | 34583 | 34585 | 34596 | 34597 | 34598 |
| 34600 | 34604 | 34605 | 34606 | 34607 | 34615 | 34617 | 34618 | 34619 | 34620 | 34628 | 34630 |
| 34632 | 34633 | 34634 | 34639 | 34641 | 34642 | 34647 | 34648 | 34651 | 34655 | 34656 | 34657 |
| 34658 | 34659 | 34660 | 34663 | 34665 | 34667 | 34672 | 34683 | 34685 | 34687 | 34690 | 34692 |
| 34693 | 34694 | 34700 | 34701 | 34704 | 34705 | 34706 | 34707 | 34711 | 34713 | 34715 | 34716 |
| 34717 | 34719 | 34720 | 34726 | 34728 | 34730 | 34732 | 34733 | 34734 | 34736 | 34737 | 34738 |
| 34739 | 34742 | 34745 | 34747 | 34748 | 34749 | 34751 | 34753 | 34754 | 34755 | 34756 | 34757 |
| 34758 | 34760 | 34761 | 34763 | 34764 | 34765 | 34766 | 34768 | 34772 | 34773 | 34775 | 34778 |
| 34779 | 34781 | 34782 | 34783 | 34785 | 34787 | 34788 | 34789 | 34790 | 34792 | 34793 | 34796 |
| 34797 | 34798 | 34799 | 34800 | 34802 | 34803 | 34804 | 34806 | 34807 | 34809 | 34810 | 34812 |
| 34813 | 34814 | 34815 | 34816 | 34818 | 34819 | 34820 | 34822 | 34823 | 34824 | 34826 | 34827 |
| 34828 | 34829 | 34830 | 34832 | 34833 | 34835 | 34836 | 34839 | 34842 | 34843 | 34845 | |
| 34846 | 34847 | 34848 | 34850 | 34852 | 34853 | 34854 | 34855 | 34858 | 34861 | 34868 | 34869 |
| 34870 | 34871 | 34872 | 34874 | 34875 | 34882 | 34883 | 34884 | 34887 | 34889 | 34890 | 34891 |
| 34892 | 34893 | 34894 | 34895 | 34896 | 34897 | 34898 | 34899 | 34901 | 34903 | 34908 | 34909 |
| 34915 | 34917 | 34923 | 34924 | 34925 | 34928 | 34929 | 34931 | 34932 | 34933 | 34935 | 34936 |
| 34937 | 34938 | 34941 | 34942 | 34944 | 34945 | 34947 | 34950 | 34953 | 34955 | 34956 | 34957 |
| 34958 | 34959 | 34964 | 34969 | 34970 | 34971 | 34972 | 34973 | 34974 | 34976 | 34977 | 34980 |
| 34981 | 34983 | 34984 | 34985 | 34986 | 34987 | 34994 | 34995 | 34996 | 34997 | 34998 | 34999 |
| 35000 | 35003 | 35006 | 35007 | 35011 | 35012 | 35013 | 35014 | 35015 | 35016 | 35019 | 35021 |
| 35023 | 35025 | 35032 | 35034 | 35035 | 35036 | 35037 | 35038 | 35043 | 35045 | 35047 | 35048 |
| 35049 | 35051 | 35052 | 35053 | 35054 | 35055 | 35057 | 35058 | 35064 | 35067 | 35068 | 35070 |
| 35074 | 35075 | 35076 | 35077 | 35079 | 35083 | 35085 | 35089 | 35090 | 35092 | 35094 | 35097 |
| 35099 | 35100 | 35104 | 35106 | 35107 | 35110 | 35112 | 35114 | 35118 | 35119 | 35120 | 35121 |
| 35122 | 35126 | 35127 | 35129 | 35130 | 35131 | 35132 | 35135 | 35136 | 35138 | 35140 | 35142 |
| 35144 | 35147 | 35150 | 35152 | 35153 | 35157 | 35158 | 35162 | 35163 | 35165 | 35166 | 35172 |
| 35176 | 35177 | 35180 | 35181 | 35185 | 35187 | 35189 | 35193 | 35202 | 35203 | 35205 | 35210 |
| 35213 | 35216 | 35217 | 35220 | 35221 | 35224 | 35225 | 35226 | 35227 | 35229 | 35231 | 35232 |
| 35237 | 35239 | 35241 | 35242 | 35244 | 35246 | 35248 | 35251 | 35252 | 35253 | 35254 | 35255 |
| 35257 | 35259 | 35261 | 35262 | 35263 | 35265 | 35268 | 35271 | 35275 | 35280 | 35281 | 35282 |
| 35284 | 35285 | 35291 | 35292 | 35293 | 35294 | 35296 | 35299 | 35301 | 35303 | 35310 | 35311 |
| 35314 | 35316 | 35319 | 35320 | 35324 | 35333 | 35335 | 35336 | 35338 | 35340 | 35343 | 35345 |
| 35346 | 35348 | 35350 | 35354 | 35372 | 35378 | 35384 | 35395 | 35396 | 35400 | 35401 | 35403 |
| 35405 | 35406 | 35409 | 35416 | 35418 | 35421 | 35423 | 35425 | 35427 | 35429 | 35430 | 35431 |
| 35433 | 35434 | 35436 | 35443 | 35447 | 35450 | 35453 | 35455 | 35456 | 35457 | 35460 | 35461 |
| 35463 | 35464 | 35465 | 35468 | 35470 | 35473 | 35475 | 35476 | 35478 | 35482 | 35483 | 35484 |
| 35487 | 35488 | 35492 | 35494 | 35498 | 35499 | 35500 | 35503 | 35512 | 35514 | 35516 | 35517 |
| 35518 | 35522 | 35525 | 35526 | 35527 | 35530 | 35531 | 35535 | 35537 | 35540 | 35542 | 35546 |
| 35548 | 35550 | 35554 | 35555 | 35557 | 35558 | 35561 | 35562 | 35563 | 35564 | 35566 | 35568 |
| 35571 | 35574 | 35575 | 35576 | 35578 | 35579 | 35581 | 35584 | 35586 | 35589 | 35590 | 35591 |
| 35592 | 35594 | 35595 | 35598 | 35599 | 35601 | 35602 | 35606 | 35609 | 35612 | 35613 | 35616 |
| 35619 | 35622 | 35623 | 35626 | 35627 | 35628 | 35633 | 35635 | 35637 | 35638 | 35640 | 35641 |
| 35644 | 35646 | 35648 | 35654 | 35657 | 35659 | 35662 | 35663 | 35664 | 35670 | 35672 | 35674 |
| 35675 | 35683 | 35684 | 35689 | 35691 | 35692 | 35694 | 35698 | 35700 | 35701 | 35704 | 35705 |
| 35707 | 35708 | 35710 | 35712 | 35717 | 35718 | 35720 | 35721 | 35722 | 35723 | 35731 | 35732 |
| 35737 | 35739 | 35740 | 35745 | 35746 | 35749 | 35751 | 35753 | 35758 | 35761 | 35764 | 35765 |
| 35766 | 35767 | 35770 | 35771 | 35773 | 35775 | 35776 | 35779 | 35780 | 35782 | 35783 | 35786 |
| 35790 | 35793 | 35796 | 35797 | 35799 | 35800 | 35804 | 35806 | 35810 | 35811 | 35815 | 35816 |
| 35818 | 35819 | 35822 | 35823 | 35824 | 35825 | 35827 | 35830 | 35831 | 35832 | 35833 | 35834 |
| 35836 | 35842 | 35843 | 35844 | 35846 | 35847 | 35848 | 35849 | 35852 | 35856 | 35857 | 35861 |
| 35862 | 35863 | 35864 | 35865 | 35866 | 35870 | 35873 | 35874 | 35875 | 35876 | 35877 | 35879 |
| 35880 | 35881 | 35882 | 35884 | 35887 | 35888 | 35889 | 35892 | 35894 | 35898 | 35899 | 35900 |
| 35903 | 35904 | 35905 | 35908 | 35909 | 35911 | 35913 | 35915 | 35918 | 35919 | 35920 | 35922 |
| 35926 | 35928 | 35929 | 35931 | 35932 | 35933 | 35934 | 35935 | 35937 | 35938 | 35940 | 35943 |
| 35947 | 35948 | 35949 | 35951 | 35952 | 35953 | 35956 | 35959 | 35960 | 35961 | 35962 | 35966 |
| 35969 | 35971 | 35979 | 35983 | 35985 | 35991 | 35992 | 35993 | 35994 | 35995 | 35999 | 36002 |
| 36003 | 36004 | 36011 | 36012 | 36017 | 36022 | 36026 | 36027 | 36028 | 36029 | 36031 | 36032 |
| 36033 | 36044 | 36045 | 36047 | 36049 | 36050 | 36051 | 36053 | 36055 | 36058 | 36059 | 36060 |
| 36063 | 36064 | 36065 | 36066 | 36067 | 36068 | 36072 | 36074 | 36076 | 36078 | 36082 | 36083 |
| 36084 | 36085 | 36086 | 36087 | 36094 | 36095 | 36096 | 36099 | 36105 | 36107 | 36110 | 36113 |
| 36114 | 36118 | 36120 | 36121 | 36123 | 36128 | 36131 | 36133 | 36137 | 36138 | 36139 | 36141 |
| 36143 | 36146 | 36147 | 36148 | 36149 | 36151 | 36152 | 36153 | 36157 | 36158 | 36159 | 36161 |
| 36162 | 36166 | 36169 | 36170 | 36171 | 36172 | 36173 | 36174 | 36175 | 36176 | 36179 | 36180 |
| 36181 | 36182 | 36183 | 36185 | 36187 | 36189 | 36191 | 36192 | 36193 | 36196 | 36200 | 36201 |
| 36202 | 36203 | 36204 | 36205 | 36208 | 36211 | 36212 | 36214 | 36217 | 36218 | 36226 | 36227 |
| 36234 | 36238 | 36239 | 36241 | 36243 | 36244 | 36251 | 36253 | 36254 | 36255 | 36258 | 36262 |
| 36263 | 36266 | 36267 | 36268 | 36269 | 36270 | 36272 | 36273 | 36276 | 36280 | 36281 | 36282 |
| 36283 | 36285 | 36287 | 36289 | 36291 | 36292 | 36295 | 36296 | 36298 | 36302 | 36303 | 36304 |
| 36309 | 36311 | 36312 | 36313 | 36314 | 36315 | 36316 | 36317 | 36320 | 36321 | 36323 | 36325 |
| 36326 | 36329 | 36330 | 36331 | 36332 | 36333 | 36334 | 36335 | 36336 | 36340 | 36342 | 36349 |
| 36351 | 36352 | 36353 | 36355 | 36359 | 36360 | 36364 | 36365 | 36366 | 36375 | 36376 | 36377 |
| 36378 | 36379 | 36381 | 36382 | 36383 | 36386 | 36387 | 36389 | 36390 | 36394 | 36396 | 36397 |
| 36404 | 36407 | 36408 | 36409 | 36410 | 36413 | 36414 | 36415 | 36416 | 36417 | 36418 | 36420 |
| 36421 | 36423 | 36424 | 36426 | 36428 | 36429 | 36432 | 36433 | 36434 | 36435 | 36438 | 36439 |
| 36441 | 36442 | 36445 | 36447 | 36451 | 36452 | 36454 | 36455 | 36458 | 36461 | 36464 | 36465 |

TABLE 19-continued

Yield: Stress Tolerance

| | | | | | | | | | | | |
|---|---|---|---|---|---|---|---|---|---|---|---|
| 36466 | 36468 | 36469 | 36471 | 36475 | 36477 | 36480 | 36481 | 36488 | 36493 | 36495 | 36497 |
| 36500 | 36502 | 36503 | 36506 | 36507 | 36509 | 36512 | 36514 | 36519 | 36522 | 36523 | 36524 |
| 36525 | 36527 | 36528 | 36529 | 36531 | 36533 | 36534 | 36538 | 36540 | 36541 | 36546 | 36548 |
| 36549 | 36550 | 36551 | 36552 | 36553 | 36556 | 36561 | 36563 | 36564 | 36566 | 36567 | 36569 |
| 36573 | 36576 | 36578 | 36579 | 36580 | 36582 | 36585 | 36586 | 36587 | 36588 | 36590 | 36593 |
| 36594 | 36598 | 36599 | 36600 | 36602 | 36603 | 36605 | 36608 | 36611 | 36612 | 36613 | 36614 |
| 36616 | 36618 | 36619 | 36621 | 36623 | 36624 | 36626 | 36628 | 36630 | 36631 | 36632 | 36634 |
| 36636 | 36638 | 36639 | 36640 | 36651 | 36653 | 36654 | 36656 | 36663 | 36664 | 36666 | 36668 |
| 36670 | 36671 | 36672 | 36673 | 36674 | 36676 | 36678 | 36679 | 36680 | 36681 | 36685 | 36688 |
| 36690 | 36693 | 36694 | 36697 | 36698 | 36701 | 36705 | 36706 | 36707 | 36709 | 36710 | 36712 |
| 36713 | 36715 | 36716 | 36719 | 36720 | 36725 | 36726 | 36727 | 36728 | 36730 | 36731 | 36733 |
| 36736 | 36738 | 36739 | 36741 | 36748 | 36749 | 36751 | 36758 | 36759 | 36760 | 36761 | 36763 |
| 36765 | 36766 | 36767 | 36768 | 36769 | 36772 | 36775 | 36777 | 36778 | 36780 | 36782 | 36783 |
| 36785 | 36787 | 36788 | 36791 | 36793 | 36795 | 36796 | 36798 | 36799 | 36800 | 36801 | 36802 |
| 36806 | 36807 | 36808 | 36809 | 36812 | 36813 | 36815 | 36817 | 36818 | 36821 | 36823 | 36824 |
| 36826 | 36828 | 36831 | 36832 | 36834 | 36835 | 36836 | 36837 | 36838 | 36839 | 36842 | 36843 |
| 36845 | 36846 | 36847 | 36848 | 36849 | 36852 | 36853 | 36856 | 36857 | 36858 | 36865 | 36866 |
| 36869 | 36870 | 36871 | 36875 | 36876 | 36878 | 36879 | 36880 | 36881 | 36882 | 36884 | 36885 |
| 36888 | 36889 | 36892 | 36895 | 36896 | 36898 | 36899 | 36900 | 36901 | 36902 | 36903 | 36904 |
| 36906 | 36908 | 36910 | 36911 | 36912 | 36915 | 36918 | 36923 | 36926 | 36929 | 36933 | 36934 |
| 36936 | 36939 | 36940 | 36941 | 36943 | 36944 | 36946 | 36948 | 36949 | 36950 | 36951 | 36952 |
| 36953 | 36956 | 36957 | 36958 | 36959 | 36964 | 36965 | 36967 | 36969 | 36970 | 36971 | 36974 |
| 36979 | 36980 | 36982 | 36983 | 36984 | 36985 | 36987 | 36989 | 36990 | 36993 | 36994 | 36997 |
| 36999 | 37000 | 37001 | 37002 | 37003 | 37004 | 37005 | 37006 | 37007 | 37009 | 37012 | 37013 |
| 37016 | 37017 | 37018 | 37020 | 37022 | 37024 | 37025 | 37027 | 37028 | 37030 | 37031 | 37032 |
| 37034 | 37036 | 37037 | 37038 | 37041 | 37042 | 37043 | 37045 | 37047 | 37049 | 37052 | 37053 |
| 37056 | 37058 | 37060 | 37061 | 37062 | 37063 | 37064 | 37066 | 37068 | 37071 | 37072 | 37073 |
| 37074 | 37076 | 37077 | 37081 | 37082 | 37087 | 37088 | 37090 | 37095 | 37096 | 37097 | 37105 |
| 37106 | 37107 | 37108 | 37109 | 37110 | 37111 | 37112 | 37114 | 37115 | 37116 | 37117 | 37121 |
| 37124 | 37128 | 37132 | 37134 | 37136 | 37137 | 37138 | 37140 | 37141 | 37146 | 37154 | 37157 |
| 37160 | 37164 | 37166 | 37167 | 37168 | 37170 | 37171 | 37172 | 37173 | 37175 | 37178 | 37180 |
| 37181 | 37186 | 37193 | 37196 | 37197 | 37198 | 37201 | 37204 | 37205 | 37206 | 37207 | 37208 |
| 37209 | 37211 | 37215 | 37216 | 37221 | 37222 | 37223 | 37225 | 37226 | 37228 | 37229 | 37230 |
| 37231 | 37236 | 37239 | 37240 | 37241 | 37242 | 37243 | 37244 | 37245 | 37246 | 37249 | 37251 |
| 37254 | 37255 | 37257 | 37258 | 37259 | 37261 | 37262 | 37263 | 37264 | 37265 | 37269 | 37274 |
| 37278 | 37279 | 37282 | 37283 | 37285 | 37293 | 37297 | 37299 | 37300 | 37303 | 37304 | 37307 |
| 37314 | 37318 | 37319 | 37320 | 37324 | 37327 | 37328 | 37330 | 37331 | 37334 | 37335 | 37336 |
| 37337 | 37340 | 37343 | 37344 | 37347 | 37348 | 37349 | 37355 | 37357 | 37358 | 37362 | 37366 |
| 37367 | 37369 | 37375 | 37377 | 37378 | 37380 | 37381 | 37386 | 37389 | 37390 | 37391 | 37393 |
| 37394 | 37397 | 37400 | 37401 | 37402 | 37404 | 37406 | 37407 | 37414 | 37415 | 37418 | 37419 |
| 37423 | 37424 | 37425 | 37427 | 37429 | 37436 | 37438 | 37439 | 37441 | 37442 | 37443 | 37445 |
| 37446 | 37451 | 37454 | 37455 | 37456 | 37460 | 37462 | 37463 | 37467 | 37468 | 37470 | 37471 |
| 37476 | 37484 | 37485 | 37489 | 37490 | 37491 | 37492 | 37493 | 37496 | 37497 | 37498 |
| 37500 | 37503 | 37504 | 37505 | 37507 | 37512 | 37516 | 37517 | 37520 | 37521 | 37522 | 37523 |
| 37524 | 37526 | 37528 | 37530 | 37531 | 37532 | 37533 | 37538 | 37542 | 37546 | 37550 | 37552 |
| 37553 | 37554 | 37555 | 37556 | 37560 | 37561 | 37564 | 37567 | 37568 | 37569 | 37571 | 37574 |
| 37577 | 37583 | 37585 | 37588 | 37589 | 37590 | 37591 | 37592 | 37593 | 37595 | 37597 | 37598 |
| 37599 | 37600 | 37601 | 37604 | 37605 | 37607 | 37611 | 37614 | 37615 | 37617 | 37619 | 37623 |
| 37626 | 37628 | 37630 | 37633 | 37635 | 37638 | 37642 | 37644 | 37645 | 37646 | 37648 | 37657 |
| 37658 | 37660 | 37661 | 37666 | 37674 | 37675 | 37677 | 37682 | 37684 | 37686 | 37687 | 37688 |
| 37689 | 37691 | 37692 | 37693 | 37694 | 37703 | 37704 | 37705 | 37707 | 37708 | 37709 | 37713 |
| 37714 | 37717 | 37720 | 37721 | 37722 | 37723 | 37726 | 37727 | 37730 | 37732 | 37735 | 37736 |
| 37737 | 37738 | 37740 | 37744 | 37747 | 37748 | 37749 | 37754 | 37755 | 37756 | 37759 | 37762 |
| 37764 | 37765 | 37773 | 37777 | 37779 | 37784 | 37785 | 37795 | 37796 | 37800 | 37804 | 37811 |
| 37812 | 37813 | 37821 | 37825 | 37828 | 37830 | 37832 | 37834 | 37836 | 37837 | 37838 | 37839 |
| 37841 | 37842 | 37848 | 37849 | 37853 | 37855 | 37857 | 37862 | 37863 | 37865 | 37868 | 37870 |
| 37873 | 37874 | 37878 | 37882 | 37884 | 37885 | 37891 | 37899 | 37900 | 37903 | 37905 | 37911 |
| 37912 | 37914 | 37915 | 37919 | 37920 | 37921 | 37923 | 37925 | 37926 | 37927 | 37929 | 37931 |
| 37933 | 37934 | 37935 | 37936 | 37940 | 37942 | 37944 | 37946 | 37947 | 37950 | 37953 | 37958 |
| 37959 | 37964 | 37965 | 37970 | 37971 | 37977 | 37980 | 37983 | 37992 | 37994 | 37995 |
| 37996 | 38000 | 38001 | 38007 | 38009 | 38011 | 38012 | 38015 | 38017 | 38020 | 38021 | 38022 |
| 38025 | 38027 | 38033 | 38035 | 38038 | 38042 | 38043 | 38046 | 38047 | 38050 | 38051 | 38052 |
| 38054 | 38055 | 38058 | 38059 | 38068 | 38070 | 38071 | 38075 | 38078 | 38079 | 38082 | 38084 |
| 38086 | 38087 | 38089 | 38090 | 38091 | 38094 | 38096 | 38098 | 38099 | 38100 | 38105 | 38108 |
| 38111 | 38118 | 38120 | 38121 | 38123 | 38128 | 38130 | 38131 | 38133 | 38135 | 38139 | 38140 |
| 38144 | 38147 | 38148 | 38151 | 38152 | 38153 | 38158 | 38159 | 38160 | 38161 | 38162 | 38163 |
| 38164 | 38166 | 38169 | 38170 | 38171 | 38174 | 38175 | 38177 | 38178 | 38180 | 38188 | 38191 |
| 38195 | 38197 | 38201 | 38202 | 38203 | 38204 | 38206 | 38208 | 38209 | 38210 | 38212 | 38213 |
| 38215 | 38216 | 38218 | 38221 | 38222 | 38227 | 38228 | 38231 | 38234 | 38235 | 38237 | 38238 |
| 38243 | 38245 | 38247 | 38250 | 38251 | 38252 | 38254 | 38255 | 38257 | 38261 | 38262 | 38267 |
| 38269 | 38273 | 38275 | 38277 | 38281 | 38284 | 38285 | 38287 | 38294 | 38297 | 38300 | 38302 |
| 38303 | 38308 | 38311 | 38313 | 38319 | 38321 | 38332 | 38334 | 38335 | 38339 | 38340 | 38343 |
| 38344 | 38346 | 38349 | 38350 | 38351 | 38353 | 38356 | 38360 | 38361 | 38362 | 38364 | 38365 |
| 38373 | 38384 | 38387 | 38388 | 38392 | 38393 | 38394 | 38395 | 38396 | 38398 | 38401 | 38404 |
| 38407 | 38409 | 38410 | 38413 | 38416 | 38417 | 38418 | 38419 | 38421 | 38427 | 38432 | 38433 |
| 38435 | 38437 | 38439 | 38444 | 38445 | 38447 | 38450 | 38451 | 38458 | 38459 | 38464 | 38475 |
| 38478 | 38479 | 38481 | 38482 | 38483 | 38486 | 38487 | 38491 | 38492 | 38493 | 38497 | 38500 |

TABLE 19-continued

Yield: Stress Tolerance

| | | | | | | | | | | | |
|---|---|---|---|---|---|---|---|---|---|---|---|
| 38503 | 38505 | 38507 | 38509 | 38511 | 38512 | 38519 | 38522 | 38527 | 38529 | 38530 | 38531 |
| 38532 | 38534 | 38535 | 38536 | 38537 | 38538 | 38540 | 38541 | 38550 | 38551 | 38554 | 38555 |
| 38556 | 38558 | 38560 | 38562 | 38563 | 38567 | 38568 | 38569 | 38572 | 38577 | 38581 | 38588 |
| 38589 | 38590 | 38594 | 38599 | 38603 | 38604 | 38607 | 38610 | 38611 | 38612 | 38618 | 38625 |
| 38630 | 38632 | 38634 | 38637 | 38638 | 38642 | 38643 | 38647 | 38649 | 38650 | 38651 | 38652 |
| 38654 | 38660 | 38661 | 38662 | 38665 | 38666 | 38668 | 38670 | 38672 | 38673 | 38674 | 38678 |
| 38679 | 38682 | 38684 | 38690 | 38691 | 38695 | 38700 | 38701 | 38702 | 38703 | 38707 | 38708 |
| 38712 | 38714 | 38716 | 38717 | 38718 | 38719 | 38721 | 38722 | 38723 | 38724 | 38725 | 38726 |
| 38727 | 38730 | 38733 | 38734 | 38738 | 38740 | 38745 | 38746 | 38747 | 38748 | 38751 | 38755 |
| 38762 | 38766 | 38767 | 38770 | 38776 | 38777 | 38779 | 38780 | 38781 | 38783 | 38790 | 38793 |
| 38794 | 38797 | 38799 | 38800 | 38802 | 38803 | 38805 | 38806 | 38807 | 38809 | 38812 | 38813 |
| 38817 | 38819 | 38820 | 38823 | 38827 | 38828 | 38829 | 38831 | 38832 | 38833 | 38836 | 38840 |
| 38841 | 38842 | 38845 | 38846 | 38847 | 38858 | 38866 | 38867 | 38870 | 38872 | 38875 | 38876 |
| 38877 | 38878 | 38879 | 38880 | 38882 | 38885 | 38889 | 38894 | 38896 | 38897 | 38898 |
| 38899 | 38901 | 38903 | 38911 | 38914 | 38915 | 38916 | 38923 | 38924 | 38927 | 38930 | 38931 |
| 38938 | 38939 | 38946 | 38950 | 38952 | 38955 | 38961 | 38962 | 38970 | 38972 | 38973 | 38974 |
| 38976 | 38979 | 38980 | 38982 | 38983 | 38984 | 38990 | 38997 | 39008 | 39009 | 39012 | 39013 |
| 39014 | 39015 | 39021 | 39022 | 39023 | 39025 | 39027 | 39029 | 39033 | 39035 | 39036 | 39040 |
| 39041 | 39043 | 39045 | 39047 | 39052 | 39056 | 39058 | 39061 | 39063 | 39064 | 39065 | 39066 |
| 39067 | 39075 | 39079 | 39080 | 39083 | 39085 | 39088 | 39090 | 39093 | 39094 | 39096 | 39097 |
| 39098 | 39101 | 39102 | 39103 | 39106 | 39108 | 39109 | 39110 | 39115 | 39116 | 39117 | 39118 |
| 39123 | 39124 | 39125 | 39127 | 39129 | 39130 | 39136 | 39137 | 39141 | 39142 | 39144 | 39145 |
| 39146 | 39150 | 39158 | 39161 | 39162 | 39164 | 39167 | 39169 | 39175 | 39176 | 39177 | 39179 |
| 39183 | 39187 | 39193 | 39197 | 39198 | 39199 | 39203 | 39205 | 39206 | 39207 | 39209 | 39212 |
| 39213 | 39217 | 39220 | 39221 | 39222 | 39225 | 39231 | 39232 | 39238 | 39239 | 39240 | 39243 |
| 39247 | 39248 | 39249 | 39250 | 39253 | 39256 | 39260 | 39262 | 39267 | 39269 | 39270 | 39271 |
| 39272 | 39274 | 39288 | 39289 | 39293 | 39296 | 39297 | 39298 | 39304 | 39306 | 39307 | 39311 |
| 39317 | 39319 | 39321 | 39323 | 39324 | 39325 | 39326 | 39329 | 39330 | 39333 | 39334 | 39335 |
| 39336 | 39337 | 39338 | 39339 | 39341 | 39342 | 39343 | 39344 | 39345 | 39346 | 39348 | 39349 |
| 39350 | 39356 | 39363 | 39374 | 39375 | 39378 | 39379 | 39380 | 39381 | 39382 | 39389 | 39390 |
| 39392 | 39394 | 39395 | 39396 | 39400 | 39402 | 39403 | 39408 | 39410 | 39412 | 39414 | 39419 |
| 39423 | 39425 | 39428 | 39431 | 39432 | 39433 | 39434 | 39435 | 39443 | 39447 | 39448 | 39451 |
| 39453 | 39456 | 39458 | 39461 | 39462 | 39464 | 39465 | 39466 | 39469 | 39470 | 39471 | 39474 |
| 39476 | 39477 | 39478 | 39483 | 39484 | 39485 | 39486 | 39487 | 39491 | 39492 | 39493 | 39495 |
| 39496 | 39498 | 39504 | 39505 | 39509 | 39510 | 39512 | 39513 | 39514 | 39517 | 39519 | 39522 |
| 39528 | 39531 | 39532 | 39534 | 39537 | 39540 | 39541 | 39545 | 39547 | 39548 | 39549 | 39550 |
| 39554 | 39558 | 39565 | 39569 | 39570 | 39571 | 39575 | 39577 | 39578 | 39580 | 39583 | 39584 |
| 39588 | 39591 | 39592 | 39593 | 39596 | 39603 | 39604 | 39611 | 39612 | 39613 | 39616 | 39620 |
| 39621 | 39622 | 39623 | 39626 | 39629 | 39633 | 39636 | 39643 | 39645 | 39646 | 39647 |
| 39648 | 39650 | 39668 | 39671 | 39672 | 39673 | 39679 | 39681 | 39682 | 39686 | 39692 | 39694 |
| 39696 | 39698 | 39699 | 39700 | 39701 | 39704 | 39705 | 39708 | 39710 | 39711 | 39712 | 39713 |
| 39714 | 39715 | 39716 | 39717 | 39718 | 39720 | 39721 | 39722 | 39723 | 39724 | 39726 | 39728 |
| 39729 | 39732 | 39733 | 39734 | 39735 | 39736 | 39739 | 39740 | 39746 | 39754 | 39757 | 39765 |
| 39766 | 39767 | 39770 | 39771 | 39772 | 39773 | 39779 | 39780 | 39781 | 39784 | 39786 | 39789 |
| 39790 | 39791 | 39794 | 39795 | 39797 | 39798 | 39804 | 39808 | 39811 | 39813 | 39815 | 39816 |
| 39817 | 39818 | 39819 | 39825 | 39826 | 39830 | 39831 | 39835 | 39837 | 39840 | 39844 | 39845 |
| 39846 | 39848 | 39849 | 39851 | 39852 | 39853 | 39856 | 39858 | 39859 | 39860 | 39865 | 39866 |
| 39867 | 39868 | 39869 | 39873 | 39874 | 39876 | 39877 | 39878 | 39880 | 39886 | 39887 | 39891 |
| 39892 | 39893 | 39894 | 39897 | 39898 | 39901 | 39902 | 39910 | 39911 | 39913 | 39915 | 39920 |
| 39921 | 39922 | 39923 | 39925 | 39927 | 39930 | 39933 | 39941 | 39942 | 39943 | 39944 | 39946 |
| 39950 | 39951 | 39953 | 39956 | 39959 | 39960 | 39963 | 39964 | 39967 | 39971 | 39978 | 39979 |
| 39981 | 39984 | 39987 | 39988 | 39989 | 39990 | 39992 | 39995 | 39996 | 40001 | 40002 | 40006 |
| 40009 | 40010 | 40011 | 40015 | 40026 | 40029 | 40031 | 40037 | 40038 | 40039 | 40046 | 40048 |
| 40050 | 40052 | 40053 | 40054 | 40057 | 40058 | 40060 | 40061 | 40062 | 40063 | 40068 | 40069 |
| 40070 | 40073 | 40075 | 40076 | 40078 | 40082 | 40083 | 40084 | 40093 | 40094 | 40095 | 40096 |
| 40098 | 40099 | 40100 | 40101 | 40106 | 40107 | 40108 | 40115 | 40116 | 40117 | 40119 | 40120 |
| 40123 | 40124 | 40131 | 40132 | 40133 | 40134 | 40135 | 40138 | 40141 | 40143 | 40144 | 40146 |
| 40149 | 40150 | 40154 | 40155 | 40156 | 40158 | 40159 | 40162 | 40164 | 40165 | 40167 | 40168 |
| 40170 | 40171 | 40172 | 40173 | 40174 | 40177 | 40182 | 40183 | 40184 | 40188 | 40189 | 40190 |
| 40197 | 40198 | 40199 | 40201 | 40206 | 40207 | 40209 | 40211 | 40212 | 40216 | 40223 | 40227 |
| 40236 | 40237 | 40238 | 40239 | 40240 | 40241 | 40242 | 40245 | 40247 | 40248 | 40249 | 40257 |
| 40258 | 40261 | 40262 | 40263 | 40264 | 40267 | 40277 | 40278 | 40279 | 40280 | 40282 | 40284 |
| 40285 | 40286 | 40290 | 40292 | 40294 | 40296 | 40297 | 40298 | 40303 | 40305 | 40307 | 40308 |
| 40311 | 40312 | 40313 | 40317 | 40318 | 40320 | 40324 | 40333 | 40336 | 40340 | 40341 |
| 40342 | 40343 | 40344 | 40345 | 40346 | 40348 | 40349 | 40351 | 40353 | 40354 | 40355 | 40356 |
| 40357 | 40361 | 40362 | 40366 | 40367 | 40368 | 40369 | 40372 | 40374 | 40379 | 40380 | 40382 |
| 40383 | 40384 | 40388 | 40389 | 40390 | 40392 | 40394 | 40396 | 40397 | 40398 | 40399 | 40400 |
| 40401 | 40402 | 40403 | 40404 | 40408 | 40409 | 40413 | 40415 | 40416 | 40419 | 40422 | 40424 |
| 40425 | 40427 | 40431 | 40436 | 40440 | 40443 | 40444 | 40445 | 40446 | 40454 | 40456 | 40457 |
| 40459 | 40463 | 40464 | 40465 | 40466 | 40467 | 40468 | 40469 | 40470 | 40474 | 40475 | 40477 |
| 40480 | 40485 | 40486 | 40490 | 40491 | 40492 | 40493 | 40494 | 40496 | 40497 | 40499 | 40500 |
| 40502 | 40504 | 40510 | 40513 | 40514 | 40515 | 40517 | 40518 | 40520 | 40522 | 40523 | 40524 |
| 40525 | 40527 | 40528 | 40530 | 40531 | 40536 | 40538 | 40541 | 40544 | 40545 | 40546 | 40548 |
| 40550 | 40551 | 40552 | 40553 | 40555 | 40557 | 40559 | 40560 | 40562 | 40564 | 40566 | 40571 |
| 40576 | 40578 | 40581 | 40582 | 40585 | 40586 | 40588 | 40591 | 40596 | 40602 | 40603 | 40604 |
| 40606 | 40607 | 40610 | 40612 | 40613 | 40617 | 40620 | 40622 | 40627 | 40628 | 40630 | 40633 |
| 40635 | 40636 | 40639 | 40644 | 40645 | 40646 | 40650 | 40651 | 40655 | 40657 | 40667 | 40668 |

TABLE 19-continued

Yield: Stress Tolerance

| | | | | | | | | | | | |
|---|---|---|---|---|---|---|---|---|---|---|---|
| 40670 | 40671 | 40672 | 40673 | 40674 | 40675 | 40680 | 40682 | 40689 | 40693 | 40696 | 40697 |
| 40698 | 40702 | 40704 | 40707 | 40711 | 40713 | 40716 | 40717 | 40718 | 40719 | 40720 | 40724 |
| 40727 | 40729 | 40731 | 40733 | 40736 | 40742 | 40744 | 40745 | 40746 | 40747 | 40748 | 40750 |
| 40752 | 40754 | 40755 | 40756 | 40758 | 40759 | 40779 | 40780 | 40781 | 40782 | 40787 | 40789 |
| 40790 | 40792 | 40798 | 40800 | 40809 | 40810 | 40812 | 40813 | 40816 | 40818 | 40823 | 40824 |
| 40825 | 40826 | 40827 | 40830 | 40836 | 40840 | 40841 | 40842 | 40844 | 40845 | 40846 | 40850 |
| 40853 | 40854 | 40855 | 40856 | 40857 | 40858 | 40859 | 40861 | 40865 | 40869 | 40870 | 40872 |
| 40873 | 40874 | 40876 | 40880 | 40881 | 40882 | 40883 | 40884 | 40885 | 40886 | 40887 | 40888 |
| 40891 | 40892 | 40894 | 40895 | 40897 | 40898 | 40904 | 40907 | 40908 | 40909 | 40913 | 40917 |
| 40918 | 40921 | 40922 | 40923 | 40924 | 40927 | 40936 | 40946 | 40952 | 40957 | 40960 | 40961 |
| 40962 | 40964 | 40965 | 40966 | 40968 | 40970 | 40971 | 40976 | 40988 | 40990 | 40994 | 40996 |
| 40997 | 41000 | 41006 | 41008 | 41009 | 41010 | 41013 | 41014 | 41015 | 41017 | 41018 | 41019 |
| 41020 | 41024 | 41032 | 41035 | 41039 | 41045 | 41046 | 41050 | 41055 | 41056 | 41057 | 41058 |
| 41059 | 41060 | 41061 | 41062 | 41064 | 41065 | 41066 | 41069 | 41070 | 41071 | 41072 | |
| 41074 | 41075 | 41076 | 41078 | 41079 | 41085 | 41086 | 41088 | 41089 | 41090 | 41091 | 41097 |
| 41099 | 41102 | 41105 | 41106 | 41108 | 41113 | 41114 | 41117 | 41123 | 41130 | 41134 | 41140 |
| 41141 | 41142 | 41143 | 41149 | 41150 | 41151 | 41153 | 41154 | 41155 | 41156 | 41158 | 41163 |
| 41164 | 41165 | 41168 | 41170 | 41171 | 41172 | 41177 | 41178 | 41181 | 41187 | 41188 | 41191 |
| 41194 | 41197 | 41202 | 41204 | 41206 | 41207 | 41209 | 41210 | 41211 | 41213 | 41214 | 41222 |
| 41223 | 41224 | 41232 | 41233 | 41234 | 41235 | 41236 | 41237 | 41238 | 41239 | 41241 | 41242 |
| 41243 | 41244 | 41246 | 41247 | 41251 | 41252 | 41253 | 41255 | 41257 | 41258 | 41259 | 41260 |
| 41261 | 41262 | 41266 | 41269 | 41270 | 41271 | 41274 | 41275 | 41277 | 41279 | 41287 | |
| 41292 | 41295 | 41301 | 41302 | 41304 | 41306 | 41309 | 41310 | 41313 | 41316 | 41328 | 41338 |
| 41339 | 41341 | 41342 | 41343 | 41344 | 41345 | 41346 | 41347 | 41348 | 41354 | 41355 | 41356 |
| 41357 | 41358 | 41359 | 41360 | 41362 | 41363 | 41365 | 41366 | 41370 | 41372 | 41374 | 41375 |
| 41376 | 41377 | 41378 | 41379 | 41380 | 41384 | 41388 | 41389 | 41393 | 41394 | 41399 | 41400 |
| 41405 | 41409 | 41410 | 41411 | 41412 | 41414 | 41415 | 41418 | 41419 | 41420 | 41424 | 41425 |
| 41426 | 41428 | 41429 | 41430 | 41431 | 41432 | 41433 | 41436 | 41439 | 41440 | 41442 | 41444 |
| 41445 | 41446 | 41447 | 41449 | 41452 | 41454 | 41457 | 41459 | 41461 | 41462 | 41463 | 41473 |
| 41475 | 41476 | 41477 | 41478 | 41480 | 41492 | 41493 | 41494 | 41496 | 41497 | 41498 | 41501 |
| 41504 | 41507 | 41508 | 41509 | 41510 | 41511 | 41517 | 41524 | 41527 | 41530 | 41536 | 41538 |
| 41539 | 41543 | 41544 | 41545 | 41547 | 41550 | 41555 | 41556 | 41557 | 41560 | 41575 | 41576 |
| 41577 | 41578 | 41582 | 41583 | 41584 | 41585 | 41586 | 41588 | 41589 | 41593 | 41600 | 41601 |
| 41604 | 41605 | 41607 | 41608 | 41609 | 41611 | 41612 | 41613 | 41614 | 41615 | 41617 | 41620 |
| 41621 | 41625 | 41626 | 41628 | 41631 | 41633 | 41635 | 41636 | 41638 | 41641 | 41642 | 41645 |
| 41646 | 41650 | 41652 | 41653 | 41655 | 41657 | 41658 | 41660 | 41666 | 41668 | 41669 | 41671 |
| 41672 | 41677 | 41679 | 41680 | 41682 | 41695 | 41696 | 41697 | 41699 | 41700 | 41704 | 41709 |
| 41712 | 41713 | 41717 | 41718 | 41719 | 41721 | 41723 | 41724 | 41725 | 41728 | 41730 | 41732 |
| 41733 | 41736 | 41737 | 41738 | 41739 | 41741 | 41742 | 41745 | 41750 | 41752 | 41753 | |
| 41754 | 41756 | 41757 | 41758 | 41760 | 41761 | 41762 | 41763 | 41764 | 41765 | 41766 | 41767 |
| 41768 | 41769 | 41773 | 41776 | 41778 | 41781 | 41782 | 41788 | 41790 | 41793 | 41800 | 41802 |
| 41805 | 41808 | 41810 | 41815 | 41818 | 41819 | 41822 | 41823 | 41830 | 41832 | 41833 | 41834 |
| 41836 | 41837 | 41838 | 41840 | 41841 | 41843 | 41847 | 41850 | 41853 | 41854 | 41855 | 41856 |
| 41857 | 41859 | 41863 | 41865 | 41867 | 41868 | 41869 | 41871 | 41873 | 41874 | 41878 | 41879 |
| 41881 | 41882 | 41883 | 41884 | 41885 | 41886 | 41890 | 41891 | 41892 | 41893 | 41895 | 41898 |
| 41900 | 41904 | 41909 | 41913 | 41914 | 41915 | 41917 | 41919 | 41921 | 41924 | 41926 | 41928 |
| 41932 | 41936 | 41938 | 41947 | 41948 | 41951 | 41952 | 41953 | 41954 | 41956 | 41957 | 41958 |
| 41965 | 41968 | 41971 | 41973 | 41977 | 41984 | 41987 | 41988 | 41989 | 41993 | 41995 | 41996 |
| 41998 | 42000 | 42002 | 42003 | 42004 | 42007 | 42008 | 42010 | 42013 | 42017 | 42019 | 42020 |
| 42021 | 42022 | 42025 | 42032 | 42037 | 42042 | 42046 | 42048 | 42049 | 42051 | 42052 | 42054 |
| 42065 | 42066 | 42067 | 42068 | 42069 | 42070 | 42074 | 42076 | 42077 | 42078 | 42084 | 42086 |
| 42087 | 42088 | 42089 | 42092 | 42103 | 42104 | 42105 | 42109 | 42110 | 42111 | 42113 | |
| 42114 | 42117 | 42118 | 42119 | 42121 | 42122 | 42123 | 42124 | 42125 | 42129 | 42130 | 42131 |
| 42133 | 42134 | 42138 | 42139 | 42143 | 42144 | 42145 | 42146 | 42147 | 42148 | 42149 | 42151 |
| 42156 | 42160 | 42161 | 42162 | 42164 | 42165 | 42166 | 42173 | 42174 | 42175 | 42176 | 42178 |
| 42183 | 42184 | 42185 | 42186 | 42187 | 42191 | 42193 | 42196 | 42197 | 42198 | 42201 | |
| 42204 | 42209 | 42212 | 42213 | 42216 | 42219 | 42220 | 42224 | 42225 | 42227 | 42231 | 42232 |
| 42233 | 42238 | 42241 | 42242 | 42244 | 42245 | 42248 | 42249 | 42250 | 42255 | 42256 | 42258 |
| 42261 | 42264 | 42265 | 42267 | 42270 | 42279 | 42280 | 42281 | 42282 | 42284 | 42285 | 42287 |
| 42288 | 42289 | 42292 | 42293 | 42294 | 42295 | 42299 | 42300 | 42301 | 42304 | 42305 | 42307 |
| 42311 | 42312 | 42315 | 42316 | 42318 | 42319 | 42320 | 42322 | 42323 | 42324 | 42326 | 42327 |
| 42328 | 42329 | 42330 | 42331 | 42333 | 42334 | 42335 | 42336 | 42337 | 42338 | 42341 | 42342 |
| 42344 | 42347 | 42352 | 42354 | 42355 | 42358 | 42359 | 42360 | 42361 | 42363 | 42365 | 42375 |
| 42378 | 42380 | 42381 | 42382 | 42383 | 42384 | 42386 | 42393 | 42394 | 42397 | 42398 | |
| 42403 | 42405 | 42406 | 42407 | 42409 | 42411 | 42412 | 42415 | 42416 | 42418 | 42420 | 42423 |
| 42424 | 42426 | 42427 | 42428 | 42429 | 42432 | 42438 | 42439 | 42441 | 42442 | 42443 | 42446 |
| 42447 | 42448 | 42449 | 42451 | 42455 | 42456 | 42458 | 42461 | 42462 | 42466 | 42467 | 42468 |
| 42473 | 42475 | 42476 | 42478 | 42480 | 42482 | 42485 | 42491 | 42492 | 42494 | 42495 | |
| 42499 | 42501 | 42502 | 42503 | 42504 | 42506 | 42507 | 42508 | 42511 | 42515 | 42517 | 42518 |
| 42519 | 42523 | 42527 | 42531 | 42532 | 42533 | 42534 | 42535 | 42537 | 42542 | 42545 | 42546 |
| 42548 | 42549 | 42550 | 42551 | 42552 | 42553 | 42554 | 42556 | 42557 | 42558 | 42559 | 42560 |
| 42561 | 42564 | 42565 | 42569 | 42571 | 42572 | 42573 | 42574 | 42575 | 42576 | 42577 | 42580 |
| 42582 | 42584 | 42588 | 42589 | 42591 | 42592 | 42593 | 42594 | 42599 | 42601 | 42603 | 42604 |
| 42606 | 42608 | 42610 | 42612 | 42613 | 42617 | 42621 | 42622 | 42623 | 42624 | 42625 | 42628 |
| 42629 | 42630 | 42631 | 42636 | 42639 | 42640 | 42641 | 42642 | 42643 | 42644 | 42647 | 42648 |
| 42649 | 42650 | 42654 | 42657 | 42661 | 42662 | 42663 | 42665 | 42666 | 42669 | 42670 | 42676 |
| 42678 | 42683 | 42685 | 42686 | 42689 | 42694 | 42695 | 42699 | 42700 | 42702 | 42703 | 42705 |

TABLE 19-continued

Yield: Stress Tolerance

| | | | | | | | | | | | |
|---|---|---|---|---|---|---|---|---|---|---|---|
| 42708 | 42709 | 42710 | 42713 | 42715 | 42716 | 42718 | 42721 | 42722 | 42726 | 42735 | 42741 |
| 42742 | 42744 | 42745 | 42746 | 42747 | 42750 | 42752 | 42756 | 42758 | 42760 | 42766 | 42768 |
| 42773 | 42774 | 42779 | 42782 | 42785 | 42790 | 42792 | 42796 | 42799 | 42801 | 42802 | 42803 |
| 42805 | 42806 | 42807 | 42808 | 42810 | 42815 | 42820 | 42821 | 42823 | 42824 | 42825 | 42826 |
| 42829 | 42830 | 42831 | 42835 | 42841 | 42843 | 42844 | 42845 | 42846 | 42847 | 42852 | 42859 |
| 42862 | 42864 | 42866 | 42878 | 42881 | 42882 | 42885 | 42886 | 42887 | 42888 | 42889 | 42890 |
| 42891 | 42892 | 42893 | 42895 | 42898 | 42900 | 42901 | 42903 | 42905 | 42907 | 42908 | 42911 |
| 42912 | 42916 | 42918 | 42919 | 42920 | 42922 | 42926 | 42927 | 42929 | 42930 | 42931 | 42934 |
| 42935 | 42936 | 42939 | 42944 | 42947 | 42948 | 42951 | 42952 | 42955 | 42958 | 42959 | 42961 |
| 42962 | 42963 | 42964 | 42965 | 42967 | 42968 | 42971 | 42973 | 42975 | 42978 | 42981 | 42982 |
| 42987 | 42988 | 42989 | 42990 | 42992 | 42993 | 42996 | 43001 | 43002 | 43004 | 43015 | 43017 |
| 43020 | 43021 | 43023 | 43024 | 43025 | 43027 | 43030 | 43037 | 43038 | 43045 | 43046 | 43047 |
| 43050 | 43051 | 43052 | 43053 | 43058 | 43059 | 43067 | 43068 | 43072 | 43073 | 43076 | 43077 |
| 43078 | 43079 | 43081 | 43082 | 43083 | 43086 | 43089 | 43091 | 43092 | 43093 | 43094 | 43097 |
| 43098 | 43101 | 43102 | 43103 | 43107 | 43110 | 43113 | 43114 | 43115 | 43120 | 43121 | 43122 |
| 43123 | 43126 | 43127 | 43128 | 43142 | 43143 | 43144 | 43145 | 43148 | 43150 | 43151 | 43152 |
| 43154 | 43158 | 43159 | 43160 | 43161 | 43163 | 43167 | 43168 | 43169 | 43170 | 43172 | 43173 |
| 43174 | 43179 | 43180 | 43187 | 43189 | 43193 | 43195 | 43197 | 43198 | 43199 | 43200 | |
| 43203 | 43205 | 43206 | 43207 | 43208 | 43209 | 43210 | 43213 | 43218 | 43219 | 43228 | 43229 |
| 43230 | 43231 | 43234 | 43236 | 43237 | 43240 | 43244 | 43245 | 43246 | 43247 | 43250 | 43251 |
| 43256 | 43258 | 43259 | 43260 | 43262 | 43264 | 43265 | 43266 | 43267 | 43270 | 43272 | 43275 |
| 43280 | 43281 | 43282 | 43286 | 43287 | 43288 | 43289 | 43291 | 43293 | 43295 | 43297 | |
| 43298 | 43299 | 43301 | 43303 | 43304 | 43305 | 43307 | 43311 | 43314 | 43315 | 43318 | 43321 |
| 43324 | 43326 | 43328 | 43329 | 43331 | 43332 | 43334 | 43340 | 43341 | 43343 | 43344 | 43346 |
| 43351 | 43352 | 43353 | 43356 | 43357 | 43358 | 43359 | 43363 | 43371 | 43373 | 43376 | 43377 |
| 43380 | 43383 | 43390 | 43391 | 43395 | 43398 | 43401 | 43403 | 43406 | 43407 | 43409 | 43411 |
| 43414 | 43415 | 43416 | 43417 | 43418 | 43419 | 43420 | 43422 | 43424 | 43426 | 43433 | 43435 |
| 43436 | 43441 | 43442 | 43446 | 43448 | 43450 | 43452 | 43453 | 43454 | 43459 | 43461 | 43463 |
| 43465 | 43466 | 43472 | 43475 | 43477 | 43478 | 43482 | 43486 | 43487 | 43489 | 43490 | 43492 |
| 43495 | 43506 | 43507 | 43508 | 43510 | 43511 | 43513 | 43516 | 43518 | 43520 | 43525 | 43526 |
| 43527 | 43528 | 43529 | 43533 | 43534 | 43537 | 43539 | 43540 | 43541 | 43542 | 43544 | 43546 |
| 43547 | 43548 | 43552 | 43555 | 43556 | 43557 | 43562 | 43564 | 43565 | 43567 | 43571 | 43572 |
| 43578 | 43579 | 43582 | 43583 | 43584 | 43589 | 43590 | 43596 | 43598 | 43601 | 43602 | 43603 |
| 43604 | 43605 | 43608 | 43609 | 43611 | 43615 | 43616 | 43617 | 43618 | 43619 | 43620 | 43622 |
| 43623 | 43624 | 43625 | 43629 | 43630 | 43632 | 43633 | 43635 | 43637 | 43641 | 43642 | 43643 |
| 43645 | 43648 | 43649 | 43651 | 43655 | 43656 | 43662 | 43664 | 43672 | 43673 | 43675 | 43677 |
| 43678 | 43681 | 43687 | 43690 | 43692 | 43693 | 43696 | 43698 | 43699 | 43700 | 43706 | 43708 |
| 43709 | 43710 | 43711 | 43712 | 43714 | 43715 | 43718 | 43719 | 43720 | 43722 | 43725 | 43729 |
| 43733 | 43735 | 43737 | 43743 | 43744 | 43745 | 43747 | 43752 | 43753 | 43754 | 43755 | 43761 |
| 43762 | 43765 | 43766 | 43771 | 43773 | 43775 | 43776 | 43790 | 43791 | 43793 | 43795 | 43798 |
| 43799 | 43800 | 43805 | 43806 | 43807 | 43809 | 43813 | 43814 | 43816 | 43817 | 43820 | 43821 |
| 43822 | 43824 | 43827 | 43828 | 43830 | 43831 | 43834 | 43835 | 43836 | 43837 | 43842 | 43844 |
| 43845 | 43849 | 43854 | 43859 | 43860 | 43861 | 43865 | 43872 | 43873 | 43879 | 43881 | 43882 |
| 43884 | 43885 | 43886 | 43888 | 43890 | 43891 | 43892 | 43894 | 43895 | 43899 | 43900 | 43901 |
| 43902 | 43903 | 43906 | 43907 | 43908 | 43910 | 43912 | 43913 | 43914 | 43916 | 43917 | 43923 |
| 43924 | 43925 | 43928 | 43929 | 43930 | 43933 | 43934 | 43935 | 43936 | 43939 | 43940 | 43942 |
| 43944 | 43946 | 43947 | 43948 | 43949 | 43950 | 43951 | 43953 | 43955 | 43956 | 43962 | 43963 |
| 43964 | 43965 | 43967 | 43969 | 43972 | 43974 | 43976 | 43978 | 43983 | 43984 | 43985 | 43986 |
| 43988 | 43991 | 43996 | 43999 | 44000 | 44001 | 44004 | 44006 | 44007 | 44008 | 44009 | 44010 |
| 44011 | 44012 | 44015 | 44019 | 44021 | 44022 | 44024 | 44029 | 44037 | 44038 | 44042 | 44043 |
| 44044 | 44045 | 44050 | 44052 | 44053 | 44055 | 44059 | 44060 | 44061 | 44062 | 44063 | 44064 |
| 44065 | 44067 | 44070 | 44071 | 44075 | 44076 | 44077 | 44079 | 44081 | 44082 | 44084 | 44087 |
| 44094 | 44095 | 44096 | 44097 | 44098 | 44099 | 44100 | 44101 | 44104 | 44105 | 44106 | 44108 |
| 44115 | 44119 | 44121 | 44122 | 44123 | 44124 | 44125 | 44126 | 44127 | 44128 | 44129 | 44130 |
| 44132 | 44133 | 44134 | 44135 | 44136 | 44137 | 44139 | 44140 | 44141 | 44142 | 44147 | 44148 |
| 44159 | 44161 | 44167 | 44171 | 44173 | 44179 | 44180 | 44181 | 44190 | 44191 | 44193 | 44194 |
| 44201 | 44202 | 44207 | 44217 | 44218 | 44222 | 44223 | 44226 | 44230 | 44233 | 44234 | 44235 |
| 44237 | 44238 | 44240 | 44241 | 44244 | 44245 | 44247 | 44249 | 44251 | 44252 | 44253 | 44255 |
| 44256 | 44257 | 44262 | 44264 | 44265 | 44267 | 44273 | 44278 | 44280 | 44284 | 44287 | 44288 |
| 44290 | 44294 | 44302 | 44306 | 44308 | 44310 | 44311 | 44312 | 44315 | 44316 | 44317 | |
| 44319 | 44320 | 44321 | 44322 | 44328 | 44330 | 44331 | 44333 | 44334 | 44335 | 44338 | 44339 |
| 44342 | 44345 | 44346 | 44347 | 44355 | 44356 | 44357 | 44362 | 44367 | 44372 | 44373 | 44374 |
| 44376 | 44381 | 44388 | 44389 | 44391 | 44393 | 44394 | 44396 | 44400 | 44401 | 44402 | 44404 |
| 44410 | 44415 | 44418 | 44420 | 44421 | 44426 | 44430 | 44432 | 44436 | 44437 | 44442 | |
| 44443 | 44444 | 44445 | 44446 | 44448 | 44452 | 44457 | 44459 | 44460 | 44461 | 44463 | 44464 |
| 44468 | 44469 | 44471 | 44473 | 44474 | 44475 | 44476 | 44482 | 44484 | 44485 | 44487 | 44488 |
| 44489 | 44492 | 44493 | 44494 | 44495 | 44496 | 44497 | 44498 | 44504 | 44506 | 44507 | 44514 |
| 44515 | 44516 | 44517 | 44519 | 44520 | 44521 | 44522 | 44523 | 44534 | 44535 | 44539 | |
| 44540 | 44541 | 44546 | 44547 | 44548 | 44549 | 44550 | 44552 | 44556 | 44557 | 44558 | 44560 |
| 44564 | 44565 | 44567 | 44568 | 44569 | 44572 | 44573 | 44578 | 44579 | 44580 | 44581 | 44582 |
| 44589 | 44591 | 44592 | 44594 | 44595 | 44596 | 44597 | 44600 | 44602 | 44605 | 44606 | 44608 |
| 44609 | 44610 | 44616 | 44617 | 44620 | 44622 | 44624 | 44627 | 44628 | 44629 | 44633 | 44634 |
| 44636 | 44637 | 44639 | 44642 | 44643 | 44644 | 44649 | 44651 | 44652 | 44653 | 44654 | 44656 |
| 44659 | 44661 | 44662 | 44665 | 44666 | 44669 | 44670 | 44671 | 44674 | 44675 | 44676 | 44677 |
| 44678 | 44679 | 44680 | 44682 | 44684 | 44689 | 44690 | 44691 | 44694 | 44695 | 44696 | 44698 |
| 44699 | 44700 | 44701 | 44707 | 44710 | 44719 | 44724 | 44726 | 44727 | 44728 | 44729 | 44730 |
| 44734 | 44737 | 44738 | 44739 | 44742 | 44745 | 44746 | 44747 | 44752 | 44754 | 44755 | 44756 |

TABLE 19-continued

Yield: Stress Tolerance

| | | | | | | | | | | | |
|---|---|---|---|---|---|---|---|---|---|---|---|
| 44760 | 44762 | 44764 | 44767 | 44768 | 44772 | 44775 | 44776 | 44778 | 44779 | 44782 | 44783 |
| 44785 | 44790 | 44792 | 44795 | 44796 | 44797 | 44798 | 44799 | 44800 | 44802 | 44803 | 44804 |
| 44805 | 44806 | 44809 | 44810 | 44811 | 44815 | 44816 | 44817 | 44823 | 44824 | 44827 | 44828 |
| 44830 | 44831 | 44834 | 44836 | 44837 | 44838 | 44840 | 44848 | 44850 | 44851 | 44852 | 44854 |
| 44857 | 44860 | 44863 | 44864 | 44865 | 44866 | 44872 | 44873 | 44875 | 44882 | 44883 | 44885 |
| 44886 | 44887 | 44889 | 44890 | 44891 | 44893 | 44895 | 44896 | 44897 | 44900 | 44906 | 44907 |
| 44911 | 44913 | 44914 | 44915 | 44916 | 44918 | 44920 | 44922 | 44925 | 44927 | 44930 | 44931 |
| 44932 | 44936 | 44937 | 44938 | 44947 | 44950 | 44951 | 44952 | 44953 | 44957 | 44958 | 44959 |
| 44962 | 44963 | 44964 | 44967 | 44968 | 44969 | 44970 | 44971 | 44972 | 44974 | 44977 | 44978 |
| 44983 | 44987 | 44991 | 44993 | 44995 | 44996 | 45000 | 45001 | 45003 | 45008 | 45010 | 45011 |
| 45015 | 45017 | 45018 | 45019 | 45020 | 45022 | 45027 | 45028 | 45029 | 45030 | 45031 | 45032 |
| 45033 | 45034 | 45035 | 45038 | 45040 | 45041 | 45043 | 45044 | 45046 | 45050 | 45051 | 45052 |
| 45053 | 45054 | 45055 | 45056 | 45058 | 45059 | 45060 | 45065 | 45066 | 45068 | 45070 | 45071 |
| 45073 | 45074 | 45076 | 45077 | 45079 | 45080 | 45081 | 45082 | 45083 | 45085 | 45089 | 45091 |
| 45092 | 45093 | 45096 | 45097 | 45098 | 45101 | 45102 | 45103 | 45105 | 45106 | 45109 | 45110 |
| 45111 | 45112 | 45115 | 45117 | 45119 | 45120 | 45121 | 45122 | 45123 | 45126 | 45128 | 45129 |
| 45130 | 45132 | 45133 | 45134 | 45135 | 45142 | 45143 | 45144 | 45149 | 45150 | 45151 | 45152 |
| 45153 | 45159 | 45160 | 45162 | 45163 | 45165 | 45166 | 45167 | 45168 | 45171 | 45173 | 45175 |
| 45178 | 45179 | 45181 | 45182 | 45183 | 45184 | 45185 | 45186 | 45189 | 45191 | 45192 | 45193 |
| 45194 | 45196 | 45197 | 45198 | 45200 | 45201 | 45202 | 45209 | 45213 | 45214 | 45215 | 45225 |
| 45228 | 45230 | 45232 | 45234 | 45236 | 45239 | 45242 | 45243 | 45244 | 45245 | 45246 | 45248 |
| 45252 | 45253 | 45254 | 45261 | 45265 | 45267 | 45270 | 45272 | 45273 | 45274 | 45275 | 45276 |
| 45277 | 45278 | 45279 | 45280 | 45285 | 45287 | 45289 | 45294 | 45295 | 45298 | 45299 | 45302 |
| 45303 | 45309 | 45310 | 45311 | 45316 | 45318 | 45324 | 45326 | 45327 | 45330 | 45332 | 45334 |
| 45336 | 45339 | 45340 | 45341 | 45342 | 45343 | 45347 | 45351 | 45353 | 45355 | 45357 | 45360 |
| 45364 | 45366 | 45367 | 45369 | 45370 | 45371 | 45376 | 45377 | 45378 | 45379 | 45380 | 45381 |
| 45383 | 45385 | 45386 | 45388 | 45389 | 45390 | 45391 | 45398 | 45399 | 45409 | 45411 | 45413 |
| 45415 | 45416 | 45418 | 45428 | 45432 | 45433 | 45434 | 45437 | 45438 | 45440 | 45443 | 45444 |
| 45445 | 45447 | 45450 | 45452 | 45457 | 45458 | 45459 | 45464 | 45465 | 45466 | 45467 | 45468 |
| 45475 | 45477 | 45478 | 45479 | 45481 | 45482 | 45483 | 45484 | 45488 | 45489 | 45490 | 45496 |
| 45497 | 45498 | 45499 | 45500 | 45501 | 45502 | 45503 | 45505 | 45506 | 45508 | 45509 | |
| 45510 | 45511 | 45512 | 45514 | 45519 | 45523 | 45524 | 45525 | 45526 | 45527 | 45528 | 45529 |
| 45531 | 45532 | 45534 | 45535 | 45537 | 45538 | 45540 | 45541 | 45545 | 45546 | 45552 | 45553 |
| 45554 | 45556 | 45560 | 45562 | 45563 | 45565 | 45569 | 45570 | 45572 | 45574 | 45576 | 45577 |
| 45578 | 45583 | 45584 | 45587 | 45589 | 45592 | 45597 | 45598 | 45599 | 45602 | 45603 | 45604 |
| 45605 | 45606 | 45608 | 45613 | 45616 | 45617 | 45621 | 45624 | 45625 | 45627 | 45629 | 45630 |
| 45632 | 45635 | 45636 | 45637 | 45640 | 45641 | 45643 | 45645 | 45646 | 45647 | 45648 | 45649 |
| 45651 | 45652 | 45656 | 45658 | 45660 | 45661 | 45662 | 45667 | 45668 | 45669 | 45670 | 45671 |
| 45672 | 45673 | 45674 | 45675 | 45676 | 45686 | 45687 | 45693 | 45694 | 45696 | 45697 | 45698 |
| 45699 | 45700 | 45702 | 45703 | 45706 | 45707 | 45708 | 45709 | 45711 | 45714 | 45717 | 45718 |
| 45720 | 45721 | 45725 | 45726 | 45727 | 45728 | 45730 | 45731 | 45732 | 45733 | 45734 | 45735 |
| 45736 | 45737 | 45740 | 45741 | 45743 | 45745 | 45747 | 45750 | 45753 | 45754 | 45758 | 45759 |
| 45762 | 45763 | 45765 | 45768 | 45769 | 45770 | 45775 | 45777 | 45780 | 45781 | 45783 | 45785 |
| 45788 | 45791 | 45794 | 45795 | 45796 | 45797 | 45801 | 45803 | 45807 | 45811 | 45812 | 45813 |
| 45814 | 45815 | 45820 | 45822 | 45824 | 45825 | 45826 | 45827 | 45828 | 45830 | 45831 | 45832 |
| 45833 | 45834 | 45835 | 45837 | 45838 | 45840 | 45841 | 45842 | 45843 | 45845 | 45847 | 45848 |
| 45851 | 45852 | 45853 | 45854 | 45855 | 45857 | 45858 | 45862 | 45863 | 45864 | 45865 | 45868 |
| 45870 | 45871 | 45872 | 45873 | 45874 | 45877 | 45878 | 45879 | 45880 | 45882 | 45885 | 45887 |
| 45888 | 45891 | 45892 | 45893 | 45894 | 45897 | 45901 | 45903 | 45904 | 45905 | 45907 | 45908 |
| 45911 | 45912 | 45913 | 45914 | 45915 | 45919 | 45920 | 45922 | 45924 | 45926 | 45927 | 45930 |
| 45931 | 45933 | 45936 | 45938 | 45939 | 45940 | 45942 | 45944 | 45951 | 45952 | 45953 | 45955 |
| 45956 | 45957 | 45958 | 45959 | 45964 | 45966 | 45967 | 45968 | 45969 | 45970 | 45971 | 45976 |
| 45978 | 45980 | 45981 | 45982 | 45983 | 45985 | 45986 | 45987 | 45988 | 45989 | 45990 | 45993 |
| 45995 | 45997 | 46000 | 46001 | 46002 | 46003 | 46006 | 46007 | 46012 | 46019 | 46020 | 46022 |
| 46023 | 46027 | 46028 | 46029 | 46033 | 46037 | 46038 | 46039 | 46040 | 46041 | 46044 | 46046 |
| 46047 | 46049 | 46051 | 46052 | 46053 | 46054 | 46055 | 46056 | 46057 | 46058 | 46059 | 46060 |
| 46062 | 46063 | 46065 | 46066 | 46067 | 46069 | 46071 | 46073 | 46074 | 46077 | 46078 | 46079 |
| 46080 | 46081 | 46083 | 46085 | 46086 | 46087 | 46088 | 46089 | 46092 | 46093 | 46094 | 46096 |
| 46097 | 46100 | 46102 | 46103 | 46104 | 46107 | 46111 | 46112 | 46114 | 46115 | 46117 | 46119 |
| 46120 | 46123 | 46125 | 46126 | 46130 | 46131 | 46133 | 46139 | 46141 | 46145 | 46146 | 46147 |
| 46148 | 46150 | 46155 | 46158 | 46159 | 46167 | 46169 | 46171 | 46174 | 46177 | 46179 | 46181 |
| 46182 | 46183 | 46184 | 46185 | 46186 | 46187 | 46188 | 46189 | 46190 | 46194 | 46196 | 46197 |
| 46198 | 46199 | 46202 | 46204 | 46207 | 46209 | 46212 | 46215 | 46220 | 46223 | 46224 | 46225 |
| 46227 | 46230 | 46231 | 46232 | 46234 | 46235 | 46237 | 46238 | 46244 | 46245 | 46251 | 46252 |
| 46255 | 46256 | 46257 | 46258 | 46260 | 46262 | 46264 | 46265 | 46266 | 46268 | 46269 | 46270 |
| 46271 | 46272 | 46275 | 46277 | 46278 | 46279 | 46280 | 46281 | 46282 | 46283 | 46284 | 46288 |
| 46292 | 46293 | 46294 | 46296 | 46297 | 46298 | 46299 | 46300 | 46303 | 46304 | 46307 | 46308 |
| 46309 | 46311 | 46312 | 46313 | 46315 | 46317 | 46318 | 46319 | 46321 | 46325 | 46328 | 46329 |
| 46333 | 46336 | 46339 | 46340 | 46341 | 46347 | 46354 | 46356 | 46359 | 46361 | 46362 | 46367 |
| 46370 | 46372 | 46374 | 46378 | 46380 | 46381 | 46383 | 46385 | 46387 | 46388 | 46389 | 46391 |
| 46392 | 46393 | 46394 | 46395 | 46399 | 46400 | 46409 | 46412 | 46413 | 46414 | 46415 | 46417 |
| 46419 | 46420 | 46424 | 46426 | 46427 | 46428 | 46429 | 46430 | 46431 | 46433 | 46435 | 46437 |
| 46439 | 46440 | 46441 | 46442 | 46444 | 46446 | 46447 | 46449 | 46450 | 46451 | 46452 | 46454 |
| 46455 | 46456 | 46458 | 46459 | 46462 | 46463 | 46464 | 46467 | 46468 | 46469 | 46473 | 46475 |
| 46476 | 46477 | 46478 | 46481 | 46485 | 46486 | 46488 | 46489 | 46491 | 46493 | 46494 | 46495 |
| 46496 | 46497 | 46498 | 46500 | 46502 | 46504 | 46508 | 46510 | 46512 | 46515 | 46518 | 46519 |
| 46521 | 46522 | 46525 | 46526 | 46527 | 46530 | 46531 | 46533 | 46535 | 46541 | 46546 | 46549 |

TABLE 19-continued

Yield: Stress Tolerance

| | | | | | | | | | | |
|---|---|---|---|---|---|---|---|---|---|---|
| 46550 | 46551 | 46552 | 46555 | 46557 | 46559 | 46560 | 46562 | 46565 | 46568 | 46572 | 46573 |
| 46577 | 46578 | 46581 | 46582 | 46584 | 46585 | 46587 | 46588 | 46589 | 46590 | 46592 | 46593 |
| 46594 | 46597 | 46598 | 46599 | 46600 | 46607 | 46608 | 46609 | 46611 | 46612 | 46614 | 46615 |
| 46617 | 46618 | 46620 | 46622 | 46623 | 46626 | 46633 | 46635 | 46640 | 46642 | 46643 | 46644 |
| 46645 | 46649 | 46651 | 46653 | 46655 | 46658 | 46659 | 46667 | 46669 | 46670 | 46673 | 46674 |
| 46676 | 46679 | 46682 | 46683 | 46684 | 46686 | 46687 | 46688 | 46690 | 46691 | 46692 | 46694 |
| 46695 | 46698 | 46700 | 46702 | 46712 | 46713 | 46715 | 46716 | 46717 | 46720 | 46724 | 46725 |
| 46731 | 46736 | 46738 | 46739 | 46741 | 46746 | 46747 | 46749 | 46750 | 46752 | 46754 | 46755 |
| 46758 | 46760 | 46762 | 46766 | 46767 | 46770 | 46774 | 46776 | 46777 | 46782 | 46784 | 46787 |
| 46788 | 46794 | 46795 | 46797 | 46798 | 46800 | 46802 | 46803 | 46804 | 46806 | 46807 | 46808 |
| 46811 | 46812 | 46813 | 46814 | 46822 | 46828 | 46829 | 46832 | 46833 | 46834 | 46835 | 46842 |
| 46844 | 46845 | 46849 | 46850 | 46853 | 46854 | 46863 | 46866 | 46867 | 46868 | 46869 | 46870 |
| 46872 | 46875 | 46885 | 46888 | 46889 | 46892 | 46894 | 46901 | 46904 | 46906 | 46907 | 46908 |
| 46909 | 46910 | 46913 | 46914 | 46917 | 46920 | 46923 | 46927 | 46928 | 46930 | 46932 | 46933 |
| 46934 | 46941 | 46942 | 46943 | 46946 | 46948 | 46950 | 46952 | 46957 | 46958 | 46959 | 46963 |
| 46968 | 46970 | 46973 | 46977 | 46979 | 46981 | 46982 | 46984 | 46985 | 46989 | 46991 | 46993 |
| 46999 | 47000 | 47003 | 47009 | 47011 | 47013 | 47016 | 47017 | 47018 | 47019 | 47021 | 47025 |
| 47030 | 47031 | 47036 | 47037 | 47039 | 47042 | 47045 | 47046 | 47047 | 47050 | 47051 | 47052 |
| 47053 | 47057 | 47058 | 47059 | 47063 | 47067 | 47068 | 47070 | 47071 | 47072 | 47078 | 47079 |
| 47081 | 47082 | 47084 | 47085 | 47088 | 47089 | 47090 | 47092 | 47094 | 47100 | 47101 | 47102 |
| 47110 | 47112 | 47113 | 47114 | 47116 | 47117 | 47121 | 47123 | 47127 | 47128 | 47133 | 47135 |
| 47136 | 47137 | 47139 | 47140 | 47144 | 47146 | 47150 | 47151 | 47152 | 47154 | 47155 | 47156 |
| 47157 | 47161 | 47166 | 47167 | 47171 | 47174 | 47175 | 47176 | 47178 | 47184 | 47185 | 47187 |
| 47189 | 47190 | 47192 | 47198 | 47199 | 47201 | 47202 | 47203 | 47207 | 47211 | 47213 | 47216 |
| 47218 | 47219 | 47221 | 47222 | 47223 | 47225 | 47226 | 47227 | 47233 | 47236 | 47237 | 47238 |
| 47239 | 47240 | 47247 | 47249 | 47252 | 47254 | 47255 | 47262 | 47269 | 47270 | 47271 | 47277 |
| 47278 | 47279 | 47282 | 47285 | 47288 | 47289 | 47291 | 47294 | 47297 | 47299 | 47300 | 47301 |
| 47302 | 47304 | 47305 | 47306 | 47309 | 47310 | 47312 | 47318 | 47321 | 47325 | 47327 | 47332 |
| 47334 | 47335 | 47336 | 47337 | 47338 | 47339 | 47340 | 47343 | 47345 | 47346 | 47349 | 47351 |
| 47353 | 47354 | 47355 | 47356 | 47358 | 47360 | 47361 | 47362 | 47363 | 47365 | 47368 | 47371 |
| 47373 | | | | | | | | | | | |

TABLE 20

Lignin Biosynthesis

Table 20A SEQ ID NOs of Polypeptides useful for improving Lignin Biosynthesis

| | | | | | | | | | | |
|---|---|---|---|---|---|---|---|---|---|---|
| 492 | 507 | 721 | 833 | 1355 | 1356 | 1472 | 1539 | 1878 | 1928 | 1932 | 2023 |
| 2335 | 2337 | 2880 | 2924 | 3135 | 3566 | 3749 | 3785 | 3812 | 3831 | 3857 | 4051 |
| 4167 | 4408 | 4456 | 4659 | 4680 | 4949 | 5302 | 5677 | 5678 | 5679 | 5897 | 6195 |
| 6275 | 6276 | 6277 | 6278 | 6290 | 6302 | 6303 | 6321 | 6507 | 6508 | 6965 | 7164 |
| 7216 | 7418 | 7439 | 7707 | 7993 | 8165 | 8236 | 8547 | 8639 | 8700 | 8722 | 8961 |
| 9079 | 9115 | 9117 | 9281 | 9309 | 9398 | 9399 | 10218 | 10562 | 10717 | 10803 | 10892 |
| 11040 | 11058 | 11065 | 11345 | 11395 | 11462 | 11527 | 11556 | 11684 | 11765 | 11860 | 11865 |
| 11934 | 12024 | 12263 | 12329 | 12460 | 12631 | 12670 | 12818 | 12853 | 12950 | 13012 | 13016 |
| 13060 | 13100 | 13135 | 13170 | 13288 | 13372 | 13381 | 13482 | 13557 | 13850 | 13927 | 14042 |
| 14080 | 14111 | 14179 | 14207 | 14280 | 14347 | 14420 | 14511 | 14593 | 14671 | 14728 | 14787 |
| 14789 | 14922 | 14948 | 14953 | 14961 | 15152 | 15208 | 15360 | 15727 | 16111 | 16399 | 16538 |
| 16543 | 17022 | 17479 | 17563 | 17612 | 17614 | 17735 | 17952 | 18204 | 18212 | 18262 | 18393 |
| 18493 | 18736 | 18975 | 18984 | 19400 | 19507 | 19509 | 19514 | 19684 | 19750 | 19972 | 20111 |
| 20427 | 20462 | 20499 | 20552 | 20590 | 20721 | 20851 | 21322 | 22735 | 22884 | 22908 | 22951 |
| 23041 | 23211 | 23680 | 23682 | 23685 | | | | | | | |

Table 20B SEQ ID NOs of Polynucleotides useful for improving Lignin Biosynthesis

| | | | | | | | | | | |
|---|---|---|---|---|---|---|---|---|---|---|
| 24179 | 24194 | 24408 | 24520 | 25042 | 25043 | 25159 | 25226 | 25565 | 25615 | 25619 | 25710 |
| 26022 | 26024 | 26567 | 26611 | 26822 | 27253 | 27436 | 27472 | 27499 | 27518 | 27544 | 27738 |
| 27854 | 28095 | 28143 | 28346 | 28367 | 28636 | 28989 | 29364 | 29365 | 29366 | 29584 | 29882 |
| 29962 | 29963 | 29964 | 29965 | 29977 | 29989 | 29990 | 30008 | 30194 | 30195 | 30652 | 30851 |
| 30903 | 31105 | 31126 | 31394 | 31680 | 31852 | 31923 | 32234 | 32326 | 32387 | 32409 | 32648 |
| 32766 | 32802 | 32804 | 32968 | 32996 | 33085 | 33086 | 33905 | 34249 | 34404 | 34490 | 34579 |
| 34727 | 34745 | 34752 | 35032 | 35082 | 35149 | 35214 | 35371 | 35452 | 35547 | 35552 |
| 35621 | 35711 | 35950 | 36016 | 36147 | 36318 | 36357 | 36505 | 36540 | 36637 | 36699 | 36703 |
| 36747 | 36787 | 36822 | 36857 | 36975 | 37059 | 37068 | 37169 | 37244 | 37537 | 37614 | 37729 |
| 37767 | 37798 | 37866 | 37894 | 37967 | 38034 | 38107 | 38198 | 38280 | 38358 | 38415 | 38474 |
| 38476 | 38609 | 38635 | 38640 | 38648 | 38839 | 38895 | 39047 | 39414 | 39798 | 40086 | 40225 |
| 40230 | 40709 | 41166 | 41250 | 41299 | 41301 | 41422 | 41639 | 41891 | 41899 | 41949 | 42080 |
| 42180 | 42423 | 42662 | 42671 | 43087 | 43194 | 43196 | 43201 | 43371 | 43437 | 43659 | 43798 |
| 44114 | 44149 | 44186 | 44239 | 44277 | 44408 | 44538 | 45009 | 46422 | 46571 | 46595 | 46638 |
| 46728 | 46898 | 47367 | 47369 | 47372 | | | | | | | |

TABLE 21

Galactomannan Biosynthesis

Table 21A SEQ ID NOs of Polypeptides useful for improving Galactomannan Biosynthesis

| 24 | 438 | 1074 | 1109 | 1177 | 1244 | 1264 | 1879 | 2511 | 2515 | 2611 | 2778 |
|---|---|---|---|---|---|---|---|---|---|---|---|
| 2897 | 3068 | 3100 | 3156 | 3389 | 3658 | 3703 | 4011 | 4017 | 4041 | 4722 | 4782 |
| 5038 | 5118 | 5582 | 6089 | 6115 | 6181 | 6511 | 6515 | 6520 | 6768 | 6780 | 6870 |
| 7481 | 7542 | 7763 | 8221 | 8246 | 8820 | 8937 | 9087 | 9210 | 9402 | 9680 | 10116 |
| 10458 | 10529 | 10549 | 10746 | 11191 | 11430 | 11543 | 11846 | 12090 | 12204 | 12230 | 12427 |
| 12730 | 12896 | 13091 | 13245 | 13474 | 13753 | 13847 | 14243 | 14505 | 14601 | 14906 | 14993 |
| 15309 | 15424 | 15675 | 15792 | 16065 | 16174 | 16699 | 16741 | 16765 | 16796 | 17119 | 17150 |
| 17493 | 18047 | 18398 | 18527 | 18948 | 19100 | 19219 | 19251 | 19598 | 19862 | 19982 | 20293 |
| 20311 | 20330 | 20678 | 21036 | 21048 | 21242 | 21548 | 21920 | 22066 | 22206 | 22242 | 22882 |
| 23056 | 23093 | 23411 | 23454 | 23611 | | | | | | | |

Table 21B SEQ ID NOs of Polynucleotides useful for improving Galactomannan Biosynthesis

| 23711 | 24125 | 24761 | 24796 | 24864 | 24931 | 24951 | 25566 | 26198 | 26202 | 26298 | 26465 |
|---|---|---|---|---|---|---|---|---|---|---|---|
| 26584 | 26755 | 26787 | 26843 | 27076 | 27345 | 27390 | 27698 | 27704 | 27728 | 28409 | 28469 |
| 28725 | 28805 | 29269 | 29776 | 29802 | 29868 | 30198 | 30202 | 30207 | 30455 | 30467 | 30557 |
| 31168 | 31229 | 31450 | 31908 | 31933 | 32507 | 32624 | 32774 | 32897 | 33089 | 33367 | 33803 |
| 34145 | 34216 | 34236 | 34433 | 34878 | 35117 | 35230 | 35533 | 35777 | 35891 | 35917 | 36114 |
| 36417 | 36583 | 36778 | 36932 | 37161 | 37440 | 37534 | 37930 | 38192 | 38288 | 38593 | 38680 |
| 38996 | 39111 | 39362 | 39479 | 39752 | 39861 | 40386 | 40428 | 40452 | 40483 | 40806 | 40837 |
| 41180 | 41734 | 42085 | 42214 | 42635 | 42787 | 42906 | 42938 | 43285 | 43549 | 43669 | 43980 |
| 43998 | 44017 | 44365 | 44723 | 44735 | 44929 | 45235 | 45607 | 45753 | 45893 | 45929 | 46569 |
| 46743 | 46780 | 47098 | 47141 | 47298 | | | | | | | |

Table 1 Column Descriptions

Seq num provides the SEQ ID NO for the listed polynucleotide sequences.

SeqID provides an arbitrary sequence name taken from the name of the clone from which the cDNA sequence was obtained.

cat_type indicates the classification scheme used to classify the sequence. GO_BP=Gene Ontology Consortium–biological process; GO_CC=Gene Ontology Consortium–cellular component; GO_MF=Gene Ontology Consortium–molecular function; KEGG=KEGG functional hierarchy (KEGG=Kyoto Encyclopedia of Genes and Genomes); EC=Enzyme Classification from ENZYME data bank release 25.0; POI=Pathways of Interest.

cat_desc provides the classification scheme subcategory to which the query sequence was assigned.

hit_desc provides the description of the BLAST hit which resulted in assignment of the sequence to the function category provided in the cat_desc column.

hit_p provides the E value for the BLAST hit in the hit_desc column.

pct_ident refers to the percentage of identically matched nucleotides (or residues) that exist along the length of that portion of the sequences which is aligned in the BLAST match provided in hit_desc.

qry_range lists the range of the query sequence aligned with the hit.

hit_range lists the range of the hit sequence aligned with the query.

qry cvrg provides the percent of query sequence length that matches to the hit (NCBI) sequence in the BLAST match (% qry cvrg=(match length/query total length)×100).

hit cvrg provides the percent of hit sequence length that matches to the query sequence in the match generated using BLAST (% hit cvrg=(match length/hit total length)×100).

Species provides the name of the organism from which the cDNA was isolated.

Product_concept column provides the plant biological properties that may be modified by expression of the listed polypeptides.

All publications and patent applications cited herein are incorporated by reference in their entirely to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07314974B2). An electronic copy of the "Sequence Listing" will also be available from the USPTO upon request and payment of the fee set forth in 37 CFR 1.19(b)(3).

What is claimed is:

1. A transformed plant comprising a recombinant DNA construct comprising a promoter functional in a plant cell positioned to provide for expression of a polynucleotide encoding a S-adenosyl-L-homocysteine hydrolase having an amino acid sequence which has at least 50% sequence identity to SEQ ID NO:1740.

2. The transformed plant according to claim 1, wherein said polynucleotide comprises a nucleic acid sequence with at least 90% identity to SEQ ID NO:25427.

3. The transformed plant according to claim 2 wherein said plant is maize.

4. The transformed plant according to claim 2 wherein said plant is soybean.

5. A method of producing a transformed plant having an improved property, wherein said method comprises transforming a plant with a recombinant construct comprising a promoter functional in a plant cell positioned to provide for expression of a polynucleotide encoding a polypeptide useful for improving plant cold tolerance or yield improvement by providing improved plant growth and development under at least one stress condition wherein said polypeptide has an amino acid sequence which has at least 50% sequence identity to SEQ ID NO:1740.

6. The method according to claim 5, wherein said transformed plant is a crop plant.

7. The transformed plant according to claim 6 wherein said plant is maize.

8. The transformed plant according to claim 6 wherein said plant is soybean.

* * * * *